US012680096B2

(12) United States Patent
Bowen et al.

(10) Patent No.: US 12,680,096 B2
(45) Date of Patent: Jul. 14, 2026

(54) RNA-GUIDED NUCLEASES AND ACTIVE FRAGMENTS AND VARIANTS THEREOF AND METHODS OF USE

(71) Applicant: Life Edit Therapeutics, Inc., Durham, NC (US)

(72) Inventors: Tyson D. Bowen, Morrisville, NC (US); Alexandra Briner Crawley, Cary, NC (US); Tedd D. Elich, Durham, NC (US); Michael Coyle, Chapel Hill, NC (US)

(73) Assignee: Life Edit Therapeutics, Inc., Durham, NC (US)

( * ) Notice: Subject to any disclaimer, the term of this patent is extended or adjusted under 35 U.S.C. 154(b) by 1059 days.

(21) Appl. No.: 17/634,723

(22) PCT Filed: Aug. 11, 2020

(86) PCT No.: PCT/US2020/045759
§ 371 (c)(1),
(2) Date: Feb. 11, 2022

(87) PCT Pub. No.: WO2021/030344
PCT Pub. Date: Feb. 18, 2021

(65) Prior Publication Data
US 2022/0364074 A1    Nov. 17, 2022

Related U.S. Application Data

(60) Provisional application No. 63/030,088, filed on May 26, 2020, provisional application No. 62/901,875, filed on Sep. 18, 2019, provisional application No. 62/885,483, filed on Aug. 12, 2019.

(51) Int. Cl.
C12N 15/10    (2006.01)
C12N 9/22    (2006.01)
C12N 15/79    (2006.01)

(52) U.S. Cl.
CPC ............ C12N 15/102 (2013.01); C12N 9/22 (2013.01); C12N 15/79 (2013.01); C12N 2310/20 (2017.05)

(58) Field of Classification Search
None
See application file for complete search history.

(56) References Cited

U.S. PATENT DOCUMENTS

| | | |
|---|---|---|
| 11,162,114 B2 | 11/2021 | Crawley et al. |
| 11,174,469 B2 | 11/2021 | Lundberg et al. |
| 11,180,778 B2 | 11/2021 | Savage et al. |
| 11,559,588 B2 | 1/2023 | Lundberg et al. |
| 11,564,997 B2 | 1/2023 | Lundberg et al. |
| 2014/0315985 A1 | 10/2014 | May et al. |
| 2016/0289659 A1 | 10/2016 | Doudna et al. |
| 2018/0362943 A1 | 12/2018 | Chittoor et al. |
| 2019/0185849 A1 | 6/2019 | Lundberg et al. |
| 2019/0211362 A1 | 7/2019 | Lundberg et al. |
| 2019/0365929 A1 | 12/2019 | Lundberg et al. |
| 2020/0040061 A1 | 2/2020 | Lundberg et al. |
| 2020/0080082 A1 | 3/2020 | Lundberg et al. |
| 2020/0095579 A1 | 3/2020 | Lundberg et al. |
| 2020/0123570 A1 | 4/2020 | Lundberg et al. |
| 2020/0216857 A1 | 7/2020 | Lundberg et al. |
| 2020/0407729 A1 | 12/2020 | Takeuchi et al. |

FOREIGN PATENT DOCUMENTS

| | | |
|---|---|---|
| CA | 2 872 241 A1 | 11/2013 |
| CA | 3 010 628 A1 | 9/2017 |
| CA | 3 029 141 A1 | 1/2018 |
| CA | 3 091 267 A1 | 8/2019 |
| CA | 3 121 191 A1 | 6/2020 |
| CA | 3 125 175 A1 | 7/2020 |
| CA | 3 132 630 A1 | 9/2020 |
| CN | 113631704 A | 11/2021 |
| EA | 201401319 | 5/2015 |
| EP | 3 245 232 | 11/2017 |
| EP | 3 699 281 A1 | 8/2020 |

(Continued)

OTHER PUBLICATIONS

Javaid & Choi, "CRISPR/Cas system and factors affecting its precision and efficiency" Fronties in Cell and Developmental Biology (Year: 2021).*

Ma et al. "Pol III promoters to express small RNAs: delineation of transcription initiation" Mol Ther Nucleic Acids (Year: 2014).*

Song & Stieger, "Optimizing the DNA donor template for homology directed repair of double stranded breaks" Molecular Therapy-Nucleic Acids (Year: 2017).*

Javiad & Choi, "CRISPR/Cas system and factors affecting its precision and efficiency" Front. Cell Dev. Diol (Year: 2021).*

Jiang, F., et al., "CRISPR-Cas9 Structures and Mechanisms," *Annu. Ref. Biophys.*, 2017, vol. 46(1), pp. 505-529.

Nam, K., et al., "Double-stranded Endonuclease Activity in *Bacillus halodurans* Clustered Regularly Interspaced Short Palindromic Repeats (CRISPR)-associate Cas2-Protein," *The Journal of Biological Chemistry*, 2012, vol. 287(43), pp. 35943-35952.

(Continued)

*Primary Examiner* — Tracy Vivlemore
*Assistant Examiner* — John David Moore
(74) *Attorney, Agent, or Firm* — Womble Bond Dickinson (US) LLP

(57)    ABSTRACT

Compositions and methods for binding to a target sequence of interest are provided. The compositions find use in cleaving or modifying a target sequence of interest, visualization of a target sequence of interest, and modifying the expression of a sequence of interest. Compositions comprise RNA-guided nuclease polypeptides, CRISPR RNAs, transactivating CRISPR RNAs, guide RNAs, and nucleic acid molecules encoding the same. Vectors and host cells comprising the nucleic acid molecules are also provided. Further provided are CRISPR systems for binding a target sequence of interest, wherein the CRISPR system comprises an RNA-guided nuclease polypeptide and one or more guide RNAs. Methods and kits for detecting a target DNA sequence are also provided.

38 Claims, No Drawings

Specification includes a Sequence Listing.

(56) References Cited

FOREIGN PATENT DOCUMENTS

| | | | |
|---|---|---|---|
| JP | 2019-520080 A | 7/2019 | |
| JP | 2020508056 A | 3/2020 | |
| JP | 2020508659 A | 3/2020 | |
| JP | 2020513824 A | 5/2020 | |
| JP | 2021518139 A | 8/2021 | |
| RU | 2015140276 A | 5/2017 | |
| RU | 2016104161 A | 8/2017 | |
| RU | 2016136702 A | 3/2018 | |
| RU | 2016101178 A | 11/2018 | |
| WO | WO 2013/176772 | 11/2013 | |
| WO | WO 2015/071474 A2 | 5/2015 | |
| WO | WO 2016/033298 A1 | 3/2016 | |
| WO | WO 2016/114972 A1 | 7/2016 | |
| WO | WO 2016/186946 A1 | 11/2016 | |
| WO | WO 2017/155714 A1 | 9/2017 | |
| WO | WO 2017/155717 A1 | 9/2017 | |
| WO | WO 2018/002886 A1 | 1/2018 | |
| WO | WO 2018/007980 A1 | 1/2018 | |
| WO | WO 2018/086623 A1 | 5/2018 | |
| WO | WO 2018/165629 A1 | 9/2018 | |
| WO | WO 2018/176009 A1 | 9/2018 | |
| WO | WO 2019/036185 A1 | 9/2018 | |
| WO | WO-2018172556 A1 * | 9/2018 | ......... A61K 31/7088 |
| WO | WO 2018/205995 A1 | 11/2018 | |
| WO | WO 2018/218188 A2 | 11/2018 | |
| WO | WO 2019/051097 A1 | 3/2019 | |
| WO | WO 2019/102381 A1 | 5/2019 | |
| WO | WO 2019/113310 A1 | 6/2019 | |
| WO | WO 2019/165168 A1 | 8/2019 | |
| WO | WO 2019/0183150 | 9/2019 | |

OTHER PUBLICATIONS

Moon, S., et al., "Improving CRISPR Genome Editing by Engineering Guide RNAs," *Trends in Biotechnology*, 2019, vol. 37(8), pp. 870-881.

Pickar-Oliver, et anan., "The next generation of CRISPR-Cas technologies and applications," *Nat Rev Mol Cell Biol.*, 2019, vol. 20(8), pp. 490-507.

Yang, Xiao, "Applications of CRISPR-Cas9 mediated genome engineering," *Military Medical Research*, 2015, vol. 2(11), pp. 1-6.

* cited by examiner

SEQUENCE LISTING

```
<160> NUMBER OF SEQ ID NOS: 742

<210> SEQ ID NO 1
<211> LENGTH: 1071
<212> TYPE: PRT
<213> ORGANISM: Bacillus sp.

<400> SEQUENCE: 1

Met Arg Glu Leu Asp Tyr Arg Ile Gly Leu Asp Ile Gly Thr Asn Ser
1               5                   10                  15

Ile Gly Trp Gly Val Ile Glu Leu Ser Trp Asn Lys Asp Arg Glu Gln
            20                  25                  30

Tyr Glu Lys Thr Arg Ile Val Asp Lys Gly Val Arg Met Phe Asp Lys
        35                  40                  45

Ala Glu Ile Pro Lys Thr Gly Ala Ser Leu Ala Glu Pro Arg Arg Ile
    50                  55                  60

Ala Arg Ser Ser Arg Arg Arg Leu Asn Arg Lys Ser Gln Arg Lys Lys
65                  70                  75                  80

Asp Ile Arg Asn Leu Leu Val Gln His Glu Ile Ile Ser Gln Lys Glu
                85                  90                  95

Leu Thr Ser Leu Tyr Pro Leu Ser Lys Ser Ser Met Asp Ile Trp Asp
            100                 105                 110

Ile Arg Leu Asp Gly Leu Asp Arg Leu Leu Asp Arg Phe Glu Trp Ala
            115                 120                 125
```

-continued

```
Arg Leu Leu Ile His Leu Ala Gln Arg Arg Gly Phe Lys Ser Asn Arg
    130                 135                 140

Lys Ser Glu Leu Lys Asp Val Glu Thr Gly Lys Val Leu Ser Ser Ile
145                 150                 155                 160

Gln Val Asn Glu Lys Arg Leu Ser Leu Tyr Arg Thr Val Gly Glu Met
                165                 170                 175

Trp Met Lys Asn Ala Asp Cys Ser Lys Tyr Gly Lys Arg Arg Asn Ser
                180                 185                 190

Pro Asn Glu Tyr Val Phe Ser Val Ser Arg Ala Asp Leu Glu Lys Glu
                195                 200                 205

Ile Val Thr Leu Phe Glu Ala Gln Arg Lys Phe His Ser Ser Tyr Ala
    210                 215                 220

Ser Val Asp Leu Gln Lys Thr Tyr Ile Gln Ile Trp Ala His Gln Leu
225                 230                 235                 240

Pro Phe Ala Ser Gly Asn Ala Ile Val Asn Lys Val Gly Tyr Cys Ser
                245                 250                 255

Leu Leu Lys Gly Lys Glu Lys Arg Val Pro Lys Ala Thr Tyr Thr Phe
                260                 265                 270

Gln Tyr Phe Asn Thr Leu Asp Gln Ile Asn Arg Thr Arg Leu Gly Pro
                275                 280                 285

Asn Phe Gln Pro Phe Thr Lys Glu Gln Arg Asp Ile Ile Leu Asp Lys
    290                 295                 300

Met Phe Gln Arg Thr Asp Tyr Tyr Lys Lys Lys Thr Ile Pro Glu Val
305                 310                 315                 320

Thr Tyr Tyr Asp Ile Arg Lys Trp Leu Ala Leu Asp Glu Thr Ile Gln
                325                 330                 335

Phe Lys Gly Leu Thr Tyr Asp Pro Asn Glu Glu Leu Lys Lys Ile Glu
                340                 345                 350

Met Lys Pro Phe Ile Asn Leu Lys Pro Phe Tyr Glu Ile Lys Lys Val
                355                 360                 365

Val Thr Asn Tyr Ala Lys Lys Thr Asn Glu Val Phe Ser Ala Leu Asp
    370                 375                 380

Tyr Asp Thr Val Ala Tyr Ala Leu Thr Val Tyr Lys Thr Asp Lys Asp
385                 390                 395                 400

Ile Arg Ser Tyr Leu Lys Arg Ser Asn Asn Leu Ser Lys Arg Cys Tyr
                405                 410                 415

Asp Asp Gln Leu Ile Glu Glu Leu Leu Thr Leu Ser Tyr Thr Lys Phe
                420                 425                 430

Gly His Leu Ser Phe Lys Ala Ile Asn His Val Leu Pro Ile Met Gln
                435                 440                 445

Glu Gly Arg Thr Tyr Gln Glu Ala Ile His Gln Leu Gly Tyr Asp Thr
    450                 455                 460

Thr Asn Leu Lys Lys Glu Asn Arg Ser Met Phe Leu Pro Ile Ile Pro
465                 470                 475                 480

Asp Glu Ile Thr Asn Pro Ile Val Lys Arg Ala Leu Thr Gln Ala Arg
                485                 490                 495

Lys Val Val Asn Ala Ile Ile Arg Arg Tyr Gly Ser Pro Asn Ser Val
                500                 505                 510

His Ile Glu Leu Ala Arg Glu Leu Ser Lys Ser His Asp Glu Arg Lys
                515                 520                 525

Lys Ile Met Thr Ala His Asp Glu Asn Tyr Lys Lys Asn Lys Gly Ala
    530                 535                 540
```

-continued

```
Ile Ser Ile Leu Ile Glu Asn Gly Ile Leu Asn Pro Thr Gly Tyr Asp
545                 550                 555                 560

Ile Val Arg Tyr Lys Leu Trp Lys Glu Gln Gly Glu Arg Cys Ala Tyr
                565                 570                 575

Ser Leu Lys Lys Ile Pro Ala Asn Thr Phe Phe Asn Glu Leu Lys Lys
            580                 585                 590

Glu Arg Ser Gly Pro Pro Val Leu Glu Val Asp His Ile Leu Pro Tyr
        595                 600                 605

Ser Gln Ser Phe Ile Asp Ser Tyr His Asn Lys Val Leu Val Tyr Gly
    610                 615                 620

Asp Glu Asn Gln Lys Lys Gly Asn Arg Ile Pro Tyr Thr Phe Phe Ser
625                 630                 635                 640

Glu Glu Asp Lys Glu Trp Glu Ser Phe Glu Ser Tyr Val Arg Ser Asn
                645                 650                 655

Ser Phe Phe Ser Lys Lys Lys Arg Gly Tyr Leu Leu Lys Lys Ala Tyr
                660                 665                 670

Leu Pro Arg Glu Ser Asn Leu Ile Lys Glu Arg His Leu Asn Asp Thr
            675                 680                 685

Arg Tyr Ala Ser Ser Tyr Leu Lys Asn Phe Ile Glu Lys Asn Leu Lys
        690                 695                 700

Phe Lys Glu Ala Val Gly Ile Thr Arg Lys Lys Tyr Val Gln Thr Val
705                 710                 715                 720

Asn Gly Val Ile Thr Ala His Leu Arg Lys Arg Trp Gly Leu Glu Lys
                725                 730                 735

Asp Arg Gln Glu Thr Tyr Leu His His Ala Met Asp Ala Ile Ile Val
            740                 745                 750

Ala Cys Thr Asp His His Met Val Thr Lys Val Thr Glu Tyr Tyr Gln
        755                 760                 765

Ile Lys Glu Gly Asn Lys Ser Ile Lys Lys Pro Tyr Phe Pro Leu Pro
    770                 775                 780

Trp Met Gly Phe Arg Glu Glu Ile Leu Ser His Leu Glu Ser Gln Pro
785                 790                 795                 800

Ile Ala Arg Lys Ile Ser Glu Glu Leu Lys Ile Gly Tyr Gln Ser Ser
                805                 810                 815

Asp Tyr Ile Leu Val Ser Arg Met Pro Lys Arg Ser Val Thr Gly Ser
            820                 825                 830

Ala His Asp Gln Thr Val Met Lys Lys Gly Gly Ile Asp Lys Lys Gly
        835                 840                 845

Lys Thr Ile Ile Ile Lys Arg Val His Leu Lys Asp Ile Lys Phe Asp
    850                 855                 860

Glu Asn Gly Asp Phe Lys Met Val Gly Lys Glu Gln Asp Leu Ala Thr
865                 870                 875                 880

Tyr Glu Ala Ile Lys Gln Arg Tyr Leu Glu Tyr Arg Lys Lys Ser Lys
                885                 890                 895

Lys Ala Phe Glu Thr Pro Leu Tyr Lys Pro Ser Lys Lys Gly Lys Gly
            900                 905                 910

Asn Leu Ile Lys Lys Ile Lys Val Glu Val Gln Thr Lys Ser Phe Val
        915                 920                 925

Arg Glu Ile Asn Gly Gly Val Ala Gln Asn Gly Asp Leu Val Arg Val
    930                 935                 940

Asp Leu Phe Glu Lys Asp Asn Arg Tyr Tyr Met Val Pro Ile Tyr Val
945                 950                 955                 960

Val Asp Thr Val Arg Ser Glu Leu Pro Asn Lys Ala Val Thr Ser Ser
```

```
                    965              970              975

Lys Gly Tyr Glu Gln Trp Leu Ser Ile Asp Asn Ser Phe Thr Phe Lys
            980              985              990

Phe Ser Leu Tyr Pro Tyr Asp Leu  Val Arg Leu Val Lys  Gly Asp Glu
        995              1000              1005

Asp Arg  Phe Leu Tyr Phe Ser  Thr Leu Asp Ile Asn  Ser Asp Arg
    1010              1015              1020

Leu Asn  Phe Lys Asp Val Asn  Lys Pro Ser Lys Gln  Ala Glu Tyr
    1025              1030              1035

Arg Tyr  Ser Leu Lys Thr Ile  Glu Asn Leu Glu Lys  Tyr Glu Ile
    1040              1045              1050

Gly Val  Leu Gly Asp Leu Arg  Leu Val Arg Gln Glu  Thr Arg Lys
    1055              1060              1065

Ile Phe  Lys
    1070
```

<210> SEQ ID NO 2
<211> LENGTH: 34
<212> TYPE: RNA
<213> ORGANISM: Bacillus sp.

<400> SEQUENCE: 2
gucauaguuc cauuaaagcc auugcuguuu uaug                            34

<210> SEQ ID NO 3
<211> LENGTH: 148
<212> TYPE: RNA
<213> ORGANISM: Bacillus sp.

<400> SEQUENCE: 3
caugauacag caauggcuuu gauguuucua ugauaagggc uucggcccgu ggcguugggg    60
aucgccugcc cauuuuaaug ggcuucuccc caucuauuua augagaaauu uacaaccuug   120
gcuauucuua aauagcuaag guuuuuuu                                       148

<210> SEQ ID NO 4
<211> LENGTH: 215
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: modified_base
<222> LOCATION: (1)..(29)
<223> OTHER INFORMATION: a, c, u, g, unknown or other

<400> SEQUENCE: 4
nnnnnnnnnn nnnnnnnnnn nnnnnnnnng ucauaguucc auuaaagcca uugcuguuuu    60
augaaagcau gauacagcaa uggcuuugau guuucauga uaagggcuuc ggcccguggc    120
guuggggauc gccugcccau uuuaaugggc uucuccccau cuauuuaaug agaaauuuac   180
aaccuuggcu auucuuaaau agcuaagguu uuuuu                              215

<210> SEQ ID NO 5
<211> LENGTH: 216
<212> TYPE: RNA
<213> ORGANISM: Artificial Sequence
<220> FEATURE:
<221> NAME/KEY: source
<223> OTHER INFORMATION: /note="Description of Artificial Sequence:

Synthetic polynucleotide"

<400> SEQUENCE: 5
gagcggacag cagcuuccua uaucucguac gucauaguuc cauuaaagcc auugcuguuu    60
uaugaaagca ugauacagca auggcuuuga uguuucuaug auaagggcuu cggcccgugg   120
cguuggggau cgccugccca uuuuaauggg cuucucccca ucuauuuaau gagaaauuua   180
caaccuuggc uauucuuaaa uagcuaaggu uuuuuu                             216

<210> SEQ ID NO 6
<211> LENGTH: 216
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 6
ccaugauaua gacguugugg cuguuguagu gucauaguuc cauuaaagcc auugcuguuu    60
uaugaaagca ugauacagca auggcuuuga uguuucuaug auaagggcuu cggcccgugg   120
cguuggggau cgccugccca uuuuaauggg cuucucccca ucuauuuaau gagaaauuua   180
caaccuuggc uauucuuaaa uagcuaaggu uuuuuu                             216

<210> SEQ ID NO 7
<211> LENGTH: 6
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(4)
<223> OTHER INFORMATION: a, c, t, g, unknown or other

<400> SEQUENCE: 7 nnnncc                                                              6

<210> SEQ ID NO 8
<211> LENGTH: 6
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (2)..(2)
<223> OTHER INFORMATION: a, c, u, g, unknown or other
<220> FEATURE:
<221> NAME/KEY: modified_base
<222> LOCATION: (4)..(5)
<223> OTHER INFORMATION: a, c, u, g, unknown or other

<400> SEQUENCE: 8 unanna                                                              6

<210> SEQ ID NO 9
<211> LENGTH: 1403
<212> TYPE: PRT
<213> ORGANISM: Chryseobacterium sp.

<400> SEQUENCE: 9

-continued

```
Met Val Glu Arg Ile Leu Gly Leu Asp Leu Gly Val Ser Ser Ile Gly
1               5                   10                  15

Trp Ala Leu Val Glu Glu Asp Val Glu Asn Pro Glu Asn Asn Lys Ile
            20                  25                  30

Ile Lys Leu Gly Val Arg Val Asn Pro Leu Thr Ile Asp Glu Lys Thr
            35                  40                  45

Asn Phe Glu Lys Gly Lys Ser Ile Thr Thr Asn Ala Gly Arg Thr Ser
    50                  55                  60

Ala Arg Ser Ala Arg Arg Asn Leu Gln Arg Phe Lys Leu Arg Arg Lys
65                  70                  75                  80

Ser Leu Trp Glu Val Leu Ile Asn Tyr Lys Ile Ile Lys Asn Asp Thr
            85                  90                  95

Val Leu Ala Glu Ile Gly Lys Asn Ser Thr Phe Gln Thr Gln Tyr Leu
            100                 105                 110

Arg Ala Lys Ala Ala Lys Glu Lys Ile Glu Leu Asp Glu Leu Ala Arg
            115                 120                 125

Val Leu Phe Leu Ile Asn Lys Lys Arg Gly Tyr Lys Ser Ser Arg Lys
    130                 135                 140

Val Gln Ser Asp Asp Glu Gly Lys Ala Ile Asp Gly Met Ser Val Ala
145                 150                 155                 160

Lys Glu Leu Tyr Glu Lys Asn Tyr Thr Pro Gly Gln Tyr Val Tyr Asp
            165                 170                 175

Leu Leu Lys Asn Gly Lys Lys Gln Ile Pro Asp Phe Tyr Arg Ser Asp
            180                 185                 190

Leu Gln Asn Glu Leu Asp Arg Val Trp Glu Phe Gln Lys Gln Tyr His
            195                 200                 205

Pro Asp Ile Leu Thr Asp Glu Tyr Lys Lys Glu Leu Glu Gly Lys Gly
    210                 215                 220

Gln Arg Ala Thr Ala Ala Ile Phe Leu Asn Arg Tyr Lys Ile Tyr Thr
225                 230                 235                 240

Ala Asp Asn Lys Gly Thr Arg Glu Glu Lys Arg Phe Gln Ala Tyr Gln
            245                 250                 255

Trp Arg Val Glu Ala Leu Ser Gln Pro Leu Asp Ile Lys Glu Val Ala
            260                 265                 270

Tyr Val Ile Thr Glu Ile Asn Asn Asn Leu Asn Asn Ser Ser Gly Tyr
            275                 280                 285

Leu Gly Ala Ile Ser Asp Arg Ser Lys Lys Leu Tyr Phe Asn Gly Gln
            290                 295                 300

Thr Ile Gly Glu Tyr Leu Tyr Glu Glu Leu Ser Leu Asn Pro His Ala
305                 310                 315                 320

Arg Leu Lys Asn Gln Val Phe Tyr Arg Gln Asp Tyr Gln Asp Glu Phe
            325                 330                 335

Glu Lys Ile Trp Glu Thr Gln Ala Lys Phe His Ser Val Leu Thr Thr
            340                 345                 350

Glu Leu Lys Glu Asp Val Arg Asp Ile Ile Ile Phe Tyr Gln Arg Lys
            355                 360                 365

Leu Lys Ser Gln Lys Gly Leu Ile Ser Phe Cys Glu Phe Glu Ser Lys
            370                 375                 380

Glu Ile Val Ile Glu Glu Asn Gly Lys Lys Lys Arg Lys Lys Val Gly
385                 390                 395                 400

Leu Lys Val Val Pro Lys Ser Ser Pro Leu Phe Gln Glu Phe Lys Ile
                405                 410                 415
```

-continued

```
Trp Gln Val Leu Asn Asn Ile Glu Ile Lys Asn Glu Asp Gly Arg Arg
            420                 425                 430

Tyr Leu Asp Gln Glu Glu Lys Glu Leu Leu Phe Asn Glu Leu Asn Cys
            435                 440                 445

Lys Gly Asn Leu Thr Ser Gln Lys Cys Leu Glu Phe Leu Gly Phe Lys
            450                 455                 460

Ser Lys Glu Thr Lys Ile Asn Phe Lys Val Ile Glu Gly Asn Arg Thr
465                 470                 475                 480

Asn Glu Lys Leu Tyr Asp Ala Phe Leu Lys Ile Leu Glu Leu Lys Gly
                485                 490                 495

Tyr Asn Val Phe Glu Leu Leu Lys Ile Lys Glu Asp Arg Asp Glu Ala
            500                 505                 510

Lys Leu Ser Glu Leu Lys Ala Ser Ala Asp Glu Ile Lys Arg Met Val
            515                 520                 525

Lys Glu Ile Phe Asn Ala Asn Leu Ile Asn Thr Ser Ile Leu Asp Phe
            530                 535                 540

Asn Ala Glu Leu Glu Gly Lys Asp Phe Glu Asn Gln Ala Ser Tyr Gln
545                 550                 555                 560

Phe Trp His Leu Ile Tyr Ser Tyr Glu Gly Asp Asn Ser Pro Ser Gly
                565                 570                 575

Asn Glu Lys Leu Tyr Glu Leu Leu Glu Asn Lys Phe Gly Phe Lys Lys
            580                 585                 590

Glu His Ser Lys Ile Leu Ser Thr Ile Val Phe Pro Gln Glu Tyr Gly
            595                 600                 605

Ser Leu Ser Ala Lys Ala Met Arg Arg Ile Tyr Pro Tyr Ile Lys Asp
            610                 615                 620

Asn Lys Tyr Ser Glu Ala Cys Leu Leu Ala Gly Tyr Asn His Ser Lys
625                 630                 635                 640

Gln Ser Leu Thr Lys Glu Glu Leu Glu Asn Arg Lys Leu Lys Glu Gln
                645                 650                 655

Leu Glu Val Leu Pro Lys Asn Ser Leu Arg Asn Pro Val Val Glu Lys
            660                 665                 670

Ile Leu Asn Gln Met Ile Asn Leu Val Asn Ala Ile Ile Ser Glu His
            675                 680                 685

Gly Lys Leu Asp Gly Val Arg Ile Glu Leu Ala Arg Glu Leu Lys Lys
            690                 695                 700

Ser Ala Gln Glu Arg Glu Asp Met Thr Lys Ser Ile Asn Glu Ala Thr
705                 710                 715                 720

Ile Leu His Gln Lys Tyr Ala Thr Val Leu Arg Gln Glu Phe Gly Val
                725                 730                 735

Val Asn Pro Ser Arg Asn Asp Ile Ile Arg Tyr Lys Leu Tyr Met Glu
                740                 745                 750

Leu Ala Gly Asn Gly Tyr Lys Asp Leu Tyr Thr Asn Val Lys Ile Glu
            755                 760                 765

Lys Glu Asn Ile Phe Thr Asp Lys Tyr Asp Ile Asp His Ile Ile Pro
            770                 775                 780

Gln Ser Arg Phe Phe Asp Asp Ser Phe Ser Asn Lys Val Leu Val Pro
785                 790                 795                 800

Arg Gln Ala Asn Leu Asp Lys Gly Asn Leu Thr Gly Tyr Asp Phe Met
                805                 810                 815

Ser Asn Lys Gly Ala Glu Arg Glu Glu His Phe Leu Asn Val Ile Lys
            820                 825                 830

Asp Leu Leu Glu Asn Gly Ser Ile Ser Lys Ala Lys Tyr Glu Lys Leu
```

```
                835                 840                 845
Lys Lys Lys Gly Ile Glu Ile Gly Asp Gly Phe Ile Glu Arg Asp Leu
    850                 855                 860
Arg Asp Thr Gln Tyr Ile Ala Arg Lys Ala Lys Glu Ile Leu Phe Glu
865                 870                 875                 880
Ile Thr Asn Ser Val Ile Ser Thr Ser Gly Arg Ile Thr Asp Lys Leu
                885                 890                 895
Arg Glu Asp Trp Asp Leu Val Asn Thr Met Lys Glu Leu Asn Leu Asp
            900                 905                 910
Lys Tyr Arg Arg Leu Gly Leu Thr Glu Ile Val Ile Asn Ser Lys Gly
        915                 920                 925
Glu Glu Lys Glu Val Ile Pro Asp Trp Thr Lys Arg Asn Asp His Arg
    930                 935                 940
His His Ala Met Asp Ala Leu Thr Val Ala Phe Thr Thr Arg Asn His
945                 950                 955                 960
Ile Gln Tyr Leu Asn Tyr Leu Asn Ala Arg Lys Asp Glu Lys His Lys
                965                 970                 975
Glu His Gln Asn Ile Tyr Ala Ile Glu Asn Ile Ile Thr Glu Ile Ile
            980                 985                 990
Glu Lys Lys Asn Gly Ser Lys Ser  Arg Arg Phe Lys Thr  Pro Met Asn
        995                 1000                1005
Arg Phe  Arg His Glu Ala Lys  Gln His Leu Lys Glu  Val Leu Val
    1010                1015                1020
Ser His  Lys Thr Lys Asn Lys  Val Val Thr Ser Asn  Ile Asn Lys
    1025                1030                1035
Thr Lys  Lys Lys Arg Gly Ile  His Lys Lys Ala Glu  Leu Thr Pro
    1040                1045                1050
Arg Gly  Gln Leu His Lys Glu  Thr Val Tyr Gly Ser  Lys Lys Phe
    1055                1060                1065
Leu Gln  Ser Arg Glu Glu Lys  Val Ser Ala Lys Phe  Asp Tyr Glu
    1070                1075                1080
Thr Ile  Leu Met Val Val Asn  Pro Ile His Arg Asn  Ala Leu Leu
    1085                1090                1095
Asn Arg  Leu Lys Glu Tyr Gly  Asn Asp Pro Lys Lys  Ala Phe Ser
    1100                1105                1110
Gly Lys  Asn Ala Val Asn Lys  Thr Pro Val Tyr Leu  Ser Asp Ser
    1115                1120                1125
Lys Ile  Glu Val Leu Pro Glu  Lys Val Thr Leu Ser  Trp Phe Glu
    1130                1135                1140
Thr Gly  Tyr Thr Ile Arg Lys  Ala Val Thr Pro Asp  Asn Phe Lys
    1145                1150                1155
Asp Tyr  Lys Asn Leu Glu Lys  Ile Thr Asp Met Gly  Ile Lys Lys
    1160                1165                1170
Ile Leu  Lys Glu Arg Leu Asp  Gln Phe Lys Gly Asn  Ala Lys Glu
    1175                1180                1185
Ala Phe  Ser Asn Leu Asp Lys  Glu Pro Ile Trp Leu  Asn Glu Glu
    1190                1195                1200
Lys Gly  Ile Ala Ile Lys Thr  Val Thr Ile Thr Gly  Val Ser Asn
    1205                1210                1215
Ala Glu  Ser Leu His Phe Lys  Lys Asp His Leu Gly  Lys Glu Ile
    1220                1225                1230
Leu Asp  Glu Asn Gly Asn Lys  Ile Pro Val Asp Phe  Val Ser Thr
    1235                1240                1245
```

```
Gly Asn  Asn His His Leu Ala  Ile Tyr Leu Asn Glu  Glu Glu Lys
    1250              1255              1260

Leu Asp  Asp Lys Met Val Thr  Phe Tyr Glu Ala Val  Leu Arg Val
    1265              1270              1275

Asn Gln  Gly Leu Pro Val Ile  Asp Lys Asn Tyr Asn  Arg Glu Lys
    1280              1285              1290

Gly Tyr  Lys Phe Leu Met Thr  Leu Lys Gln Asn Glu  Met Phe Val
    1295              1300              1305

Phe Pro  Asn Glu Glu Phe Asp  Pro Ser Glu Ile Asp  Leu Leu Asp
    1310              1315              1320

Glu Lys  Asn Leu Glu Gln Ile  Ser Gln Asn Leu Phe  Arg Val Gln
    1325              1330              1335

Lys Ile  Ser Lys Val Gly Tyr  Gly Asn Ser Phe Ile  Arg Asp Phe
    1340              1345              1350

Val Phe  Arg His His Leu Glu  Thr Thr Val Glu Asp  Arg Lys Glu
    1355              1360              1365

Leu Arg  Asn Thr Thr Tyr Ile  Gln Leu Lys Ser Leu  Glu Gly Leu
    1370              1375              1380

Arg Asn  Ile Val Lys Val Arg  Leu Asn His Leu Gly  Lys Ile Val
    1385              1390              1395

Gln Ile  Gly Glu Tyr
    1400

<210> SEQ ID NO 10
<211> LENGTH: 24
<212> TYPE: RNA
<213> ORGANISM: Chryseobacterium sp.

<400> SEQUENCE: 10
guugugaaau gcuuucaaaa cuua                                        24

<210> SEQ ID NO 11
<211> LENGTH: 78
<212> TYPE: RNA
<213> ORGANISM: Chryseobacterium sp.

<400> SEQUENCE: 11
auaaauuuug aaagcacuuc acaauaagga uuauuccguu gugaaaacau ucaaggcggg   60
gcaacucgcc uuuuuuuu                                               78

<210> SEQ ID NO 12
<211> LENGTH: 135
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: modified_base
<222> LOCATION: (1)..(29)
<223> OTHER INFORMATION: a, c, u, g, unknown or other

<400> SEQUENCE: 12
nnnnnnnnnn nnnnnnnnnn nnnnnnnnng uugugaaaug cuuucaaaac uuaaaagaua   60
aauuuugaaa gcacuucaca auaaggauua uuccguugug aaaacauuca aggcggggca  120
acucgccuuu uuuuu                                                  135
```

-continued

<210> SEQ ID NO 13
<211> LENGTH: 136
<212> TYPE: RNA
<213> ORGANISM: Artificial Sequence
<220> FEATURE:
<221> NAME/KEY: source
<223> OTHER INFORMATION: /note="Description of Artificial Sequence:
     Synthetic polynucleotide"

<400> SEQUENCE: 13
gagcggacag cagcuuccua uaucucguac guugugaaau gcuuucaaaa cuuaaaagau      60
aaauuuugaa agcacuucac aauaaggauu auuccguugu gaaaacauuc aaggcggggc     120
aacucgccuu uuuuuu                                                     136

<210> SEQ ID NO 14
<211> LENGTH: 136
<212> TYPE: RNA
<213> ORGANISM: Artificial Sequence
<220> FEATURE:
<221> NAME/KEY: source
<223> OTHER INFORMATION: /note="Description of Artificial Sequence:
     Synthetic polynucleotide"

<400> SEQUENCE: 14
ccaugauaua gacguugugg cuguuguagu guugugaaau gcuuucaaaa cuuaaaagau      60
aaauuuugaa agcacuucac aauaaggauu auuccguugu gaaaacauuc aaggcggggc     120
aacucgccuu uuuuuu                                                     136

<210> SEQ ID NO 15
<211> LENGTH: 6
<212> TYPE: DNA
<213> ORGANISM: Artificial Sequence
<220> FEATURE:
<221> NAME/KEY: source
<223> OTHER INFORMATION: /note="Description of Artificial Sequence:
     Synthetic oligonucleotide"
<220> FEATURE:
<221> NAME/KEY: modified_base
<222> LOCATION: (1)..(1)
<223> OTHER INFORMATION: a, c, t, g, unknown or other

<400> SEQUENCE: 15 nrrttt                                                                 6

<210> SEQ ID NO 16
<211> LENGTH: 1404
<212> TYPE: PRT
<213> ORGANISM: Sphingobacterium sp.

<400> SEQUENCE: 16

Met Met Lys Arg Ile Leu Gly Leu Asp Leu Gly Thr Ser Ser Ile Gly
1               5                   10                  15

Trp Ala Tyr Val Leu Glu Ala Gln Asp Glu Asn Glu Ile Ser Gln Ile
            20                  25                  30

Lys Lys Leu Gly Val Arg Val Asn Pro Leu Thr Thr Asp Glu Gln Leu
        35                  40                  45

Asn Phe Glu Lys Gly Lys Pro Ile Thr Thr Asn Ala Gly Arg Thr Leu
    50                  55                  60

Ala Arg Ser Ala Arg Arg Asn Leu Gln Arg Tyr Lys Leu Arg Arg Glu
65                  70                  75                  80

Asn Leu Ile Glu Val Leu Lys Arg Glu Lys Trp Ile Asp Asp Lys Ser
                85                  90                  95

```
Ile Leu Ala Glu Asn Gly Asn Lys Ser Thr Phe Glu Thr Tyr Ala Leu
            100                 105                 110

Arg Ala Ala Ala Ala Ser Lys Glu Ile Lys Leu Glu Glu Leu Ala Arg
            115                 120                 125

Val Leu Leu Met Ile Asn Lys Lys Arg Gly Tyr Lys Ser Ser Arg Lys
            130                 135                 140

Val Asn Lys Glu Asp Asp Gly Gln Leu Val Asp Gly Met Glu Val Ala
145                 150                 155                 160

Lys Lys Leu Tyr His Glu Asn Leu Thr Pro Gly Glu Phe Val Tyr Arg
                165                 170                 175

Leu Leu Lys Glu Gly Lys Lys Lys Ile Pro Asp Phe Tyr Arg Ser Asp
            180                 185                 190

Leu Gln Arg Glu Leu Asp Leu Ile Trp Asp Phe Gln Phe Lys Tyr Tyr
            195                 200                 205

Pro Asp Leu Leu Thr Gln Asp Leu Lys Glu Glu Leu Lys Gly Lys Gly
            210                 215                 220

Leu Arg Ala Thr Ser Ala Ile Phe Trp Ser Lys Tyr Lys Phe Asn Thr
225                 230                 235                 240

Ala Glu Asn Lys Gly Thr Arg Glu Glu Lys Lys Ile Gln Ala Tyr Gln
                245                 250                 255

Trp Arg Lys Asp Gly Leu Thr Lys Gln Leu Glu Gln Glu Glu Val Ala
            260                 265                 270

Tyr Ile Ile Ala Glu Ile Asn Gly Gln Leu Ala Asn Ser Ser Gly Tyr
            275                 280                 285

Leu Gly Ala Ile Ser Asp Arg Ser Lys Glu Leu Tyr Phe Asn Lys Gln
            290                 295                 300

Thr Val Gly Gln Phe Leu Phe Asn Gln Leu Gln His Asn Thr His Ala
305                 310                 315                 320

Arg Val Lys Asn Gln Val Phe Tyr Arg Gln Asp Tyr Leu Asp Glu Phe
                325                 330                 335

Glu Lys Ile Trp Ser Val Gln Ser Gln Tyr His Gln Gly Leu Thr Glu
            340                 345                 350

Gln Leu Lys Glu Glu Ile Arg Asp Ile Ile Ile Phe Tyr Gln Arg Lys
            355                 360                 365

Leu Lys Ser Gln Lys Gly Leu Ile Ser Phe Cys Glu Phe Glu Gln His
            370                 375                 380

Glu Val Val Ile Asn Gly Lys Asn Lys Ile Val Gly Leu Arg Val Ala
385                 390                 395                 400

Pro Lys Ser Ser Pro Ile Phe Gln Glu Phe Lys Ile Trp Gln Gln Ile
                405                 410                 415

Asn Asn Val Lys Leu Arg Asn Lys Ile Thr Lys Glu Val Tyr Asn Leu
            420                 425                 430

Ala Glu Glu Gln Lys Arg Ser Leu Phe Glu Thr Leu Asn Leu Lys Gly
            435                 440                 445

Lys Leu Ser Ala Tyr Gln Val Leu Asn Leu Ile Glu Val Lys Pro Lys
            450                 455                 460

Glu Trp Glu Leu Asn Tyr Thr Glu Leu Glu Gly Asn Ser Thr Asn Leu
465                 470                 475                 480

Ala Leu Tyr Asn Ala Tyr Leu Asp Ile Leu Asp Ile Glu Gly Tyr Asp
                485                 490                 495

Val Arg Ser Glu Leu Lys Ile Lys Leu Asn Lys Asp Glu Ile Thr Leu
            500                 505                 510

Ser Asp Leu Asp Ile Pro Val Ser Glu Ile Lys Gly Met Ile Arg Arg
```

```
             515              520              525

Ile Phe Gln His Leu Gly Ile Asn Thr Ser Ile Leu Asp Phe Asn Ala
    530              535              540

Gln Met Gln Gly Asp Asp Phe Glu Lys Gln Leu Ser Tyr Gln Leu Trp
545              550              555              560

His Leu Leu Tyr Ser Tyr Glu Glu Asp Asn Ser Lys Thr Gly Met Glu
             565              570              575

Arg Leu Tyr Asn Gln Leu Asn Leu Lys Phe Gly Phe Ser Leu Asp Gln
             580              585              590

Ala Lys Ile Phe Gly Lys Ile Ala Leu Gln Glu Asp Tyr Gly Asn Leu
             595              600              605

Ser Thr Lys Ala Ile Arg Lys Ile Tyr Pro Tyr Ile Gln Asp Val Glu
    610              615              620

Tyr Ser Val Ala Cys Lys Gln Ala Gly Tyr Asn His Ser Lys Ser Ser
625              630              635              640

Leu Thr Lys Glu Gln Leu Thr Asn Arg Val Leu Lys Asp His Leu Asp
             645              650              655

Ile Leu Pro Lys Asn Ser Leu Arg Asn Pro Val Val Glu Lys Ile Leu
             660              665              670

Asn Gln Met Val Asn Val Val Asn Thr Leu Ile Glu Thr Glu Asn Asp
             675              680              685

Lys Leu Ile Lys Glu Gly Lys Asn Ala Asp Phe Arg Phe Asp Glu Ile
    690              695              700

Arg Ile Glu Leu Ala Arg Glu Leu Lys Lys Asn Ala Lys Glu Arg Glu
705              710              715              720

Glu Leu Thr Lys Ala Ile Asn Thr Ser Lys Ser Glu His Glu Lys Ile
             725              730              735

Ile Lys Ile Leu Gln Thr Glu Asp Gly Ile Lys Asn Pro Thr Arg Asn
             740              745              750

Asp Ile Ile Arg Phe Lys Leu Tyr Gln Glu Leu Lys Asn Asn Gly Tyr
             755              760              765

Lys Asn Leu Tyr Thr Asn Glu Tyr Ile Gln Arg Lys Asp Leu Phe Thr
    770              775              780

Asn Val Tyr Asp Ile Asp His Ile Ile Pro Gln Ser Arg Leu Phe Asp
785              790              795              800

Asp Ser Phe Ser Asn Lys Val Leu Val Pro Arg Asn Ile Asn Ile Glu
             805              810              815

Lys Gly Asn Gln Thr Ala Phe Asp Tyr Val His Ala Lys Phe Gly Glu
             820              825              830

Asp Gly Ile Glu Ala Tyr Glu Ala Arg Val Glu Arg Leu Phe Asn Leu
             835              840              845

Lys Glu Glu Gly Val Ser Arg Ser Lys Tyr Lys Lys Leu Leu Met Arg
    850              855              860

Gly Leu Asp Ile Gly Glu Gly Phe Ile Glu Arg Asp Leu Arg Asp Ser
865              870              875              880

Gln Tyr Ile Ala Lys Lys Ala Lys Ala Met Leu Phe Glu Ile Ala Pro
             885              890              895

Ser Val Ile Ser Thr Ser Gly Ser Val Thr Asp Arg Leu Arg Glu Asp
             900              905              910

Trp Gly Leu Val Ser Val Met Lys Glu Leu Asn Leu Pro Lys Phe Lys
             915              920              925

Ala Val Gly Leu Thr Glu Tyr Leu Glu Thr Lys Asp Gly Asn Arg Lys
    930              935              940
```

-continued

```
Glu Val Ile Lys Asp Trp Ser Lys Arg Asn Asp His Arg His His Ala
945             950             955             960

Met Asp Ala Leu Thr Val Ala Phe Thr Lys His Ser His Ile His Tyr
            965             970             975

Leu Asn His Leu Asn Ala Arg Lys Asn Glu Lys Ser Glu Phe Phe Ser
        980             985             990

Thr Ile Lys Ala Ile Glu Ile Lys  Glu Thr Tyr Val Glu  Arg Asp Asp
        995             1000            1005

Leu Gly  Asn Arg Lys Arg Leu  Phe Lys Glu Pro Ile  Pro His Phe
    1010            1015            1020

Arg Ser  Ile Ala Lys Glu His  Leu Glu Ser Val Leu  Val Ser His
    1025            1030            1035

Lys Ala  Lys Asn Lys Val Val  Thr Lys Asn Arg Asn  Lys Ile Asp
    1040            1045            1050

Gly Lys  Lys Gln Ala Gln Glu  Val Leu Thr Pro Arg  Gly Gln Leu
    1055            1060            1065

His Lys  Glu Ser Ile Tyr Gly  Lys Ile Leu Gln Tyr  Ala Ser Lys
    1070            1075            1080

Glu Glu  Lys Ile Ser Ala Lys  Phe Asp Ala Ala Thr  Ile Ala Met
    1085            1090            1095

Val Ser  Asn Pro Arg Tyr Arg  Ser Ala Leu Leu Asp  Arg Leu Ser
    1100            1105            1110

Ala Tyr  Gly Asn Asp Pro Lys  Lys Ala Phe Thr Gly  Lys Asn Ser
    1115            1120            1125

Pro Asn  Lys Ser Pro Ile Tyr  Leu Asp Gln Glu Lys  Gln Leu Ala
    1130            1135            1140

Val Pro  Glu Lys Val Lys Leu  Val Trp Leu Glu Glu  Asp Tyr Thr
    1145            1150            1155

Ile Arg  Lys Glu Ile Gly Pro  Asp Leu Lys Ile Glu  Lys Val Ile
    1160            1165            1170

Asp Gln  Gly Val Lys Arg Ile  Leu Glu Gln Arg Leu  Thr Glu Tyr
    1175            1180            1185

Gly Gly  Asp Ser Lys Lys Ala  Phe Ser Asp Leu Asp  Asn Asn Pro
    1190            1195            1200

Ile Trp  Leu Asn Lys Glu Lys  Gly Ile Ala Ile Lys  Arg Val Thr
    1205            1210            1215

Ile Ser  Gly Val Lys Asn Ala  Glu Ala Leu His Ile  Lys Lys Asp
    1220            1225            1230

His Leu  Gly Gln Val Leu Lys  Asp Lys Asp Gly Lys  Pro Met Pro
    1235            1240            1245

Val Asp  Phe Val Ser Thr Gly  Asn Asn His His Val  Ala Ile Tyr
    1250            1255            1260

Glu Asp  Asp Asn Gly Ala Leu  Gln Glu Arg Ile Val  Pro Phe Tyr
    1265            1270            1275

Glu Ala  Val Ala Arg Val Asn  Asn Gly Phe Pro Ile  Ile Asp Lys
    1280            1285            1290

His Tyr  Asn Gln His Leu Gly  Trp Lys Phe Leu Phe  Ser Met Lys
    1295            1300            1305

Gln Asn  Glu Met Phe Leu Phe  Pro Ser Glu Glu Phe  Asp Pro Lys
    1310            1315            1320

Gln Ile  Asn Leu Leu Asp Arg  Ser Asn Tyr Arg Leu  Ile Ser Lys
    1325            1330            1335
```

-continued

```
Asn Leu  Phe Arg Val Gln Lys  Phe Gly Glu Leu Ser  Lys Ser Gly
    1340                 1345                 1350

Phe Trp  Phe Arg His His Leu  Glu Thr Ser Val Asp  Val Asn Lys
    1355                 1360                 1365

Ser Leu  Arg Ser Ile Ser Tyr  Phe Asp Phe Tyr Ser  Lys Asp Phe
    1370                 1375                 1380

Met Lys  Asn Ile Ala Lys Val  Arg Ile Asn His Leu  Gly Glu Ile
    1385                 1390                 1395

Ile His  Val Gly Glu Tyr
    1400
```

```
<210> SEQ ID NO 17
<211> LENGTH: 18
<212> TYPE: RNA
<213> ORGANISM: Sphingobacterium sp.

<400> SEQUENCE: 17
guugugaauu gcuuucau                                                    18

<210> SEQ ID NO 18
<211> LENGTH: 72
<212> TYPE: RNA
<213> ORGANISM: Sphingobacterium sp.

<400> SEQUENCE: 18
augaaagcaa uucacaauaa ggauuauuuc cguuguguaa acauuuagcg ccucgucuau     60
cuacggggca uu                                                         72

<210> SEQ ID NO 19
<211> LENGTH: 123
<212> TYPE: RNA
<213> ORGANISM: Artificial Sequence
<220> FEATURE:
<221> NAME/KEY: source
<223> OTHER INFORMATION: /note="Description of Artificial Sequence:
     Synthetic polynucleotide"
<220> FEATURE:
<221> NAME/KEY: modified_base
<222> LOCATION: (1)..(29)
<223> OTHER INFORMATION: a, c, u, g, unknown or other

<400> SEQUENCE: 19
nnnnnnnnnn nnnnnnnnnn nnnnnnnnng uugugaauug cuuucauaaa gaugaaagca     60
auucacaaua aggauuauuu ccguugugua aacauuuagc gccucgucua ucuacggggc    120
auu                                                                  123

<210> SEQ ID NO 20
<211> LENGTH: 124
<212> TYPE: RNA
<213> ORGANISM: Artificial Sequence
<220> FEATURE:
<221> NAME/KEY: source
<223> OTHER INFORMATION: /note="Description of Artificial Sequence:
     Synthetic polynucleotide"

<400> SEQUENCE: 20
gagcggacag cagcuuccua uaucucguac guugugaauu gcuuucauaa agaugaaagc     60
aauucacaau aaggauuauu ccguugugu aaacauuuag cgccucgucu aucuacgggg    120
cauu                                                                 124

<210> SEQ ID NO 21
```

<211> LENGTH: 124
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 21
ccaugauaua gacguugugg cguuguagu guugugaauu gcuuucauaa agaugaaagc          60
aauucacaau aaggauuauu uccguugugu aaacauuuag cgccucgucu aucuacgggg        120
cauu                                                                     124

<210> SEQ ID NO 22
<211> LENGTH: 7
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(2)
<223> OTHER INFORMATION: a, c, t, g, unknown or other
<220> FEATURE:
<221> NAME/KEY: modified_base
<222> LOCATION: (5)..(5)
<223> OTHER INFORMATION: a, c, t, g, unknown or other

<400> SEQUENCE: 22 nnrrngg                                                                    7

<210> SEQ ID NO 23
<211> LENGTH: 1453
<212> TYPE: PRT
<213> ORGANISM: Chryseobacterium sp.

<400> SEQUENCE: 23

Met Met Ile Lys Asn Ile Leu Gly Leu Asp Leu Gly Thr Asn Ser Ile
1               5                   10                  15

Gly Trp Ala Leu Ile Lys Gln Asp Phe Glu Asn Lys Tyr Gly Glu Ile
            20                  25                  30

Leu Gly Met Gly Ser Arg Ile Ile Pro Met Asp Gln Lys Val Leu Gly
        35                  40                  45

Glu Phe Gly Ser Gly Asn Ser Val Ser Gln Thr Ala Asp Arg Thr Lys
    50                  55                  60

Tyr Arg Gly Val Arg Arg Leu Arg Glu Arg Phe Leu Leu Arg Arg Glu
65                  70                  75                  80

Arg Leu His Arg Val Leu Asn Val Leu Asn Phe Leu Pro Ile His Tyr
                85                  90                  95

Ala Ser Gln Ile Asp Phe Glu Lys Arg Phe Gly Lys Phe Arg Glu Glu
            100                 105                 110

Ile Glu Pro Lys Leu Val Tyr Asn Asn Asp Gly Phe Ile Phe Lys Asn
            115                 120                 125

Ser Phe Glu Glu Met Leu Ser Asp Phe Arg Lys His Gln Pro Gln Ile
    130                 135                 140

Leu Glu Asn Asp Lys Lys Ile Pro Tyr Asp Trp Thr Ile Tyr Tyr Leu
145                 150                 155                 160

Arg Lys Lys Ala Leu Thr Gln Lys Ile Glu Lys Glu Glu Leu Ala Trp
                165                 170                 175

```
Ile Leu Leu Asn Phe Asn Gln Lys Arg Gly Tyr Tyr Gln Leu Arg Gly
            180                 185                 190

Glu Asp Ile Glu Glu Glu Lys Asp Lys Thr Phe Val Arg Leu Lys Val
        195                 200                 205

Glu Lys Ile Val Asp Ser Gly Asp Asn Val Lys Gly Lys Ile Leu Tyr
    210                 215                 220

Asp Val Tyr Phe Asp Asn Gly Trp Lys Tyr Asp Lys Gln Ile Val Lys
225                 230                 235                 240

Thr Glu Asp Trp Ile Glu Arg Val Lys Glu Phe Ile Val Thr Glu Ser
                245                 250                 255

Phe Leu Lys Asn Gly Asp Ile Lys Arg Thr Tyr Lys Ala Val Asp Ser
            260                 265                 270

Glu Lys Asp Trp Ile Ala Ile Lys Thr Lys Thr Glu Gln Glu Ile Glu
        275                 280                 285

Lys Ser His Lys Thr Val Gly Thr Tyr Ile Tyr Glu Thr Ile Leu His
    290                 295                 300

Asn Pro Lys Gln Lys Ile Lys Gly Lys Leu Val Arg Thr Ile Glu Arg
305                 310                 315                 320

Lys Phe Tyr Lys Asp Glu Leu Arg Gln Ile Leu Glu Lys Gln Lys Glu
                325                 330                 335

Phe His Pro Glu Leu Gln Asn Asp Asp Leu Tyr Ser Asp Cys Val Arg
            340                 345                 350

Glu Leu Tyr Arg Asn Asn Glu Ala His Gln Leu Thr Leu Ser Lys Lys
            355                 360                 365

Asp Phe Val His Leu Phe Ile Glu Asp Ile Ile Phe Tyr Gln Arg Pro
    370                 375                 380

Leu Arg Ser Gln Lys Ser Ser Ile Ser Asn Cys Thr Leu Glu Tyr Arg
385                 390                 395                 400

Arg Tyr Lys Asp Lys His Gly Val Glu His Ile Gln Tyr Leu Lys Ala
                405                 410                 415

Ile Pro Lys Ser Asn Pro Tyr Tyr Gln Glu Phe Arg Ile Trp Gln Trp
            420                 425                 430

Met Tyr Asn Leu Asn Ile Tyr Lys Arg Asp Asp Asp Thr Asn Val Thr
            435                 440                 445

Lys Glu Phe Leu Asn Ser Thr Glu Asp Phe Glu Asn Leu Phe Asp Phe
    450                 455                 460

Leu Asn Asn Arg Lys Glu Val Glu Gln Lys Ala Leu Leu Lys His Phe
465                 470                 475                 480

Lys Leu Asn Glu Lys Thr His Arg Trp Asn Phe Val Glu Asn Lys Lys
                485                 490                 495

Tyr Pro Cys Asn Glu Thr Lys Thr Met Ile Ser Ser Arg Leu Asp Lys
            500                 505                 510

Val Glu Asn Ile Ser Glu Asn Phe Leu Thr Ser Glu Ile Glu His Lys
        515                 520                 525

Ile Trp His Ile Ile Tyr Ser Val Asn Asp Lys Ile Glu Tyr Glu Lys
    530                 535                 540

Ala Leu Lys Ser Phe Ala Asn Lys Asn Asn Leu Asp Glu Val Ser Phe
545                 550                 555                 560

Phe Glu Ala Phe Lys Lys Phe Pro Pro Phe Lys Asn Glu Tyr Gly Ser
                565                 570                 575

Phe Ser Glu Lys Ala Ile Lys Lys Leu Leu Pro Leu Met Arg Val Gly
            580                 585                 590

Lys Tyr Trp Asp Glu Asp Glu Ile Val Lys Asn Ser Asp Thr Tyr Phe
```

```
            595                 600                 605

Lys Asn Ile Glu Asp Leu Leu Gly Asn Ile Ala Arg Lys Glu Glu Asn
    610                 615                 620

Ile Ser Asp Asp Asp Arg Lys Lys Tyr Asn Lys Thr Val Asn Leu Lys
625                 630                 635                 640

Leu Arg Glu Glu Leu Glu Ile Phe Gln Asp Ala Glu Ile Ala Ser Phe
                645                 650                 655

Gln Lys Leu Arg Leu His Ile Ala Gln Tyr Leu Val Tyr Gly Arg His
                660                 665                 670

Ser Glu Ala Ser Ile Ile Gly Lys Trp Asn Ser Ala Asp Asp Leu Glu
                675                 680                 685

Glu Phe Leu Lys Glu Phe Lys Gln His Ser Leu Arg Asn Pro Ile Val
                690                 695                 700

Glu Gln Val Ile Thr Glu Thr Leu Arg Val Val Lys Asp Ile Trp Met
705                 710                 715                 720

Lys Tyr Gly Asn Gly Ala Lys Asp Phe Phe Asn Glu Ile His Ile Glu
                725                 730                 735

Leu Gly Arg Glu Met Lys Leu Pro Ala Glu Asp Arg Lys Lys Leu Thr
                740                 745                 750

Ser Gln Ile Ser Glu Asn Glu Asn Thr Asn Leu Arg Ile Lys Ala Leu
                755                 760                 765

Leu Ala Glu Met Met Asn Asp Ser Ser Val Glu Asn Val Arg Pro Phe
                770                 775                 780

Ser Pro Met Gln Gln Glu Ile Leu Lys Ile Tyr Glu Asp Gly Val Leu
785                 790                 795                 800

Asn Ser Gly Ile Glu Ile Glu Asp Glu Tyr Leu Lys Ile Ser Lys Thr
                805                 810                 815

Ala Gln Pro Ser Ser Ser Asp Leu Lys Arg Tyr Lys Leu Trp Leu Glu
                820                 825                 830

Gln Lys Tyr Lys Ser Pro Tyr Thr Gly Gln Ile Ile Pro Leu Asn Lys
                835                 840                 845

Leu Phe Thr Pro Glu Tyr Glu Ile Glu His Ile Ile Pro Lys Ser Arg
                850                 855                 860

Tyr Phe Asp Asp Ser Phe Ser Asn Lys Ile Ile Cys Glu Ser Ala Val
865                 870                 875                 880

Asn Lys Leu Lys Asp Asn Tyr Ile Gly Leu Gly Phe Ile Lys Gln Phe
                885                 890                 895

Ala Gly Ala Ile Val Glu Leu Gly Phe Gly Lys Asn Val Lys Val Phe
                900                 905                 910

Glu Ile Glu Glu Tyr Glu Asp Phe Val Lys Lys His Tyr Ala Asn Asn
                915                 920                 925

Arg Gly Lys Arg Asn Lys Leu Leu Leu Glu Glu Ile Pro Glu Lys Met
                930                 935                 940

Ile Glu Arg Gln Leu Asn Asp Thr Arg His Ile Ser Lys Tyr Ile Ser
945                 950                 955                 960

Ser Val Leu Ser Asn Ile Val Arg Val Glu Asp Gly Thr Asp Glu Gly
                965                 970                 975

Val Asn Ser Lys Asn Ile Val Pro Gly Asn Gly Lys Ile Thr Ile Gln
                980                 985                 990

Leu Lys Gln Asp Trp Gly Leu Asn  Asp Val Trp Asn Asp  Leu Ile Leu
                995                 1000                1005

Pro Arg  Phe Glu Arg Met Asn  Gln Leu Thr Asn Ser  Thr Asp Phe
    1010                1015                1020
```

-continued

```
Thr Ala Trp Asn Lys Asn His  Gln Lys Tyr Leu Pro  Thr Val Pro
    1025            1030            1035

Ile Glu Phe Ser Lys Gly Phe  Ser Lys Lys Arg Ile  Asp His Arg
    1040            1045            1050

His His Ala Leu Asp Ala Leu  Val Ile Ala Cys Thr  Thr Lys Asp
    1055            1060            1065

His Val Asn Leu Leu Asn Asn  Gln Ser Ala Lys Ser  Asp Thr Lys
    1070            1075            1080

Arg Tyr Asp Leu Lys Lys Lys  Leu Met Lys Phe Glu  Lys Val Val
    1085            1090            1095

Tyr Asn His Thr Gln Thr Gly  Glu Lys Ile Glu Arg  Asp Ile Pro
    1100            1105            1110

Lys Gln Phe Leu Lys Pro Trp  Glu Thr Phe Thr Ile  Asp Ala Lys
    1115            1120            1125

Asn Arg Leu Glu Thr Ile Ile  Val Ser Phe Lys Gln  Asn Leu Arg
    1130            1135            1140

Val Ile Asn Lys Ala Thr Asn  His Tyr Glu Lys Tyr  Val Glu Lys
    1145            1150            1155

Glu Gly Val Lys Met Lys Glu  Arg Val Glu Gln Thr  Gly Thr Asn
    1160            1165            1170

Trp Ala Ile Arg Lys Ser Leu  His Glu Glu Thr Val  Ser Gly Lys
    1175            1180            1185

Ile Thr Leu Ser Trp Val Glu  Thr Ser Lys Gly Glu  Phe Ile Thr
    1190            1195            1200

Ala Thr Arg Lys Pro Leu Asp  Ser Ser Phe Thr Phe  Glu Lys Ile
    1205            1210            1215

Asn Lys Ile Thr Asp Thr Gly  Ile Gln Lys Ile Leu  Asn Asn Tyr
    1220            1225            1230

Leu Glu Ala Lys Asp Asn Asn  Pro Glu Leu Ala Phe  Ser Ala Glu
    1235            1240            1245

Gly Ile Glu Asp Leu Asn Lys  Asn Ile Glu Lys Tyr  Asn Asp Gly
    1250            1255            1260

Lys Ser His Gln Pro Ile Ile  Lys Ile Arg Leu Tyr  Glu Lys Gly
    1265            1270            1275

Lys Gly Arg Phe Val Leu Gly  Gln Thr Gly Asn Lys  Ile Asn Lys
    1280            1285            1290

Tyr Val Gln Gly Ser Pro Asn  Leu Phe Phe Ala Ile  Tyr Lys Asp
    1295            1300            1305

Glu Asn Gly Lys Lys Ile Phe  Glu Ser Ile Arg Leu  Asp Ile Val
    1310            1315            1320

Ile Glu Arg Leu Lys Gln Gly  Leu Gln Ala Ile Pro  Glu Thr Asn
    1325            1330            1335

Gln Asn Gly Val Ser Leu Tyr  Gln Ser Leu Ser Pro  Leu Asp Leu
    1340            1345            1350

Val Tyr Ile Pro Thr Glu Tyr  Glu Leu Glu Ser Pro  His Ile Leu
    1355            1360            1365

Asp Phe Ser Lys Leu Asn Lys  Thr Gln Ile Thr Arg  Leu Tyr Asn
    1370            1375            1380

Thr Asn Asp Phe Ser Gly Val  Thr Ala Tyr Phe Ser  Gln Asn Ser
    1385            1390            1395

Phe Ala Lys His Ile Tyr Pro  Lys Glu Met Asp Leu  Ser Trp Asn
    1400            1405            1410
```

-continued

```
Glu Lys  Lys Gln Lys Leu Ser  Gly Ser Phe Asp Ser  Lys Thr Ala
    1415                1420             1425

Ser Tyr  Asn Asn Thr Ser Ile  Lys Asp Ile Phe Ile  Lys Val Lys
    1430                1435             1440

Val Asp  Arg Leu Gly Asn Ile  Ser Lys Ala
    1445                1450
```

```
<210> SEQ ID NO 24
<211> LENGTH: 29
<212> TYPE: RNA
<213> ORGANISM: Chryseobacterium sp.

<400> SEQUENCE: 24
guugugaauu gcuuucaaaa auuauuauc                                        29

<210> SEQ ID NO 25
<211> LENGTH: 83
<212> TYPE: RNA
<213> ORGANISM: Chryseobacterium sp.

<400> SEQUENCE: 25
uaauaauuuu gaaagcaauu cacaauaagg auuauuccgu ugugaaaaca uucaaggcgg      60
ggcaacucgc cuuuuuucgu uuu                                              83

<210> SEQ ID NO 26
<211> LENGTH: 145
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: modified_base
<222> LOCATION: (1)..(29)
<223> OTHER INFORMATION: a, c, u, g, unknown or other

<400> SEQUENCE: 26
nnnnnnnnnn nnnnnnnnnn nnnnnnnnng uugugaauug cuuucaaaaa uuauuaucaa      60
aguaauaauu uugaaagcaa uucacaauaa ggauuauucc guugugaaaa cauucaaggc     120
ggggcaacuc gccuuuuuuc guuuu                                           145

<210> SEQ ID NO 27
<211> LENGTH: 146
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 27
gagcggacag cagcuuccua uaucucguac guugugaauu gcuuucaaaa auuauuauca      60
aaguaauaau uuugaaagca auucacaaua aggauuauuc cguugugaaa acauucaagg     120
cggggcaacu cgccuuuuuu cguuuu                                          146

<210> SEQ ID NO 28
<211> LENGTH: 146
<212> TYPE: RNA
<213> ORGANISM: Artificial Sequence
<220> FEATURE:
<221> NAME/KEY: source
<223> OTHER INFORMATION: /note="Description of Artificial Sequence:
```

-continued

Synthetic polynucleotide"

<400> SEQUENCE: 28
ccaugauaua gacguugugg cuguuguagu guugugaauu gcuuucaaaa auuauuauca      60
aaguaauaau uuugaaagca auucacaaua aggauuauuc cguugugaaa acauucaagg     120
cggggcaacu cgccuuuuuu cguuuu                                          146

<210> SEQ ID NO 29
<211> LENGTH: 6
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(2)
<223> OTHER INFORMATION: a, c, t, g, unknown or other

<400> SEQUENCE: 29 nnraar                                                                 6

<210> SEQ ID NO 30
<211> LENGTH: 1093
<212> TYPE: PRT
<213> ORGANISM: Brucella sp.

<400> SEQUENCE: 30

Met Lys Thr Leu Gly Ile Asp Leu Gly Thr Ala Ser Ile Gly Trp Ala
1               5                   10                  15

Ile Leu Asp Glu Ala Ser Ile Ile Ala Ser Gly Val Arg Ile Phe Ser
                20                  25                  30

Gln Ser Glu Met Ala Gly Arg Asp Pro Gln Ser Lys Ala Ser Leu Ala
            35                  40                  45

Val Ala Arg Arg Asp Ala Arg Gly Ala Arg Arg Arg Asp Arg Tyr
        50                  55                  60

Leu Lys Arg Arg Arg Leu Leu Asp Leu Leu Thr Glu His Gly Leu
65                  70                  75                  80

Ala Pro Ala Asp Glu Lys Ser Arg Lys Ala Leu Val Arg Glu Tyr Glu
                85                  90                  95

Asp Gly Lys Asp Gly Asp Leu Ser Asn Ser Val Tyr Ala Leu Arg Ala
            100                 105                 110

Arg Ala Leu Asp Glu Ala Leu Thr Pro Tyr Glu Ile Gly Arg Ala Ile
        115                 120                 125

Phe Gln Leu Asn Gln Arg Arg Gly Phe Lys Ser Asn Arg Lys Thr Asp
    130                 135                 140

Ser Asn Asp Pro Glu Gln Gly Lys Ile Ala Thr Ala Ile His Val Leu
145                 150                 155                 160

Asp Ala Lys Met Asp Glu Asp Lys Ala Arg Thr Phe Gly Glu Trp Leu
                165                 170                 175

His Met Arg Arg Leu Lys Gly Leu Ser Val Arg Ala Arg Met Thr Ala
            180                 185                 190

Asp Gly Asp Ser Tyr Asp Phe Tyr Pro Ser Arg Ala Ala Leu Glu Arg
        195                 200                 205

Glu Phe Asp Arg Leu Met Ala Ser Gln Lys Arg Phe His Pro Asp Leu
    210                 215                 220

Leu Asn Ser Ser Val Ile Asp Asp Ile Arg Lys Val Val Phe His Gln

-continued

```
225                 230                 235                 240

Arg Pro Leu Lys Pro Val Gln Pro Gly Lys Cys Ser Tyr Asn His Arg
            245                 250                 255

Glu Ser Arg Leu Pro Lys Ala His Pro Leu Phe Gln Lys Phe Arg Leu
            260                 265                 270

Leu Lys Glu Val Asn Glu Leu Glu Ile Val Gly Glu Asp Gln Arg Tyr
            275                 280                 285

Val Lys Leu Thr Pro Ala Gln Arg Asp Val Leu Thr Leu Ala Leu Arg
    290                 295                 300

Thr Gly Leu Thr Lys Gln Gly Arg Leu Pro Phe Ser Lys Leu Arg Ser
305                 310                 315                 320

Ile Leu Lys Leu Gly Lys Glu Val Arg Phe Asn Lys Glu Lys Asp Asn
                325                 330                 335

Arg Thr Asp Leu Glu Gly Asp Val Ile His Phe Arg Val Ser Arg Pro
            340                 345                 350

Asp Cys Phe Gly Asn Arg Trp Ala Ala Met Pro Val Glu Glu Gln Ala
            355                 360                 365

Ala Val Thr Glu Lys Leu Arg Thr Glu Pro Asp Tyr Ser Ala Leu Leu
    370                 375                 380

Asp Trp Leu Lys Asn Glu Ala Gly Leu Asp Glu Ala His Ala Arg Ala
385                 390                 395                 400

Val Ala Asp Thr Pro Val Pro Asp Gly Phe Gly Arg Met Gly Pro Ser
                405                 410                 415

Ala Leu Ser Ala Leu Ala Asp Ala Met Glu His Glu Ile Asp Ala Gln
            420                 425                 430

Gly Phe Val Ile Thr Glu Ala Glu Ala Ala Lys Arg Val Tyr Gly Arg
            435                 440                 445

Thr Asn Ser Glu Ala Asp Pro Gly Arg Lys Gly Val Asp Gln Leu Pro
    450                 455                 460

Lys Tyr Gln Glu Val Leu Gln Arg His Ile Pro Pro Gly Thr Gly Glu
465                 470                 475                 480

Pro Asp Asp Pro Tyr Asp Glu Tyr Met Gly Arg Ile Thr Asn Pro Thr
                485                 490                 495

Val His Ile Ala Leu Asn Gln Leu Arg Arg Leu Val Asn Ala Leu Ile
            500                 505                 510

Arg Lys Tyr Gly Lys Pro Asn Lys Ile Ala Ile Glu Val Gly Arg Glu
            515                 520                 525

Leu Lys Leu Asn Glu Lys Gln Arg Asn Glu Val Asn Arg Glu Ile Gly
    530                 535                 540

Gln Asn Thr Arg Ala Ala Met Ala Arg Gly Gln Gln Leu Val Glu Ile
545                 550                 555                 560

Phe Lys Gln Pro Asn Thr Gly Tyr Asn Arg Leu Arg Leu Glu Leu Trp
                565                 570                 575

Glu Asp Leu Asn Arg Glu Gln Pro Leu Lys Arg Leu Cys Thr Tyr Cys
            580                 585                 590

Gly Lys Ala Ile Ala Ala His Met Leu Phe Asn Gly Glu Thr Asp Ile
            595                 600                 605

Asp His Ile Leu Pro Tyr Ser Lys Thr Leu Asp Asp Ser Lys Ala Asn
    610                 615                 620

Arg Leu Leu Cys Cys Thr Pro Cys Asn Arg Glu Lys Lys Asn Tyr Ala
625                 630                 635                 640

Pro Ala Asn Val Leu Gln Trp Arg Asp His Tyr Gly Glu Ile Leu Ala
                645                 650                 655
```

```
Arg Ala Thr Ala Leu Pro Lys Asn Lys Gln Trp Arg Phe Ala Glu Asp
            660                 665             670

Ala Met Thr Arg Tyr Glu Ala Glu Gly Gly Phe Leu Ala Arg Gln Leu
            675                 680             685

Thr Asp Met Gln Tyr Ile Ser Arg Leu Ala Leu Thr Tyr Leu Ala His
            690                 695             700

Leu Tyr Asp Tyr Glu Glu Pro Asp Leu Asp Gly Val Tyr Lys Arg His
705                 710             715                 720

Asp Arg Val Arg Ala Leu Pro Gly Arg Met Thr Glu Met Leu Arg Arg
                725             730             735

Gln Trp Ala Leu Asn Glu Leu Leu His Gly His Asn Leu Ala Gly Gly
            740                 745             750

Asp Gly Ala Lys Glu Lys Asn Arg Leu Asp His Arg His His Ala Ile
            755                 760             765

Asp Ala Ile Val Ile Ala Cys Thr Ser Gln Ser Leu Ile Asn Arg Leu
            770                 775             780

Ser Thr Ala Ala Gly Glu Ala Glu Glu Arg Gly Ala Ala Arg Val Val
785                 790             795                 800

Glu Arg Ile Asp Pro Pro Trp Pro Ser Phe Arg Glu Asp Val Arg Glu
                805             810             815

Ala Val Asn Ala Ile Val Val Ser His Lys Pro Asp His Gly Thr Ala
            820                 825             830

Ser Arg Ser Gly Tyr Asp Lys Gly Arg Gly Gln Thr Ala Gly Lys Leu
            835                 840             845

His Asn Asp Thr Ala Tyr Gly Glu Thr Gly Glu Lys Asp His Asn Gly
            850                 855             860

Asn Asn Leu Val Val Arg Arg Ile Ala Ile Ser Asp Ile Lys Arg Ser
865                 870             875                 880

Ala Asp Ile Met Lys Ile Arg Thr Asn Ala His Gly His Ser Glu Leu
                885             890             895

Arg Asp Arg Leu Tyr Glu Ala Thr Arg Asp Leu Glu Gly Lys Ala Phe
                900             905             910

Glu Gln Ala Val Thr Ala Phe Val Lys His Asp Ala Lys Phe Lys Gly
            915                 920             925

Ile Arg His Val Arg Val Thr Glu Val Gln Asn Pro Val Trp Ile Thr
            930                 935             940

His Gly Gly Gly Lys Tyr Lys Lys Gly Tyr Leu Pro Gly Gly Asn Asp
945                 950             955                 960

Arg Phe Asp Val Trp Glu Leu Pro Asp Gly Lys Trp Asp Ala Glu Val
                965             970             975

Val Thr Thr Phe Asp Ala His Arg Pro Asp Phe Thr Pro Arg Met Arg
                980             985             990

Ile Glu His His Asn Ala Arg Lys  Ile Met Ser Leu Lys  Lys Gly Asp
            995             1000                1005

Met Ile  Ala Tyr Asp Asp Pro  Asp Ser Gly Lys Arg  Val Ile Ala
    1010                1015                1020

Ile Val  Arg Lys Phe Asp Gln  Arg Asn Lys Gln Leu  Tyr Leu Asp
    1025                1030                1035

Pro His  Asn Glu Ala Gly Asn  Leu Asp Gln Arg Glu  Lys Glu Lys
    1040                1045                1050

Thr Tyr  Lys Pro Leu Arg Pro  Met Pro Asn Pro Leu  Lys Lys Tyr
    1055                1060                1065
```

```
Arg Pro  Arg Gln Val Arg Val  Asp Glu Ile Gly Gln  Val Phe Asp
    1070              1075                1080

Pro Gly  Pro Trp Trp Glu Lys  Arg Ser Asp
    1085              1090
```

```
<210> SEQ ID NO 31
<211> LENGTH: 27
<212> TYPE: RNA
<213> ORGANISM: Brucella sp.

<400> SEQUENCE: 31
guugcgguug gccugcgauu ucugaac                                          27

<210> SEQ ID NO 32
<211> LENGTH: 81
<212> TYPE: RNA
<213> ORGANISM: Brucella sp.

<400> SEQUENCE: 32
guucagaaau cgcaguccag ccguuaacaa gcugagauau gcaccaaaua aggcgcucgc      60
uucggcgggc gcuuuuucgu u                                                81

<210> SEQ ID NO 33
<211> LENGTH: 141
<212> TYPE: RNA
<213> ORGANISM: Artificial Sequence
<220> FEATURE:
<221> NAME/KEY: source
<223> OTHER INFORMATION: /note="Description of Artificial Sequence:
     Synthetic polynucleotide"
<220> FEATURE:
<221> NAME/KEY: modified_base
<222> LOCATION: (1)..(29)
<223> OTHER INFORMATION: a, c, u, g, unknown or other

<400> SEQUENCE: 33
nnnnnnnnnn nnnnnnnnnn nnnnnnnnng uugcgguugg ccugcgauuu cugaacaaag      60
guucagaaau cgcaguccag ccguuaacaa gcugagauau gcaccaaaua aggcgcucgc      120
uucggcgggc gcuuuuucgu u                                                141

<210> SEQ ID NO 34
<211> LENGTH: 142
<212> TYPE: RNA
<213> ORGANISM: Artificial Sequence
<220> FEATURE:
<221> NAME/KEY: source
<223> OTHER INFORMATION: /note="Description of Artificial Sequence:
     Synthetic polynucleotide"

<400> SEQUENCE: 34
gagcggacag cagcuuccua uaucucguac guugcgguug gccugcgauu ucgaacaaa       60 gguucagaaa ucgcagucca gccguuaaca agcugagaua ugcaccaaau aaggcgcucg     120
cuucggcggg cgcuuuuucg uu                                              142

<210> SEQ ID NO 35
<211> LENGTH: 142
<212> TYPE: RNA
<213> ORGANISM: Artificial Sequence
<220> FEATURE:
<221> NAME/KEY: source
<223> OTHER INFORMATION: /note="Description of Artificial Sequence:
     Synthetic polynucleotide"

<400> SEQUENCE: 35
```

-continued

```
ccaugauaua gacguugugg cuguuguagu guugcgguug gccugcgauu ucugaacaaa      60
gguucagaaa ucgcagucca gccguuaaca agcugagaua ugcaccaaau aaggcgcucg     120
cuucggcggg cgcuuuuucg uu                                             142
```

<210> SEQ ID NO 36
<211> LENGTH: 6
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(2)
<223> OTHER INFORMATION: a, c, t, g, unknown or other
<220> FEATURE:
<221> NAME/KEY: modified_base
<222> LOCATION: (4)..(4)
<223> OTHER INFORMATION: a, c, t, g, unknown or other

<400> SEQUENCE: 36

```
nnrnat                                                                6
```

<210> SEQ ID NO 37
<211> LENGTH: 6
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (2)..(2)
<223> OTHER INFORMATION: a, c, u, g, unknown or other
<220> FEATURE:
<221> NAME/KEY: modified_base
<222> LOCATION: (4)..(5)
<223> OTHER INFORMATION: a, c, u, g, unknown or other

<400> SEQUENCE: 37

```
cnanng                                                                6
```

<210> SEQ ID NO 38
<211> LENGTH: 1054
<212> TYPE: PRT
<213> ORGANISM: Staphylococcus sp.

<400> SEQUENCE: 38

```
Met Lys Glu Lys Tyr Ile Leu Gly Leu Asp Leu Gly Ile Thr Ser Val
1               5                   10                  15

Gly Tyr Gly Ile Ile Asn Phe Glu Thr Lys Lys Ile Ile Asp Ala Gly
            20                  25                  30

Val Arg Leu Phe Pro Glu Ala Asn Val Asp Asn Asn Glu Gly Arg Arg
        35                  40                  45

Ser Lys Arg Gly Ser Arg Arg Leu Lys Arg Arg Arg Ile His Arg Leu
    50                  55                  60

Glu Arg Val Lys Leu Leu Leu Thr Glu Tyr Asp Leu Ile Asn Lys Glu
65                  70                  75                  80

Gln Ile Pro Thr Ser Asn Asn Pro Tyr Gln Ile Arg Val Lys Gly Leu
                85                  90                  95

Ser Glu Ile Leu Ser Lys Asp Glu Leu Ala Ile Ala Leu Leu His Leu
            100                 105                 110
```

```
Ala Lys Arg Arg Gly Ile His Asn Ile Asn Val Ser Ser Glu Asp Glu
        115                 120                 125

Asp Ala Ser Asn Glu Leu Ser Thr Lys Glu Gln Ile Asn Arg Asn Asn
        130                 135                 140

Lys Leu Leu Lys Asp Lys Tyr Val Cys Glu Val Gln Leu Gln Arg Leu
145                 150                 155                 160

Lys Glu Gly Gln Ile Arg Gly Glu Lys Asn Arg Phe Lys Thr Thr Asp
                165                 170                 175

Ile Leu Lys Glu Ile Asp Gln Leu Leu Lys Val Gln Lys Asp Tyr His
                180                 185                 190

Asn Leu Asp Ile Asp Phe Ile Asn Gln Tyr Lys Glu Ile Val Glu Thr
                195                 200                 205

Arg Arg Glu Tyr Phe Glu Gly Pro Gly Gln Gly Ser Pro Phe Gly Trp
        210                 215                 220

Asn Gly Asp Leu Lys Lys Trp Tyr Glu Met Leu Met Gly His Cys Thr
225                 230                 235                 240

Tyr Phe Pro Gln Glu Leu Arg Ser Val Lys Tyr Ala Tyr Ser Ala Asp
                245                 250                 255

Leu Phe Asn Ala Leu Asn Asp Leu Asn Asn Leu Ile Ile Gln Arg Asp
                260                 265                 270

Asn Ser Glu Lys Leu Glu Tyr His Glu Lys Tyr His Ile Ile Glu Asn
        275                 280                 285

Val Phe Lys Gln Lys Lys Lys Pro Thr Leu Lys Gln Ile Ala Lys Glu
        290                 295                 300

Ile Gly Val Asn Pro Glu Asp Ile Lys Gly Tyr Arg Ile Thr Lys Ser
305                 310                 315                 320

Gly Thr Pro Gln Phe Thr Glu Phe Lys Leu Tyr His Asp Leu Lys Ser
                325                 330                 335

Ile Val Phe Asp Lys Ser Ile Leu Glu Asn Glu Ala Ile Leu Asp Gln
                340                 345                 350

Ile Ala Glu Ile Leu Thr Ile Tyr Gln Asp Glu Gln Ser Ile Lys Glu
        355                 360                 365

Glu Leu Asn Lys Leu Pro Glu Ile Leu Asn Glu Gln Asp Lys Ala Glu
        370                 375                 380

Ile Ala Lys Leu Ile Gly Tyr Asn Gly Thr His Arg Leu Ser Leu Lys
385                 390                 395                 400

Cys Ile His Leu Ile Asn Glu Glu Leu Trp Gln Thr Ser Arg Asn Gln
                405                 410                 415

Met Glu Ile Phe Asn Tyr Leu Asn Ile Lys Pro Asn Lys Val Asp Leu
                420                 425                 430

Ser Glu Gln Asn Lys Ile Pro Lys Asp Met Val Asn Asp Phe Ile Leu
        435                 440                 445

Ser Pro Val Val Lys Arg Thr Phe Ile Gln Ser Ile Asn Val Ile Asn
        450                 455                 460

Lys Val Ile Glu Lys Tyr Gly Ile Pro Glu Asp Ile Ile Ile Glu Leu
465                 470                 475                 480

Ala Arg Glu Asn Asn Ser Asp Asp Arg Lys Lys Phe Ile Asn Asn Leu
                485                 490                 495

Gln Lys Lys Asn Glu Ala Thr Arg Lys Arg Ile Asn Glu Ile Ile Gly
        500                 505                 510

Gln Thr Gly Asn Gln Asn Ala Lys Arg Ile Val Glu Lys Ile Arg Leu
        515                 520                 525
```

```
His Asp Gln Gln Glu Gly Lys Cys Leu Tyr Ser Leu Glu Ser Ile Ala
    530                 535                 540

Leu Met Asp Leu Leu Asn Asn Pro Gln Asn Tyr Glu Val Asp His Ile
545                 550                 555                 560

Ile Pro Arg Ser Val Ala Phe Asp Asn Ser Ile His Asn Lys Val Leu
                565                 570                 575

Val Lys Gln Ile Glu Asn Ser Lys Lys Gly Asn Arg Thr Pro Tyr Gln
                580                 585                 590

Tyr Leu Asn Ser Ser Asp Ala Lys Leu Ser Tyr Asn Gln Phe Lys Gln
        595                 600                 605

His Ile Leu Asn Leu Ser Lys Ser Lys Asp Arg Ile Ser Lys Lys Lys
    610                 615                 620

Lys Asp Tyr Leu Leu Glu Glu Arg Asp Ile Asn Lys Phe Glu Val Gln
625                 630                 635                 640

Lys Glu Phe Ile Asn Arg Asn Leu Val Asp Thr Arg Tyr Ala Thr Arg
                645                 650                 655

Glu Leu Thr Ser Tyr Leu Lys Ala Tyr Phe Ser Ala Asn Asn Met Asp
                660                 665                 670

Val Lys Val Lys Thr Ile Asn Gly Ser Phe Thr Asn His Leu Arg Lys
                675                 680                 685

Val Trp Arg Phe Asp Lys Tyr Arg Asn His Gly Tyr Lys His His Ala
    690                 695                 700

Glu Asp Ala Leu Ile Ile Ala Asn Ala Asp Phe Leu Phe Lys Glu Asn
705                 710                 715                 720

Lys Lys Leu Gln Asn Ala Asn Lys Ile Leu Glu Lys Pro Thr Ile Glu
                725                 730                 735

Asn Asn Thr Lys Lys Val Thr Val Glu Lys Glu Glu Asp Tyr Asn Asn
                740                 745                 750

Val Phe Glu Thr Pro Lys Leu Val Glu Asp Ile Lys Gln Tyr Arg Asp
                755                 760                 765

Tyr Lys Phe Ser His Arg Val Asp Lys Lys Pro Asn Arg Gln Leu Ile
    770                 775                 780

Asn Asp Thr Leu Tyr Ser Thr Arg Met Lys Asp Glu His Asp Tyr Ile
785                 790                 795                 800

Val Gln Thr Ile Thr Asp Ile Tyr Gly Lys Asp Asn Thr Asn Leu Lys
                805                 810                 815

Lys Gln Phe Asn Lys Asn Pro Glu Lys Phe Leu Met Tyr Gln Asn Asp
                820                 825                 830

Pro Lys Thr Phe Glu Lys Leu Ser Ile Ile Met Lys Gln Tyr Ser Asp
                835                 840                 845

Glu Lys Asn Pro Leu Ala Lys Tyr Tyr Glu Glu Thr Gly Glu Tyr Leu
    850                 855                 860

Thr Lys Tyr Ser Lys Lys Asn Asn Gly Pro Ile Val Lys Lys Ile Lys
865                 870                 875                 880

Leu Leu Gly Asn Lys Val Gly Asn His Leu Asp Val Thr Asn Lys Tyr
                885                 890                 895

Glu Asn Ser Thr Lys Lys Leu Val Lys Leu Ser Ile Lys Asn Tyr Arg
                900                 905                 910

Phe Asp Val Tyr Leu Thr Glu Lys Gly Tyr Lys Phe Val Thr Ile Ala
        915                 920                 925

Tyr Leu Asn Val Phe Lys Lys Asp Asn Tyr Tyr Ile Pro Lys Asp
    930                 935                 940

Lys Tyr Gln Glu Leu Lys Glu Lys Lys Ile Lys Asp Thr Asp Gln
```

-continued

```
945           950           955           960

Phe Ile Ala Ser Phe Tyr Lys Asn Asp Leu Ile Lys Leu Asn Gly Asp
                965                970                975

Leu Tyr Lys Ile Ile Gly Val Asn Ser Asp Asp Arg Asn Ile Ile Glu
            980                985                990

Leu Asp Tyr Tyr Asp Ile Lys Tyr  Lys Asp Tyr Cys Glu  Ile Asn Asn
        995              1000              1005

Ile Lys  Gly Glu Pro Arg Ile  Lys Lys Thr Ile Gly  Lys Lys Thr
    1010              1015              1020

Glu Ser  Ile Glu Lys Phe Thr  Thr Asp Val Leu Gly  Asn Leu Tyr
    1025              1030              1035

Leu His  Ser Thr Glu Lys Ala  Pro Gln Leu Ile Phe  Lys Arg Gly
    1040              1045              1050

Leu
```

```
<210> SEQ ID NO 39
<211> LENGTH: 28
<212> TYPE: RNA
<213> ORGANISM: Staphylococcus sp.

<400> SEQUENCE: 39
guuuuaguac ucuguaauuu uagguaug                                    28

<210> SEQ ID NO 40
<211> LENGTH: 85
<212> TYPE: RNA
<213> ORGANISM: Staphylococcus sp.

<400> SEQUENCE: 40
ucauaccuaa aauuacagaa ucuacugaaa caagacuaua ugucguguuu aucccacuaa    60
uuuauuagug ggauuuuuuu guuuu                                       85

<210> SEQ ID NO 41
<211> LENGTH: 146
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: modified_base
<222> LOCATION: (1)..(29)
<223> OTHER INFORMATION: a, c, u, g, unknown or other

<400> SEQUENCE: 41
nnnnnnnnnn nnnnnnnnnn nnnnnnnng uuuuaguacu cuguaauuuu agguaugaaa    60
gucauaccua aaauuacaga aucuacugaa acaagacuau augucguguu uaucccacua    120
auuuauuagu gggauuuuuu uguuuu                                      146

<210> SEQ ID NO 42
<211> LENGTH: 147
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 42
gagcggacag cagcuuccua uaucucguac guuuuaguac ucuguaauuu uagguaugaa    60
```

```
agucauaccu aaaauuacag aaucuacuga aacaagacua uaugucgugu uuaucccacu      120
aauuuauuag ugggauuuuu uuguuuu                                          147
```

```
<210> SEQ ID NO 43
<211> LENGTH: 147
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 43
ccaugauaua gacguugugg cguuuguagu guuuuaguac ucuguaauuu uagguaugaa       60
agucauaccu aaaauuacag aaucuacuga aacaagacua uaugucgugu uuaucccacu      120
aauuuauuag ugggauuuuu uuguuuu                                          147
```

```
<210> SEQ ID NO 44
<211> LENGTH: 4
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(2)
<223> OTHER INFORMATION: a, c, t, g, unknown or other

<400> SEQUENCE: 44 nngg                                                                    4
```

```
<210> SEQ ID NO 45
<211> LENGTH: 6
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (2)..(2)
<223> OTHER INFORMATION: a, c, u, g, unknown or other
<220> FEATURE:
<221> NAME/KEY: modified_base
<222> LOCATION: (4)..(5)
<223> OTHER INFORMATION: a, c, u, g, unknown or other

<400> SEQUENCE: 45 cnannu                                                                  6
```

```
<210> SEQ ID NO 46
<211> LENGTH: 1076
<212> TYPE: PRT
<213> ORGANISM: Bacillus sp.

<400> SEQUENCE: 46

Met Ser Glu Leu Asp Tyr Arg Ile Gly Leu Asp Ile Gly Thr Asn Ser
1               5                   10                  15

Ile Gly Trp Gly Val Ile Glu Leu Phe Trp Asn Lys Asp Arg Glu Arg
                20                  25                  30

Tyr Glu Lys Val Arg Ile Val Asp Lys Gly Val Arg Met Phe Asp Lys
        35                  40                  45
```

-continued

```
Ala Glu Ile Pro Lys Thr Gly Ala Ser Leu Ala Glu Pro Arg Arg Ile
    50              55              60

Ala Arg Ser Ser Arg Arg Arg Leu Asn Arg Lys Ser Gln Arg Lys Lys
65              70              75              80

Glu Ile Arg Asn Leu Leu Val Gln His Gly Val Ile Thr Gln Glu Glu
                85              90              95

Leu Asp Leu Leu Tyr Pro Leu Ser Lys Lys Ser Met Asp Ile Trp Asp
            100             105             110

Ile Arg Leu Asp Gly Leu Asp Arg Leu Leu Asn His Leu Glu Trp Thr
        115             120             125

Arg Leu Leu Ile His Leu Ala Gln Arg Arg Gly Phe Lys Ser Asn Arg
    130             135             140

Lys Ser Glu Leu Lys Asp Ala Glu Thr Gly Lys Val Leu Ser Ser Ile
145             150             155             160

Gln Val Asn Glu Lys Arg Leu Ser Leu Tyr Arg Thr Val Gly Glu Met
            165             170             175

Trp Ile Lys Asp Ala Glu Phe Ser Lys Tyr Asp Arg Arg Arg Asn Ser
        180             185             190

Pro Asn Glu Tyr Val Phe Ser Val Ser Arg Ala Asp Leu Glu Lys Glu
            195             200             205

Ile Val Thr Leu Phe Glu Ala Gln Arg Lys Phe Gln Ser Ser Tyr Ser
    210             215             220

Ser Lys Asn Leu Gln Glu Thr Tyr Leu Gln Ile Trp Ala His Gln Leu
225             230             235             240

Pro Phe Ala Ser Gly Asn Ala Ile Leu Asn Lys Val Gly Tyr Cys Ser
            245             250             255

Leu Leu Lys Gly Lys Glu Arg Arg Ile Pro Lys Ala Thr Tyr Thr Phe
            260             265             270

Gln Tyr Phe Ser Ala Leu Asp Gln Val Asn Arg Thr Arg Leu Gly Pro
    275             280             285

Asp Phe Gln Pro Phe Thr Gln Glu Gln Lys Glu Ile Ile Leu Asp Lys
    290             295             300

Met Phe Gln Arg Thr Asp Tyr Tyr Lys Lys Lys Thr Ile Pro Glu Val
305             310             315             320

Ser Tyr Tyr Asp Ile Arg Lys Trp Leu Glu Leu Asp Glu Thr Ile Gln
            325             330             335

Phe Lys Gly Leu Asn Tyr Asp Pro Asn Glu Glu Leu Lys Lys Ile Glu
            340             345             350

Lys Lys Pro Phe Ile Asn Leu Lys Ala Phe Tyr Glu Ile Lys Lys Val
    355             360             365

Val Ala Asn Tyr Ala Glu Arg Thr Asn Glu Ala Phe Ser Thr Leu Asp
    370             375             380

Tyr Asp Ala Ile Ala Tyr Ala Leu Thr Val Tyr Lys Thr Asp Lys Asp
385             390             395             400

Ile Arg Ser Tyr Leu Lys Lys Ser Asn Asn Leu Ser Lys Arg Cys Tyr
            405             410             415

Asp Asp Gln Leu Ile Glu Glu Leu Phe Thr Leu Ser Tyr Thr Lys Phe
            420             425             430

Gly His Leu Ser Phe Lys Ala Ile Asn Arg Val Leu Pro Ile Met Gln
        435             440             445

Glu Gly Arg Thr Tyr Gln Glu Ala Ile Gln Gln Leu Gly Tyr Asp Thr
    450             455             460
```

-continued

```
Thr Asn Leu Lys Lys Glu Asn Arg Ser Met Phe Leu Pro Leu Ile Pro
465                 470                 475                 480

Asp Glu Ile Thr Asn Pro Ile Val Lys Arg Ala Leu Thr Gln Ala Arg
                485                 490                 495

Lys Val Val Asn Ala Ile Ile Arg Arg Tyr Gly Ser Pro Asn Ser Val
                500                 505                 510

His Ile Glu Leu Ala Arg Glu Leu Ser Lys Ser His Asp Glu Arg Lys
            515                 520                 525

Lys Ile Met Thr Ala His Asp Glu Asn Tyr Lys Lys Asn Lys Gly Ala
        530                 535                 540

Ile Ser Ile Leu Ile Glu Asn Gly Ile Leu Asn Pro Thr Gly Tyr Asp
545                 550                 555                 560

Ile Val Arg Tyr Lys Leu Trp Lys Glu Gln Gly Glu Arg Cys Ala Tyr
                565                 570                 575

Ser Leu Lys Glu Ile Pro Pro Asp Thr Phe Phe Asn Glu Leu Lys Lys
                580                 585                 590

Glu Arg Asn Gly Ser Ser Ile Leu Glu Val Asp His Ile Leu Pro Tyr
                595                 600                 605

Ser Gln Ser Phe Ile Asp Ser Tyr His Asn Lys Val Leu Val Tyr Ser
            610                 615                 620

Asp Glu Asn Arg Asn Lys Gly Asn Arg Ile Pro Tyr Thr Tyr Phe Leu
625                 630                 635                 640

Glu Thr Asn Lys Asp Trp Glu Ala Phe Glu Arg Tyr Val Arg Ser Asn
                645                 650                 655

Lys Leu Phe Ser Lys Lys Lys Arg Glu Tyr Leu Leu Lys Lys Ala Tyr
                660                 665                 670

Leu Pro Arg Glu Ser Glu Leu Ile Lys Glu Arg His Leu Asn Asp Thr
                675                 680                 685

Arg Tyr Ala Ser Thr Phe Leu Lys Asn Phe Ile Glu Gln Asn Leu Gln
            690                 695                 700

Phe Lys Glu Val Glu Val Asn Leu Arg Lys Lys Arg Val Gln Thr Val
705                 710                 715                 720

Asn Gly Val Ile Thr Ala His Leu Arg Lys Arg Trp Gly Leu Glu Lys
                725                 730                 735

Asn Arg Gln Glu Thr Tyr Leu His His Ala Met Asp Ala Ile Ile Val
            740                 745                 750

Ala Cys Thr Asp His His Met Val Thr Arg Ile Thr Glu Tyr Tyr Gln
            755                 760                 765

Ile Lys Glu Ser Asn Lys Ser Val Lys Lys Pro Tyr Phe Pro Met Pro
        770                 775                 780

Trp Glu Gly Phe Arg Asp Glu Leu Leu Ser His Leu Ala Ser Gln Pro
785                 790                 795                 800

Ile Ala Lys Lys Ile Ser Glu Glu Leu Lys Ala Gly Tyr Gln Ser Ser
                805                 810                 815

Asp Tyr Ile Phe Val Ser Arg Met Pro Lys Arg Ser Val Thr Gly Ala
            820                 825                 830

Ala His Asn Gln Met Ile Arg Arg Lys Gly Gly Ile Asp Lys Lys Gly
        835                 840                 845

Lys Thr Ile Ile Ile Lys Arg Val Arg Leu Lys Asp Ile Lys Phe Asp
        850                 855                 860

Glu Asn Gly Asp Phe Lys Met Val Gly Lys Glu Gln Asp Leu Ala Thr
865                 870                 875                 880

Tyr Glu Ala Ile Lys Gln Arg Tyr Leu Asp His Gly Lys Asn Leu Lys
```

-continued

```
                885                 890                 895

Lys Ala Phe Glu Thr Pro Leu Tyr Lys Pro Ser Lys Lys Gly Thr Gly
            900                 905                 910

Asn Leu Ile Lys Arg Val Lys Ile Glu Gly Gln Thr Lys Ala Phe Val
            915                 920                 925

Arg Glu Val Asn Gly Gly Val Ala Gln Asn Ser Asp Leu Val Arg Val
        930                 935                 940

Asp Leu Phe Glu Lys Asp Asp Lys Tyr Tyr Met Val Pro Ile Tyr Val
945                 950                 955                 960

Pro Asp Thr Val Cys Ser Glu Leu Pro Lys Lys Val Val Lys Ser Gly
                965                 970                 975

Lys Gly Tyr Glu Gln Trp Leu Thr Leu Asp Asn Ser Phe Thr Phe Lys
                980                 985                 990

Phe Ser Leu Tyr Pro Tyr Asp Leu  Val Arg Leu Val Lys  Gly Asp Glu
                995                 1000                1005

Asp Arg  Phe Leu Tyr Phe Gly  Thr Leu Asp Ile Asp  Ser Asp Arg
    1010                 1015                1020

Leu Asn  Phe Lys Asp Val Asn  Lys Pro Ser Lys Gln  Asn Glu Tyr
    1025                 1030                1035

Arg Tyr  Ser Leu Lys Thr Ile  Glu Asp Leu Glu Lys  Tyr Glu Val
    1040                 1045                1050

Gly Val  Leu Gly Asp Leu Arg  Leu Val Arg Lys Glu  Thr Arg Arg
    1055                 1060                1065

Asn Phe  His Glu Ile Lys Ile  Asn
    1070                 1075
```

```
<210> SEQ ID NO 47
<211> LENGTH: 20
<212> TYPE: RNA
<213> ORGANISM: Bacillus sp.

<400> SEQUENCE: 47
gucauaguuc cauuaaagcc                                                20

<210> SEQ ID NO 48
<211> LENGTH: 84
<212> TYPE: RNA
<213> ORGANISM: Bacillus sp.

<400> SEQUENCE: 48
ggcuuugaug uuucuaugau aaggguuucg gcccguggcg ucggggaucg ccugcccauu    60
ccgaugggcu ucuccccauu uauu                                          84

<210> SEQ ID NO 49
<211> LENGTH: 137
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: modified_base
<222> LOCATION: (1)..(29)
<223> OTHER INFORMATION: a, c, u, g, unknown or other

<400> SEQUENCE: 49
nnnnnnnnnn nnnnnnnnnn nnnnnnnnng ucauaguucc auuaaagcca aagggcuuug    60
auguuucuau gauaaggguu ucggcccgug gcgucgggga ucgccugccc auuccgaugg   120
```

-continued

```
gcuucucccc auuuauu                                                    137

<210> SEQ ID NO 50
<211> LENGTH: 138
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 50
gagcggacag cagcuuccua uaucucguac gucauaguuc cauuaaagcc aaagggcuuu       60
gauguuucua ugauaagggu uucggcccgu ggcgucgggg aucgccugcc cauuccgaug      120
ggcuucuccc cauuuauu                                                   138

<210> SEQ ID NO 51
<211> LENGTH: 138
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 51
ccaugauaua gacguugugg cuguuguagu gucauaguuc cauuaaagcc aaagggcuuu       60
gauguuucua ugauaagggu uucggcccgu ggcgucgggg aucgccugcc cauuccgaug      120
ggcuucuccc cauuuauu                                                   138

<210> SEQ ID NO 52
<211> LENGTH: 6
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(4)
<223> OTHER INFORMATION: a, c, t, g, unknown or other

<400> SEQUENCE: 52 nnnncc                                                                 6

<210> SEQ ID NO 53
<211> LENGTH: 6
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (2)..(2)
<223> OTHER INFORMATION: a, c, u, g, unknown or other
<220> FEATURE:
<221> NAME/KEY: modified_base
<222> LOCATION: (4)..(5)
<223> OTHER INFORMATION: a, c, u, g, unknown or other

<400> SEQUENCE: 53 unanng                                                                 6
```

-continued

<210> SEQ ID NO 54
<211> LENGTH: 1108
<212> TYPE: PRT
<213> ORGANISM: Brevibacillus sp.

<400> SEQUENCE: 54

Met Ala Ile Arg Ser Ile Lys Leu Lys Leu Lys Thr Arg Thr Gly Pro
1               5                   10                  15

Glu Ala Gln Asn Leu Arg Lys Gly Ile Trp Arg Thr His Arg Leu Leu
            20                  25                  30

Asn Glu Gly Val Ala Tyr Tyr Met Lys Met Leu Leu Leu Phe Arg Gln
        35                  40                  45

Glu Ser Thr Gly Gly Gln Thr Lys Lys Glu Leu Gln Glu Glu Leu Val
    50                  55                  60

Arg His Ile Arg Glu Gln Gln Gln Lys Asn Arg Ala Asp Lys Asn Thr
65                  70                  75                  80

Gln Ala Leu Pro Leu Asp Lys Ala Phe Ala Ala Leu Arg Gln Leu Tyr
                85                  90                  95

Glu Leu Leu Val Pro Ser Ser Ile Gly Gln Ser Gly Asp Ala Gln Ile
            100                 105                 110

Ile Ser Arg Lys Phe Leu Ser Pro Leu Val Asp Pro Asn Ser Glu Gly
        115                 120                 125

Gly Lys Gly Thr Ser Lys Ala Gly Ala Lys Pro Thr Trp Gln Lys Lys
    130                 135                 140

Lys Glu Ala Asn Asp Pro Thr Trp Glu Gln Asp Tyr Glu Lys Trp Lys
145                 150                 155                 160

Lys Arg Arg Glu Glu Asp Pro Thr Ala Ser Val Ile Thr Thr Leu Glu
                165                 170                 175

Glu Tyr Gly Ile Arg Pro Ile Phe Pro Leu Tyr Thr Asn Thr Val Ala
            180                 185                 190

Asp Ile Ala Trp Leu Pro Leu Gln Ser Asn Gln Phe Val Arg Thr Trp
        195                 200                 205

Asp Arg Asp Met Leu Gln Gln Ala Ile Glu Arg Leu Leu Ser Trp Glu
    210                 215                 220

Ser Trp Asn Lys Arg Val Gln Glu Glu Tyr Ser Lys Leu Gln Glu Lys
225                 230                 235                 240

Met Thr Gln Leu Asn Glu Gln Leu Glu Gly Gly Gln Glu Trp Ile Ser
                245                 250                 255

Leu Leu Glu Gln Tyr Glu Glu Gln Arg Glu Gln Glu Leu Ile Glu Asn
            260                 265                 270

Met Thr Ala Ala Asn Asp Lys Tyr Arg Ile Thr Lys Arg Gln Met Lys
        275                 280                 285

Gly Trp Asn Glu Leu Tyr Glu Gln Trp Ser Thr Val Leu Pro Asn Ala
    290                 295                 300

Ser His Glu Gln Tyr Arg Glu Ala Leu Lys Arg Val Gln Gln Arg Leu
305                 310                 315                 320

Arg Gly Arg Phe Gly Asp Ala His Phe Phe Gln Tyr Leu Met Lys Glu
                325                 330                 335

Glu His His Leu Ile Trp Lys Gly Asn Pro Gln Arg Ile His Tyr Phe
            340                 345                 350

Val Ala Arg Asn Glu Leu Lys Lys Arg Leu Glu Glu Ala Lys Gln Asn
        355                 360                 365

Ala Thr Met Thr Leu Pro Asp Ala Arg Lys His Pro Leu Trp Val Arg
    370                 375                 380

-continued

```
Phe Asp Ala Arg Gly Gly Asn Leu Gln Asp Tyr Tyr Leu Thr Ala Glu
385                 390                 395                 400

Ala Asp Asn Pro Arg Ser Arg Arg Phe Val Thr Phe Ser Gln Leu Ile
                405             410             415

Trp Pro Asn Glu Ser Gly Trp Met Glu Lys Gln Asp Val Glu Val Glu
            420             425             430

Leu Ala Leu Ser Lys Gln Phe Tyr Gln Gln Val Thr Leu Gln Lys Asn
        435             440             445

Asp Lys Gly Lys Gln Glu Ile Glu Phe Lys Asp Lys Gly Ser Gly Ser
    450             455             460

Thr Phe Ser Gly His Leu Gly Gly Ala Lys Leu Gln Leu Glu Arg Gly
465             470             475             480

Asp Leu Glu Lys Glu Glu Lys Asp Phe Glu Gly Gly Glu Ile Gly Ser
            485             490             495

Val Tyr Leu Asn Ile Val Ile Asp Phe Glu Pro Leu Gln Glu Val Lys
            500             505             510

Asn Gly Arg Leu Gln Ser Pro Tyr Gly Gln Val Leu Gln Leu Val Arg
        515             520             525

Arg Pro Asn Glu Phe Pro Lys Val Thr Thr Tyr Lys Ser Glu Glu Leu
    530             535             540

Val Glu Trp Met Lys Ala Ser Gln Asn His Ser Ser Gly Val Glu Ser
545             550             555             560

Leu Glu Ser Gly Phe Arg Val Met Ser Ile Asp Leu Gly Leu Arg Thr
            565             570             575

Ala Ala Ala Thr Ser Ile Phe Ser Val Glu Glu Ser Asn Asp Ala Asn
        580             585             590

Ala Ala Gly Phe Ser Tyr Trp Ile Glu Gly Thr Pro Leu Val Ala Val
        595             600             605

His Lys Arg Ser Tyr Met Leu Lys Leu Pro Gly Glu Gln Val Glu Lys
    610             615             620

Gln Val Arg Glu Lys Arg Asp Glu Arg Gln Asp Gln Gln Arg Arg Val
625             630             635             640

Arg Phe Gln Ile Arg Ile Leu Ser Gln Val Ile Arg Met Ala Lys Lys
            645             650             655

Gln Asn Arg Glu Arg Ala Asp Glu Leu Asp His Leu Ser Gln Ala Leu
        660             665             670

Glu Lys Gln Lys Ser Leu Leu Asp Gln Thr Asp Arg Thr Phe Trp Asn
    675             680             685

Gly Ile Val Cys Asp Leu Thr Asp Ala Leu Arg Glu Lys Glu Gly Gly
    690             695             700

Trp Glu Gln Ala Val Val Gln Ile His Arg Lys Ala Glu Glu His Val
705             710             715             720

Gly Lys Val Val Gln Ala Trp Arg Lys Arg Phe Asp Ala Asp Glu Arg
            725             730             735

Lys Gly Ile Ala Gly Leu Ser Met Trp Ser Ile Glu Glu Leu Asp Ser
        740             745             750

Leu Arg Lys Leu Leu Ile Ser Trp Ser Arg Arg Thr Arg Asn Pro Gln
        755             760             765

Glu Ile Asn Arg Phe Glu Gln Gly His Thr Ser His Gln Arg Leu Leu
    770             775             780

Thr His Ile Gln Asn Val Lys Glu Asp Arg Leu Lys Gln Leu Ser His
785             790             795             800
```

-continued

```
Ala Ile Val Met Thr Ala Leu Gly Tyr Val Tyr Asp Glu Lys Lys Leu
            805                 810                 815

Glu Trp Phe Ala Lys Tyr Pro Ala Cys Gln Val Ile Leu Phe Glu Asn
            820                 825                 830

Leu Ser Gln Tyr Arg Ser His Met Asp Arg Ser Thr Lys Glu Asn Ser
            835                 840                 845

Thr Leu Met Lys Trp Ala His Arg Ser Ile Pro Lys Tyr Val His Met
    850                 855                 860

Gln Ala Glu Pro Tyr Gly Ile Gln Ile Gly Asp Val Arg Ala Glu Tyr
865                 870                 875                 880

Ser Ser Arg Phe His Ala Lys Thr Gly Thr Pro Gly Ile Arg Cys Lys
            885                 890                 895

Met Val Lys Gly Gln Glu Leu Gln Gly Lys Arg Phe Glu Asn Leu Gln
            900                 905                 910

Lys Arg Leu Val Ser Glu Gln Phe Leu Thr Glu Glu Gln Val Lys Gln
            915                 920                 925

Leu Arg Pro Gly Asp Ile Val Pro Asp Asp Ser Gly Glu Trp Phe Met
    930                 935                 940

Thr Leu Ser Asp Gly Ser Glu Gly Lys Glu Val Val Phe Leu Gln Ala
945                 950                 955                 960

Asp Ile Asn Ala Ala Gln Asn Leu Gln Lys Arg Phe Trp Gln Arg Tyr
            965                 970                 975

Asn Glu Leu Phe Lys Val Ser Cys Arg Val Leu Ile Arg Gly Glu Glu
            980                 985                 990

Glu Tyr Leu Ile Pro Lys Ala Lys  Ser Val Gln Ala Lys  Leu Gly Lys
            995                 1000                1005

Gly Leu Phe Val Lys Lys Thr  Asp Thr Val Met Lys  Asp Val Tyr
    1010                1015                1020

Val Trp Asp Ser Gln Ala Lys  Leu Lys Gly Lys Thr  Thr Phe Thr
    1025                1030                1035

Glu Glu Ser Glu Ser Pro Glu  Gln Leu Glu Asp Phe  Gln Glu Ile
    1040                1045                1050

Ile Glu Glu Ala Glu Glu Ala  Lys Gly Thr Tyr Arg  Thr Leu Phe
    1055                1060                1065

Arg Asp Pro Ser Gly Val Phe  Phe Pro Glu Phe Val  Trp Asn Thr
    1070                1075                1080

Gln Lys Asp Phe Trp Ser Glu  Val Lys Arg Arg Leu  Tyr Gly Lys
    1085                1090                1095

Leu Arg Glu Arg Phe Leu Met  Lys Thr Arg
    1100                1105
```

<210> SEQ ID NO 55
<211> LENGTH: 22
<212> TYPE: RNA
<213> ORGANISM: Brevibacillus sp.

<400> SEQUENCE: 55
uggaaagcuu cgagguuagc ac                                                    22

<210> SEQ ID NO 56
<211> LENGTH: 105
<212> TYPE: RNA
<213> ORGANISM: Brevibacillus sp.

<400> SEQUENCE: 56
cgacgguuag aggccguaug ucgauuugcu uuaauuucgu gcgugugcau ugucguccuc          60

```
cauuacaggg cggcuaccac gaauagucac gaaguuccac ugagu               105

<210> SEQ ID NO 57
<211> LENGTH: 160
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: modified_base
<222> LOCATION: (132)..(160)
<223> OTHER INFORMATION: a, c, u, g, unknown or other

<400> SEQUENCE: 57
cgacgguuag aggccguaug ucgauuugcu uuaauuucgu gcgugugcau ugucguccuc      60
cauuacaggg cggcuaccac gaauagucac gaaguuccac ugaguaaagu ggaaagcuuc     120
gagguuagca cnnnnnnnnn nnnnnnnnnn nnnnnnnnnn                          160

<210> SEQ ID NO 58
<211> LENGTH: 161
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 58
cgacgguuag aggccguaug ucgauuugcu uuaauuucgu gcgugugcau ugucguccuc      60
cauuacaggg cggcuaccac gaauagucac gaaguuccac ugaguaaagu ggaaagcuuc     120
gagguuagca cguacgagau auaggaagcu gcguccgcu c                         161

<210> SEQ ID NO 59
<211> LENGTH: 161
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 59
cgacgguuag aggccguaug ucgauuugcu uuaauuucgu gcgugugcau ugucguccuc      60
cauuacaggg cggcuaccac gaauagucac gaaguuccac ugaguaaagu ggaaagcuuc     120
gagguuagca cacuacaaca gccacaacgu cuauaucaug g                        161

<210> SEQ ID NO 60
<211> LENGTH: 4
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (4)..(4)
<223> OTHER INFORMATION: a, c, t, g, unknown or other

<400> SEQUENCE: 60 dttn                                                                4
```

<210> SEQ ID NO 61
<211> LENGTH: 1150
<212> TYPE: PRT
<213> ORGANISM: Enterococcus sp.

<400> SEQUENCE: 61

Met Tyr Ser Ile Gly Leu Asp Leu Gly Ile Ser Ser Val Gly Trp Ser
1               5                   10                  15

Val Ile Asp Glu Arg Thr Gly Asn Val Ile Asp Leu Gly Ile Arg Leu
                20                  25                  30

Phe Ser Ala Lys Asn Ser Glu Lys Asn Leu Glu Arg Arg Thr Asn Arg
            35                  40                  45

Gly Gly Arg Arg Leu Ile Arg Arg Lys Thr Asn Arg Leu Lys Asp Ala
        50                  55                  60

Lys Lys Ile Leu Ala Ala Val Gly Phe Tyr Glu Asp Lys Ser Leu Lys
65                  70                  75                  80

Asn Ser Cys Pro Tyr Gln Leu Arg Val Lys Gly Leu Thr Glu Pro Leu
                85                  90                  95

Ser Lys Gly Glu Ile Tyr Lys Val Thr Leu His Ile Leu Lys Lys Arg
            100                 105                 110

Gly Ile Ser Tyr Leu Asp Glu Asp Thr Glu Ala Ala Lys Glu Ser
            115                 120                 125

Gln Asp Tyr Lys Glu Gln Val Arg Glu Asn Ala Gln Leu Leu Thr Lys
        130                 135                 140

Tyr Thr Pro Gly Gln Ile Gln Leu Gln Arg Leu Lys Glu Asn Asn Arg
145                 150                 155                 160

Val Lys Thr Gly Ile Asn Ala Gln Gly Asn Tyr Gln Leu Asn Val Phe
                165                 170                 175

Lys Val Ser Ala Tyr Ala Asn Glu Leu Ala Thr Ile Leu Lys Thr Gln
            180                 185                 190

Gln Ala Phe Tyr Pro Asn Glu Leu Thr Asp Asp Trp Ile Ala Leu Phe
            195                 200                 205

Val Gln Pro Gly Ile Ala Glu Glu Ala Gly Leu Ile Tyr Arg Lys Arg
        210                 215                 220

Pro Tyr Tyr His Gly Pro Gly Asn Glu Ala Asn Asn Ser Pro Tyr Gly
225                 230                 235                 240

Arg Trp Ser Asp Phe Lys Lys Thr Gly Gln Pro Ala Thr Asn Ile Phe
                245                 250                 255

Asp Lys Leu Ile Gly Lys Asp Phe Gln Gly Glu Leu Arg Ala Ser Gly
            260                 265                 270

Leu Ser Leu Ser Ala Gln Gln Tyr Asn Leu Leu Asn Asp Leu Thr Asn
        275                 280                 285

Leu Lys Ile Asp Gly Glu Ile Pro Leu Ser Pro Glu Gln Lys Glu Tyr
        290                 295                 300

Ile Leu Ala Glu Leu Met Thr Lys Glu Phe Thr Arg Phe Gly Val Asn
305                 310                 315                 320

Asp Val Val Lys Leu Leu Gly Val Lys Lys Glu Arg Leu Ser Gly Trp
                325                 330                 335

Arg Leu Asp Lys Lys Gly Lys Pro Glu Ile His Thr Leu Lys Gly Tyr
            340                 345                 350

Arg Asn Trp Arg Lys Ile Phe Ala Glu Ser Gly Ile Asp Leu Ala Thr
            355                 360                 365

Leu Pro Thr Glu Thr Ile Asp Cys Leu Ala Lys Val Leu Thr Leu Asn
        370                 375                 380

-continued

```
Thr Glu Arg Glu Gly Ile Glu Asn Thr Leu Ala Phe Glu Leu Ser Glu
385                 390                 395                 400

Leu Ala Glu Ser Val Lys Leu Leu Val Leu Asp Arg Tyr Lys Glu Leu
                405                 410                 415

Ser Gln Ser Val Ser Thr Gln Ala Trp His Arg Phe Ser Leu Lys Thr
                420                 425                 430

Leu His Leu Leu Ile Pro Glu Leu Met Asn Ala Thr Ser Glu Gln Asn
            435                 440                 445

Thr Leu Leu Glu Gln Phe Gln Leu Lys Ser Asp Val Arg Lys Arg Tyr
        450                 455                 460

Ser Glu Tyr Lys Lys Leu Pro Thr Lys Asp Val Leu Thr Glu Ile Tyr
465                 470                 475                 480

Asn Pro Thr Val Asn Lys Thr Val Ser Gln Ala Phe Lys Val Ile Asp
                485                 490                 495

Ala Leu Leu Val Lys Tyr Gly Lys Glu Gln Ile Arg Tyr Ile Thr Ile
                500                 505                 510

Glu Met Pro Arg Asp Asp Asn Glu Glu Asp Glu Lys Lys Arg Ile Lys
            515                 520                 525

Glu Leu His Ala Lys Asn Ser Gln Arg Lys Asn Asp Ser Gln Ser Tyr
        530                 535                 540

Phe Met Gln Lys Ser Gly Trp Ser Gln Glu Lys Phe Gln Thr Thr Ile
545                 550                 555                 560

Gln Lys Asn Arg Arg Phe Leu Ala Lys Leu Leu Tyr Tyr Tyr Glu Gln
                565                 570                 575

Asp Gly Ile Cys Ala Tyr Thr Gly Leu Ser Ile Ser Pro Glu Leu Leu
                580                 585                 590

Val Ser Asp Ser Thr Glu Ile Asp His Ile Ile Pro Ile Ser Ile Ser
            595                 600                 605

Leu Asp Asp Ser Ile Asn Asn Lys Val Leu Val Leu Ser Lys Ala Asn
        610                 615                 620

Gln Val Lys Gly Gln Gln Thr Pro Tyr Asp Ala Trp Met Asp Gly Ser
625                 630                 635                 640

Phe Lys Lys Ile Asn Gly Lys Phe Ser Asn Trp Asp Asp Tyr Gln Lys
                645                 650                 655

Trp Val Glu Ser Cys His Phe Ser His Lys Lys Glu Asn Asn Leu Leu
                660                 665                 670

Glu Thr Arg Asn Ile Phe Asp Ser Glu Gln Val Glu Lys Phe Leu Ala
            675                 680                 685

Arg Asn Leu Asn Asp Thr Arg Tyr Ala Ser Arg Leu Val Leu Asn Thr
        690                 695                 700

Leu Gln Ser Phe Phe Ala Asn Gln Glu Thr Lys Val Arg Val Val Asn
705                 710                 715                 720

Gly Ser Phe Thr His Thr Leu Arg Lys Lys Trp Gly Ala Asp Leu Asp
                725                 730                 735

Lys Thr Arg Glu Thr His His His His Ala Val Asp Ala Thr Leu Cys
            740                 745                 750

Ala Val Thr Pro Phe Val Lys Val Ser Arg Tyr His Tyr Ala Val Lys
            755                 760                 765

Glu Glu Thr Gly Glu Lys Val Met Arg Glu Ile Asp Phe Glu Thr Gly
        770                 775                 780

Glu Ile Val Asp Glu Met Ser Tyr Arg Glu Phe Lys Lys Ser Lys Lys
785                 790                 795                 800
```

```
Tyr Glu Arg Lys Thr Tyr Gln Val Lys Trp Pro Asn Phe Arg Glu Gln
            805             810             815

Leu Lys Pro Val Asn Leu His Pro Arg Ile Lys Phe Ser His Gln Val
            820             825             830

Asp Arg Lys Ala Asn Arg Lys Leu Ser Asp Ala Thr Ile Tyr Ser Val
            835             840             845

Arg Glu Lys Thr Glu Val Lys Thr Leu Lys Ser Gly Lys Gln Lys Ile
    850             855             860

Thr Thr Asp Glu Tyr Thr Ile Gly Lys Ile Lys Asp Ile Tyr Thr Val
865             870             875             880

Asp Gly Trp Glu Ala Phe Lys Lys Lys Gln Asp Lys Leu Leu Met Lys
            885             890             895

Asp Leu Asp Glu Lys Thr Tyr Glu Arg Leu Leu Ser Ile Ala Glu Thr
            900             905             910

Thr Pro Asp Phe Gln Glu Val Glu Glu Lys Asn Gly Lys Val Lys Arg
            915             920             925

Val Lys Arg Ser Pro Phe Ala Val Tyr Cys Glu Glu Asn Asp Ile Pro
    930             935             940

Ala Ile Arg Lys Tyr Ala Lys Lys Asn Asn Gly Pro Leu Ile Arg Ser
945             950             955             960

Leu Lys Tyr Tyr Asp Gly Lys Leu Asn Lys His Ile Asn Ile Thr Lys
            965             970             975

Asp Ser Gln Gly Arg Pro Val Glu Lys Thr Lys Asn Gly Arg Lys Val
            980             985             990

Thr Leu Gln Ser Leu Lys Pro Tyr  Arg Tyr Asp Ile Tyr  Gln Asp Leu
            995             1000             1005

Glu Thr  Lys Ala Tyr Tyr Thr  Val Gln Leu Tyr Tyr  Ser Asp Leu
    1010             1015             1020

Arg Phe  Val Glu Gly Lys Tyr  Gly Ile Thr Glu Lys  Glu Tyr Met
    1025             1030             1035

Lys Lys  Val Ala Glu Gln Thr  Lys Gly Gln Val Val  Arg Phe Cys
    1040             1045             1050

Phe Ser  Leu Gln Lys Asn Asp  Gly Leu Glu Ile Glu  Trp Lys Asp
    1055             1060             1065

Ser Gln  Cys Tyr Asp Val Arg  Phe Tyr Asn Phe Gln  Ser Ala Asn
    1070             1075             1080

Ser Ile  Asn Phe Lys Gly Leu  Glu Gln Glu Met Met  Pro Ala Glu
    1085             1090             1095

Asn Gln  Phe Lys Gln Lys Pro  Tyr Asn Asn Gly Ala  Ile Asn Leu
    1100             1105             1110

Asn Ile  Ala Lys Tyr Gly Lys  Glu Gly Lys Lys Leu  Arg Lys Phe
    1115             1120             1125

Asn Thr  Asp Ile Leu Gly Lys  Lys His Tyr Leu Tyr  Tyr Glu Lys
    1130             1135             1140

Glu Pro  Lys Asn Ile Ile Lys
    1145             1150
```

<210> SEQ ID NO 62
<211> LENGTH: 19
<212> TYPE: RNA
<213> ORGANISM: Enterococcus sp.

<400> SEQUENCE: 62
guuuuuguac ucucaauaa                                                        19

```
<210> SEQ ID NO 63
<211> LENGTH: 73
<212> TYPE: RNA
<213> ORGANISM: Enterococcus sp.

<400> SEQUENCE: 63
uuauugagaa ucuacaaaaa uaaggcauuu ugccgaauuu accgcccuac auauguaggg      60
cgguuuuuuu auu                                                        73

<210> SEQ ID NO 64
<211> LENGTH: 125
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: modified_base
<222> LOCATION: (1)..(29)
<223> OTHER INFORMATION: a, c, u, g, unknown or other

<400> SEQUENCE: 64
nnnnnnnnnn nnnnnnnnnn nnnnnnnnng uuuuuguacu cucaauaaaa aguuauugag      60
aaucuacaaa aauaaggcau uuugccgaau uuaccgcccu acauauguag ggcgguuuuu     120
uuauu                                                               125

<210> SEQ ID NO 65
<211> LENGTH: 126
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 65
gagcggacag cagcuuccua uaucucguac guuuuuguac ucucaauaaa aaguuauuga      60
gaaucuacaa aaauaaggca uuuugccgaa uuuaccgccc uacauaugua gggcgguuuu     120
uuuauu                                                              126

<210> SEQ ID NO 66
<211> LENGTH: 126
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 66
ccaugauaua gacguugugg cuguuguagu guuuuuguac ucucaauaaa aaguuauuga      60
gaaucuacaa aaauaaggca uuuugccgaa uuuaccgccc uacauaugua gggcgguuuu     120
uuuauu                                                              126

<210> SEQ ID NO 67
<211> LENGTH: 5
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

<220> FEATURE:
<221> NAME/KEY: modified_base
<222> LOCATION: (1)..(4)
<223> OTHER INFORMATION: a, c, t, g, unknown or other

<400> SEQUENCE: 67 nnnna                                                                                        5

<210> SEQ ID NO 68
<211> LENGTH: 6
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (2)..(2)
<223> OTHER INFORMATION: a, c, u, g, unknown or other
<220> FEATURE:
<221> NAME/KEY: modified_base
<222> LOCATION: (4)..(5)
<223> OTHER INFORMATION: a, c, u, g, unknown or other

<400> SEQUENCE: 68 unannc                                                                                       6

<210> SEQ ID NO 69
<211> LENGTH: 1408
<212> TYPE: PRT
<213> ORGANISM: Sphingobacterium sp.

<400> SEQUENCE: 69

Met Lys Arg Ile Leu Gly Leu Asp Leu Gly Thr Ser Ser Ile Gly Trp
1               5                   10                  15

Ala Tyr Val Leu Glu Ala Gln Asp Glu Asn Glu Ile Ser Lys Ile Glu
                20                  25                  30

Lys Leu Gly Val Arg Val Asn Pro Leu Thr Thr Asp Glu Gln Leu Asn
            35                  40                  45

Phe Glu Lys Gly Lys Pro Ile Thr Thr Asn Ala Gly Arg Thr Leu Ala
        50                  55                  60

Arg Ser Ala Arg Arg Asn Leu Gln Arg Phe Lys Leu Arg Arg Asn Asn
65                  70                  75                  80

Leu Ile Glu Val Leu Lys Arg Glu Lys Trp Ile Asp Asp Lys Ser Ile
                85                  90                  95

Leu Ala Glu Asn Gly Asn Lys Ser Thr Phe Glu Thr Tyr Ala Leu Arg
            100                 105                 110

Ala Ala Ala Ala Ser Lys Glu Ile Lys Leu Glu Glu Leu Ala Arg Val
            115                 120                 125

Leu Leu Met Ile Asn Lys Lys Arg Gly Tyr Lys Ser Ser Arg Lys Val
        130                 135                 140

Ile Lys Glu Asp Asp Gly Gln Leu Val Asp Gly Met Glu Val Ala Lys
145                 150                 155                 160

Lys Leu Tyr His Glu Asn Leu Thr Pro Gly Glu Phe Val Cys Arg Leu
                165                 170                 175

Leu Lys Glu Gly Lys Lys Lys Leu Pro Asp Phe Tyr Arg Ser Asp Leu
            180                 185                 190

Gln Arg Glu Leu Asp Leu Ile Trp Asp Phe Gln Phe Lys Tyr Tyr Pro
        195                 200                 205

Glu Leu Leu Thr Arg Asp Phe Lys Glu Glu Leu Lys Gly Lys Gly Leu

```
              210             215               220

Arg Ala Thr Ser Ala Ile Phe Trp Ser Lys Tyr Lys Phe Asn Thr Ala
225                 230                 235                 240

Glu Asn Lys Gly Thr Lys Glu Glu Lys Lys Ile Gln Ala Tyr Gln Trp
                245                 250                 255

Arg Lys Asp Gly Leu Thr Lys Gln Leu Ala Lys Glu Glu Val Ala Tyr
                260                 265                 270

Ile Ile Ala Glu Ile Asn Gly Gln Leu Ala Asn Ser Ser Gly Tyr Leu
                275                 280                 285

Gly Ala Ile Ser Asp Arg Ser Lys Glu Leu Tyr Phe Asn Lys Gln Thr
                290                 295                 300

Val Gly Gln Phe Leu Phe Asn Gln Leu Gln Gln Asn Thr His Ala Arg
305                 310                 315                 320

Leu Lys Asn Gln Val Phe Tyr Arg Gln Asp Tyr Leu Asp Glu Phe Glu
                325                 330                 335

Lys Ile Trp Cys Ile Gln Ser Gln Phe His Gln Ala Leu Thr Glu Gln
                340                 345                 350

Leu Lys Glu Glu Ile Arg Asp Ile Ile Ile Phe Tyr Gln Arg Lys Leu
                355                 360                 365

Lys Ser Gln Lys Gly Leu Ile Ser Phe Cys Glu Phe Glu Gln His Glu
                370                 375                 380

Val Val Val Asn Gly Lys Asn Lys Val Val Gly Leu Arg Val Ala Pro
385                 390                 395                 400

Lys Ser Ser Pro Ile Phe Gln Glu Phe Lys Ile Trp Gln Gln Leu Asn
                405                 410                 415

Asn Val Lys Leu Arg Asn Asn Ile Thr Lys Glu Val Tyr Asn Leu Ala
                420                 425                 430

Glu Glu Gln Lys Lys Leu Leu Phe Glu Thr Leu Asn Leu Lys Gly Lys
                435                 440                 445

Leu Ser Ala Tyr Gln Val Leu Ser Leu Ile Glu Gly Lys Pro Lys Glu
                450                 455                 460

Trp Glu Leu Asn Tyr Thr Glu Leu Glu Gly Asn Ser Thr Asn Ser Ala
465                 470                 475                 480

Leu Tyr Asn Ala Tyr Leu Asn Ile Leu Asp Ile Glu Gly Tyr Asp Val
                485                 490                 495

Arg Ser Glu Leu Lys Ile Lys Leu Asn Lys Asp Glu Ile Thr Leu Ser
                500                 505                 510

Asp Leu Asp Ile Pro Val Ser Glu Ile Lys Asp Met Ile Arg Arg Ile
                515                 520                 525

Phe Gln His Leu Gly Ile Asn Thr Ser Ile Leu Asp Phe Asp Ala Gln
                530                 535                 540

Met Gln Gly Asp Asp Phe Glu Lys Gln Leu Ser Tyr Gln Leu Trp His
545                 550                 555                 560

Leu Leu Tyr Ser Tyr Glu Glu Asp Asp Ser Lys Thr Gly Met Asp Arg
                565                 570                 575

Leu Tyr Asn Gln Leu Asn Leu Lys Phe Gly Phe Ser Leu Asp Gln Ala
                580                 585                 590

Lys Phe Ile Gly Lys Ile Ala Leu Gln Asp Asp Tyr Gly Asn Leu Ser
                595                 600                 605

Thr Lys Ala Ile Arg Gln Ile Tyr Pro Tyr Ile Gln Asp Ala Glu Tyr
                610                 615                 620

Ser Ala Ala Cys Lys Leu Ala Gly Tyr Asn His Ser Lys Ser Ser Leu
625                 630                 635                 640
```

-continued

Thr Lys Glu Gln Leu Thr Asn Arg Val Leu Lys Asp His Leu Asp Ile
                645                 650             655

Leu Pro Lys Asn Ser Leu Arg Asn Pro Val Val Glu Lys Ile Leu Asn
                660             665             670

Gln Met Val Asn Val Val Asn Thr Leu Ile Asp Thr Glu Asn Asp Lys
        675                 680             685

Leu Ile Lys Glu Gly Lys Asn Ala Asp Phe Arg Phe Asp Glu Ile Arg
    690             695             700

Ile Glu Leu Ala Arg Glu Leu Lys Lys Asn Ala Lys Glu Arg Glu Glu
705             710             715             720

Leu Thr Lys Ala Ile Asn Thr Ser Lys Glu Gln His Glu Lys Ile Ile
                725             730             735

Lys Ile Leu Gln Thr Glu Asp Gly Ile Lys Asn Pro Thr Arg Asn Asp
            740             745             750

Ile Ile Arg Phe Lys Leu Tyr Gln Glu Leu Lys Asn Asn Gly Tyr Lys
        755             760             765

Asn Leu Tyr Thr Asn Glu Tyr Ile Gln Arg Lys Asp Leu Phe Thr Asn
770             775             780

Ile Tyr Asp Ile Asp His Ile Val Pro Gln Ser Arg Leu Phe Asp Asp
785             790             795             800

Ser Phe Ser Asn Lys Val Leu Val Pro Arg Asn Ile Asn Ile Glu Lys
            805             810             815

Gly Asn Gln Thr Ala Phe Asp Tyr Val Arg Thr Lys Phe Gly Glu Asp
            820             825             830

Gly Ile Glu Ala Tyr Glu Ala Arg Val Glu Arg Leu Phe Asn Leu Lys
            835             840             845

Glu Glu Gly Val Ser Arg Ser Lys Tyr Lys Lys Leu Leu Met Arg Gly
    850             855             860

Ser Asp Ile Gly Glu Gly Phe Ile Glu Arg Asp Leu Arg Asp Ser Gln
865             870             875             880

Tyr Ile Ala Lys Lys Ala Lys Ala Met Leu Phe Glu Ile Thr Pro Ser
            885             890             895

Val Ile Ser Thr Ser Gly Ser Val Thr Asp Arg Leu Arg Glu Asp Trp
            900             905             910

Gly Leu Val Ser Val Met Lys Glu Leu Asn Leu Pro Lys Phe Lys Ala
            915             920             925

Val Gly Leu Thr Glu Tyr Leu Glu Thr Lys Asp Gly Asn Arg Lys Glu
    930             935             940

Val Ile Lys Asp Trp Ser Lys Arg Asn Asp His Arg His His Ala Met
945             950             955             960

Asp Ala Leu Thr Val Ala Phe Thr Lys His Ser His Ile Gln Tyr Leu
            965             970             975

Asn His Leu Asn Ala Arg Lys Asn Glu Lys Ser Glu Phe Phe Ser Ser
            980             985             990

Ile Lys Ala Ile Glu Ile Lys Glu  Thr Tyr Val Glu Arg  Asp Asp Leu
            995             1000                1005

Gly Asn Arg Lys Arg Leu Phe  Lys Glu Pro Ile Ala  His Phe Arg
    1010            1015            1020

Thr Ile Val Lys Glu His Leu  Glu Arg Val Leu Val  Ser His Lys
    1025            1030            1035

Ala Lys Asn Lys Val Val Thr  Lys Asn Arg Asn Lys  Ile Asp Gly
    1040            1045            1050

```
Lys Lys Glu Ala Gln Glu Val Leu Thr Pro Arg Gly Gln Leu His
    1055                1060                1065

Lys Glu Thr Ile Tyr Gly Lys Ile Leu Gln Tyr Ala Ser Lys Glu
    1070                1075                1080

Glu Lys Ile Ser Ala Lys Phe Asp Ala Ala Thr Ile Ala Met Val
    1085                1090                1095

Ser Asn Pro Arg Tyr Arg Ser Ala Leu Leu Asp Arg Leu Ile Glu
    1100                1105                1110

Tyr Gly Asn Asp Pro Lys Lys Ala Phe Thr Gly Lys Asn Ser Pro
    1115                1120                1125

Ser Lys Ser Pro Ile Tyr Leu Asp Gln Gln Arg Gln Leu Ala Val
    1130                1135                1140

Pro Glu Lys Val Lys Leu Val Trp Leu Glu Ala Asp Tyr Thr Ile
    1145                1150                1155

Arg Lys Glu Ile Gly Pro Asp Leu Lys Ile Glu Lys Val Ile Asp
    1160                1165                1170

Gln Gly Val Lys Arg Ile Leu Lys Gln Arg Leu Ser Val Tyr Asp
    1175                1180                1185

Gly Asp Thr Lys Lys Ala Phe Ser Asp Leu Asp Asn Asn Pro Ile
    1190                1195                1200

Trp Leu Asn Glu Glu Lys Gly Ile Ala Ile Lys Arg Val Thr Ile
    1205                1210                1215

Ser Gly Val Lys Asn Ala Glu Ala Leu His Thr Lys Lys Asp His
    1220                1225                1230

Leu Gly Gln Val Leu Glu Asp Lys Asp Gly Asn Thr Met Pro Val
    1235                1240                1245

Asp Phe Val Ser Thr Gly Asn Asn His His Val Ala Ile Tyr Glu
    1250                1255                1260

Asp Ser Glu Gly Asn Leu Tyr Asp Arg Val Val Ser Phe Tyr Glu
    1265                1270                1275

Ala Val Glu Arg Ile Asn Gln Asn Leu Pro Ile Val Asp Arg His
    1280                1285                1290

Tyr Lys Gln Glu Glu Gly Trp Lys Phe Leu Phe Ser Met Lys Gln
    1295                1300                1305

Asn Glu Leu Phe Val Phe Pro Ser Ile Asn Phe Asp Pro Lys Glu
    1310                1315                1320

Ile Asp Leu Leu Asp Lys Lys Asn Tyr Lys Glu Val Ser Lys His
    1325                1330                1335

Leu Phe Arg Met Gln Lys Phe Ser Lys Val Glu Tyr Gly Asn Ser
    1340                1345                1350

Ala Val Arg Asp Tyr Val Phe Arg His His Leu Glu Thr Ser Ile
    1355                1360                1365

Ile Asp Thr Lys Glu Leu Arg Asp Ile Ala Tyr Lys Val Phe Lys
    1370                1375                1380

Ser Ile Gly Glu Phe Lys Ser Phe Val Lys Ile Arg Thr Asn His
    1385                1390                1395

Leu Gly Glu Ile Val His Leu Gly Glu Tyr
    1400                1405
```

<210> SEQ ID NO 70
<211> LENGTH: 16
<212> TYPE: RNA
<213> ORGANISM: Sphingobacterium sp.

<400> SEQUENCE: 70
guugugaauu gcuuuc                                                          16

<210> SEQ ID NO 71
<211> LENGTH: 72
<212> TYPE: RNA
<213> ORGANISM: Sphingobacterium sp.

<400> SEQUENCE: 71
gaaagcaauu cacaauaagg auuauuuccg uuguguaaac auuuagcgcc ucgucuaucu         60
acggggcauu uu                                                             72

<210> SEQ ID NO 72
<211> LENGTH: 121
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: modified_base
<222> LOCATION: (1)..(29)
<223> OTHER INFORMATION: a, c, u, g, unknown or other

<400> SEQUENCE: 72
nnnnnnnnnn nnnnnnnnnn nnnnnnnnng uugugaauug cuuucaaagg aaagcaauuc         60
acaauaagga uuauuuccgu uguguaaaca uuuagcgccu cgucuaucua cggggcauuu        120
u                                                                        121

<210> SEQ ID NO 73
<211> LENGTH: 122
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 73
gagcggacag cagcuuccua uaucucguac guugugaauu gcuuucaaag gaaagcaauu         60
cacaauaagg auuauuuccg uuguguaaac auuuagcgcc ucgucuaucu acggggcauu        120
uu                                                                       122

<210> SEQ ID NO 74
<211> LENGTH: 122
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 74
ccaugauaua gacguugugg cuguuguagu guugugaauu gcuuucaaag gaaagcaauu         60
cacaauaagg auuauuuccg uuguguaaac auuuagcgcc ucgucuaucu acggggcauu        120
uu                                                                       122

<210> SEQ ID NO 75
<211> LENGTH: 1429
<212> TYPE: PRT
<213> ORGANISM: Chryseobacterium sp.

-continued

<400> SEQUENCE: 75

```
Met Met Ile Lys His Ile Leu Gly Leu Asp Leu Gly Thr Asn Ser Ile
1               5                   10                  15

Gly Trp Ala Leu Ile Lys Gln Asn Phe Glu Asn Lys Tyr Gly Glu Ile
            20                  25                  30

Leu Gly Met Gly Ser Arg Ile Ile Pro Met Ser Gln Asp Ile Leu Gly
        35                  40                  45

Glu Phe Gly Lys Gly Asn Ser Val Ser Gln Thr Ala Ala Arg Thr Asp
    50                  55                  60

Tyr Arg Gly Ile Arg Arg Leu Arg Glu Arg Phe Leu Leu Arg Arg Glu
65                  70                  75                  80

Arg Leu His Arg Ile Leu Asn Val Leu Asn Phe Leu Pro Glu His Tyr
                85                  90                  95

Ala Ser Gln Ile Asp Phe Asp Lys Arg Phe Gly Lys Phe Lys Val Glu
            100                 105                 110

Thr Glu Pro Lys Leu Ala Trp Lys Asn Ser Asp Gly Lys Phe Ser Phe
            115                 120                 125

Leu Phe Gln Thr Ser Phe Asn Glu Met Leu Glu Asp Phe Lys Ala His
        130                 135                 140

Gly Gln Asp Leu Lys Val Pro Tyr Asp Trp Thr Ile Tyr Tyr Leu Arg
145                 150                 155                 160

Lys Lys Ala Leu Ser Gln Lys Ile Glu Lys Glu Glu Leu Ala Trp Ile
                165                 170                 175

Leu Leu Asn Phe Asn Gln Lys Arg Gly Tyr Tyr Gln Leu Arg Gly Glu
            180                 185                 190

Glu Glu Glu Glu Asn Pro Asn Lys Leu Ile Glu Phe Tyr Ser Leu Lys
            195                 200                 205

Ile Ile Asp Val Leu Ala Asp Glu Pro Gln Lys Gly Lys Ser Asp Ile
    210                 215                 220

Trp Tyr Ser Leu Val Leu Glu Asn Gly Trp Ile Tyr Arg Arg Ser Ser
225                 230                 235                 240

Lys Thr Ser Leu Leu Asp Trp Lys Asp Lys Ile Arg Asp Phe Ile Val
                245                 250                 255

Thr Thr Asp Leu Asn Asp Asn Gly Ser Val Lys Thr Asp Lys Glu Gly
            260                 265                 270

Asn Glu Lys Arg Ser Phe Arg Ala Pro Gly Glu Asn Asp Trp Thr Leu
            275                 280                 285

Val Lys Thr Lys Thr Glu Gln Glu Ile Asp Arg Ser Arg Lys Thr Val
    290                 295                 300

Gly Thr Tyr Ile Tyr Glu Thr Leu Leu Gln Asn Pro Lys Gln Lys Ile
305                 310                 315                 320

Lys Gly Lys Leu Val Arg Thr Ile Glu Arg Lys Phe Tyr Lys Glu Glu
                325                 330                 335

Leu Lys Gln Ile Leu Glu Lys Gln Lys Glu Phe His Tyr Glu Leu Gln
            340                 345                 350

Ser Asp Asp Leu Tyr Asp Asp Cys Ile Arg Glu Leu Tyr Arg Asn Asn
            355                 360                 365

Glu Ala His Gln Leu Thr Leu Ser Lys Lys Asp Phe Val His Leu Phe
    370                 375                 380

Met Glu Asp Ile Ile Phe Tyr Gln Arg Pro Leu Lys Ser Gln Lys Ser
385                 390                 395                 400

Ser Ile Ser Asn Cys Thr Leu Glu Phe Arg Lys Tyr Lys Asp Glu Asn
                405                 410                 415
```

-continued

```
Gly Val Glu His Thr Gln Phe Leu Lys Ala Ile Pro Lys Ser Asn Pro
            420             425             430

Tyr Tyr Gln Glu Phe Arg Ile Trp Gln Trp Ile Phe Asn Leu Asn Ile
            435             440             445

Tyr Lys Lys Asp Asn Asp Asp Asn Val Thr Lys Glu Phe Leu Ser Thr
            450             455             460

Thr Glu Asp Phe Glu Asn Leu Phe Glu Phe Leu Asn Asn Arg Lys Glu
465             470             475             480

Ile Asp Gln Lys Ala Leu Leu Lys His Phe Lys Leu Asn Glu Lys Thr
            485             490             495

His Arg Trp Lys Tyr Val Glu Asp Lys Lys Tyr Pro Cys Asn Glu Thr
            500             505             510

Lys Thr Met Ile Ser Glu Arg Leu Lys Lys Val Glu Asn Ile Ser Asp
            515             520             525

Asp Phe Leu Thr Arg Gly Met Glu Gln Lys Ile Trp His Ile Ile Tyr
            530             535             540

Ser Val Asn Asp Lys Thr Glu Tyr Glu Lys Ala Leu Lys Ser Phe Ala
545             550             555             560

Glu Lys Asn Asn Leu Asp Glu Asn Ser Phe Phe Glu Ala Phe Arg Lys
            565             570             575

Phe Pro Pro Phe Lys Ser Glu Tyr Gly Ser Phe Ser Glu Lys Ala Ile
            580             585             590

Lys Lys Leu Leu Pro Leu Met Arg Leu Gly Lys Tyr Trp Ser Tyr Ala
            595             600             605

Asn Ile Asp Leu Tyr Ser Lys Asn Arg Ile Gln Lys Ile Ile Thr Gly
            610             615             620

Glu Phe Asp Glu Asn Ile Lys Asp Arg Val Arg Glu Lys Ala Ile His
625             630             635             640

Leu Thr Ala Glu Asn Asp Phe Gln Gly Leu Gln Leu Trp Leu Ala Gln
            645             650             655

Tyr Ile Val Tyr Gly Arg His Ser Glu Ala Thr Met Ile Gly Lys Trp
            660             665             670

Asn Ser Ala Asp Asp Leu Glu Glu Phe Leu Lys Glu Phe Lys Gln His
            675             680             685

Ser Leu Arg Asn Pro Ile Val Glu Gln Val Ile Thr Glu Thr Leu Arg
            690             695             700

Val Val Lys Asp Ile Trp Leu Lys Tyr Gly Asn Gly Ala Lys Asp Phe
705             710             715             720

Phe Asn Glu Val His Ile Glu Leu Gly Arg Glu Met Lys Gln Thr Lys
            725             730             735

Asp Glu Arg Ala Asn Ala Thr Lys Thr Ile Thr Glu Asn Glu Asn Thr
            740             745             750

Asn Leu Arg Ile Lys Ala Leu Leu Ala Glu Met Met Asn Asp His Ser
            755             760             765

Val Glu Asn Val Arg Pro Tyr Ser Pro Met Gln Gln Glu Ile Leu Lys
            770             775             780

Ile Tyr Glu Asp Gly Ile Leu Lys Ser Asp Ile Glu Ile Asp Asp Asp
785             790             795             800

Ile Leu Lys Ile Ser Lys Thr Ala Gln Pro Ser Ser Ser Asp Leu Lys
            805             810             815

Arg Tyr Lys Leu Trp Leu Glu Gln Lys Tyr Lys Ser Pro Tyr Thr Gly
            820             825             830
```

```
Gln Ile Ile Pro Leu Asn Lys Leu Phe Thr Pro Glu Tyr Glu Ile Glu
        835                 840                 845

His Ile Ile Pro Gln Ser Arg Tyr Phe Asp Asp Ser Leu Ser Asn Lys
        850                 855                 860

Ile Ile Cys Glu Ser Ala Val Asn Lys Leu Lys Asp Asn Tyr Ile Gly
865                 870                 875                 880

Leu Gly Phe Ile Lys Gln Phe Gly Gly Thr Ile Ile Glu Cys Gly Phe
                885                 890                 895

Gly Lys Arg Val Lys Val Phe Lys Ala Glu Glu Tyr Glu Glu Phe Val
                900                 905                 910

Lys Lys His Tyr Ala Asn Asn Arg Gly Lys Arg Asn Lys Leu Leu Leu
        915                 920                 925

Glu Asp Ile Pro Glu Lys Met Ile Glu Arg Gln Met Asn Asp Thr Arg
        930                 935                 940

His Ile Ser Lys Tyr Ile Ser Gly Ile Leu Ser His Ile Val Arg Val
945                 950                 955                 960

Glu Asp Gly Thr Asp Glu Gly Val Asn Ser Lys Asn Val Ile Pro Gly
                965                 970                 975

Asn Gly Lys Ile Thr Thr Gln Leu Arg Gln Asp Trp Gly Leu Asn Asp
                980                 985                 990

Val Trp Asn Glu Leu Val Leu Pro  Arg Phe Glu Arg Met  Asn Gln Leu
                995                 1000                1005

Thr Asn  Ser Thr Asp Phe Thr  Ser Trp Asn Glu Asn  His Gln Lys
        1010                1015                1020

Tyr Leu  Pro Thr Val Pro Val  Glu Phe Ser Lys Gly  Phe Ser Lys
        1025                1030                1035

Lys Arg  Ile Asp His Arg His  His Ala Leu Asp Ala  Leu Val Ile
        1040                1045                1050

Ala Cys  Ala Thr Lys Asp His  Val Asn Leu Leu Asn  Asn Gln Ser
        1055                1060                1065

Ala Lys  Ser Asp Thr Lys Arg  Tyr Asp Leu Lys Lys  Lys Leu Met
        1070                1075                1080

Lys Phe  Glu Lys Thr Val Tyr  Lys Asp Pro Gln Thr  Glu Lys Arg
        1085                1090                1095

Ile Glu  Arg Glu Val Pro Lys  Tyr Phe Leu Lys Pro  Trp Glu Thr
        1100                1105                1110

Phe Thr  Val Asp Ala Lys Asn  Lys Leu Glu Thr Ile  Ile Val Ser
        1115                1120                1125

Phe Lys  Gln Asn Leu Arg Val  Ile Asn Lys Ala Thr  Asn Tyr Tyr
        1130                1135                1140

Glu Lys  Tyr Val Asp Lys Asp  Gly Val Lys Thr Lys  Glu Arg Val
        1145                1150                1155

Glu Gln  Thr Gly Thr Asn Trp  Ala Ile Arg Lys Pro  Met His Lys
        1160                1165                1170

Glu Thr  Val Ser Gly Lys Ile  Asp Leu Pro Trp Val  Lys Val Pro
        1175                1180                1185

Lys Gly  Lys Ile Leu Thr Ala  Thr Arg Lys Ser Leu  Asp Thr Ser
        1190                1195                1200

Phe Asp  Leu Lys Ala Ile Ala  Ser Ile Thr Asp Thr  Gly Ile Gln
        1205                1210                1215

Lys Ile  Leu Lys Asn Tyr Leu  Glu Phe Lys Glu Ser  Pro Glu Leu
        1220                1225                1230

Ala Phe  Ser Pro Glu Gly Ile  Glu Asp Met Asn Lys  Asn Ile Lys
```

-continued

```
     1235              1240              1245

Lys Tyr  Asn Gly Gly Lys Pro  His Gln Pro Ile Ser  Lys Val Arg
    1250              1255              1260

Val Phe  Glu Leu Gly Ser Lys  Phe Gln Val Gly Gln  Thr Gly Asn
    1265              1270              1275

Lys Lys  Asp Lys Tyr Val Glu  Ala Ala Lys Gly Thr  Asn Leu Phe
    1280              1285              1290

Phe Ala  Ile Tyr Glu Asp Arg  Lys Gly Lys Arg Ser  Tyr Glu Thr
    1295              1300              1305

Ile Pro  Leu Asn Glu Val Ile  Glu Arg Gln Lys Gln  Gly Leu Ser
    1310              1315              1320

Val Val  Asp Leu Lys Asn Ile  Asn Asp Phe Phe Leu  Cys Pro Asn
    1325              1330              1335

Asp Leu  Val Tyr Ile Pro Ser  Gly Asp Glu Leu Glu  Asn Gly Gly
    1340              1345              1350

Ser Ile  Glu Ile Lys Asn Ile  Thr Lys Glu Lys Ser  Glu Arg Phe
    1355              1360              1365

Tyr Lys  Val Val Ser Phe Ser  Gly Ser Gln Ile Phe  Phe Val Arg
    1370              1375              1380

His Asp  Ile Ala Val Ser Ile  Val Asn Lys Gly Glu  Phe Ser Thr
    1385              1390              1395

Leu Asn  Lys Met Glu Arg Ala  Ile Asp Gly Ser Met  Val Lys Glu
    1400              1405              1410

Ser Cys  Ile Lys Leu Lys Ile  Asp Arg Leu Gly Asn  Val Leu Lys
    1415              1420              1425

Ala
```

```
<210> SEQ ID NO 76
<211> LENGTH: 19
<212> TYPE: RNA
<213> ORGANISM: Chryseobacterium sp.

<400> SEQUENCE: 76
guugugaauu gcuuucaaa                                                 19

<210> SEQ ID NO 77
<211> LENGTH: 75
<212> TYPE: RNA
<213> ORGANISM: Chryseobacterium sp.

<400> SEQUENCE: 77
uuugaaaagc aauucacaau aaggauuauu ccguugugaa aacauucaag gcggggcaac   60
ucgccuuuuu ucguu                                                     75

<210> SEQ ID NO 78
<211> LENGTH: 127
<212> TYPE: RNA
<213> ORGANISM: Artificial Sequence
<220> FEATURE:
<221> NAME/KEY: source
<223> OTHER INFORMATION: /note="Description of Artificial Sequence:
     Synthetic polynucleotide"
<220> FEATURE:
<221> NAME/KEY: modified_base
<222> LOCATION: (1)..(29)
<223> OTHER INFORMATION: a, c, u, g, unknown or other

<400> SEQUENCE: 78
nnnnnnnnnn nnnnnnnnnn nnnnnnnnng uugugaauug cuuucaaaaa aguuugaaaa   60
```

-continued

```
gcaauucaca auaaggauua uuccguugug aaaacauuca aggcggggca acucgccuuu      120
uuucguu                                                                127

<210> SEQ ID NO 79
<211> LENGTH: 128
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 79
gagcggacag cagcuuccua uaucucguac guugugaauu gcuuucaaaa aaguuugaaa      60
agcaauucac aauaaggauu auuccguugu gaaaacauuc aaggcggggc aacucgccuu      120
uuuucguu                                                               128

<210> SEQ ID NO 80
<211> LENGTH: 128
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 80
ccaugauaua gacguugugg cuguuguagu guugugaauu gcuuucaaaa aaguuugaaa      60
agcaauucac aauaaggauu auuccguugu gaaaacauuc aaggcggggc aacucgccuu      120
uuuucguu                                                               128

<210> SEQ ID NO 81
<211> LENGTH: 6
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(2)
<223> OTHER INFORMATION: a, c, t, g, unknown or other

<400> SEQUENCE: 81 nnraat                                                                 6

<210> SEQ ID NO 82
<211> LENGTH: 1440
<212> TYPE: PRT
<213> ORGANISM: Chryseobacterium sp.

<400> SEQUENCE: 82

Met Lys Asn Ile Leu Gly Leu Asp Leu Gly Thr Asn Ser Ile Gly Trp
1               5                   10                  15

Ala Leu Val Lys Gln Asp Phe Lys Asn Lys Gln Gly Glu Ile Leu Gly
            20                  25                  30

Met Gly Thr Arg Ile Ile Pro Met Ser Gln Asp Ile Leu Gly Asp Phe
        35                  40                  45

Gly Lys Gly Asn Ser Val Ser Gln Thr Ala Glu Arg Thr Lys Tyr Arg
    50                  55                  60
```

Ser Ala Arg Arg Leu Arg Glu Arg Phe Leu Leu Arg Arg Glu Arg Leu
65               70                   75                   80

His Arg Val Leu Asn Ile Leu Asn Phe Leu Pro Glu His Tyr Ala Ser
                85                   90                   95

Gln Ile Asp Phe Glu Lys Arg Phe Gly Lys Phe Lys Val Glu Thr Glu
            100                 105                 110

Pro Lys Leu Ala Trp Lys Asn Ile Glu Gly Gln Phe Ser Phe Leu Phe
        115                 120                 125

Gln Asn Ser Phe Asn Glu Met Leu Glu Asp Phe Lys Ala Asn Ala Gln
        130                 135                 140

Asp Leu Arg Ile Pro Tyr Asp Trp Thr Ile Tyr Tyr Leu Arg Lys Lys
145                 150                 155                 160

Ala Leu Ser Gln Lys Ile Glu Lys Glu Glu Leu Val Trp Ile Leu Leu
                165                 170                 175

Asn Phe Asn Gln Lys Arg Gly Tyr Tyr Gln Leu Arg Gly Glu Glu Glu
            180                 185                 190

Glu Glu Asn Pro Asn Lys Leu Val Glu Leu Tyr Ser Leu Lys Val Val
            195                 200                 205

Asp Val Phe Val Asp Glu Pro Gln Lys Gly Lys Ser Asp Ile Trp Tyr
        210                 215                 220

Ser Leu Val Leu Glu Asn Gly Trp Ile Tyr Arg Arg Ala Ser Lys Ile
225                 230                 235                 240

Ser Leu Phe Asp Trp Lys Asp Lys Ile Arg Asp Phe Ile Val Thr Thr
                245                 250                 255

Asp Leu Asn Asp Asp Gly Ser Val Lys Thr Asp Lys Asp Gly Asn Glu
            260                 265                 270

Lys Arg Ser Phe Arg Ala Pro Gly Glu Asn Asp Trp Thr Leu Val Lys
            275                 280                 285

Lys Lys Thr Glu Gln Glu Ile Glu Gln Ser His Lys Thr Val Gly Met
        290                 295                 300

Tyr Ile Tyr Glu Thr Leu Arg Ala Asn Pro Lys Gln Lys Ile Lys Gly
305                 310                 315                 320

Lys Leu Val Arg Thr Ile Glu Arg Lys Phe Tyr Lys Glu Glu Leu Arg
                325                 330                 335

Gln Ile Leu Glu Lys Gln Lys Glu Phe His Gln Glu Leu Gln Asn Asp
            340                 345                 350

Asp Leu Tyr Asn Asp Cys Ile Arg Glu Leu Tyr Arg Asn Asn Glu Ala
            355                 360                 365

His Gln Leu Thr Leu Ser Lys Lys Asp Phe Val His Leu Phe Ile Glu
        370                 375                 380

Asp Ile Val Phe Tyr Gln Arg Pro Leu Arg Ser Gln Lys Ser Ser Ile
385                 390                 395                 400

Ser Asn Cys Thr Leu Glu Phe Arg Lys Tyr Lys Asp Glu Asn Gly Ala
                405                 410                 415

Glu His Thr Gln Tyr Leu Lys Ala Ile Pro Lys Ser Asn Pro Tyr Tyr
            420                 425                 430

Gln Glu Phe Arg Leu Trp Gln Trp Ile Phe Asn Leu Asn Leu Tyr Lys
            435                 440                 445

Lys Asp Asn Asp Glu Asn Val Ile Lys Glu Phe Leu Thr Thr Thr Gln
        450                 455                 460

Asp Val Glu Asn Leu Phe Glu Phe Leu Asn Asn Arg Lys Glu Ile Asp
465                 470                 475                 480

Gln Lys Ala Leu Leu Lys His Phe Lys Leu Ser Glu Lys Thr His Arg

```
                    485                     490                     495
Trp Asn Phe Val Glu Asp Lys Lys Tyr Pro Cys Asn Glu Thr Lys Thr
            500                     505                     510

Met Ile Ala Thr Arg Leu Glu Lys Val Glu Asn Ile Ser Asp Asp Phe
            515                     520                     525

Leu Thr Arg Glu Ile Glu Gln Lys Ile Trp His Ile Ile Tyr Ser Val
        530                     535                     540

Asn Asp Lys Ile Glu Tyr Glu Lys Ala Leu Lys Ser Phe Ala Leu Lys
545                     550                     555                     560

His Asn Leu Asp Glu Asn Ser Phe Phe Glu Ala Phe Arg Lys Phe Pro
                565                     570                     575

Pro Phe Lys Ser Glu Tyr Gly Ser Phe Ser Glu Lys Ala Ile Lys Lys
            580                     585                     590

Leu Leu Pro Leu Met Arg Leu Gly Lys Tyr Trp Asp Tyr Ala Asn Ile
            595                     600                     605

Asp Gln Phe Ser Lys Gly Arg Ile Gln Lys Ile Ile Asn Gly Glu Tyr
        610                     615                     620

Asp Glu Asn Ile Lys Asp Arg Val Arg Glu Lys Ala Val His Leu Thr
625                     630                     635                     640

Ser Glu Asn Asp Phe Gln Gly Leu Gln Leu Trp Leu Ala Gln Tyr Ile
                645                     650                     655

Val Tyr Gly Arg His Ser Glu Ala Ser Ile Ala Gly Lys Trp Asn Ser
            660                     665                     670

Ala Asp Asp Leu Glu Glu Phe Leu Lys Asp Phe Lys His His Ser Leu
            675                     680                     685

Arg Asn Pro Ile Val Glu Gln Val Ile Thr Glu Thr Leu Arg Val Val
        690                     695                     700

Lys Asp Ile Trp Leu Lys Tyr Gly Lys Gly Ala Lys Asp Phe Phe Asn
705                     710                     715                     720

Glu Ile His Ile Glu Leu Gly Arg Glu Met Lys Leu Pro Ala Asp Asp
                725                     730                     735

Arg Lys Lys Leu Thr Asn Gln Ile Thr Glu Asn Glu Asn Thr Asn Leu
            740                     745                     750

Arg Ile Lys Ala Leu Leu Ala Glu Met Met Asn Asp His Gly Val Glu
            755                     760                     765

Asn Val Arg Pro Phe Ser Pro Gln Gln Gln Glu Ile Leu Lys Ile Tyr
        770                     775                     780

Glu Asp Gly Val Leu Asn Ser Asp Ile Glu Ile Glu Asp Glu Tyr Leu
785                     790                     795                     800

Lys Ile Ser Lys Thr Ala Gln Pro Ser Pro Ser Asp Leu Lys Arg Tyr
                805                     810                     815

Lys Leu Trp Leu Glu Gln Lys Tyr Lys Ser Pro Tyr Thr Gly Gln Ile
            820                     825                     830

Ile Pro Leu Asn Lys Leu Phe Thr Pro Glu Tyr Glu Ile Glu His Ile
            835                     840                     845

Ile Pro Gln Ser Arg Tyr Phe Asp Asp Ser Phe Ser Asn Lys Ile Ile
        850                     855                     860

Cys Glu Ser Ala Val Asn Lys Leu Lys Asp Asn Tyr Ile Gly Leu Gly
865                     870                     875                     880

Phe Ile Lys Gln Phe Gly Gly Thr Ile Ile Glu Leu Gly Phe Gly Lys
                885                     890                     895

Ser Val Lys Val Phe Asp Ile Asp Glu Tyr Glu Asp Phe Val Lys Lys
            900                     905                     910
```

His Tyr Ala Asn Asn Arg Ser Lys Arg Asn Lys Leu Leu Leu Glu Asp
        915                 920                 925

Ile Pro Glu Lys Met Ile Glu Arg Gln Ile Asn Asp Thr Arg Tyr Ile
    930                 935                 940

Ser Lys Tyr Ile Ser Gly Ile Leu Ser Asn Ile Val Arg Leu Glu Asp
945                 950                 955                 960

Gly Ser Asp Glu Gly Ile Asn Ser Lys Asn Ile Val Pro Gly Asn Gly
                965                 970                 975

Lys Ile Thr Thr Gln Leu Lys Lys Asp Trp Gly Leu Asn Asp Val Trp
                980                 985                 990

Asn Asp Leu Ile Leu Pro Arg Phe Lys Arg Met Asn Gln Leu Thr Asn
        995                 1000                1005

Ser Thr Asp Phe Ile Ala Trp Asn Glu Asn Phe Gln Lys Phe Leu
    1010                1015                1020

Pro Thr Val Pro Ile Glu Tyr Ser Lys Gly Phe Ser Lys Lys Arg
    1025                1030                1035

Ile Asp His Arg His His Ala Leu Asp Ala Leu Val Ile Ala Cys
    1040                1045                1050

Ala Thr Lys Asp His Val Asn Leu Leu Asn Asn Gln Ser Ala Lys
    1055                1060                1065

Ser Glu Thr Lys Arg Tyr Asp Leu Lys Lys Lys Leu Met Lys Phe
    1070                1075                1080

Glu Arg Val Val Tyr Leu His Thr Gln Thr Gly Glu Lys Ile Glu
    1085                1090                1095

Arg Glu Val Pro Lys His Phe Leu Lys Pro Trp Glu Asn Phe Thr
    1100                1105                1110

Val Asp Val Lys His Asn Leu Asp Thr Val Ile Val Ser Phe Lys
    1115                1120                1125

Gln Asn Leu Arg Val Ile Asn Lys Ala Thr Asn Tyr Tyr Glu Lys
    1130                1135                1140

Tyr Ala Glu Asn Gly Gly Ala Arg Asn Lys Ala Arg Val Glu Gln
    1145                1150                1155

Lys Gly Ile Asn Trp Ala Ile Arg Lys Pro Met His Lys Asp Thr
    1160                1165                1170

Val Ser Gly Lys Val Asp Leu Pro Trp Val Lys Val Pro Lys Gly
    1175                1180                1185

Lys Ile Leu Thr Ala Thr Arg Lys Ser Leu Asp Thr Ser Phe Asp
    1190                1195                1200

Leu Lys Ser Ile Gly Ser Ile Thr Asp Thr Gly Ile Gln Lys Ile
    1205                1210                1215

Leu Lys Asn Tyr Leu Met Leu Lys Asp Gly Asn Pro Glu Leu Ala
    1220                1225                1230

Phe Ser Pro Glu Gly Ile Glu Asp Leu Asn Lys Ser Ile Glu Lys
    1235                1240                1245

Tyr Asn Asp Gly Lys Pro His Gln Pro Ile Asn Lys Val Arg Val
    1250                1255                1260

Phe Glu Leu Gly Ser Lys Phe Gln Ile Gly Gln Ala Gly Asn Lys
    1265                1270                1275

Lys Asp Lys Tyr Val Glu Ala Ala Lys Gly Thr Asn Leu Phe Phe
    1280                1285                1290

Ala Val Tyr Glu Asp Lys Asn Gly Lys Arg Ser Tyr Glu Thr Ile
    1295                1300                1305

```
Pro Leu  Asn Glu Val Ile Glu  Arg Gln Lys Gln Gly  Leu Pro Val
    1310             1315             1320

Val Asp  Leu Arg Ser Thr Asn  Asp Phe Tyr Leu Cys  Pro Asn Asp
    1325             1330             1335

Leu Val  Tyr Ile Leu Ser Asp  Asp Glu Arg Gly Asn  Met Thr Asn
    1340             1345             1350

Asn Asp  Phe Glu Asn Leu Ser  Asp Glu Gln Val Lys  Arg Ile Tyr
    1355             1360             1365

Lys Phe  Val Ser Cys Thr Gly  Gly Glu Gly His Phe  Ile Pro Tyr
    1370             1375             1380

Ala Asn  Ala Thr Glu Ile Ile  Lys Asn Glu Asn Gly  Thr Asn Ser
    1385             1390             1395

Lys Ser  Glu Arg Met Gln Asn  Phe Tyr Asp Gly Ser  Cys Met Leu
    1400             1405             1410

Asp Lys  Asn Ser Lys Pro Ile  Met Ile Lys Glu Asn  Cys Val Lys
    1415             1420             1425

Leu Lys  Val Asp Arg Leu Gly  Asn Ile Ser Lys Ile
    1430             1435             1440

<210> SEQ ID NO 83
<211> LENGTH: 20
<212> TYPE: RNA
<213> ORGANISM: Chryseobacterium sp.

<400> SEQUENCE: 83
guugugaauu gcuuucaaaa                                              20

<210> SEQ ID NO 84
<211> LENGTH: 79
<212> TYPE: RNA
<213> ORGANISM: Chryseobacterium sp.

<400> SEQUENCE: 84
uuuugaaagc aauucacaau aaggauuauu ccguugugaa aacauuuaga gccucgacua   60
ccuucggggc auuuuuauu                                               79

<210> SEQ ID NO 85
<211> LENGTH: 132
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: modified_base
<222> LOCATION: (1)..(29)
<223> OTHER INFORMATION: a, c, u, g, unknown or other

<400> SEQUENCE: 85
nnnnnnnnnn nnnnnnnnnn nnnnnnnnng uugugaauug cuuucaaaaa aaguuuugaa   60
agcaauucac aauaaggauu auuccguugu gaaaacauuu agagccucga cuaccuucgg  120
ggcauuuuua uu                                                     132

<210> SEQ ID NO 86
<211> LENGTH: 133
<212> TYPE: RNA
<213> ORGANISM: Artificial Sequence
<220> FEATURE:
<221> NAME/KEY: source
<223> OTHER INFORMATION: /note="Description of Artificial Sequence:
```

-continued

Synthetic polynucleotide"

<400> SEQUENCE: 86

```
gagcggacag cagcuuccua uaucucguac guugugaauu gcuuucaaaa aaaguuuuga      60
aagcaauuca caauaaggau uauuccguug ugaaaacauu uagagccucg acuaccuucg     120
gggcauuuuu auu                                                       133
```

<210> SEQ ID NO 87
<211> LENGTH: 133
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 87

```
ccaugauaua gacguugugg cuguuguagu guugugaauu gcuuucaaaa aaaguuuuga      60
aagcaauuca caauaaggau uauuccguug ugaaaacauu uagagccucg acuaccuucg     120
gggcauuuuu auu                                                       133
```

<210> SEQ ID NO 88
<211> LENGTH: 6
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(2)
<223> OTHER INFORMATION: a, c, t, g, unknown or other
<220> FEATURE:
<221> NAME/KEY: modified_base
<222> LOCATION: (5)..(5)
<223> OTHER INFORMATION: a, c, t, g, unknown or other

<400> SEQUENCE: 88 nnrrng                                                                 6
```

<210> SEQ ID NO 89
<211> LENGTH: 1071
<212> TYPE: PRT
<213> ORGANISM: Bacillus sp.

<400> SEQUENCE: 89

```
Met Arg Glu Leu Asp Tyr Arg Ile Gly Leu Asp Ile Gly Thr Asn Ser
1               5                   10                  15

Ile Gly Trp Gly Val Ile Glu Leu Ser Trp Asn Lys Asp Arg Glu Gln
            20                  25                  30

Tyr Glu Lys Thr Arg Ile Val Asp Lys Gly Val Arg Met Phe Asp Lys
        35                  40                  45

Ala Glu Ile Pro Lys Thr Gly Ala Ser Leu Ala Glu Pro Arg Arg Ile
    50                  55                  60

Ala Arg Ser Ser Arg Arg Arg Leu Asn Arg Lys Ser Gln Arg Lys Lys
65                  70                  75                  80

Asp Ile Arg Asn Leu Leu Val Gln His Glu Ile Ile Ser Gln Lys Glu
                85                  90                  95

Leu Thr Ser Leu Tyr Pro Leu Ser Lys Ser Ser Met Asp Ile Trp Asp
            100                 105                 110
```

Ile Arg Leu Asp Gly Leu Asp Arg Leu Leu Asp Arg Phe Glu Trp Ala
        115                 120                 125

Arg Leu Leu Ile His Leu Ala Gln Arg Arg Gly Phe Lys Ser Asn Arg
    130                 135                 140

Lys Ser Glu Leu Lys Asp Val Glu Thr Gly Lys Val Leu Ser Ser Ile
145                 150                 155                 160

Gln Val Asn Glu Lys Arg Leu Ser Leu Tyr Arg Thr Val Gly Glu Met
                165                 170                 175

Trp Met Lys Asn Ala Asp Phe Ser Lys Tyr Gly Lys Arg Arg Asn Ser
            180                 185                 190

Pro Asn Glu Tyr Val Phe Ser Val Ser Arg Ala Asp Leu Glu Lys Glu
        195                 200                 205

Ile Val Thr Leu Phe Glu Ala Gln Arg Lys Phe His Ser Ser Tyr Ala
    210                 215                 220

Ser Val Asp Leu Gln Lys Thr Tyr Ile Gln Ile Trp Ala His Gln Leu
225                 230                 235                 240

Pro Phe Ala Ser Gly Asn Ala Ile Val Asn Lys Val Gly Tyr Cys Ser
                245                 250                 255

Leu Leu Lys Gly Lys Glu Lys Arg Val Pro Lys Ala Thr Tyr Thr Phe
            260                 265                 270

Gln Tyr Phe Asn Thr Leu Asp Gln Ile Asn Arg Thr Arg Leu Gly Pro
        275                 280                 285

Asn Phe Gln Pro Phe Thr Lys Glu Gln Arg Asp Ile Ile Leu Asp Lys
    290                 295                 300

Met Phe Gln Arg Thr Asp Tyr Tyr Lys Lys Lys Thr Ile Pro Glu Val
305                 310                 315                 320

Thr Tyr Tyr Asp Ile Arg Lys Trp Leu Ala Leu Asp Glu Thr Ile Gln
                325                 330                 335

Phe Lys Gly Leu Thr Tyr Asp Pro Asn Glu Glu Leu Lys Lys Ile Glu
            340                 345                 350

Met Lys Pro Phe Ile Asn Leu Lys Pro Phe Tyr Glu Ile Lys Lys Val
        355                 360                 365

Val Thr Asn Tyr Ala Lys Lys Thr Asn Glu Val Phe Ser Ala Leu Asp
    370                 375                 380

Tyr Asp Thr Val Ala Tyr Ala Leu Thr Val Tyr Lys Thr Asp Lys Asp
385                 390                 395                 400

Ile Arg Ser Tyr Leu Lys Arg Ser Asn Asn Leu Ser Lys Arg Cys Tyr
                405                 410                 415

Asp Asp Gln Leu Ile Glu Glu Leu Leu Thr Leu Ser Tyr Thr Lys Phe
            420                 425                 430

Gly His Leu Ser Phe Lys Ala Ile Asn His Val Leu Pro Ile Met Gln
        435                 440                 445

Glu Gly Arg Thr Tyr Gln Glu Ala Ile His Gln Leu Gly Tyr Asp Thr
    450                 455                 460

Thr Asn Leu Lys Lys Glu Asn Arg Ser Met Phe Leu Pro Ile Ile Pro
465                 470                 475                 480

Asp Glu Ile Thr Asn Pro Ile Val Lys Arg Ala Leu Thr Gln Ala Arg
                485                 490                 495

Lys Val Val Asn Ala Ile Ile Arg Arg Tyr Gly Ser Pro Asn Ser Val
            500                 505                 510

His Ile Glu Leu Ala Arg Glu Leu Ser Lys Ser His Asp Glu Arg Lys
        515                 520                 525

Lys Ile Met Thr Ala His Asp Glu Asn Tyr Lys Lys Asn Lys Gly Ala

-continued

```
        530              535              540

Ile Ser Ile Leu Ile Glu Asn Gly Ile Leu Asn Pro Thr Gly Tyr Asp
545              550              555              560

Ile Val Arg Tyr Lys Leu Trp Lys Glu Gln Gly Glu Arg Cys Ala Tyr
                565              570              575

Ser Leu Lys Lys Ile Ser Ala Asn Thr Phe Phe Asn Glu Leu Lys Lys
            580              585              590

Glu Arg Ser Gly Pro Pro Val Leu Glu Val Asp His Ile Leu Pro Tyr
            595              600              605

Ser Gln Ser Phe Ile Asp Ser Tyr His Asn Lys Val Leu Val Tyr Gly
            610              615              620

Asp Glu Asn Gln Lys Lys Gly Asn Arg Ile Pro Tyr Thr Phe Phe Ser
625              630              635              640

Glu Glu Asp Lys Glu Trp Glu Ser Phe Glu Ser Tyr Val Arg Ser Asn
                645              650              655

Ser Phe Phe Ser Lys Lys Lys Arg Gly Tyr Leu Leu Lys Lys Ala Tyr
                660              665              670

Leu Pro Arg Glu Ser Asn Leu Ile Lys Glu Arg His Leu Asn Asp Thr
            675              680              685

Arg Tyr Ala Ser Ser Tyr Leu Lys Asn Phe Ile Glu Lys Asn Leu Lys
            690              695              700

Phe Lys Glu Ala Val Gly Ile Thr Arg Lys Lys Tyr Val Gln Thr Val
705              710              715              720

Asn Gly Val Ile Thr Ala His Leu Arg Lys Arg Trp Gly Leu Glu Lys
                725              730              735

Asp Arg Gln Glu Thr Tyr Leu His His Ala Met Asp Ala Ile Ile Val
                740              745              750

Ala Cys Thr Asp His His Met Val Thr Lys Val Thr Glu Tyr Tyr Gln
            755              760              765

Ile Lys Glu Gly Asn Lys Ser Ile Lys Lys Pro Tyr Phe Pro Leu Pro
            770              775              780

Trp Met Gly Phe Arg Glu Glu Ile Leu Ser His Leu Glu Ser Gln Pro
785              790              795              800

Ile Ala Arg Lys Ile Ser Glu Glu Leu Lys Ile Gly Tyr Gln Ser Ser
                805              810              815

Asp Tyr Ile Leu Val Ser Arg Met Pro Lys Arg Ser Val Thr Gly Ser
            820              825              830

Ala His Asp Gln Thr Val Met Lys Lys Gly Gly Ile Asp Lys Lys Gly
            835              840              845

Lys Thr Ile Ile Ile Lys Arg Val His Leu Lys Asp Ile Lys Phe Asp
            850              855              860

Glu Asn Gly Asp Phe Lys Met Val Gly Lys Glu Gln Asp Leu Ala Thr
865              870              875              880

Tyr Glu Ala Ile Lys Gln Arg Tyr Leu Glu Tyr Arg Lys Glu Ser Lys
                885              890              895

Lys Ala Phe Glu Thr Pro Leu Tyr Lys Pro Ser Lys Lys Gly Lys Gly
            900              905              910

Asn Leu Ile Lys Lys Ile Lys Val Glu Val Gln Thr Lys Ser Phe Val
            915              920              925

Arg Glu Ile Asn Gly Gly Val Ala Gln Asn Gly Asp Leu Val Arg Val
            930              935              940

Asp Leu Phe Glu Lys Asp Asn Arg Tyr Tyr Met Val Pro Ile Tyr Val
945              950              955              960
```

Val Asp Thr Val Arg Ser Glu Leu Pro Asn Lys Ala Val Thr Ser Ser
                965                 970                 975

Lys Gly Tyr Glu Gln Trp Leu Ser Ile Asp Asn Ser Phe Thr Phe Lys
            980                 985                 990

Phe Ser Leu Tyr Pro Tyr Asp Leu  Val Arg Leu Val Lys  Gly Asp Glu
        995                 1000                 1005

Asp Arg  Phe Leu Tyr Phe Ser  Thr Leu Asp Ile Asn  Ser Asp Arg
    1010                 1015                 1020

Leu Asn  Phe Lys Asp Val Asn  Lys Pro Ser Lys Gln  Ala Glu Tyr
    1025                 1030                 1035

Arg Tyr  Ser Leu Lys Thr Ile  Glu Asn Leu Glu Lys  Tyr Glu Ile
    1040                 1045                 1050

Gly Val  Leu Gly Asp Leu Arg  Leu Val Arg Gln Glu  Thr Arg Lys
    1055                 1060                 1065

Ile Phe  Lys
    1070

<210> SEQ ID NO 90
<211> LENGTH: 24
<212> TYPE: RNA
<213> ORGANISM: Bacillus sp.

<400> SEQUENCE: 90
gucauaguuc cauuaaagcc auug                                              24

<210> SEQ ID NO 91
<211> LENGTH: 138
<212> TYPE: RNA
<213> ORGANISM: Bacillus sp.

<400> SEQUENCE: 91
caauggcuuu gauguuucua ugauaagggc uucggcccgu ggcguugggg aucgccugcc      60
cauuuuaaug ggcuucuccc caucuauuua augagaauuu uacaaccuug gcuauucuua     120
aauagcuaag guuuuuuu                                                   138

<210> SEQ ID NO 92
<211> LENGTH: 195
<212> TYPE: RNA
<213> ORGANISM: Artificial Sequence
<220> FEATURE:
<221> NAME/KEY: source
<223> OTHER INFORMATION: /note="Description of Artificial Sequence:
     Synthetic polynucleotide"
<220> FEATURE:
<221> NAME/KEY: modified_base
<222> LOCATION: (1)..(29)
<223> OTHER INFORMATION: a, c, u, g, unknown or other

<400> SEQUENCE: 92
nnnnnnnnnn nnnnnnnnnn nnnnnnnng ucauaguucc auuaaagcca uugaaagcaa      60
uggcuuugau guuucuauga uaagggcuuc ggcccguggc guuggggauc gccugcccau     120
uuuaaugggc uucuccccau cuauuuaaug agaauuuuac aaccuuggcu auucuuaaau     180
agcuaagguu uuuuu                                                      195

<210> SEQ ID NO 93
<211> LENGTH: 196
<212> TYPE: RNA
<213> ORGANISM: Artificial Sequence
<220> FEATURE:

-continued

<221> NAME/KEY: source
<223> OTHER INFORMATION: /note="Description of Artificial Sequence:
      Synthetic polynucleotide"
<400> SEQUENCE: 93
gagcggacag cagcuuccua uaucucguac gucauaguuc cauuaaagcc auugaaagca      60
auggcuuuga uguuucuaug auaagggcuu cggcccgugg cguuggggau cgccugccca     120
uuuuaauggg cuucucccca ucuauuuaau gagaauuuua caaccuuggc uauucuuaaa     180
uagcuaaggu uuuuuu                                                    196

<210> SEQ ID NO 94
<211> LENGTH: 196
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<400> SEQUENCE: 94
ccaugauaua gacguugugg cguuguagu gucauaguuc cauuaaagcc auugaaagca       60
auggcuuuga uguuucuaug auaagggcuu cggcccgugg cguuggggau cgccugccca     120
uuuuaauggg cuucucccca ucuauuuaau gagaauuuua caaccuuggc uauucuuaaa     180
uagcuaaggu uuuuuu                                                    196

<210> SEQ ID NO 95
<211> LENGTH: 1091
<212> TYPE: PRT
<213> ORGANISM: Rhizobium sp.
<400> SEQUENCE: 95

Met Asp Ile Glu Thr Leu Phe Ala Phe Asp Ile Gly Thr Asn Ser Ile
1               5                   10                  15

Gly Phe Cys Val Phe Ala Leu Asp Glu Asn Gly Glu Pro Tyr Arg Ile
                20                  25                  30

Ile Asp Ile Gly Thr Arg Ile Tyr Ala Asp Gly Arg Asp Pro Gln Ser
        35                  40                  45

Lys Ala Ser Leu Ala Val Ala Arg Arg Glu Ala Arg Ala Met Ser Arg
    50                  55                  60

Arg Arg Asp Arg Tyr Val Asn Arg Arg Lys Ala Val Leu Arg Thr Leu
65                  70                  75                  80

Thr Glu Tyr Gly Leu Met Pro Ala Glu Ala Ser Ala Arg Gln Ala Leu
                85                  90                  95

Ile Ala Glu Thr Ser Asp Arg Asn Gly Ala Ala Gly Glu Ala Ser Ala
            100                 105                 110

Asn Pro Tyr Ala Leu Arg Ala Met Ala Leu Asp Glu Lys Leu Pro Leu
        115                 120                 125

Tyr Trp Ile Gly Arg Val Leu Phe His Leu Asn Gln Arg Arg Gly Phe
    130                 135                 140

Lys Ser Asn Arg Lys Thr Asp Arg Lys Asp Asn Glu Lys Gly Val Ile
145                 150                 155                 160

Ala Leu Gly Ile Gly Glu Leu Arg Ala Ala Met His Lys Thr Lys Ala
                165                 170                 175

Arg Thr Tyr Gly Glu Trp Leu Ala Ala Arg Arg Glu Asp Gly His Val
            180                 185                 190

Thr Arg Leu Arg Ala Gly Ser Asp Ala Phe Glu Gly Asp Gly Tyr Ala

-continued

```
              195                 200                 205

Phe Tyr Pro Glu Arg Ser Leu Leu Glu Ala Glu Phe Arg Glu Ile Trp
    210                 215                 220

Ala Arg Gln Ser Ser Phe Tyr Pro Asp Val Leu Thr Glu Ala Arg Gly
225                 230                 235                 240

Asp His Leu Phe Gln Val Met Phe Tyr Gln Arg Pro Leu Lys Lys Pro
                245                 250                 255

Arg Val Gly Lys Cys Ala Phe Asn Pro Leu Glu Glu Arg Leu Ala Lys
                260                 265                 270

Ala His Pro Leu Phe Gln Glu Phe Arg Leu Tyr Lys Glu Val Asn Glu
                275                 280                 285

Leu Glu Leu Val Leu Pro Asp His Ser His Lys Lys Leu Asp Ile Glu
    290                 295                 300

Gln Arg Asn Ala Leu Val Ile Leu Leu Arg Ala Asn Arg Glu Val Thr
305                 310                 315                 320

Phe Lys Lys Leu Arg Thr Ala Leu Lys Leu Ala Pro Asp Ile Val Phe
                325                 330                 335

Asn Lys Glu Ser Glu Ser Arg Glu Lys Leu Arg Gly Asp Glu Val His
                340                 345                 350

Ser Val Leu Ala Asp Lys Lys Arg Phe Gly Pro Gln Trp Gly Ala Leu
                355                 360                 365

Ser Arg Glu Arg Gln Trp Gln Ile Ile Gln Thr Leu Lys Asp Glu Glu
    370                 375                 380

Asn Pro Glu Lys Leu Phe Gly Trp Leu Lys Glu Glu Phe Gly Phe Glu
385                 390                 395                 400

Gly Glu Lys Ala Asp Ala Ile Ala Asn Ala Pro Leu Pro Glu Gly Tyr
                405                 410                 415

Gly Arg Leu Gly Glu Thr Ala Leu Ser Ser Met Leu Asp Glu Met Lys
                420                 425                 430

Ala Ala Val Ile Pro Glu Ala Glu Ala Ala Lys Asn Cys Gly Tyr Asp
                435                 440                 445

His Ser Lys Leu Gly Glu Asp Arg Glu Glu Gly Glu Ala Phe Leu Pro
    450                 455                 460

Pro Tyr Gln Glu Ile Leu Ser Arg Gln Ile Pro Pro Gly Thr Asn Asp
465                 470                 475                 480

Pro Ala Asp Ile Tyr Asp Ile Arg Met Gly Arg Phe Thr Asn Pro Thr
                485                 490                 495

Val His Ile Gly Leu Asn Gln Leu Arg Arg Val Val Asn Ala Leu Ile
                500                 505                 510

Ala Arg His Gly Lys Pro Gln Phe Val Ser Leu Glu Leu Ala Arg Asp
                515                 520                 525

Leu Gln Leu Ser Glu Lys Gln Lys Ala Glu Ala Asn Arg Ala Ile Ala
    530                 535                 540

Lys Asn Thr Arg Glu Ala Ala Ala Arg Ser Lys Lys Leu Gly Glu Met
545                 550                 555                 560

Gly Gln Leu Asp Thr Gly Tyr Asn Arg Leu Leu Leu Lys Leu Trp Glu
                565                 570                 575

Glu Leu Asn Pro Ser Lys Pro Glu Asp Arg Val Cys Ile Tyr Ser Gly
                580                 585                 590

Lys Pro Ile Gly Ile Asp Met Leu Phe Ser Ala Glu Val Asp Val Asp
                595                 600                 605

His Ile Leu Pro Trp Ser Lys Thr Leu Asp Asp Ser Gln Ala Asn Lys
    610                 615                 620
```

```
Leu Leu Cys Leu Lys Ser Ala Asn Arg Gln Lys Arg Asn Arg Ala Pro
625                 630                 635                 640

Ala Asp Val Pro Glu Trp Arg Asp Arg Tyr Glu Glu Ile Leu Ala Arg
                645                 650                 655

Ala Ala Arg Leu Ala Pro Asn Lys Arg Arg Arg Phe Ala Pro Asn Ala
                660                 665                 670

Met Ala Glu Phe Glu Ala Glu Gly Gly Phe Leu Ala Arg Gln Leu Thr
                675                 680                 685

Asp Thr Gln Tyr Leu Ser Arg Met Ala Arg Glu Tyr Leu Ser Cys Leu
                690                 695                 700

Phe Pro Ser Ala Glu Ile Asp Arg Arg Gly Glu Arg Lys Lys Lys Ile
705                 710                 715                 720

Arg Val Ile Val Ser Pro Gly Arg Leu Thr Glu Met Leu Arg Arg Asn
                725                 730                 735

Trp Gly Leu Asn Asn Ile Leu Pro Asp His Asn Leu Gly Glu Met Thr
                740                 745                 750

Gln Ala Lys Asn Arg Lys Asp His Arg His His Ala Ile Asp Ala Ala
                755                 760                 765

Val Val Gly Val Thr Thr Arg Ser Leu Leu Gln Arg Ile Ala Thr Ala
                770                 775                 780

Ala Gly Arg Leu Asp Glu Ala Asp Phe Glu Asn Leu Val Arg Lys Met
785                 790                 795                 800

Val Ser Glu Asn Pro Pro Trp Pro Thr Phe Arg Glu Glu Leu Gln Ala
                805                 810                 815

Ala Val Asn Gly Ile Val Val Ser His Lys Pro Asp His Gly Thr Val
                820                 825                 830

Ser Arg Lys Gly Tyr Ala Glu Gly Lys Gly Arg Thr Ala Gly Arg Leu
                835                 840                 845

His Asn Asp Thr Ala Tyr Gly Phe Gly Thr Asp Ala Ser Gly Asn Pro
                850                 855                 860

Val Ala Val Arg Arg Lys Leu Phe Thr Ser Leu Glu Ala Lys Asp Ile
865                 870                 875                 880

Pro Met Ile Arg Asp Pro Glu Leu Gln Ala Glu Leu Tyr Ala Ala Ile
                885                 890                 895

Asp Gly Leu Asp Asp Arg Arg Ala Leu Gln Asp Ala Leu Leu Ser Phe
                900                 905                 910

Arg Arg Thr His Pro Lys Phe Lys Gly Ile Arg Arg Val Arg Met Ala
                915                 920                 925

Glu Thr Leu Ser Phe Ile Pro Ile Arg Asp Ser Gln Gly Asn Val Tyr
                930                 935                 940

Lys Gly Tyr Lys Gly Asp Ala Asn Tyr Arg Tyr Asp Val Trp Glu Thr
945                 950                 955                 960

Leu Asp Gly Lys Trp His Ala Asp Val Val Thr Met Phe Asn Ala His
                965                 970                 975

Gln Pro Asp Trp Arg Ser Pro Val His Gln Glu His Pro Thr Ala Arg
                980                 985                 990

Arg Val Leu Arg Leu Gln Gln Asn  Asp Met Val Ala Tyr  Glu His Pro
                995                 1000                1005

Asn Asp  Gly Tyr Thr Ile Ala  Arg Val Val Lys Phe  Asn Thr Ala
    1010                1015                1020

Gly Ile  Val Tyr Phe Ala Ser  His Arg Glu Ser Gly  Ser Leu Lys
    1025                1030                1035
```

-continued

```
Ala Arg  Asp Ala Asp Lys Gln  Asp Pro Phe Lys Tyr  Phe Ser Lys
    1040             1045              1050

Ser Ala  Ala Gly Leu Lys Asp  Ile Gln Cys Arg Gln  Ile Arg Ile
    1055             1060              1065

Asp Ala  Ala Gly Arg Val Phe  Asp Pro Gly Pro Gln  Asp Arg Ala
    1070             1075              1080

Ser Lys  Ser Thr Arg Lys Thr  Asn
    1085             1090
```

<210> SEQ ID NO 96
<211> LENGTH: 29
<212> TYPE: RNA
<213> ORGANISM: Rhizobium sp.

<400> SEQUENCE: 96
guugcggcug gaccgcguuu ucugaucug                                             29

<210> SEQ ID NO 97
<211> LENGTH: 78
<212> TYPE: RNA
<213> ORGANISM: Rhizobium sp.

<400> SEQUENCE: 97
cagaucagaa aacgcggucu ggccguuaac aagcuagaag caccaaauaa ggccguuccu          60
ucgggagcgg cuuuuucu                                                        78

<210> SEQ ID NO 98
<211> LENGTH: 140
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: modified_base
<222> LOCATION: (1)..(29)
<223> OTHER INFORMATION: a, c, u, g, unknown or other

<400> SEQUENCE: 98
nnnnnnnnnn nnnnnnnnnn nnnnnnnnng uugcggcugg accgcguuuu cugaucugaa          60
agcagaucag aaaacgcggu cuggccguua acaagcuaga agcaccaaau aaggccguuc          120
cuucgggagc ggcuuuuucu                                                      140

<210> SEQ ID NO 99
<211> LENGTH: 141
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 99
gagcggacag cagcuuccua uaucucguac guugcggcug gaccgcguuu ucugaucuga          60
aagcagauca gaaaacgcgg ucuggccguu aacaagcuag aagcaccaaa uaaggccguu          120
ccuucgggag cggcuuuuuc u                                                    141

<210> SEQ ID NO 100
<211> LENGTH: 141
<212> TYPE: RNA
<213> ORGANISM: Artificial Sequence
<220> FEATURE:
<221> NAME/KEY: source
<223> OTHER INFORMATION: /note="Description of Artificial Sequence:
     Synthetic polynucleotide"

<400> SEQUENCE: 100
ccaugauaua gacguugugg cguuguagu guugcggcug gaccgcguuu ucgaucuga        60 aagcagauca gaaaacgcgg ucuggccguu aacaagcuag aagcaccaaa uaaggccguu       120
ccuucgggag cggcuuuuc u                                                  141

<210> SEQ ID NO 101
<211> LENGTH: 3
<212> TYPE: DNA
<213> ORGANISM: Artificial Sequence
<220> FEATURE:
<221> NAME/KEY: source
<223> OTHER INFORMATION: /note="Description of Artificial Sequence:
     Synthetic oligonucleotide"
<220> FEATURE:
<221> NAME/KEY: modified_base
<222> LOCATION: (1)..(1)
<223> OTHER INFORMATION: a, c, t, g, unknown or other

<400> SEQUENCE: 101 ngg                                                                      3

<210> SEQ ID NO 102
<211> LENGTH: 6
<212> TYPE: RNA
<213> ORGANISM: Artificial Sequence
<220> FEATURE:
<221> NAME/KEY: source
<223> OTHER INFORMATION: /note="Description of Artificial Sequence:
     Synthetic oligonucleotide"
<220> FEATURE:
<221> NAME/KEY: modified_base
<222> LOCATION: (2)..(2)
<223> OTHER INFORMATION: a, c, u, g, unknown or other
<220> FEATURE:
<221> NAME/KEY: modified_base
<222> LOCATION: (4)..(5)
<223> OTHER INFORMATION: a, c, u, g, unknown or other

<400> SEQUENCE: 102 cnannu                                                                   6

<210> SEQ ID NO 103
<211> LENGTH: 1401
<212> TYPE: PRT
<213> ORGANISM: Myroides sp.

<400> SEQUENCE: 103

Met Lys Arg Ile Leu Gly Ile Asp Leu Gly Thr Thr Ser Ile Gly Trp
1               5                   10                  15

Ala Tyr Val His Glu Ala Glu Asn Glu Asn Glu Ile Ser Ser Ile Glu
            20                  25                  30

Lys Leu Gly Val Arg Val Asn Pro Leu Thr Val Asp Glu Gln Ile Asn
        35                  40                  45

Phe Glu Lys Gly Lys Pro Ile Thr Thr Asn Ala Thr Arg Thr Leu Phe
    50                  55                  60

Arg Ser Ala Arg Arg Asn Leu Gln Arg Phe Lys Leu Arg Arg Lys His
65                  70                  75                  80

Leu Ile Glu Ile Leu Lys His Asn Asn Trp Ile Ser Lys Gln Thr Leu
                85                  90                  95

-continued

```
Leu Thr Glu Asn Gly Asn His Thr Thr Phe Glu Thr Ile Ser Leu Arg
            100                 105                 110

Asp Lys Ala Ala Thr Gln Lys Val Thr Leu Glu Glu Leu Ala Arg Val
            115                 120                 125

Leu Leu Met Ile Asn Lys Lys Arg Gly Tyr Lys Ser Ser Arg Lys Val
        130                 135                 140

Asn Asn Thr Glu Glu Gly Gln Leu Ile Asp Gly Met Glu Val Ala Lys
145                 150                 155                 160

Lys Leu Tyr His Glu Gln Leu Thr Pro Gly Gln Leu Ser Leu Gln Leu
                165                 170                 175

Ile Lys Gln Gly Val Lys Arg Leu Pro Asp Tyr Tyr Arg Ser Asp Leu
            180                 185                 190

Asn His Glu Leu Asp Leu Ile Trp Ala Phe Gln Gln Lys Phe Tyr Pro
            195                 200                 205

His Ile Leu Thr Ser Glu Phe Lys Glu Leu Leu Lys Gly Lys Gly Leu
        210                 215                 220

Arg Ala Thr Ser Asn Gln Phe Trp Thr Asn Tyr Asn Phe Asn Thr Ala
225                 230                 235                 240

Asp Asn Lys Gly Thr Arg Glu Glu Lys Lys Leu Gln Asn Tyr Gln Trp
                245                 250                 255

Arg Ser Asp Ala Leu Ile Lys Gln Leu Asp Lys Glu Ile Val Ala Tyr
                260                 265                 270

Val Ile Ser Glu Ile Asn Gly Gln Ile Asn Asn Ser Ser Gly Tyr Leu
            275                 280                 285

Gly Ala Ile Ser Asp Arg Ser Lys Glu Leu Tyr Phe Asn Gln Leu Thr
        290                 295                 300

Val Gly Gln Tyr Leu His Arg Gln Leu Ile Ala Asn Pro His Thr Arg
305                 310                 315                 320

Leu Lys Ser Gln Val Phe Tyr Arg Gln Asp Tyr Leu Asp Glu Phe Glu
                325                 330                 335

Lys Ile Trp Glu Thr Gln Ser Lys Phe Tyr Pro Lys Glu Leu Thr Thr
                340                 345                 350

Val Leu Lys Asn Glu Ile Arg Asp Thr Val Ile Phe Tyr Gln Arg Lys
            355                 360                 365

Leu Lys Ser Gln Lys Gly Leu Ile Ser Phe Cys Glu Phe Glu Gln Glu
        370                 375                 380

Gln Lys Ile Ile Asn Gly Lys Thr Lys Thr Ile Gly His Arg Val Ile
385                 390                 395                 400

Pro Lys Ser Ser Pro Leu Phe Gln Glu Phe Lys Ile Trp Gln Gln Leu
                405                 410                 415

His Asn Val Val Leu Arg Asn Lys Lys Thr Asn Val Ile Thr Pro Leu
            420                 425                 430

Ala Glu Glu Gln Lys Ser His Leu Phe Glu Glu Leu Asn Leu Lys Gly
            435                 440                 445

Lys Leu Ser Ser Thr Gln Ile Leu Lys Leu Ile Glu Asp Lys Pro Lys
        450                 455                 460

Asp Trp Glu Leu Asn Tyr Ser Glu Leu Glu Gly Asn Asn Thr Asn Lys
465                 470                 475                 480

Ala Leu Tyr Asn Ala Tyr Leu Asp Ile Leu Asp Leu Glu Gly Tyr Asp
                485                 490                 495

Ile Arg Asp Glu Leu Lys Ile Lys Leu Asn Lys Asp Asp Ile Glu Leu
            500                 505                 510

Ser Asp Leu Asp Val Asn Ala Ser Glu Ile Lys Glu Met Ile Phe Ser
```

-continued

```
                    515                        520                        525
        Ile Phe Lys His Leu Gly Ile Asn Thr Glu Ile Leu Glu Phe Asp Ala
            530                        535                        540

Thr Leu Lys Asp Lys Ala Phe Glu Lys Gln Ala Ser Tyr Gln Leu Trp
        545                        550                        555                        560

His Leu Leu Tyr Ser Tyr Glu Glu Asp Asn Ser Pro Thr Gly Leu Asp
                            565                        570                        575

Arg Leu His Asn Leu Leu Gln Lys Lys Phe Asn Phe Thr Leu Asp Gln
                            580                        585                        590

Ala Lys Leu Val Gly Asn Val Leu Phe Gln Asp Asp Tyr Gly Asn Leu
                            595                        600                        605

Ser Ser Lys Ala Ile Lys Asn Ile Phe Pro Tyr Ile Thr Asp Asn Asn
                610                        615                        620

Tyr Ser Thr Ala Cys Glu Leu Ala Gly Tyr Lys His Ser Lys His Ser
        625                        630                        635                        640

Leu Thr Lys Glu Glu Asn Glu Lys Arg Glu Leu Lys Ser Arg Leu Thr
                            645                        650                        655

Ile Leu Thr Lys Asn Ser Leu Arg Asn Pro Val Val Glu Lys Ile Leu
                            660                        665                        670

Asn Gln Met Ile Asn Val Ile Asn Thr Leu Ile Glu Ser Glu Asn Asp
                            675                        680                        685

Lys Leu Val Ala Gln Gly Lys Glu Pro Asn Phe Gln Phe Asp Glu Ile
                690                        695                        700

Arg Ile Glu Leu Ala Arg Glu Leu Lys Lys Asn Ala Lys Glu Arg Glu
        705                        710                        715                        720

Glu Leu Thr Lys Ser Met Thr Gln Gly Lys Thr Asn His Glu Lys Ile
                            725                        730                        735

Ile Lys Ile Leu Gln Lys Glu Asp Gly Ile Lys Asn Pro Thr Arg Asn
                            740                        745                        750

Asp Ile Thr Arg Phe Lys Leu Tyr Ser Glu Leu Lys Asn Asn Gly Tyr
                            755                        760                        765

Lys Asp Leu Tyr Thr Asn Glu Tyr Ile Glu Arg Lys Asp Ile Phe Ser
                770                        775                        780

Lys Glu Tyr Asp Ile Glu His Ile Ile Pro Gln Ser Lys Leu Phe Asp
        785                        790                        795                        800

Asp Ser Phe Ser Asn Lys Thr Leu Val Arg Arg Asn Val Asn Leu Lys
                            805                        810                        815

Lys Gly Asn Gln Thr Ala Tyr Asp Phe Ile Leu Ser Glu Tyr Gly Gln
                            820                        825                        830

Glu Lys Ala Asn Glu Phe Glu Thr Arg Ile Thr Asn Leu Tyr Ser Leu
                            835                        840                        845

Gly Lys Asp Glu Gly Ile Ser Lys Ser Lys Tyr Lys Lys Leu Leu Met
                850                        855                        860

Gln Glu Ser Glu Ile Gly Lys Gly Phe Ile Glu Arg Asp Leu Arg Glu
        865                        870                        875                        880

Thr Gln Tyr Ile Ala Lys Lys Ala Lys Ser Leu Leu Leu Glu Ile Thr
                            885                        890                        895

Arg Asn Val Val Ser Thr Ser Gly Gly Ile Thr Asp Arg Leu Arg Glu
                            900                        905                        910

Asp Trp Gly Leu Val Asn Val Met Lys Glu Leu Asn Leu Lys Lys Phe
                            915                        920                        925

Arg Asp Ala Gly Leu Thr Glu Phe Val Glu Met Lys Asp Gly Asn Lys
                930                        935                        940
```

-continued

```
Lys Glu Val Ile Ile Asp Trp Thr Lys Arg Asn Asp His Arg His His
945              950              955              960

Ala Met Asp Ala Leu Thr Ile Ala Phe Thr Lys His Asn His Ile Gln
             965              970              975

Tyr Leu Asn His Leu Asn Ala Arg Lys Asn Thr Lys Asp Glu Leu His
             980              985              990

Thr Asn Ile Ile Ala Ile Glu Lys  Lys Glu Thr Thr Ile  Ile Thr Asp
         995              1000              1005

Glu Arg  Gly Asn Lys Lys Arg  Ile Phe Lys Glu Pro  Ile Pro Asn
    1010              1015              1020

Phe Arg  Asn Ile Ala Lys Ser  His Leu Glu Ala Ile  Leu Val Ser
    1025              1030              1035

His Lys  Ala Lys Asn Lys Val  Val Thr Lys Asn Ile  Asn Lys Ile
    1040              1045              1050

Ser Gly  Lys Lys Ile Gly Gln  Gln Thr Leu Thr Pro  Arg Gly Gln
    1055              1060              1065

Leu His  Lys Glu Thr Val Tyr  Gly Lys Ile Arg Gln  Tyr Val Ser
    1070              1075              1080

Lys Glu  Glu Lys Val Gly Pro  Lys Phe Thr Lys Glu  Val Ile Glu
    1085              1090              1095

Leu Val  Ser Asn Pro Thr Tyr  Arg Asp Leu Leu Leu  Lys Arg Leu
    1100              1105              1110

Gln Glu  Asn Asn Asn Asp Pro  Lys Lys Ala Phe Gly  Gly Lys Asn
    1115              1120              1125

Ala Leu  Ser Lys Ser Pro Ile  Tyr Ile Asn Leu Glu  Lys Asn Ile
    1130              1135              1140

Ile Val  Pro Glu Val Val Lys  Leu Val Trp Leu Glu  Asp Asp Tyr
    1145              1150              1155

Thr Ile  Arg Lys Glu Ile Ser  Pro Glu Leu Lys Ile  Asp Lys Val
    1160              1165              1170

Val Asp  Glu Gly Val Lys Arg  Ile Leu Gln Asn Arg  Leu Ala Leu
    1175              1180              1185

Tyr Asn  Gly Asp Ala Lys Ile  Ala Phe Ser Asp Leu  Asp Asn Asn
    1190              1195              1200

Pro Ile  Trp Leu Ser Lys Asp  Lys Gly Ile Thr Ile  Lys Arg Val
    1205              1210              1215

Thr Leu  Ser Gly Val Lys Asn  Ala Thr Ala Leu His  Thr Lys Lys
    1220              1225              1230

Asp His  Leu Gly Gln Pro Ile  Leu Asp His Lys Gly  Gln Glu Ile
    1235              1240              1245

Pro Val  Asp Phe Ile Ser Thr  Gly Asn Asn His His  Val Ala Ile
    1250              1255              1260

Tyr Glu  Asp Lys Asn Gly Lys  Leu Gln Glu Ser Val  Val Ser His
    1265              1270              1275

Phe Glu  Ala Val Glu Arg Val  Asn Gln Gln Leu Pro  Ile Ile Asp
    1280              1285              1290

Lys Thr  Phe Asn Gln His Leu  Gly Trp Lys Phe Leu  Phe Thr Met
    1295              1300              1305

Lys Gln  Asn Glu Leu Phe Leu  Phe Pro Ser Asp Asp  Phe Asn Pro
    1310              1315              1320

Asn Glu  Ile Asp Leu Phe Asp  Thr Arg Asn Tyr Ala  Val Ile Ser
    1325              1330              1335
```

```
Lys His  Leu Phe Arg Ala Gln  Lys Leu Ser Thr  Lys  Asp Tyr Ser
    1340                    1345                1350

Phe Arg  His His Leu Glu Thr  Asn Val Glu Asp  Ile  Lys Asp Leu
    1355                    1360                1365

Lys Thr  Ile Thr Trp Arg Arg  Glu Gly Leu Asn  Gly  Ile Gln Asn
    1370                    1375                1380

Ile Val  Lys Ile Arg Thr Asn  His Leu Gly Glu  Ile  Val His Ile
    1385                    1390                1395

Gly Glu  Tyr
    1400
```

```
<210> SEQ ID NO 104
<211> LENGTH: 21
<212> TYPE: RNA
<213> ORGANISM: Myroides sp.

<400> SEQUENCE: 104
guugugaauu gcuuucaaac a                                              21
```

```
<210> SEQ ID NO 105
<211> LENGTH: 105
<212> TYPE: RNA
<213> ORGANISM: Myroides sp.

<400> SEQUENCE: 105
ugaaagcaau ucacaauaag gauuauuccg uugugaaaac aucuaguccu cgacuaauuu    60
cggggaauaa agccuuaacu cuguuaaggc uuuuuuuagu uuuuu                   105
```

```
<210> SEQ ID NO 106
<211> LENGTH: 159
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: modified_base
<222> LOCATION: (1)..(29)
<223> OTHER INFORMATION: a, c, u, g, unknown or other

<400> SEQUENCE: 106
nnnnnnnnnn nnnnnnnnnn nnnnnnnnng uugugaauug cuuucaaaca aaagugaaag    60
caauucacaa uaaggauuau uccguuguga aaacaucuag uccucgacua auuucgggga   120
auaaagccuu aacucuguua aggcuuuuuu uaguuuuuu                          159
```

```
<210> SEQ ID NO 107
<211> LENGTH: 160
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 107
gagcggacag cagcuuccua uaucucguac guugugaauu gcuuucaaac aaaagugaaa    60
gcaauucaca auaaggauua uuccguugug aaaacaucua guccucgacu aauuucgggg   120
aauaaagccu uaacucuguu aaggcuuuuu uuaguuuuuu                         160
```

```
<210> SEQ ID NO 108
```

-continued

```
<211> LENGTH: 160
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 108
ccaugauaua gacguugugg cguuguagu guugugaauu gcuuucaaac aaaagugaaa      60
gcaauucaca auaaggauua uuccguugug aaaacaucua guccucgacu aauuucgggg     120
aauaaagccu uaacucuguu aaggcuuuuu uuaguuuuuu                            160

<210> SEQ ID NO 109
<211> LENGTH: 5
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(4)
<223> OTHER INFORMATION: a, c, t, g, unknown or other

<400> SEQUENCE: 109 nnnnc                                                                   5

<210> SEQ ID NO 110
<211> LENGTH: 1432
<212> TYPE: PRT
<213> ORGANISM: Chryseobacterium sp.

<400> SEQUENCE: 110

Met Ala Lys Asn Ile Leu Gly Leu Asp Leu Gly Thr Asn Ser Ile Gly
1               5                   10                  15

Trp Ala Leu Ile Asn Gln Asp Phe Glu Asn Lys Gln Gly Lys Ile Leu
            20                  25                  30

Gly Met Gly Ser Arg Ile Ile Pro Met Ser Gln Asp Ile Leu Gly Asp
        35                  40                  45

Phe Gly Lys Gly Asn Ser Val Ser Gln Thr Ala Ala Arg Thr Gly Tyr
    50                  55                  60

Arg Gly Val Arg Arg Leu Arg Glu Arg Phe Leu Leu Arg Arg Glu Arg
65                  70                  75                  80

Leu His Arg Val Leu Asn Ile Ile Asn Phe Leu Pro Glu His Tyr Ala
                85                  90                  95

Ser Gln Ile Asp Phe Glu Lys Arg Phe Gly Lys Phe Lys Glu Glu Thr
                100                 105                 110

Glu Pro Lys Leu Ala Tyr Asn Lys Asp Gly Phe Val Phe Lys Asp Ser
        115                 120                 125

Phe Glu Glu Met Leu Ala Asp Phe Lys Asn Tyr Gln Pro Gln Leu Leu
    130                 135                 140

Glu Asn Asp Lys Lys Ile Pro Tyr Asp Trp Thr Ile Tyr Tyr Leu Arg
145                 150                 155                 160

Lys Lys Ala Leu Ser Gln Lys Ile Glu Lys Glu Glu Leu Ala Trp Ile
                165                 170                 175

Leu Leu Asn Phe Asn Gln Lys Arg Gly Tyr Tyr Gln Leu Arg Gly Glu
                180                 185                 190

Asp Phe Glu Glu Glu Lys Asp Lys Met Phe Val Arg Leu Lys Val Glu
```

-continued

```
         195                200                205

Lys Ile Ile Asp Ser Gly Asp Asn Val Lys Gly Lys Ile Leu Tyr Asp
    210                215                220

Val Tyr Phe Glu Asn Gly Trp Lys Tyr Asp Lys Gln Ile Val Lys Thr
225                230                235                240

Glu Asp Trp Ile Glu Arg Val Lys Glu Phe Ile Val Thr Glu Ser Phe
                245                250                255

Leu Lys Asn Gly Asp Ile Lys Arg Thr Phe Lys Ala Val Asp Ser Glu
                260                265                270

Lys Asp Trp Ile Ala Ile Lys Thr Lys Thr Glu Gln Glu Ile Asp Lys
                275                280                285

Ser His Lys Thr Val Gly Val Tyr Ile Tyr Glu Thr Leu Leu Gln Asn
    290                295                300

Pro Lys Gln Lys Ile Lys Gly Lys Leu Val Arg Thr Ile Glu Arg Lys
305                310                315                320

Phe Tyr Lys Asp Glu Leu Lys Gln Ile Leu Glu Lys Gln Lys Glu Phe
                325                330                335

His Gln Glu Leu Lys Asn Asp Asp Leu Tyr Asn Asp Cys Val Arg Glu
                340                345                350

Leu Tyr Arg Asn Asn Glu Ala His Gln Leu Thr Leu Ser Lys Lys Glu
                355                360                365

Phe Val His Leu Leu Met Glu Asp Ile Ile Phe Tyr Gln Arg Pro Leu
    370                375                380

Arg Ser Gln Lys Ser Ser Ile Ser Asn Cys Ser Leu Glu Phe Arg Lys
385                390                395                400

Tyr Lys Asp Glu Asn Gly Val Glu His Ile Gln Tyr Leu Lys Ala Val
                405                410                415

Pro Lys Ser Asn Pro Tyr Tyr Gln Glu Phe Arg Ile Trp Gln Trp Ile
                420                425                430

Phe Asn Leu Asn Ile Tyr Lys Arg Asp Asp Glu Gln Asn Pro Val Thr
                435                440                445

Thr Glu Phe Leu Asn Thr Thr Thr Asp Ile Glu Asn Leu Phe Glu Phe
    450                455                460

Leu Asn Asn Arg Lys Glu Val Asp Gln Lys Ala Leu Leu Lys His Phe
465                470                475                480

Lys Leu Asn Glu Lys Thr His Arg Trp Lys Tyr Val Glu Asp Lys Lys
                485                490                495

Tyr Pro Cys Asn Glu Thr Lys Ser Met Ile Ser Glu Arg Leu Lys Lys
                500                505                510

Val Glu Asn Ile Ala Asn Asp Phe Leu Thr Arg Glu Ile Glu Gln Lys
                515                520                525

Ile Trp His Ile Ile Tyr Ser Val Asn Asp Lys Ile Glu Tyr Glu Lys
    530                535                540

Ala Leu Lys Ser Phe Ala Lys Lys Asn Asn Leu Asp Glu Asn Ser Phe
545                550                555                560

Phe Glu Ala Phe Lys Lys Phe Pro Pro Phe Lys Ser Glu Tyr Gly Ser
                565                570                575

Phe Ser Glu Lys Ala Ile Lys Lys Leu Leu Pro Leu Met Arg Leu Gly
                580                585                590

Lys Tyr Trp Asn Cys Glu Asn Ile Ser Asp Asp Ser Lys Glu Arg Ile
                595                600                605

Gln Lys Ile Ile Asn Gly Glu Tyr Asp Glu Asn Ile Lys Asp Arg Val
    610                615                620
```

```
Arg Glu Lys Ala Ile His Leu Thr Ser Glu Asn Asn Phe Gln Gly Leu
625                 630                 635                 640

Gln Leu Trp Leu Ala Gln Tyr Val Val Tyr Asp Arg His Ser Glu Ala
                645                 650                 655

Ser Met Ile Gly Lys Trp Asn Ser Ala Asp Asp Leu Glu Glu Phe Leu
                660                 665                 670

Lys Glu Phe Lys Gln His Ser Leu Arg Asn Pro Ile Val Glu Gln Val
                675                 680                 685

Ile Thr Glu Thr Leu Arg Val Val Lys Asp Ile Trp Leu Lys Tyr Gly
690                 695                 700

Asn Gly Ala Lys Asp Phe Phe Asn Glu Ile His Ile Glu Leu Gly Arg
705                 710                 715                 720

Glu Met Lys Gln Thr Lys Asp Glu Arg Leu Asp Ala Thr Lys Arg Ile
                725                 730                 735

Thr Glu Asn Glu Asn Thr Asn Leu Arg Ile Lys Ala Leu Leu Ala Glu
                740                 745                 750

Met Met Asn Asp Asn Ser Val Glu Asn Val Arg Pro Tyr Ser Pro Met
                755                 760                 765

Gln Gln Glu Ile Leu Lys Ile Tyr Glu Asp Gly Val Leu Asn Ser Gly
        770                 775                 780

Ile Glu Ile Glu Asp Glu Tyr Leu Lys Ile Ser Lys Thr Ala Gln Pro
785                 790                 795                 800

Ser Pro Ser Asp Leu Lys Arg Tyr Lys Leu Trp Leu Glu Gln Arg Tyr
                805                 810                 815

Lys Ser Pro Tyr Thr Gly Gln Ile Ile Pro Leu Asn Lys Leu Phe Thr
                820                 825                 830

Pro Glu Tyr Glu Ile Glu His Ile Ile Pro Gln Ser Arg Tyr Phe Asp
                835                 840                 845

Asp Ser Phe Ser Asn Lys Ile Ile Cys Glu Ser Ala Val Asn Lys Leu
        850                 855                 860

Lys Asp Asn Tyr Ile Gly Leu Gly Phe Ile Lys Gln Phe Gly Gly Thr
865                 870                 875                 880

Ile Val Glu Cys Gly Leu Gly Lys Asn Val Lys Val Phe Glu Val Asn
                885                 890                 895

Glu Tyr Glu Asp Phe Val Lys Lys His Tyr Ala Asn Asn Arg Gly Lys
                900                 905                 910

Arg Asn Lys Leu Leu Leu Glu Glu Ile Pro Glu Lys Met Ile Glu Arg
        915                 920                 925

Gln Leu Asn Asp Thr Arg His Ile Ser Lys Tyr Ile Ser Gly Val Leu
        930                 935                 940

Ser Asn Ile Val Arg Val Glu Asp Gly Ser Asp Glu Gly Val Asn Ser
945                 950                 955                 960

Lys Asn Ile Val Pro Gly Asn Gly Lys Ile Thr Thr Gln Leu Lys Gln
                965                 970                 975

Asp Trp Gly Leu Asn Asp Val Trp Asn Asp Leu Ile Leu Pro Arg Phe
                980                 985                 990

Glu Arg Met Asn Gln Leu Thr Asn  Ser Thr Asp Phe Thr  Ala Trp Asn
        995                 1000                1005

Glu Asn  His Gln Lys Phe Leu  Pro Thr Val Pro Ile  Glu Phe Ser
    1010                1015                1020

Lys Gly  Phe Ser Lys Lys Arg  Ile Asp His Arg His  His Ala Leu
    1025                1030                1035
```

-continued

Asp Ala  Leu Val Ile Ala Cys  Ala Thr Lys Asp His  Ile Asn Leu
    1040             1045             1050

Leu Asn  Asn Gln Ser Ala Lys  Ser Asp Thr Lys Arg  Tyr Asp Leu
    1055             1060             1065

Lys Lys  Lys Leu Met Lys Phe  Glu Lys Gly Val Tyr  Asn His Pro
    1070             1075             1080

Gln Thr  Gly Glu Arg Ile Gln  Arg Asp Val Pro Lys  Gln Phe Leu
    1085             1090             1095

Lys Pro  Trp Glu Ser Phe Thr  Ile Asp Ala Lys Asn  Asn Leu Asp
    1100             1105             1110

Lys Ile  Ile Ile Ser Phe Lys  Gln Asn Leu Arg Val  Ile Asn Lys
    1115             1120             1125

Ala Thr  Asn Tyr Tyr Glu Lys  Tyr Val Glu Lys Asn  Gly Ile Lys
    1130             1135             1140

Thr Lys  Glu Arg Val Glu Gln  Thr Gly Thr Asn Trp  Ala Ile Arg
    1145             1150             1155

Lys Pro  Met His Lys Glu Thr  Val Ser Gly Ile Val  Asn Leu Pro
    1160             1165             1170

Trp Val  Lys Val Pro Lys Gly  Lys Ile Leu Thr Ala  Thr Arg Lys
    1175             1180             1185

Ser Leu  Asp Thr Thr Phe Asp  Leu Lys Ser Ile Asn  Ser Ile Thr
    1190             1195             1200

Asp Thr  Gly Ile Gln Lys Ile  Leu Arg Asn Tyr Leu  Glu Phe Lys
    1205             1210             1215

Gly Ser  Pro Glu Leu Ala Phe  Ser Pro Glu Gly Ile  Glu Asp Met
    1220             1225             1230

Asn Lys  Asn Ile Glu Lys Tyr  Asn Asp Gly Lys Leu  His Gln Pro
    1235             1240             1245

Ile Asn  Lys Val Arg Val Phe  Glu Leu Gly Ser Lys  Phe Gln Val
    1250             1255             1260

Gly Gln  Thr Gly Asn Lys Lys  Asp Lys Tyr Val Glu  Ala Ala Lys
    1265             1270             1275

Gly Thr  Asn Leu Phe Phe Ala  Val Tyr Glu Asp Lys  Asn Gly Lys
    1280             1285             1290

Arg Asn  Tyr Glu Thr Ile Pro  Leu Asn Ile Val Ile  Glu Arg Gln
    1295             1300             1305

Lys Gln  Gly Leu Leu Ala Cys  Pro Glu Ser Asn Glu  Lys Gly Glu
    1310             1315             1320

Lys Leu  Leu Phe Gln Leu Ser  Pro Asn Asp Phe Val  Tyr Leu Thr
    1325             1330             1335

Thr Glu  Glu Glu Asn Asp Asn  Ala Thr Pro Ile Asn  Phe Ser Leu
    1340             1345             1350

Leu Ser  Lys Glu Gln Ile Asn  Asn Leu Tyr Lys Ile  Val Ser Phe
    1355             1360             1365

Thr Gly  Asn Arg Leu Tyr Gly  Ile Pro Ile Cys Val  Ala Thr Thr
    1370             1375             1380

Ile Val  Asn Lys Ala Glu Tyr  Thr Gln Leu Asn Lys  Ile Glu Phe
    1385             1390             1395

Thr Lys  Glu Lys Asp Leu Leu  Leu Lys Leu Asn Val  Asn Arg Leu
    1400             1405             1410

Gly Asp  Val Lys Thr Phe Thr  Ala Asn Asp Ile Arg  Lys Ile Phe
    1415             1420             1425

Asn Arg  Gln Glu

1430

<210> SEQ ID NO 111
<211> LENGTH: 16
<212> TYPE: RNA
<213> ORGANISM: Chryseobacterium sp.

<400> SEQUENCE: 111
guugugaauu gcuuuc                                                     16

<210> SEQ ID NO 112
<211> LENGTH: 73
<212> TYPE: RNA
<213> ORGANISM: Chryseobacterium sp.

<400> SEQUENCE: 112
gaaagcaauu cacaauaagg auuauuccgu ugugaaaaca uuuagcgccu cgacuaucuu     60
cggggcauuu uuu                                                        73

<210> SEQ ID NO 113
<211> LENGTH: 122
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: modified_base
<222> LOCATION: (1)..(29)
<223> OTHER INFORMATION: a, c, u, g, unknown or other

<400> SEQUENCE: 113
nnnnnnnnnn nnnnnnnnnn nnnnnnnnng uugugaauug cuuucaaagg aaagcaauuc     60
acaauaagga uuauuccguu gugaaaacau uuagcgccuc gacuaucuuc ggggcauuuu    120
uu                                                                  122

<210> SEQ ID NO 114
<211> LENGTH: 123
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 114
gagcggacag cagcuuccua uaucucguac guugugaauu gcuuucaaag gaaagcaauu     60
cacaauaagg auuauuccgu ugugaaaaca uuuagcgccu cgacuaucuu cggggcauuu    120
uuu                                                                  123

<210> SEQ ID NO 115
<211> LENGTH: 123
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 115
ccaugauaua gacguugugg cuguuguagu guugugaauu gcuuucaaag gaaagcaauu     60
cacaauaagg auuauuccgu ugugaaaaca uuuagcgccu cgacuaucuu cggggcauuu    120

-continued uuu                                                                                  123

<210> SEQ ID NO 116
<211> LENGTH: 6
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(5)
<223> OTHER INFORMATION: a, c, t, g, unknown or other

<400> SEQUENCE: 116 nnnnnc                                                                               6

<210> SEQ ID NO 117
<211> LENGTH: 1092
<212> TYPE: PRT
<213> ORGANISM: Bacillus sp.

<400> SEQUENCE: 117

Met Arg Tyr Ser Ile Gly Leu Asp Ile Gly Thr Thr Ser Ile Gly Asn
1               5                   10                  15

Ala Val Ile Asn Lys Asp Leu Gln Arg Phe Glu His Leu Gly Val Arg
                20                  25                  30

Ile Phe Asp Ala Ala Glu Asn Pro Lys Asp Gly Ser Ser Leu Ser Ala
            35                  40                  45

Pro Arg Arg Leu Ala Arg Ser Ser Arg Arg Arg Leu Arg Arg Arg Lys
        50                  55                  60

His Arg Val Glu Arg Thr Lys Gln Leu Leu Ile Asn Lys Gly Leu Leu
65                  70                  75                  80

Thr Lys Thr Gln Val Lys Asn Leu Tyr Asn Ser Lys Asn Ile Asn Leu
                85                  90                  95

Asp Ile Trp Asp Ile Arg Val Ser Gly Ile Asp Arg Lys Leu Phe Asn
                100                 105                 110

Asn Glu Phe Ala Arg Val Leu Ile His Phe Ser Lys Asn Arg Gly Phe
            115                 120                 125

Lys Ser Asn Arg Lys Ser Glu Leu Lys Glu Asp Asp Asn Gly Ala Ile
        130                 135                 140

Leu Ser Ala Val Lys Glu Asn Arg Glu Leu Met Asp Glu Lys Gly Tyr
145                 150                 155                 160

Arg Thr Ile Ala Glu Met Leu Val Ser Asp Glu Lys Tyr Glu Gly Thr
                165                 170                 175

Lys Arg Asn Lys Gly Gly Asp Tyr Ser His Val Val Ala Arg Ser Asp
                180                 185                 190

Ile Glu Asn Glu Ile Cys Leu Leu Phe Gln Lys Gln Arg Glu Tyr Gly
            195                 200                 205

His Pro Phe Ala Thr Glu Glu Asn Glu Glu Ala Phe Leu Ser Ile Trp
        210                 215                 220

Ser Ser Gln Arg Pro Phe Ser Thr Lys Asp Asp Ile Val Lys Lys Ile
225                 230                 235                 240

Gly Asn Cys Thr Leu Glu Pro Lys Glu Lys Arg Ala Pro Lys Ser Thr
                245                 250                 255

Tyr Thr Phe Glu Arg Phe Arg Ala Leu Asp Lys Leu Asn Arg Leu Arg
                260                 265                 270

-continued

```
Ile Leu Ser Thr Thr Ala Pro Ser Arg Pro Leu Thr Asn Glu Glu Arg
        275             280             285

Lys Ser Ile Leu Ser Ser Leu Phe Ser Lys Lys Glu Val Lys Tyr Lys
    290             295             300

Glu Leu Arg Lys Leu Leu Lys Leu Thr Asp Asp Gln Arg Phe Asn Glu
305             310             315             320

Ile Tyr Tyr Ser Pro Asp Glu Thr Ile Glu Lys Thr Glu Asn Arg Thr
            325             330             335

Phe Leu Ser Leu Glu Ser Gln Tyr Lys Ile Lys Lys Ile Ile Glu Lys
            340             345             350

Thr Glu Ser Lys Asn Met Gln Ser Ser Tyr His Pro Ile Asp Tyr Asp
            355             360             365

Thr Ile Gly Tyr Ala Leu Thr Val Phe Lys Asp Asp Lys Asp Ile Gln
        370             375             380

His Tyr Leu Gln Asn Ser Tyr Ile Asp Ser Lys Gly Lys Ala Ile Pro
385             390             395             400

Asn Met Ala Asn Arg Glu Tyr Asn Leu Glu Leu Ile Glu Glu Leu Leu
                405             410             415

Gly Leu Ser Phe Ala Lys Phe Gly His Leu Ser Leu Lys Ala Leu Asn
            420             425             430

Asn Ile Leu Pro Tyr Met Glu Glu Gly Glu Pro Tyr His Ile Ala Cys
            435             440             445

Glu Met Ala Ser Tyr Gln Phe Ser Gln Arg Leu Ser Lys Glu Lys His
        450             455             460

Arg Leu Leu Pro Pro Ile Pro Val Asp Glu Ile Pro Asn Pro Val Val
465             470             475             480

Val Arg Ala Leu Thr Gln Val Arg Lys Val Leu Asn Ser Ile Ile Lys
                485             490             495

Lys Tyr Gly Pro Pro Ser Asp Ile Tyr Ile Glu Leu Ala Arg Glu Met
            500             505             510

Ser Lys Pro Phe Lys Glu Arg Lys Ser Leu Glu Arg Glu Phe Asn Glu
            515             520             525

Asn Arg Gln Ile Asn Glu Lys Ala Lys Ala His Ile Ser Glu Leu Tyr
        530             535             540

Arg Ile Pro Asn Asp Pro Arg Pro His Asp Ile Leu Lys Phe Lys Leu
545             550             555             560

Trp Asn Glu Gln Asn Gly Ile Cys Pro Tyr Ser Leu Lys Pro Ile Ser
            565             570             575

Ile Glu Tyr Leu Phe Asn Ile Gly Tyr Ala Glu Val Asp His Ile Ile
            580             585             590

Pro Tyr Ser Arg Ser Phe Asp Asp Ser Asn Gly Asn Lys Val Leu Val
            595             600             605

Leu Thr Arg Glu Asn Gln Asn Lys Leu Asn Arg Thr Pro Tyr Glu Trp
        610             615             620

Phe Gly His Glu Glu Asn Arg Trp Glu Asp Phe Val Ser Phe Ile Arg
625             630             635             640

Thr Met Lys Val Gly Lys Lys Lys Asn Met Leu Leu Lys Lys Asn
                645             650             655

Phe Asp Glu Glu Gln Glu Glu Gln Ile Leu Ser Arg Asn Leu Asn Asp
            660             665             670

Thr Arg Tyr Ile Thr Arg Tyr Ile Lys Ser Phe Ile Glu Asp Asn Leu
        675             680             685
```

-continued

```
Glu Phe Arg Thr Glu Glu Asn Lys Glu Gln Tyr Val His Thr Val Asn
    690                 695                 700

Gly Ala Tyr Thr Ser Leu Met Arg Lys Arg Trp Gly Leu Asn Lys Asp
705                 710                 715                 720

Arg Arg Gly Asn Asp Leu His His Ala Val Asp Ala Ala Ile Ile Ala
                725                 730                 735

Val Ser Leu Pro Phe Lys Asn Lys Val Asn Ala Tyr Phe Lys Arg Gln
            740                 745                 750

Glu Thr Gly Leu Ser Lys Leu Leu Asn Asn Lys Lys Asp Ile Phe Pro
        755                 760                 765

Glu Pro Trp Arg Asn Phe Ile Lys Glu Leu Glu Ala Arg Met Ile Gln
    770                 775                 780

Asp Pro Glu Lys Met Lys Arg Ala Leu Glu Ser Leu Glu Leu Glu Thr
785                 790                 795                 800

Tyr Gly Glu Ile Phe Leu Asn Lys Leu Lys Pro Ile Phe Val Ser Arg
                805                 810                 815

Met Pro Lys His Ser Ile Lys Gly Gln Ile His Glu Glu Thr Ile Arg
            820                 825                 830

Arg Val Arg Gly Phe Thr Glu Glu Gly Phe Leu Val Thr Val Lys Lys
        835                 840                 845

Thr Arg Leu Asp Gln Ile Pro Phe Asp Lys Asn Gly Asp Phe Pro Met
    850                 855                 860

Tyr Gly Lys Glu Thr Asp Ile Lys Thr Tyr Met Ala Ile Lys Gln Arg
865                 870                 875                 880

Tyr Leu Glu Tyr Gly Gln Asp Lys Gln Lys Ala Phe Ala Val Pro Leu
                885                 890                 895

Arg Lys Pro Ser Lys Asn Pro Lys Asn Ala Pro Ile Val Arg Ser Val
            900                 905                 910

Lys Ile Glu Gly Lys Ala Asn Arg Val Val Met Leu Asp Asp Lys Ala
        915                 920                 925

Ala Ala Asp Asn Ala Ser Ile Val Arg Thr Glu Val Phe Arg His Lys
    930                 935                 940

Lys Thr Gly Glu Tyr Tyr Leu Thr Pro Val Tyr Val Ala Asp Ile Leu
945                 950                 955                 960

Ser Asn Lys Ile Pro Asp Arg Leu Ile Thr Ile Lys Lys Ser Tyr Ser
                965                 970                 975

Asp Trp Asp Arg Ile Thr Asp Glu His Glu Tyr Leu Phe Ser Leu Tyr
            980                 985                 990

Asn Asn Asp Leu Val Lys Ile Ile  Leu Pro Lys Glu Lys  Glu Thr Lys
        995                 1000                1005

Lys Tyr  Thr Gly Gly Asn His  Leu Trp Gln Glu Gly  Phe Phe Tyr
    1010                1015                1020

Phe Lys  Gly Val Asp Ser Ser  Asn Ala Gly Ile Lys  Ile Ile Asn
    1025                1030                1035

His Leu  Asn Ser Phe Glu Ala  Arg Ile Gly Thr Lys  Arg Leu Ile
    1040                1045                1050

Ala Phe  Glu Lys Tyr Gln Val  Asn Pro Leu Gly Glu  Ile Asn Lys
    1055                1060                1065

Val His  Gly Glu Lys Arg Pro  Gly Glu Leu Leu Asn  Lys Glu Glu
    1070                1075                1080

Ile Lys  Glu Asn Arg Lys Asn  Ile Ser
    1085                1090
```

-continued

```
<210> SEQ ID NO 118
<211> LENGTH: 23
<212> TYPE: RNA
<213> ORGANISM: Bacillus sp.

<400> SEQUENCE: 118
gccauaauuc cucuguaaaa cuu                                              23

<210> SEQ ID NO 119
<211> LENGTH: 112
<212> TYPE: RNA
<213> ORGANISM: Bacillus sp.

<400> SEQUENCE: 119
aagguuuaua gaguuauuau gguaaggcaa uaugccgugg cguuggggau cgccuauguc     60
cgguuuuacc ggaucucccu aaaggugacu aacuuugguu agucaccuuu uu            112

<210> SEQ ID NO 120
<211> LENGTH: 168
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: modified_base
<222> LOCATION: (1)..(29)
<223> OTHER INFORMATION: a, c, u, g, unknown or other

<400> SEQUENCE: 120
nnnnnnnnnn nnnnnnnnnn nnnnnnnng ccauaauucc ucuguaaaac uuaaagaagg     60
uuuauagagu uauuauggua aggcaauaug ccguggcguu ggggaucgcc uauguccggu    120
uuuaccggau cucccuaaag gugacuaacu uugguuaguc accuuuu                  168

<210> SEQ ID NO 121
<211> LENGTH: 169
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 121
gagcggacag cagcuuccua uaucucguac gccauaauuc cucuguaaaa cuuaaagaag     60
guuuauagag uuauuauggu aaggcaauau gccguggcgu uggggaucgc cuauguccgg    120
uuuuaccgga ucucccuaaa ggugacuaac uuugguuagu caccuuuuu               169

<210> SEQ ID NO 122
<211> LENGTH: 169
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 122
ccaugauaua gacguugugg cuguuguagu gccauaauuc cucuguaaaa cuuaaagaag     60
guuuauagag uuauuauggu aaggcaauau gccguggcgu uggggaucgc cuauguccgg    120
uuuuaccgga ucucccuaaa ggugacuaac uuugguuagu caccuuuuu               169
```

```
<210> SEQ ID NO 123
<211> LENGTH: 4
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 123 aaag                                                                          4

<210> SEQ ID NO 124
<211> LENGTH: 13
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 124
gccgccrcca tgg                                                                13

<210> SEQ ID NO 125
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 125

Pro Lys Lys Lys Arg Lys Val
1               5

<210> SEQ ID NO 126
<211> LENGTH: 22
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 126

Asp Tyr Lys Asp His Asp Gly Asp Tyr Lys Asp His Asp Ile Asp Tyr
1               5                   10                  15

Lys Asp Asp Asp Asp Lys
            20

<210> SEQ ID NO 127
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 127

Lys Arg Pro Ala Ala Thr Lys Lys Ala Gly Gln Ala Lys Lys Lys Lys
1               5                   10                  15

<210> SEQ ID NO 128
<211> LENGTH: 1092
```

<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 128

Met Arg Tyr Ser Ile Gly Leu Ala Ile Gly Thr Thr Ser Ile Gly Asn
1               5                   10                  15

Ala Val Ile Asn Lys Asp Leu Gln Arg Phe Glu His Leu Gly Val Arg
                20                  25                  30

Ile Phe Asp Ala Ala Glu Asn Pro Lys Asp Gly Ser Ser Leu Ser Ala
            35                  40                  45

Pro Arg Arg Leu Ala Arg Ser Ser Arg Arg Arg Leu Arg Arg Arg Lys
        50                  55                  60

His Arg Val Glu Arg Thr Lys Gln Leu Leu Ile Asn Lys Gly Leu Leu
65                  70                  75                  80

Thr Lys Thr Gln Val Lys Asn Leu Tyr Asn Ser Lys Asn Ile Asn Leu
                85                  90                  95

Asp Ile Trp Asp Ile Arg Val Ser Gly Ile Asp Arg Lys Leu Phe Asn
                100                 105                 110

Asn Glu Phe Ala Arg Val Leu Ile His Phe Ser Lys Asn Arg Gly Phe
            115                 120                 125

Lys Ser Asn Arg Lys Ser Glu Leu Lys Glu Asp Asp Asn Gly Ala Ile
        130                 135                 140

Leu Ser Ala Val Lys Glu Asn Arg Glu Leu Met Asp Glu Lys Gly Tyr
145                 150                 155                 160

Arg Thr Ile Ala Glu Met Leu Val Ser Asp Glu Lys Tyr Glu Gly Thr
                165                 170                 175

Lys Arg Asn Lys Gly Gly Asp Tyr Ser His Val Val Ala Arg Ser Asp
                180                 185                 190

Ile Glu Asn Glu Ile Cys Leu Leu Phe Gln Lys Gln Arg Glu Tyr Gly
            195                 200                 205

His Pro Phe Ala Thr Glu Glu Asn Glu Glu Ala Phe Leu Ser Ile Trp
        210                 215                 220

Ser Ser Gln Arg Pro Phe Ser Thr Lys Asp Asp Ile Val Lys Lys Ile
225                 230                 235                 240

Gly Asn Cys Thr Leu Glu Pro Lys Glu Lys Arg Ala Pro Lys Ser Thr
                245                 250                 255

Tyr Thr Phe Glu Arg Phe Arg Ala Leu Asp Lys Leu Asn Arg Leu Arg
                260                 265                 270

Ile Leu Ser Thr Thr Ala Pro Ser Arg Pro Leu Thr Asn Glu Glu Arg
            275                 280                 285

Lys Ser Ile Leu Ser Ser Leu Phe Ser Lys Lys Glu Val Lys Tyr Lys
        290                 295                 300

Glu Leu Arg Lys Leu Leu Lys Leu Thr Asp Asp Gln Arg Phe Asn Glu
305                 310                 315                 320

Ile Tyr Tyr Ser Pro Asp Glu Thr Ile Glu Lys Thr Glu Asn Arg Thr
                325                 330                 335

Phe Leu Ser Leu Glu Ser Gln Tyr Lys Ile Lys Lys Ile Ile Glu Lys
            340                 345                 350

Thr Glu Ser Lys Asn Met Gln Ser Ser Tyr His Pro Ile Asp Tyr Asp
        355                 360                 365

Thr Ile Gly Tyr Ala Leu Thr Val Phe Lys Asp Asp Lys Asp Ile Gln

-continued

```
              370               375               380

His Tyr Leu Gln Asn Ser Tyr Ile Asp Ser Lys Gly Lys Ala Ile Pro
385               390               395               400

Asn Met Ala Asn Arg Glu Tyr Asn Leu Glu Leu Ile Glu Glu Leu Leu
              405               410               415

Gly Leu Ser Phe Ala Lys Phe Gly His Leu Ser Leu Lys Ala Leu Asn
              420               425               430

Asn Ile Leu Pro Tyr Met Glu Glu Gly Glu Pro Tyr His Ile Ala Cys
              435               440               445

Glu Met Ala Ser Tyr Gln Phe Ser Gln Arg Leu Ser Lys Glu Lys His
              450               455               460

Arg Leu Leu Pro Pro Ile Pro Val Asp Glu Ile Pro Asn Pro Val Val
465               470               475               480

Val Arg Ala Leu Thr Gln Val Arg Lys Val Leu Asn Ser Ile Ile Lys
              485               490               495

Lys Tyr Gly Pro Pro Ser Asp Ile Tyr Ile Glu Leu Ala Arg Glu Met
              500               505               510

Ser Lys Pro Phe Lys Glu Arg Lys Ser Leu Glu Arg Glu Phe Asn Glu
              515               520               525

Asn Arg Gln Ile Asn Glu Lys Ala Lys Ala His Ile Ser Glu Leu Tyr
              530               535               540

Arg Ile Pro Asn Asp Pro Arg Pro His Asp Ile Leu Lys Phe Lys Leu
545               550               555               560

Trp Asn Glu Gln Asn Gly Ile Cys Pro Tyr Ser Leu Lys Pro Ile Ser
              565               570               575

Ile Glu Tyr Leu Phe Asn Ile Gly Tyr Ala Glu Val Asp His Ile Ile
              580               585               590

Pro Tyr Ser Arg Ser Phe Asp Asp Ser Asn Gly Asn Lys Val Leu Val
              595               600               605

Leu Thr Arg Glu Asn Gln Asn Lys Leu Asn Arg Thr Pro Tyr Glu Trp
              610               615               620

Phe Gly His Glu Glu Asn Arg Trp Glu Asp Phe Val Ser Phe Ile Arg
625               630               635               640

Thr Met Lys Val Gly Lys Lys Lys Asn Met Leu Leu Lys Lys Asn
              645               650               655

Phe Asp Glu Glu Gln Glu Glu Gln Ile Leu Ser Arg Asn Leu Asn Asp
              660               665               670

Thr Arg Tyr Ile Thr Arg Tyr Ile Lys Ser Phe Ile Glu Asp Asn Leu
              675               680               685

Glu Phe Arg Thr Glu Glu Asn Lys Glu Gln Tyr Val His Thr Val Asn
              690               695               700

Gly Ala Tyr Thr Ser Leu Met Arg Lys Arg Trp Gly Leu Asn Lys Asp
705               710               715               720

Arg Arg Gly Asn Asp Leu His His Ala Val Asp Ala Ala Ile Ile Ala
              725               730               735

Val Ser Leu Pro Phe Lys Asn Lys Val Asn Ala Tyr Phe Lys Arg Gln
              740               745               750

Glu Thr Gly Leu Ser Lys Leu Leu Asn Asn Lys Lys Asp Ile Phe Pro
              755               760               765

Glu Pro Trp Arg Asn Phe Ile Lys Glu Leu Glu Ala Arg Met Ile Gln
              770               775               780

Asp Pro Glu Lys Met Lys Arg Ala Leu Glu Ser Leu Glu Leu Glu Thr
785               790               795               800
```

-continued

Tyr Gly Glu Ile Phe Leu Asn Lys Leu Lys Pro Ile Phe Val Ser Arg
                805                 810                 815

Met Pro Lys His Ser Ile Lys Gly Gln Ile His Glu Glu Thr Ile Arg
                820                 825                 830

Arg Val Arg Gly Phe Thr Glu Glu Gly Phe Leu Val Thr Val Lys Lys
            835                 840                 845

Thr Arg Leu Asp Gln Ile Pro Phe Asp Lys Asn Gly Asp Phe Pro Met
    850                 855                 860

Tyr Gly Lys Glu Thr Asp Ile Lys Thr Tyr Met Ala Ile Lys Gln Arg
865                 870                 875                 880

Tyr Leu Glu Tyr Gly Gln Asp Lys Gln Lys Ala Phe Ala Val Pro Leu
                885                 890                 895

Arg Lys Pro Ser Lys Asn Pro Lys Asn Ala Pro Ile Val Arg Ser Val
            900                 905                 910

Lys Ile Glu Gly Lys Ala Asn Arg Val Val Met Leu Asp Asp Lys Ala
            915                 920                 925

Ala Ala Asp Asn Ala Ser Ile Val Arg Thr Glu Val Phe Arg His Lys
    930                 935                 940

Lys Thr Gly Glu Tyr Tyr Leu Thr Pro Val Tyr Val Ala Asp Ile Leu
945                 950                 955                 960

Ser Asn Lys Ile Pro Asp Arg Leu Ile Thr Ile Lys Lys Ser Tyr Ser
                965                 970                 975

Asp Trp Asp Arg Ile Thr Asp Glu His Glu Tyr Leu Phe Ser Leu Tyr
                980                 985                 990

Asn Asn Asp Leu Val Lys Ile Ile Leu Pro Lys Glu Lys  Glu Thr Lys
            995                 1000                1005

Lys Tyr  Thr Gly Gly Asn His  Leu Trp Gln Glu Gly  Phe Phe Tyr
    1010                1015                1020

Phe Lys  Gly Val Asp Ser Ser  Asn Ala Gly Ile Lys  Ile Ile Asn
    1025                1030                1035

His Leu  Asn Ser Phe Glu Ala  Arg Ile Gly Thr Lys  Arg Leu Ile
    1040                1045                1050

Ala Phe  Glu Lys Tyr Gln Val  Asn Pro Leu Gly Glu  Ile Asn Lys
    1055                1060                1065

Val His  Gly Glu Lys Arg Pro  Gly Glu Leu Leu Asn  Lys Glu Glu
    1070                1075                1080

Ile Lys  Glu Asn Arg Lys Asn  Ile Ser
    1085                1090

<210> SEQ ID NO 129
<211> LENGTH: 230
<212> TYPE: PRT
<213> ORGANISM: Unknown
<220> FEATURE:
<221> NAME/KEY: source
<223> OTHER INFORMATION: /note="Description of Unknown:
    APG09980 deaminase sequence"

<400> SEQUENCE: 129

Met Ala Ala Gly Pro Ala Pro Glu Ala Arg Ser Leu Met Asp Glu Gln
1                 5                 10                  15

Thr Phe Leu Asp Asn Phe Asn Asn Leu Lys Tyr Pro Arg Lys Thr Tyr
                20                  25                  30

Leu Cys Tyr Glu Val Glu Leu Leu Val Gly Glu Asn His Ile Pro Leu
        35                  40                  45

-continued

```
Asp Asp Tyr Lys Gly Phe Val His Asn Glu Gly Phe Asp Met Gly Leu
    50              55                  60

Glu Arg Cys His Ala Glu Leu Ile Phe Leu Glu Arg Met Ala Ser Trp
65              70                  75                  80

Asn Leu Asp Thr Glu Leu Arg Tyr Arg Ile Thr Val Phe Ile Ser Trp
                85                  90                  95

Ser Pro Cys Pro Glu Cys Ala Asp Glu Leu Val Lys Phe Leu Arg Glu
            100             105             110

Asn Arg His Val Asn Leu Arg Ile Phe Ala Ala Arg Ile Tyr Asp Trp
            115             120             125

Tyr Gln Gly Tyr Glu Ala Gly Leu Arg Ala Leu Lys Ala Ala Gly Ala
    130             135             140

Glu Val Ala Met Met Thr Leu His Glu Phe Glu Tyr Cys Trp Asn Asn
145             150             155             160

Phe Val Asp His Gln Gln Asp Glu Asp Thr Pro Phe Pro Pro Trp Asp
            165             170             175

Asn Leu Val Ala Arg Ser Glu Glu Leu Ser Gln Arg Leu Glu Gly Ile
            180             185             190

Leu Gln Pro Ser Val Leu Val Phe Cys Trp Pro Ser Gln Val Ser Val
    195             200             205

Thr Ala Ala His Ser Asp Ile Met Ser Gln Ala Ser Arg Ala Trp Glu
    210             215             220

Lys Arg Arg Asp Pro Pro
225             230
```

```
<210> SEQ ID NO 130
<211> LENGTH: 182
<212> TYPE: PRT
<213> ORGANISM: Unknown
<220> FEATURE:
<221> NAME/KEY: source
<223> OTHER INFORMATION: /note="Description of Unknown:
      APG07386 CTD sequence"

<400> SEQUENCE: 130
```

```
Met Glu Ala Thr Tyr Pro His Ile Phe Tyr Phe His Phe Lys Asn Leu
1               5                   10                  15

Arg Lys Ala Tyr Gly Arg Asn Glu Thr Trp Leu Cys Phe Thr Met Glu
            20                  25                  30

Ile Ile Lys Gln His Ser Thr Val Phe Trp Glu Thr Gly Val Phe Arg
        35                  40                  45

Asn Gln Val Tyr Pro Glu Ser Leu Cys His Ala Glu Arg Cys Phe Leu
    50                  55                  60

Ser Trp Phe Cys Glu Asp Ile Leu Ser Pro Asn Thr Asp Tyr Arg Val
65              70                  75                  80

Thr Trp Tyr Thr Ser Trp Ser Pro Cys Leu Asp Cys Ala Gly Glu Val
                85                  90                  95

Ala Glu Phe Leu Ala Arg His Ser Asn Val Lys Leu Ala Ile Phe Ala
            100             105             110

Ala Arg Leu Tyr Tyr Phe Trp Asp Pro His Tyr Gln Gln Gly Leu Arg
            115             120             125

Ser Leu Ser Glu Lys Gly Ala Ser Val Glu Ile Met Gly Tyr Lys Asp
    130             135             140

Phe Lys Tyr Cys Trp Glu Asn Phe Val Tyr Asn Gly Asp Glu Pro Phe
145             150             155             160

Lys Pro Trp Lys Gly Leu Lys Tyr Asn Phe Leu Phe Leu Asp Ser Lys
```

-continued

```
                    165                 170                 175

Leu Gln Glu Ile Leu Gln
                180

<210> SEQ ID NO 131
<211> LENGTH: 201
<212> TYPE: PRT
<213> ORGANISM: Unknown
<220> FEATURE:
<221> NAME/KEY: source
<223> OTHER INFORMATION: /note="Description of Unknown:
      APG05840 deaminase sequence"

<400> SEQUENCE: 131

Met Glu Ala Ser Pro Ala Ser Arg Pro Arg Pro Leu Met Asp Pro His
1               5                   10                  15

Met Phe Thr Gly Asn Phe Thr Asn Asn Pro Arg Val Phe Gly Leu His
                20                  25                  30

Gln Thr Tyr Leu Cys Tyr Glu Val Lys Arg Gln Gly Pro Asp Gly Thr
            35                  40                  45

Arg Asp Leu Met Asn Glu Gln Arg Asp Phe Leu Cys Asn Gln Ala Lys
        50                  55                  60

Asn His Phe Ser Gly Ser Glu Asp His His Ala Glu Arg Cys Phe Leu
65                  70                  75                  80

Asp Arg Ile Pro Ser Trp Gln Leu Asp Pro Ala Gln Thr Tyr Arg Val
                85                  90                  95

Thr Cys Phe Ile Ser Trp Ser Pro Cys Phe Ser Cys Ala Gln Glu Val
                100                 105                 110

Ala Glu Phe Leu His Glu Asn Pro His Val Asn Leu Arg Ile Phe Ala
            115                 120                 125

Ala Arg Ile Tyr Asp Tyr Leu Pro Arg Tyr Glu Glu Gly Leu Gln Met
        130                 135                 140

Leu Gln Asn Ala Gly Ala Gln Val Ser Ile Met Thr Ser Glu Glu Phe
145                 150                 155                 160

Gly His Cys Trp Asp Thr Phe Val Asp Arg Gln Gly His Pro Phe Gln
                165                 170                 175

Pro Trp Glu Gly Leu Asp Glu His Ser Gln Ala Leu Ser Gly Arg Leu
                180                 185                 190

Gln Ala Ile Leu Gln Asn Gln Gly Asn
            195                 200

<210> SEQ ID NO 132
<211> LENGTH: 192
<212> TYPE: PRT
<213> ORGANISM: Unknown
<220> FEATURE:
<221> NAME/KEY: source
<223> OTHER INFORMATION: /note="Description of Unknown:
      APG00868 deaminase sequence"

<400> SEQUENCE: 132

Met Glu Pro Trp Arg Pro Ser Pro Arg Asn Pro Met Asp Arg Ile Asp
1               5                   10                  15

Pro Asn Thr Phe Arg Phe His Phe Pro Asn Leu Leu Tyr Ala Ser Gly
                20                  25                  30

Arg Lys Leu Cys Tyr Leu Cys Phe Gln Val Glu Thr Gly Asp Tyr Phe
            35                  40                  45

Ser Cys Asp Asp Ser Asp Arg Gly Val Phe Arg Asn Lys Val His Pro
        50                  55                  60
```

```
Trp Ala Arg Cys His Ala Glu Gln Cys Phe Leu Ser Trp Phe Arg Asp
65                  70                  75                  80

Gln Tyr Pro Cys Arg Asp Glu Tyr Tyr Asn Val Thr Trp Phe Leu Ser
                85                  90                  95

Trp Ser Pro Cys Pro Thr Cys Ala Glu Glu Val Val Glu Phe Leu Glu
            100                 105                 110

Glu Tyr Arg Asn Leu Thr Leu Ser Ile Phe Thr Ser Arg Leu Tyr Tyr
        115                 120                 125

Phe Tyr His Pro Asn Tyr Gln Gln Gly Leu Arg Lys Leu Trp Asp Ala
    130                 135                 140

Gly Val Gln Leu Asp Ile Met Ser Cys Asp Asp Phe Glu His Cys Trp
145                 150                 155                 160

Asp Asn Phe Val Asp His Lys Gly Met Arg Phe Gln Arg Arg Asn Leu
                165                 170                 175

Leu Lys Asp Tyr Asp Phe Leu Ala Ala Glu Leu Gln Glu Ile Leu Arg
            180                 185                 190
```

<210> SEQ ID NO 133
<211> LENGTH: 32
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 133

```
Ser Gly Gly Ser Ser Gly Gly Ser Ser Gly Ser Glu Thr Pro Gly Thr
1               5                   10                  15

Ser Glu Ser Ala Thr Pro Glu Ser Ser Gly Gly Ser Ser Gly Gly Ser
            20                  25                  30
```

<210> SEQ ID NO 134
<211> LENGTH: 159
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 134

```
gggccattaa aacctctcca gccataattc ctctgtaaaa cttaaagaag gtttatagag      60
ttattatggt aaggcaatat gccgtggcgt tggggatcgc ctatgtccgg ttttaccgga     120
tctccctaaa ggtgactaac tttggttagt caccttttt                            159
```

<210> SEQ ID NO 135
<211> LENGTH: 159
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 135

```
catggcagta cattagagca gccataattc ctctgtaaaa cttaaagaag gtttatagag      60
ttattatggt aaggcaatat gccgtggcgt tggggatcgc ctatgtccgg ttttaccgga     120
tctccctaaa ggtgactaac tttggttagt caccttttt                            159
```

```
<210> SEQ ID NO 136
<211> LENGTH: 164
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 136
agctgtttgg gaggtcagaa atagggccat aattcctctg taaaacttaa agaaggttta        60
tagagttatt atggtaaggc aatatgccgt ggcgttgggg atcgcctatg tccggtttta       120
ccggatctcc ctaaaggtga ctaactttgg ttagtcacct tttt                        164

<210> SEQ ID NO 137
<211> LENGTH: 1151
<212> TYPE: PRT
<213> ORGANISM: Brevibacillus sp.

<400> SEQUENCE: 137

Met Ala Lys Arg Pro Ala Ala Thr Lys Lys Ala Gly Gln Ala Lys Lys
1               5                   10                  15

Lys Lys Ala Ile Arg Ser Ile Lys Leu Lys Leu Lys Thr Arg Thr Gly
            20                  25                  30

Pro Glu Ala Gln Asn Leu Arg Lys Gly Ile Trp Arg Thr His Arg Leu
        35                  40                  45

Leu Asn Glu Gly Val Ala Tyr Tyr Met Lys Met Leu Leu Leu Phe Arg
    50                  55                  60

Gln Glu Ser Thr Gly Gly Gln Thr Lys Lys Glu Leu Gln Glu Glu Leu
65                  70                  75                  80

Val Arg His Ile Arg Glu Gln Gln Gln Lys Asn Arg Ala Asp Lys Asn
                85                  90                  95

Thr Gln Ala Leu Pro Leu Asp Lys Ala Phe Ala Ala Leu Arg Gln Leu
            100                 105                 110

Tyr Glu Leu Leu Val Pro Ser Ser Ile Gly Gln Ser Gly Asp Ala Gln
        115                 120                 125

Ile Ile Ser Arg Lys Phe Leu Ser Pro Leu Val Asp Pro Asn Ser Glu
    130                 135                 140

Gly Gly Lys Gly Thr Ser Lys Ala Gly Ala Lys Pro Thr Trp Gln Lys
145                 150                 155                 160

Lys Lys Glu Ala Asn Asp Pro Thr Trp Glu Gln Asp Tyr Glu Lys Trp
                165                 170                 175

Lys Lys Arg Arg Glu Glu Asp Pro Thr Ala Ser Val Ile Thr Thr Leu
            180                 185                 190

Glu Glu Tyr Gly Ile Arg Pro Ile Phe Pro Leu Tyr Thr Asn Thr Val
        195                 200                 205

Ala Asp Ile Ala Trp Leu Pro Leu Gln Ser Asn Gln Phe Val Arg Thr
    210                 215                 220

Trp Asp Arg Asp Met Leu Gln Gln Ala Ile Glu Arg Leu Leu Ser Trp
225                 230                 235                 240

Glu Ser Trp Asn Lys Arg Val Gln Glu Glu Tyr Ser Lys Leu Gln Glu
                245                 250                 255

Lys Met Thr Gln Leu Asn Glu Gln Leu Glu Gly Gly Gln Glu Trp Ile
            260                 265                 270

Ser Leu Leu Glu Gln Tyr Glu Glu Gln Arg Glu Gln Glu Leu Ile Glu
        275                 280                 285
```

-continued

```
Asn Met Thr Ala Ala Asn Asp Lys Tyr Arg Ile Thr Lys Arg Gln Met
    290                 295                 300

Lys Gly Trp Asn Glu Leu Tyr Glu Gln Trp Ser Thr Val Leu Pro Asn
305                 310                 315                 320

Ala Ser His Glu Gln Tyr Arg Glu Ala Leu Lys Arg Val Gln Gln Arg
                325                 330                 335

Leu Arg Gly Arg Phe Gly Asp Ala His Phe Phe Gln Tyr Leu Met Lys
                340                 345                 350

Glu Glu His His Leu Ile Trp Lys Gly Asn Pro Gln Arg Ile His Tyr
                355                 360                 365

Phe Val Ala Arg Asn Glu Leu Lys Lys Arg Leu Glu Glu Ala Lys Gln
    370                 375                 380

Asn Ala Thr Met Thr Leu Pro Asp Ala Arg Lys His Pro Leu Trp Val
385                 390                 395                 400

Arg Phe Asp Ala Arg Gly Gly Asn Leu Gln Asp Tyr Tyr Leu Thr Ala
                405                 410                 415

Glu Ala Asp Asn Pro Arg Ser Arg Arg Phe Val Thr Phe Ser Gln Leu
                420                 425                 430

Ile Trp Pro Asn Glu Ser Gly Trp Met Glu Lys Gln Asp Val Glu Val
                435                 440                 445

Glu Leu Ala Leu Ser Lys Gln Phe Tyr Gln Gln Val Thr Leu Gln Lys
    450                 455                 460

Asn Asp Lys Gly Lys Gln Glu Ile Glu Phe Lys Asp Lys Gly Ser Gly
465                 470                 475                 480

Ser Thr Phe Ser Gly His Leu Gly Gly Ala Lys Leu Gln Leu Glu Arg
                485                 490                 495

Gly Asp Leu Glu Lys Glu Glu Lys Asp Phe Glu Gly Gly Glu Ile Gly
                500                 505                 510

Ser Val Tyr Leu Asn Ile Val Ile Asp Phe Glu Pro Leu Gln Glu Val
                515                 520                 525

Lys Asn Gly Arg Leu Gln Ser Pro Tyr Gly Gln Val Leu Gln Leu Val
    530                 535                 540

Arg Arg Pro Asn Glu Phe Pro Lys Val Thr Thr Tyr Lys Ser Glu Glu
545                 550                 555                 560

Leu Val Glu Trp Ile Lys Ser Ser Thr Lys Asp Ser Ala Gly Val Glu
                565                 570                 575

Ser Leu Glu Ser Gly Phe Arg Val Met Ser Ile Asp Leu Gly Leu Arg
                580                 585                 590

Thr Ala Ala Ala Thr Ser Ile Phe Ser Val Glu Glu Ser Asn Asp Ala
                595                 600                 605

Asn Ala Ala Gly Phe Ser Tyr Trp Ile Glu Gly Thr Pro Leu Val Ala
    610                 615                 620

Val His Lys Arg Ser Tyr Met Leu Lys Leu Pro Gly Glu Gln Val Glu
625                 630                 635                 640

Lys Gln Val Arg Glu Lys Arg Asp Glu Arg Gln Asp Gln Gln Arg Arg
                645                 650                 655

Val Arg Phe Gln Ile Arg Ile Leu Ser Gln Val Ile Arg Met Ala Lys
                660                 665                 670

Lys Gln Asn Arg Glu Arg Ala Asp Glu Leu Asp His Leu Ser Gln Ala
                675                 680                 685

Leu Glu Lys Gln Lys Ser Leu Leu Asp Gln Thr Asp Arg Thr Phe Trp
    690                 695                 700
```

-continued

```
Asn Gly Ile Val Cys Asp Leu Thr Asp Ala Leu Arg Glu Lys Glu Gly
705             710             715             720

Gly Trp Glu Gln Ala Val Val Gln Ile His Arg Lys Ala Glu Glu His
            725             730             735

Val Gly Lys Val Val Gln Ala Trp Arg Lys Arg Phe Asp Ala Asp Glu
            740             745             750

Arg Lys Gly Ile Ala Gly Leu Ser Met Trp Ser Ile Glu Glu Leu Asp
            755             760             765

Ser Leu Arg Lys Leu Leu Ile Ser Trp Ser Arg Arg Thr Arg Asn Pro
770             775             780

Arg Glu Ile Asn Cys Phe Glu Gln Gly His Thr Ser His Gln Arg Leu
785             790             795             800

Leu Thr His Ile Gln Asn Val Lys Glu Asp Arg Leu Lys Gln Leu Ser
            805             810             815

His Ala Ile Val Met Thr Ala Leu Gly Tyr Val Tyr Asp Glu Lys Lys
            820             825             830

Leu Glu Trp Phe Ala Lys Tyr Pro Ala Cys Gln Val Ile Leu Phe Glu
            835             840             845

Asn Leu Ser Gln Tyr Arg Ser Asn Met Asp Arg Ser Thr Lys Glu Asn
850             855             860

Ser Thr Leu Met Lys Trp Ala His Arg Ser Ile Pro Lys Tyr Val His
865             870             875             880

Met Gln Ala Glu Pro Tyr Gly Ile Gln Ile Gly Asp Val Arg Ala Glu
            885             890             895

Tyr Ser Ser Arg Phe His Ala Lys Thr Gly Thr Pro Gly Ile Arg Cys
            900             905             910

Lys Met Val Ser Gly His Asp Leu Gln Gly Arg Arg Phe Glu Asn Leu
            915             920             925

Gln Lys Arg Leu Ile Ser Glu Gln Phe Leu Thr Glu Glu Gln Val Lys
930             935             940

Gln Leu Arg Pro Gly Asp Ile Val Pro Asp Asp Ser Gly Glu Trp Phe
945             950             955             960

Met Thr Leu Ser Asp Gly Ser Glu Gly Lys Glu Val Val Phe Leu Gln
            965             970             975

Ala Asp Ile Asn Ala Ala Gln Asn Leu Gln Lys Arg Phe Trp Gln Arg
            980             985             990

Tyr Asn Glu Leu Phe Lys Val Ser  Cys Arg Val Leu Ile  Arg Gly Glu
            995             1000            1005

Glu Glu  Tyr Leu Ile Pro Lys  Thr Lys Ser Val Gln  Ala Lys Leu
    1010            1015            1020

Gly Lys  Gly Leu Phe Val Lys  Lys Thr Asp Thr Val  Met Lys Asp
    1025            1030            1035

Val Tyr  Val Trp Asp Ser Gln  Ala Lys Leu Lys Gly  Lys Thr Thr
    1040            1045            1050

Phe Thr  Glu Glu Ser Glu Ser  Pro Glu Gln Leu Glu  Asp Phe Gln
    1055            1060            1065

Glu Ile  Ile Glu Glu Ala Glu  Glu Ala Lys Gly Thr  Tyr Arg Thr
    1070            1075            1080

Leu Phe  Arg Asp Pro Ser Gly  Val Phe Phe Pro Glu  Phe Val Trp
    1085            1090            1095

Ser Thr  Gln Lys Asp Phe Trp  Ser Glu Val Lys Arg  Arg Leu Tyr
    1100            1105            1110

Gly Lys  Leu Arg Glu Arg Phe  Leu Met Lys Thr Arg  Pro Lys Lys
```

-continued

```
    1115              1120              1125

Lys Arg  Lys Val Glu Asn Leu  Tyr Phe Gln Ser Gly  Ser His His
    1130              1135              1140

His His  His His His His His  His
    1145              1150
```

```
<210> SEQ ID NO 138
<211> LENGTH: 11
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 138
aaaggaatcc c                                                          11
```

```
<210> SEQ ID NO 139
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 139
ttcgattccg gagagggagc ct                                              22
```

```
<210> SEQ ID NO 140
<211> LENGTH: 50
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 140
aggagcggac agcagcttcc tatatctcgt acagggaact caacatggtt              50
```

```
<210> SEQ ID NO 141
<211> LENGTH: 50
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 141
agccatgata tagacgttgt ggctgttgta gtagggaact caacatggtt              50
```

```
<210> SEQ ID NO 142
<211> LENGTH: 50
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 142
aggagcggac agcagcttcc tatatctcgt acaggaccgt caacatggtt              50
```

```
<210> SEQ ID NO 143
<211> LENGTH: 50
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 143
agccatgata tagacgttgt ggctgttgta gtaggaccgt caacatggtt                50

<210> SEQ ID NO 144
<211> LENGTH: 142
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 144
ggcgacgguu agaggccgua ugucgauuug cuuuaauuuc gugcgugugc auugucgucc     60
uccauuacag ggcggcuacc acgaauagcc acgaaguaaa agcuucgugg cuagcacgua    120
cgagauauag gaagcugcug uc                                            142

<210> SEQ ID NO 145
<211> LENGTH: 137
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 145
ggcgacgguu agaggccgua ugucgauuug cuuuaauuuc gugcgugugc auugucgucc     60
uccauuacag ggcggcuacc acgaauagcc acgaaguaaa agcuucgugg cuagcacacu    120
acaacagcca caacguc                                                  137

<210> SEQ ID NO 146
<211> LENGTH: 4
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 146 cttc                                                                 4

<210> SEQ ID NO 147
<211> LENGTH: 5
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 147 atatg                                                                5

<210> SEQ ID NO 148
```

```
<211> LENGTH: 5
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 148 tattg                                                                          5

<210> SEQ ID NO 149
<211> LENGTH: 5
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 149 cgttc                                                                          5

<210> SEQ ID NO 150
<211> LENGTH: 5
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 150 ttttt                                                                          5

<210> SEQ ID NO 151
<211> LENGTH: 5
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 151 caatc                                                                          5

<210> SEQ ID NO 152
<211> LENGTH: 5
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 152 aatct                                                                          5

<210> SEQ ID NO 153
<211> LENGTH: 5
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 153
```

-continued aaatt                                                                                              5

<210> SEQ ID NO 154
<211> LENGTH: 5
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 154 catcc                                                                                              5

<210> SEQ ID NO 155
<211> LENGTH: 5
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 155 agata                                                                                              5

<210> SEQ ID NO 156
<211> LENGTH: 5
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 156 tattc                                                                                              5

<210> SEQ ID NO 157
<211> LENGTH: 5
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 157 atttt                                                                                              5

<210> SEQ ID NO 158
<211> LENGTH: 5
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 158 tcttt                                                                                              5

<210> SEQ ID NO 159
<211> LENGTH: 5
<212> TYPE: DNA
<213> ORGANISM: Artificial Sequence
<220> FEATURE:

US 12,680,096 B2

269

270

-continued

<221> NAME/KEY: source
<223> OTHER INFORMATION: /note="Description of Artificial Sequence:
      Synthetic oligonucleotide"

<400> SEQUENCE: 159 agatc                                                                    5

<210> SEQ ID NO 160
<211> LENGTH: 5
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 160 aataa                                                                    5

<210> SEQ ID NO 161
<211> LENGTH: 5
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 161 gatcc                                                                    5

<210> SEQ ID NO 162
<211> LENGTH: 5
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 162 attca                                                                    5

<210> SEQ ID NO 163
<211> LENGTH: 5
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 163 aaaat                                                                    5

<210> SEQ ID NO 164
<211> LENGTH: 5
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 164 ttatc                                                                    5

-continued

```
<210> SEQ ID NO 165
<211> LENGTH: 5
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 165 tatca                                                             5

<210> SEQ ID NO 166
<211> LENGTH: 5
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 166 tcact                                                             5

<210> SEQ ID NO 167
<211> LENGTH: 5
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 167 cttat                                                             5

<210> SEQ ID NO 168
<211> LENGTH: 5
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 168 tgata                                                             5

<210> SEQ ID NO 169
<211> LENGTH: 5
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 169 tacta                                                             5

<210> SEQ ID NO 170
<211> LENGTH: 5
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

```
<400> SEQUENCE: 170 atata                                                              5

<210> SEQ ID NO 171
<211> LENGTH: 5
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 171 gactc                                                              5

<210> SEQ ID NO 172
<211> LENGTH: 5
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 172 gctca                                                              5

<210> SEQ ID NO 173
<211> LENGTH: 5
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 173 taacc                                                              5

<210> SEQ ID NO 174
<211> LENGTH: 5
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 174 cgtgt                                                              5

<210> SEQ ID NO 175
<211> LENGTH: 5
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 175 tttcg                                                              5

<210> SEQ ID NO 176
<211> LENGTH: 5
<212> TYPE: DNA
<213> ORGANISM: Artificial Sequence
```

```
<220> FEATURE:
<221> NAME/KEY: source
<223> OTHER INFORMATION: /note="Description of Artificial Sequence:
      Synthetic oligonucleotide"

<400> SEQUENCE: 176 cagta                                                              5

<210> SEQ ID NO 177
<211> LENGTH: 5
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 177 ccctt                                                              5

<210> SEQ ID NO 178
<211> LENGTH: 5
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 178 cctat                                                              5

<210> SEQ ID NO 179
<211> LENGTH: 5
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 179 tccct                                                              5

<210> SEQ ID NO 180
<211> LENGTH: 5
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 180 aggtt                                                              5

<210> SEQ ID NO 181
<211> LENGTH: 5
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 181 taacg                                                              5
```

```
<210> SEQ ID NO 182
<211> LENGTH: 5
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 182 aacag                                                                          5

<210> SEQ ID NO 183
<211> LENGTH: 5
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 183 tgaac                                                                          5

<210> SEQ ID NO 184
<211> LENGTH: 5
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 184 taagt                                                                          5

<210> SEQ ID NO 185
<211> LENGTH: 5
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 185 ctgta                                                                          5

<210> SEQ ID NO 186
<211> LENGTH: 5
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 186 agggg                                                                          5

<210> SEQ ID NO 187
<211> LENGTH: 5
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

-continued

<400> SEQUENCE: 187 gctgt                                                                    5

<210> SEQ ID NO 188
<211> LENGTH: 5
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 188 atcta                                                                    5

<210> SEQ ID NO 189
<211> LENGTH: 5
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 189 tcagg                                                                    5

<210> SEQ ID NO 190
<211> LENGTH: 5
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 190 atgtc                                                                    5

<210> SEQ ID NO 191
<211> LENGTH: 5
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 191 tgcta                                                                    5

<210> SEQ ID NO 192
<211> LENGTH: 5
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 192 taaaa                                                                    5

<210> SEQ ID NO 193
<211> LENGTH: 5
<212> TYPE: DNA

-continued

```
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 193 atcag                                                             5

<210> SEQ ID NO 194
<211> LENGTH: 5
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 194 cgggg                                                             5

<210> SEQ ID NO 195
<211> LENGTH: 5
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 195 ttctc                                                             5

<210> SEQ ID NO 196
<211> LENGTH: 5
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 196 gtcat                                                             5

<210> SEQ ID NO 197
<211> LENGTH: 5
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 197 gcgtg                                                             5

<210> SEQ ID NO 198
<211> LENGTH: 5
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 198 gcaat                                                             5
```

-continued

```
<210> SEQ ID NO 199
<211> LENGTH: 5
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 199 ttctc                                                             5

<210> SEQ ID NO 200
<211> LENGTH: 5
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 200 agcat                                                             5

<210> SEQ ID NO 201
<211> LENGTH: 5
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 201 gtcaa                                                             5

<210> SEQ ID NO 202
<211> LENGTH: 5
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 202 agagc                                                             5

<210> SEQ ID NO 203
<211> LENGTH: 5
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 203 gtggg                                                             5

<210> SEQ ID NO 204
<211> LENGTH: 5
<212> TYPE: DNA
<213> ORGANISM: Artificial Sequence
<220> FEATURE:
<221> NAME/KEY: source
<223> OTHER INFORMATION: /note="Description of Artificial Sequence:
```

-continued

Synthetic oligonucleotide"

<400> SEQUENCE: 204 ctgaa                                                                          5

<210> SEQ ID NO 205
<211> LENGTH: 5
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 205 ctgat                                                                          5

<210> SEQ ID NO 206
<211> LENGTH: 5
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 206 atgaa                                                                          5

<210> SEQ ID NO 207
<211> LENGTH: 5
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 207 acctt                                                                          5

<210> SEQ ID NO 208
<211> LENGTH: 5
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 208 aacca                                                                          5

<210> SEQ ID NO 209
<211> LENGTH: 5
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 209 gtaaa                                                                          5

<210> SEQ ID NO 210
<211> LENGTH: 5

```
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 210 tagga                                                                    5

<210> SEQ ID NO 211
<211> LENGTH: 5
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 211 ccgaa                                                                    5

<210> SEQ ID NO 212
<211> LENGTH: 5
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 212 tacga                                                                    5

<210> SEQ ID NO 213
<211> LENGTH: 5
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 213 tggct                                                                    5

<210> SEQ ID NO 214
<211> LENGTH: 5
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 214 ccaag                                                                    5

<210> SEQ ID NO 215
<211> LENGTH: 5
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 215
```

-continued

```
tgctt                                                             5

<210> SEQ ID NO 216
<211> LENGTH: 5
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 216 ctaaa                                                             5

<210> SEQ ID NO 217
<211> LENGTH: 5
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 217 tcgat                                                             5

<210> SEQ ID NO 218
<211> LENGTH: 5
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 218 gtaac                                                             5

<210> SEQ ID NO 219
<211> LENGTH: 5
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 219 gtaac                                                             5

<210> SEQ ID NO 220
<211> LENGTH: 500
<212> TYPE: DNA
<213> ORGANISM: Homo sapiens

<400> SEQUENCE: 220
aaaaatggac aattatgagg aggggagagt gcagacaggg gaagcttcac ctcctttaca      60
attttgggag tccacacggc atggcataca aattatttca ttcccattga gaaataaaat     120
ccaattctcc atcaccaaga gagccttccg aaagaggccc ccctgggcaa acggccaccg     180
atggagaggt ctgccagtcc tcttctaccc cacccacgcc cccaccctaa tcagaggcca     240
aacccttcct ggagcctgtg ataaaagcaa ctgttagctt gcactagact agcttcaaag     300
ttgtattgac cctggtgtgt tatgtctaag agtagatgcc atatctcttt tctggcctat     360
gttattacct gtatggactt tgcactggaa tcagctatct gctcttactt atgcacacct     420
```

```
gggggcataga gccagccctg tatcgctttt cagccatctc actacagata actcccaagt      480
cctgtctagc tgccttcctt                                                    500

<210> SEQ ID NO 221
<211> LENGTH: 20
<212> TYPE: DNA
<213> ORGANISM: Homo sapiens

<400> SEQUENCE: 221
tattgaccct ggtgtgttat                                                    20

<210> SEQ ID NO 222
<211> LENGTH: 20
<212> TYPE: DNA
<213> ORGANISM: Homo sapiens

<400> SEQUENCE: 222
gcttgcacta gactagcttc                                                    20

<210> SEQ ID NO 223
<211> LENGTH: 20
<212> TYPE: DNA
<213> ORGANISM: Homo sapiens

<400> SEQUENCE: 223
cttttatcac aggctccagg                                                    20

<210> SEQ ID NO 224
<211> LENGTH: 135
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 224
cgacgguuag aggccguaug ucgauuugcu uuaauuucgu gcgugugcau ugucguccuc      60
cauuacaggg cggcuaccac gaauagccac gaaguaaaag cuucguggcu agcacuauug     120
acccuggugu guuau                                                        135

<210> SEQ ID NO 225
<211> LENGTH: 1977
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 225
caagcatgag gagggaagta ggcagaatcc tctggagcca aagctctgga tgtctctccc      60
ctctgaccat ggagcccacc cctgctccac tgctccaggg acagccctat gctgcaggca     120
gctctgcccc cactcagcat cccaggggct gatttctttg gttttggatc cagctggatg     180
tctgcattgc cgaggccacc agggctggct cagcaactgt cggggaatca ccagggtctg     240
agaaatcttg tgcgcatgtg aggggctgtg ggagcagaga accactgggt gggaaattct     300
aatccccacc ctgctggaaa ctctctgggt ggccccaaca tgctaatcct ccggcaaacc     360
tctgtttcct cctcaaaagg caggaggtcg gaaagaataa acaatgagag tcacattaaa     420
```

-continued

```
aacacaaaat cctacggaaa tactgaagaa tgagtctcag cactaaggaa aagcctccag      480
cagctcctgc tttctgaggg tgaaggatag acgctgtggc tctgcatgac tcactagcac      540
tctatcacgg ccatattctg gcagggtcag tggctccaac taacatttgt ttggtacttt      600
acagtttatt aaatagatgt ttatatggag aagctctcat ttctttctca gaagagcctg      660
gctaggaagg tggatgaggc accatattca ttttgcaggt gaaattcctg agatgtaagg      720
agctgctgtg acttgctcaa ggccttatat cgagtaaacg gtagtgctgg ggcttagacg      780
caggtgttct gatttatagt tcaaaacctc tatcaatgag agagcaatct cctggtaatg      840
tgatagattt cccaacttaa tgccaacata ccataaacct cccattctgc taatgcccag      900
cctaagttgg ggagaccact ccagattcca agatgtacag tttgctttgc tgggcctttt      960
tcccatgcct gcctttactc tgccagagtt atattgctgg ggttttgaag aagatcctat     1020
taaataaaag aataagcagt attattaagt agccctgcat ttcaggtttc cttgagtggc     1080
aggccaggcc tggccgtgaa cgttcactga aatcatggcc tcttggccaa gattgatagc     1140
ttgtgcctgt ccctgagtcc cagtccatca cgagcagctg gtttctaaga tgctatttcc     1200
cgtataaagc atgagaccgt gacttgccag ccccacagag ccccgccctt gtccatcact     1260
ggcatctgga ctccagcctg ggttggggca aagagggaaa tgagatcatg tcctaaccct     1320
gatcctcttg tcccacagat atccagaacc ctgaccctgc cgtgtaccag ctgagagact     1380
ctaaatccag tgacaagtct gtctgcctat tcaccgattt tgattctcaa acaaatgtgt     1440
cacaaagtaa ggattctgat gtgtatatca cagacaaaac tgtgctagac atgaggtcta     1500
tggacttcaa gagcaacagt gctgtggcct ggagcaacaa atctgacttt gcatgtgcaa     1560
acgccttcaa caacagcatt attccagaag acaccttctt ccccagccca ggtaagggca     1620
gctttggtgc cttcgcaggc tgtttccttg cttcaggaat ggccaggttc tgcccagagc     1680
tctggtcaat gatgtctaaa actcctctga ttggtggtct cggccttatc cattgccacc     1740
aaaaccctct ttttactaag aaacagtgag ccttgttctg gcagtccaga gaatgacacg     1800
ggaaaaaagc agatgaagag aaggtggcag gagagggcac gtggcccagc ctcagtctct     1860
ccaactgagt tcctgcctgc ctgcctttgc tcagactgtt tgccccttac tgctcttcta     1920
ggcctcattc taagcccctt ctccaagttg cctctcctta tttctccctg tctgcca       1977
```

<210> SEQ ID NO 226
<211> LENGTH: 566
<212> TYPE: DNA
<213> ORGANISM: Artificial Sequence
<220> FEATURE:
<221> NAME/KEY: source
<223> OTHER INFORMATION: /note="Description of Artificial Sequence:
     Synthetic polynucleotide"

<400> SEQUENCE: 226

```
tcgtcggcag cgtcagatgt gtataagaga cagtttgggt tttgccagac tccacagtgc       60
atacgtgggc tccaacaggt cctcttccct cccagtcact gactaacccc ggaaccacac      120
agcttcccgt tctcagctcc acaaacttgg tgccaaattc ttctcccctg ggaagcatcc      180
ctggacactt cccaaaggac cccagtcact ccagcctgtt ggctgccgct cactttgatg      240
tctgcaggcc agatgagggc tccagatggc acattgtcag agggacacac tgtggcccct      300
gtgcccagcc ctgggctctc tgtacatgaa gcaactccag tcccaaatat gtagctgttt      360
gggaggtcag aaatagggggg tccaggagca aactccccccc accccctttc caaagcccat      420
tccctcttta gccagagccg gggtgtgcag acggcagtca ctagggggcg ctcggccacc      480
```

-continued

```
acagggaagc tgggtgaatg gagcgagcag cgtcttcgag agtgaggacg tgctgtctct     540
tatacacatc tccgagccca cgagac                                          566

<210> SEQ ID NO 227
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 227
gaaagggggt ggggggagtt tgctc                                            25

<210> SEQ ID NO 228
<211> LENGTH: 53
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 228
tcgtcggcag cgtcagatgt gtataagaga cagtttgggt tttgccagac tcc            53

<210> SEQ ID NO 229
<211> LENGTH: 54
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 229
gtctcgtggg ctcggagatg tgtataagag acagcctctg acaatgtgcc atct           54

<210> SEQ ID NO 230
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 230
cccgtataaa gcatgagacc                                                  20

<210> SEQ ID NO 231
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 231
caagcatgag gagggaagta g                                                21

<210> SEQ ID NO 232
<211> LENGTH: 21
<212> TYPE: DNA
```

<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 232
tggcagacag ggagaaataa g                                                                            21

<210> SEQ ID NO 233
<211> LENGTH: 137
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 233
ggcgacgguu agaggccgua ugucgauuug cuuuaauuuc gugcgugugc auugucgucc          60
uccauuacag ggcggcuacc acgaauagcc acgaaguaaa agcuucgugg cuagcacgaa          120
aggggguggg gggaguu                                                        137

<210> SEQ ID NO 234
<211> LENGTH: 137
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 234
ggcgacgguu agaggccgua ugucgauuug cuuuaauuuc gugcgugugc auugucgucc          60
uccauuacag ggcggcuacc acgaauagcc acgaaguaaa agcuucgugg cuagcacccc          120
guauaaagca ugagacc                                                        137

<210> SEQ ID NO 235
<211> LENGTH: 1071
<212> TYPE: PRT
<213> ORGANISM: Bacillus sp.

<400> SEQUENCE: 235

Met Arg Glu Leu Asp Tyr Arg Ile Gly Leu Asp Ile Gly Thr Asn Ser
1               5                   10                  15

Ile Gly Trp Gly Val Ile Glu Leu Ser Trp Asn Lys Asp Arg Glu Arg
            20                  25                  30

Tyr Glu Lys Val Arg Ile Val Asp Gln Gly Val Arg Met Phe Asp Arg
        35                  40                  45

Ala Glu Met Pro Lys Thr Gly Ala Ser Leu Ala Glu Pro Arg Arg Ile
    50                  55                  60

Ala Arg Ser Ser Arg Arg Arg Leu Asn Arg Lys Ser Gln Arg Lys Lys
65                  70                  75                  80

Asn Ile Arg Asn Leu Leu Val Gln His Gly Val Ile Thr Gln Glu Glu
                85                  90                  95

Leu Asp Ser Leu Tyr Pro Leu Ser Lys Lys Ser Met Asp Ile Trp Gly
            100                 105                 110

Ile Arg Leu Asp Gly Leu Asp Arg Leu Leu Asn His Phe Glu Trp Ala
        115                 120                 125

Arg Leu Leu Ile His Leu Ala Gln Arg Arg Gly Phe Lys Ser Asn Arg

```
        130                135                140

Lys Ser Glu Leu Lys Asp Thr Glu Thr Gly Lys Val Leu Ser Ser Ile
145                150                155                160

Gln Leu Asn Glu Lys Arg Leu Ser Leu Tyr Arg Thr Val Gly Glu Met
                165                170                175

Trp Met Lys Asp Pro Asp Phe Ser Lys Tyr Asp Arg Lys Arg Asn Ser
                180                185                190

Pro Asn Glu Tyr Val Phe Ser Val Ser Arg Ala Glu Leu Glu Lys Glu
                195                200                205

Ile Val Thr Leu Phe Ala Ala Gln Arg Arg Phe Gln Ser Pro Tyr Ala
        210                215                220

Ser Lys Asp Leu Gln Glu Thr Tyr Leu Gln Ile Trp Thr His Gln Leu
225                230                235                240

Pro Phe Ala Ser Gly Asn Ala Ile Leu Asn Lys Val Gly Tyr Cys Ser
                245                250                255

Leu Leu Lys Gly Lys Glu Arg Arg Ile Pro Lys Ala Thr Tyr Thr Phe
                260                265                270

Gln Tyr Phe Ser Ala Leu Asp Gln Val Asn Arg Thr Arg Leu Gly Pro
                275                280                285

Asp Phe Gln Pro Phe Thr Lys Glu Gln Arg Glu Ile Ile Leu Asn Asn
        290                295                300

Met Phe Gln Arg Thr Asp Tyr Tyr Lys Lys Lys Thr Ile Pro Glu Val
305                310                315                320

Thr Tyr Tyr Asp Ile Arg Lys Trp Leu Glu Leu Asp Glu Thr Ile Gln
                325                330                335

Phe Lys Gly Leu Asn Tyr Asp Pro Asn Glu Glu Leu Lys Lys Ile Glu
                340                345                350

Lys Lys Pro Phe Ile Asn Leu Lys Ala Phe Tyr Glu Ile Asn Lys Val
                355                360                365

Val Ala Asn Tyr Ser Glu Arg Thr Asn Glu Thr Phe Ser Thr Leu Asp
        370                375                380

Tyr Asp Gly Ile Gly Tyr Ala Leu Thr Val Tyr Lys Thr Asp Lys Asp
385                390                395                400

Ile Arg Ser Tyr Leu Lys Ser Ser His Asn Leu Pro Lys Arg Cys Tyr
                405                410                415

Asp Asp Gln Leu Ile Glu Glu Leu Leu Ser Leu Ser Tyr Thr Lys Phe
                420                425                430

Gly His Leu Ser Leu Lys Ala Ile Asn His Val Leu Ser Ile Met Gln
                435                440                445

Lys Gly Asn Thr Tyr Lys Glu Ala Val Asp Gln Leu Gly Tyr Asp Thr
        450                455                460

Ser Gly Leu Lys Lys Glu Lys Arg Ser Lys Phe Leu Pro Pro Ile Ser
465                470                475                480

Asp Glu Ile Thr Asn Pro Ile Val Lys Arg Ala Leu Thr Gln Ala Arg
                485                490                495

Lys Val Val Asn Ala Ile Ile Arg Arg His Gly Ser Pro His Ser Val
                500                505                510

His Ile Glu Leu Ala Arg Glu Leu Ser Lys Asn His Asp Glu Arg Thr
                515                520                525

Lys Ile Val Ser Ala Gln Asp Glu Asn Tyr Lys Lys Asn Lys Gly Ala
        530                535                540

Ile Ser Ile Leu Ser Glu His Gly Ile Leu Asn Pro Thr Gly Tyr Asp
545                550                555                560
```

-continued

```
Ile Val Arg Tyr Lys Leu Trp Lys Glu Gln Gly Glu Arg Cys Ala Tyr
                565             570             575

Ser Leu Lys Glu Ile Pro Ala Asp Thr Phe Phe Asn Glu Leu Lys Lys
            580             585             590

Glu Arg Asn Gly Ala Pro Ile Leu Glu Val Asp His Ile Leu Pro Tyr
            595             600             605

Ser Gln Ser Phe Ile Asp Ser Tyr His Asn Lys Val Leu Val Tyr Ser
        610             615             620

Asp Glu Asn Arg Lys Lys Gly Asn Arg Ile Pro Tyr Thr Tyr Phe Leu
625             630             635             640

Glu Thr Asn Lys Asp Trp Glu Ala Phe Glu Arg Tyr Val Arg Ser Asn
            645             650             655

Lys Phe Phe Ser Lys Lys Lys Arg Glu Tyr Leu Leu Lys Arg Ala Tyr
            660             665             670

Leu Pro Arg Glu Ser Glu Leu Ile Lys Glu Arg His Leu Asn Asp Thr
            675             680             685

Arg Tyr Ala Ser Thr Phe Leu Lys Asn Phe Ile Glu Gln Asn Leu Gln
        690             695             700

Phe Lys Glu Ala Glu Asp Asn Pro Arg Lys Arg Arg Val Gln Thr Val
705             710             715             720

Asn Gly Val Ile Thr Ala His Phe Arg Lys Arg Trp Gly Leu Glu Lys
            725             730             735

Asp Arg Gln Glu Thr Tyr Leu His His Ala Met Asp Ala Ile Ile Val
            740             745             750

Ala Cys Thr Asp His His Met Val Thr Arg Val Thr Glu Tyr Tyr Gln
            755             760             765

Ile Lys Glu Ser Asn Lys Ser Val Lys Lys Pro Tyr Phe Pro Met Pro
        770             775             780

Trp Glu Gly Phe Arg Asp Glu Leu Leu Ser His Leu Ala Ser Gln Pro
785             790             795             800

Ile Ala Lys Lys Ile Ser Glu Glu Leu Lys Ala Gly Tyr Gln Ser Leu
            805             810             815

Asp Tyr Ile Phe Val Ser Arg Met Pro Lys Arg Ser Ile Thr Gly Ala
            820             825             830

Ala His Lys Gln Thr Ile Met Arg Lys Gly Gly Ile Asp Lys Lys Gly
            835             840             845

Lys Thr Ile Ile Ile Glu Arg Leu His Leu Lys Asp Ile Lys Phe Asp
        850             855             860

Glu Asn Gly Asp Phe Lys Met Val Gly Lys Glu Gln Asp Met Ala Thr
865             870             875             880

Tyr Glu Ala Ile Lys Gln Arg Tyr Leu Glu His Gly Lys Asn Ser Lys
            885             890             895

Lys Ala Phe Glu Thr Pro Leu Tyr Lys Pro Ser Lys Lys Gly Thr Gly
            900             905             910

Asn Leu Ile Lys Arg Val Lys Val Glu Gly Gln Ala Lys Ser Phe Val
            915             920             925

Arg Glu Val Asn Gly Gly Val Ala Gln Asn Gly Asp Leu Val Arg Val
        930             935             940

Asp Leu Phe Glu Lys Asp Asp Lys Tyr Tyr Met Val Pro Ile Tyr Val
945             950             955             960

Pro Asp Thr Val Cys Ser Glu Leu Pro Lys Lys Val Val Ala Ser Ser
            965             970             975
```

```
Lys Gly Tyr Glu Gln Trp Leu Thr Leu Asp Asn Ser Phe Thr Phe Lys
        980                 985                 990

Phe Ser Leu Tyr Pro Tyr Asp Leu  Val Arg Leu Val Lys  Gly Asp Glu
        995                 1000                1005

Asp Arg  Phe Leu Tyr Phe Gly  Thr Leu Asp Ile Asp  Ser Asp Arg
    1010                1015                1020

Leu Asn  Phe Lys Asp Val Asn  Lys Pro Ser Lys Lys  Asn Glu Tyr
    1025                1030                1035

Arg Tyr  Ser Leu Lys Thr Ile  Glu Asp Leu Glu Lys  Tyr Glu Val
    1040                1045                1050

Gly Val  Leu Gly Asp Leu Arg  Leu Val Arg Lys Glu  Thr Arg Arg
    1055                1060                1065

Asn Phe  His
    1070
```

<210> SEQ ID NO 236
<211> LENGTH: 46
<212> TYPE: RNA
<213> ORGANISM: Bacillus sp.

<400> SEQUENCE: 236
gacagcagcu uccuauaucu cguacgucau aguuccauua aagcca                     46

<210> SEQ ID NO 237
<211> LENGTH: 85
<212> TYPE: RNA
<213> ORGANISM: Bacillus sp.

<400> SEQUENCE: 237
uggcuuugau guuucuauga uaaggguuuc dacccguggc gucggggauc gccugcccau      60
ugaaaugggc uucuccccau uuauu                                            85

<210> SEQ ID NO 238
<211> LENGTH: 32
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 238
gacagcagcu uccuauaucu cguacgucau ag                                    32

<210> SEQ ID NO 239
<211> LENGTH: 71
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 239
cuaugauaag gguuucgacc cguggcgucg gggaucgccu gcccauugaa augggcuucu      60
ccccauuuau u                                                           71

<210> SEQ ID NO 240
<211> LENGTH: 36
<212> TYPE: RNA
<213> ORGANISM: Artificial Sequence
<220> FEATURE:

<221> NAME/KEY: source
<223> OTHER INFORMATION: /note="Description of Artificial Sequence:
      Synthetic oligonucleotide"

<400> SEQUENCE: 240
gacagcagcu uccuauaucu cguacgucau agccau                                          36

<210> SEQ ID NO 241
<211> LENGTH: 75
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 241
augucuauga uaaggguuuc gacccguggc gucggggauc gccugcccau ugaaaugggc      60
uucuccccau uuauu                                                       75

<210> SEQ ID NO 242
<211> LENGTH: 40
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 242
gacagcagcu uccuauaucu cguacgucau aguuccauua                            40

<210> SEQ ID NO 243
<211> LENGTH: 79
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 243
ugauguuucu augauaaggg uuucgacccg uggcgucggg gaucgccugc ccauugaaau      60
gggcuucucc ccauuuauu                                                   79

<210> SEQ ID NO 244
<211> LENGTH: 46
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 244
gacagcagcu uccuauaucu cguacgucau aguuccauua aagcca                     46

<210> SEQ ID NO 245
<211> LENGTH: 78
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 245

-continued

```
uggcuuugau guuucuauga uaaggguuuc gacccguggc gucggggauc gccugcccau        60
ugaaaugggc uucucccc                                                       78

<210> SEQ ID NO 246
<211> LENGTH: 46
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 246
gacagcagcu uccuauaucu cguacgucau aguuccauua aagcca                        46

<210> SEQ ID NO 247
<211> LENGTH: 75
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 247
uggcuuugau guuucuauga uaaggguuuc gacccguggc gucggggacc gcccauugaa        60
augggccucc ccuuu                                                          75

<210> SEQ ID NO 248
<211> LENGTH: 46
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 248
gacagcagcu uccuauaucu cguacgucau aguuccauua aagcca                        46

<210> SEQ ID NO 249
<211> LENGTH: 71
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 249
uggcuuugau guuucuauga uaaggguuuc gacccguggc gucgggaccg ccauugaaau        60
ggccucccuu u                                                              71

<210> SEQ ID NO 250
<211> LENGTH: 38
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 250
gacagcagcu uccuauaucu cguacgucau aguuccau                                 38
```

```
<210> SEQ ID NO 251
<211> LENGTH: 77
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 251
auguuucuau gauaaggguu ucgacccgug gcgucgggga ucgccugccc auugaaaugg      60
gcuucccccc auuuauu                                                    77

<210> SEQ ID NO 252
<211> LENGTH: 38
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 252
gacagcagcu uccuauaucu cguacgucau aguuccau                             38

<210> SEQ ID NO 253
<211> LENGTH: 70
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 253
auguuucuau gauaaggguu ucgacccgug gcgucgggga ucgccugccc auugaaaugg      60
gcuucccccc                                                            70

<210> SEQ ID NO 254
<211> LENGTH: 46
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 254
gacagcagcu uccuauaucu cguacgucau aguuccauua aagcca                    46

<210> SEQ ID NO 255
<211> LENGTH: 76
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 255
uggcuuugau guuucuauga uaaggguuuc gacccguggc gucggggauc gccugcccau      60
ugaaaugggc uucucc                                                     76

<210> SEQ ID NO 256
<211> LENGTH: 39
```

<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 256
gcuuccuaua ucucguacgu cauaguucca uuaaaagcca                              39

<210> SEQ ID NO 257
<211> LENGTH: 85
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 257
uggcuuugau guuucuauga uaaggguuuc gacccguggc gucggggauc gccugcccau      60
ugaaaugggc uucuccccau uuauu                                             85

<210> SEQ ID NO 258
<211> LENGTH: 38
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 258
gacagcagcu uccuauaucu cguacgucau aguuccau                               38

<210> SEQ ID NO 259
<211> LENGTH: 71
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 259
uggcuuugau guuucuauga uaaggguuuc gacccguggc gucgggaccg ccauugaaau      60
ggccucccuu u                                                            71

<210> SEQ ID NO 260
<211> LENGTH: 682
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 260
ttgtctcatg agcggataca tatttgaatg tatttagaaa aataaacaaa tagggttcc       60 gcgcacattt ccccgaaaag tgccagatac ctgaaacaaa acccatcgta cggccaagga     120
agtctccaat aactgtgatc caccacaagc gccagggttt tcccagtcac gacgttgtaa     180
aacgacggcc agtcatgcat aatccgcacg catctggaat aaggaagtgc cattccgcct     240
gacctgaaga ccaggctcga aagccttcac accctcagta agagctttct caatgtcgat     300

-continued

```
tgtgccacac accctgtcct cagtagcacc tagcggtaaa tcaaccatgt tgacggtcct    360
gtacgagata taggaagctg ctgtccgctc ctcaatttgt cacggacttc tgcactcatt    420
acttcttggt catctggatc tgaattgaac ggatcaccag aaataacttt gatttcagga    480
agtaaatcta ccaaagatct aaccgtggtg gacttcccgg ttcctctatc acccattatc    540
atcacaggct aggtggaggc tcagtgatga taagtctgcg atggtggatg catgtgtcat    600
ggtcatagct gtttcctgtg tgaaattgtt atccgctcag agggcacaat cctattccgc    660
gctatccgac aatctccaag ac                                              682
```

```
<210> SEQ ID NO 261
<211> LENGTH: 82
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 261

Thr Asn Leu Ser Asp His Glu Lys Glu Thr Gly Lys Gln Leu Val Ile
1               5                   10                  15

Gln Glu Ser Ile Leu Met Leu Pro Glu Glu Val Glu Glu Val Ile Gly
            20                  25                  30

Asn Lys Pro Glu Ser Asp Ile Leu Val His Thr Ala Tyr Asp Glu Ser
        35                  40                  45

Thr Asp Glu Asn Val Met Leu Leu Thr Ser Asp Ala Pro Glu Tyr Lys
    50                  55                  60

Pro Trp Ala Leu Val Ile Gln Asp Ser Asn Gly Glu Asn Lys Ile Lys
65                  70                  75                  80

Met Leu
```

```
<210> SEQ ID NO 262
<211> LENGTH: 1072
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 262

Met Ser Glu Leu Asp Tyr Arg Ile Gly Leu Ala Ile Gly Thr Asn Ser
1               5                   10                  15

Ile Gly Trp Gly Val Ile Glu Leu Phe Trp Asn Lys Asp Arg Glu Arg
            20                  25                  30

Tyr Glu Lys Val Arg Ile Val Asp Lys Gly Val Arg Met Phe Asp Lys
        35                  40                  45

Ala Glu Ile Pro Asn Lys Gly Ala Ser Leu Ala Glu Pro Arg Arg Ile
    50                  55                  60

Ala Arg Ser Ser Arg Arg Arg Leu Asn Arg Lys Ser Gln Arg Lys Lys
65                  70                  75                  80

Glu Ile Arg Asn Leu Leu Val Gln His Gly Met Ile Thr Gln Glu Glu
                85                  90                  95

Leu Asp Leu Leu Tyr Pro Leu Ser Lys Lys Ser Ile Asp Ile Trp Asp
            100                 105                 110

Ile Arg Leu Asp Gly Leu Asp Arg Leu Leu Asn His Leu Glu Trp Ala
        115                 120                 125
```

Arg Leu Leu Ile His Leu Ala Gln Arg Arg Gly Phe Lys Ser Asn Arg
    130                 135                 140

Lys Ser Glu Leu Lys Asp Ala Glu Thr Gly Lys Val Leu Ser Ser Ile
145                 150                 155                 160

Gln Val Asn Glu Lys Arg Leu Phe Leu Tyr Arg Thr Val Gly Glu Met
                165                 170                 175

Trp Ile Lys Asp Ala Glu Phe Ser Lys Tyr Asp Arg Arg Arg Asn Ser
                180                 185                 190

Pro Asn Glu Tyr Val Phe Ser Val Ser Arg Ala Asp Leu Glu Lys Glu
                195                 200                 205

Ile Val Thr Leu Phe Glu Ala Gln Arg Lys Phe Gln Ser Ser Tyr Ala
    210                 215                 220

Ser Lys Asn Leu Gln Glu Thr Tyr Leu Gln Ile Trp Ala His Gln Leu
225                 230                 235                 240

Pro Phe Ala Ser Gly Asn Ala Ile Leu Asn Lys Val Gly Tyr Cys Ser
                245                 250                 255

Leu Leu Lys Gly Lys Glu Arg Arg Ile Pro Lys Ala Thr Tyr Thr Phe
                260                 265                 270

Gln Tyr Phe Ser Ala Leu Asp Gln Val Asn Arg Thr Arg Leu Gly Pro
                275                 280                 285

Asp Phe Gln Pro Phe Thr Gln Glu Gln Lys Glu Ile Ile Leu Asp Lys
    290                 295                 300

Met Phe Gln Arg Thr Asp Tyr Tyr Lys Lys Lys Thr Ile Pro Glu Val
305                 310                 315                 320

Ser Tyr Tyr Asp Ile Arg Lys Trp Leu Glu Leu Asp Glu Thr Ile Gln
                325                 330                 335

Phe Lys Gly Leu Asn Tyr Asp Pro Asn Glu Glu Leu Lys Lys Ile Glu
                340                 345                 350

Lys Lys Pro Phe Ile Asn Leu Lys Ala Phe Tyr Glu Ile Lys Lys Val
                355                 360                 365

Val Ala Asn Tyr Ala Glu Arg Thr Asn Glu Ala Phe Ser Thr Leu Asp
    370                 375                 380

Tyr Asp Ala Ile Ala Tyr Ala Leu Thr Val Tyr Lys Thr Asp Lys Asp
385                 390                 395                 400

Ile Arg Ser Tyr Leu Lys Lys Ser Asn Asn Leu Ser Lys Arg Cys Tyr
                405                 410                 415

Asp Asp Gln Leu Ile Glu Glu Leu Phe Thr Leu Ser Tyr Thr Lys Phe
                420                 425                 430

Gly His Leu Ser Phe Lys Ala Ile Asn His Val Leu Pro Ile Met Gln
                435                 440                 445

Glu Gly Arg Thr Tyr Gln Glu Ala Ile His Gln Leu Gly Tyr Asp Thr
    450                 455                 460

Thr Asn Leu Lys Lys Glu Asn Arg Ser Met Phe Leu Pro Leu Ile Pro
465                 470                 475                 480

Asp Glu Ile Thr Asn Pro Ile Val Lys Arg Ala Ile Thr Gln Ala Arg
                485                 490                 495

Lys Val Val Asn Ala Ile Ile Arg Arg Tyr Gly Ser Pro Asn Ser Val
                500                 505                 510

His Ile Glu Leu Ala Arg Glu Leu Ser Lys Ser His Asp Glu Arg Lys
                515                 520                 525

Lys Ile Met Thr Ala His Asp Glu Asn Tyr Lys Lys Asn Lys Gly Ala
    530                 535                 540

Ile Ser Ile Leu Ile Glu Asn Gly Ile Leu Asn Pro Thr Gly Tyr Asp

-continued

```
545              550              555              560

Ile Val Arg Tyr Lys Leu Trp Lys Glu Gln Gly Glu Arg Cys Ala Tyr
             565              570              575

Ser Leu Lys Glu Ile Pro Pro Asp Thr Phe Phe Asn Glu Leu Lys Lys
             580              585              590

Glu Arg Asn Gly Ser Pro Ile Leu Glu Val Asp His Ile Leu Pro Tyr
             595              600              605

Ser Gln Ser Phe Ile Asp Ser Tyr His Asn Lys Val Leu Val Tyr Ser
610              615              620

Asp Glu Asn Arg Asn Lys Gly Asn Arg Ile Pro Tyr Thr Tyr Phe Leu
625              630              635              640

Glu Thr Asn Lys Asp Trp Glu Ala Phe Glu Arg Tyr Val Arg Ser Asn
             645              650              655

Lys Leu Phe Ser Lys Lys Lys Arg Glu Tyr Leu Leu Lys Lys Thr Tyr
             660              665              670

Leu Pro Arg Glu Ser Glu Leu Ile Lys Glu Arg His Leu Asn Asp Thr
             675              680              685

Arg Tyr Ala Ser Thr Phe Leu Lys Asn Phe Ile Glu Gln Asn Leu Gln
             690              695              700

Phe Lys Glu Val Glu Val Asn Leu Arg Lys Lys Arg Val Gln Thr Val
705              710              715              720

Asn Gly Val Ile Thr Ala His Leu Arg Lys Arg Trp Gly Leu Glu Lys
             725              730              735

Asn Arg Gln Glu Thr Tyr Leu His His Ala Met Asp Ala Ile Ile Val
             740              745              750

Ala Cys Thr Asp His His Met Val Thr Arg Ile Thr Glu Tyr Tyr Gln
             755              760              765

Ile Lys Glu Ser Asn Lys Ser Val Lys Lys Pro Tyr Phe Pro Met Pro
             770              775              780

Trp Glu Gly Phe Arg Asp Glu Leu Leu Ser His Leu Ala Ser Gln Pro
785              790              795              800

Ile Ala Lys Lys Ile Ser Glu Glu Leu Lys Ala Gly Tyr Gln Ser Ser
             805              810              815

Asp Tyr Ile Phe Val Ser Arg Met Pro Lys Arg Ser Val Thr Gly Ala
             820              825              830

Ala His Asp Gln Thr Ile Arg Arg Lys Gly Gly Ile Asp Lys Lys Gly
             835              840              845

Lys Thr Ile Ile Ile Lys Arg Val Arg Leu Lys Asp Ile Lys Phe Asp
850              855              860

Glu Asn Gly Asp Phe Lys Met Val Gly Lys Glu Gln Asp Leu Ala Thr
865              870              875              880

Tyr Glu Ala Ile Lys Gln Arg Tyr Leu Glu His Arg Lys Asn Ser Lys
             885              890              895

Lys Ala Phe Glu Thr Pro Leu Tyr Lys Pro Ser Lys Lys Gly Thr Gly
             900              905              910

Asn Leu Ile Lys Arg Val Lys Ile Glu Gly Gln Thr Lys Ala Phe Val
             915              920              925

Arg Glu Val Asn Gly Gly Val Ala Gln Asn Ser Asp Leu Val Arg Val
             930              935              940

Asp Leu Phe Glu Lys Asp Asp Lys Tyr Tyr Met Val Pro Ile Tyr Val
945              950              955              960

Pro Asp Thr Val Cys Ser Glu Leu Pro Lys Lys Val Val Lys Ser Gly
             965              970              975
```

```
Lys Gly Tyr Glu Gln Trp Leu Thr Leu Asp Asn Ser Phe Thr Phe Lys
        980                 985                 990

Ser Ser Leu Tyr Pro Tyr Asp Leu  Val Arg Leu Val Lys  Gly Asn Glu
        995                 1000                1005

Asp Arg  Phe Leu Tyr Phe Gly  Thr Leu Asp Ile Asp  Ser Asp Arg
    1010                1015                1020

Leu Asn  Phe Lys Asp Val Asn  Lys Pro Ser Lys Gln  Asn Glu Tyr
    1025                1030                1035

Arg Tyr  Ser Leu Lys Thr Ile  Glu Asn Leu Glu Lys  Tyr Glu Val
    1040                1045                1050

Gly Val  Leu Gly Asp Leu Arg  Leu Val Lys Gln Glu  Thr Arg Arg
    1055                1060                1065

Ile Phe  Asn Arg
    1070
```

```
<210> SEQ ID NO 263
<211> LENGTH: 130
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 263
catggcagta cattagagca gtcatagttc cattaaagcc aaaagtggct ttgatgtttc      60
tatgataagg gtttcgaccc gtggcgtcgg ggatcgcctg cccattgaaa tgggcttctc     120
cccatttatt                                                            130
```

```
<210> SEQ ID NO 264
<211> LENGTH: 130
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 264
cacatctcga gcaagacgtt gtcatagttc cattaaagcc aaaagtggct ttgatgtttc      60
tatgataagg gtttcgaccc gtggcgtcgg ggatcgcctg cccattgaaa tgggcttctc     120
cccatttatt                                                            130
```

```
<210> SEQ ID NO 265
<211> LENGTH: 130
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 265
cttctatagc ctccttcccc gtcatagttc cattaaagcc aaaagtggct ttgatgtttc      60
tatgataagg gtttcgaccc gtggcgtcgg ggatcgcctg cccattgaaa tgggcttctc     120
cccatttatt                                                            130
```

```
<210> SEQ ID NO 266
<211> LENGTH: 50
```

```
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 266
caggtcgact ctagaggatc ccatgatata gacgttgtgg ctgttgtagt              50

<210> SEQ ID NO 267
<211> LENGTH: 53
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (19)..(23)
<223> OTHER INFORMATION: a, c, t, g, unknown or other

<400> SEQUENCE: 267
aacgacggcc agtgaattnn nnnactacaa cagccacaac gtctatatca tgg           53

<210> SEQ ID NO 268
<211> LENGTH: 1493
<212> TYPE: PRT
<213> ORGANISM: Homo sapiens

<400> SEQUENCE: 268

Met Pro Asn Glu Gly Ile Pro His Ser Ser Gln Thr Gln Glu Gln Asp
1               5                   10                  15

Cys Leu Gln Ser Gln Pro Val Ser Asn Asn Glu Glu Met Ala Ile Lys
            20                  25                  30

Gln Glu Ser Gly Gly Asp Gly Glu Val Glu Glu Tyr Leu Ser Phe Arg
        35                  40                  45

Ser Val Gly Asp Gly Leu Ser Thr Ser Ala Val Gly Cys Ala Ser Ala
    50                  55                  60

Ala Pro Arg Arg Gly Pro Ala Leu Leu His Ile Asp Arg His Gln Ile
65                  70                  75                  80

Gln Ala Val Glu Pro Ser Ala Gln Ala Leu Glu Leu Gln Gly Leu Gly
                85                  90                  95

Val Asp Val Tyr Asp Gln Asp Val Leu Glu Gln Gly Val Leu Gln Gln
            100                 105                 110

Val Asp Asn Ala Ile His Glu Ala Ser Arg Ala Ser Gln Leu Val Asp
        115                 120                 125

Val Glu Lys Glu Tyr Arg Ser Val Leu Asp Asp Leu Thr Ser Cys Thr
    130                 135                 140

Thr Ser Leu Arg Gln Ile Asn Lys Ile Ile Glu Gln Leu Ser Pro Gln
145                 150                 155                 160

Ala Ala Thr Ser Arg Asp Ile Asn Arg Lys Leu Asp Ser Val Lys Arg
                165                 170                 175

Gln Lys Tyr Asn Lys Glu Gln Gln Leu Lys Lys Ile Thr Ala Lys Gln
            180                 185                 190

Lys His Leu Gln Ala Ile Leu Gly Gly Ala Glu Val Lys Ile Glu Leu
        195                 200                 205

Asp His Ala Ser Leu Glu Glu Asp Ala Glu Pro Gly Pro Ser Ser Leu
    210                 215                 220
```

-continued

```
Gly Ser Met Leu Met Pro Val Gln Glu Thr Ala Trp Glu Glu Leu Ile
225             230                 235                 240

Arg Thr Gly Gln Met Thr Pro Phe Gly Thr Gln Ile Pro Gln Lys Gln
                245                 250                 255

Glu Lys Lys Pro Arg Lys Ile Met Leu Asn Glu Ala Ser Gly Phe Glu
                260                 265                 270

Lys Tyr Leu Ala Asp Gln Ala Lys Leu Ser Phe Glu Arg Lys Lys Gln
        275                 280                 285

Gly Cys Asn Lys Arg Ala Ala Arg Lys Ala Pro Ala Pro Val Thr Pro
        290                 295                 300

Pro Ala Pro Val Gln Asn Lys Asn Lys Pro Asn Lys Lys Ala Arg Val
305                 310                 315                 320

Leu Ser Lys Lys Glu Glu Arg Leu Lys Lys His Ile Lys Lys Leu Gln
                325                 330                 335

Lys Arg Ala Leu Gln Phe Gln Gly Lys Val Gly Leu Pro Lys Ala Arg
                340                 345                 350

Arg Pro Trp Glu Ser Asp Met Arg Pro Glu Ala Glu Gly Asp Ser Glu
        355                 360                 365

Gly Glu Glu Ser Glu Tyr Phe Pro Thr Glu Glu Glu Glu Glu Glu Glu
        370                 375                 380

Asp Asp Glu Val Glu Gly Ala Glu Ala Asp Leu Ser Gly Asp Gly Thr
385                 390                 395                 400

Asp Tyr Glu Leu Lys Pro Leu Pro Lys Gly Gly Lys Arg Gln Lys Lys
                405                 410                 415

Val Pro Val Gln Glu Ile Asp Asp Asp Phe Phe Pro Ser Ser Gly Glu
                420                 425                 430

Glu Ala Glu Ala Ala Ser Val Gly Glu Gly Gly Gly Gly Arg Lys
        435                 440                 445

Val Gly Arg Tyr Arg Asp Asp Gly Asp Glu Asp Tyr Tyr Lys Gln Arg
        450                 455                 460

Leu Arg Arg Trp Asn Lys Leu Arg Leu Gln Asp Lys Glu Lys Arg Leu
465                 470                 475                 480

Lys Leu Glu Asp Asp Ser Glu Glu Ser Asp Ala Glu Phe Asp Glu Gly
                485                 490                 495

Phe Lys Val Pro Gly Phe Leu Phe Lys Lys Leu Phe Lys Tyr Gln Gln
                500                 505                 510

Thr Gly Val Arg Trp Leu Trp Glu Leu His Cys Gln Gln Ala Gly Gly
        515                 520                 525

Ile Leu Gly Asp Glu Met Gly Leu Gly Lys Thr Ile Gln Ile Ile Ala
        530                 535                 540

Phe Leu Ala Gly Leu Ser Tyr Ser Lys Ile Arg Thr Arg Gly Ser Asn
545                 550                 555                 560

Tyr Arg Phe Glu Gly Leu Gly Pro Thr Val Ile Val Cys Pro Thr Thr
                565                 570                 575

Val Met His Gln Trp Val Lys Glu Phe His Thr Trp Trp Pro Pro Phe
        580                 585                 590

Arg Val Ala Ile Leu His Glu Thr Gly Ser Tyr Thr His Lys Lys Glu
        595                 600                 605

Lys Leu Ile Arg Asp Val Ala His Cys His Gly Ile Leu Ile Thr Ser
        610                 615                 620

Tyr Ser Tyr Ile Arg Leu Met Gln Asp Asp Ile Ser Arg Tyr Asp Trp
625                 630                 635                 640

His Tyr Val Ile Leu Asp Glu Gly His Lys Ile Arg Asn Pro Asn Ala
```

-continued

```
              645            650             655

Ala Val Thr Leu Ala Cys Lys Gln Phe Arg Thr Pro His Arg Ile Ile
             660             665             670

Leu Ser Gly Ser Pro Met Gln Asn Asn Leu Arg Glu Leu Trp Ser Leu
             675             680             685

Phe Asp Phe Ile Phe Pro Gly Lys Leu Gly Thr Leu Pro Val Phe Met
         690             695             700

Glu Gln Phe Ser Val Pro Ile Thr Met Gly Gly Tyr Ser Asn Ala Ser
     705             710             715             720

Pro Val Gln Val Lys Thr Ala Tyr Lys Cys Ala Cys Val Leu Arg Asp
             725             730             735

Thr Ile Asn Pro Tyr Leu Leu Arg Arg Met Lys Ser Asp Val Lys Met
             740             745             750

Ser Leu Ser Leu Pro Asp Lys Asn Glu Gln Val Leu Phe Cys Arg Leu
             755             760             765

Thr Asp Glu Gln His Lys Val Tyr Gln Asn Phe Val Asp Ser Lys Glu
         770             775             780

Val Tyr Arg Ile Leu Asn Gly Glu Met Gln Ile Phe Ser Gly Leu Ile
     785             790             795             800

Ala Leu Arg Lys Ile Cys Asn His Pro Asp Leu Phe Ser Gly Gly Pro
             805             810             815

Lys Asn Leu Lys Gly Leu Pro Asp Asp Glu Leu Glu Glu Asp Gln Phe
             820             825             830

Gly Tyr Trp Lys Arg Ser Gly Lys Met Ile Val Val Glu Ser Leu Leu
             835             840             845

Lys Ile Trp His Lys Gln Gly Gln Arg Val Leu Leu Phe Ser Gln Ser
     850             855             860

Arg Gln Met Leu Asp Ile Leu Glu Val Phe Leu Arg Ala Gln Lys Tyr
865             870             875             880

Thr Tyr Leu Lys Met Asp Gly Thr Thr Thr Ile Ala Ser Arg Gln Pro
             885             890             895

Leu Ile Thr Arg Tyr Asn Glu Asp Thr Ser Ile Phe Val Phe Leu Leu
             900             905             910

Thr Thr Arg Val Gly Gly Leu Gly Val Asn Leu Thr Gly Ala Asn Arg
             915             920             925

Val Val Ile Tyr Asp Pro Asp Trp Asn Pro Ser Thr Asp Thr Gln Ala
     930             935             940

Arg Glu Arg Ala Trp Arg Ile Gly Gln Lys Lys Gln Val Thr Val Tyr
945             950             955             960

Arg Leu Leu Thr Ala Gly Thr Ile Glu Glu Lys Ile Tyr His Arg Gln
             965             970             975

Ile Phe Lys Gln Phe Leu Thr Asn Arg Val Leu Lys Asp Pro Lys Gln
             980             985             990

Arg Arg Phe Phe Lys Ser Asn Asp Leu Tyr Glu Leu Phe Thr Leu Thr
             995             1000            1005

Ser Pro Asp Ala Ser Gln Ser Thr Glu Thr Ser Ala Ile Phe Ala
     1010            1015            1020

Gly Thr Gly Ser Asp Val Gln Thr Pro Lys Cys His Leu Lys Arg
     1025            1030            1035

Arg Ile Gln Pro Ala Phe Gly Ala Asp His Asp Val Pro Lys Arg
     1040            1045            1050

Lys Lys Phe Pro Ala Ser Asn Ile Ser Val Asn Asp Ala Thr Ser
     1055            1060            1065
```

-continued

```
Ser Glu  Glu Lys Ser Glu Ala  Lys Gly Ala Glu Val  Asn Ala Val
    1070             1075             1080

Thr Ser  Asn Arg Ser Asp Pro  Leu Lys Asp Asp Pro  His Met Ser
    1085             1090             1095

Ser Asn  Val Thr Ser Asn Asp  Arg Leu Gly Glu Glu  Thr Asn Ala
    1100             1105             1110

Val Ser  Gly Pro Glu Glu Leu  Ser Val Ile Ser Gly  Asn Gly Glu
    1115             1120             1125

Cys Ser  Asn Ser Ser Gly Thr  Gly Lys Thr Ser Met  Pro Ser Gly
    1130             1135             1140

Asp Glu  Ser Ile Asp Glu Lys  Leu Gly Leu Ser Tyr  Lys Arg Glu
    1145             1150             1155

Arg Pro  Ser Gln Ala Gln Thr  Glu Ala Phe Trp Glu  Asn Lys Gln
    1160             1165             1170

Met Glu  Asn Asn Phe Tyr Lys  His Lys Ser Lys Thr  Lys His His
    1175             1180             1185

Ser Val  Ala Glu Glu Glu Thr  Leu Glu Lys His Leu  Arg Pro Lys
    1190             1195             1200

Gln Lys  Pro Lys Asn Ser Lys  His Cys Arg Asp Ala  Lys Phe Glu
    1205             1210             1215

Gly Thr  Arg Ile Pro His Leu  Val Lys Lys Arg Arg  Tyr Gln Lys
    1220             1225             1230

Gln Asp  Ser Glu Asn Lys Ser  Glu Ala Lys Glu Gln  Ser Asn Asp
    1235             1240             1245

Asp Tyr  Val Leu Glu Lys Leu  Phe Lys Lys Ser Val  Gly Val His
    1250             1255             1260

Ser Val  Met Lys His Asp Ala  Ile Met Asp Gly Ala  Ser Pro Asp
    1265             1270             1275

Tyr Val  Leu Val Glu Ala Glu  Ala Asn Arg Val Ala  Gln Asp Ala
    1280             1285             1290

Leu Lys  Ala Leu Arg Leu Ser  Arg Gln Arg Cys Leu  Gly Ala Val
    1295             1300             1305

Ser Gly  Val Pro Thr Trp Thr  Gly His Arg Gly Ile  Ser Gly Ala
    1310             1315             1320

Pro Ala  Gly Lys Lys Ser Arg  Phe Gly Lys Lys Arg  Asn Ser Asn
    1325             1330             1335

Phe Ser  Val Gln His Pro Ser  Ser Thr Ser Pro Thr  Glu Lys Cys
    1340             1345             1350

Gln Asp  Gly Ile Met Lys Lys  Glu Gly Lys Asp Asn  Val Pro Glu
    1355             1360             1365

His Phe  Ser Gly Arg Ala Glu  Asp Ala Asp Ser Ser  Ser Gly Pro
    1370             1375             1380

Leu Ala  Ser Ser Ser Leu Leu  Ala Lys Met Arg Ala  Arg Asn His
    1385             1390             1395

Leu Ile  Leu Pro Glu Arg Leu  Glu Ser Glu Ser Gly  His Leu Gln
    1400             1405             1410

Glu Ala  Ser Ala Leu Leu Pro  Thr Thr Glu His Asp  Asp Leu Leu
    1415             1420             1425

Val Glu  Met Arg Asn Phe Ile  Ala Phe Gln Ala His  Thr Asp Gly
    1430             1435             1440

Gln Ala  Ser Thr Arg Glu Ile  Leu Gln Glu Phe Glu  Ser Lys Leu
    1445             1450             1455
```

```
Ser Ala  Ser Gln Ser Cys Val  Phe Arg Glu Leu Leu  Arg Asn Leu
    1460             1465               1470

Cys Thr  Phe His Arg Thr Ser  Gly Gly Glu Gly Ile  Trp Lys Leu
    1475             1480               1485

Lys Pro  Glu Tyr Cys
    1490
```

```
<210> SEQ ID NO 269
<211> LENGTH: 135
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 269
cgacgguuag aggccguaug ucgauuugcu uuaauuucgu gcgugugcau ugucguccuc      60
cauuacaggg cggcuaccac gaauagccac gaaguaaaag cuucguggcu agcacgcuug     120
cacuagacua gcuuc                                                      135

<210> SEQ ID NO 270
<211> LENGTH: 135
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 270
cgacgguuag aggccguaug ucgauuugcu uuaauuucgu gcgugugcau ugucguccuc      60
cauuacaggg cggcuaccac gaauagccac gaaguaaaag cuucguggcu agcaccuuuu     120
aucacaggcu ccagg                                                      135

<210> SEQ ID NO 271
<211> LENGTH: 25
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 271
gacagcagcu uccuauaucu cguac                                            25

<210> SEQ ID NO 272
<211> LENGTH: 18
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 272
gcuuccuaua ucucguac                                                    18

<210> SEQ ID NO 273
<211> LENGTH: 22
<212> TYPE: RNA
<213> ORGANISM: Brevibacillus sp.
```

-continued

<400> SEQUENCE: 273
uggaaagcuu cgagguuagc ac                                        22

<210> SEQ ID NO 274
<211> LENGTH: 95
<212> TYPE: RNA
<213> ORGANISM: Brevibacillus sp.

<400> SEQUENCE: 274
cgacgguuag aggccguaug ucgauuugcu uuaauuucgu gcgugugcau ugucguccuc    60
cauuacaggg cggcuaccac gaauagccac gaagu                            95

<210> SEQ ID NO 275
<211> LENGTH: 151
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: modified_base
<222> LOCATION: (132)..(151)
<223> OTHER INFORMATION: a, c, u, g, unknown or other

<400> SEQUENCE: 275
cgacgguuag aggccguaug ucgauuugcu uuaauuucgu gcgugugcau ugucguccuc    60
cauuacaggg cggcuaccac gaauagucac gaaguuccac ugaguaaagu ggaaagcuuc   120
gagguuagca cnnnnnnnnn nnnnnnnnnn n                               151

<210> SEQ ID NO 276
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic 6xHis tag"

<400> SEQUENCE: 276

His His His His His His
1               5

<210> SEQ ID NO 277
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic 10xHis tag"

<400> SEQUENCE: 277

His His His His His His His His His His
1               5                   10

<210> SEQ ID NO 278
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 278
cccgtataaa gcatgagacc gtgac                                              25

<210> SEQ ID NO 279
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 279
ctcagactgt ttgcccctta ctgct                                             25

<210> SEQ ID NO 280
<211> LENGTH: 135
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 280
cgacgguuag aggccguaug ucgauuugcu uuaauuucgu gcgugugcau ugucguccuc       60
cauuacaggg cggcuaccac gaauagccac gaaguaaaag cuucguggcu agcaccccgu       120
auaaagcaug agacc                                                        135

<210> SEQ ID NO 281
<211> LENGTH: 135
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 281
cgacgguuag aggccguaug ucgauuugcu uuaauuucgu gcgugugcau ugucguccuc       60
cauuacaggg cggcuaccac gaauagccac gaaguaaaag cuucguggcu agcaccucag       120
acuguuugcc ccuua                                                        135

<210> SEQ ID NO 282
<211> LENGTH: 156
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 282
cgacgguuag aggccguaug ucgauuugcu uuaauuucgu gcgugugcau ugucguccuc       60
cauuacaggg cggcuaccac gaauagucac gaaguuccac ugaguaaagu ggaaagcuuc       120
gagguuagca ccccguauaa agcaugagac cgugac                                 156

<210> SEQ ID NO 283
<211> LENGTH: 156
<212> TYPE: RNA
<213> ORGANISM: Artificial Sequence
<220> FEATURE:
<221> NAME/KEY: source
<223> OTHER INFORMATION: /note="Description of Artificial Sequence:

-continued

Synthetic polynucleotide"

<400> SEQUENCE: 283
cgacgguuag aggccguaug ucgauuugcu uuaauuucgu gcgugugcau ugucguccuc      60
cauuacaggg cggcuaccac gaauagucac gaaguuccac ugaguaaagu ggaaagcuuc     120
gagguuagca ccucagacug uuugcccuu acugcu                                156

<210> SEQ ID NO 284
<211> LENGTH: 4
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 284 aaaa                                                                    4

<210> SEQ ID NO 285
<211> LENGTH: 135
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: modified_base
<222> LOCATION: (116)..(135)
<223> OTHER INFORMATION: a, c, u, g, unknown or other

<400> SEQUENCE: 285
cgacgguuag aggccguaug ucgauuugcu uuaauuucgu gcgugugcau ugucguccuc      60
cauuacaggg cggcuaccac gaauagccac gaaguaaaag cuucguggcu agcacnnnnn     120
nnnnnnnnnn nnnnn                                                       135

<210> SEQ ID NO 286
<211> LENGTH: 95
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 286
cgacgguuag aggccguaug ucgauuugcu uuaauuucgu gcgugugcau ugucguccuc      60
cauuacaggg cggcuaccac gaauagccac gaagu                                 95

<210> SEQ ID NO 287
<211> LENGTH: 16
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 287
gcuucguggc uagcac                                                       16

<210> SEQ ID NO 288
<211> LENGTH: 151

```
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: modified_base
<222> LOCATION: (132)..(151)
<223> OTHER INFORMATION: a, c, u, g, unknown or other

<400> SEQUENCE: 288
cgacgguuag aggccguaug ucgauuugcu uuaauuucgu gcgugugcau ugucguccuc      60
cauuacaggg cggcuaccac gaauagucac gaaguuccac ugaguaaagu ggaaagcuuc     120
gagguuagca cnnnnnnnnn nnnnnnnnnn n                                    151

<210> SEQ ID NO 289
<211> LENGTH: 135
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: modified_base
<222> LOCATION: (116)..(135)
<223> OTHER INFORMATION: a, c, u, g, unknown or other

<400> SEQUENCE: 289
cgacgguuag aggccguaug ucgauuugcu uuaauuucgu gcgugugcau ugucguccuc      60
cauuacaggg cggcuaccac gaauagucac gaaguaaaag cuucgagguu agcacnnnnn     120
nnnnnnnnnn nnnnn                                                      135

<210> SEQ ID NO 290
<211> LENGTH: 144
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: modified_base
<222> LOCATION: (125)..(144)
<223> OTHER INFORMATION: a, c, u, g, unknown or other

<400> SEQUENCE: 290
cgacgguuag aggccguaug ucgauuugcu uuaauuucgu gcgugugcau ugucguccuc      60
cauuacaggg cggcuaccac gaauagccac gaaguuccaa aauggaaagc uucguggcua     120
gcacnnnnnn nnnnnnnnnn nnnn                                            144

<210> SEQ ID NO 291
<211> LENGTH: 135
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: modified_base
<222> LOCATION: (116)..(135)
<223> OTHER INFORMATION: a, c, u, g, unknown or other

<400> SEQUENCE: 291
```

-continued

```
cgacgguuag aggccguaug ucgauuugcu uuaauuucgu gcgugugcau ugucguccuc     60
cauuacaggg cggcuaccac gaauagccac gaaguaaaag cuucguggcu agcacnnnnn    120
nnnnnnnnnn nnnnn                                                     135

<210> SEQ ID NO 292
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
     Synthetic oligonucleotide"

<400> SEQUENCE: 292
gtacgagata taggaagctg ctgtccgctc                                      30

<210> SEQ ID NO 293
<211> LENGTH: 29
<212> TYPE: DNA
<213> ORGANISM: Artificial Sequence
<220> FEATURE:
<221> NAME/KEY: source
<223> OTHER INFORMATION: /note="Description of Artificial Sequence:
     Synthetic oligonucleotide"

<400> SEQUENCE: 293
actacaacag ccacaacgtc tatatcatg                                       29

<210> SEQ ID NO 294
<211> LENGTH: 149
<212> TYPE: RNA
<213> ORGANISM: Artificial Sequence
<220> FEATURE:
<221> NAME/KEY: source
<223> OTHER INFORMATION: /note="Description of Artificial Sequence:
     Synthetic polynucleotide"

<400> SEQUENCE: 294
cgacgguuag aggccguaug ucgauuugcu uuaauuucgu gcgugugcau ugucguccuc     60
cauuacaggg cggcuaccac gaauagucac gaaguuccac ugaguaaagu ggaaagcuuc    120
gagguuagca cacuacaaca gccacaacg                                      149

<210> SEQ ID NO 295
<211> LENGTH: 151
<212> TYPE: RNA
<213> ORGANISM: Artificial Sequence
<220> FEATURE:
<221> NAME/KEY: source
<223> OTHER INFORMATION: /note="Description of Artificial Sequence:
     Synthetic polynucleotide"

<400> SEQUENCE: 295
cgacgguuag aggccguaug ucgauuugcu uuaauuucgu gcgugugcau ugucguccuc     60
cauuacaggg cggcuaccac gaauagucac gaaguuccac ugaguaaagu ggaaagcuuc    120
gagguuagca cguacgagau auaggaagcu g                                   151

<210> SEQ ID NO 296
<211> LENGTH: 151
<212> TYPE: RNA
<213> ORGANISM: Artificial Sequence
<220> FEATURE:
<221> NAME/KEY: source
<223> OTHER INFORMATION: /note="Description of Artificial Sequence:
     Synthetic polynucleotide"
```

```
<400> SEQUENCE: 296
cgacgguuag aggccguaug ucgauuugcu uuaauuucgu gcgugugcau ugucguccuc      60
cauuacaggg cggcuaccac gaauagucac gaaguuccac ugaguaaagu ggaaagcuuc     120
gagguuagca cacuacaaca gccacaacgu c                                    151

<210> SEQ ID NO 297
<211> LENGTH: 156
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 297
cgacgguuag aggccguaug ucgauuugcu uuaauuucgu gcgugugcau ugucguccuc      60
cauuacaggg cggcuaccac gaauagucac gaaguuccac ugaguaaagu ggaaagcuuc     120
gagguuagca cguacgagau auaggaagcu gcuguc                               156

<210> SEQ ID NO 298
<211> LENGTH: 156
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 298
cgacgguuag aggccguaug ucgauuugcu uuaauuucgu gcgugugcau ugucguccuc      60
cauuacaggg cggcuaccac gaauagucac gaaguuccac ugaguaaagu ggaaagcuuc     120
gagguuagca cacuacaaca gccacaacgu cuauau                               156

<210> SEQ ID NO 299
<211> LENGTH: 140
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 299
cgacgguuag aggccguaug ucgauuugcu uuaauuucgu gcgugugcau ugucguccuc      60
cauuacaggg cggcuaccac gaauagucac gaaguaaaag cuucgagguu agcacacuac     120
aacagccaca acgucuauau                                                 140

<210> SEQ ID NO 300
<211> LENGTH: 149
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 300
cgacgguuag aggccguaug ucgauuugcu uuaauuucgu gcgugugcau ugucguccuc      60
cauuacaggg cggcuaccac gaauagccac gaaguuccaa aauggaaagc uucguggcua     120
```

-continued

```
gcacacuaca acagccacaa cgucuauau                                        149

<210> SEQ ID NO 301
<211> LENGTH: 140
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 301
cgacgguuag aggccguaug ucgauuugcu uuaauuucgu gcgugugcau ugucguccuc      60
cauuacaggg cggcuaccac gaauagccac gaaguaaaag cuucguggcu agcacacuac     120
aacagccaca acgucuauau                                                 140

<210> SEQ ID NO 302
<211> LENGTH: 135
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 302
cgacgguuag aggccguaug ucgauuugcu uuaauuucgu gcgugugcau ugucguccuc      60
cauuacaggg cggcuaccac gaauagccac gaaguaaaag cuucguggcu agcacacuac     120
aacagccaca acguc                                                     135

<210> SEQ ID NO 303
<211> LENGTH: 140
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 303
cgacgguuag aggccguaug ucgauuugcu uuaauuucgu gcgugugcau ugucguccuc      60
cauuacaggg cggcuaccac gaauagccac gaaguaaaag cuucguggcu agcacguacg     120
agauauagga agcugcuguc                                                 140

<210> SEQ ID NO 304
<211> LENGTH: 3324
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 304
atggccattc ggagcatcaa gctcaagctg aagaccagaa ccggtcctga ggctcagaac      60
ctgcggaagg gcatctggag aacccaccgg ctgctgaacg agggcgtggc ctactacatg     120
aagatgctgc tgctcttccg gcaggaatcc actggcggcc agacaaagaa ggaactgcag     180
gaggaactgg tgcggcacat ccgggagcag cagcagaaaa acagagccga caagaatacc     240
caggccctgc ctctggataa ggccttcgcc gctctgagac aactgtacga gctgctcgtg     300
ccatctagca tcggccagag cggcgatgcc cagatcatct ctagaaaatt cctgtctcct     360
```

-continued

```
ttggtggacc ctaacagcga gggcggcaag ggcactagca aggccggagc caagcccaca      420
tggcagaaaa agaaggaggc caatgaccct acatgggagc aagattacga gaagtggaaa      480
aagcgtagag aggaagatcc taccgccagt gtgataacaa ccctggaaga atatggaatt      540
agacctatct ttccactgta caccaacacc gtggccgata tcgcctggct gcctctgcag      600
tctaaccagt ttgtccggac atgggatcgg gacatgctgc agcaggccat cgagaggcta      660
ctctcttggg agtcttggaa caagcgggtg caagaggaat acagcaagct gcaggagaag      720
atgacgcaac tgaacgagca actggagggc ggacaggagt ggatcagcct gctggaacaa      780
tacgaggaac agagagagca ggagctgatc gaaaacatga ccgccgcaaa cgataaatac      840
cgcatcacca agcggcagat gaagggctgg aatgagctgt atgagcagtg gtctaccgtg      900
ctgcccaatg ccagccacga gcagtacaga gaggcactga aaagagtgca acagcggctg      960
aggggcagat tcggcgacgc tcatttcttc cagtatctga tgaaagaaga acaccacctg     1020
atctggaagg ggaaccctca gagaatccac tacttcgtgg ccagaaacga gctgaagaaa     1080
agactggaag aagccaagca gaacgccacc atgaccctgc ctgatgccag aaagcaccct     1140
ctgtgggtca gatttgacgc cagaggcggc aacctgcaag actactacct gacggccgaa     1200
gccgacaacc ccagaagcag aaggttcgtg accttcagcc aactgatctg gcctaacgag     1260
agcggctgga tggaaaaaca ggacgtggaa gttgaactgg ccctgagcaa gcagttctac     1320
cagcaagtga cactgcagaa aaacgacaag gggaagcagg aaatcgagtt caaagacaag     1380
ggcagtggca gcaccttcag cggccacctg ggcgggggcca agctgcaact ggagagagga     1440
gatctggaga aggaagaaaa agactttgaa ggcggcgaaa tcggcagcgt gtacctgaac     1500
atcgtgatcg acttcgagcc actgcaggag gtgaagaacg gccgactgca atctccttac     1560
ggccaggtgc tgcaactggt cagaaggcct aatgagttcc ccaaggtgac cacctacaag     1620
tctgaggaac tggtcgagtg gatcaagagc agcaccaagg acagcgccgg cgtggagtcc     1680
ttagagagcg gttttagagt gatgagcatc gacctgggac tgcggaccgc cgccgcaaca     1740
agcatcttct ctgtagagga atccaacgac gccaacgccg cgggtttcag ctactggatc     1800
gagggaactc ctctggttgc cgttcataag cggtcatata tgctgaaact gcccggagag     1860
caagtcgaaa agcaggtgcg agagaagcgg gacgagcggc aggatcagca gagaagagtg     1920
aggttccaaa tcagaatcct gagccaggtg atccggatgg ccaagaagca gaaccgggag     1980
cgggctgatg agctggacca cctgtcccag gccctggaga gcaaaaatc tctgctggac     2040 cagaccgatc ggaccttttg gaacggcatc gtgtgcgacc tgacagacgc tctgagagag     2100
aaagagggcg atgggaaca ggccgtggtc cagatccaca ggaaggccga ggagcacgtg     2160
ggcaaggtgt gcaagcctg gcggaaacgg ttcgacgccg atgaacgcaa gggcatcgcc     2220
ggcctgtcta tgtggtctat cgaggagctg gacagcctgc ggaagctgct gatctcttgg     2280
agcagaagaa caagaaaccc cagagaaatc aactgcttcg agcagggcca caccagccac     2340
cagcggctgc tgacacacat ccagaactg aaggaggacc ggctgaagca actgagccac     2400
gccattgtga tgacagcctt gggctacgtg tacgacgaga agaaattgga atggtttgcc     2460
aagtaccctg cttgtcaggt gatcctgttc gagaacctgt cccagtaccg gtccaacatg     2520
gacagaagca ccaaagagaa tagcaccctg atgaaatggg cccacaggag catccctaag     2580
tacgtgcaca tgcaggccga gccttacggc atccagatcg cgatgtgcg ggccgagtac     2640 tccagcagat tccacgccaa gacaggcaca cctggcatcc ggtgcaagat ggtgtccgga     2700
```

-continued

```
cacgacctgc aaggcaggcg cttcgagaac ctgcagaagc ggttaatctc tgaacagttc      2760
ctgacagagg agcaagtgaa gcagctcaga cccggcgaca tcgtgcccga cgactccggc      2820
gagtggttca tgaccctgag cgacggcagc gaaggcaaag aggttgtgtt cctccaagcc      2880
gacatcaacg ccgcccaaaa tctgcaaaag agattctggc agcggtacaa cgagctgttt      2940
aaggtctcct gcagagtgct gatccgagga gaagaggaat acctgatccc caagacaaag      3000
tccgtgcaag ccaagctggg caaaggcctg ttcgtgaaaa aaaccgacac cgtgatgaag      3060
gacgtgtacg tgtgggacag ccaggctaag ctgaagggca aaaccacatt caccgaggag      3120
tccgaaagcc ctgagcaact ggaggatttt caggagatca tcgaagaagc cgaagaagct      3180
aagggcacat acagaacact gtttagagac cccagcggag tgttcttccc tgagttcgtg      3240
tggtccaccc agaaagattt ctggtccgag gtgaagagac ggctgtacgg caagctgaga      3300
gagcggttcc tgatgaagac cagg                                            3324
```

```
<210> SEQ ID NO 305
<211> LENGTH: 3324
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 305
```

```
atggccatca gatctatcaa gctgaagctc aagaccagaa caggtcctga ggcccagaac        60
ctgcggaagg gcatttggcg gacacaccgc ctcctcaacg agggcgtcgc ctattatatg       120
aaaatgctgc tgctgttcag acaggagagc acaggcggcc agaccaagaa agagctgcag       180
gaagaactgg tccggcacat cagagagcag cagcagaaga tcgggccga caagaacacc        240 caggccctgc ctctggacaa ggcttttgcc gctctgcggc agctctacga gctgctggtg       300
ccttcttcta tcggccagag cggagacgcg cagatcatca gcagaaagtt cctgtcccct       360
ctcgtggacc ccaacagcga gggcggcaag ggcacatcta agctggcgc caagcctaca        420 tggcagaaaa agaaggaggc caacgacccc acctgggaac aggattacga gaaatggaag       480
aagcggagag aggaggaccc taccgccagc gtgattacca ccctggaaga atacggcatc       540
agaccaatct ccccactgta caccaacacc gtggccgaca tcgcctggct gcctctgcag       600
tccaaccagt tcgtgcggac atgggacaga gacatgctgc agcaggctat cgagagactg       660
ctgagctggg aaagctggaa caagagagtg caagaggaat acagcaagct gcaagagaag       720
atgacacagc tcaacgagca actggagggc ggccaggagt ggatcagcct gctggaacag       780
tacgaggagc aacgggagca ggagctgatc gagaacatga ccgccgctaa cgacaaatat       840
agaataacaa agcggcagat gaagggctgg aacgagctgt acgagcagtg gagcaccgtg       900
ctgcccaatg cctctcacga gcagtaccgg gaagccctta gcgggtcca gcaaagactg        960 cggggcagat cggcgacgc tcatttcttc cagtatctga tgaaggaaga gcaccacctg      1020
atttggaagg gcaaccccca gagaatccac tactttgtgg ccagaaacga gctgaagaaa      1080
agactggaag aggccaagca gaacgccact atgaccctgc agacgccag aaagcacccc       1140 ctgtgggtgc ggttcgacgc cagaggcgga aatctgcagg actactacct gaccgccgag      1200
gccgataacc ccagatctag aagattcgtt acctttagcc agttgatctg gcctaacgag      1260
tccggctgga tggaaaagca ggacgtggaa gtggaactcg ccctgagcaa gcagttctac      1320
cagcaagtga ccctgcagaa gaacgataag gggaaacagg agatcgagtt taaggacaag      1380
```

-continued

```
ggctccggat ctacgttcag tggccatctg ggcggggcta agctgcaact ggagcgaggc    1440
gacctggaga aagaagagaa ggactttgag ggcggagaaa tcggaagcgt gtacctgaac    1500
atcgtgatcg acttcgagcc cttgcaggag gtgaaaaacg gcagactgca gagcccatac    1560
ggccaggtgc tgcagctcgt tcggagacct aatgagttcc ctaaggtgac cacatacaag    1620
tctgaagaac ttgttgagtg gatgaaggcc agccagaatc acagcagcgg cgtggagtct    1680
ctggagtcgg gcttcagagt gatgagcatc gatctgggac tgaggacagc cgctgccacc    1740
agcattttct ctgtggaaga aagcaacgat gccaacgccg ctggcttcag ctactggatc    1800
gagggcaccc ctctggtcgc cgtgcacaag agaagctaca tgctgaagct gccaggcgaa    1860
caagtggaaa aacaggtgcg ggaaaagaga gatgagagac aagaccagca gaggcgcgtc    1920
agatttcaga tcagaatcct gagccaggtg atcaggatgg ccaagaaaca aaacagagaa    1980
agagctgacg aactggacca cctgagccag gcactggaga agcagaagtc cctgctcgat    2040
cagaccgata gaaccttctg gaacggcatc gtttgtgacc tgaccgatgc gctgcgcgaa    2100
aaggagggag gctgggagca agccgtggtc caaatccaca gaaaggccga ggaacacgtg    2160
ggcaaggtgg tgcaagcctg gcggaaaaga tttgacgccg atgagcggaa gggcatcgcc    2220
ggcctgagca tgtggtccat agaagagctg gacagcctcc ggaagctgct cattagctgg    2280
agcagaagga caagaaaccc tcaggagatc aacagattcg agcagggcca cacctctcac    2340
cagcggctgc tgacacatat ccagaacgtg aaggaagata gactgaagca actgagccac    2400
gccatcgtga tgaccgccct gggctacgtg tacgacgaga agaagctgga gtggttcgcc    2460
aaataccccg cctgccaggt gatcctgttc gagaatctgt ctcagtacag aagccacatg    2520
gacagatcca cgaaggaaaa tagcaccctg atgaaatggg cccacagaag catccctaag    2580
tacgtccaca tgcaggccga gccttacgga atccagatcg gagatgtgag agccgaatat    2640
agcagcaggt tccacgccaa gacagggaca cctggcatcc gttgcaagat ggtgaaggga    2700
caagaactgc aaggcaagcg attcgagaac ctgcaaaaga gactggtgtc cgaacagttt    2760
ctgaccgagg aacaggtgaa gcagcttcgg cctggagata tcgtgccaga tgacagcgga    2820
gagtggttca tgaccctgag tgatggcagc gaaggcaagg aagtggtgtt cctgcaagcc    2880
gacatcaacg ccgcccagaa ccttcagaaa cgattctggc agagatacaa cgaactgttc    2940
aaggtgtcat gcagagtgct gatcagaggc gaggaagagt acctgatccc caaggccaag    3000
agcgtgcaag ccaaactcgg caagggactg ttcgtgaaga aaaccgacac cgtgatgaag    3060
gacgtgtacg tgtgggatag ccaggccaaa ctgaagggca aaacaacctt caccgaggaa    3120
agcgagagcc ctgagcaact ggaggacttc caggagatca tcgaagaagc cgaggaagcc    3180
aagggcacct acagaacact gtttagagat cctagcggcg ttttcttccc cgagttcgtg    3240
tggaataccc agaaagactt ctggtccgag gtgaagagaa ggctgtacgg caagctgcgc    3300
gagagattcc tgatgaagac ccgg                                          3324
```

```
<210> SEQ ID NO 306
<211> LENGTH: 203
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 306
```

-continued

```
tgatgcggtt ttggcagtac atcaatgggc gtggatagcg gtttgactca cggggatttc      60
caagtctcca ccccattgac gtcaatggga gtttgttttg gcaccaaaat caacgggact     120
ttccaaaatg tcgtaacaac tccgccccat tgacgcaaat gggcggtagg cgtgtacggt     180
gggaggtcta tataagcaga gct                                             203

<210> SEQ ID NO 307
<211> LENGTH: 304
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 307
cgttacataa cttacggtaa atggcccgcc tggctgaccg cccaacgacc cccgcccatt      60
gacgtcaata atgacgtatg ttcccatagt aacgccaata gggactttcc attgacgtca     120
atgggtggag tatttacggt aaactgccca cttggcagta catcaagtgt atcatatgcc     180
aagtacgccc cctattgacg tcaatgacgg taaatggccc gcctggcatt atgcccagta     240
catgacctta tgggactttc ctacttggca gtacatctac gtattagtca tcgctattac     300
catg                                                                  304

<210> SEQ ID NO 308
<211> LENGTH: 318
<212> TYPE: DNA
<213> ORGANISM: Homo sapiens

<400> SEQUENCE: 308
tgtacaaaaa agcaggcttt aaaggaacca attcagtcga ctggatccgg taccaaggtc      60
gggcaggaag agggcctatt tcccatgatt ccttcatatt tgcatatacg atacaaggct     120
gttagagaga taattagaat taatttgact gtaaacacaa agatattagt acaaaatacg     180
tgacgtagaa agtaataatt tcttgggtag tttgcagttt taaaattatg ttttaaaatg     240
gactatcata tgcttaccgt aacttgaaag tatttcgatt tcttggcttt atatatcttg     300
tggaaaggac gaaacacc                                                   318

<210> SEQ ID NO 309
<211> LENGTH: 3324
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 309
atggccatca gatctatcaa gctgaagctc aagaccagaa caggtcctga ggcccagaac      60
ctgcggaagg gcatttggcg gacacaccgc ctcctcaacg agggcgtcgc ctattatatg     120
aaaatgctgc tgctgttcag acaggagagc acaggcggcc agaccaagaa agagctgcag     180
gaagaactgg tccggcacat cagagagcag cagcagaaga tcgggccga caagaacacc     240 caggccctgc tctctggacaa ggcttttgcc gctctgcggc agctctacga gctgctggtg     300
ccttcttcta tcggccagag cggagacgcg cagatcatca gcagaaagtt cctgtcccct     360
ctcgtggacc ccaacagcga gggcggcaag ggcacatcta agctggcgc caagcctaca     420 tggcagaaaa agaaggaggc caacgacccc acctgggaac aggattacga gaaatggaag     480
```

-continued

```
aagcggagag aggaggaccc taccgccagc gtgattacca ccctggaaga atacggcatc      540
agaccaatct tcccactgta caccaacacc gtggccgaca tcgcctggct gcctctgcag      600
tccaaccagt tcgtgcggac atgggacaga gacatgctgc agcaggctat cgagagactg      660
ctgagctggg aaagctggaa caagagagtg caagaggaat acagcaagct gcaagagaag      720
atgacacagc tcaacgagca actggagggc ggccaggagt ggatcagcct gctggaacag      780
tacgaggagc aacgggagca ggagctgatc gagaacatga ccgccgctaa cgacaaatat      840
agaataacaa agcggcagat gaagggctgg aacgagctgt acgagcagtg gagcaccgtg      900
ctgcccaatg cctctcacga gcagtaccgg gaagccctta agcgggtcca gcaaagactg      960
cggggcagat tcggcgacgc tcatttcttc cagtatctga tgaaggaaga gcaccacctg     1020
atttggaagg gcaacccca gagaatccac tactttgtgg ccagaaacga gctgaagaaa      1080
agactggaag aggccaagca gaacgccact atgaccctgc cagacgccag aaagcacccc     1140
ctgtgggtgc ggttcgacgc cagaggcgga aatctgcagg actactacct gaccgccgag     1200
gccgataacc ccagatctag aagattcgtt acctttagcc agttgatctg gcctaacgag     1260
tccggctgga tggaaaagca ggacgtggaa gtggaactcg ccctgagcaa gcagttctac     1320
cagcaagtga ccctgcagaa gaacgataag gggaaacagg agatcgagtt taaggacaag     1380
ggctccggat ctacgttcag tggccatctg ggcggggcta agctgcaact ggagcgaggc     1440
gacctggaga aagaagagaa ggactttgag ggcggagaaa tcggaagcgt gtacctgaac     1500
atcgtgatcg acttcgagcc cttgcaggag gtgaaaaacg gcagactgca gagcccatac     1560
ggccaggtgc tgcagctcgt tcggagacct aatgagttcc ctaaggtgac cacatacaag     1620
tctgaagaac ttgttgagtg gatgaaggcc agccagaatc acagcagcgg cgtggagtct     1680
ctggagtcgg gcttcagagt gatgagcatc gatctgggac tgaggacagc cgctgccacc     1740
agcattttct ctgtggaaga aagcaacgat gccaacgccg ctggcttcag ctactggatc     1800
gagggcaccc ctctggtcgc cgtgcacaag agaagctaca tgctgaagct gccaggcgaa     1860
caagtggaaa aacaggtgcg ggaaaagaga gatgagagac aagaccagca gaggcgcgtc     1920
agatttcaga tcagaatcct gagccaggtg atcaggatgg ccaagaaaca aaacagagaa     1980
agagctgacg aactgaccca cctgagccag gcactggaga agcagaagtc cctgctcgat     2040
cagaccgata gaaccttctg gaacggcatc gtttgtgacc tgaccgatgc gctgcgcgaa     2100
aaggagggag ctgggagca agccgtggtc caaatccaca gaaaggccga ggaacacgtg     2160
ggcaaggtgg tgcaagcctg gcggaaaaga tttgacgccg atgagcggaa gggcatcgcc     2220
ggcctgagca tgtggtccat agaagagctg gacagcctcc ggaagctgct cattagctgg     2280
agcagaagga caagaaaccc tcaggagatc aacagattcg agcagggcca cacctctcac     2340
cagcggctgc tgacacatat ccagaacgtg aaggaagata gactgaagca actgagccac     2400
gccatcgtga tgaccgccct gggctacgtg tacgacgaga agaagctgga gtggttcgcc     2460
aaataccccg cctgccaggt gatcctgttc gagaatctgt ctcagtacag aagccacatg     2520
gacagatcca cgaaggaaaa tagccgcctg atgaaatggg cccacagaag catccctaag     2580
tacgtccaca tgcaggccga gccttacgga atccagatcg agatgtgag agccgaatat     2640 agcagcaggt tccacgccaa gacagggaca cctggcatcc gttgcaagat ggtgaaggga     2700
caagaactgc aaggcaagcg attcgagaac ctgcaaaaga gactggtgtc cgaacagttt     2760
ctgaccgagg aacaggtgaa gcagcttcgg cctggagata tcgtgccaga tgacagcgga     2820
```

-continued

```
gagtggttca tgaccctgag tgatggcagc gaaggcaagg aagtggtgtt cctgcaagcc      2880
gacatcaacg ccgcccagaa ccttcagaaa cgattctggc agagatacaa cgaactgttc      2940
aaggtgtcat gcagagtgct gatcagaggc gaggaagagt acctgatccc caaggccaag      3000
agcgtgcaag ccaaactcgg caagggactg ttcgtgaaga aaaccgacac cgtgatgaag      3060
gacgtgtacg tgtgggatag ccaggccaaa ctgaagggca aaacaacctt caccgaggaa      3120
agcgagagcc ctgagcaact ggaggacttc caggagatca tcgaagaagc cgaggaagcc      3180
aagggcacct acagaacact gtttagagat cctagcggcg tttttcttccc cgagttcgtg     3240 tggaataccc agaaagactt ctggtccgag gtgaagagaa ggctgtacgg caagctgcgc      3300
gagagattcc tgatgaagac ccgg                                             3324
```

```
<210> SEQ ID NO 310
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 310
cccagcccta ggttgtttat t                                                21
```

```
<210> SEQ ID NO 311
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 311
ctggctacat cttccttgac tac                                              23
```

```
<210> SEQ ID NO 312
<211> LENGTH: 140
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 312
cgacgguuag aggccguaug ucgauuugcu uuaauuucgu gcgugugcau ugucguccuc      60
cauuacaggg cggcuaccac gaauagccac gaaguaaaag cuucguggcu agcacccuug     120
gcuagucuug aauuccuagg                                                 140
```

```
<210> SEQ ID NO 313
<211> LENGTH: 25
<212> TYPE: DNA
<213> ORGANISM: Homo sapiens

<400> SEQUENCE: 313
ccaacagtcc tacttccctg tttca                                            25
```

```
<210> SEQ ID NO 314
<211> LENGTH: 25
<212> TYPE: DNA
<213> ORGANISM: Artificial Sequence
```

```
<220> FEATURE:
<221> NAME/KEY: source
<223> OTHER INFORMATION: /note="Description of Artificial Sequence:
      Synthetic oligonucleotide"

<400> SEQUENCE: 314
gagatgtccc cagtgaactc caaat                                              25

<210> SEQ ID NO 315
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 315
cctgtcgttg cccctcccag atcat                                             25

<210> SEQ ID NO 316
<211> LENGTH: 49
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 316
gucugauugc cugucguugc cccucccaga ucauggagga guuggcaga                   49

<210> SEQ ID NO 317
<211> LENGTH: 41
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 317
gtctgattgc ctgtcgttgc ccctcccaag gagttggcag a                          41

<210> SEQ ID NO 318
<211> LENGTH: 69
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 318
gtctgattgc ctgtcgttgc ccctaagtgt attaagcatt gtctcagaga ttttggagga      60
gttggcaga                                                              69

<210> SEQ ID NO 319
<211> LENGTH: 39
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 319
```
gtctgattgc ctgtcgttgc ccctggagga gttggcaga                        39

<210> SEQ ID NO 320
<211> LENGTH: 47
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 320
gtctgattgc ctgtcgttgc ccctcccaga tcggaggagt tggcaga                47

<210> SEQ ID NO 321
<211> LENGTH: 44
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 321
gtctgattgc ctgtcgttgc ccctcccaga taggagttgg caga                   44

<210> SEQ ID NO 322
<211> LENGTH: 39
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 322
gtctgattgc ctgtcgttgc ccatctggga gttggcaga                        39

<210> SEQ ID NO 323
<211> LENGTH: 41
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 323
gtctgattgc ctgtcgttgc ccctctggag gagttggcag a                     41

<210> SEQ ID NO 324
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 324
gtctgattgg aggagttggc aga                                          23

<210> SEQ ID NO 325
<211> LENGTH: 40
<212> TYPE: DNA
<213> ORGANISM: Artificial Sequence
<220> FEATURE:
<221> NAME/KEY: source -continued

```
<223> OTHER INFORMATION: /note="Description of Artificial Sequence:
      Synthetic oligonucleotide"

<400> SEQUENCE: 325
gtctgattgc ctgtcgttgc ccctcggagg agttggcaga                              40

<210> SEQ ID NO 326
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 326
gtctgattgc ctgtcgttgc ccctccagga ggagttggca ga                          42

<210> SEQ ID NO 327
<211> LENGTH: 34
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 327
gtctgattgc ctgtcgttgc ccggagttgg caga                                   34

<210> SEQ ID NO 328
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 328
gtctgattgc ctgtcgttgc ccatcatgga ggagttggca ga                          42

<210> SEQ ID NO 329
<211> LENGTH: 43
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 329
gtctgattgc ctgtcgttgc ccctccatgg aggagttggc aga                         43

<210> SEQ ID NO 330
<211> LENGTH: 33
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 330
gtctgattgc ctgtcgttgc ccctcccagt act                                    33

<210> SEQ ID NO 331
```

-continued

```
<211> LENGTH: 44
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 331
gtctgattgc ctgtcgttgc cccaatcttg gaggagttgg caga                          44

<210> SEQ ID NO 332
<211> LENGTH: 43
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 332
gtctgattgc ctgtcgttgc cctgggatgg aggagttggc aga                           43

<210> SEQ ID NO 333
<211> LENGTH: 35
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 333
gtctgattgc ctgtcgttgc ccctcagttg gcaga                                    35

<210> SEQ ID NO 334
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 334
gtctgattgc ctgtcgttgc ccctcatgga ggagttggca ga                            42

<210> SEQ ID NO 335
<211> LENGTH: 25
<212> TYPE: DNA
<213> ORGANISM: Homo sapiens

<400> SEQUENCE: 335
tctttggaca gtgtccatac tggtg                                               25

<210> SEQ ID NO 336
<211> LENGTH: 25
<212> TYPE: DNA
<213> ORGANISM: Homo sapiens

<400> SEQUENCE: 336
tggtgagcac acctcgggac tgggc                                               25

<210> SEQ ID NO 337
<211> LENGTH: 25
<212> TYPE: DNA
<213> ORGANISM: Homo sapiens
```

-continued

---

<400> SEQUENCE: 337
ctgccacaat accttggccc ttctc                                     25

<210> SEQ ID NO 338
<211> LENGTH: 25
<212> TYPE: DNA
<213> ORGANISM: Homo sapiens

<400> SEQUENCE: 338
gctgcgaccc atacacccaa aggat                                     25

<210> SEQ ID NO 339
<211> LENGTH: 25
<212> TYPE: DNA
<213> ORGANISM: Homo sapiens

<400> SEQUENCE: 339
ttgtcgatgg tcagcacagc cttat                                     25

<210> SEQ ID NO 340
<211> LENGTH: 25
<212> TYPE: DNA
<213> ORGANISM: Homo sapiens

<400> SEQUENCE: 340
tgacttcatg gtaactggga gaggg                                     25

<210> SEQ ID NO 341
<211> LENGTH: 25
<212> TYPE: DNA
<213> ORGANISM: Homo sapiens

<400> SEQUENCE: 341
tgtagtccag aaccgtgctg gcagc                                     25

<210> SEQ ID NO 342
<211> LENGTH: 25
<212> TYPE: DNA
<213> ORGANISM: Homo sapiens

<400> SEQUENCE: 342
cacttcaggt cctgacagac actag                                     25

<210> SEQ ID NO 343
<211> LENGTH: 25
<212> TYPE: DNA
<213> ORGANISM: Homo sapiens

<400> SEQUENCE: 343
cacaggtcct caagggcaga agagt                                     25

<210> SEQ ID NO 344
<211> LENGTH: 25
<212> TYPE: DNA
<213> ORGANISM: Homo sapiens

<400> SEQUENCE: 344
ccaagaaacg gggctgaaag ccggg                                     25

<210> SEQ ID NO 345
<211> LENGTH: 25
<212> TYPE: DNA

<213> ORGANISM: Homo sapiens

<400> SEQUENCE: 345
tccttcacca ttatcaccac ccagt                                                 25

<210> SEQ ID NO 346
<211> LENGTH: 25
<212> TYPE: DNA
<213> ORGANISM: Homo sapiens

<400> SEQUENCE: 346
ggcttagggt taccgaagag gggcc                                                 25

<210> SEQ ID NO 347
<211> LENGTH: 25
<212> TYPE: DNA
<213> ORGANISM: Homo sapiens

<400> SEQUENCE: 347
ggctcagggt tactgaagag gggcc                                                 25

<210> SEQ ID NO 348
<211> LENGTH: 20
<212> TYPE: DNA
<213> ORGANISM: Homo sapiens

<400> SEQUENCE: 348
cctaaaggaa atgactgcag                                                       20

<210> SEQ ID NO 349
<211> LENGTH: 20
<212> TYPE: DNA
<213> ORGANISM: Homo sapiens

<400> SEQUENCE: 349
acttcgtcta ttcccagatc                                                       20

<210> SEQ ID NO 350
<211> LENGTH: 20
<212> TYPE: DNA
<213> ORGANISM: Homo sapiens

<400> SEQUENCE: 350
tggactgcat cttagcccta                                                       20

<210> SEQ ID NO 351
<211> LENGTH: 25
<212> TYPE: DNA
<213> ORGANISM: Homo sapiens

<400> SEQUENCE: 351
tgggtaggta ggctgggctg tgggt                                                 25

<210> SEQ ID NO 352
<211> LENGTH: 25
<212> TYPE: DNA
<213> ORGANISM: Homo sapiens

<400> SEQUENCE: 352
ttgctcattg acctccactc agtgt                                                 25

<210> SEQ ID NO 353
<211> LENGTH: 25

-continued

<212> TYPE: DNA
<213> ORGANISM: Homo sapiens

<400> SEQUENCE: 353 taaccccccac ccccactgcc gggta                                          25

<210> SEQ ID NO 354
<211> LENGTH: 25
<212> TYPE: DNA
<213> ORGANISM: Homo sapiens

<400> SEQUENCE: 354
ttgctcgttg atctccactc agtgt                                          25

<210> SEQ ID NO 355
<211> LENGTH: 20
<212> TYPE: DNA
<213> ORGANISM: Homo sapiens

<400> SEQUENCE: 355
caccacggct gtcgacacca                                                20

<210> SEQ ID NO 356
<211> LENGTH: 20
<212> TYPE: DNA
<213> ORGANISM: Homo sapiens

<400> SEQUENCE: 356
caacagtgga ggaaagcctt                                                20

<210> SEQ ID NO 357
<211> LENGTH: 25
<212> TYPE: DNA
<213> ORGANISM: Homo sapiens

<400> SEQUENCE: 357
ctatctggtc gtgggagtac gggat                                          25

<210> SEQ ID NO 358
<211> LENGTH: 20
<212> TYPE: DNA
<213> ORGANISM: Homo sapiens

<400> SEQUENCE: 358
aaataagcag caggaagcag                                                20

<210> SEQ ID NO 359
<211> LENGTH: 20
<212> TYPE: DNA
<213> ORGANISM: Homo sapiens

<400> SEQUENCE: 359
ctcgatatag gtggagtctt                                                20

<210> SEQ ID NO 360
<211> LENGTH: 25
<212> TYPE: DNA
<213> ORGANISM: Homo sapiens

<400> SEQUENCE: 360
tggttgtgca gccagatgcc tagac                                          25

<210> SEQ ID NO 361

-continued

```
<211> LENGTH: 25
<212> TYPE: DNA
<213> ORGANISM: Homo sapiens

<400> SEQUENCE: 361
tcttgctcac tttggacctt ggtgg                                          25

<210> SEQ ID NO 362
<211> LENGTH: 25
<212> TYPE: DNA
<213> ORGANISM: Homo sapiens

<400> SEQUENCE: 362
ctggctgtaa gtcgggcttt cttca                                          25

<210> SEQ ID NO 363
<211> LENGTH: 25
<212> TYPE: DNA
<213> ORGANISM: Homo sapiens

<400> SEQUENCE: 363
ctgcaagcaa cctccagtgg tgacc                                          25

<210> SEQ ID NO 364
<211> LENGTH: 20
<212> TYPE: DNA
<213> ORGANISM: Homo sapiens

<400> SEQUENCE: 364
aggagctctc gagccagttt                                                20

<210> SEQ ID NO 365
<211> LENGTH: 20
<212> TYPE: DNA
<213> ORGANISM: Homo sapiens

<400> SEQUENCE: 365
gtcagaggaa ggttgagccc                                                20

<210> SEQ ID NO 366
<211> LENGTH: 25
<212> TYPE: DNA
<213> ORGANISM: Homo sapiens

<400> SEQUENCE: 366
gggtctgttt gaacatggag aacac                                          25

<210> SEQ ID NO 367
<211> LENGTH: 25
<212> TYPE: DNA
<213> ORGANISM: Homo sapiens

<400> SEQUENCE: 367
gaaagatcta gctcaccgtc ctctt                                          25

<210> SEQ ID NO 368
<211> LENGTH: 25
<212> TYPE: DNA
<213> ORGANISM: Homo sapiens

<400> SEQUENCE: 368
tgcaagccca ccttggtcca tgtgg                                          25
```

<210> SEQ ID NO 369
<211> LENGTH: 25
<212> TYPE: DNA
<213> ORGANISM: Homo sapiens

<400> SEQUENCE: 369
ttccctccat catgtgtccc agggc                                          25

<210> SEQ ID NO 370
<211> LENGTH: 25
<212> TYPE: DNA
<213> ORGANISM: Homo sapiens

<400> SEQUENCE: 370
ggaagtggtt ggacaagtaa gcgcc                                          25

<210> SEQ ID NO 371
<211> LENGTH: 25
<212> TYPE: DNA
<213> ORGANISM: Homo sapiens

<400> SEQUENCE: 371
cccgcctgct tacagatttc agttt                                          25

<210> SEQ ID NO 372
<211> LENGTH: 20
<212> TYPE: DNA
<213> ORGANISM: Homo sapiens

<400> SEQUENCE: 372
gagagtacag ccacaccatt                                                20

<210> SEQ ID NO 373
<211> LENGTH: 25
<212> TYPE: DNA
<213> ORGANISM: Homo sapiens

<400> SEQUENCE: 373
tatcacttac ggatcacaga ggggg                                          25

<210> SEQ ID NO 374
<211> LENGTH: 25
<212> TYPE: DNA
<213> ORGANISM: Homo sapiens

<400> SEQUENCE: 374
gtgacagagc tggtttcaaa gttgc                                          25

<210> SEQ ID NO 375
<211> LENGTH: 25
<212> TYPE: DNA
<213> ORGANISM: Homo sapiens

<400> SEQUENCE: 375
cctgaagcca tcaaggggct gcagc                                          25

<210> SEQ ID NO 376
<211> LENGTH: 25
<212> TYPE: DNA
<213> ORGANISM: Homo sapiens

<400> SEQUENCE: 376
tttactctcc cacagtggcg ctgct                                          25

-continued

<210> SEQ ID NO 377
<211> LENGTH: 25
<212> TYPE: DNA
<213> ORGANISM: Homo sapiens

<400> SEQUENCE: 377
ctccaattca ggacccacat gacgg                                          25

<210> SEQ ID NO 378
<211> LENGTH: 25
<212> TYPE: DNA
<213> ORGANISM: Homo sapiens

<400> SEQUENCE: 378
atctcctcct catcctccag cctct                                          25

<210> SEQ ID NO 379
<211> LENGTH: 25
<212> TYPE: DNA
<213> ORGANISM: Homo sapiens

<400> SEQUENCE: 379
gggggctggt ttgccatcca agggg                                          25

<210> SEQ ID NO 380
<211> LENGTH: 25
<212> TYPE: DNA
<213> ORGANISM: Homo sapiens

<400> SEQUENCE: 380
gccggacagg gatgttcatt gtgat                                          25

<210> SEQ ID NO 381
<211> LENGTH: 25
<212> TYPE: DNA
<213> ORGANISM: Homo sapiens

<400> SEQUENCE: 381
gccattttgg ctgagttggt ccagt                                          25

<210> SEQ ID NO 382
<211> LENGTH: 25
<212> TYPE: DNA
<213> ORGANISM: Homo sapiens

<400> SEQUENCE: 382
gccactttgg ctgagttggt ccggt                                          25

<210> SEQ ID NO 383
<211> LENGTH: 25
<212> TYPE: DNA
<213> ORGANISM: Homo sapiens

<400> SEQUENCE: 383
agctgctagt cccagctgag gacgt                                          25

<210> SEQ ID NO 384
<211> LENGTH: 25
<212> TYPE: DNA
<213> ORGANISM: Homo sapiens

<400> SEQUENCE: 384
ttggactccc ttgatgccca ggaga                                          25

-continued

```
<210> SEQ ID NO 385
<211> LENGTH: 20
<212> TYPE: DNA
<213> ORGANISM: Homo sapiens

<400> SEQUENCE: 385
cctaccctga aaatccgaaa                                                        20

<210> SEQ ID NO 386
<211> LENGTH: 25
<212> TYPE: DNA
<213> ORGANISM: Homo sapiens

<400> SEQUENCE: 386
tagtagcaca cactctgcac cttga                                                  25

<210> SEQ ID NO 387
<211> LENGTH: 25
<212> TYPE: DNA
<213> ORGANISM: Homo sapiens

<400> SEQUENCE: 387
ccctcgttga catcgatgct tgaga                                                  25

<210> SEQ ID NO 388
<211> LENGTH: 25
<212> TYPE: DNA
<213> ORGANISM: Homo sapiens

<400> SEQUENCE: 388
gacagcggaa accccggaaa agcag                                                  25

<210> SEQ ID NO 389
<211> LENGTH: 25
<212> TYPE: DNA
<213> ORGANISM: Homo sapiens

<400> SEQUENCE: 389
acctgagtgt tttagctacg gtgag                                                  25

<210> SEQ ID NO 390
<211> LENGTH: 20
<212> TYPE: DNA
<213> ORGANISM: Homo sapiens

<400> SEQUENCE: 390
gaaggtctcc tccctggtca                                                        20

<210> SEQ ID NO 391
<211> LENGTH: 25
<212> TYPE: DNA
<213> ORGANISM: Homo sapiens

<400> SEQUENCE: 391
ctgctgaatc agccggcaga accag                                                  25

<210> SEQ ID NO 392
<211> LENGTH: 20
<212> TYPE: DNA
<213> ORGANISM: Homo sapiens

<400> SEQUENCE: 392
```

-continued

```
tgtgcccgca ctcgaaaaag                                              20

<210> SEQ ID NO 393
<211> LENGTH: 20
<212> TYPE: DNA
<213> ORGANISM: Homo sapiens

<400> SEQUENCE: 393
cttgggactg taaaagctgt                                              20

<210> SEQ ID NO 394
<211> LENGTH: 20
<212> TYPE: DNA
<213> ORGANISM: Homo sapiens

<400> SEQUENCE: 394
gtaagtgatc catcctaggt                                              20

<210> SEQ ID NO 395
<211> LENGTH: 20
<212> TYPE: DNA
<213> ORGANISM: Homo sapiens

<400> SEQUENCE: 395
aacgaagccc tccgtgagag                                              20

<210> SEQ ID NO 396
<211> LENGTH: 20
<212> TYPE: DNA
<213> ORGANISM: Homo sapiens

<400> SEQUENCE: 396
caagaatctg accatcttgg                                              20

<210> SEQ ID NO 397
<211> LENGTH: 20
<212> TYPE: DNA
<213> ORGANISM: Homo sapiens

<400> SEQUENCE: 397
tcgtccgtga cctgggagcc                                              20

<210> SEQ ID NO 398
<211> LENGTH: 20
<212> TYPE: DNA
<213> ORGANISM: Homo sapiens

<400> SEQUENCE: 398
acagatgaac actggtcagc                                              20

<210> SEQ ID NO 399
<211> LENGTH: 20
<212> TYPE: DNA
<213> ORGANISM: Homo sapiens

<400> SEQUENCE: 399
tcagtgccaa cctcctcaca                                              20

<210> SEQ ID NO 400
<211> LENGTH: 20
<212> TYPE: DNA
<213> ORGANISM: Homo sapiens

<400> SEQUENCE: 400
```
ttgatcttgt cgggagttcc                                                          20

<210> SEQ ID NO 401
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 401
aagactaacc tggccaacat                                                          20

<210> SEQ ID NO 402
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 402
gtcttgaact ccggacctca                                                          20

<210> SEQ ID NO 403
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 403
gccgggcgtg gtgtcgcgcg                                                          20

<210> SEQ ID NO 404
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 404
tcctgccgca gcctctggag                                                          20

<210> SEQ ID NO 405
<211> LENGTH: 135
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 405
cgacgguuag aggccguaug ucgauuugcu uuaauuucgu gcgugugcau ugucguccuc      60
cauuacaggg cggcuaccac gaauagccac gaaguaaaag cuucguggcu agcacaagac      120
uaaccuggcc aacau                                                              135

<210> SEQ ID NO 406

```
<211> LENGTH: 135
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 406
cgacgguuag aggccguaug ucgauuugcu uuaauuucgu gcgugugcau ugucguccuc      60
cauuacaggg cggcuaccac gaauagccac gaaguaaaag cuucguggcu agcacgucuu     120
gaacuccgga ccuca                                                     135

<210> SEQ ID NO 407
<211> LENGTH: 135
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 407
cgacgguuag aggccguaug ucgauuugcu uuaauuucgu gcgugugcau ugucguccuc      60
cauuacaggg cggcuaccac gaauagccac gaaguaaaag cuucguggcu agcacgccgg     120 gcguggguc gcgcg                                                       135

<210> SEQ ID NO 408
<211> LENGTH: 135
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 408
cgacgguuag aggccguaug ucgauuugcu uuaauuucgu gcgugugcau ugucguccuc      60
cauuacaggg cggcuaccac gaauagccac gaaguaaaag cuucguggcu agcacuccug     120
ccgcagccuc uggag                                                      135

<210> SEQ ID NO 409
<211> LENGTH: 3324
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 409
atggccattc ggagcatcaa gctcaagctg aagaccagaa ccggtcctga ggctcagaac      60
ctgcggaagg gcatctggag aacccaccgg ctgctgaacg agggcgtggc ctactacatg     120
aagatgctgc tgctcttccg gcaggaatcc actggcggcc agacaaagaa ggaactgcag     180
gaggaactgg tgcggcacat ccgggagcag cagcagaaaa acagagccga caagaatacc     240
caggccctgc tctctggataa ggccttcgcc gctctgagac aactgtacga gctgctcgtg     300
ccatctagca tcggccagag cggcgatgcc cagatcatct ctagaaaatt cctgtctcct     360
ttggtggacc ctaacagcga gggcggcaag ggcactagca aggccggagc caagcccaca     420
tggcagaaaa agaaggaggc caatgaccct acatgggagc aagattacga gaagtggaaa     480
```

```
aagcgtagag aggaagatcc taccgccagt gtgataacaa ccctggaaga atatggaatt      540
agacctatct ttccactgta caccaacacc gtggccgata tcgcctggct gcctctgcag      600
tctaaccagt ttgtccggac atgggatcgg acatgctgc agcaggccat cgagaggcta       660
ctctcttggg agtcttggaa caagcgggtg caagaggaat acagcaagct gcaggagaag      720
atgacgcaac tgaacgagca actggagggc ggacaggagt ggatcagcct gctggaacaa      780
tacgaggaac agagagagca ggagctgatc gaaaacatga ccgccgcaaa cgataaatac      840
cgcatcacca agcggcagat gaagggctgg aatgagctgt atgagcagtg gtctaccgtg      900
ctgcccaatg ccagccacga gcagtacaga gaggcactga aaagagtgca acagcggctg      960
aggggcagat tcggcgacgc tcatttcttc cagtatctga tgaaagaaga acaccacctg     1020
atctggaagg ggaaccctca gagaatccac tacttcgtgg ccagaaacga gctgaagaaa     1080
agactggaag aagccaagca gaacgccacc atgaccctgc ctgatgccag aaagcaccct     1140
ctgtgggtca gatttgacgc cagaggcggc aacctgcaag actactacct gacggccgaa     1200
gccgacaacc ccagaagcag aaggttcgtg accttcagcc aactgatctg gcctaacgag     1260
agcggctgga tggaaaaaca ggacgtggaa gttgaactgg ccctgagcaa gcagttctac     1320
cagcaagtga cactgcagaa aaacgacaag gggaagcagg aaatcgagtt caaagacaag     1380
ggcagtggca gcaccttcag cggccacctg ggcgggggcca agctgcaact ggagagagga     1440
gatctggaga aggaagaaaa agactttgaa ggcggcgaaa tcggcagcgt gtacctgaac     1500
atcgtgatcg acttcgagcc actgcaggag gtgaagaacg gccgactgca atctccttac     1560
ggccaggtgc tgcaactggt cagaaggcct aatgagttcc ccaaggtgac cacctacaag     1620
tctgaggaac tggtcgagtg gatcaagagc agcaccaagg acagcgccgg cgtggagtcc     1680
ttagagagcg gttttagagt gatgagcatc gacctgggac tgcggaccgc cgccgcaaca     1740
agcatcttct ctgtagagga atccaacgac gccaacgccg cgggtttcag ctactggatc     1800
gagggaactc ctctggttgc cgttcataag cggtcatata tgctgaaact gcccggagag     1860
caagtcgaaa agcaggtgcg agagaagcgg gacgagcggc aggatcagca gagaagagtg     1920
aggttccaaa tcagaatcct gagccaggtg atccggatgg ccaagaagca gaaccgggag     1980
cgggctgatg agctgaacca cctgtcccag gccctggaga gcaaaaaatc tctgctggac     2040
cagaccgatc ggacctttttg gaacggcatc gtgtgcgacc tgacagacgc tctgagagag     2100
aaagagggcg gatgggaaca ggccgtggtc cagatccaca ggaaggccga ggagcacgtg     2160
ggcaaggtgg tgcaagcctg gcggaaacgg ttcgacgccg atgaacgcaa gggcatcgcc     2220
ggcctgtcta tgtggtctat cgaggagctg gacagcctgc ggaagctgct gatctcttgg     2280
agcagaagaa caagaaaccc cagagaaatc aactgcttcg agcagggcca caccagccac     2340
cagcggctgc tgacacacat ccagaacgtg aaggaggacc ggctgaagca actgagccac     2400
gccattgtga tgacagcctt gggctacgtg tacgacgaga agaaattgga atggtttgcc     2460
aagtaccctg cttgtcaggt gatcctgttc gagaacctgt cccagtaccg gtccaacatg     2520
gacagaagca ccaaagagaa tagcaccctg atgaaatggg cccacaggag catccctaag     2580
tacgtgcaca tgcaggccga gccttacggc atccagatcg gcgatgtgcg ggccgagtac     2640
tccagcagat tccacgccaa gacaggcaca cctggcatcc ggtgcaagat ggtgtccgga     2700
cacgacctgc aaggcaggcg cttcgagaac ctgcagaagc ggttaatctc tgaacagttc     2760
ctgacagagg agcaagtgaa gcagctcaga cccggcgaca tcgtgcccga cgactccggc     2820
```

-continued

```
gagtggttca tgaccctgag cgacggcagc gaaggcaaag aggttgtgtt cctccaagcc     2880
gacatcaacg ccgcccaaaa tctgcaaaag agattctggc agcggtacaa cgagctgttt     2940
aaggtctcct gcagagtgct gatccgagga gaagaggaat acctgatccc caagacaaag     3000
tccgtgcaag ccaagctggg caaaggcctg ttcgtgaaaa aaaccgacac cgtgatgaag     3060
gacgtgtacg tgtgggacag ccaggctaag ctgaagggca aaaccacatt caccgaggag     3120
tccgaaagcc ctgagcaact ggaggatttt caggagatca tcgaagaagc cgaagaagct     3180
aagggcacat acagaacact gtttagagac cccagcggag tgttcttccc tgagttcgtg     3240
tggtccaccc agaaagattt ctggtccgag gtgaagagac ggctgtacgg caagctgaga     3300
gagcggttcc tgatgaagac cagg                                            3324

<210> SEQ ID NO 410
<211> LENGTH: 3324
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 410
atggccatca gatctatcaa gctgaagctc aagaccagaa caggtcctga ggcccagaac       60
ctgcggaagg gcatttggcg gacacaccgc ctcctcaacg agggcgtcgc ctattatatg      120
aaaatgctgc tgctgttcag acaggagagc acaggcggcc agaccaagaa agagctgcag      180
gaagaactgg tccggcacat cagagagcag cagcagaaga atcgggccga caagaacacc      240
caggccctgc ctctggacaa ggcttttgcc gctctgcggc agctctacga gctgctggtg      300
ccttcttcta tcggccagag cggagacgcg cagatcatca gcagaaagtt cctgtccccct     360 ctcgtggacc ccaacagcga gggcggcaag ggcacatcta aagctggcgc caagcctaca      420
tggcagaaaa agaaggaggc caacgacccc acctgggaac aggattacga gaaatggaag      480
aagcggagag aggaggaccc taccgccagc gtgattacca ccctggaaga atacggcatc      540
agaccaatct ccccactgta caccaacacc gtggccgaca tcgcctggct gcctctgcag      600
tccaaccagt tcgtgcggac atgggacaga gacatgctgc agcaggctat cgagagactg      660
ctgagctggg aaagctggaa caagagagtg caagaggaat acagcaagct gcaagagaag      720
atgacacagc tcaacgagca actggagggc ggccaggagt ggatcagcct gctggaacag      780
tacgaggagc aacgggagca ggagctgatc gagaacatga ccgccgctaa cgacaaatat      840
agaataacaa agcggcagat gaagggctgg aacgagctgt acgagcagtg gagcaccgtg      900
ctgcccaatg cctctcacga gcagtaccgg gaagcccctta agcgggtcca gcaaagactg      960
cggggcagat cggcgacgc tcatttcttc cagtatctga tgaaggaaga gcaccacctg     1020
atttggaagg caaccccca gagaatccac tactttgtgg ccagaaacga gctgaagaaa     1080
agactggaag aggccaagca gaacgccact atgaccctgc cagacgccag aaagcacccc     1140
ctgtgggtgc ggttcgacgc cagaggcgga aatctgcagg actactacct gaccgccgag     1200
gccgataacc ccagatctag aagattcgtt acctttagcc agttgatctg gcctaacgag     1260
tccggctgga tggaaaagca ggacgtggaa gtggaactcg ccctgagcaa gcagttctac     1320
cagcaagtga ccctgcagaa gaacgataag gggaaacagg agatcgagtt taaggacaag     1380
ggctccggat ctacgttcag tggccatctg ggcgggggcta agctgcaact ggagcgaggc     1440
gacctggaga aagaagagaa ggactttgag ggcgagaaaa tcggaagcgt gtacctgaac     1500
```

```
atcgtgatcg acttcgagcc cttgcaggag gtgaaaaacg gcagactgca gagcccatac      1560
ggccaggtgc tgcagctcgt tcggagacct aatgagttcc ctaaggtgac cacatacaag      1620
tctgaagaac ttgttgagtg gatgaaggcc agccagaatc acagcagcgg cgtggagtct      1680
ctggagtcgg gcttcagagt gatgagcatc gatctgggac tgaggacagc cgctgccacc      1740
agcattttct ctgtggaaga aagcaacgat gccaacgccg ctggcttcag ctactggatc      1800
gagggcaccc ctctggtcgc cgtgcacaag agaagctaca tgctgaagct gccaggcgaa      1860
caagtggaaa aacaggtgcg ggaaaagaga gatgagagac aagaccagca gaggcgcgtc      1920
agatttcaga tcagaatcct gagccaggtg atcaggatgg ccaagaaaca aaacagagaa      1980
agagctgacg aactggacca cctgagccag gcactggaga agcagaagtc cctgctcgat      2040
cagaccgata gaaccttctg gaacggcatc gtttgtgacc tgaccgatgc gctgcgcgaa      2100
aaggagggag gctgggagca agccgtggtc caaatccaca gaaaggccga ggaacacgtg      2160
ggcaaggtgg tgcaagcctg gcggaaaaga tttgacgccg atgagcggaa gggcatcgcc      2220
ggcctgagca tgtggtccat agaagagctg gacagcctcc ggaagctgct cattagctgg      2280
agcagaagga caagaaaccc tcaggagatc aacagattcg agcagggcca cacctctcac      2340
cagcggctgc tgacacatat ccagaacgtg aaggaagata gactgaagca actgagccac      2400
gccatcgtga tgaccgccct gggctacgtg tacgacgaga agaagctgga gtggttcgcc      2460
aaataccccg cctgccaggt gatcctgttc gagaatctgt ctcagtacag aagccacatg      2520
gacagatcca cgaaggaaaa tagcaccctg atgaaatggg cccacagaag catccctaag      2580
tacgtccaca tgcaggccga gccttacgga atccagatcg gagatgtgag agccgaatat      2640
agcagcaggt tccacgccaa gacagggaca cctggcatcc gttgcaagat ggtgaaggga      2700
caagaactgc aaggcaagcg attcgagaac ctgcaaaaga gactggtgtc cgaacagttt      2760
ctgaccgagg aacaggtgaa gcagcttcgg cctggagata tcgtgccaga tgacagcgga      2820
gagtggttca tgaccctgag tgatggcagc gaaggcaagg aagtggtgtt cctgcaagcc      2880
gacatcaacg ccgcccagaa ccttcagaaa cgattctggc agagatacaa cgaactgttc      2940
aaggtgtcat gcagagtgct gatcagaggc gaggaagagt acctgatccc caaggccaag      3000
agcgtgcaag ccaaactcgg caagggactg ttcgtgaaga aaaccgacac cgtgatgaag      3060
gacgtgtacg tgtgggatag ccaggccaaa ctgaagggca aacaacctt caccgaggaa      3120 agcgagagcc ctgagcaact ggaggacttc caggagatca tcgaagaagc cgaggaagcc      3180
aagggcaccg acagaacact gtttagagat cctagcggcg ttttcttccc cgagttcgtg      3240
tggaataccc agaaagactt ctggtccgag gtgaagagaa ggctgtacgg caagctgcgc      3300
gagagattcc tgatgaagac ccgg                                            3324
```

<210> SEQ ID NO 411
<211> LENGTH: 3279
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 411

```
atgaaaaccc tggggatcga tctgggaacc gccagcatcg gctgggctat cctggacgag        60
gccagcatca tcgcctccgg cgtgcggatc tttagccaga gcgagatggc tggcagagat       120
```

-continued

```
ccccagagca aggccagcct ggccgtcgcc cggagggacg ccagaggagc tagaaggagg      180
agagacagat acctgaaaag acggaggaga ctgctggacc tgctgacaga gcacggcctg      240
gctccagccg atgagaaaag ccggaaggcc ctggtgcggg aatacgagga tggcaaagat      300
ggagatctga gcaacagcgt gtacgccctt agagctagag ccttggatga agccctgacc      360
ccttacgaga tcgggcgggc catcttccaa ctgaaccagc ggcggggctt taagtctaac      420
agaaagaccg acagcaacga ccccgagcag ggaaaaatcg ccacagcaat ccacgtgctg      480
gatgccaaaa tggacgagga taaggcccgg accttcggag agtggctgca catgagaaga      540
ctcaaaggcc tgagcgtgcg cgctcggatg accgccgacg gcgattctta cgatttctac      600
cctagccgtg ccgccctgga aagagagttc gacagactga tggccagcca gaagagattc      660
caccctgacc tgctgaactc aagcgtgatc gacgacatca ggaaggtggt gtttcaccag      720
cggcctctga gcctgtgca acctggcaag tgtagctaca accacagaga atctcggctg      780
cccaaggcac accccttgtt tcagaaattc cggctgctga agaggtgaa tgagctggaa      840 atcgtcggcg aagatcagag atacgtgaag ctgacccctg cccagcgcga tgtgctgaca      900
ctggccctca gaacaggcct gaccaagcaa ggtagactgc cgttctctaa gctgcggagc      960
attctgaagc tgggcaagga ggttcggttt aacaaggaaa aggacaaccg gaccgacctg     1020
gaaggcgatg tgatccactt cagagtgtcc aggcccgact gcttcggcaa tagatgggcc     1080
gctatgcctg tggaagagca agccgctgtg accgagaagc tgagaaccga gccagattac     1140
agcgccctgc tcgattggct gaagaacgag gctggcttgg atgaggctca tgcccgagcc     1200
gtggccgaca cacctgtgcc cgacggcttc ggcagaatgg acccagcgc cttgtctgcc     1260 ctggctgatg ctatggaaca cgagattgat gcacagggct tcgtgatcac cgaggccgag     1320
gccgccaaga gagtgtacgg cagaaccaat agcgaggctg accccggccg gaaaggagtg     1380
gaccaactgc ctaagtacca ggaggtcctg cagaggcata ttcctcctgg aacaggcgaa     1440
cctgatgacc cctacgacga gtacatgggc agaatcacca accccaccgt gcacatcgcc     1500
ctgaaccaac tgagaagact ggtcaacgca ctgatccgga agtacggcaa gcccaacaaa     1560
atcgccatcg aagtgggccg ggagctgaaa ctgaacgaaa agcagagaaa cgaggtcaac     1620
cgagaaatcg gccaaaatac cagagccgct atggccagag ccagcaact ggtggaaatc     1680 ttcaagcagc aaacaccggg atacaaccgg ctgagactgg aactgtggga agatctgaac     1740
cgggaacagc ctctgaaacg gctctgtacc tactgcggca aggccatcgc tgcccacatg     1800
ctgttcaacg gcgagacaga tatcgatcac atcctgccat attccaagac actggatgac     1860
tccaaggcca acaggctgtt gtgctgcaca ccttgcaaca gagagaagaa gaactacgcc     1920
cctgccaacg tgctgcagtg gcgggaccac tacggcgaga tcctggccag agccaccgcc     1980
ctccctaaga acaagcagtg gagattcgcc gaggatgcta tgaccagata cgaggccgag     2040
ggcggtttcc tggcccggca gctcacagat atgcagtaca tcagcagact cgccctgaca     2100
tacctggccc acctgtacga ctacgaggaa cccgacctgg acggcgtgta caagagacac     2160
gacagagtga gagccctccc tgggcgcatg accgagatgc tgagacggca gtgggccctg     2220
aacgaactgc tccacggcca caacctggct ggtggcgacg cgccaagga aaagaacaga     2280 ctggatcaca gacaccacgc cattgatgct atcgtgatcg cttgtaccag ccagtctctt     2340
attaacagac tgtccaccgc cgccggcgag gccgaagaac ggggcgccgc cagagtggtc     2400
gagagaatcg accctccttg gcctagcttc cgggaagatg tgagagaagc tgttaatgcc     2460
attgtggttt ctcacaagcc tgaccacggc accgctagcc ggagcggcta cgacaagggc     2520
```

```
agaggccaga ccgccggcaa gctgcacaac gacactgcct atggcgagac aggcgagaaa   2580
gaccacaacg gcaacaacct ggtggtgcgg cggatcgcca tcagcgacat caagcggagc   2640
gccgacatca tgaagatcag aacaaacgcc cacggccaca gcgagctgag agacagactg   2700
tacgaagcca ctcgggatct ggaaggcaag gctttcgagc aggccgtgac agcttttgtg   2760
aagcacgacg ccaagttcaa ggggatcaga cacgtgcgag tgaccgaagt tcagaacccc   2820
gtctggatca cccacggcgg aggcaaatac aagaagggct acctgcctgg aggcaatgat   2880
cggttcgacg tgtgggagct gcctgatggt aaatgggacg ccgaggtggt gacgaccttt   2940
gatgcccatc ggcctgactt caccctaga atgcggatcg agcaccacaa cgctcggaag   3000
atcatgtctc tgaagaaagg cgacatgatc gcctacgacg atcctgacag cgggaagcgc   3060
gtgattgcca tcgtgcggaa attcgaccag cggaacaagc aactgtacct ggaccctcac   3120
aatgaggccg gcaacctgga ccagagagaa aaagaaaaaa catacaagcc cctaagacct   3180
atgcccaacc ctctgaaaaa gtacagaccc agacaggtgc gggtggacga gattggacaa   3240
gtgttcgacc ctggcccttg gtgggagaag cgctctgat                          3279
```

```
<210> SEQ ID NO 412
<211> LENGTH: 3162
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 412
```

```
atgaaagaga agtatatcct gggcctagac ctgggcatta catctgtggg atacggcatc     60
atcaacttcg agacaaagaa aatcattgac gccggcgtgc ggctgtttcc tgaagccaac    120
gtggacaaca tgagggaag acggagcaag agaggcagca gaaggctgaa gagaagaaga    180
attcacagac tggaaagagt gaagctgctg ctgaccgagt acgacctgat taacaaggaa    240
cagatcccta caagcaacaa cccctaccag atcagagtga aggactgag cgagatactg    300 agcaaggatg aactggccat cgctcttctg cacctggcta aaagacgggg aatccacaac    360
atcaacgtca gcagcgaaga tgaggatgct agcaacgagc tgtccaccaa ggaacagatt    420
aaccggaaca acaagctgct caaggacaaa tacgtgtgcg aggtgcaact gcagcggctg    480
aaggagggcc agatccgggg cgagaagaac agattcaaga caaccgacat cctgaaagaa    540
atcgaccaac tgctgaaggt gcaaaaagat taccacaacc tggacatcga cttcatcaat    600
caatacaagg agatcgtgga aacacggaga gagtacttcg agggccccgg ccagggctct    660
ccattcggct ggaacgggga tctgaagaaa tggtatgaga tgctgatggg ccactgcacc    720
tacttccccc aggagctgag aagcgtgaag tacgcctaca gcgccgactt gtttaacgcc    780
ctcaatgatc tgaacaatct gatcattcag agagacaact ccgagaaact ggaataccac    840
gagaagtacc acataattga aaatgtgttc aaacagaaga gaaacccac cctgaagcag    900 attgctaaag atatcggcgt gaaccctgag gacatcaagg gctacagaat caccaagagc    960 ggcacccac agttcaccga gttcaagtta taccacgatc tgaagagcat cgtctttgac   1020
aagtccatcc tggaaaacga ggccatcctc gatcagatcg ccgagatcct gaccatctac   1080
caagatgaac agagcatcaa ggaagagctg aacaaactgc ctgagattct gaatgagcag   1140
gacaaggccg agattgccaa actcattggc tacaacggta cacacagact gagcctgaag   1200
```

-continued

```
tgtatccacc tgatcaatga ggaactgtgg cagacaagta gaaaccagat ggaaatcttc      1260
aactacctga acatcaagcc caacaaggtg gacctgtctg aacagaacaa gatccccaag      1320
gacatggtga acgacttcat tctgagccct gtggtgaaaa gaaccttcat ccagagcatc      1380
aatgtgatca ataaggtgat cgagaagtac ggcatcccag aggacatcat cattgagctg      1440
gccagagaga acaacagcga cgaccggaag aagttcatca acaacctgca gaagaagaac      1500
gaggccacaa gaaagcggat taacgagatc atcggccaga ccggcaacca gaatgccaaa      1560
cgcatcgtgg aaaagatcag actgcacgac cagcaggagg gcaagtgcct gtacagcctg      1620
gaaagcattg ctctgatgga cctgctgaac aatcctcaga attacgaggt ggaccacatc      1680
atccccagaa gcgtggcctt cgacaacagc atccacaaca aggtgctggt gaagcagatc      1740
gagaatagca agaagggcaa ccggacccct taccaatacc tgaattctag cgatgccaag      1800
ctgtcttaca accagttcaa gcaacacatc ctgaacctgt ccaaaagcaa ggatagaatc      1860
agcaaaaaga agaaggacta cctgctggaa gagagagata tcaacaagtt cgaggtgcaa      1920
aaggagttca tcaaccgaaa cctggtggac accagatacg ccaccagaga actgacgtct      1980
tatctgaagg cctactttttc tgccaacaac atggatgtga aagtcaagac catcaacggc      2040
tccttcacca accacctgcg gaaagtgtgg cggttcgaca gtaccgcaa ccacggctac      2100 aagcaccacg ccgaggatgc cctgatcatc gcaaacgccg atttcctgtt taaggaaaac      2160
aaaaagctgc agaacgctaa caagattctg gaaaagccca caatcgagaa caataccaag      2220
aaggtgaccg tggaaaaaga ggaagattat aataatgtgt tcgagactcc taagctggtc      2280
gaggatatca aacagtaccg ggactacaag ttcagccacc gggtggataa gaagcctaac      2340
agacaactga tcaacgacac tctgtattcc acaagaatga aggacgagca cgactatatc      2400
gttcagacca tcaccgacat ctacggcaag gataacacca atctgaaaaa gcagttcaac      2460
aagaaccccg aaaaattcct gatgtaccag aacgatccta agaccttcga gaagctgtcc      2520
atcatcatga acagtacag cgacgagaag aaccctctgg ccaagtatta tgaggaaacc      2580
ggagagtatc tgacaaagta ctcaaagaag aataacggcc caatcgtgaa gaagatcaag      2640
ctgctgggca acaaggtggg caatcacctg gatgtcacca caaatacga gaacagcacg      2700 aaaaagctgg tgaagctgag tatcaagaac tacagattcg acgtctacct gacagagaag      2760
ggctacaaat cgtgaccat cgcttactta aatgtgttca agaaggacaa ctactactac      2820
attcctaagg acaagtacca ggagttgaag gaaaaaaaga agatcaaaga taccgaccag      2880
tttatcgctt cttttttacaa gaatgacctg atcaagctga acggcgacct ttataagatc      2940
atcggcgtga actccgatga cagaaatatc atcgagctgg actactacga cataaaatac      3000
aaggactact gcgaaatcaa caacatcaag ggagagccta gaatcaagaa aaccatcgga      3060
aaaaagacag agagcatcga gaagttcacc acagatgtgc tgggaaatct gtacctgcat      3120
tctaccgaaa aggcccctca actgatcttc aagagagggc tg                          3162
```

<210> SEQ ID NO 413
<211> LENGTH: 3213
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 413

```
atgagggagc tggactacag gatcggcctg gacatcggca ccaacagcat cggctggggc      60
```

-continued

```
gtgatcgagc tgagctggaa caaggacagg gagcagtacg agaagaccag gatcgtggac    120
aagggcgtga ggatgttcga caaggccgag atccccaaga ccggcgccag cctggccgag    180
cccaggagga tcgccaggag cagcaggagg aggctgaaca ggaagagcca gaggaagaag    240
gacatcagga acctgctggt gcagcacgag atcatcagcc agaaggagct gaccagcctg    300
taccccctga gcaagagcag catggacatc tgggacatca ggctggacgg cctggacagg    360
ctgctggaca ggttcgagtg ggccaggctg ctgatccacc tggcccagag gagggggcttc    420 aagagcaaca ggaagagcga gctgaaggac gtggagaccg gcaaggtgct gagcagcatc    480
caggtgaacg agaagaggct gagcctgtac aggaccgtgg gcgagatgtg gatgaagaac    540
gccgactgca gcaagtacgg caagaggagg aacagcccca acgagtacgt gttcagcgtg    600
agcagggccg acctggagaa ggagatcgtg accctgttcg aggcccagag gaagttccac    660
agcagctacg ccagcgtgga cctgcagaag acctacatcc agatctgggc ccaccagctg    720
cccttcgcca gcggcaacgc catcgtgaac aaggtgggct actgcagcct gctgaagggc    780
aaggagaaga gggtgcccaa ggccacctac accttccagt acttcaacac cctggaccag    840
atcaacagga ccaggctggg ccccaacttc cagcccttca ccaaggagca gagggacatc    900
atcctggaca agatgttcca gaggaccgac tactacaaga agaagaccat ccccgaggtg    960
acctactacg acatcaggaa gtggctggcc ctggacgaga ccatccagtt caagggcctg   1020
acctacgacc ccaacgagga gctgaagaag atcgagatga gcccttcat caacctgaag   1080 cccttctacg agatcaagaa ggtggtgacc aactacgcca agaagaccaa cgaggtgttc   1140
agcgccctgg actacgacac cgtggcctac gccctgaccg tgtacaagac cgacaaggac   1200
atcaggagct acctgaagag gagcaacaac ctgagcaaga ggtgctacga cgaccagctg   1260
atcgaggagc tgctgaccct gagctacacc aagttcggcc acctgagctt caaggccatc   1320
aaccacgtgc tgcccatcat gcaggagggc aggacctacc aggaggccat ccaccagctg   1380
ggctacgaca ccaccaacct gaagaaggag aacaggagca tgttcctgcc catcatcccc   1440
gacgagatca ccaaccccat cgtgaagagg gccctgaccc aggccaggaa ggtggtgaac   1500
gccatcatca ggaggtacgg cagccccaac agcgtgcaca tcgagctggc cagggagctg   1560
agcaagagcc acgacgagag gaagaagatc atgaccgccc acgacgagaa ctacaagaag   1620
aacaagggcg ccatcagcat cctgatcgag aacggcatcc tgaaccccac cggctacgac   1680
atcgtgaggt acaagctgtg gaaggagcag ggcgagaggt gcgcctacag cctgaagaag   1740
atccccgcca acaccttctt caacgagctg aagaaggaga ggagcggccc ccccgtgctg   1800
gaggtggacc acatcctgcc ctacagccag agcttcatcg acagctacca acaaggtg   1860 ctggtgtacg gcgacgagaa ccagaagaag ggcaacagga tcccctacac cttcttcagc   1920
gaggaggaca aggagtggga gagcttcgag agctacgtga ggagcaacag cttcttcagc   1980
aagaagaaga ggggctacct gctgaagaag gcctacctgc ccaggagagag caacctgatc   2040 aaggagaggc acctgaacga caccaggtac gccagcagct acctgaagaa cttcatcgag   2100
aagaacctga agttcaagga ggccgtgggc atcaccagga agaagtacgt gcagaccgtg   2160
aacggcgtga tcaccgccca cctgaggaag aggtgggggcc tggagaagga caggcaggag   2220
acctacctgc accacgccat ggacgccatc atcgtggcct gcaccgacca ccacatggtg   2280
accaaggtga ccgagtacta ccagatcaag gaggcaaca agagcatcaa gaagccctac   2340
ttccccctgc cctggatggg cttcagggag gagatcctga ccacctgga gagccagccc   2400
```

-continued

```
atcgccagga agatcagcga ggagctgaag atcggctacc agagcagcga ctacatcctg    2460
gtgagcagga tgcccaagag gagcgtgacc ggcagcgccc acgaccagac cgtgatgaag    2520
aagggcggca tcgacaagaa gggcaagacc atcatcatca agagggtgca cctgaaggac    2580
atcaagttcg acgagaacgg cgacttcaag atggtgggca aggagcagga cctggccacc    2640
tacgaggcca tcaagcagag gtacctggag tacaggaaga agagcaagaa ggccttcgag    2700
acccccctgt acaagcccag caagaagggc aagggcaacc tgatcaagaa gatcaaggtg    2760
gaggtgcaga ccaagagctt cgtgagggag atcaacggcg gcgtggccca gaacggcgac    2820
ctggtgaggg tggacctgtt cgagaaggac aacaggtact acatggtgcc catctacgtg    2880
gtggacaccg tgaggagcga gctgcccaac aaggccgtga ccagcagcaa gggctacgag    2940
cagtggctga gcatcgacaa cagcttcacc ttcaagttca gcctgtaccc ctacgacctg    3000
gtgaggctgg tgaagggcga cgaggacagg ttcctgtact tcagcaccct ggacatcaac    3060
agcgacaggc tgaacttcaa ggacgtgaac aagcccagca gcaggccga gtacaggtac    3120 agcctgaaga ccatcgagaa cctggagaag tacgagatcg gcgtgctggg cgacctgagg    3180
ctggtgaggc aggagaccag gaagatcttc aag    3213
```

<210> SEQ ID NO 414
<211> LENGTH: 3228
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 414

```
atgagcgagc tggactacag aatcggcctg gacataggaa caaacagcat cggctggggc     60
gttatagaac tgttttggaa caaggacaga gaaagatacg agaaggtgag gatagtggac    120
aagggcgtgc ggatgtttga caaggctgaa atccccaaga ccggagcctc tctggccgaa    180
cctagaagaa tcgccagaag cagcagaagg agacttaata gaaagagcca gagaaaaaag    240
gagatcagaa acctgctggt gcaacacggc gtgatcaccc aggaagagct ggacctgctg    300
taccccctgt ctaagaagag catggacatt tgggacatcc gcctggacgg cctcgacaga    360
ctgctgaacc acctggaatg gacacggctg ctgattcacc tggctcagag gcgtggattt    420
aagtctaacc ggaagtctga gctgaaagac gccgaaacag gcaaagttct gagcagcatc    480
caggtgaacg agaaaagact gagcctgtat agaaccgtgg gcgaaatgtg gatcaaggac    540
gccgaattct caaaatacga tagacggaga aatagcccta cgaatacgt ctttagcgtg    600 tccagagccg acctggagaa ggaaatcgtt accctcttcg aggcccagcg gaaattccag    660
agcagctaca gcagcaaaaa cctccaggag acctacctgc aaatctgggc ccaccaactg    720
cctttcgcca gcggcaacgc catcttaaac aaggtgggct actgcagcct cctgaaaggc    780
aaggagcgga gaatccctaa ggctacatac accttccagt acttcagcgc cctggaccaa    840
gtgaaccgga ccagactcgg tcctgacttc caacctttta cacaggagca gaaagaaatc    900
atcctggaca gatgttcca gcggaccgac tactacaaga agaagaccat tcccgaggtg    960
tcctattatg atatcagaaa gtggctggaa ctcgacgaaa ctatccaatt taagggcctg    1020
aactacgatc ctaacgagga actgaaaaag atcgagaaga agcctttcat caacctgaag    1080
gccttctacg agatcaaaaa ggttgttgcc aactacgccg agagaaccaa cgaggccttc    1140 tccacccctgg actacgacgc catcgcttac gctctgacag tgtacaagac agacaaggat    1200
```

-continued

```
attagaagtt atctgaagaa aagcaacaac ctcagcaaac ggtgctacga cgaccaactg      1260
atcgaagaac tcttcaccct gagctatacc aagttcggcc acctgagctt caaggccatc      1320
aacagagtgc tgcctatcat gcaggagggc agaacctacc aggaggccat ccagcaactg      1380
ggctacgaca ccaccaacct gaagaaagag aatagaagca tgttcctgcc tctgatcccc      1440
gatgagatca ccaatcctat cgtgaagcgg gccctgaccc aggccagaaa agtggtgaac      1500
gccatcatcc gccgctacgg atctccaaac tccgtgcaca tcgagctggc tagagagctg      1560
tcaaagagcc acgatgagag aaagaagatc atgacagccc acgacgaaaa ctacaagaag      1620
aataagggcg ccatcagcat cctgatcgag aacggcatcc tgaaccccac aggctacgat      1680
atcgtgcggt acaaactgtg gaaggagcag ggcgagcggt gcgcctactc cctgaaggaa      1740
attccacctg acactttttt caacgagctg aaaaaagaac gcaacggcag tagcatcctg      1800
gaagtggacc acattctccc ctactcccag tcttttatcg atagctacca caacaaagtg      1860
ctggtctaca gcgacgaaaa tcggaacaag ggcaacagaa tcccttacac ctacttcctg      1920
gaaacaaaca aagattggga agccttcgag agatacgtgc ggagcaataa gctcttcagc      1980
aagaaaaaga gagagtacct gctgaagaag gcttacctgc cacgggagtc tgaactgatc      2040
aaggaaagac acctgaacga caccagatac gccagcacct tcctgaagaa cttcatcgag      2100
cagaacctgc agttcaagga agtggaagtg aacctgagaa aaaagcgggt gcaaaccgtg      2160
aacggcgtga tcaccgccca cctcagaaag cggtggggcc tggaaaagaa ccggcaggag      2220
acctacctgc accacgctat ggacgctatt atcgtggctt gtacagacca tcacatggtc      2280
accagaatca cagagtacta ccagatcaag gagagcaaca agtccgtgaa gaaaccttat      2340
ttccccatgc cctgggaggg cttcagagat gagctgctga gccatctggc tagccagcct      2400
atcgccaaga agatttctga agagctgaaa gccggatacc agagcagcga ttacatcttc      2460
gtgagcagaa tgcctaagcg gtccgtgacc ggcgccgccc ataatcagat gatccggaga      2520
aagggcggaa tcgacaaaaa gggcaagacg atcatcatta agagagtgag actgaaagat      2580
atcaaattcg atgagaacgg cgatttcaag atggtgggaa aagaacaaga cctggccaca      2640
tacgaggcca ttaaacagag ataccttggat cacggcaaga acctcaaaaa ggccttttgaa      2700 acccctctgt acaagccttc taaaaaaggc accggaaacc tgatcaagcg ggtgaagatc      2760
gagggacaga ccaaggcatt cgtgagagag gtgaacggcg gagtggccca aaattctgac      2820
ctcgtgcggg tggacctttt cgagaaggat gacaagtact acatggtgcc catctacgtg      2880
cctgatacag tgtgtagcga gctgcctaag aaagtggtca aaagtggcaa gggctatgag      2940
cagtggctga ccctggacaa cagcttcacc ttcaagttct ccctgtaccc ttacgactta      3000
gtgagactgg tgaagggcga cgaagataga ttcctgtact ttggcacact ggatatcgac      3060
agcgaccggc tgaacttcaa ggacgtgaat aaaccttcta agcagaacga gtacagatat      3120
agcctgaaga ccatcgagga cctcgaaaag tacgaggtgg gcgtgctggg cgacctgcgg      3180
ctggtgcgaa aagaaactcg gcggaatttc cacgagatca aaattaac                  3228
```

<210> SEQ ID NO 415
<211> LENGTH: 3276
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

-continued

```
<400> SEQUENCE: 415
atgcggtaca gcattggact ggatatcgga accacatcta tcggaaatgc cgtgatcaac      60
aaggatctgc agaggtttga gcacctgggc gtgagaatct tcgatgccgc agagaacccg     120
aaagacggct cttctctgag cgcccctaga agactggccc ggagcagcag acggcggctg     180
cggagaagaa agcaccgggt cgagcggacc aaacaactgc tgatcaacaa gggtctgctg     240
accaagaccc aggtgaagaa cctgtacaac agcaaaaaca tcaacctgga catctgggac     300
atccgggtgt caggcatcga tagaaagctg ttcaacaacg agttcgccag ggtgctgatc     360
cacttcagca aaaaccgagg attcaagtcc aacaggaaaa gcgagctgaa agaagatgac     420
aatggcgcta tcctgagcgc cgtcaaggaa aacagagagc tgatggacga aagggctac      480 agaacaatcg ccgagatgct ggtgtccgat gagaagtacg agggcaccaa gagaaacaag     540
ggcggcgatt acagccacgt ggtggcccga agcgacatcg agaacgaaat ctgcctgctg     600
ttccagaagc agagggagta cggccacccc ttcgccacag aggagaacga ggaagccttc     660
ctgagcatct ggagcagcca gagacctttt agcaccaaag acgacatcgt caagaagatc     720
ggcaactgca ccctggaacc taaggaaaag agggcccta agtccactta caccttcgag       780
cggttcagag ccctggacaa gctcaacaga ctgagaatcc tgtctaccac cgcccttct       840 cggcccctga ctaacgaaga aagaaagagc atcctgagca gcctgttctc caagaaggaa     900
gtgaaataca aggaactgcg gaagctcctc aaactgacag acgaccagcg gttcaacgag     960
atctactact ctccagatga gacaatcgag aaaaccgaga atagaacatt cctgagcctt    1020
gagtcccagt acaagatcaa gaagatcatc gagaagaccg aaagcaagaa tatgcagagc    1080
agctaccacc ctattgacta cgacaccatc ggctatgccc tgaccgtgtt caaagacgac    1140
aaggacatcc aacactacct gcagaacagc tacatcgaca gcaagggcaa ggccatcccc    1200
aacatggcca acagagagta caacctggaa ctgatcgagg agctgcttgg cctgagcttt    1260
gccaaattcg gccacctgag cctcaaggct ctgaacaaca tcctgccta tatggaagag     1320 ggcgagccct atcacatcgc ttgtgaaatg gctagctacc agttcagcca gcggctgtcc    1380
aaagaaaagc acagactgct gcctccaatc ccagtggacg agatccccaa ccccgtggtc    1440
gtgcgggccc tgacgcaggt gcgcaaagtg ctgaacagca tcatcaagaa gtacggccct    1500
cctagcgaca tctacatcga gctagccaga gaaatgagca gcccttcaa ggagagaaaa      1560 tctctggaaa gagaattcaa cgagaaccgg cagatcaacg agaaggccaa ggcccacatc    1620
agcgagctgt atagaatccc caatgacccc agaccccacg acatcctgaa gttcaagctg    1680
tggaacgagc aaaacggcat ctgcccctac tccctgaagc ctatttctat cgagtacctg    1740
ttcaacatcg gtacgccga ggtggaccac attatcccat acagccggag cttcgacgac      1800
agcaacggaa acaaggtgct ggtcctgacc agagaaaacc agaacaaact gaaccggacc    1860
ccttatgagt ggttcggcca tgaggaaaac cggtgggagg atttcgtgtc gtttatcagg    1920
acaatgaagg tgggcaagaa gaaaaaaaat atgctgctga aaagaatttt cgacgaagag    1980
caagaggagc agatcctgtc tagaaatctg aatgacacca gatacatcac aagatacatc    2040
aagagcttca tcgaagataa cctggagttc cggacagaag aaaacaagga acagtacgtg    2100
cacaccgtga atgggcccta tacaagcctg atgagaaaga gatggggcct gaacaaggac    2160
cggagaggaa atgatctgca ccacgccgtg acgccgcca tcattgccgt cagcctccct       2220
ttcaagaaca aggtgaacgc ctactttaag agacaggaga ccggcctgag caagctgctg    2280
aacaacaaga aggacatctt ccccgagcct tggcggaact tcatcaagga actggaagcc    2340
```

-continued

```
agaatgatcc aggaccctga gaagatgaag agagccctgg agagcctgga gctggaaaca     2400
tacggagaaa tcttcctgaa caagctgaag cccatctttg tgtccagaat gcctaagcat     2460
tctatcaaag gccagatcca cgaggaaaca attagacggg tgcggggctt taccgaggaa     2520
ggctttctgg tgaccgtgaa gaagaccaga ctggatcaga tcccttttcga caagaacggc     2580 gacttcccta tgtacggcaa ggaaaccgac atcaagacct acatggccat caagcagcga     2640
tacctggaat acggccagga caaacaaaag gcttttgctg ttcctctgag aaagcctagc     2700
aaaaacccca aaaatgcccc tatcgtgcgg agcgtgaaga tcgagggcaa ggccaataga     2760
gtggtgatgc tggacgataa ggccgctgcc gacaacgcca gcattgtgcg gaccgaagtg     2820
tttagacaca agaagaccgg cgagtactac ctgacacctg tgtacgtggc cgatatcctg     2880
tccaataaaa tcccagacag actgattacc atcaagaaga gctacagcga ctgggataga     2940
atcacagacg aacacgagta tctgtttttct ctgtacaaca acgacctcgt gaaaattatc     3000
ctgcccaagg agaaagagac aaagaagtac accggaggca tcacctctg gcaggagggt     3060 ttcttctact tcaagggagt tgatagctcc aacgccggca tcaagataat caaccacctg     3120
aattctttcg aggccaggat cggcaccaag cggctgattg catttgagaa gtatcaggtg     3180
aaccctctgg gcgaaatcaa caaagtgcat ggcgagaaac ggcctggcga gttgctgaat     3240
aaagaagaga tcaaagaaaa tagaaagaat atctct                              3276
```

<210> SEQ ID NO 416
<211> LENGTH: 3450
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 416

```
atgtacagca tcggcctgga cctggggatc agcagcgtgg gctggagtgt tatagatgag       60
agaaccggca acgtgatcga cctcggcatc agactgtttt cagccaagaa cagcgaaaag      120
aatctggaac ggcgcaccaa caggggcgga cgacggctga tccggcgaaa gaccaaccgg      180
ctgaaggacg ccaagaagat cctcgccgcc gtgggcttct acgaggacaa gagcctcaaa      240
aactcttgcc cttatcaact gagagtgaaa ggcctgacag agcctctgtc taaggggggaa      300 atctacaagg tgaccctcca tatcctgaag aagcggggca tcagctacct ggatgaagat      360
gatacagagg ccgctaagga gagccaggac tacaaagagc aagtgcggga aaacgcccaa      420
ctgctgacaa agtacacccc tggacaaatc caactgcagc ggctgaaaga aaacaacaga      480
gtgaagactg gcatcaacgc ccagggcaat taccaactga acgtgttcaa ggtgtccgct      540
tacgccaacg agctggccac tattctgaag acacagcagg ccttctaccc caacgagctg      600
accgatgact ggatcgccct gttcgtgcaa cctggcatcg ccgaggaggc cggcctgatc      660
tatagaaaac ggccttacta ccacggccct ggcaacgaag ctaacaatag ccccctacggc      720 agatggagcg attttaagaa aacaggacag cctgctacca acatcttcga caagctgatc      780
ggcaaagact tccaaggaga actcagagcc agcggactca gcctgagcgc tcaacagtac      840
aacctgctga cgaccttac aaacctgaag atcgacggcg agattcccct gagccctgag      900
cagaaggagt acatcctggc cgagctgatg accaaggagt tcaccagatt cggcgtgaac      960
gacgtggtga agctgctggg agtgaagaag gaacggctga gcggctggcg gctggataag     1020
```

-continued

```
aagggcaagc ctgagatcca caccctgaaa ggctacagaa actggagaaa gatcttcgcc      1080
gagagcggga tcgacctcgc tacactgcct acggagacca tcgactgcct ggccaaggtg      1140
ctgaccctga acactgagag agaaggcatc gagaacaccc ttgcctttga gctgtctgaa      1200
ctggccgaga gcgtcaagct gctggtgctg gaccggtaca aggaactgag ccagagcgtg      1260
agcacccagg cctggcacag attttctctg aaaaccctgc acctgctgat ccctgagctg      1320
atgaacgcca ccagcgagca gaacaccctt ctggaacagt ttcaactgaa gtccgatgtg      1380
cggaaaagat acagcgagta caagaagctg cctacaaagg atgtcctgac cgaaatctac      1440
aaccctaccg tgaacaaaac cgttagccaa gccttcaagg tgatcgatgc cctgctcgtg      1500
aagtacggaa aagagcagat cagatacatt accatcgaga tgcccagaga tgacaacgag      1560
gaggatgaga agaaaagaat taaggaactg cacgccaaaa acagccagag aaaaaacgac      1620
tcacagagct acttcatgca gaaaagcgga tggtcccaag agaagttcca gacaaccatc      1680
cagaagaaca aagatttct ggctaagctg ctgtactact acgagcagga tggcatctgc      1740
gcctacaccg gcctgtctat ctctccagag ctgctggtgt ccgactccac cgagatcgac      1800
cacattatcc ctatcagcat cagcctggac gacagtatca acaacaaggt gctggtgctg      1860
tccaaggcca accaggtgaa aggccagcag acccccttacg acgcctggat ggacggatct      1920
ttcaagaaga tcaacggcaa gtttagcaac tgggacgatt accagaagtg ggtcgaaagc      1980
tgtcacttca gccacaagaa agagaacaac ctgctggaaa ccagaaacat ctttgactcc      2040
gagcaagtcg aaaaatttct ggctagaaac ctgaacgaca ccagatacgc ttctagactg      2100
gtgctgaaca ccctgcagag cttcttcgct aaccaggaga caaaagtgcg ggtggtgaat      2160
ggcagcttca cccacaccct gcggaaaaag tggggcgccg acctcgacaa gacaagagag      2220
acacaccacc accatgccgt tgatgccacc ctgtgcgccg tgaccccttt cgtgaaggtg      2280
tctcggtatc actacgcggt gaaagaagaa acaggcgaga aggtgatgag agagatcgac      2340
ttcgagaccg gcgagatcgt ggacgaaatg tcttatagag aattcaagaa gagcaagaag      2400
tacgagcgga agacgtacca ggtgaagtgg cctaacttca gagagcaact gaagcccgtg      2460
aacctgcatc ctagaatcaa gttcagtcac caggtggaca gaaaagccaa tagaaaactg      2520
agcgacgcca cgatctatag cgtgcgggaa aagaccgagg tgaagaccct caagtcagga      2580
aaacagaaaa taacaacaga cgagtacacc atcggcaaga tcaaggacat ctacaccgtg      2640
gatgggtggg aggccttcaa gaaaaagcag gacaagctgc tgatgaaaga cctggacgag      2700
aagacctacg aaagactgct gtccatcgcc gaaaccaccc ccgacttcca ggaggtggaa      2760
gagaagaacg gcaaggtgaa gcgggtgaag aggtccccat tcgccgtgta ctgcgaggaa      2820
aatgacatcc ccgctatccg gaaatacgcc aagaaaaaca acggcccct gatcagatct      2880 ctgaagtatt acgacggcaa actgaacaag cacatcaaca ttacaaaaga tagtcaaggc      2940
agacctgtgg aaaaaaccaa gaatggcaga aaggtgacac tgcagagcct gaaaccctac      3000
agatatgata tctaccaaga cctggaaacc aaggcctact atacagtgca actgtactac      3060
agcgacctgc ggttcgtgga aggcaagtac ggcataacag agaaagaata catgaagaag      3120
gtggccgagc agaccaaggg ccaagtggtt agattctgct tcagcctgca aaagaacgat      3180
ggactggaaa tcgagtggaa ggacagccaa tgttacgacg tgcgatttta caacttccag      3240
tctgctaatt ctatcaactt caagggcctg gaacaggaga tgatgccagc cgaaaatcag      3300
ttcaagcaaa agccatataa caacgggccc atcaacctga atatcgctaa gtacggcaag      3360
gaaggtaaga aactgagaaa gttcaacacc gacatcctgg gcaaaaagca ctacctgtac      3420
```

-continued

```
tacgagaagg aacccaagaa tatcatcaaa                                    3450
```

<210> SEQ ID NO 417
<211> LENGTH: 4287
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 417

```
atgatgatca aacacattct gggcctggat ctgggcacga acagcatcgg atgggccctc      60
atcaagcaaa atttcgagaa caaatatgga gagatcctgg gaatgggcag cagaatcata     120
cctatgagcc aagatattct cggcgagttc ggcaagggaa atagcgtgtc acagaccgcc     180
gctagaaccg actaccgggg catccgccgg ctgagagaaa ggtttctgct gcggagagaa     240
cggctgcaca gaatcctgaa cgtgctgaac ttcctgcctg aacactacgc cagccagatc     300
gacttcgaca aacgcttcgg caagtttaaa gtcgagacag aacctaagct ggcctggaaa     360
aacagcgacg gcaaattctc attcctgttc cagaccagct tcaacgagat gctggaggac     420
ttcaaggccc acggccagga cctgaaggtg ccctatgact ggaccatcta ttacctgcgg     480
aaaaaagctc tgagccagaa aatcgaaaaa gaggaactcg cctggattct gctgaacttc     540
aaccagaaga gaggctacta ccaactgaga ggagaagagg aagaagaaaa tcccaataaa     600
ctgatcgagt tctacagcct gaaaatcatc gacgtgctgg ccgacgagcc tcagaagggc     660
aaatctgata tctggtacag ccttgtcctt gagaacggct ggatctacag aagatcctcc     720
aaaacaagcc tgctggactg gaaggataag atcagagatt ttatcgtcac caccgatctt     780
aacgacaacg gctccgtgaa gacagacaag gagggaaatg aaaagcggag cttcagagcc     840
cctggcgaga cgactggac acttgttaag accaaaaccg agcaggagat agaccgctcc     900
agaaagaccg tcggcacgta catctacgag acactgctgc agaaccccaa gcagaagatc     960
aagggcaagc tcgtgagaac aatcgagaga aaattctaca aggaggagct gaaacagatc    1020
ctggaaaagc aaaaggaatt ccactacgag ctgcagtccg acgatctgta cgacgactgc    1080
atccgggagc tgtacagaaa caacgaggcc catcaactga ccctcagcaa gaaagacttc    1140
gtgcacctgt tcatggaaga tataattttc tatcaaagac tctctgaagtc ccagaaaagc    1200 agcatatcta actgcaccct ggagttcaga aagtacaaag acgagaacgg cgtggagcac    1260
acccagttcc tgaaggccat tcctaagagc aaccccctatt atcaggaatt cagaatttgg    1320
cagtggattt tcaatctgaa catctacaag aaggacaacg atgacaacgt gaccaaggaa    1380
ttcctgagca ccaccgaaga cttcgagaac ctgttcgagt ttctgaataa tcggaaaagag    1440 atcgatcaga aggctcttct gaaacacttc aagctcaatg agaaaactca cagatggaag    1500
tacgtggaag ataagaagta tccttgcaac gagacaaaaa ccatgatttc cgagagattg    1560
aaaaaggtgg aaaatatctc cgacgacttt ctgacaagag gcatggaaca gaagatctgg    1620
cacatcatct actccgtgaa tgacaaaacc gaatacgaga aagctctgaa gagctttgcc    1680
gaaaagaaca atctggatga gaatagcttc ttcgaggcct ttcggaaatt tccacctttc    1740
aagtccgaat acggctcttt ctccgaaaag gccatcaaga agctgctccc actgatgaga    1800
ctgggcaagt attggagcta cgccaacatc gacctctact caaagaacag aatccagaaa    1860
atcatcaccg gcgaattcga cgagaacatc aaggatagag tgcgggagaa agcaatccac    1920
```

-continued

```
ctgaccgccg agaatgactt ccagggcctg caactgtggc tggcccagta catcgtgtac    1980
gggagacata gcgaggcaac catgatcggc aagtggaact ctgccgatga tctggaggaa    2040
tttctgaagg agtttaagca gcacagcctg cggaacccaa tcgtggagca ggtgattaca    2100
gaaaccctgc gtgtggtgaa ggacatttgg ctgaaatacg aaacggcgc caaggacttc    2160 tttaacgagg tgcacatcga gctgggaaga gagatgaagc agacaaagga cgaacgggct    2220
aatgccacaa agacaatcac cgaaaatgaa aacaccaacc tgagaatcaa agccctgctg    2280
gctgagatga tgaacgacca cagcgtggaa aacgtgcggc cttattctcc tatgcagcag    2340
gagatcctga aaatctacga ggacggcatc ctgaaatcgg atatcgagat cgatgacgac    2400
atcctgaaga tcagcaaaac cgcccaacct agcagcagcg atctgaaaag atacaaactg    2460
tggctggagc agaaatacaa gtccccttac accggacaga tcatccccct gaataagctc    2520
ttcacccctg agtacgaaat cgaacacatc atccctcagt ccagatactt cgacgacagc    2580
ctgagcaaca aaattatctg cgagagcgcc gtgaacaagc tgaaagataa ctacatcggc    2640
ctgggtttca tcaagcaatt cggcggcaca atcatcgagt gcggcttcgg caagagagtg    2700
aaggtttcta aggccgagga atacgaggaa ttcgtgaaga agcactacgc caacaaccgg    2760
ggcaagagaa acaagctgct gctggaagac atcccagaga agatgatcga gcggcagatg    2820
aacgacaccc ggcatatctc taagtacatc agcggcattc tgtcccacat cgtccgggtg    2880
gaagacggca ccgacgaggg cgttaacagc aaaaatgtga tccccggcaa cggcaaaatc    2940
accacacaac tgagacagga ctggggactg aatgatgtgt ggaacgagct tgtgctgccg    3000
cgattcgaga gaatgaacca actgaccaac agcacagatt ttacaagctg gaacgagaac    3060
caccagaagt acctgcctac agtgcctgtg gagtttagca agggattctc taagaaaaga    3120
atcgaccacc ggcaccacgc cctggacgcc ctggtgatcg cctgcgccac caaggatcat    3180
gtgaacctgc tgaacaatca gagcgccaag agcgacacga agcgatacga tctgaagaag    3240
aagctgatga agttcgagaa gacagtgtac aaggacccc agaccgagaa gcgaatcgag    3300
cgagaagtgc caaagtactt tctgaagcct tgggagactt ttaccgtgga cgccaagaac    3360
aagctggaaa ccatcatcgt gtccttcaaa cagaacctca gagtcatcaa caaggccaca    3420
aactactacg agaagtacgt ggacaaggac ggcgtgaaga cgaaggagcg ggttgagcag    3480
actggaacaa actgggccat cagaaaacct atgcacaagg aaaccgtgtc cggcaaaatt    3540
gacctgcctt gggtgaaagt gcccaagggc aagatcctga ccgccaccag aaagagcctg    3600
gacaccagct tcgacctcaa ggctatcgcc agcatcacgg acaccggcat ccagaagatc    3660
ctgaagaact acctggagtt caaggaatcc cctgagctgg ccttcagccc tgagggcatc    3720
gaggacatga acaagaacat caaaaagtac aacggcggaa agcccaccca gcctatctct    3780
aaggtgcgcg tctttgagct gggcagcaag ttccaagtgg gccagaccgg caataagaag    3840
gacaagtacg tggaagccgc caagggacc aacctgttct cgccatcta tgaggacaga    3900 aagggcaagc gctcctacga gaccatccct ctgaacgagg tgatcgagag acagaagcag    3960
ggtctgtctg tggtggacct gaagaacatt aacgacttct tcctgtgtcc taacgacctg    4020
gtgtacattc ccagcggcga cgagttggaa aacggcggct ccatagagat caaaaacatc    4080
accaaagaaa agtccgaaag attttataag gtggtctctt tttctggcag ccaaatcttc    4140
ttcgtgcggc acgacattgc cgtgtccatc gtgaacaagg gggaattctc caccctaaac    4200
aagatggaac gcgccatcga tggctctatg gtgaaggaat cttgtatcaa gctgaagatc    4260
gacagactgg gcaacgtgct gaaagcg                                        4287
```

-continued

```
<210> SEQ ID NO 418
<211> LENGTH: 4296
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 418
atggccaaga atatcctcgg cctggacctg ggcaccaaca gcatcggctg ggcccttatc      60
aaccaagact tcgagaacaa gcagggtaag atcctcggaa tgggcagccg gatcattcca     120
atgagccaag atatcctggg cgacttcggc aagggcaact ctgtgtccca gaccgccgct     180
agaaccggct accggggcgt gcggagactc agagagcggg ttctgctgag aagagagaga     240
ctgcaccggg tgctgaatat aatcaacttc ctgcccgaac attacgcctc tcagatcgac     300
tttgagaaaa gattcggcaa gttcaaggaa gaaaccgagc ctaagctggc ctacaacaaa     360
gacggcttcg tgttcaagga tagctttgag gaaatgctgg ccgattttaa gaactaccag     420
cctcaactgc tggaaaacga caagaaaatt ccctacgact ggaccatcta ctacctgaga     480
aagaaggccc tgtcccagaa aatcgagaag gaagagttgg cctggattct gctcaatttc     540
aaccagaaga gaggctatta ccaactgagg ggcgaagact cgaggaaga gaaggacaaa     600 atgttcgtcc gcctgaaggt ggagaagatc atcgatagcg gcgacaacgt gaagggtaag     660
attctgtacg acgtctactt cgagaacggc tggaaatacg acaaacagat cgttaagacc     720
gaggactgga tcgaaagagt gaaggaattc atcgtcaccg aatctttcct gaagaatggc     780
gacatcaaga gaacatttaa ggccgtggac tccgagaagg attggatcgc catcaaaaca     840
aaaacagaac aagagattga caagtcccac aagaccgtgg gcgtgtacat ctacgaaaca     900
ctgctccaga accctaagca gaagattaag ggcaagctgg tgagaacaat cgagcgcaag     960 tttttacaagg acgaactgaa gcagatcttg gagaagcaga aagagttcca ccaggagctg    1020
aagaacgatg acctgtataa cgactgcgtg agagaactgt acagaaacaa tgaagctcat    1080
caactgaccc tctctaagaa ggagtttgtg cacctgctga tggaagatat catttctctac    1140 caaagacccc tgaggtccca gaagagcagc atcagcaatt gcagcctgga attcagaaag    1200
tacaaggacg agaacggcgt ggagcatatc caatatctga agccgtgcc taagagcaat    1260 ccttactacc aggagtttcg gatctggcag tggatcttta acctgaacat ctacaagcgg    1320
gacgatgagc aaaaccccgt gaccacagag ttcctgaaca ccaccaccga tattgaaaac    1380
ctcttcgagt tcctcaacaa ccggaaggaa gtggatcaga agccctgct gaaacatttc    1440 aagctgaacg agaagaccca gatggaag tacgtggagg ataagaaata cccctgcaac    1500
gaaaccaaga gcatgatttc cgagcggctg aagaaggtgg agaacatagc taacgacttc    1560
ctgaccagag agattgagca gaaaatctgg catatcatct attctgtgaa cgacaaaatc    1620
gaatacgaaa aagccctgaa gagttttgcc aagaagaaca acctggacga gaactccttt    1680
ttcgaggctt tcaagaaatt ccccccccttc aaaagcgagt acggcagttt cagcgaaaag    1740
gccatcaaga agctgctgcc tctgatgcgg cttggcaagt actggaactg cgagaacatc    1800
agcgacgaca gcaaggaaag aatccagaag attatcaacg gcgagtacga cgagaatatc    1860
aaggatagag tgcgcgagaa agccattcac ctgaccagcg aaaacaactt ccagggcctg    1920
cagctctggc tggcccagta cgtggtgtac gacagacatt cggaagccag catgatcggc    1980
```

```
aagtggaata gcgccgacga cctcgaagaa ttcctgaagg agttcaaaca gcacagcctt          2040
agaaacccta ttgtggagca ggtgatcaca gagacactgc gggtggtgaa ggacatctgg          2100
ctgaagtacg gcaatggagc caaagatttc ttcaatgaga ttcacatcga actgggaaga          2160
gagatgaagc aaaccaaaga cgagcgcctc gatgctacga agcggatcac cgagaacgag          2220
aataccaatc tgagaatcaa ggctctgctg gctgagatga tgaatgataa cagcgtggaa          2280
aacgtccggc cttacagccc tatgcagcag gagatcctga agatctacga ggatggcgtg          2340
ctgaatagtg gaattgagat tgaagatgaa tacctgaaga tttctaagac cgcccagcct          2400
agcccttctg acctcaagcg gtacaagctg tggctggaac agagatacaa gagcccatac          2460
accggccaga tcattcccct gaacaagctg tttacccctg aatacgagat tgagcacatc          2520
atccctcaga gcagatactt cgacgacagc ttcagcaaca agatcatctg tgaaagcgcc          2580
gtgaacaagc tgaaggacaa ctatatcgga ctgggcttca tcaagcagtt cggcggaacc          2640
atcgtggagt gcggcctggg aaaaaacgtg aaggtgtttg aagtgaacga gtacgaggac          2700
ttcgtgaaga aacactacgc caacaacaga ggaaagagga ataagctgct cctggaggaa          2760
atccctgaga aaatgatcga gaggcaactg aacgacacca ggcatatcag caagtacatc          2820
tccggcgtgc tgagcaacat cgtgcgggtg gaagacggct ctgacgaggg agtgaacagc          2880
aaaaacatcg tgccaggcaa tggcaagatc accacccaac tgaagcagga ttggggactg          2940
aacgatgtgt ggaacgacct gatcctgcct agattcgaga gaatgaacca actgaccaat          3000
tcaacagact tcaccgcctg gaacgaaaat caccagaagt ttctccctac agtgcccatc          3060
gaatttagca agggatttag caagaaaaga atcgaccaca gacaccacgc cctggacgcc          3120
ctcgtgatcg cctgtgccac caaggaccac atcaatctgc tgaacaatca gtctgccaaa          3180
agcgacacca aacggtacga cctgaagaaa aagctcatga aattcgagaa gggcgtgtac          3240
aaccaccctc agaccggcga gagaatccag cgggacgtgc cgaagcaatt tctgaagcct          3300
tgggagagct tcaccatcga cgctaagaac aacctggaca agatcatcat cagcttcaag          3360
cagaacttga gggtgatcaa caaagccaca aactactacg agaagtatgt ggaaaagaac          3420
ggcatcaaga caaaagagag agtcgaacag acaggcacaa actgggccat ccggaagccc          3480
atgcacaagg aaaccgtgtc tggcatcgtt aacctgcctt gggtgaaagt gcctaaaggc          3540
aaaatcctga ccgccacccg gaaaagcctg gacaccacat ttgacctgaa aagcatcaac          3600
tccataacag ataccggcat tcagaagatc ttgagaaact acctggaatt caaaggcagt          3660
cctgaactgg ccttcagccc agagggcatc gaggacatga acaagaacat cgagaaatac          3720
aacgatggca agctgcacca acctataaac aaagtgagag ttttcgagct gggcagcaaa          3780
ttccaagtgg gacagaccgg caacaagaag gacaagtacg tggaggccgc caagggcacc          3840
aacctgttct cgccgtcta cgaggacaag aacggcaaaa gaaactacga aacaatccct          3900
ctgaacatag tgatcgagag acagaagcag ggcctcctgg cctgccccga gagtaatgaa          3960
aaaggcgaga agctgctgtt ccaactgagc ccaaacgact cgtgtatct cacgacagag          4020 gaagaaaatg ataacgccac acctatcaat ttctctctgc tgagcaagga acagattaac          4080
aacctgtaca aaatcgtgtc ctttaccggc aacagactgt acggcatccc tatctgcgtg          4140
gccaccacaa tcgtgaacaa agccgagtac acccaactga acaagatcga gttcaccaaa          4200
gagaaagatc tgctgctgaa gctcaatgtc aatagactgg cgacgtgaa gacctttaca          4260 gccaatgaca tcagaaagat tttcaaccgg caggag                                    4296
```

```
<210> SEQ ID NO 419
<211> LENGTH: 137
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 419
aagugggaga guacugaaug ggcacguugc gguuggccug cgauuucuga acaaagguuc      60
agaaaucgca guccagccgu uaacaagcug agauaugcac caaauaaggc gcucgcuucg     120
gcgggcgcuu uuucguu                                                    137

<210> SEQ ID NO 420
<211> LENGTH: 137
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 420
accuucuucc cauggcagua cauuaguugc gguuggccug cgauuucuga acaaagguuc      60
agaaaucgca guccagccgu uaacaagcug agauaugcac caaauaaggc gcucgcuucg     120
gcgggcgcuu uuucguu                                                    137

<210> SEQ ID NO 421
<211> LENGTH: 137
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 421
gcccacaacu gcgauaauga cucuaguugc gguuggccug cgauuucuga acaaagguuc      60
agaaaucgca guccagccgu uaacaagcug agauaugcac caaauaaggc gcucgcuucg     120
gcgggcgcuu uuucguu                                                    137

<210> SEQ ID NO 422
<211> LENGTH: 137
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 422 uggggcgcu caguuuccag aaccuguugc gguuggccug cgauuucuga acaaagguuc      60
agaaaucgca guccagccgu uaacaagcug agauaugcac caaauaaggc gcucgcuucg     120
gcgggcgcuu uuucguu                                                    137

<210> SEQ ID NO 423
<211> LENGTH: 133
<212> TYPE: RNA
<213> ORGANISM: Artificial Sequence
<220> FEATURE:
<221> NAME/KEY: source
<223> OTHER INFORMATION: /note="Description of Artificial Sequence:
```

Synthetic polynucleotide"

<400> SEQUENCE: 423
acagugcgca ucucccuggu caccguuuua guacucugua auuuuaggua ugaaagucau      60
accuaaaauu acagaaucua cugaaacaag acuauaugc guguuuaucc cacuaauuua      120 uuaguggau uuu                                                          133

<210> SEQ ID NO 424
<211> LENGTH: 131
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 424
auuuacagcc uggccuuugg ggguuuuagu acucuguaau uuuagguaug aaagucauac      60
cuaaaauuac agaaucuacu gaaacaagac uauaugucgu guuuauccca cuaauuuauu      120 aguggauuu u                                                            131

<210> SEQ ID NO 425
<211> LENGTH: 134
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 425
ccuuggggcc cagacugagc acgugguuuu aguacucugu aauuuuaggu augaaaguca      60
uaccuaaaau uacagaaucu acugaaacaa gacuauaugu cguguuuauc ccacuaauuu      120
auuaguggga uuuu                                                        134

<210> SEQ ID NO 426
<211> LENGTH: 134
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 426
cuucuccuca ggagucagau gcaccguuuu aguacucugu aauuuuaggu augaaaguca      60
uaccuaaaau uacagaaucu acugaaacaa gacuauaugu cguguuuauc ccacuaauuu      120
auuaguggga uuuu                                                        134

<210> SEQ ID NO 427
<211> LENGTH: 132
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 427
gaugauauuu ucuuuaaugg ugcguuuuag uacucuguaa uuuuagguau gaaagucaua      60
ccuaaaauua cagaaucuac ugaaacaaga cuauaugucg uguuuauccc acuaauuuau      120

-continued uaguggggauu uu                                                          132

<210> SEQ ID NO 428
<211> LENGTH: 133
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 428
ggcugggcca uuaaaaccuc uccaguuuua guacucugua auuuuaggua ugaaagucau       60
accuaaaauu acagaaucua cugaaacaag acuauaugc guguuuaucc cacuaauuua        120 uuaguggggau uuu                                                         133

<210> SEQ ID NO 429
<211> LENGTH: 206
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 429
cacaucucga gcaagacguu gucauaguuc cauuaaagcc auugcuguuu uaugaaagca       60
ugauacagca auggcuuuga uguuucuaug auaagggcuu cggcccgugg cguuggggau       120
cgccugccca uuuuaauggg cuucucccca ucuauuuaau gagaaauuua caaccuuggc       180
uauucuuaaa uagcuaaggu uuuuuu                                            206

<210> SEQ ID NO 430
<211> LENGTH: 206
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 430
cauggcagua cauuagagca gucauaguuc cauuaaagcc auugcuguuu uaugaaagca       60
ugauacagca auggcuuuga uguuucuaug auaagggcuu cggcccgugg cguuggggau       120
cgccugccca uuuuaauggg cuucucccca ucuauuuaau gagaaauuua caaccuuggc       180
uauucuuaaa uagcuaaggu uuuuuu                                            206

<210> SEQ ID NO 431
<211> LENGTH: 206
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 431
ccugaaugcu gugcggcucu gucauaguuc cauuaaagcc auugcuguuu uaugaaagca       60
ugauacagca auggcuuuga uguuucuaug auaagggcuu cggcccgugg cguuggggau       120
cgccugccca uuuuaauggg cuucucccca ucuauuuaau gagaaauuua caaccuuggc       180

-continued

```
uauucuuaaa uagcuaaggu uuuuuu                                        206
```

```
<210> SEQ ID NO 432
<211> LENGTH: 206
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 432
cuucuauagc cuccuucccc gucauaguuc cauuaaagcc auugcuguuu uaugaaagca      60
ugauacagca auggcuuuga uguuucuaug auaagggcuu cggcccgugg cguuggggau     120
cgccugccca uuuuaauggg cuucucccca ucuauuuaau gagaaauuua caaccuuggc     180
uauucuuaaa uagcuaaggu uuuuuu                                        206
```

```
<210> SEQ ID NO 433
<211> LENGTH: 206
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 433
ggacagugcg caucucccug gucauaguuc cauuaaagcc auugcuguuu uaugaaagca      60
ugauacagca auggcuuuga uguuucuaug auaagggcuu cggcccgugg cguuggggau     120
cgccugccca uuuuaauggg cuucucccca ucuauuuaau gagaaauuua caaccuuggc     180
uauucuuaaa uagcuaaggu uuuuuu                                        206
```

```
<210> SEQ ID NO 434
<211> LENGTH: 133
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 434
aagacauuac acucauauua cacccgucau aguuccauua aagccaaagg gcuuugaugu      60
uucuaugaua aggguuucgg cccguggcgu cggggaucgc cugcccauuc cgaugggcuu     120
cuccccauuu auu                                                     133
```

```
<210> SEQ ID NO 435
<211> LENGTH: 133
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 435
agagccauca ccaucacauc ccuaagucau aguuccauua aagccaaagg gcuuugaugu      60
uucuaugaua aggguuucgg cccguggcgu cggggaucgc cugcccauuc cgaugggcuu     120
cuccccauuu auu                                                     133
```

```
<210> SEQ ID NO 436
<211> LENGTH: 133
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 436
aucuggaggg aacuuacagc auauggucau aguuccauua aagccaaagg gcuuugaugu     60
uucuaugaua aggguuucgg cccguggcgu cggggaucgc cugcccauuc cgaugggcuu    120
cuccccauuu auu                                                       133

<210> SEQ ID NO 437
<211> LENGTH: 133
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 437
ccacccagcc ugcucugccu uggggggucau aguuccauua aagccaaagg gcuuugaugu    60
uucuaugaua aggguuucgg cccguggcgu cggggaucgc cugcccauuc cgaugggcuu    120
cuccccauuu auu                                                       133

<210> SEQ ID NO 438
<211> LENGTH: 133
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 438
gaacaacuca aauggaaaug aauaugucau aguuccauua aagccaaagg gcuuugaugu     60
uucuaugaua aggguuucgg cccguggcgu cggggaucgc cugcccauuc cgaugggcuu    120
cuccccauuu auu                                                       133

<210> SEQ ID NO 439
<211> LENGTH: 133
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 439
gcuucuacuc uuggcuuaca acccagucau aguuccauua aagccaaagg gcuuugaugu     60
uucuaugaua aggguuucgg cccguggcgu cggggaucgc cugcccauuc cgaugggcuu    120
cuccccauuu auu                                                       133

<210> SEQ ID NO 440
<211> LENGTH: 133
<212> TYPE: RNA
<213> ORGANISM: Artificial Sequence
<220> FEATURE:
<221> NAME/KEY: source
<223> OTHER INFORMATION: /note="Description of Artificial Sequence:
```

-continued

Synthetic polynucleotide"

<400> SEQUENCE: 440
ggccaaaauc cagcugccuu ccuuggucau aguuccauua aagccaaagg gcuuugaugu        60
uucuaugaua aggguuucgg cccguggcgu cggggaucgc cugcccauuc cgaugggcuu       120
cuccccauuu auu                                                          133

<210> SEQ ID NO 441
<211> LENGTH: 133
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 441
uaaaaugauu uggaagagca gagacgucau aguuccauua aagccaaagg gcuuugaugu        60
uucuaugaua aggguuucgg cccguggcgu cggggaucgc cugcccauuc cgaugggcuu       120
cuccccauuu auu                                                          133

<210> SEQ ID NO 442
<211> LENGTH: 133
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 442
uccuguucca ucaccaucaa aaaaagucau aguuccauua aagccaaagg gcuuugaugu        60
uucuaugaua aggguuucgg cccguggcgu cggggaucgc cugcccauuc cgaugggcuu       120
cuccccauuu auu                                                          133

<210> SEQ ID NO 443
<211> LENGTH: 164
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 443
aagacauuac acucauauua cacccgccau aauuccucug uaaaacuuaa agaagguuua        60
uagaguuauu augguaaggc aauaugccgu ggcguugggg aucgccuaug uccgguuuua       120
ccggaucucc cuaaagguga cuaacuuugg uuagucaccu uuuu                        164

<210> SEQ ID NO 444
<211> LENGTH: 164
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 444
agcuguuugg gaggucagaa auagggccau aauuccucug uaaaacuuaa agaagguuua        60
uagaguuauu augguaaggc aauaugccgu ggcguugggg aucgccuaug uccgguuuua       120

```
ccggaucucc cuaaaggug cuaacuuugg uuagucaccu uuuu                        164

<210> SEQ ID NO 445
<211> LENGTH: 159
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 445
agguuuuaau ggcccagccu gccauaauuc cucguguaaaa cuuaaagaag guuuauagag       60
uuauuauggu aaggcaauau gccguggcgu uggggaucgc cuauguccgg uuuuaccgga      120
ucucccuaaa ggugacuaac uuugguuagu caccuuuuu                             159

<210> SEQ ID NO 446
<211> LENGTH: 164
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 446
auguacugcc augggaagaa ggugagccau aauuccucug uaaaacuuaa agaagguuua       60
uagaguuauu augguaaggc aauaugccgu ggcguugggg aucgccuaug uccgguuuua      120
ccggaucucc cuaaaggug cuaacuuugg uuagucaccu uuuu                        164

<210> SEQ ID NO 447
<211> LENGTH: 164
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 447
cagaagucag gcuggacacu gaggagccau aauuccucug uaaaacuuaa agaagguuua       60
uagaguuauu augguaaggc aauaugccgu ggcguugggg aucgccuaug uccgguuuua      120
ccggaucucc cuaaaggug cuaacuuugg uuagucaccu uuuu                        164

<210> SEQ ID NO 448
<211> LENGTH: 164
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 448
cagggccucg auaaugagau aauuugccau aauuccucug uaaaacuuaa agaagguuua       60
uagaguuauu augguaaggc aauaugccgu ggcguugggg aucgccuaug uccgguuuua      120
ccggaucucc cuaaaggug cuaacuuugg uuagucaccu uuuu                        164

<210> SEQ ID NO 449
<211> LENGTH: 164
<212> TYPE: RNA
```

-continued

```
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 449
caucuacuaa uuucuucccca cucccgccau aauuccucug uaaaacuuaa agaagguuua      60
uagaguuauu augguaaggc aauaugccgu ggcguugggg aucgccuaug uccgguuuua     120
ccggaucucc cuaaagguga cuaacuuugg uuagucaccu uuuu                      164

<210> SEQ ID NO 450
<211> LENGTH: 159
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 450
cauggcagua cauuagagca gccauaauuc cucuguaaaa cuuaaagaag guuuauagag      60
uuauuauggu aaggcaauau gccguggcgu ugggggaucgc cuauguccgg uuuuaccgga    120
ucucccuaaa ggugacuaac uuugguuagu caccuuuuu                            159

<210> SEQ ID NO 451
<211> LENGTH: 164
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 451
cccuggcugu gcacauuccc uccuggccau aauuccucug uaaaacuuaa agaagguuua      60
uagaguuauu augguaaggc aauaugccgu ggcguugggg aucgccuaug uccgguuuua     120
ccggaucucc cuaaagguga cuaacuuugg uuagucaccu uuuu                      164

<210> SEQ ID NO 452
<211> LENGTH: 164
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 452
ccgcuguuuc cauuccucau cauucgccau aauuccucug uaaaacuuaa agaagguuua      60
uagaguuauu augguaaggc aauaugccgu ggcguugggg aucgccuaug uccgguuuua     120
ccggaucucc cuaaagguga cuaacuuugg uuagucaccu uuuu                      164

<210> SEQ ID NO 453
<211> LENGTH: 164
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 453
```

-continued

_____ ccuagagccc aagagaaccc acugagccau aauuccucug uaaaacuuaa agaagguuua      60
uagaguuauu augguaaggc aauaugccgu ggcguugggg aucgccuaug uccgguuuua     120
ccggaucucc cuaaaggguga cuaacuuugg uuagucaccu uuuu                     164

<210> SEQ ID NO 454
<211> LENGTH: 164
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 454
cgcacagcau ucaggucgua gucccgccau aauuccucug uaaaacuuaa agaagguuua     60
uagaguuauu augguaaggc aauaugccgu ggcguugggg aucgccuaug uccgguuuua    120
ccggaucucc cuaaagguga cuaacuuugg uuagucaccu uuuu                     164

<210> SEQ ID NO 455
<211> LENGTH: 164
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 455
cggcacuauc auugacucag cugcugccau aauuccucug uaaaacuuaa agaagguuua     60
uagaguuauu augguaaggc aauaugccgu ggcguugggg aucgccuaug uccgguuuua    120
ccggaucucc cuaaagguga cuaacuuugg uuagucaccu uuuu                     164

<210> SEQ ID NO 456
<211> LENGTH: 164
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 456
cucaacauuc cagggcucaa gcgaugccau aauuccucug uaaaacuuaa agaagguuua     60
uagaguuauu augguaaggc aauaugccgu ggcguugggg aucgccuaug uccgguuuua    120
ccggaucucc cuaaagguga cuaacuuugg uuagucaccu uuuu                     164

<210> SEQ ID NO 457
<211> LENGTH: 164
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 457
gaaugcugug cggcucugcu uccaggccau aauuccucug uaaaacuuaa agaagguuua     60
uagaguuauu augguaaggc aauaugccgu ggcguugggg aucgccuaug uccgguuuua    120
ccggaucucc cuaaagguga cuaacuuugg uuagucaccu uuuu                     164

<210> SEQ ID NO 458
<211> LENGTH: 164
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 458
gcuaccaccu cugugccccc ccggcgccau aauuccucug uaaaacuuaa agaagguuua      60
uagaguuauu augguaaggc aauaugccgu ggcguugggg aucgccuaug uccgguuuua     120
ccggaucucc cuaaagguga cuaacuuugg uuagucaccu uuuu                       164

<210> SEQ ID NO 459
<211> LENGTH: 164
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 459
ggaggccugc agcuccugca ccuccgccau aauuccucug uaaaacuuaa agaagguuua      60
uagaguuauu augguaaggc aauaugccgu ggcguugggg aucgccuaug uccgguuuua     120
ccggaucucc cuaaagguga cuaacuuugg uuagucaccu uuuu                       164

<210> SEQ ID NO 460
<211> LENGTH: 159
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 460
gggccauuaa aaccucucca gccauaauuc cucuguaaaa cuuaaagaag guuuauagag      60
uuauuauggu aaggcaauau gccguggcgu ugggggaucgc cuauguccgg uuuuaccgga    120
ucucccuaaa ggugacuaac uuugguuagu caccuuuuu                            159

<210> SEQ ID NO 461
<211> LENGTH: 164
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 461
gggccauuaa aaccucucca ggggcgccau aauuccucug uaaaacuuaa agaagguuua      60
uagaguuauu augguaaggc aauaugccgu ggcguugggg aucgccuaug uccgguuuua     120
ccggaucucc cuaaagguga cuaacuuugg uuagucaccu uuuu                       164

<210> SEQ ID NO 462
<211> LENGTH: 164
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 462
guuuuaaugg cccagccuca cacccgccau aauuccucug uaaaacuuaa agaagguuua      60
uagaguuauu augguaaggc aauaugccgu ggcguugggg aucgccuaug uccgguuuua     120
ccggaucucc cuaaagguga cuaacuuugg uuagucaccu uuu                       164

<210> SEQ ID NO 463
<211> LENGTH: 164
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 463
uaaaaugauu uggaagagca gagacgccau aauuccucug uaaaacuuaa agaagguuua      60
uagaguuauu augguaaggc aauaugccgu ggcguugggg aucgccuaug uccgguuuua     120
ccggaucucc cuaaagguga cuaacuuugg uuagucaccu uuu                       164

<210> SEQ ID NO 464
<211> LENGTH: 164
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 464
uccuguucca ucaccaucaa aaaaagccau aauuccucug uaaaacuuaa agaagguuua      60
uagaguuauu augguaaggc aauaugccgu ggcguugggg aucgccuaug uccgguuuua     120
ccggaucucc cuaaagguga cuaacuuugg uuagucaccu uuu                       164

<210> SEQ ID NO 465
<211> LENGTH: 164
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 465
ugucucaaau aauaaaaaaa auaaggccau aauuccucug uaaaacuuaa agaagguuua      60
uagaguuauu augguaaggc aauaugccgu ggcguugggg aucgccuaug uccgguuuua     120
ccggaucucc cuaaagguga cuaacuuugg uuagucaccu uuu                       164

<210> SEQ ID NO 466
<211> LENGTH: 164
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 466
uguugguuac cucccugcca ccaccgccau aauuccucug uaaaacuuaa agaagguuua      60

-continued uagaguuauu augguaaggc aauaugccgu ggcguugggg aucgccuaug uccgguuuua        120
ccggaucucc cuaaaggug a cuaacuuugg uuagucaccu uuuu                        164

<210> SEQ ID NO 467
<211> LENGTH: 164
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 467
uuuagguucg uaucuguaaa accaagccau aauuccucug uaaaacuuaa agaagguuua        60
uagaguuauu augguaaggc aauaugccgu ggcguugggg aucgccuaug uccgguuuua       120
ccggaucucc cuaaaggug a cuaacuuugg uuagucaccu uuuu                        164

<210> SEQ ID NO 468
<211> LENGTH: 118
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 468
aagugggaga guacugaaug ggcacguuuu uguacucuca auaaaaaguu auugagaauc        60
uacaaaaaua aggcauuuug ccgaauuuac cgcccuacau auguagggcg guuuuuuu        118

<210> SEQ ID NO 469
<211> LENGTH: 113
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 469
accggaggac aaaguacaaa guuuuuguac ucucaauaaa aaguuauuga gaaucuacaa        60
aaauaaggca uuuugccgaa uuuaccgccc uacauaugua gggcgguuuu uuu             113

<210> SEQ ID NO 470
<211> LENGTH: 113
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 470
ccacggcucc uccgaagcga guuuuuguac ucucaauaaa aaguuauuga gaaucuacaa        60
aaauaaggca uuuugccgaa uuuaccgccc uacauaugua gggcgguuuu uuu             113

<210> SEQ ID NO 471
<211> LENGTH: 113
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

-continued

<400> SEQUENCE: 471
cccugauccu cuugucccac guuuuuguac ucucaauaaa aaguuauuga gaaucuacaa        60
aaauaaggca uuuugccgaa uuuaccgccc uacauaugua gggcgguuuu uuu             113

<210> SEQ ID NO 472
<211> LENGTH: 113
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 472
cuggagcaac aaaucugacu guuuuuguac ucucaauaaa aaguuauuga gaaucuacaa        60
aaauaaggca uuuugccgaa uuuaccgccc uacauaugua gggcgguuuu uuu             113

<210> SEQ ID NO 473
<211> LENGTH: 113
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 473
gggggucggg gcucgcggcg guuuuuguac ucucaauaaa aaguuauuga gaaucuacaa        60
aaauaaggca uuuugccgaa uuuaccgccc uacauaugua gggcgguuuu uuu             113

<210> SEQ ID NO 474
<211> LENGTH: 113
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 474
uggauuuaga gucucucagc guuuuuguac ucucaauaaa aaguuauuga gaaucuacaa        60
aaauaaggca uuuugccgaa uuuaccgccc uacauaugua gggcgguuuu uuu             113

<210> SEQ ID NO 475
<211> LENGTH: 123
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 475
aagugggaga guacugaaug ggcacguugu gaauugcuuu caaaaaaguu ugaaaagcaa        60
uucacaauaa ggauuauucc guugugaaaa cauucaaggc ggggcaacuc gccuuuuuuc       120
guu                                                                    123

<210> SEQ ID NO 476
<211> LENGTH: 123
<212> TYPE: RNA
<213> ORGANISM: Artificial Sequence
<220> FEATURE:

-continued

<221> NAME/KEY: source
<223> OTHER INFORMATION: /note="Description of Artificial Sequence:
      Synthetic polynucleotide"

<400> SEQUENCE: 476
aggugauuca cagagacaua aagccguugu gaauugcuuu caaaaaaguu ugaaaagcaa       60
uucacaauaa ggauuauucc guugugaaaa cauucaaggc ggggcaacuc gccuuuuuuc      120
guu                                                                    123

<210> SEQ ID NO 477
<211> LENGTH: 123
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 477
auuuagcucu uaguccuggc aagccguugu gaauugcuuu caaaaaaguu ugaaaagcaa       60
uucacaauaa ggauuauucc guugugaaaa cauucaaggc ggggcaacuc gccuuuuuuc      120
guu                                                                    123

<210> SEQ ID NO 478
<211> LENGTH: 123
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 478
cugggagguc aagacugcaa ugagaguugu gaauugcuuu caaaaaaguu ugaaaagcaa       60
uucacaauaa ggauuauucc guugugaaaa cauucaaggc ggggcaacuc gccuuuuuuc      120
guu                                                                    123

<210> SEQ ID NO 479
<211> LENGTH: 123
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 479
gcccacaacu gcgauaauga cucuaguugu gaauugcuuu caaaaaaguu ugaaaagcaa       60
uucacaauaa ggauuauucc guugugaaaa cauucaaggc ggggcaacuc gccuuuuuuc      120
guu                                                                    123

<210> SEQ ID NO 480
<211> LENGTH: 118
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 480
aagcaacucu ccugucucag ccuccguugu gaauugcuuu caaaggaaag caauucacaa       60
uaaggauuau uccguuguga aaacauuuag cgccucgacu aucuucgggg cauuuuuu       118

<210> SEQ ID NO 481
<211> LENGTH: 118
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 481
gggaagaagg ugauucacag agacaguugu gaauugcuuu caaaggaaag caauucacaa       60
uaaggauuau uccguuguga aaacauuuag cgccucgacu aucuucgggg cauuuuuu       118

<210> SEQ ID NO 482
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 482
aagtgggaga gtactgaatg ggcac                                            25

<210> SEQ ID NO 483
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 483
accttcttcc catggcagta catta                                           25

<210> SEQ ID NO 484
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 484
gcccacaact gcgataatga ctcta                                           25

<210> SEQ ID NO 485
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 485
tgggggcgct cagtttccag aacct                                           25

<210> SEQ ID NO 486
<211> LENGTH: 24
<212> TYPE: DNA

<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 486
acagtgcgca tctccctggt cacc                                          24

<210> SEQ ID NO 487
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 487
atttacagcc tggcctttgg gg                                            22

<210> SEQ ID NO 488
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 488
ccttggggcc cagactgagc acgtg                                         25

<210> SEQ ID NO 489
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 489
cttctcctca ggagtcagat gcacc                                         25

<210> SEQ ID NO 490
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 490
gatgatattt tctttaatgg tgc                                           23

<210> SEQ ID NO 491
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 491
ggctgggcca ttaaaacctc tcca                                          24

<210> SEQ ID NO 492
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 492
cacatctcga gcaagacgtt                                                        20

<210> SEQ ID NO 493
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 493
catggcagta cattagagca                                                        20

<210> SEQ ID NO 494
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 494
cctgaatgct gtgcggctct                                                        20

<210> SEQ ID NO 495
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 495
cttctatagc ctccttcccc                                                        20

<210> SEQ ID NO 496
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 496
ggacagtgcg catctccctg                                                        20

<210> SEQ ID NO 497
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:

Synthetic oligonucleotide"

<400> SEQUENCE: 497
aagacattac actcatatta caccc                                        25

<210> SEQ ID NO 498
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 498
agagccatca ccatcacatc cctaa                                        25

<210> SEQ ID NO 499
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 499
atctggaggg aacttacagc atatg                                        25

<210> SEQ ID NO 500
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 500
ccacccagcc tgctctgcct tgggg                                        25

<210> SEQ ID NO 501
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 501
gaacaactca aatggaaatg aatat                                        25

<210> SEQ ID NO 502
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 502
gcttctactc ttggcttaca accca                                        25

<210> SEQ ID NO 503
<211> LENGTH: 25

```
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 503
ggccaaaatc cagctgcctt ccttg                                              25

<210> SEQ ID NO 504
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 504
taaaatgatt tggaagagca gagac                                              25

<210> SEQ ID NO 505
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 505
tcctgttcca tcaccatcaa aaaaa                                              25

<210> SEQ ID NO 506
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 506
agctgtttgg gaggtcagaa atagg                                              25

<210> SEQ ID NO 507
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 507
aggttttaat ggcccagcct                                                    20

<210> SEQ ID NO 508
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 508
```
atgtactgcc atgggaagaa ggtga 25

<210> SEQ ID NO 509
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 509
cagaagtcag gctggacact gagga 25

<210> SEQ ID NO 510
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 510
cagggcctcg ataatgagat aattt 25

<210> SEQ ID NO 511
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 511
catctactaa tttcttccca ctccc 25

<210> SEQ ID NO 512
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 512
ccctggctgt gcacattccc tcctg 25

<210> SEQ ID NO 513
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 513
ccgctgtttc cattcctcat cattc 25

<210> SEQ ID NO 514
<211> LENGTH: 25
<212> TYPE: DNA
<213> ORGANISM: Artificial Sequence
<220> FEATURE:
<221> NAME/KEY: source -continued
<223> OTHER INFORMATION: /note="Description of Artificial Sequence:
      Synthetic oligonucleotide"

<400> SEQUENCE: 514
cctagagccc aagagaaccc actga                                                    25

<210> SEQ ID NO 515
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 515
cgcacagcat tcaggtcgta gtccc                                                    25

<210> SEQ ID NO 516
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 516
cggcactatc attgactcag ctgct                                                    25

<210> SEQ ID NO 517
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 517
ctcaacattc cagggctcaa gcgat                                                    25

<210> SEQ ID NO 518
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 518
gaatgctgtg cggctctgct tccag                                                    25

<210> SEQ ID NO 519
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 519
gctaccacct ctgtgccccc ccggc                                                    25

<210> SEQ ID NO 520

```
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 520
ggaggcctgc agctcctgca cctcc                                                    25

<210> SEQ ID NO 521
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 521
gggccattaa aacctctcca                                                          20

<210> SEQ ID NO 522
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 522
gggccattaa aacctctcca ggggc                                                    25

<210> SEQ ID NO 523
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 523
gttttaatgg cccagcctca caccc                                                    25

<210> SEQ ID NO 524
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 524
tgtctcaaat aataaaaaaa ataag                                                    25

<210> SEQ ID NO 525
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 525
```

-continued

```
tgttggttac ctccctgcca ccacc                                                    25

<210> SEQ ID NO 526
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 526
tttaggttcg tatctgtaaa accaa                                                    25

<210> SEQ ID NO 527
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 527
accggaggac aaagtacaaa                                                          20

<210> SEQ ID NO 528
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 528
ccacggctcc tccgaagcga                                                          20

<210> SEQ ID NO 529
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 529
ccctgatcct cttgtcccac                                                          20

<210> SEQ ID NO 530
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 530
ctggagcaac aaatctgact                                                          20

<210> SEQ ID NO 531
<211> LENGTH: 20
<212> TYPE: DNA
<213> ORGANISM: Artificial Sequence
<220> FEATURE:
```

-continued

```
<221> NAME/KEY: source
<223> OTHER INFORMATION: /note="Description of Artificial Sequence:
      Synthetic oligonucleotide"

<400> SEQUENCE: 531
gggggtcggg gctcgcggcg                                          20

<210> SEQ ID NO 532
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 532
tggatttaga gtctctcagc                                          20

<210> SEQ ID NO 533
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 533
aggtgattca cagagacata aagcc                                    25

<210> SEQ ID NO 534
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 534
atttagctct tagtcctggc aagcc                                    25

<210> SEQ ID NO 535
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 535
ctgggaggtc aagactgcaa tgaga                                    25

<210> SEQ ID NO 536
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 536
aagcaactct cctgtctcag cctcc                                    25
```

-continued

```
<210> SEQ ID NO 537
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 537
gggaagaagg tgattcacag agaca                                            25

<210> SEQ ID NO 538
<211> LENGTH: 25
<212> TYPE: DNA
<213> ORGANISM: Homo sapiens

<400> SEQUENCE: 538
gacaggctgt gtgtcagagt tcgcc                                            25

<210> SEQ ID NO 539
<211> LENGTH: 25
<212> TYPE: DNA
<213> ORGANISM: Homo sapiens

<400> SEQUENCE: 539
agtggacagg ctgtgtgtca gagtt                                            25

<210> SEQ ID NO 540
<211> LENGTH: 25
<212> TYPE: DNA
<213> ORGANISM: Homo sapiens

<400> SEQUENCE: 540
ctgcgattgc agaagatgac ctggg                                            25

<210> SEQ ID NO 541
<211> LENGTH: 25
<212> TYPE: DNA
<213> ORGANISM: Homo sapiens

<400> SEQUENCE: 541
acgcgcggac tgcgattgca gaaga                                            25

<210> SEQ ID NO 542
<211> LENGTH: 25
<212> TYPE: DNA
<213> ORGANISM: Homo sapiens

<400> SEQUENCE: 542
agtactcacg attcgggggt ataca                                            25

<210> SEQ ID NO 543
<211> LENGTH: 25
<212> TYPE: DNA
<213> ORGANISM: Homo sapiens

<400> SEQUENCE: 543
agtactcacg attcgggggt ataca                                            25

<210> SEQ ID NO 544
<211> LENGTH: 25
<212> TYPE: DNA
<213> ORGANISM: Homo sapiens
```

<400> SEQUENCE: 544
atcacgtgcc ttgtacactg tccca                                                    25

<210> SEQ ID NO 545
<211> LENGTH: 25
<212> TYPE: DNA
<213> ORGANISM: Homo sapiens

<400> SEQUENCE: 545
gtggggatca cgtgccttgt acact                                                    25

<210> SEQ ID NO 546
<211> LENGTH: 25
<212> TYPE: DNA
<213> ORGANISM: Homo sapiens

<400> SEQUENCE: 546
ctttgatggg ttcatccgac cagtc                                                    25

<210> SEQ ID NO 547
<211> LENGTH: 25
<212> TYPE: DNA
<213> ORGANISM: Homo sapiens

<400> SEQUENCE: 547
tgggttcatc cgaccagtcc cggca                                                    25

<210> SEQ ID NO 548
<211> LENGTH: 25
<212> TYPE: DNA
<213> ORGANISM: Homo sapiens

<400> SEQUENCE: 548
cttggacctg gttccatgtc cccac                                                    25

<210> SEQ ID NO 549
<211> LENGTH: 25
<212> TYPE: DNA
<213> ORGANISM: Homo sapiens

<400> SEQUENCE: 549
accaggaagt ggccatgcgc aagct                                                    25

<210> SEQ ID NO 550
<211> LENGTH: 25
<212> TYPE: DNA
<213> ORGANISM: Homo sapiens

<400> SEQUENCE: 550
cacagatcga atagaagact ccttc                                                    25

<210> SEQ ID NO 551
<211> LENGTH: 25
<212> TYPE: DNA
<213> ORGANISM: Homo sapiens

<400> SEQUENCE: 551
cacagatcga atagaagact ccttc                                                    25

<210> SEQ ID NO 552
<211> LENGTH: 25
<212> TYPE: DNA
<213> ORGANISM: Homo sapiens

<400> SEQUENCE: 552
ccctaactga gcagctcagg ctgcc                                          25

<210> SEQ ID NO 553
<211> LENGTH: 25
<212> TYPE: DNA
<213> ORGANISM: Homo sapiens

<400> SEQUENCE: 553
caggctgccg tggctcacct gtcca                                          25

<210> SEQ ID NO 554
<211> LENGTH: 25
<212> TYPE: DNA
<213> ORGANISM: Homo sapiens

<400> SEQUENCE: 554
cttccatgaa gataacattc cccag                                          25

<210> SEQ ID NO 555
<211> LENGTH: 25
<212> TYPE: DNA
<213> ORGANISM: Homo sapiens

<400> SEQUENCE: 555
attccccagc tggaagaagt ttctc                                          25

<210> SEQ ID NO 556
<211> LENGTH: 25
<212> TYPE: DNA
<213> ORGANISM: Homo sapiens

<400> SEQUENCE: 556
ggtacaagct gcagtcattt ccttt                                          25

<210> SEQ ID NO 557
<211> LENGTH: 25
<212> TYPE: DNA
<213> ORGANISM: Homo sapiens

<400> SEQUENCE: 557
gtcatttcct ttagggaatc atctt                                          25

<210> SEQ ID NO 558
<211> LENGTH: 25
<212> TYPE: DNA
<213> ORGANISM: Homo sapiens

<400> SEQUENCE: 558
catcaccccc tagactatag ttagc                                          25

<210> SEQ ID NO 559
<211> LENGTH: 25
<212> TYPE: DNA
<213> ORGANISM: Homo sapiens

<400> SEQUENCE: 559 tcaccccca gactatagtt agcca                                           25

<210> SEQ ID NO 560
<211> LENGTH: 25
<212> TYPE: DNA

-continued

<213> ORGANISM: Homo sapiens

<400> SEQUENCE: 560
acttcttggc aagtcggtta agatc                                          25

<210> SEQ ID NO 561
<211> LENGTH: 25
<212> TYPE: DNA
<213> ORGANISM: Homo sapiens

<400> SEQUENCE: 561
aagatctggg aatagacgaa gtaaa                                          25

<210> SEQ ID NO 562
<211> LENGTH: 25
<212> TYPE: DNA
<213> ORGANISM: Homo sapiens

<400> SEQUENCE: 562
aaaatggctg gtagtacata tggaa                                          25

<210> SEQ ID NO 563
<211> LENGTH: 25
<212> TYPE: DNA
<213> ORGANISM: Homo sapiens

<400> SEQUENCE: 563
tggctggtag tacatatgga acagg                                          25

<210> SEQ ID NO 564
<211> LENGTH: 25
<212> TYPE: DNA
<213> ORGANISM: Homo sapiens

<400> SEQUENCE: 564
caattgactg tcaccagccc ctact                                          25

<210> SEQ ID NO 565
<211> LENGTH: 25
<212> TYPE: DNA
<213> ORGANISM: Homo sapiens

<400> SEQUENCE: 565
agcccctact agggctaaga tgcag                                          25

<210> SEQ ID NO 566
<211> LENGTH: 25
<212> TYPE: DNA
<213> ORGANISM: Homo sapiens

<400> SEQUENCE: 566
catcagtcga gttccaacct tcgcc                                          25

<210> SEQ ID NO 567
<211> LENGTH: 25
<212> TYPE: DNA
<213> ORGANISM: Homo sapiens

<400> SEQUENCE: 567
atacactgtt tctatggctt ttctc                                          25

<210> SEQ ID NO 568
<211> LENGTH: 25

-continued

```
<212> TYPE: DNA
<213> ORGANISM: Homo sapiens

<400> SEQUENCE: 568
aggaagttga ttctaccaga tgatc                                          25

<210> SEQ ID NO 569
<211> LENGTH: 25
<212> TYPE: DNA
<213> ORGANISM: Homo sapiens

<400> SEQUENCE: 569
accgtggaca atattcgctc catct                                          25

<210> SEQ ID NO 570
<211> LENGTH: 25
<212> TYPE: DNA
<213> ORGANISM: Homo sapiens

<400> SEQUENCE: 570
ggaaatgctg ttagtcgtta tgtcg                                          25

<210> SEQ ID NO 571
<211> LENGTH: 25
<212> TYPE: DNA
<213> ORGANISM: Homo sapiens

<400> SEQUENCE: 571
taccatgaat agaacatttc ctttc                                          25

<210> SEQ ID NO 572
<211> LENGTH: 25
<212> TYPE: DNA
<213> ORGANISM: Homo sapiens

<400> SEQUENCE: 572
gtgtcttact agccatttta atact                                          25

<210> SEQ ID NO 573
<211> LENGTH: 25
<212> TYPE: DNA
<213> ORGANISM: Homo sapiens

<400> SEQUENCE: 573
ggacctacac aagcagcatc ttctt                                          25

<210> SEQ ID NO 574
<211> LENGTH: 25
<212> TYPE: DNA
<213> ORGANISM: Homo sapiens

<400> SEQUENCE: 574
tggtggacct acacaagcag catct                                          25

<210> SEQ ID NO 575
<211> LENGTH: 25
<212> TYPE: DNA
<213> ORGANISM: Homo sapiens

<400> SEQUENCE: 575
aaagtgactc tctaattttc tattt                                          25

<210> SEQ ID NO 576
```

-continued

```
<211> LENGTH: 25
<212> TYPE: DNA
<213> ORGANISM: Homo sapiens

<400> SEQUENCE: 576
tttttggtaa tagaacatct ccaag                                          25

<210> SEQ ID NO 577
<211> LENGTH: 25
<212> TYPE: DNA
<213> ORGANISM: Homo sapiens

<400> SEQUENCE: 577
caccacggct gtcgacacca atccc                                          25

<210> SEQ ID NO 578
<211> LENGTH: 25
<212> TYPE: DNA
<213> ORGANISM: Homo sapiens

<400> SEQUENCE: 578
tattccacca cggctgtcga cacca                                          25

<210> SEQ ID NO 579
<211> LENGTH: 25
<212> TYPE: DNA
<213> ORGANISM: Homo sapiens

<400> SEQUENCE: 579
actttgcaac agtggaggaa agcct                                          25

<210> SEQ ID NO 580
<211> LENGTH: 25
<212> TYPE: DNA
<213> ORGANISM: Homo sapiens

<400> SEQUENCE: 580
aacagtggag gaaagccttt ggagt                                          25

<210> SEQ ID NO 581
<211> LENGTH: 25
<212> TYPE: DNA
<213> ORGANISM: Homo sapiens

<400> SEQUENCE: 581
aggtggctgc ttctttggtt gtgct                                          25

<210> SEQ ID NO 582
<211> LENGTH: 25
<212> TYPE: DNA
<213> ORGANISM: Homo sapiens

<400> SEQUENCE: 582
tggctccttg gaaagtgaga attcc                                          25

<210> SEQ ID NO 583
<211> LENGTH: 25
<212> TYPE: DNA
<213> ORGANISM: Homo sapiens

<400> SEQUENCE: 583
tcaaataagc agcaggaagc agacc                                          25
```

-continued

```
<210> SEQ ID NO 584
<211> LENGTH: 25
<212> TYPE: DNA
<213> ORGANISM: Homo sapiens

<400> SEQUENCE: 584
aaataagcag caggaagcag accca                                              25

<210> SEQ ID NO 585
<211> LENGTH: 25
<212> TYPE: DNA
<213> ORGANISM: Homo sapiens

<400> SEQUENCE: 585
atgctggcat tgttaaatcc atccc                                              25

<210> SEQ ID NO 586
<211> LENGTH: 25
<212> TYPE: DNA
<213> ORGANISM: Homo sapiens

<400> SEQUENCE: 586
atccatccca agggggtgag tgtgg                                              25

<210> SEQ ID NO 587
<211> LENGTH: 25
<212> TYPE: DNA
<213> ORGANISM: Homo sapiens

<400> SEQUENCE: 587
gataggtagt acatgcacag ttgct                                              25

<210> SEQ ID NO 588
<211> LENGTH: 25
<212> TYPE: DNA
<213> ORGANISM: Homo sapiens

<400> SEQUENCE: 588
ccatcattag atgataggta gtaca                                              25

<210> SEQ ID NO 589
<211> LENGTH: 25
<212> TYPE: DNA
<213> ORGANISM: Homo sapiens

<400> SEQUENCE: 589
acaatttcaa cacaagctaa actag                                              25

<210> SEQ ID NO 590
<211> LENGTH: 25
<212> TYPE: DNA
<213> ORGANISM: Homo sapiens

<400> SEQUENCE: 590
taaactagta ggatatagtt cttca                                              25

<210> SEQ ID NO 591
<211> LENGTH: 25
<212> TYPE: DNA
<213> ORGANISM: Homo sapiens

<400> SEQUENCE: 591
aatttcaaaa aatgttggcc tctct                                              25
```

-continued

```
<210> SEQ ID NO 592
<211> LENGTH: 25
<212> TYPE: DNA
<213> ORGANISM: Homo sapiens

<400> SEQUENCE: 592
tccaatagtc atttttacct acgat                                              25

<210> SEQ ID NO 593
<211> LENGTH: 25
<212> TYPE: DNA
<213> ORGANISM: Homo sapiens

<400> SEQUENCE: 593
tctgagtgtt tccctccttc ataaa                                             25

<210> SEQ ID NO 594
<211> LENGTH: 25
<212> TYPE: DNA
<213> ORGANISM: Homo sapiens

<400> SEQUENCE: 594
ccttcataaa caggccagat aattt                                             25

<210> SEQ ID NO 595
<211> LENGTH: 25
<212> TYPE: DNA
<213> ORGANISM: Homo sapiens

<400> SEQUENCE: 595
cagttaacag ttctttattt gaagt                                             25

<210> SEQ ID NO 596
<211> LENGTH: 25
<212> TYPE: DNA
<213> ORGANISM: Homo sapiens

<400> SEQUENCE: 596
tgtgtattta caagaaagag cagat                                             25

<210> SEQ ID NO 597
<211> LENGTH: 25
<212> TYPE: DNA
<213> ORGANISM: Homo sapiens

<400> SEQUENCE: 597
agttctactg tgctcataga taata                                             25

<210> SEQ ID NO 598
<211> LENGTH: 25
<212> TYPE: DNA
<213> ORGANISM: Homo sapiens

<400> SEQUENCE: 598
acaatcttag atcttttatt gtgcc                                             25

<210> SEQ ID NO 599
<211> LENGTH: 25
<212> TYPE: DNA
<213> ORGANISM: Homo sapiens

<400> SEQUENCE: 599
cataaacaat cttagatctt ttatt                                             25
```

-continued

<210> SEQ ID NO 600
<211> LENGTH: 25
<212> TYPE: DNA
<213> ORGANISM: Homo sapiens

<400> SEQUENCE: 600
cttaattagc atatcctgta tatct                                          25

<210> SEQ ID NO 601
<211> LENGTH: 25
<212> TYPE: DNA
<213> ORGANISM: Homo sapiens

<400> SEQUENCE: 601
tcttcttaat tagcatatcc tgtat                                          25

<210> SEQ ID NO 602
<211> LENGTH: 25
<212> TYPE: DNA
<213> ORGANISM: Homo sapiens

<400> SEQUENCE: 602
tgctttcaga gagattagag gcaga                                          25

<210> SEQ ID NO 603
<211> LENGTH: 25
<212> TYPE: DNA
<213> ORGANISM: Homo sapiens

<400> SEQUENCE: 603
cctactgctg ctttcagaga gatta                                          25

<210> SEQ ID NO 604
<211> LENGTH: 25
<212> TYPE: DNA
<213> ORGANISM: Homo sapiens

<400> SEQUENCE: 604
ggtggatgac tcataccctc caatg                                          25

<210> SEQ ID NO 605
<211> LENGTH: 25
<212> TYPE: DNA
<213> ORGANISM: Homo sapiens

<400> SEQUENCE: 605
gttggctgat ggtggatgac tcata                                          25

<210> SEQ ID NO 606
<211> LENGTH: 25
<212> TYPE: DNA
<213> ORGANISM: Homo sapiens

<400> SEQUENCE: 606
ggtggatgga tcataccctc caatg                                          25

<210> SEQ ID NO 607
<211> LENGTH: 25
<212> TYPE: DNA
<213> ORGANISM: Homo sapiens

<400> SEQUENCE: 607

-continued

```
gttggctgat ggtggatgga tcata                                                25

<210> SEQ ID NO 608
<211> LENGTH: 25
<212> TYPE: DNA
<213> ORGANISM: Homo sapiens

<400> SEQUENCE: 608
tcactataga tggctcatat ggaaa                                                25

<210> SEQ ID NO 609
<211> LENGTH: 25
<212> TYPE: DNA
<213> ORGANISM: Homo sapiens

<400> SEQUENCE: 609
ataatcacta tagatggctc atatg                                                25

<210> SEQ ID NO 610
<211> LENGTH: 25
<212> TYPE: DNA
<213> ORGANISM: Homo sapiens

<400> SEQUENCE: 610
aaagcattac attacgtaat catat                                                25

<210> SEQ ID NO 611
<211> LENGTH: 25
<212> TYPE: DNA
<213> ORGANISM: Homo sapiens

<400> SEQUENCE: 611
cttcaactaa aatacagcca agttt                                                25

<210> SEQ ID NO 612
<211> LENGTH: 25
<212> TYPE: DNA
<213> ORGANISM: Homo sapiens

<400> SEQUENCE: 612
acagttggac agaagattat tcttc                                                25

<210> SEQ ID NO 613
<211> LENGTH: 25
<212> TYPE: DNA
<213> ORGANISM: Homo sapiens

<400> SEQUENCE: 613
gcagactgac agttggacag aagat                                                25

<210> SEQ ID NO 614
<211> LENGTH: 25
<212> TYPE: DNA
<213> ORGANISM: Homo sapiens

<400> SEQUENCE: 614
gaataaggct tctagtctct ttagt                                                25

<210> SEQ ID NO 615
<211> LENGTH: 25
<212> TYPE: DNA
<213> ORGANISM: Homo sapiens

<400> SEQUENCE: 615
```

-continued

```
ggcttctagt ctctttagtt gggcc                                    25

<210> SEQ ID NO 616
<211> LENGTH: 22
<212> TYPE: DNA
<213> ORGANISM: Homo sapiens

<400> SEQUENCE: 616
gcttacaata cgcaacttcc ac                                       22

<210> SEQ ID NO 617
<211> LENGTH: 25
<212> TYPE: DNA
<213> ORGANISM: Homo sapiens

<400> SEQUENCE: 617
ccttgataaa cctagttcct tttgt                                    25

<210> SEQ ID NO 618
<211> LENGTH: 25
<212> TYPE: DNA
<213> ORGANISM: Homo sapiens

<400> SEQUENCE: 618
tgtcgctgct aacagtatgt tagct                                    25

<210> SEQ ID NO 619
<211> LENGTH: 25
<212> TYPE: DNA
<213> ORGANISM: Homo sapiens

<400> SEQUENCE: 619
acctcagaac aagatggcag aaagt                                    25

<210> SEQ ID NO 620
<211> LENGTH: 25
<212> TYPE: DNA
<213> ORGANISM: Homo sapiens

<400> SEQUENCE: 620
ctcagaacaa gatggcagaa agtct                                    25

<210> SEQ ID NO 621
<211> LENGTH: 25
<212> TYPE: DNA
<213> ORGANISM: Homo sapiens

<400> SEQUENCE: 621
acaaatcaaa gagaagctgc aagtc                                    25

<210> SEQ ID NO 622
<211> LENGTH: 25
<212> TYPE: DNA
<213> ORGANISM: Homo sapiens

<400> SEQUENCE: 622
agtcatggca agtcctctgt ttagt                                    25

<210> SEQ ID NO 623
<211> LENGTH: 25
<212> TYPE: DNA
<213> ORGANISM: Homo sapiens
```

-continued

```
<400> SEQUENCE: 623
atttcatctg aaacatacag aaaac                                              25

<210> SEQ ID NO 624
<211> LENGTH: 25
<212> TYPE: DNA
<213> ORGANISM: Homo sapiens

<400> SEQUENCE: 624
gctctcgagc cagtttttct gatct                                             25

<210> SEQ ID NO 625
<211> LENGTH: 25
<212> TYPE: DNA
<213> ORGANISM: Homo sapiens

<400> SEQUENCE: 625
taaggagctc tcgagccagt ttttc                                             25

<210> SEQ ID NO 626
<211> LENGTH: 25
<212> TYPE: DNA
<213> ORGANISM: Homo sapiens

<400> SEQUENCE: 626
gtgagcccac accattagtc agagg                                             25

<210> SEQ ID NO 627
<211> LENGTH: 25
<212> TYPE: DNA
<213> ORGANISM: Homo sapiens

<400> SEQUENCE: 627
cacaccatta gtcagaggaa ggttg                                             25

<210> SEQ ID NO 628
<211> LENGTH: 25
<212> TYPE: DNA
<213> ORGANISM: Homo sapiens

<400> SEQUENCE: 628
caagttctca gtaataagat cttgg                                             25

<210> SEQ ID NO 629
<211> LENGTH: 25
<212> TYPE: DNA
<213> ORGANISM: Homo sapiens

<400> SEQUENCE: 629
tggttggaga gtacagccac accat                                             25

<210> SEQ ID NO 630
<211> LENGTH: 20
<212> TYPE: DNA
<213> ORGANISM: Homo sapiens

<400> SEQUENCE: 630
taccagctct cctagataca                                                   20

<210> SEQ ID NO 631
<211> LENGTH: 25
<212> TYPE: DNA
<213> ORGANISM: Homo sapiens
```

-continued

```
<400> SEQUENCE: 631
ctaccctgaa aatccgaaag tgttt                                          25

<210> SEQ ID NO 632
<211> LENGTH: 25
<212> TYPE: DNA
<213> ORGANISM: Homo sapiens

<400> SEQUENCE: 632
aattcaccgt tgacattaac ttcaa                                          25

<210> SEQ ID NO 633
<211> LENGTH: 25
<212> TYPE: DNA
<213> ORGANISM: Homo sapiens

<400> SEQUENCE: 633
gcagactctc ttccgaggca acagc                                          25

<210> SEQ ID NO 634
<211> LENGTH: 25
<212> TYPE: DNA
<213> ORGANISM: Homo sapiens

<400> SEQUENCE: 634
gcagactctc ttccgaggca acagc                                          25

<210> SEQ ID NO 635
<211> LENGTH: 25
<212> TYPE: DNA
<213> ORGANISM: Homo sapiens

<400> SEQUENCE: 635
agagcggtcc cggaagctgg cggag                                          25

<210> SEQ ID NO 636
<211> LENGTH: 25
<212> TYPE: DNA
<213> ORGANISM: Homo sapiens

<400> SEQUENCE: 636
tgattgagac tagtgagagg gtgca                                          25

<210> SEQ ID NO 637
<211> LENGTH: 25
<212> TYPE: DNA
<213> ORGANISM: Homo sapiens

<400> SEQUENCE: 637
ctcacgcatt ggctggctgc acaac                                          25

<210> SEQ ID NO 638
<211> LENGTH: 25
<212> TYPE: DNA
<213> ORGANISM: Homo sapiens

<400> SEQUENCE: 638
cacacatgga ctcacgcatt ggctg                                          25

<210> SEQ ID NO 639
<211> LENGTH: 25
<212> TYPE: DNA
```

-continued

<213> ORGANISM: Homo sapiens

<400> SEQUENCE: 639
tcctccatgt attccactcg aggga                                          25

<210> SEQ ID NO 640
<211> LENGTH: 25
<212> TYPE: DNA
<213> ORGANISM: Homo sapiens

<400> SEQUENCE: 640
tgtattccac tcgagggatg ggctg                                          25

<210> SEQ ID NO 641
<211> LENGTH: 25
<212> TYPE: DNA
<213> ORGANISM: Homo sapiens

<400> SEQUENCE: 641
cgccagtaag tctgccttgc ttgtt                                          25

<210> SEQ ID NO 642
<211> LENGTH: 25
<212> TYPE: DNA
<213> ORGANISM: Homo sapiens

<400> SEQUENCE: 642
gacattgcct acaactaccg ccagt                                          25

<210> SEQ ID NO 643
<211> LENGTH: 25
<212> TYPE: DNA
<213> ORGANISM: Homo sapiens

<400> SEQUENCE: 643
gccacccacc cacccggcta ggctg                                          25

<210> SEQ ID NO 644
<211> LENGTH: 25
<212> TYPE: DNA
<213> ORGANISM: Homo sapiens

<400> SEQUENCE: 644
ggacggggtg gagctgacca gggag                                          25

<210> SEQ ID NO 645
<211> LENGTH: 25
<212> TYPE: DNA
<213> ORGANISM: Homo sapiens

<400> SEQUENCE: 645
gatcagctga tcacagcgct cctca                                          25

<210> SEQ ID NO 646
<211> LENGTH: 25
<212> TYPE: DNA
<213> ORGANISM: Homo sapiens

<400> SEQUENCE: 646
gaccggctca ctggactacg agacc                                          25

<210> SEQ ID NO 647
<211> LENGTH: 25

<212> TYPE: DNA
<213> ORGANISM: Homo sapiens

<400> SEQUENCE: 647
accggctcac tggactacga gaccg                                                    25

<210> SEQ ID NO 648
<211> LENGTH: 25
<212> TYPE: DNA
<213> ORGANISM: Homo sapiens

<400> SEQUENCE: 648
aactactact catggtgact caagc                                                    25

<210> SEQ ID NO 649
<211> LENGTH: 25
<212> TYPE: DNA
<213> ORGANISM: Homo sapiens

<400> SEQUENCE: 649
cctaaactac tactcatggt gactc                                                    25

<210> SEQ ID NO 650
<211> LENGTH: 25
<212> TYPE: DNA
<213> ORGANISM: Homo sapiens

<400> SEQUENCE: 650
tgcatctcct acaagtgagt ctgcg                                                    25

<210> SEQ ID NO 651
<211> LENGTH: 25
<212> TYPE: DNA
<213> ORGANISM: Homo sapiens

<400> SEQUENCE: 651
tgcatctcct acaagtgagt ctgcg                                                    25

<210> SEQ ID NO 652
<211> LENGTH: 25
<212> TYPE: DNA
<213> ORGANISM: Homo sapiens

<400> SEQUENCE: 652
tcaaccgtaa gttaaaaaga accac                                                    25

<210> SEQ ID NO 653
<211> LENGTH: 25
<212> TYPE: DNA
<213> ORGANISM: Homo sapiens

<400> SEQUENCE: 653
actcttcatc aaccgtaagt taaaa                                                    25

<210> SEQ ID NO 654
<211> LENGTH: 25
<212> TYPE: DNA
<213> ORGANISM: Homo sapiens

<400> SEQUENCE: 654
atactcattt atgattttgc caatt                                                    25

<210> SEQ ID NO 655

-continued

```
<211> LENGTH: 25
<212> TYPE: DNA
<213> ORGANISM: Homo sapiens

<400> SEQUENCE: 655 ttcatttttta ttttcagtga agaac                                             25

<210> SEQ ID NO 656
<211> LENGTH: 25
<212> TYPE: DNA
<213> ORGANISM: Homo sapiens

<400> SEQUENCE: 656
agccagcatg tgaatgaggg aggaa                                              25

<210> SEQ ID NO 657
<211> LENGTH: 25
<212> TYPE: DNA
<213> ORGANISM: Homo sapiens

<400> SEQUENCE: 657
catctgggcc attacagcta ataag                                             25

<210> SEQ ID NO 658
<211> LENGTH: 25
<212> TYPE: DNA
<213> ORGANISM: Homo sapiens

<400> SEQUENCE: 658
ccctgggctc agcatggtct tcttg                                             25

<210> SEQ ID NO 659
<211> LENGTH: 25
<212> TYPE: DNA
<213> ORGANISM: Homo sapiens

<400> SEQUENCE: 659
ccctgggctc agcatggtct tcttg                                             25

<210> SEQ ID NO 660
<211> LENGTH: 25
<212> TYPE: DNA
<213> ORGANISM: Homo sapiens

<400> SEQUENCE: 660
ggggcagaac agcaggctca cctgc                                             25

<210> SEQ ID NO 661
<211> LENGTH: 25
<212> TYPE: DNA
<213> ORGANISM: Homo sapiens

<400> SEQUENCE: 661
acagtgcctc gaagctcctg cagca                                             25

<210> SEQ ID NO 662
<211> LENGTH: 25
<212> TYPE: DNA
<213> ORGANISM: Homo sapiens

<400> SEQUENCE: 662
gtgtgcccgc actcgaaaaa gcagc                                             25
```

```
<210> SEQ ID NO 663
<211> LENGTH: 25
<212> TYPE: DNA
<213> ORGANISM: Homo sapiens

<400> SEQUENCE: 663
gcccgcactc gaaaaagcag ccggg                                          25

<210> SEQ ID NO 664
<211> LENGTH: 25
<212> TYPE: DNA
<213> ORGANISM: Homo sapiens

<400> SEQUENCE: 664
gtttattttg tgtagatgta tacgt                                          25

<210> SEQ ID NO 665
<211> LENGTH: 25
<212> TYPE: DNA
<213> ORGANISM: Homo sapiens

<400> SEQUENCE: 665
gtttattttg tgtagatgta tacgt                                          25

<210> SEQ ID NO 666
<211> LENGTH: 25
<212> TYPE: DNA
<213> ORGANISM: Homo sapiens

<400> SEQUENCE: 666
ttacagtgga tggagaagac atcat                                          25

<210> SEQ ID NO 667
<211> LENGTH: 25
<212> TYPE: DNA
<213> ORGANISM: Homo sapiens

<400> SEQUENCE: 667
taacacatta ttacagtgga tggag                                          25

<210> SEQ ID NO 668
<211> LENGTH: 25
<212> TYPE: DNA
<213> ORGANISM: Homo sapiens

<400> SEQUENCE: 668
tattgacgtt cccaaaacca tccag                                          25

<210> SEQ ID NO 669
<211> LENGTH: 25
<212> TYPE: DNA
<213> ORGANISM: Homo sapiens

<400> SEQUENCE: 669
gcggtctcag aggtcagaga tggtc                                          25

<210> SEQ ID NO 670
<211> LENGTH: 25
<212> TYPE: DNA
<213> ORGANISM: Homo sapiens

<400> SEQUENCE: 670
agataaatcg gtactgtgct tctgt                                          25
```

-continued

```
<210> SEQ ID NO 671
<211> LENGTH: 25
<212> TYPE: DNA
<213> ORGANISM: Homo sapiens

<400> SEQUENCE: 671
gtctggaccc tccctgacct ctgag                                          25

<210> SEQ ID NO 672
<211> LENGTH: 25
<212> TYPE: DNA
<213> ORGANISM: Homo sapiens

<400> SEQUENCE: 672
agttccctct gcgtgttctc ataaa                                          25

<210> SEQ ID NO 673
<211> LENGTH: 25
<212> TYPE: DNA
<213> ORGANISM: Homo sapiens

<400> SEQUENCE: 673
cgtgttctca taaacaggca tgtgt                                          25

<210> SEQ ID NO 674
<211> LENGTH: 25
<212> TYPE: DNA
<213> ORGANISM: Homo sapiens

<400> SEQUENCE: 674
gagtgtattg gtaagtgatc catcc                                          25

<210> SEQ ID NO 675
<211> LENGTH: 25
<212> TYPE: DNA
<213> ORGANISM: Homo sapiens

<400> SEQUENCE: 675
cgtggggagt gtattggtaa gtgat                                          25

<210> SEQ ID NO 676
<211> LENGTH: 25
<212> TYPE: DNA
<213> ORGANISM: Homo sapiens

<400> SEQUENCE: 676
acttcaatct cactgtccaa ggtga                                          25

<210> SEQ ID NO 677
<211> LENGTH: 25
<212> TYPE: DNA
<213> ORGANISM: Homo sapiens

<400> SEQUENCE: 677
cttcaatctc actgtccaag gtgag                                          25

<210> SEQ ID NO 678
<211> LENGTH: 25
<212> TYPE: DNA
<213> ORGANISM: Homo sapiens

<400> SEQUENCE: 678
gcaggcgctg ctgggggccc gggct                                          25
```

-continued

<210> SEQ ID NO 679
<211> LENGTH: 25
<212> TYPE: DNA
<213> ORGANISM: Homo sapiens

<400> SEQUENCE: 679
ggcgctgctg ggggcccggg ctaag                                                                          25

<210> SEQ ID NO 680
<211> LENGTH: 25
<212> TYPE: DNA
<213> ORGANISM: Homo sapiens

<400> SEQUENCE: 680
agtttaacga agccctccgt gagag                                                                          25

<210> SEQ ID NO 681
<211> LENGTH: 25
<212> TYPE: DNA
<213> ORGANISM: Homo sapiens

<400> SEQUENCE: 681
gtgaagttta acgaagccct ccgtg                                                                          25

<210> SEQ ID NO 682
<211> LENGTH: 25
<212> TYPE: DNA
<213> ORGANISM: Homo sapiens

<400> SEQUENCE: 682
aagctgctct gagggctccc aggtc                                                                          25

<210> SEQ ID NO 683
<211> LENGTH: 25
<212> TYPE: DNA
<213> ORGANISM: Homo sapiens

<400> SEQUENCE: 683
gtcacggacg agaactccca cagtc                                                                          25

<210> SEQ ID NO 684
<211> LENGTH: 25
<212> TYPE: DNA
<213> ORGANISM: Homo sapiens

<400> SEQUENCE: 684
tggggatgag gctggtgtac tcgct                                                                          25

<210> SEQ ID NO 685
<211> LENGTH: 25
<212> TYPE: DNA
<213> ORGANISM: Homo sapiens

<400> SEQUENCE: 685
tgtactcgct caggtccagc gtcat                                                                          25

<210> SEQ ID NO 686
<211> LENGTH: 25
<212> TYPE: DNA
<213> ORGANISM: Homo sapiens

<400> SEQUENCE: 686
acctcacctt gtgaaaaagt tatat                                          25

<210> SEQ ID NO 687
<211> LENGTH: 25
<212> TYPE: DNA
<213> ORGANISM: Homo sapiens

<400> SEQUENCE: 687
gtaaatctgt gaaagagaat ggatt                                          25

<210> SEQ ID NO 688
<211> LENGTH: 25
<212> TYPE: DNA
<213> ORGANISM: Homo sapiens

<400> SEQUENCE: 688
tgacagaaac actttttgac atagt                                          25

<210> SEQ ID NO 689
<211> LENGTH: 25
<212> TYPE: DNA
<213> ORGANISM: Homo sapiens

<400> SEQUENCE: 689
gaaacacttt ttgacatagt gtggt                                          25

<210> SEQ ID NO 690
<211> LENGTH: 25
<212> TYPE: DNA
<213> ORGANISM: Homo sapiens

<400> SEQUENCE: 690
acttcttggc aagtaggtta agatc                                          25

<210> SEQ ID NO 691
<211> LENGTH: 25
<212> TYPE: DNA
<213> ORGANISM: Homo sapiens

<400> SEQUENCE: 691
tggcaagtag gttaagatct gggaa                                          25

<210> SEQ ID NO 692
<211> LENGTH: 25
<212> TYPE: DNA
<213> ORGANISM: Homo sapiens

<400> SEQUENCE: 692
tcgctccata gatgcaacac ccgat                                          25

<210> SEQ ID NO 693
<211> LENGTH: 25
<212> TYPE: DNA
<213> ORGANISM: Homo sapiens

<400> SEQUENCE: 693
cttacagcta atctctagaa tttca                                          25

<210> SEQ ID NO 694
<211> LENGTH: 25
<212> TYPE: DNA
<213> ORGANISM: Homo sapiens

<400> SEQUENCE: 694

-continued

```
tcttttctta cagctaatct ctaga                                    25

<210> SEQ ID NO 695
<211> LENGTH: 25
<212> TYPE: DNA
<213> ORGANISM: Homo sapiens

<400> SEQUENCE: 695
gacagcccac tgcctataag tacaa                                    25

<210> SEQ ID NO 696
<211> LENGTH: 25
<212> TYPE: DNA
<213> ORGANISM: Homo sapiens

<400> SEQUENCE: 696
ggtccatccc tacgctgacc agtgt                                    25

<210> SEQ ID NO 697
<211> LENGTH: 25
<212> TYPE: DNA
<213> ORGANISM: Homo sapiens

<400> SEQUENCE: 697
ccacttacat ttgcaaatgc tgatt                                    25

<210> SEQ ID NO 698
<211> LENGTH: 25
<212> TYPE: DNA
<213> ORGANISM: Homo sapiens

<400> SEQUENCE: 698
aaatgctttt gaagcaccac ttaca                                    25

<210> SEQ ID NO 699
<211> LENGTH: 25
<212> TYPE: DNA
<213> ORGANISM: Homo sapiens

<400> SEQUENCE: 699
cccgcccggc acccgcgtct gcgcc                                    25

<210> SEQ ID NO 700
<211> LENGTH: 25
<212> TYPE: DNA
<213> ORGANISM: Homo sapiens

<400> SEQUENCE: 700
cccgcccggc acccgcgtct gcgcc                                    25

<210> SEQ ID NO 701
<211> LENGTH: 25
<212> TYPE: DNA
<213> ORGANISM: Homo sapiens

<400> SEQUENCE: 701
gctgccagaa catccttggg ggcta                                    25

<210> SEQ ID NO 702
<211> LENGTH: 25
<212> TYPE: DNA
<213> ORGANISM: Homo sapiens
```

-continued

```
<400> SEQUENCE: 702
catggctgcc agaacatcct tgggg                                        25

<210> SEQ ID NO 703
<211> LENGTH: 25
<212> TYPE: DNA
<213> ORGANISM: Homo sapiens

<400> SEQUENCE: 703
atgattctga attagctata tcgtc                                        25

<210> SEQ ID NO 704
<211> LENGTH: 25
<212> TYPE: DNA
<213> ORGANISM: Homo sapiens

<400> SEQUENCE: 704
gaattagcta tatcgtcaag gcact                                        25

<210> SEQ ID NO 705
<211> LENGTH: 25
<212> TYPE: DNA
<213> ORGANISM: Homo sapiens

<400> SEQUENCE: 705
acctgtgagg aggttggcac tgaaa                                        25

<210> SEQ ID NO 706
<211> LENGTH: 25
<212> TYPE: DNA
<213> ORGANISM: Homo sapiens

<400> SEQUENCE: 706
acctgtgagg aggttggcac tgaaa                                        25

<210> SEQ ID NO 707
<211> LENGTH: 25
<212> TYPE: DNA
<213> ORGANISM: Homo sapiens

<400> SEQUENCE: 707
ggacggctca gacgtggcct cctgc                                        25

<210> SEQ ID NO 708
<211> LENGTH: 25
<212> TYPE: DNA
<213> ORGANISM: Homo sapiens

<400> SEQUENCE: 708
tgcttggacg gctcagacgt ggcct                                        25

<210> SEQ ID NO 709
<211> LENGTH: 25
<212> TYPE: DNA
<213> ORGANISM: Homo sapiens

<400> SEQUENCE: 709
cccctgacct cgctccccga acccc                                        25

<210> SEQ ID NO 710
<211> LENGTH: 25
<212> TYPE: DNA
<213> ORGANISM: Homo sapiens
```

<400> SEQUENCE: 710
cccctgacct cgctccccga acccc                                          25

<210> SEQ ID NO 711
<211> LENGTH: 25
<212> TYPE: DNA
<213> ORGANISM: Homo sapiens

<400> SEQUENCE: 711
tggggaactc ccgacaagat caaga                                         25

<210> SEQ ID NO 712
<211> LENGTH: 25
<212> TYPE: DNA
<213> ORGANISM: Homo sapiens

<400> SEQUENCE: 712
ggaactcccg acaagatcaa gaaag                                         25

<210> SEQ ID NO 713
<211> LENGTH: 25
<212> TYPE: DNA
<213> ORGANISM: Homo sapiens

<400> SEQUENCE: 713
cttcgcatct tagctgggcc accag                                         25

<210> SEQ ID NO 714
<211> LENGTH: 25
<212> TYPE: DNA
<213> ORGANISM: Homo sapiens

<400> SEQUENCE: 714
cgcatcttag ctgggccacc agctg                                         25

<210> SEQ ID NO 715
<211> LENGTH: 25
<212> TYPE: DNA
<213> ORGANISM: Homo sapiens

<400> SEQUENCE: 715
acttggccgt cgcacctcca gaact                                         25

<210> SEQ ID NO 716
<211> LENGTH: 25
<212> TYPE: DNA
<213> ORGANISM: Homo sapiens

<400> SEQUENCE: 716
cagtccactt ggccgtcgca cctcc                                         25

<210> SEQ ID NO 717
<211> LENGTH: 25
<212> TYPE: DNA
<213> ORGANISM: Homo sapiens

<400> SEQUENCE: 717
tgccatctat tgatgggacc cagac                                         25

<210> SEQ ID NO 718
<211> LENGTH: 25
<212> TYPE: DNA

-continued

<213> ORGANISM: Homo sapiens

<400> SEQUENCE: 718
caagaaattt gccatctatt gatgg                                        25

<210> SEQ ID NO 719
<211> LENGTH: 25
<212> TYPE: DNA
<213> ORGANISM: Homo sapiens

<400> SEQUENCE: 719
gtgctcagtc gcgacatacc gacag                                        25

<210> SEQ ID NO 720
<211> LENGTH: 25
<212> TYPE: DNA
<213> ORGANISM: Homo sapiens

<400> SEQUENCE: 720
agggtgctca gtcgcgacat accga                                        25

<210> SEQ ID NO 721
<211> LENGTH: 25
<212> TYPE: DNA
<213> ORGANISM: Homo sapiens

<400> SEQUENCE: 721
gactgcaagg acatgagcgt tgaag                                        25

<210> SEQ ID NO 722
<211> LENGTH: 25
<212> TYPE: DNA
<213> ORGANISM: Homo sapiens

<400> SEQUENCE: 722
gactgcaagg acatgagcgt tgaag                                        25

<210> SEQ ID NO 723
<211> LENGTH: 25
<212> TYPE: DNA
<213> ORGANISM: Homo sapiens

<400> SEQUENCE: 723
ggagggtggc tacaagtgcc agtgt                                        25

<210> SEQ ID NO 724
<211> LENGTH: 25
<212> TYPE: DNA
<213> ORGANISM: Homo sapiens

<400> SEQUENCE: 724
tgcgtgaacc tggagggtgg ctaca                                        25

<210> SEQ ID NO 725
<211> LENGTH: 25
<212> TYPE: DNA
<213> ORGANISM: Homo sapiens

<400> SEQUENCE: 725
ctcacctgca gatcattctc tggga                                        25

<210> SEQ ID NO 726
<211> LENGTH: 25

```
<212> TYPE: DNA
<213> ORGANISM: Homo sapiens

<400> SEQUENCE: 726
tgcagatcat tctctgggac aggtc                                          25

<210> SEQ ID NO 727
<211> LENGTH: 25
<212> TYPE: DNA
<213> ORGANISM: Homo sapiens

<400> SEQUENCE: 727
ccacttgtgt gtctagatct cctca                                          25

<210> SEQ ID NO 728
<211> LENGTH: 25
<212> TYPE: DNA
<213> ORGANISM: Homo sapiens

<400> SEQUENCE: 728
ctcagtggcc gcctctactg ggttg                                          25

<210> SEQ ID NO 729
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 729
tttcaccatg ttggccaggt                                                20

<210> SEQ ID NO 730
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 730
tactgggttt caccatgttg                                                20

<210> SEQ ID NO 731
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 731
agaaaagtta gccgggcgtg                                                20

<210> SEQ ID NO 732
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

-continued

<400> SEQUENCE: 732
acaggcgcgc gacaccacgc                                                                    20

<210> SEQ ID NO 733
<211> LENGTH: 159
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 733
uuucaccaug uuggccaggu gccauaauuc cucuguaaaa cuuaaagaag guuuauagag        60
uuauuauggu aaggcaauau gccguggcgu uggggaucgc cuauguccgg uuuuaccgga       120
ucucccuaaa ggugacuaac uuugguuagu caccuuuuu                              159

<210> SEQ ID NO 734
<211> LENGTH: 159
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 734
uacuggguuu caccauguug gccauaauuc cucuguaaaa cuuaaagaag guuuauagag        60
uuauuauggu aaggcaauau gccguggcgu uggggaucgc cuauguccgg uuuuaccgga       120
ucucccuaaa ggugacuaac uuugguuagu caccuuuuu                              159

<210> SEQ ID NO 735
<211> LENGTH: 159
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 735
agaaaaguua gccgggcgug gccauaauuc cucuguaaaa cuuaaagaag guuuauagag        60
uuauuauggu aaggcaauau gccguggcgu uggggaucgc cuauguccgg uuuuaccgga       120
ucucccuaaa ggugacuaac uuugguuagu caccuuuuu                              159

<210> SEQ ID NO 736
<211> LENGTH: 159
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 736
acaggcgcgc gacaccacgc gccauaauuc cucuguaaaa cuuaaagaag guuuauagag        60
uuauuauggu aaggcaauau gccguggcgu uggggaucgc cuauguccgg uuuuaccgga       120
ucucccuaaa ggugacuaac uuugguuagu caccuuuuu                              159

<210> SEQ ID NO 737
<211> LENGTH: 20

```
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 737
tcctggagcc tgtgataaaa                                                20

<210> SEQ ID NO 738
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 738
gctaacagtt gcttttatca                                                20

<210> SEQ ID NO 739
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 739
taacagttgc ttttatcaca                                                20

<210> SEQ ID NO 740
<211> LENGTH: 159
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 740
uccuggagcc ugugauaaaa gccauaauuc cucuguaaaa cuuaaagaag guuuauagag      60
uuauuauggu aaggcaauau gccguggcgu uggggaucgc cuauguccgg uuuuaccgga     120
ucucccuaaa ggugacuaac uuugguuagu caccuuuuu                           159

<210> SEQ ID NO 741
<211> LENGTH: 159
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 741
gcuaacaguu gcuuuuauca gccauaauuc cucuguaaaa cuuaaagaag guuuauagag      60
uuauuauggu aaggcaauau gccguggcgu uggggaucgc cuauguccgg uuuuaccgga     120
ucucccuaaa ggugacuaac uuugguuagu caccuuuuu                           159

<210> SEQ ID NO 742
<211> LENGTH: 159
<212> TYPE: RNA
```

-continued

```
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 742
uaacaguugc uuuuaucaca gccauaauuc cucuguaaaa cuuaaagaag guuuauagag        60
uuauuauggu aaggcaauau gccguggcgu uggggaucgc cuauguccgg uuuuaccgga       120
ucucccuaaa ggugacuaac uuugguuagu caccuuuuu                            159
```

RNA-GUIDED NUCLEASES AND ACTIVE FRAGMENTS AND VARIANTS THEREOF AND METHODS OF USE

CROSS-REFERENCE TO RELATED APPLICATIONS

This application is a national stage filing under 35 U.S.C. 371 of PCT/US2020/045759 filed Aug. 11, 2020, which International Application was published by the International Bureau in English on Feb. 18, 2021, and application claims priority from U.S. Provisional Application Nos. 62/885,483, filed Aug. 12, 2019, 62/901,875, filed Sep. 18, 2019, and 63/030,088, filed May 26, 2020, which applications are hereby incorporated in their entirety by reference in this application.

FIELD OF THE INVENTION

The present invention relates to the field of molecular biology and gene editing.

REFERENCE TO A SEQUENCE LISTING SUBMITTED AS A TEXT FILE VIA EFS-WEB

The instant application contains a Sequence Listing which has been submitted in ASCII format via EFS-Web and is hereby incorporated by reference in its entirety. Said ASCII copy, created on Aug. 11, 2020, is named L103438_1170 WO_0049_2_Seq_List.txt, and is 489,326 bytes in size.

BACKGROUND OF THE INVENTION

Targeted genome editing or modification is rapidly becoming an important tool for basic and applied research. Initial methods involved engineering nucleases such as meganucleases, zinc finger fusion proteins or TALENs, requiring the generation of chimeric nucleases with engineered, programmable, sequence-specific DNA-binding domains specific for each particular target sequence. RNA-guided nucleases, such as the Clustered Regularly Interspaced Short Palindromic Repeats (CRISPR)-associated (Cas) proteins of the CRISPR-Cas bacterial system, allow for the targeting of specific sequences by complexing the nucleases with guide RNA that specifically hybridizes with a particular target sequence. Producing target-specific guide RNAs is less costly and more efficient than generating chimeric nucleases for each target sequence. Such RNA-guided nucleases can be used to edit genomes optionally through the introduction of a sequence-specific, double-stranded break that is repaired via error-prone non-homologous end-joining (NHEJ) to introduce a mutation at a specific genomic location. Alternatively, heterologous DNA may be introduced into the genomic site via homology-directed repair.

BRIEF SUMMARY OF THE INVENTION

Compositions and methods for binding a target sequence of interest are provided. The compositions find use in cleaving or modifying a target sequence of interest, detection of a target sequence of interest, and modifying the expression of a sequence of interest. Compositions comprise RNA-guided nuclease (RGN) polypeptides, CRISPR RNAs (crRNAs), trans-activating CRISPR RNAs (tracrRNAs), guide RNAs (gRNAs), nucleic acid molecules encoding the same, and vectors and host cells comprising the nucleic acid molecules. Also provided are CRISPR systems for binding a target sequence of interest, wherein the CRISPR system comprises an RNA-guided nuclease polypeptide and one or more guide RNAs. Thus, methods disclosed herein are drawn to binding a target sequence of interest, and in some embodiments, cleaving or modifying the target sequence of interest. The target sequence of interest can be modified, for example, as a result of non-homologous end joining or homology-directed repair with an introduced donor sequence. Further provided are methods and kits for detecting a target DNA sequence of a DNA molecule using detector single-stranded DNA.

DETAILED DESCRIPTION

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended embodiments. Although specific terms are employed herein, they are used in a generic and descriptive sense only and not for purposes of limitation.

I. Overview

RNA-guided nucleases (RGNs) allow for the targeted manipulation of a single site within a genome and are useful in the context of gene targeting for therapeutic and research applications. In a variety of organisms, including mammals, RNA-guided nucleases have been used for genome engineering by stimulating non-homologous end joining and homologous recombination, for example. The compositions and methods described herein are useful for creating single- or double-stranded breaks in polynucleotides, modifying polynucleotides, detecting a particular site within a polynucleotide, or modifying the expression of a particular gene.

The RNA-guided nucleases disclosed herein can alter gene expression by modifying a target sequence. In specific embodiments, the RNA-guided nucleases are directed to the target sequence by a guide RNA (gRNA) as part of a Clustered Regularly Interspaced Short Palindromic Repeats (CRISPR) RNA-guided nuclease system. The RGNs are considered "RNA-guided" because guide RNAs form a complex with the RNA-guided nucleases to direct the RNA-guided nuclease to bind to a target sequence and in some embodiments, introduce a single-stranded or double-stranded break at the target sequence. After the target sequence has been cleaved, the break can be repaired such that the DNA sequence of the target sequence is modified during the repair process. Thus, provided herein are methods for using the RNA-guided nucleases to modify a target sequence in the DNA of host cells. For example, RNA-guided nucleases can be used to modify a target sequence at a genomic locus of eukaryotic cells or prokaryotic cells.

II. RNA-Guided Nucleases

Provided herein are RNA-guided nucleases. The term RNA-guided nuclease (RGN) refers to a polypeptide that binds to a particular target nucleotide sequence in a sequence-specific manner and is directed to the target nucleotide sequence by a guide RNA molecule that is complexed with the polypeptide and hybridizes with the target sequence. Although an RNA-guided nuclease can be capable of cleaving the target sequence upon binding, the term RNA-guided nuclease also encompasses nuclease-dead RNA-guided nucleases that are capable of binding to, but not cleaving, a target sequence. Cleavage of a target sequence by an RNA-guided nuclease can result in a single- or double-stranded break. RNA-guided nucleases only capable of cleaving a single strand of a double-stranded nucleic acid molecule are referred to herein as nickases.

The RNA-guided nucleases disclosed herein include the APG05733.1, APG06207.1, APG01647.1, APG08032.1, APG05712.1, APG01658.1, APG06498.1, APG09106.1, APG09882.1, APG02675.1, APG01405.1, APG06250.1, APG06877.1, APG09053.1, APG04293.1, APG01308.1, APG06646.1, APG09748, and APG07433.1 RNA-guided nucleases, the amino acid sequences of which are set forth, respectively, as SEQ ID NO: 1, 9, 16, 23, 30, 38, 46, 54, 61, 69, 75, 82, 89, 95, 103, 110, 117, 137 or 235, and active fragments or variants thereof that retain the ability to bind to a target nucleotide sequence in an RNA-guided sequence-specific manner. In some of these embodiments, the active fragment or variant of the APG05733.1, APG06207.1, APG01647.1, APG08032.1, APG05712.1, APG01658.1, APG06498.1, APG09106.1, APG09882.1, APG02675.1, APG01405.1, APG06250.1, APG06877.1, APG09053.1, APG04293.1, APG01308.1, APG06646.1, APG09748, or APG07433.1 RGN is capable of cleaving a single- or double-stranded target sequence. In some embodiments, an active variant of the APG05733.1, APG06207.1, APG01647.1, APG08032.1, APG05712.1, APG01658.1, APG06498.1, APG09106.1, APG09882.1, APG02675.1, APG01405.1, APG06250.1, APG06877.1, APG09053.1, APG04293.1, APG01308.1, APG06646.1, APG09748, or APG07433.1 RGN comprises an amino acid sequence having at least 40%, 45%, 50%, 55%, 60%, 65%, 70%, 75%, 80%, 85%, 90%, 91%, 92%, 93%, 94%, 95%, 96%, 97%, 98%, 99% or more sequence identity to the amino acid sequence set forth as SEQ ID NO: 1, 9, 16, 23, 30, 38, 46, 54, 61, 69, 75, 82, 89, 95, 103, 110, 117, 137 or 235. In certain embodiments, an active fragment of the APG05733.1, APG06207.1, APG01647.1, APG08032.1, APG05712.1, APG01658.1, APG06498.1, APG09106.1, APG09882.1, APG02675.1, APG01405.1, APG06250.1, APG06877.1, APG09053.1, APG04293.1, APG01308.1, APG06646.1, APG09748, or APG07433.1 RGN comprises at least 50, 100, 150, 200, 250, 300, 350, 400, 450, 500, 550, 600, 650, 700, 750, 800, 850, 900, 950, 1000, 1050 or more contiguous amino acid residues of the amino acid sequence set forth as SEQ ID NO: 1, 9, 16, 23, 30, 38, 46, 54, 61, 69, 75, 82, 89, 95, 103, 110, 117, 137, or 235. RNA-guided nucleases provided herein can comprise at least one nuclease domain (e.g., DNase, RNase domain) and at least one RNA recognition and/or RNA binding domain to interact with guide RNAs. Further domains that can be found in RNA-guided nucleases provided herein include, but are not limited to: DNA binding domains, helicase domains, protein-protein interaction domains, and dimerization domains. In specific embodiments, the RNA-guided nucleases provided herein can comprise at least 70%, 75%, 80%, 85%, 90%, 91%, 92%, 93%, 94%, 95%, 96%, 97%, 98%, 99% to one or more of a DNA binding domains, helicase domains, protein-protein interaction domains, and dimerization domains.

A target nucleotide sequence is bound by an RNA-guided nuclease provided herein and hybridizes with the guide RNA associated with the RNA-guided nuclease. The target sequence can then be subsequently cleaved by the RNA-guided nuclease if the polypeptide possesses nuclease activity. The terms "cleave" or "cleavage" refer to the hydrolysis of at least one phosphodiester bond within the backbone of a target nucleotide sequence that can result in either single-stranded or double-stranded breaks within the target sequence. The presently disclosed RGNs can cleave nucleotides within a polynucleotide, functioning as an endonuclease or can be an exonuclease, removing successive nucleotides from the end (the 5' and/or the 3' end) of a polynucleotide. In other embodiments, the disclosed RGNs can cleave nucleotides of a target sequence within any position of a polynucleotide and thus function as both an endonuclease and exonuclease. The cleavage of a target polynucleotide by the presently disclosed RGNs can result in staggered breaks or blunt ends.

The presently disclosed RNA-guided nucleases can be wild-type sequences derived from bacterial or archaeal species. Alternatively, the RNA-guided nucleases can be variants or fragments of wild-type polypeptides. The wild-type RGN can be modified to alter nuclease activity or alter PAM specificity, for example. In some embodiments, the RNA-guided nuclease is not naturally-occurring.

In certain embodiments, the RNA-guided nuclease functions as a nickase, only cleaving a single strand of the target nucleotide sequence. Such RNA-guided nucleases have a single functioning nuclease domain. In some of these embodiments, additional nuclease domains have been mutated such that the nuclease activity is reduced or eliminated.

In other embodiments, the RNA-guided nuclease lacks nuclease activity altogether or exhibits reduced nuclease activity, and is referred to herein as nuclease-dead or nuclease inactive. Any method known in the art for introducing mutations into an amino acid sequence, such as PCR-mediated mutagenesis and site-directed mutagenesis, can be used for generating nickases or nuclease-dead RGNs. See, e.g., U.S. Publ. No. 2014/0068797 and U.S. Pat. No. 9,790, 490; each of which is incorporated by reference in its entirety.

RNA-guided nucleases that lack nuclease activity can be used to deliver a fused polypeptide, polynucleotide, or small molecule payload to a particular genomic location. In some of these embodiments, the RGN polypeptide or guide RNA can be fused to a detectable label to allow for detection of a particular sequence. As a non-limiting example, a nuclease-dead RGN can be fused to a detectable label (e.g., fluorescent protein) and targeted to a particular sequence associated with a disease to allow for detection of the disease-associated sequence.

Alternatively, nuclease-dead RGNs can be targeted to particular genomic locations to alter the expression of a desired sequence. In some embodiments, the binding of a nuclease-dead RNA-guided nuclease to a target sequence results in the repression of expression of the target sequence or a gene under transcriptional control by the target sequence by interfering with the binding of RNA polymerase or transcription factors within the targeted genomic region. In other embodiments, the RGN (e.g., a nuclease-dead RGN) or its complexed guide RNA further comprises an expression modulator that, upon binding to a target sequence, serves to either repress or activate the expression of the target sequence or a gene under transcriptional control by the target sequence. In some of these embodiments, the expression modulator modulates the expression of the target sequence or regulated gene through epigenetic mechanisms.

In other embodiments, the nuclease-dead RGNs or a RGN with only nickase activity can be targeted to particular genomic locations to modify the sequence of a target polynucleotide through fusion to a base-editing polypeptide, for example a deaminase polypeptide or active variant or fragment thereof that deaminates a nucleotide base, resulting in conversion from one nucleotide base to another. The base-editing polypeptide can be fused to the RGN at its N-terminal or C-terminal end. Additionally, the base-editing polypeptide may be fused to the RGN via a peptide linker. A non-limiting example of a deaminase polypeptide that is useful for such compositions and methods include a cytidine deaminase or an adenosine deaminase (such as the adenosine deaminase base editor described in Gaudelli et al. (2017) *Nature* 551:464-471, U.S. Publ. Nos. 2017/0121693 and 2018/0073012, and International Publ. No. WO/2018/027078, or any of the deaminases disclosed in International Appl. No. PCT/US2019/068079, each of which is herein incorporated by reference in its entirety). Further, it is known in the art that certain fusion proteins between an RGN and a base-editing enzyme may also comprise at least one uracil stabilizing polypeptide that increases the mutation rate of a cytidine, deoxycytidine, or cytosine to a thymidine, deoxythymidine, or thymine in a nucleic acid molecule by a deaminase. Non-limiting examples of uracil stabilizing polypeptides include those disclosed in U.S. Provisional Appl. No. 63/052,175, filed Jul. 15, 2020, and a uracil glycosylase inhibitor (UGI) domain (SEQ ID NO: 261), which may increase base editing efficiency (U.S. Pat. No. 10,167,547, herein incorporated by reference). Therefore, a fusion protein may comprise an RGN described herein or a variant thereof, a deaminase, and optionally at least one uracil stabilizing polypeptides, such as UGI.

RNA-guided nucleases that are fused to a polypeptide or domain can be separated or joined by a linker. The term "linker," as used herein, refers to a chemical group or a molecule linking two molecules or moieties, e.g., a binding domain and a cleavage domain of a nuclease. In some embodiments, a linker joins a gRNA binding domain of an RNA guided nuclease and a base-editing polypeptide, such as a deaminase. In some embodiments, a linker joins a nuclease-dead RGN and a deaminase. Typically, the linker is positioned between, or flanked by, two groups, molecules, or other moieties and connected to each one via a covalent bond, thus connecting the two. In some embodiments, the linker is an amino acid or a plurality of amino acids (e.g., a peptide or protein). In some embodiments, the linker is an organic molecule, group, polymer, or chemical moiety. In some embodiments, the linker is 5-100 amino acids in length, for example, 5, 6, 7, 8, 9, 10, 11, 12, 13, 14, 15, 16, 17, 18, 19, 20, 21, 22, 23, 24, 25, 26, 27, 28, 29, 30, 30-35, 35-40, 40-45, 45-50, 50-60, 60-70, 70-80, 80-90, 90-100, 100-150, or 150-200 amino acids in length. Longer or shorter linkers are also contemplated.

The presently disclosed RNA-guided nucleases can comprise at least one nuclear localization signal (NLS) to enhance transport of the RGN to the nucleus of a cell. Nuclear localization signals are known in the art and generally comprise a stretch of basic amino acids (see, e.g., Lange et al., *J. Biol. Chem.* (2007) 282:5101-5105). In particular embodiments, the RGN comprises 2, 3, 4, 5, 6 or more nuclear localization signals. The nuclear localization signal(s) can be a heterologous NLS. Non-limiting examples of nuclear localization signals useful for the presently disclosed RGNs are the nuclear localization signals of SV40 Large T-antigen, nucleoplasmin, and c-Myc (see, e.g., Ray et al. (2015) *Bioconjug Chem* 26(6):1004-7). In particular embodiments, the RGN comprises the NLS sequence set forth as SEQ ID NO: 125 or 127. The RGN can comprise one or more NLS sequences at its N-terminus, C-terminus, or both the N-terminus and C-terminus. For example, the RGN can comprise two NLS sequences at the N-terminal region and four NLS sequences at the C-terminal region.

Other localization signal sequences known in the art that localize polypeptides to particular subcellular location(s) can also be used to target the RGNs, including, but not limited to, plastid localization sequences, mitochondrial localization sequences, and dual-targeting signal sequences that target to both the plastid and mitochondria (see, e.g., Nassoury and Morse (2005) *Biochim Biophys Acta* 1743:5-19; Kunze and Berger (2015) *Front Physiol* dx.doi.org/10.3389/fphys.2015.00259; Hellmann and Neupert (2003) *IUBMB Life* 55:219-225; Soll (2002) *Curr Opin Plant Biol* 5:529-535; Carrie and Small (2013) *Biochim Biophys Acta* 1833:253-259; Carrie et al. (2009) *FEBS J* 276:1187-1195; Silva-Filho (2003) *Curr Opin Plant Biol* 6:589-595; Peeters and Small (2001) *Biochim Biophys Acta* 1541:54-63; Murcha et al. (2014) *J Exp Bot* 65:6301-6335; Mackenzie (2005) *Trends Cell Biol* 15:548-554; Glaser et al. (1998) *Plant Mol Biol* 38:311-338).

In certain embodiments, the presently disclosed RNA-guided nucleases comprise at least one cell-penetrating domain that facilitates cellular uptake of the RGN. Cell-penetrating domains are known in the art and generally comprise stretches of positively charged amino acid residues (i.e., polycationic cell-penetrating domains), alternating polar amino acid residues and non-polar amino acid residues (i.e., amphipathic cell-penetrating domains), or hydrophobic amino acid residues (i.e., hydrophobic cell-penetrating domains) (see, e.g., Milletti F. (2012) *Drug Discov Today* 17:850-860). A non-limiting example of a cell-penetrating domain is the trans-activating transcriptional activator (TAT) from the human immunodeficiency virus 1.

The nuclear localization signal, plastid localization signal, mitochondrial localization signal, dual-targeting localization signal, and/or cell-penetrating domain can be located at the amino-terminus (N-terminus), the carboxyl-terminus (C-terminus), or in an internal location of the RNA-guided nuclease.

The presently disclosed RGNs can be fused to an effector domain, such as a cleavage domain, a deaminase domain, or an expression modulator domain, either directly or indirectly via a linker peptide. Such a domain can be located at the N-terminus, the C-terminus, or an internal location of the RNA-guided nuclease. In some of these embodiments, the RGN component of the fusion protein is a nuclease-dead RGN.

In some embodiments, the RGN fusion protein comprises a cleavage domain, which is any domain that is capable of cleaving a polynucleotide (i.e., RNA, DNA, or RNA/DNA hybrid) and includes, but is not limited to, restriction endonucleases and homing endonucleases, such as Type IIS endonucleases (e.g., FokI) (see, e.g., Belfort et al. (1997) *Nucleic Acids Res.* 25:3379-3388; Linn et al. (eds.) Nucleases, Cold Spring Harbor Laboratory Press, 1993).

In other embodiments, the RGN fusion protein comprises a deaminase domain that deaminates a nucleotide base, resulting in conversion from one nucleotide base to another, and includes, but is not limited to, a cytidine deaminase or an adenosine deaminase base editor (see, e.g., Gaudelli et al. (2017) *Nature* 551:464-471, U.S. Publ. Nos. 2017/0121693 and 2018/0073012, U.S. Pat. No. 9,840,699, and International Publ. No. WO/2018/027078).

In some embodiments, the effector domain of the RGN fusion protein can be an expression modulator domain, which is a domain that either serves to upregulate or downregulate transcription. The expression modulator domain can be an epigenetic modification domain, a transcriptional repressor domain or a transcriptional activation domain.

In some of these embodiments, the expression modulator of the RGN fusion protein comprises an epigenetic modification domain that covalently modifies DNA or histone proteins to alter histone structure and/or chromosomal structure without altering the DNA sequence, leading to changes in gene expression (i.e., upregulation or downregulation). Non-limiting examples of epigenetic modifications include acetylation or methylation of lysine residues, arginine methylation, serine and threonine phosphorylation, and lysine ubiquitination and sumoylation of histone proteins, and methylation and hydroxymethylation of cytosine residues in DNA. Non-limiting examples of epigenetic modification domains include histone acetyltransferase domains, histone deacetylase domains, histone methyltransferase domains, histone demethylase domains, DNA methyltransferase domains, and DNA demethylase domains.

In other embodiments, the expression modulator of the fusion protein comprises a transcriptional repressor domain, which interacts with transcriptional control elements and/or transcriptional regulatory proteins, such as RNA polymerases and transcription factors, to reduce or terminate transcription of at least one gene. Transcriptional repressor domains are known in the art and include, but are not limited to, Sp1-like repressors, IκB, and Krüppel associated box (KRAB) domains.

In yet other embodiments, the expression modulator of the fusion protein comprises a transcriptional activation domain, which interacts with transcriptional control elements and/or transcriptional regulatory proteins, such as RNA polymerases and transcription factors, to increase or activate transcription of at least one gene. Transcriptional activation domains are known in the art and include, but are not limited to, a herpes simplex virus VP16 activation domain and an NFAT activation domain.

The presently disclosed RGN polypeptides can comprise a detectable label or a purification tag. The detectable label or purification tag can be located at the N-terminus, the C-terminus, or an internal location of the RNA-guided nuclease, either directly or indirectly via a linker peptide. In some of these embodiments, the RGN component of the fusion protein is a nuclease-dead RGN. In other embodiments, the RGN component of the fusion protein is an RGN with nickase activity.

A detectable label is a molecule that can be visualized or otherwise observed. The detectable label may be fused to the RGN as a fusion protein (e.g., fluorescent protein) or may be a small molecule conjugated to the RGN polypeptide that can be detected visually or by other means. Detectable labels that can be fused to the presently disclosed RGNs as a fusion protein include any detectable protein domain, including but not limited to, a fluorescent protein or a protein domain that can be detected with a specific antibody. Non-limiting examples of fluorescent proteins include green fluorescent proteins (e.g., GFP, EGFP, ZsGreen1) and yellow fluorescent proteins (e.g., YFP, EYFP, ZsYellow1). Non-limiting examples of small molecule detectable labels include radioactive labels, such as $^3$H and $^{35}$S.

RGN polypeptides can also comprise a purification tag, which is any molecule that can be utilized to isolate a protein or fused protein from a mixture (e.g., biological sample, culture medium). Non-limiting examples of purification tags include biotin, myc, maltose binding protein (MBP), and glutathione-S-transferase (GST).

II. Guide RNA

The present disclosure provides guide RNAs and polynucleotides encoding the same. The term "guide RNA" refers to a nucleotide sequence having sufficient complementarity with a target nucleotide sequence to hybridize with the target sequence and direct sequence-specific binding of an associated RNA-guided nuclease to the target nucleotide sequence. Thus, a RGN's respective guide RNA is one or more RNA molecules (generally, one or two), that can bind to the RGN and guide the RGN to bind to a particular target nucleotide sequence, and in those instances wherein the RGN has nickase or nuclease activity, also cleave the target nucleotide sequence. In general, a guide RNA comprises a CRISPR RNA (crRNA) and in some embodiments, a trans-activating CRISPR RNA (tracrRNA). Native guide RNAs that comprise both a crRNA and a tracrRNA generally comprise two separate RNA molecules that hybridize to each other through the repeat sequence of the crRNA and the anti-repeat sequence of the tracrRNA.

Native direct repeat sequences within a CRISPR array generally range in length from 28 to 37 base pairs, although the length can vary between about 23 bp to about 55 bp. Spacer sequences within a CRISPR array generally range from about 32 to about 38 bp in length, although the length can be between about 21 bp to about 72 bp. Each CRISPR array generally comprises less than 50 units of the CRISPR repeat-spacer sequence. The CRISPRs are transcribed as part of a long transcript termed the primary CRISPR transcript, which comprises much of the CRISPR array. The primary CRISPR transcript is cleaved by Cas proteins to produce crRNAs or in some cases, to produce pre-crRNAs that are further processed by additional Cas proteins into mature crRNAs. Mature crRNAs comprise a spacer sequence and a CRISPR repeat sequence. In some embodiments in which pre-crRNAs are processed into mature (or processed) crRNAs, maturation involves the removal of about one to about six or more 5', 3', or 5' and 3' nucleotides. For the purposes of genome editing or targeting a particular target nucleotide sequence of interest, these nucleotides that are removed during maturation of the pre-crRNA molecule are not necessary for generating or designing a guide RNA.

A CRISPR RNA (crRNA) comprises a spacer sequence and a CRISPR repeat sequence. The "spacer sequence" is the nucleotide sequence that directly hybridizes with the target nucleotide sequence of interest. The spacer sequence is engineered to be fully or partially complementary with the target sequence of interest. In various embodiments, the spacer sequence can comprise from about 8 nucleotides to about 30 nucleotides, or more. For example, the spacer sequence can be about 8, about 9, about 10, about 11, about 12, about 13, about 14, about 15, about 16, about 17, about 18, about 19, about 20, about 21, about 22, about 23, about 24, about 25, about 26, about 27, about 28, about 29, about 30, or more nucleotides in length. In some embodiments, the spacer sequence is about 10 to about 26 nucleotides in length, or about 12 to about 30 nucleotides in length. In particular embodiments, the spacer sequence is about 30 nucleotides in length. In some embodiments, the degree of complementarity between a spacer sequence and its corresponding target sequence, when optimally aligned using a suitable alignment algorithm, is about or more than about 50%, about 60%, about 70%, about 75%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or more. In particular embodiments, the spacer sequence is free of secondary structure, which can be predicted using any suitable polynucleotide folding algorithm known in the art, including but not limited to mFold (see, e.g., Zuker and Stiegler (1981) *Nucleic Acids Res.* 9:133-148) and RNAfold (see, e.g., Gruber et al. (2008) *Cell* 106(1):23-24).

The CRISPR RNA repeat sequence comprises a nucleotide sequence that comprises a region with sufficient complementarity to hybridize to a tracrRNA. In various embodiments, the CRISPR RNA repeat sequence can comprise from about 8 nucleotides to about 30 nucleotides, or more. For example, the CRISPR repeat sequence can be about 8, about 9, about 10, about 11, about 12, about 13, about 14, about 15, about 16, about 17, about 18, about 19, about 20, about 21, about 22, about 23, about 24, about 25, about 26, about 27, about 28, about 29, about 30, or more nucleotides in length. In some embodiments, the CRISPR repeat sequence is about 21 nucleotides in length. In some embodiments, the degree of complementarity between a CRISPR repeat sequence and its corresponding tracrRNA sequence, when optimally aligned using a suitable alignment algorithm, is about or more than about 50%, about 60%, about 70%, about 75%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or more. In particular embodiments, the CRISPR repeat sequence comprises the nucleotide sequence of SEQ ID NO: 2, 10, 17, 24, 31, 39, 47, 55, 62, 70, 76, 83, 90, 96, 104, 111, 118, 240, 273, or 287, or an active variant or fragment thereof that when comprised within a guide RNA, is capable of directing the sequence-specific binding of an associated RNA-guided nuclease provided herein to a target sequence of interest. In certain embodiments, an active CRISPR repeat sequence variant of a wild-type sequence comprises a nucleotide sequence having at least 40%, 45%, 50%, 55%, 60%, 65%, 70%, 75%, 80%, 85%, 90%, 91%, 92%, 93%, 94%, 95%, 96%, 97%, 98%, 99% or more sequence identity to the nucleotide sequence set forth as SEQ ID NO: 2, 10, 17, 24, 31, 39, 47, 55, 62, 70, 76, 83, 90, 96, 104, 111, 118, 240, 273 or 287. In certain embodiments, an active CRISPR repeat sequence fragment of a wild-type sequence comprises at least 5, 6, 7, 8, 9, 10, 11, 12, 13, 14, 15, 16, 17, 18, 19, or 20 contiguous nucleotides of the nucleotide sequence set forth as SEQ ID NO: 2, 10, 17, 24, 31, 39, 47, 55, 62, 70, 76, 83, 90, 96, 104, 111, 118, 240, 273, or 287.

In certain embodiments, the crRNA is not naturally-occurring. In some of these embodiments, the specific CRISPR repeat sequence is not linked to the engineered spacer sequence in nature and the CRISPR repeat sequence is considered heterologous to the spacer sequence. In certain embodiments, the spacer sequence is an engineered sequence that is not naturally occurring.

A trans-activating CRISPR RNA or tracrRNA molecule comprises a nucleotide sequence comprising a region that has sufficient complementarity to hybridize to a CRISPR repeat sequence of a crRNA, which is referred to herein as the anti-repeat region. In some embodiments, the tracrRNA molecule further comprises a region with secondary structure (e.g., stem-loop) or forms secondary structure upon hybridizing with its corresponding crRNA. In particular embodiments, the region of the tracrRNA that is fully or partially complementary to a CRISPR repeat sequence is at the 5' end of the molecule and the 3' end of the tracrRNA comprises secondary structure. This region of secondary structure generally comprises several hairpin structures, including the nexus hairpin, which is found adjacent to the anti-repeat sequence. The nexus hairpin often has a conserved nucleotide sequence in the base of the hairpin stem, with the motif UNANNA, CNANNG, CNANNU, UNANNG, UNANNC, or CNANNU (SEQ ID NOs: 8, 37, 45, 53, 68, and 102, respectively) found in many nexus hairpins in tracrRNAs. There are often terminal hairpins at the 3' end of the tracrRNA that can vary in structure and number, but often comprise a GC-rich Rho-independent transcriptional terminator hairpin followed by a string of U's at the 3' end. See, for example, Briner et al. (2014) *Molecular Cell* 56:333-339, Briner and Barrangou (2016) *Cold Spring Haab Protoc*; doi: 10.1101/pdb.top090902, and U.S. Publication No. 2017/0275648, each of which is herein incorporated by reference in its entirety.

In various embodiments, the anti-repeat region of the tracrRNA that is fully or partially complementary to the CRISPR repeat sequence comprises from about 8 nucleotides to about 30 nucleotides, or more. For example, the region of base pairing between the tracrRNA anti-repeat sequence and the CRISPR repeat sequence can be about 8, about 9, about 10, about 11, about 12, about 13, about 14, about 15, about 16, about 17, about 18, about 19, about 20, about 21, about 22, about 23, about 24, about 25, about 26, about 27, about 28, about 29, about 30, or more nucleotides in length. In particular embodiments, the anti-repeat region of the tracrRNA that is fully or partially complementary to a CRISPR repeat sequence is about 20 nucleotides in length. In some embodiments, the degree of complementarity between a CRISPR repeat sequence and its corresponding tracrRNA anti-repeat sequence, when optimally aligned using a suitable alignment algorithm, is about or more than about 50%, about 60%, about 70%, about 75%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or more.

In various embodiments, the entire tracrRNA can comprise from about 60 nucleotides to more than about 140 nucleotides. For example, the tracrRNA can be about 60, about 65, about 70, about 75, about 80, about 85, about 90, about 95, about 100, about 105, about 110, about 115, about 120, about 125, about 130, about 135, about 140, or more nucleotides in length. In particular embodiments, the tracrRNA is about 80 to about 90 nucleotides in length, including about 80, about 81, about 82, about 83, about 84, about 85, about 86, about 87, about 88, about 89, and about 90 nucleotides in length. In certain embodiments, the tracrRNA is about 85 nucleotides in length.

In particular embodiments, the tracrRNA comprises the nucleotide sequence of SEQ ID NO: 3, 11, 18, 25, 32, 40, 48, 56, 63, 71, 77, 84, 91, 97, 105, 112, or 119, or an active variant or fragment thereof that when comprised within a guide RNA is capable of directing the sequence-specific binding of an associated RNA-guided nuclease provided herein to a target sequence of interest. In certain embodiments, an active tracrRNA sequence variant of a wild-type sequence comprises a nucleotide sequence having at least 40%, 45%, 50%, 55%, 60%, 65%, 70%, 75%, 80%, 85%, 90%, 91%, 92%, 93%, 94%, 95%, 96%, 97%, 98%, 99% or more sequence identity to the nucleotide sequence set forth as SEQ ID NO: 3, 11, 18, 25, 32, 40, 48, 56, 63, 71, 77, 84, 91, 97, 105, 112, 119, 241, 274, or 286. In certain embodiments, an active tracrRNA sequence fragment of a wild-type sequence comprises at least 5, 10, 15, 20, 25, 30, 35, 40, 45, 50, 55, 60, 65, 70, 75, 80, or more contiguous nucleotides of the nucleotide sequence set forth as SEQ ID NO: 3, 11, 18, 25, 32, 40, 48, 56, 63, 71, 77, 84, 91, 97, 105, 112, 119, 241, 274, or 286.

Two polynucleotide sequences can be considered to be substantially complementary when the two sequences hybridize to each other under stringent conditions. Likewise, an RGN is considered to bind to a particular target sequence within a sequence-specific manner if the guide RNA bound to the RGN binds to the target sequence under stringent conditions. By "stringent conditions" or "stringent hybridization conditions" is intended conditions under which the two polynucleotide sequences will hybridize to each other to a detectably greater degree than to other sequences (e.g., at least 2-fold over background). Stringent conditions are sequence-dependent and will be different in different circumstances. Typically, stringent conditions will be those in which the salt concentration is less than about 1.5 M Na ion, typically about 0.01 to 1.0 M Na ion concentration (or other salts) at pH 7.0 to 8.3, and the temperature is at least about 30° C. for short sequences (e.g., 10 to 50 nucleotides) and at least about 60° C. for long sequences (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulfate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C. Optionally, wash buffers may comprise about 0.1% to about 1% SDS. Duration of hybridization is generally less than about 24 hours, usually about 4 to about 12 hours. The duration of the wash time will be at least a length of time sufficient to reach equilibrium.

The Tm is the temperature (under defined ionic strength and pH) at which 50% of a complementary target sequence hybridizes to a perfectly matched sequence. For DNA-DNA hybrids, the Tm can be approximated from the equation of Meinkoth and Wahl (1984) Anal. Biochem. 138:267-284: $Tm=81.5° C.+16.6 (\log M)+0.41 (\% GC)−0.61 (\% form)−500/L$; where M is the molarity of monovalent cations, % GC is the percentage of guanosine and cytosine nucleotides in the DNA, % form is the percentage of formamide in the hybridization solution, and L is the length of the hybrid in base pairs. Generally, stringent conditions are selected to be about 5° C. lower than the thermal melting point (Tm) for the specific sequence and its complement at a defined ionic strength and pH. However, severely stringent conditions can utilize a hybridization and/or wash at 1, 2, 3, or 4° C. lower than the thermal melting point (Tm); moderately stringent conditions can utilize a hybridization and/or wash at 6, 7, 8, 9, or 10° C. lower than the thermal melting point (Tm); low stringency conditions can utilize a hybridization and/or wash at 11, 12, 13, 14, 15, or 20° C. lower than the thermal melting point (Tm). Using the equation, hybridization and wash compositions, and desired Tm, those of ordinary skill will understand that variations in the stringency of hybridization and/or wash solutions are inherently described. An extensive guide to the hybridization of nucleic acids is found in Tijssen (1993) Laboratory Techniques in Biochemistry and Molecular Biology—Hybridization with Nucleic Acid Probes, Part I, Chapter 2 (Elsevier, New York); and Ausubel et al., eds. (1995) Current Protocols in Molecular Biology, Chapter 2 (Greene Publishing and Wiley-Interscience, New York). See Sambrook et al. (1989) Molecular Cloning: A Laboratory Manual (2d ed., Cold Spring Harbor Laboratory Press, Plainview, New York).

The guide RNA can be a single guide RNA or a dual-guide RNA system. A single guide RNA comprises the crRNA and tracrRNA on a single molecule of RNA, whereas a dual-guide RNA system comprises a crRNA and a tracrRNA present on two distinct RNA molecules, hybridized to one another through at least a portion of the CRISPR repeat sequence of the crRNA and at least a portion of the tracrRNA, which may be fully or partially complementary to the CRISPR repeat sequence of the crRNA. In some of those embodiments wherein the guide RNA is a single guide RNA, the crRNA and tracrRNA are separated by a linker nucleotide sequence. In general, the linker nucleotide sequence is one that does not include complementary bases in order to avoid the formation of secondary structure within or comprising nucleotides of the linker nucleotide sequence. In some embodiments, the linker nucleotide sequence between the crRNA and tracrRNA is at least 3, at least 4, at least 5, at least 6, at least 7, at least 8, at least 9, at least 10, at least 11, at least 12, or more nucleotides in length. In particular embodiments, the linker nucleotide sequence of a single guide RNA is at least 4 nucleotides in length. In certain embodiments, the linker nucleotide sequence is the nucleotide sequence set forth as SEQ ID NO: 123.

The single guide RNA or dual-guide RNA can be synthesized chemically or via in vitro transcription. Assays for determining sequence-specific binding between a RGN and a guide RNA are known in the art and include, but are not limited to, in vitro binding assays between an expressed RGN and the guide RNA, which can be tagged with a detectable label (e.g., biotin) and used in a pull-down detection assay in which the guide RNA:RGN complex is captured via the detectable label (e.g., with streptavidin beads). A control guide RNA with an unrelated sequence or structure to the guide RNA can be used as a negative control for non-specific binding of the RGN to RNA. In certain embodiments, the guide RNA is SEQ ID NO: 4, 12, 19, 26, 33, 41, 49, 57, 64, 72, 78, 85, 92, 98, 106, 113, or 120, wherein the spacer sequence can be any sequence and is indicated as a poly-N sequence.

In certain embodiments, the guide RNA can be introduced into a target cell, organelle, or embryo as an RNA molecule. The guide RNA can be transcribed in vitro or chemically synthesized. In other embodiments, a nucleotide sequence encoding the guide RNA is introduced into the cell, organelle, or embryo. In some of these embodiments, the nucleotide sequence encoding the guide RNA is operably linked to a promoter (e.g., an RNA polymerase III promoter). The promoter can be a native promoter or heterologous to the guide RNA-encoding nucleotide sequence.

In various embodiments, the guide RNA can be introduced into a target cell, organelle, or embryo as a ribonucleoprotein complex, as described herein, wherein the guide RNA is bound to an RNA-guided nuclease polypeptide.

The guide RNA directs an associated RNA-guided nuclease to a particular target nucleotide sequence of interest through hybridization of the guide RNA to the target nucleotide sequence. A target nucleotide sequence can comprise DNA, RNA, or a combination of both and can be single-stranded or double-stranded. A target nucleotide sequence can be genomic DNA (i.e., chromosomal DNA), plasmid DNA, or an RNA molecule (e.g., messenger RNA, ribosomal RNA, transfer RNA, micro RNA, small interfering RNA). The target nucleotide sequence can be bound (and in some embodiments, cleaved) by an RNA-guided nuclease in vitro or in a cell. The chromosomal sequence targeted by the RGN can be a nuclear, plastid or mitochondrial chromosomal sequence. In some embodiments, the target nucleotide sequence is unique in the target genome.

The target nucleotide sequence is adjacent to a protospacer adjacent motif (PAM). A protospacer adjacent motif is generally within about 1 to about 10 nucleotides from the target nucleotide sequence, including about 1, about 2, about 3, about 4, about 5, about 6, about 7, about 8, about 9, or about 10 nucleotides from the target nucleotide sequence. The PAM can be 5' or 3' of the target sequence. In some embodiments, the PAM is 3' of the target sequence for the presently disclosed RGNs. Generally, the PAM is a consensus sequence of about 3-4 nucleotides, but in particular embodiments, can be 2, 3, 4, 5, 6, 7, 8, 9, or more nucleotides in length. In various embodiments, the PAM sequence recognized by the presently disclosed RGNs comprises the consensus sequence set forth as SEQ ID NO: 7, 15, 22, 29, 36, 44, 52, 60, 67, 81, 88, 101, 109, or 116.

In particular embodiments, an RNA-guided nuclease having SEQ ID NO: 1, 9, 16, 23, 30, 38, 46, 54, 61, 69, 75, 82, 89, 95, 103, 110, or 117 or an active variant or fragment thereof binds a target nucleotide sequence adjacent to a PAM sequence set forth as SEQ ID NO: 7, 15, 22, 29, 36, 44, 52, 60, 67, 81, 88, 101, 109, or 116. In some embodiments, an RNA-guided nuclease having SEQ ID NO: 54 or 137 or an active variant or fragment thereof binds a target nucleotide sequence adjacent to a PAM sequence set forth as SEQ ID NO: 147. In some of these embodiments, the RGN binds to a guide sequence comprising a CRISPR repeat sequence set forth in SEQ ID NO: 2, 10, 17, 24, 31, 39, 47, 55, 62, 70, 76, 83, 90, 96, 104, 111, or 118, respectively, or an active variant or fragment thereof, and a tracrRNA sequence set forth in SEQ ID NO: 3, 11, 18, 25, 32, 40, 48, 56, 63, 71, 77, 84, 91, 97, 105, 112, or 119, respectively, or an active variant or fragment thereof. The RGN systems are described further in Example 1 and Tables 1 and 2 of the present specification.

It is well-known in the art that PAM sequence specificity for a given nuclease enzyme is affected by enzyme concentration (see, e.g., Karvelis et al. (2015) *Genome Biol* 16:253), which may be modified by altering the promoter used to express the RGN, or the amount of ribonucleoprotein complex delivered to the cell, organelle, or embryo.

Upon recognizing its corresponding PAM sequence, the RGN can cleave the target nucleotide sequence at a specific cleavage site. As used herein, a cleavage site is made up of the two particular nucleotides within a target nucleotide sequence between which the nucleotide sequence is cleaved by an RGN. The cleavage site can comprise the $1^{st}$ and $2^{nd}$, $2^{nd}$ and $3^{rd}$, $3^{rd}$ and $4^{th}$, $4^{th}$ and $5^{th}$, $5^{th}$ and $6^{th}$, $7^{th}$ and $8^{th}$, or $8^{th}$ and $9^{th}$ nucleotides from the PAM in either the 5' or 3' direction. In some embodiments, the cleavage site may be over 10, 11, 12, 13, 14, 15, 16, 17, 18, 19, or 20 nucleotides from the PAM in either the 5' or 3' direction. In some embodiments, the cleavage site is 4 nucleotides away from the PAM. In other embodiments, the cleavage site is at least 15 nucleotides away from the PAM. As RGNs can cleave a target nucleotide sequence resulting in staggered ends, in some embodiments, the cleavage site is defined based on the distance of the two nucleotides from the PAM on the positive (+) strand of the polynucleotide and the distance of the two nucleotides from the PAM on the negative (−) strand of the polynucleotide.

The PAM is regarded as a hallmark of the RNA-guided nucleases of Type II CRISPR systems (Szczelkun et al., PNAS, 111: 9798-9803, 2014; Sternberg et al., Nature 507: 62-67, 2014). Interestingly, although APG06646.1 and APG04293.1 function as RNA-guided nucleases and possess many of the same domains as Type II CRISPR Cas9 nucleases, they each lack the typical PAM-Interacting domain (PID; Interpro: IPR032237; Pfam: PF16595). Accordingly, APG06646.1 and APG04293.1 also do not possess the typical PAM requirement, which is a motif of 2-5 nucleotides as described above. Instead, these proteins have unique DNA recognition domains at their C-termini (residues 821-1092 of APG06646.1 (full length sequence is SEQ ID NO: 117); residues 1064-1401 of APG04293.1 (full-length sequence is SEQ ID NO: 103). These unique DNA recognition domains enable the nucleases to cleave at a genomic target site based on a single-nucleotide motif in the vicinity of the genomic target sequence (SEQ ID NO: 109; see Table 2).

APG04293.1 also possesses a unique signature domain of 133 amino acid residues proximal to its N-terminus (residues 144-276). The function of this domain is not known in either Type II CRISPR Cas9 nucleases or generally in the art.

III. Nucleotides Encoding RNA-Guided Nucleases, CRISPR RNA, and/or tracrRNA

The present disclosure provides polynucleotides comprising the presently disclosed CRISPR RNAs, tracrRNAs, and/or sgRNAs and polynucleotides comprising a nucleotide sequence encoding the presently disclosed RNA-guided nucleases, CRISPR RNAs, tracrRNAs, and/or sgRNAs. Presently disclosed polynucleotides include those comprising or encoding a CRISPR repeat sequence comprising the nucleotide sequence of SEQ ID NO: 2, 10, 17, 24, 31, 39, 47, 55, 62, 70, 76, 83, 90, 96, 104, 111, 118, 240, 273, or 287, or an active variant or fragment thereof that when comprised within a guide RNA is capable of directing the sequence-specific binding of an associated RNA-guided nuclease to a target sequence of interest. Also disclosed are polynucleotides comprising or encoding a tracrRNA comprising the nucleotide sequence of SEQ ID NO: 3, 11, 18, 25, 32, 40, 48, 56, 63, 71, 77, 84, 91, 97, 105, 112, 119, 241, 274, or 286, or an active variant or fragment thereof that when comprised within a guide RNA is capable of directing the sequence-specific binding of an associated RNA-guided nuclease to a target sequence of interest. Polynucleotides are also provided that encode an RNA-guided nuclease comprising the amino acid sequence set forth as SEQ ID NO: 1, 9, 16, 23, 30, 38, 46, 54, 61, 69, 75, 82, 89, 95, 103, 110, 117, 137, or 235, and active fragments or variants thereof that retain the ability to bind to a target nucleotide sequence in an RNA-guided sequence-specific manner.

The use of the term "polynucleotide" is not intended to limit the present disclosure to polynucleotides comprising DNA. Those of ordinary skill in the art will recognize that polynucleotides can comprise ribonucleotides (RNA) and combinations of ribonucleotides and deoxyribonucleotides. Such deoxyribonucleotides and ribonucleotides include both naturally occurring molecules and synthetic analogues. These include peptide nucleic acids (PNAs), PNA-DNA chimers, locked nucleic acids (LNAs), and phosphothioate linked sequences. The polynucleotides disclosed herein also encompass all forms of sequences including, but not limited to, single-stranded forms, double-stranded forms, DNA-RNA hybrids, triplex structures, stem-and-loop structures, and the like.

The nucleic acid molecules encoding RGNs can be codon optimized for expression in an organism of interest. A "codon-optimized" coding sequence is a polynucleotide coding sequence having its frequency of codon usage designed to mimic the frequency of preferred codon usage or transcription conditions of a particular host cell. Expression in the particular host cell or organism is enhanced as a result of the alteration of one or more codons at the nucleic acid level such that the translated amino acid sequence is not changed. Nucleic acid molecules can be codon optimized, either wholly or in part. Codon tables and other references providing preference information for a wide range of organisms are available in the art (see, e.g., Campbell and Gowri (1990) *Plant Physiol.* 92:1-11 for a discussion of plant-preferred codon usage). Methods are available in the art for synthesizing plant-preferred genes. See, for example, U.S. Pat. Nos. 5,380,831, and 5,436,391, and Murray et al. (1989) *Nucleic Acids Res.* 17:477-498, herein incorporated by reference.

Polynucleotides encoding the RGNs, crRNAs, tracrR-NAs, and/or sgRNAs provided herein can be provided in expression cassettes for in vitro expression or expression in a cell, organelle, embryo, or organism of interest. The cassette will include 5' and 3' regulatory sequences operably linked to a polynucleotide encoding an RGN, crRNA, tracrRNAs, and/or sgRNAs provided herein that allows for expression of the polynucleotide. The cassette may additionally contain at least one additional gene or genetic element to be cotransformed into the organism. Where additional genes or elements are included, the components are operably linked. The term "operably linked" is intended to mean a functional linkage between two or more elements. For example, an operable linkage between a promoter and a coding region of interest (e.g., region coding for an RGN, crRNA, tracrRNAs, and/or sgRNAs) is a functional link that allows for expression of the coding region of interest. Operably linked elements may be contiguous or non-contiguous. When used to refer to the joining of two protein coding regions, by operably linked is intended that the coding regions are in the same reading frame. Alternatively, the additional gene(s) or element(s) can be provided on multiple expression cassettes. For example, the nucleotide sequence encoding a presently disclosed RGN can be present on one expression cassette, whereas the nucleotide sequence encoding a crRNA, tracrRNA, or complete guide RNA can be on a separate expression cassette. Such an expression cassette is provided with a plurality of restriction sites and/or recombination sites for insertion of the polynucleotides to be under the transcriptional regulation of the regulatory regions. The expression cassette may additionally contain a selectable marker gene.

The expression cassette will include in the 5'-3' direction of transcription, a transcriptional (and, in some embodiments, translational) initiation region (i.e., a promoter), an RGN-, crRNA-, tracrRNA- and/or sgRNA-encoding polynucleotide of the invention, and a transcriptional (and in some embodiments, translational) termination region (i.e., termination region) functional in the organism of interest. The promoters of the invention are capable of directing or driving expression of a coding sequence in a host cell. The regulatory regions (e.g., promoters, transcriptional regulatory regions, and translational termination regions) may be endogenous or heterologous to the host cell or to each other. As used herein, "heterologous" in reference to a sequence is a sequence that originates from a foreign species, or, if from the same species, is substantially modified from its native form in composition and/or genomic locus by deliberate human intervention. As used herein, a chimeric gene comprises a coding sequence operably linked to a transcription initiation region that is heterologous to the coding sequence.

Convenient termination regions are available from the Ti-plasmid of *A. tumefaciens*, such as the octopine synthase and nopaline synthase termination regions. See also Guerineau et al. (1991) *Mol. Gen. Genet.* 262:141-144; Proudfoot (1991) *Cell* 64:671-674; Sanfacon et al. (1991) *Genes Dev.* 5:141-149; Mogen et al. (1990) *Plant Cell* 2:1261-1272; Munroe et al. (1990) *Gene* 91:151-158; Ballas et al. (1989) *Nucleic Acids Res.* 17:7891-7903; and Joshi et al. (1987) *Nucleic Acids Res.* 15:9627-9639.

Additional regulatory signals include, but are not limited to, transcriptional initiation start sites, operators, activators, enhancers, other regulatory elements, ribosomal binding sites, an initiation codon, termination signals, and the like. See, for example, U.S. Pat. Nos. 5,039,523 and 4,853,331; EPO 0480762A2; Sambrook et al. (1992) Molecular Cloning: A Laboratory Manual, ed. Maniatis et al. (Cold Spring Harbor Laboratory Press, Cold Spring Harbor, N.Y.), hereinafter "Sambrook 11"; Davis et al., eds. (1980) Advanced Bacterial Genetics (Cold Spring Harbor Laboratory Press), Cold Spring Harbor, N.Y., and the references cited therein.

In preparing the expression cassette, the various DNA fragments may be manipulated, so as to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, resubstitutions, e.g., transitions and transversions, may be involved.

A number of promoters can be used in the practice of the invention. The promoters can be selected based on the desired outcome. The nucleic acids can be combined with constitutive, inducible, growth stage-specific, cell type-specific, tissue-preferred, tissue-specific, or other promoters for expression in the organism of interest. See, for example, promoters set forth in WO 99/43838 and in U.S. Pat. Nos. 8,575,425; 7,790,846; 8,147,856; 8,586,832; 7,772,369; 7,534,939; 6,072,050; 5,659,026; 5,608,149; 5,608,144; 5,604,121; 5,569,597; 5,466,785; 5,399,680; 5,268,463; 5,608,142; and 6,177,611; herein incorporated by reference.

For expression in plants, constitutive promoters also include CaMV 35S promoter (Odell et al. (1985) *Nature* 313:810-812); rice actin (McElroy et al. (1990) *Plant Cell* 2:163-171); ubiquitin (Christensen et al. (1989) *Plant Mol. Biol.* 12:619-632 and Christensen et al. (1992) *Plant Mol. Biol.* 18:675-689); pEMU (Last et al. (1991) *Theor. Appl. Genet.* 81:581-588); and MAS (Velten et al. (1984) *EMBO J* 3:2723-2730).

Examples of inducible promoters are the Adh1 promoter which is inducible by hypoxia or cold stress, the Hsp70 promoter which is inducible by heat stress, the PPDK promoter and the pepcarboxylase promoter which are both inducible by light. Also useful are promoters which are chemically inducible, such as the In2-2 promoter which is safener induced (U.S. Pat. No. 5,364,780), the Axig1 promoter which is auxin induced and tapetum specific but also active in callus (PCT US01/22169), the steroid-responsive promoters (see, for example, the ERE promoter which is estrogen induced, and the glucocorticoid-inducible promoter in Schena et al. (1991) *Proc. Natl. Acad. Sci. USA* 88:10421-10425 and McNellis et al. (1998) *Plant J.* 14(2):247-257) and tetracycline-inducible and tetracycline-repressible promoters (see, for example, Gatz et al. (1991) *Mol. Gen.*

*Genet.* 227:229-237, and U.S. Pat. Nos. 5,814,618 and 5,789,156), herein incorporated by reference.

Tissue-specific or tissue-preferred promoters can be utilized to target expression of an expression construct within a particular tissue. In certain embodiments, the tissue-specific or tissue-preferred promoters are active in plant tissue. Examples of promoters under developmental control in plants include promoters that initiate transcription preferentially in certain tissues, such as leaves, roots, fruit, seeds, or flowers. A "tissue specific" promoter is a promoter that initiates transcription only in certain tissues. Unlike constitutive expression of genes, tissue-specific expression is the result of several interacting levels of gene regulation. As such, promoters from homologous or closely related plant species can be preferable to use to achieve efficient and reliable expression of transgenes in particular tissues. In some embodiments, the expression comprises a tissue-preferred promoter. A "tissue preferred" promoter is a promoter that initiates transcription preferentially, but not necessarily entirely or solely in certain tissues.

In some embodiments, the nucleic acid molecules encoding a RGN, crRNA, and/or tracrRNA comprise a cell type-specific promoter. A "cell type specific" promoter is a promoter that primarily drives expression in certain cell types in one or more organs. Some examples of plant cells in which cell type specific promoters functional in plants may be primarily active include, for example, BETL cells, vascular cells in roots, leaves, stalk cells, and stem cells. The nucleic acid molecules can also include cell type preferred promoters. A "cell type preferred" promoter is a promoter that primarily drives expression mostly, but not necessarily entirely or solely in certain cell types in one or more organs. Some examples of plant cells in which cell type preferred promoters functional in plants may be preferentially active include, for example, BETL cells, vascular cells in roots, leaves, stalk cells, and stem cells.

The nucleic acid sequences encoding the RGNs, crRNAs, tracrRNAs, and/or sgRNAs can be operably linked to a promoter sequence that is recognized by a phage RNA polymerase for example, for in vitro mRNA synthesis. In such embodiments, the in vitro-transcribed RNA can be purified for use in the methods described herein. For example, the promoter sequence can be a T7, T3, or SP6 promoter sequence or a variation of a T7, T3, or SP6 promoter sequence. In such embodiments, the expressed protein and/or RNAs can be purified for use in the methods of genome modification described herein.

In certain embodiments, the polynucleotide encoding the RGN, crRNA, tracrRNA, and/or sgRNA also can be linked to a polyadenylation signal (e.g., SV40 polyA signal and other signals functional in plants) and/or at least one transcriptional termination sequence. Additionally, the sequence encoding the RGN also can be linked to sequence(s) encoding at least one nuclear localization signal, at least one cell-penetrating domain, and/or at least one signal peptide capable of trafficking proteins to particular subcellular locations, as described elsewhere herein.

The polynucleotide encoding the RGN, crRNA, tracrRNA, and/or sgRNA can be present in a vector or multiple vectors. A "vector" refers to a polynucleotide composition for transferring, delivering, or introducing a nucleic acid into a host cell. Suitable vectors include plasmid vectors, phagemids, cosmids, artificial/mini-chromosomes, transposons, and viral vectors (e.g., lentiviral vectors, adeno-associated viral vectors, baculoviral vector). The vector can comprise additional expression control sequences (e.g., enhancer sequences, Kozak sequences, polyadenylation sequences, transcriptional termination sequences), selectable marker sequences (e.g., antibiotic resistance genes), origins of replication, and the like. Additional information can be found in "Current Protocols in Molecular Biology" Ausubel et al., John Wiley & Sons, New York, 2003 or "Molecular Cloning: A Laboratory Manual" Sambrook & Russell, Cold Spring Harbor Press, Cold Spring Harbor, N.Y., 3rd edition, 2001.

The vector can also comprise a selectable marker gene for the selection of transformed cells. Selectable marker genes are utilized for the selection of transformed cells or tissues. Marker genes include genes encoding antibiotic resistance, such as those encoding neomycin phosphotransferase II (NEO) and hygromycin phosphotransferase (HPT), as well as genes conferring resistance to herbicidal compounds, such as glufosinate ammonium, bromoxynil, imidazolinones, and 2,4-dichlorophenoxyacetate (2,4-D).

In some embodiments, the expression cassette or vector comprising the sequence encoding the RGN polypeptide can further comprise a sequence encoding a crRNA and/or a tracrRNA, or the crRNA and tracrRNA combined to create a guide RNA. The sequence(s) encoding the crRNA and/or tracrRNA can be operably linked to at least one transcriptional control sequence for expression of the crRNA and/or tracrRNA in the organism or host cell of interest. For example, the polynucleotide encoding the crRNA and/or tracrRNA can be operably linked to a promoter sequence that is recognized by RNA polymerase III (Pol III). Examples of suitable Pol III promoters include, but are not limited to, mammalian U6, U3, H1, and 7SL RNA promoters and rice U6 and U3 promoters.

As indicated, expression constructs comprising nucleotide sequences encoding the RGNs, crRNA, tracrRNA, and/or sgRNA can be used to transform organisms of interest. Methods for transformation involve introducing a nucleotide construct into an organism of interest. By "introducing" is intended to introduce the nucleotide construct to the host cell in such a manner that the construct gains access to the interior of the host cell. The methods of the invention do not require a particular method for introducing a nucleotide construct to a host organism, only that the nucleotide construct gains access to the interior of at least one cell of the host organism. The host cell can be a eukaryotic or prokaryotic cell. In particular embodiments, the eukaryotic host cell is a plant cell, a mammalian cell, or an insect cell. Methods for introducing nucleotide constructs into plants and other host cells are known in the art including, but not limited to, stable transformation methods, transient transformation methods, and virus-mediated methods.

The methods result in a transformed organism, such as a plant, including whole plants, as well as plant organs (e.g., leaves, stems, roots, etc.), seeds, plant cells, propagules, embryos and progeny of the same. Plant cells can be differentiated or undifferentiated (e.g. callus, suspension culture cells, protoplasts, leaf cells, root cells, phloem cells, pollen).

"Transgenic organisms" or "transformed organisms" or "stably transformed" organisms or cells or tissues refers to organisms that have incorporated or integrated a polynucleotide encoding a RGN, crRNA, and/or tracrRNA of the invention. It is recognized that other exogenous or endogenous nucleic acid sequences or DNA fragments may also be incorporated into the host cell. *Agrobacterium*- and biolistic-mediated transformation remain the two predominantly employed approaches for transformation of plant cells. However, transformation of a host cell may be performed by infection, transfection, microinjection, electroporation, microprojection, biolistics or particle bombardment, electroporation, silica/carbon fibers, ultrasound mediated, PEG mediated, calcium phosphate co-precipitation, polycation DMSO technique, DEAE dextran procedure, and viral mediated, liposome mediated and the like. Viral-mediated introduction of a polynucleotide encoding an RGN, crRNA, and/or tracrRNA includes retroviral, lentiviral, adenoviral, and adeno-associated viral mediated introduction and expression, as well as the use of Caulimoviruses, Geminiviruses, and RNA plant viruses.

Transformation protocols as well as protocols for introducing polypeptides or polynucleotide sequences into plants may vary depending on the type of host cell (e.g., monocot or dicot plant cell) targeted for transformation. Methods for transformation are known in the art and include those set forth in U.S. Pat. Nos. 8,575,425; 7,692,068; 8,802,934; 7,541,517; each of which is herein incorporated by reference. See, also, Rakoczy-Trojanowska, M. (2002) *Cell Mol Biol Lett.* 7:849-858; Jones et al. (2005) *Plant Methods* 1:5; Rivera et al. (2012) *Physics of Life Reviews* 9:308-345; Bartlett et al. (2008) *Plant Methods* 4:1-12; Bates, G. W. (1999) *Methods in Molecular Biology* 111:359-366; Binns and Thomashow (1988) *Annual Reviews in Microbiology* 42:575-606; Christou, P. (1992) *The Plant Journal* 2:275-281; Christou, P. (1995) *Euphytica* 85:13-27; Tzfira et al. (2004) *TRENDS in Genetics* 20:375-383; Yao et al. (2006) *Journal of Experimental Botany* 57:3737-3746; Zupan and Zambryski (1995) *Plant Physiology* 107:1041-1047; Jones et al. (2005) *Plant Methods* 1:5;

Transformation may result in stable or transient incorporation of the nucleic acid into the cell. "Stable transformation" is intended to mean that the nucleotide construct introduced into a host cell integrates into the genome of the host cell and is capable of being inherited by the progeny thereof. "Transient transformation" is intended to mean that a polynucleotide is introduced into the host cell and does not integrate into the genome of the host cell.

Methods for transformation of chloroplasts are known in the art. See, for example, Svab et al. (1990) *Proc. Natl. Acad. Sci. USA* 87:8526-8530; Svab and Maliga (1993) *Proc. Natl. Acad. Sci. USA* 90:913-917; Svab and Maliga (1993) *EMBO J.* 12:601-606. The method relies on particle gun delivery of DNA containing a selectable marker and targeting of the DNA to the plastid genome through homologous recombination. Additionally, plastid transformation can be accomplished by transactivation of a silent plastid-borne transgene by tissue-preferred expression of a nuclear-encoded and plastid-directed RNA polymerase. Such a system has been reported in McBride et al. (1994) *Proc. Natl. Acad. Sci. USA* 91:7301-7305.

The cells that have been transformed may be grown into a transgenic organism, such as a plant, in accordance with conventional ways. See, for example, McCormick et al. (1986) *Plant Cell Reports* 5:81-84. These plants may then be grown, and either pollinated with the same transformed strain or different strains, and the resulting hybrid having constitutive expression of the desired phenotypic characteristic identified. Two or more generations may be grown to ensure that expression of the desired phenotypic characteristic is stably maintained and inherited and then seeds harvested to ensure expression of the desired phenotypic characteristic has been achieved. In this manner, the present invention provides transformed seed (also referred to as "transgenic seed") having a nucleotide construct of the invention, for example, an expression cassette of the invention, stably incorporated into their genome.

Alternatively, cells that have been transformed may be introduced into an organism. These cells could have originated from the organism, wherein the cells are transformed in an ex vivo approach.

The sequences provided herein may be used for transformation of any plant species, including, but not limited to, monocots and dicots. Examples of plants of interest include, but are not limited to, corn (maize), sorghum, wheat, sunflower, tomato, crucifers, peppers, potato, cotton, rice, soybean, sugarbeet, sugarcane, tobacco, barley, and oilseed rape, *Brassica* sp., alfalfa, rye, millet, safflower, peanuts, sweet potato, cassava, coffee, coconut, pineapple, citrus trees, cocoa, tea, banana, avocado, fig, guava, mango, olive, papaya, cashew, macadamia, almond, oats, vegetables, ornamentals, and conifers.

Vegetables include, but are not limited to, tomatoes, lettuce, green beans, lima beans, peas, and members of the genus *Curcumins* such as cucumber, cantaloupe, and musk melon. Ornamentals include, but are not limited to, azalea, hydrangea, hibiscus, roses, tulips, daffodils, petunias, carnation, poinsettia, and chrysanthemum. Preferably, plants of the present invention are crop plants (for example, maize, sorghum, wheat, sunflower, tomato, crucifers, peppers, potato, cotton, rice, soybean, sugarbeet, sugarcane, tobacco, barley, oilseed rape, etc.).

As used herein, the term plant includes plant cells, plant protoplasts, plant cell tissue cultures from which plants can be regenerated, plant calli, plant clumps, and plant cells that are intact in plants or parts of plants such as embryos, pollen, ovules, seeds, leaves, flowers, branches, fruit, kernels, ears, cobs, husks, stalks, roots, root tips, anthers, and the like. Grain is intended to mean the mature seed produced by commercial growers for purposes other than growing or reproducing the species. Progeny, variants, and mutants of the regenerated plants are also included within the scope of the invention, provided that these parts comprise the introduced polynucleotides. Further provided is a processed plant product or byproduct that retains the sequences disclosed herein, including for example, soymeal.

The polynucleotides encoding the RGNs, crRNAs, and/or tracrRNAs can also be used to transform any prokaryotic species, including but not limited to, archaea and bacteria (e.g., *Bacillus* sp., *Klebsiella* sp. *Streptomyces* sp., *Rhizobium* sp., *Escherichia* sp., *Pseudomonas* sp., *Salmonella* sp., *Shigella* sp., *Vibrio* sp., *Yersinia* sp., *Mycoplasma* sp., *Agrobacterium*, *Lactobacillus* sp.).

The polynucleotides encoding the RGNs, crRNAs, and/or tracrRNAs can be used to transform any eukaryotic species, including but not limited to animals (e.g., mammals, insects, fish, birds, and reptiles), fungi, amoeba, algae, and yeast.

Conventional viral and non-viral based gene transfer methods can be used to introduce nucleic acids in mammalian cells or target tissues. Such methods can be used to administer nucleic acids encoding components of a CRISPR system to cells in culture, or in a host organism. Non-viral vector delivery systems include DNA plasmids, RNA (e.g. a transcript of a vector described herein), naked nucleic acid, and nucleic acid complexed with a delivery vehicle, such as a liposome. Viral vector delivery systems include DNA and RNA viruses, which have either episomal or integrated genomes after delivery to the cell. For a review of gene therapy procedures, see Anderson, Science 256: 808-813 (1992); Nabel & Feigner, TIBTECH 11:211-217 (1993); Mitani & Caskey, TIBTECH 11:162-166 (1993); Dillon, TIBTECH 11:167-175 (1993); Miller, Nature 357:455-460 (1992); Van Brunt, Biotechnology 6(10): 1149-1154 (1988); Vigne, Restorative Neurology and Neuroscience 8:35-36

(1995); Kremer & Perricaudet, British Medical Bulletin 51(1):31-44 (1995); Haddada et al., in Current Topics in Microbiology and Immunology, Doerfler and Bohm (eds) (1995); and Yu et al., Gene Therapy 1:13-26 (1994).

Methods of non-viral delivery of nucleic acids include lipofection, nucleofection, microinjection, biolistics, virosomes, liposomes, immunoliposomes, polycation or lipid: nucleic acid conjugates, naked DNA, artificial virions, and agent-enhanced uptake of DNA. Lipofection is described in e.g., U.S. Pat. Nos. 5,049,386, 4,946,787; and 4,897,355) and lipofection reagents are sold commercially (e.g., Transfectam™ and Lipofectin™). Cationic and neutral lipids that are suitable for efficient receptor-recognition lipofection of polynucleotides include those of Feigner, WO 91/17424; WO 91/16024. Delivery can be to cells (e.g. in vitro or ex vivo administration) or target tissues (e.g. in vivo administration). The preparation of lipid:nucleic acid complexes, including targeted liposomes such as immunolipid complexes, is well known to one of skill in the art (see, e.g., Crystal, Science 270:404-410 (1995); Blaese et al., Cancer Gene Ther. 2:291-297 (1995); Behr et al., Bioconjugate Chem. 5:382-389 (1994); Remy et al., Bioconjugate Chem. 5:647-654 (1994); Gao et al., Gene Therapy 2:710-722 (1995); Ahmad et al., Cancer Res. 52:4817-4820 (1992); U.S. Pat. Nos. 4,186,183, 4,217,344, 4,235,871, 4,261,975, 4,485,054, 4,501,728, 4,774,085, 4,837,028, and 4,946, 787).

The use of RNA or DNA viral based systems for the delivery of nucleic acids takes advantage of highly evolved processes for targeting a virus to specific cells in the body and trafficking the viral payload to the nucleus. Viral vectors can be administered directly to patients (in vivo) or they can be used to treat cells in vitro, and the modified cells may optionally be administered to patients (ex vivo). Conventional viral based systems could include retroviral, lentivirus, adenoviral, adeno-associated and herpes simplex virus vectors for gene transfer. Integration in the host genome is possible with the retrovirus, lentivirus, and adeno-associated virus gene transfer methods, often resulting in long term expression of the inserted transgene. Additionally, high transduction efficiencies have been observed in many different cell types and target tissues.

The tropism of a retrovirus can be altered by incorporating foreign envelope proteins, expanding the potential target population of target cells. Lentiviral vectors are retroviral vectors that are able to transduce or infect non-dividing cells and typically produce high viral titers. Selection of a retroviral gene transfer system would therefore depend on the target tissue. Retroviral vectors are comprised of cis-acting long terminal repeats with packaging capacity for up to 6-10 kb of foreign sequence. The minimum cis-acting LTRs are sufficient for replication and packaging of the vectors, which are then used to integrate the therapeutic gene into the target cell to provide permanent transgene expression. Widely used retroviral vectors include those based upon murine leukemia virus (MuLV), gibbon ape leukemia virus (GaLV), Simian Immuno deficiency virus (SIV), human immuno deficiency virus (HIV), and combinations thereof (see, e.g., Buchscher et al., J. Viral. 66:2731-2739 (1992); Johann et al., J. Viral. 66:1635-1640 (1992); Sommnerfelt et al., Viral. 176:58-59 (1990); Wilson et al., J. Viral. 63:2374-2378 (1989); Miller et al., I. Viral. 65:2220-2224 (1991); PCT/US94/05700).

In applications where transient expression is preferred, adenoviral based systems may be used. Adenoviral based vectors are capable of very high transduction efficiency in many cell types and do not require cell division. With such vectors, high titer and levels of expression have been obtained. This vector can be produced in large quantities in a relatively simple system. Adeno-associated virus ("AAV") vectors may also be used to transduce cells with target nucleic acids, e.g., in the in vitro production of nucleic acids and peptides, and for in vivo and ex vivo gene therapy procedures (see, e.g., West et al., Virology 160:38-47 (1987); U.S. Pat. No. 4,797,368; WO 93/24641; Katin, Human Gene Therapy 5:793-801 (1994); Muzyczka, I. Clin. Invest. 94:1351 (1994). Construction of recombinant AAV vectors are described in a number of publications, including U.S. Pat. No. 5,173,414; Tratschin et al., Mol. Cell. Biol. 5:3251-3260 (1985); Tratschin, et al., Mol. Cell. Biol. 4:2072-2081 (1984); Hermonat & Muzyczka, PNAS 81:6466-6470 (1984); and Samulski et al., I. Viral. 63:03822-3828 (1989). Packaging cells are typically used to form virus particles that are capable of infecting a host cell. Such cells include 293 cells, which package adenovirus, and ψJ2 cells or PA317 cells, which package retrovirus.

Viral vectors used in gene therapy are usually generated by producing a cell line that packages a nucleic acid vector into a viral particle. The vectors typically contain the minimal viral sequences required for packaging and subsequent integration into a host, other viral sequences being replaced by an expression cassette for the polynucleotide(s) to be expressed. The missing viral functions are typically supplied in trans by the packaging cell line. For example, AAV vectors used in gene therapy typically only possess ITR sequences from the AAV genome which are required for packaging and integration into the host genome. Viral DNA is packaged in a cell line, which contains a helper plasmid encoding the other AAV genes, namely rep and cap, but lacking ITR sequences.

The cell line may also be infected with adenovirus as a helper. The helper virus promotes replication of the AAV vector and expression of AAV genes from the helper plasmid. The helper plasmid is not packaged in significant amounts due to a lack of ITR sequences. Contamination with adenovirus can be reduced by, e.g., heat treatment to which adenovirus is more sensitive than AAV. Additional methods for the delivery of nucleic acids to cells are known to those skilled in the art. See, for example, US20030087817, incorporated herein by reference.

In some embodiments, a host cell is transiently or nontransiently transfected with one or more vectors described herein. In some embodiments, a cell is transfected as it naturally occurs in a subject. In some embodiments, a cell that is transfected is taken from a subject. In some embodiments, the cell is derived from cells taken from a subject, such as a cell line. A wide variety of cell lines for tissue culture are known in the art. Examples of cell lines include, but are not limited to, C8161, CCRF-CEM, MOLT, mIMCD-3, NHDF, HeLaS3, Huh1, Huh4, Huh7, HUVEC, HASMC, HEKn, HEKa, MiaPaCell, Panel, PC-3, TF1, CTLL-2, CIR, Rath, CVI, RPTE, A10, T24, 182, A375, ARH-77, Calu1, SW480, SW620, SKOV3, SK-UT, CaCo2, P388D1, SEM-K2, WEHI-231, HB56, TIB55, Iurkat, 145.01, LRMB, Bcl-1, BC-3, IC21, DLD2, Raw264.7, NRK, NRK-52E, MRC5, MEF, Hep G2, HeLa B, HeLa T4. COS, COS-1, COS-6, COS-M6A, BS-C-1 monkey kidney epithelial, BALB/3T3 mouse embryo fibroblast, 3T3 Swiss, 3T3-L1, 132-d5 human fetal fibroblasts; 10.1 mouse fibroblasts, 293-T, 3T3, 721, 9L, A2780, A2780ADR, A2780cis, A172, A20, A253, A431, A-549, ALC, B16, B35, BCP-I cells, BEAS-2B, bEnd.3, BHK-21, BR 293, BxPC3, C3H-10Tl/2, C6/36, Cal-27, CHO, CHO-7, CHO-IR, CHO-K1, CHO-K2, CHO-T, CHO Dhfr−/−, COR-L23, COR-L23/ CPR, COR-L235010, CORL23/R23, COS-7, COV-434, CML Tl, CMT, CT26, D17, DH82, DU145, DuCaP, EL4, EM2, EM3, EMT6/AR1, EMT6/AR10.0, FM3, H1299, H69, HB54, HB55, HCA2, HEK-293, HeLa, Hepalclc7, HL-60, HMEC, HT-29, lurkat, lY cells, K562 cells, Ku812, KCL22, KGl, KYO1, LNCap, Ma-Mel 1-48, MC-38, MCF-7, MCF-10A, MDA-MB-231, MDA-MB-468, MDA-MB-435, MDCKII, MDCKII, MOR/0.2R, MONO-MAC 6, MTD-1A, MyEnd, NCI-H69/CPR, NCI-H69/LX10, NCI-H69/LX20, NCI-H69/LX4, NIH-3T3, NALM-1, NW-145, OPCN/OPCT cell lines, Peer, PNT-1A/PNT 2, RenCa, RIN-5F, RMA/RMAS, Saos-2 cells, Sf-9, SkBr3, T2, T-47D, T84, THP1 cell line, U373, U87, U937, VCaP, Vero cells, WM39, WT-49, X63, YAC-1, YAR, and transgenic varieties thereof. Cell lines are available from a variety of sources known to those with skill in the art (see, e.g., the American Type Culture Collection (ATCC) (Manassas, Va.)).

In some embodiments, a cell transfected with one or more vectors described herein is used to establish a new cell line comprising one or more vector-derived sequences. In some embodiments, a cell transiently transfected with the components of a CRISPR system as described herein (such as by transient transfection of one or more vectors, or transfection with RNA), and modified through the activity of a CRISPR complex, is used to establish a new cell line comprising cells containing the modification but lacking any other exogenous sequence. In some embodiments, cells transiently or non-transiently transfected with one or more vectors described herein, or cell lines derived from such cells are used in assessing one or more test compounds.

In some embodiments, one or more vectors described herein are used to produce a non-human transgenic animal or transgenic plant. In some embodiments, the transgenic animal is a mammal, such as a mouse, rat, or rabbit.

IV. Variants and Fragments of Polypeptides and Polynucleotides

The present disclosure provides active variants and fragments of a naturally-occurring (i.e., wild-type) RNA-guided nuclease, the amino acid sequence of which is set forth as SEQ ID NO: 1, 9, 16, 23, 30, 38, 46, 54, 61, 69, 75, 82, 89, 95, 103, 110, 117, 137, or 235, as well as active variants and fragments of naturally-occurring CRISPR repeats, such as the sequence set forth as SEQ ID NO: 2, 10, 17, 24, 31, 39, 47, 55, 62, 70, 76, 83, 90, 96, 104, 111, 118, 240, 273, or 287, and active variant and fragments of naturally-occurring tracrRNAs, such as the sequence set forth as SEQ ID NO: 3, 11, 18, 25, 32, 40, 48, 56, 63, 71, 77, 84, 91, 97, 105, 112, 119, 241, 274, or 286, and polynucleotides encoding the same.

While the activity of a variant or fragment may be altered compared to the polynucleotide or polypeptide of interest, the variant and fragment should retain the functionality of the polynucleotide or polypeptide of interest. For example, a variant or fragment may have increased activity, decreased activity, different spectrum of activity or any other alteration in activity when compared to the polynucleotide or polypeptide of interest.

Fragments and variants of naturally-occurring RGN polypeptides, such as those disclosed herein, will retain sequence-specific, RNA-guided DNA-binding activity. In particular embodiments, fragments and variants of naturally-occurring RGN polypeptides, such as those disclosed herein, will retain nuclease activity (single-stranded or double-stranded).

Fragments and variants of naturally-occurring CRISPR repeats, such as those disclosed herein, will retain the ability, when part of a guide RNA (comprising a tracrRNA), to bind to and guide an RNA-guided nuclease (complexed with the guide RNA) to a target nucleotide sequence in a sequence-specific manner.

Fragments and variants of naturally-occurring tracrRNAs, such as those disclosed herein, will retain the ability, when part of a guide RNA (comprising a CRISPR RNA), to guide an RNA-guided nuclease (complexed with the guide RNA) to a target nucleotide sequence in a sequence-specific manner.

The term "fragment" refers to a portion of a polynucleotide or polypeptide sequence of the invention. "Fragments" or "biologically active portions" include polynucleotides comprising a sufficient number of contiguous nucleotides to retain the biological activity (i.e., binding to and directing an RGN in a sequence-specific manner to a target nucleotide sequence when comprised within a guideRNA). "Fragments" or "biologically active portions" include polypeptides comprising a sufficient number of contiguous amino acid residues to retain the biological activity (i.e., binding to a target nucleotide sequence in a sequence-specific manner when complexed with a guide RNA). Fragments of the RGN proteins include those that are shorter than the full-length sequences due to the use of an alternate downstream start site. A biologically active portion of an RGN protein can be a polypeptide that comprises, for example, 10, 25, 50, 100, 150, 200, 250, 300, 350, 400, 450, 500, 550, 600, 650, 700, 750, 800, 850, 900, 950, 1000, 1050 or more contiguous amino acid residues of SEQ ID NO: 1, 9, 16, 23, 30, 38, 46, 54, 61, 69, 75, 82, 89, 95, 103, 110, 117, 137, or 235. Such biologically active portions can be prepared by recombinant techniques and evaluated for sequence-specific, RNA-guided DNA-binding activity. A biologically active fragment of a CRISPR repeat sequence can comprise at least 8 contiguous amino acids of SEQ ID NO: 2, 10, 17, 24, 31, 39, 47, 55, 62, 70, 76, 83, 90, 96, 104, 111, 118, 240, 273, or 287. A biologically active portion of a CRISPR repeat sequence can be a polynucleotide that comprises, for example, 8, 9, 10, 11, 12, 13, 14, 15, 16, 17, 18, 19, or 20 contiguous nucleotides of SEQ ID NO: 2, 10, 17, 24, 31, 39, 47, 55, 62, 70, 76, 83, 90, 96, 104, 111, 118, 240, 273, or 287. A biologically active portion of a tracrRNA can be a polynucleotide that comprises, for example, 8, 9, 10, 11, 12, 13, 14, 15, 16, 17, 18, 19, 20, 21, 22, 23, 24, 25, 26, 27, 28, 29, 30, 35, 40, 45, 50, 55, 60, 65, 70, 75, 80 or more contiguous nucleotides of SEQ ID NO: 3, 11, 18, 25, 32, 40, 48, 56, 63, 71, 77, 84, 91, 97, 105, 112, 119, 241, 274, or 286.

In general, "variants" is intended to mean substantially similar sequences. For polynucleotides, a variant comprises a deletion and/or addition of one or more nucleotides at one or more internal sites within the native polynucleotide and/or a substitution of one or more nucleotides at one or more sites in the native polynucleotide. As used herein, a "native" or "wild type" polynucleotide or polypeptide comprises a naturally occurring nucleotide sequence or amino acid sequence, respectively. For polynucleotides, conservative variants include those sequences that, because of the degeneracy of the genetic code, encode the native amino acid sequence of the gene of interest. Naturally occurring allelic variants such as these can be identified with the use of well-known molecular biology techniques, as, for example, with polymerase chain reaction (PCR) and hybridization techniques as outlined below. Variant polynucleotides also include synthetically derived polynucleotides, such as those generated, for example, by using site-directed mutagenesis but which still encode the polypeptide or the polynucleotide of interest. Generally, variants of a particular polynucleotide disclosed herein will have at least about 40%, 45%, 50%, 55%, 60%, 65%, 70%, 75%, 80%, 85%, 90%, 91%, 92%, 93%, 94%, 95%, 96%, 97%, 98%, 99% or more sequence identity to that particular polynucleotide as determined by sequence alignment programs and parameters described elsewhere herein.

Variants of a particular polynucleotide disclosed herein (i.e., the reference polynucleotide) can also be evaluated by comparison of the percent sequence identity between the polypeptide encoded by a variant polynucleotide and the polypeptide encoded by the reference polynucleotide. Percent sequence identity between any two polypeptides can be calculated using sequence alignment programs and parameters described elsewhere herein. Where any given pair of polynucleotides disclosed herein is evaluated by comparison of the percent sequence identity shared by the two polypeptides they encode, the percent sequence identity between the two encoded polypeptides is at least about 40%, 45%, 50%, 55%, 60%, 65%, 70%, 75%, 80%, 85%, 90%, 91%, 92%, 93%, 94%, 95%, 96%, 97%, 98%, 99% or more sequence identity.

In particular embodiments, the presently disclosed polynucleotides encode an RNA-guided nuclease polypeptide comprising an amino acid sequence having at least 40%, 45%, 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, or greater identity to an amino acid sequence of SEQ ID NO: 1, 9, 16, 23, 30, 38, 46, 54, 61, 69, 75, 82, 89, 95, 103, 110, 117, 137, or 235.

A biologically active variant of an RGN polypeptide of the invention may differ by as few as about 1-15 amino acid residues, as few as about 1-10, such as about 6-10, as few as 5, as few as 4, as few as 3, as few as 2, or as few as 1 amino acid residue. In specific embodiments, the polypeptides can comprise an N-terminal or a C-terminal truncation, which can comprise at least a deletion of 10, 15, 20, 25, 30, 35, 40, 45, 50, 55, 60, 65, 70, 75, 80, 85, 90, 95, 100, 150, 200, 250, 300, 350, 400, 450, 500, 550, 600, 650, 700, 750, 800, 850, 900, 950, 1000, 1050 amino acids or more from either the N or C terminus of the polypeptide. In certain embodiments, the presently disclosed polynucleotides comprise or encode a CRISPR repeat comprising a nucleotide sequence having at least 40%, 45%, 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, or greater identity to the nucleotide sequence set forth as SEQ ID NO: 2, 10, 17, 24, 31, 39, 47, 55, 62, 70, 76, 83, 90, 96, 104, 111, 118, 240, 273, or 287.

The presently disclosed polynucleotides can comprise or encode a tracrRNA comprising a nucleotide sequence having at least 40%, 45%, 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, or greater identity to the nucleotide sequence set forth as SEQ ID NO: 3, 11, 18, 25, 32, 40, 48, 56, 63, 71, 77, 84, 91, 97, 105, 112, 119, 241, 274, or 286.

Biologically active variants of a CRISPR repeat or tracrRNA of the invention may differ by as few as about 1-15 nucleotides, as few as about 1-10, such as about 6-10, as few as 5, as few as 4, as few as 3, as few as 2, or as few as 1 nucleotide. In specific embodiments, the polynucleotides can comprise a 5' or 3' truncation, which can comprise at least a deletion of 10, 15, 20, 25, 30, 35, 40, 45, 50, 55, 60, 65, 70, 75, 80 nucleotides or more from either the 5' or 3' end of the polynucleotide.

It is recognized that modifications may be made to the RGN polypeptides, CRISPR repeats, and tracrRNAs provided herein creating variant proteins and polynucleotides. Changes designed by man may be introduced through the application of site-directed mutagenesis techniques. Alternatively, native, as yet-unknown or as yet unidentified polynucleotides and/or polypeptides structurally and/or functionally-related to the sequences disclosed herein may also be identified that fall within the scope of the present invention. Conservative amino acid substitutions may be made in nonconserved regions that do not alter the function of the RGN proteins. Alternatively, modifications may be made that improve the activity of the RGN.

Variant polynucleotides and proteins also encompass sequences and proteins derived from a mutagenic and recombinogenic procedure such as DNA shuffling. With such a procedure, one or more different RGN proteins disclosed herein (e.g., SEQ ID NO: 1, 9, 16, 23, 30, 38, 46, 54, 61, 69, 75, 82, 89, 95, 103, 110, 117, 137, or 235) is manipulated to create a new RGN protein possessing the desired properties. In this manner, libraries of recombinant polynucleotides are generated from a population of related sequence polynucleotides comprising sequence regions that have substantial sequence identity and can be homologously recombined in vitro or in vivo. For example, using this approach, sequence motifs encoding a domain of interest may be shuffled between the RGN sequences provided herein and other known RGN genes to obtain a new gene coding for a protein with an improved property of interest, such as an increased $K_m$ in the case of an enzyme. Strategies for such DNA shuffling are known in the art. See, for example, Stemmer (1994) *Proc. Natl. Acad. Sci. USA* 91:10747-10751; Stemmer (1994) *Nature* 370:389-391; Crameri et al. (1997) *Nature Biotech.* 15:436-438; Moore et al. (1997) *J Mol. Biol.* 272:336-347; Zhang et al. (1997) *Proc. Natl. Acad. Sci. USA* 94:4504-4509; Crameri et al. (1998) *Nature* 391:288-291; and U.S. Pat. Nos. 5,605,793 and 5,837,458. A "shuffled" nucleic acid is a nucleic acid produced by a shuffling procedure such as any shuffling procedure set forth herein. Shuffled nucleic acids are produced by recombining (physically or virtually) two or more nucleic acids (or character strings), for example in an artificial, and optionally recursive, fashion. Generally, one or more screening steps are used in shuffling processes to identify nucleic acids of interest; this screening step can be performed before or after any recombination step. In some (but not all) shuffling embodiments, it is desirable to perform multiple rounds of recombination prior to selection to increase the diversity of the pool to be screened. The overall process of recombination and selection are optionally repeated recursively. Depending on context, shuffling can refer to an overall process of recombination and selection, or, alternately, can simply refer to the recombinational portions of the overall process.

As used herein, "sequence identity" or "identity" in the context of two polynucleotides or polypeptide sequences makes reference to the residues in the two sequences that are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity". Means for making this adjustment are well known to those of skill in the art. Typically, this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, California).

As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

Unless otherwise stated, sequence identity/similarity values provided herein refer to the value obtained using GAP Version 10 using the following parameters: % identity and % similarity for a nucleotide sequence using GAP Weight of 50 and Length Weight of 3, and the nwsgapdna.cmp scoring matrix; % identity and % similarity for an amino acid sequence using GAP Weight of 8 and Length Weight of 2, and the BLOSUM62 scoring matrix; or any equivalent program thereof. By "equivalent program" is intended any sequence comparison program that, for any two sequences in question, generates an alignment having identical nucleotide or amino acid residue matches and an identical percent sequence identity when compared to the corresponding alignment generated by GAP Version 10.

Two sequences are "optimally aligned" when they are aligned for similarity scoring using a defined amino acid substitution matrix (e.g., BLOSUM62), gap existence penalty and gap extension penalty so as to arrive at the highest score possible for that pair of sequences. Amino acid substitution matrices and their use in quantifying the similarity between two sequences are well-known in the art and described, e.g., in Dayhoff et al. (1978) "A model of evolutionary change in proteins." In "Atlas of Protein Sequence and Structure," Vol. 5, Suppl. 3 (ed. M. O. Dayhoff), pp. 345-352. Natl. Biomed. Res. Found., Washington, D.C. and Henikoff et al. (1992) Proc. Natl. Acad. Sci. USA 89:10915-10919. The BLOSUM62 matrix is often used as a default scoring substitution matrix in sequence alignment protocols. The gap existence penalty is imposed for the introduction of a single amino acid gap in one of the aligned sequences, and the gap extension penalty is imposed for each additional empty amino acid position inserted into an already opened gap. The alignment is defined by the amino acids positions of each sequence at which the alignment begins and ends, and optionally by the insertion of a gap or multiple gaps in one or both sequences, so as to arrive at the highest possible score. While optimal alignment and scoring can be accomplished manually, the process is facilitated by the use of a computer-implemented alignment algorithm, e.g., gapped BLAST 2.0, described in Altschul et al. (1997) *Nucleic Acids Res.* 25:3389-3402, and made available to the public at the National Center for Biotechnology Information Website (www.ncbi.nlm.nih.gov). Optimal alignments, including multiple alignments, can be prepared using, e.g., PSI-BLAST, available through www.ncbi.nlm.nih.gov and described by Altschul et al. (1997) *Nucleic Acids Res.* 25:3389-3402.

With respect to an amino acid sequence that is optimally aligned with a reference sequence, an amino acid residue "corresponds to" the position in the reference sequence with which the residue is paired in the alignment. The "position" is denoted by a number that sequentially identifies each amino acid in the reference sequence based on its position relative to the N-terminus. Owing to deletions, insertion, truncations, fusions, etc., that must be taken into account when determining an optimal alignment, in general the amino acid residue number in a test sequence as determined by simply counting from the N-terminal will not necessarily be the same as the number of its corresponding position in the reference sequence. For example, in a case where there is a deletion in an aligned test sequence, there will be no amino acid that corresponds to a position in the reference sequence at the site of deletion. Where there is an insertion in an aligned reference sequence, that insertion will not correspond to any amino acid position in the reference sequence. In the case of truncations or fusions there can be stretches of amino acids in either the reference or aligned sequence that do not correspond to any amino acid in the corresponding sequence.

V. Antibodies

Antibodies to the RGN polypeptides or ribonucleoproteins comprising the RGN polypeptides of the present invention, including those having the amino acid sequence set forth as SEQ ID NO: 1, 9, 16, 23, 30, 38, 46, 54, 61, 69, 75, 82, 89, 95, 103, 110, or 117 or active variants or fragments thereof, are also encompassed. Methods for producing antibodies are well known in the art (see, for example, Harlow and Lane (1988) Antibodies: A Laboratory Manual, Cold Spring Harbor Laboratory, Cold Spring Harbor, N.Y.; and U.S. Pat. No. 4,196,265). These antibodies can be used in kits for the detection and isolation of RGN polypeptides or ribonucleoproteins. Thus, this disclosure provides kits comprising antibodies that specifically bind to the polypeptides or ribonucleoproteins described herein, including, for example, polypeptides having the sequence of SEQ ID NO: 1, 9, 16, 23, 30, 38, 46, 54, 61, 69, 75, 82, 89, 95, 103, 110, or 117.

VI. Systems and Ribonucleoprotein Complexes for Binding a Target Sequence of Interest and Methods of Making the Same The present disclosure provides a system for binding a target sequence of interest, wherein the system comprises at least one guide RNA or a nucleotide sequence encoding the same, and at least one RNA-guided nuclease or a nucleotide sequence encoding the same. The guide RNA hybridizes to the target sequence of interest and also forms a complex with the RGN polypeptide, thereby directing the RGN polypeptide to bind to the target sequence. In some of these embodiments, the RGN comprises an amino acid sequence of SEQ ID NO: 1, 9, 16, 23, 30, 38, 46, 54, 61, 69, 75, 82, 89, 95, 103, 110, 117, 137, or 235, or an active variant or fragment thereof. In various embodiments, the guide RNA comprises a CRISPR repeat sequence comprising the nucleotide sequence of SEQ ID NO: 2, 10, 17, 24, 31, 39, 47, 55, 62, 70, 76, 83, 90, 96, 104, 111, 118, 240, 273, or 287, or an active variant or fragment thereof. In particular embodiments, the guide RNA comprises a tracrRNA comprising a nucleotide sequence of SEQ ID NO: 3, 11, 18, 25, 32, 40, 48, 56, 63, 71, 77, 84, 91, 97, 105, 112, 119, 241, 274, or 286, or an active variant or fragment thereof. The guide RNA of the system can be a single guide RNA or a dual-guide RNA. In particular embodiments, the system comprises a RNA-guided nuclease that is heterologous to the guideRNA, wherein the RGN and guideRNA are not naturally complexed in nature.

The system for binding a target sequence of interest provided herein can be a ribonucleoprotein complex, which is at least one molecule of an RNA bound to at least one protein. The ribonucleoprotein complexes provided herein comprise at least one guide RNA as the RNA component and an RNA-guided nuclease as the protein component. Such ribonucleoprotein complexes can be purified from a cell or organism that naturally expresses an RGN polypeptide and has been engineered to express a particular guide RNA that is specific for a target sequence of interest. Alternatively, the ribonucleoprotein complex can be purified from a cell or organism that has been transformed with polynucleotides that encode an RGN polypeptide and a guide RNA and cultured under conditions to allow for the expression of the RGN polypeptide and guide RNA. Thus, methods are provided for making an RGN polypeptide or an RGN ribonucleoprotein complex. Such methods comprise culturing a cell comprising a nucleotide sequence encoding an RGN polypeptide, and in some embodiments a nucleotide sequence encoding a guide RNA, under conditions in which the RGN polypeptide (and in some embodiments, the guide RNA) is expressed. The RGN polypeptide or RGN ribonucleoprotein can then be purified from a lysate of the cultured cells.

Methods for purifying an RGN polypeptide or RGN ribonucleoprotein complex from a lysate of a biological sample are known in the art (e.g., size exclusion and/or affinity chromatography, 2D-PAGE, HPLC, reversed-phase chromatography, immunoprecipitation). In particular methods, the RGN polypeptide is recombinantly produced and comprises a purification tag to aid in its purification, including but not limited to, glutathione-S-transferase (GST), chitin binding protein (CBP), maltose binding protein, thioredoxin (TRX), poly(NANP), tandem affinity purification (TAP) tag, myc, AcV5, AU1, AU5, E, ECS, E2, FLAG, HA, nus, Softag 1, Softag 3, Strep, SBP, Glu-Glu, HSV, KT3, S, S1, T7, V5, VSV-G, 6×His, 10×His, biotin carboxyl carrier protein (BCCP), and calmodulin. Generally, the tagged RGN polypeptide or RGN ribonucleoprotein complex is purified using immobilized metal affinity chromatography. It will be appreciated that other similar methods known in the art may be used, including other forms of chromatography or for example immunoprecipitation, either alone or in combination.

An "isolated" or "purified" polypeptide, or biologically active portion thereof, is substantially or essentially free from components that normally accompany or interact with the polypeptide as found in its naturally occurring environment. Thus, an isolated or purified polypeptide is substantially free of other cellular material, or culture medium when produced by recombinant techniques, or substantially free of chemical precursors or other chemicals when chemically synthesized. A protein that is substantially free of cellular material includes preparations of protein having less than about 30%, 20%, 10%, 5%, or 1% (by dry weight) of contaminating protein. When the protein of the invention or biologically active portion thereof is recombinantly produced, optimally culture medium represents less than about 30%, 20%, 10%, 5%, or 1% (by dry weight) of chemical precursors or non-protein-of-interest chemicals.

Particular methods provided herein for binding and/or cleaving a target sequence of interest involve the use of an in vitro assembled RGN ribonucleoprotein complex. In vitro assembly of an RGN ribonucleoprotein complex can be performed using any method known in the art in which an RGN polypeptide is contacted with a guide RNA under conditions to allow for binding of the RGN polypeptide to the guide RNA. As used herein, "contact", contacting", "contacted," refer to placing the components of a desired reaction together under conditions suitable for carrying out the desired reaction. The RGN polypeptide can be purified from a biological sample, cell lysate, or culture medium, produced via in vitro translation, or chemically synthesized. The guide RNA can be purified from a biological sample, cell lysate, or culture medium, transcribed in vitro, or chemically synthesized. The RGN polypeptide and guide RNA can be brought into contact in solution (e.g., buffered saline solution) to allow for in vitro assembly of the RGN ribonucleoprotein complex.

VII. Methods of Binding, Cleaving, or Modifying a Target Sequence

The present disclosure provides methods for binding, cleaving, and/or modifying a target nucleotide sequence of interest. The methods include delivering a system comprising at least one guide RNA or a polynucleotide encoding the same, and at least one RGN polypeptide or a polynucleotide encoding the same to the target sequence or a cell, organelle, or embryo comprising the target sequence. In some of these embodiments, the RGN comprises the amino acid sequence of SEQ ID NO: 1, 9, 16, 23, 30, 38, 46, 54, 61, 69, 75, 82, 89, 95, 103, 110, 117, 137, or 235, or an active variant or fragment thereof. In various embodiments, the guide RNA comprises a CRISPR repeat sequence comprising the nucleotide sequence of SEQ ID NO: 2, 10, 17, 24, 31, 39, 47, 55, 62, 70, 76, 83, 90, 96, 104, 111, 118, 240, 273, or 287, or an active variant or fragment thereof. In particular embodiments, the guide RNA comprises a tracrRNA comprising the nucleotide sequence of SEQ ID NO: 3, 11, 18, 25, 32, 40, 48, 56, 63, 71, 77, 84, 91, 97, 105, 112, 119, 241, 274, or 286, or an active variant or fragment thereof. The guide RNA of the system can be a single guide RNA or a dual-guide RNA. The RGN of the system may be nuclease dead RGN, have nickase activity, or may be a fusion polypeptide. In some embodiments, the fusion polypeptide comprises a base-editing polypeptide, for example a cytidine deaminase or an adenosine deaminase. In other embodiments, the RGN fusion protein comprises a reverse transcriptase. In other embodiments, the RGN fusion protein comprises a polypeptide that recruits members of a functional nucleic acid repair complex, such as a member of the nucleotide excision repair (NER) or transcription coupled-nucleotide excision repair (TC-NER) pathway (Wei et al., 2015, *PNAS USA* 112(27):E3495-504; Troelstra et al., 1992, *Cell* 71:939-953; Marnef et al., 2017, *J Mol Biol* 429(9): 1277-1288), as described in U.S. Provisional Application No. 62/966,203, which was filed on Jan. 27, 2020, and is incorporated by reference in its entirety. In some embodiments, the RGN fusion protein comprises CSB (van den Boom et al., 2004, *J Cell Biol* 166(1):27-36; van Gool et al., 1997, *EMBO J* 16(19):5955-65; an example of which is set forth as SEQ ID NO: 268), which is a member of the TC-NER (nucleotide excision repair) pathway and functions in the recruitment of other members. In further embodiments, the RGNABP fusion protein comprises an active domain of CSB, such as the acidic domain of CSB which comprises amino acid residues 356-394 of SEQ ID NO: 268 (Teng et al., 2018, *Nat Commun* 9(1):4115).

In particular embodiments, the RGN and/or guide RNA is heterologous to the cell, organelle, or embryo to which the RGN and/or guide RNA (or polynucleotide(s) encoding at least one of the RGN and guide RNA) are introduced.

In those embodiments wherein the method comprises delivering a polynucleotide encoding a guide RNA and/or an RGN polypeptide, the cell or embryo can then be cultured under conditions in which the guide RNA and/or RGN polypeptide are expressed. In various embodiments, the method comprises contacting a target sequence with an RGN ribonucleoprotein complex. The RGN ribonucleoprotein complex may comprise an RGN that is nuclease dead or has nickase activity. In some embodiments, the RGN of the ribonucleoprotein complex is a fusion polypeptide comprising a base-editing polypeptide. In certain embodiments, the method comprises introducing into a cell, organelle, or embryo comprising a target sequence an RGN ribonucleoprotein complex. The RGN ribonucleoprotein complex can be one that has been purified from a biological sample, recombinantly produced and subsequently purified, or in vitro-assembled as described herein. In those embodiments wherein the RGN ribonucleoprotein complex that is contacted with the target sequence or a cell organelle, or embryo has been assembled in vitro, the method can further comprise the in vitro assembly of the complex prior to contact with the target sequence, cell, organelle, or embryo.

A purified or in vitro assembled RGN ribonucleoprotein complex can be introduced into a cell, organelle, or embryo using any method known in the art, including, but not limited to electroporation. Alternatively, an RGN polypeptide and/or polynucleotide encoding or comprising the guide RNA can be introduced into a cell, organelle, or embryo using any method known in the art (e.g., electroporation).

Upon delivery to or contact with the target sequence or cell, organelle, or embryo comprising the target sequence, the guide RNA directs the RGN to bind to the target sequence in a sequence-specific manner. In those embodiments wherein the RGN has nuclease activity, the RGN polypeptide cleaves the target sequence of interest upon binding. The target sequence can subsequently be modified via endogenous repair mechanisms, such as non-homologous end joining, or homology-directed repair with a provided donor polynucleotide.

Methods to measure binding of an RGN polypeptide to a target sequence are known in the art and include chromatin immunoprecipitation assays, gel mobility shift assays, DNA pull-down assays, reporter assays, microplate capture and detection assays. Likewise, methods to measure cleavage or modification of a target sequence are known in the art and include in vitro or in vivo cleavage assays wherein cleavage is confirmed using PCR, sequencing, or gel electrophoresis, with or without the attachment of an appropriate label (e.g., radioisotope, fluorescent substance) to the target sequence to facilitate detection of degradation products. Alternatively, the nicking triggered exponential amplification reaction (NTEXPAR) assay can be used (see, e.g., Zhang et al. (2016) *Chem. Sci.* 7:4951-4957). In vivo cleavage can be evaluated using the Surveyor assay (Guschin et al. (2010) *Methods Mol Biol* 649:247-256).

In some embodiments, the methods involve the use of a single type of RGN complexed with more than one guide RNA. The more than one guide RNA can target different regions of a single gene or can target multiple genes.

In those embodiments wherein a donor polynucleotide is not provided, a double-stranded break introduced by an RGN polypeptide can be repaired by a non-homologous end-joining (NHEJ) repair process. Due to the error-prone nature of NHEJ, repair of the double-stranded break can result in a modification to the target sequence. As used herein, a "modification" in reference to a nucleic acid molecule refers to a change in the nucleotide sequence of the nucleic acid molecule, which can be a deletion, insertion, or substitution of one or more nucleotides, or a combination thereof. Modification of the target sequence can result in the expression of an altered protein product or inactivation of a coding sequence.

In those embodiments wherein a donor polynucleotide is present, the donor sequence in the donor polynucleotide can be integrated into or exchanged with the target nucleotide sequence during the course of repair of the introduced double-stranded break, resulting in the introduction of the exogenous donor sequence. A donor polynucleotide thus comprises a donor sequence that is desired to be introduced into a target sequence of interest. In some embodiments, the donor sequence alters the original target nucleotide sequence such that the newly integrated donor sequence will not be recognized and cleaved by the RGN. Integration of the donor sequence can be enhanced by the inclusion within the donor polynucleotide of flanking sequences that have substantial sequence identity with the sequences flanking the target nucleotide sequence, allowing for a homology-directed repair process. In those embodiments wherein the RGN polypeptide introduces double-stranded staggered breaks, the donor polynucleotide can comprise a donor sequence flanked by compatible overhangs, allowing for direct ligation of the donor sequence to the cleaved target nucleotide sequence comprising overhangs by a non-homologous repair process during repair of the double-stranded break.

In those embodiments wherein the method involves the use of an RGN that is a nickase (i.e., is only able to cleave a single strand of a double-stranded polynucleotide), the method can comprise introducing two RGN nickases that target identical or overlapping target sequences and cleave different strands of the polynucleotide. For example, an RGN nickase that only cleaves the positive (+) strand of a double-stranded polynucleotide can be introduced along with a second RGN nickase that only cleaves the negative (−) strand of a double-stranded polynucleotide.

In various embodiments, a method is provided for binding a target nucleotide sequence and detecting the target sequence, wherein the method comprises introducing into a cell, organelle, or embryo at least one guide RNA or a polynucleotide encoding the same, and at least one RGN polypeptide or a polynucleotide encoding the same, expressing the guide RNA and/or RGN polypeptide (if coding sequences are introduced), wherein the RGN polypeptide is a nuclease-dead RGN and further comprises a detectable label, and the method further comprises detecting the detectable label. The detectable label may be fused to the RGN as a fusion protein (e.g., fluorescent protein) or may be a small molecule conjugated to or incorporated within the RGN polypeptide that can be detected visually or by other means.

Also provided herein are methods for modulating the expression of a target sequence or a gene of interest under the regulation of a target sequence. The methods comprise introducing into a cell, organelle, or embryo at least one guide RNA or a polynucleotide encoding the same, and at least one RGN polypeptide or a polynucleotide encoding the same, expressing the guide RNA and/or RGN polypeptide (if coding sequences are introduced), wherein the RGN polypeptide is a nuclease-dead RGN. In some of these embodiments, the nuclease-dead RGN is a fusion protein comprising an expression modulator domain (i.e., epigenetic modification domain, transcriptional activation domain or a transcriptional repressor domain) as described herein.

The present disclosure also provides methods for binding and/or modifying a target nucleotide sequence of interest. The methods include delivering a system comprising at least one guide RNA or a polynucleotide encoding the same, and at least one fusion polypeptide comprises an RGN of the invention and a base-editing polypeptide, for example a cytidine deaminase or an adenosine deaminase, or a polynucleotide encoding the fusion polypeptide, to the target sequence or a cell, organelle, or embryo comprising the target sequence.

One of ordinary skill in the art will appreciate that any of the presently disclosed methods can be used to target a single target sequence or multiple target sequences. Thus, methods comprise the use of a single RGN polypeptide in combination with multiple, distinct guide RNAs, which can target multiple, distinct sequences within a single gene and/or multiple genes. Also encompassed herein are methods wherein multiple, distinct guide RNAs are introduced in combination with multiple, distinct RGN polypeptides. These guide RNAs and guide RNA/RGN polypeptide systems can target multiple, distinct sequences within a single gene and/or multiple genes.

In one aspect, the invention provides kits containing any one or more of the elements disclosed in the above methods and compositions. In some embodiments, the kit comprises a vector system and instructions for using the kit. In some embodiments, the vector system comprises (a) a first regulatory element operably linked to a DNA sequence encoding the crRNA sequence and one or more insertion sites for inserting a guide sequence upstream of the encoded crRNA sequence, wherein when expressed, the guide sequence directs sequence-specific binding of a CRISPR complex to a target sequence in a eukaryotic cell, wherein the CRISPR complex comprises a CRISPR enzyme complexed with the guide RNA polynucleotide; and/or (b) a second regulatory element operably linked to an enzyme coding sequence encoding said CRISPR enzyme comprising a nuclear localization sequence. Elements may be provided individually or in combinations, and may be provided in any suitable container, such as a vial, a bottle, or a tube.

In some embodiments, the kit includes instructions in one or more languages. In some embodiments, a kit comprises one or more reagents for use in a process utilizing one or more of the elements described herein. Reagents may be provided in any suitable container. For example, a kit may provide one or more reaction or storage buffers. Reagents may be provided in a form that is usable in a particular assay, or in a form that requires addition of one or more other components before use (e.g. in concentrate or lyophilized form). A buffer can be any buffer, including but not limited to a sodium carbonate buffer, a sodium bicarbonate buffer, a borate buffer, a Tris buffer, a MOPS buffer, a HEPES buffer, and combinations thereof. In some embodiments, the buffer is alkaline. In some embodiments, the buffer has a pH from about 7 to about 10.

In some embodiments, the kit comprises one or more oligonucleotides corresponding to a guide sequence for insertion into a vector so as to operably link the guide sequence and a regulatory element. In some embodiments, the kit comprises a homologous recombination template polynucleotide. In one aspect, the invention provides methods for using one or more elements of a CRISPR system. The CRISPR complex of the invention provides an effective means for modifying a target polynucleotide. The CRISPR complex of the invention has a wide variety of utility including modifying (e.g., deleting, inserting, translocating, inactivating, activating, base editing) a target polynucleotide in a multiplicity of cell types. As such the CRISPR complex of the invention has a broad spectrum of applications in, e.g., gene therapy, drug screening, disease diagnosis, and prognosis. An exemplary CRISPR complex comprises a CRISPR enzyme complexed with a guide sequence hybridized to a target sequence within the target polynucleotide.

VIII. Target Polynucleotides

In one aspect, the invention provides for methods of modifying a target polynucleotide in a eukaryotic cell, which may be in vivo, ex vivo or in vitro. In some embodiments, the method comprises sampling a cell or population of cells from a human or non-human animal or plant (including microalgae) and modifying the cell or cells. Culturing may occur at any stage ex vivo. The cell or cells may even be re-introduced into the non-human animal or plant (including micro-algae).

Using natural variability, plant breeders combine most useful genes for desirable qualities, such as yield, quality, uniformity, hardiness, and resistance against pests. These desirable qualities also include growth, day length preferences, temperature requirements, initiation date of floral or reproductive development, fatty acid content, insect resistance, disease resistance, nematode resistance, fungal resistance, herbicide resistance, tolerance to various environmental factors including drought, heat, wet, cold, wind, and adverse soil conditions including high salinity The sources of these useful genes include native or foreign varieties, heirloom varieties, wild plant relatives, and induced mutations, e.g., treating plant material with mutagenic agents. Using the present invention, plant breeders are provided with a new tool to induce mutations. Accordingly, one skilled in the art can analyze the genome for sources of useful genes, and in varieties having desired characteristics or traits employ the present invention to induce the rise of useful genes, with more precision than previous mutagenic agents and hence accelerate and improve plant breeding programs.

The target polynucleotide of an RGN system can be any polynucleotide endogenous or exogenous to the eukaryotic cell. For example, the target polynucleotide can be a polynucleotide residing in the nucleus of the eukaryotic cell. The target polynucleotide can be a sequence coding a gene product (e.g., a protein) or a non-coding sequence (e.g., a regulatory polynucleotide or a junk DNA). Without wishing to be bound by theory, it is believed that the target sequence should be associated with a PAM (protospacer adjacent motif); that is, a short sequence recognized by the CRISPR complex. The precise sequence and length requirements for the PAM differ depending on the CRISPR enzyme used, but PAMs are typically 2-5 base pair sequences adjacent the protospacer (that is, the target sequence).

The target polynucleotide of a CRISPR complex may include a number of disease-associated genes and polynucleotides as well as signaling biochemical pathway-associated genes and polynucleotides. Examples of target polynucleotides include a sequence associated with a signaling bio-chemical pathway, e.g., a signaling biochemical pathway-associated gene or polynucleotide. Examples of target polynucleotides include a disease associated gene or poly-nucleotide. A "disease-associated" gene or polynucleotide refers to any gene or polynucleotide which is yielding transcription or translation products at an abnormal level or in an abnormal form in cells derived from a disease-affected tissues compared with tissues or cells of a non-disease control. It may be a gene that becomes expressed at an abnormally high level; it may be a gene that becomes expressed at an abnormally low level, where the altered expression correlates with the occurrence and/or progression of the disease. A disease-associated gene also refers to a gene possessing mutation(s) or genetic variation that is directly responsible or is in linkage disequilibrium with a gene(s) that is responsible for the etiology of a disease (e.g., a causal mutation). The transcribed or translated products may be known or unknown, and further may be at a normal or abnormal level. Examples of disease-associated genes and polynucleotides are available from McKusick-Nathans Institute of Genetic Medicine, Johns Hopkins University (Baltimore, Md.) and National Center for Biotechnology Information, National Library of Medicine (Bethesda, Md.), available on the World Wide Web.

Although CRISPR systems are particularly useful for their relative ease in targeting to genomic sequences of interest, there still remains an issue of what the RGN can do to address a causal mutation. One approach is to produce a fusion protein between an RGN (preferably an inactive or nickase variant of the RGN) and a base-editing enzyme or the active domain of a base editing enzyme, such as a cytidine deaminase or an adenosine deaminase base editor (U.S. Pat. No. 9,840,699, herein incorporated by reference). In some embodiments, the methods comprise contacting a DNA molecule with (a) a fusion protein comprising an RGN of the invention and a base-editing polypeptide such as a deaminase; and (b) a gRNA targeting the fusion protein of (a) to a target nucleotide sequence of the DNA strand; wherein the DNA molecule is contacted with the fusion protein and the gRNA in an amount effective and under conditions suitable for the deamination of a nucleotide base. In some embodiments, the target DNA sequence comprises a sequence associated with a disease or disorder, and wherein the deamination of the nucleotide base results in a sequence that is not associated with a disease or disorder. In some embodiments, the target DNA sequence resides in an allele of a crop plant, wherein the particular allele of the trait of interest results in a plant of lesser agronomic value. The deamination of the nucleotide base results in an allele that improves the trait and increases the agronomic value of the plant.

In some embodiments, the DNA sequence comprises a T→C or A→G point mutation associated with a disease or disorder, and wherein the deamination of the mutant C or G base results in a sequence that is not associated with a disease or disorder. In some embodiments, the deamination corrects a point mutation in the sequence associated with the disease or disorder.

In some embodiments, the sequence associated with the disease or disorder encodes a protein, and wherein the deamination introduces a stop codon into the sequence associated with the disease or disorder, resulting in a trun-cation of the encoded protein. In some embodiments, the contacting is performed in vivo in a subject susceptible to having, having, or diagnosed with the disease or disorder. In some embodiments, the disease or disorder is a disease associated with a point mutation, or a single-base mutation, in the genome. In some embodiments, the disease is a genetic disease, a cancer, a metabolic disease, or a lysosomal storage disease.

Modifying Causal Mutations Using Base-Editing

An example of a genetically inherited disease which could be corrected using an approach that relies on an RGN-base editor fusion protein of the invention is Hurler Syndrome. Hurler Syndrome, also known as MPS-1, is the result of a deficiency of α-L-iduronidase (IDUA) resulting in a lyso-somal storage disease characterized at the molecular level by the accumulation of dermatan sulfate and heparan sulfate in lysosomes. This disease is generally an inherited genetic disorder caused by mutations in the IDUA gene encoding α-L-iduronidase. Common IDUA mutations are W402X and Q70X, both nonsense mutations resulting in premature termination of translation. Such mutations are well addressed by precise genome editing (PGE) approaches, since reversion of a single nucleotide, for example by a base-editing approach, would restore the wild-type coding sequence and result in protein expression controlled by the endogenous regulatory mechanisms of the genetic locus. Additionally, since heterozygotes are known to be asymp-tomatic, a PGE therapy that targets one of these mutations would be useful to a large proportion of patients with this disease, as only one of the mutated alleles needs to be corrected (Bunge et al. (1994) Hum. Mol. Genet. 3(6): 861-866, herein incorporated by reference).

Current treatments for Hurler Syndrome include enzyme replacement therapy and bone marrow transplants (Vellodi et al. (1997) Arch. Dis. Child. 76(2): 92-99; Peters et al. (1998) Blood 91(7): 2601-2608, herein incorporated by reference). While enzyme replacement therapy has had a dramatic effect on the survival and quality of life of Hurler Syndrome patients, this approach requires costly and time-consuming weekly infusions. Additional approaches include the delivery of the IDUA gene on an expression vector or the insertion of the gene into a highly expressed locus such as that of serum albumin (U.S. Pat. No. 9,956,247, herein incorporated by reference). However, these approaches do not restore the original IDUA locus to the correct coding sequence. A genome-editing strategy would have a number of advantages, most notably that regulation of gene expres-sion would be controlled by the natural mechanisms present in healthy individuals. Additionally, using base editing does not necessitate causing a double stranded DNA breaks, which could lead to large chromosomal rearrangements, cell death, or oncogenicity by the disruption of tumor suppres-sion mechanisms. A general strategy may be directed toward using RGN-base editor fusion proteins of the invention to target and correct certain disease-causing mutations in the human genome. It will be appreciated that similar approaches to target diseases that can be corrected by base-editing may also be pursued. It will be further appre-ciated that similar approaches to target disease-causing mutations in other species, particularly common household pets or livestock, can also be deployed using the RGNs of the invention. Common household pets and livestock include dogs, cats, horses, pigs, cows, sheep, chickens, donkeys, snakes, ferrets, and fish including salmon and shrimp.

Modifying Causal Mutations by Targeted Deletion

RGNs of the invention could also be useful in human therapeutic approaches where the causal mutation is more complicated. For example, some diseases such as Friedre-ich's Ataxia and Huntington's Disease are the result of a significant increase in repeats of a three nucleotide motif at a particular region of a gene, which affects the ability of the expressed protein to function or to be expressed. Friedreich's Ataxia (FRDA) is an autosomal recessive disease resulting in progressive degeneration of nervous tissue in the spinal cord. Reduced levels of the frataxin (FXN) protein in the mitochondria cause oxidative damages and iron deficiencies at the cellular level. The reduced FXN expression has been linked to a GAA triplet expansion within the intron 1 of the somatic and germline FXN gene. In FRDA patients, the GAA repeat frequently consists of more than 70, sometimes even more than 1000 (most commonly 600-900) triplets, whereas unaffected individuals have about 40 repeats or less (Pandolfo et al. (2012) Handbook of Clinical Neurology 103: 275-294; Campuzano et al. (1996) Science 271: 1423-1427; Pandolfo (2002) Adv. Exp. Med. Biol. 516: 99-118; all herein incorporated by reference).

The expansion of the trinucleotide repeat sequence causing Friedreich's Ataxia (FRDA) occurs in a defined genetic locus within the FXN gene, referred to as the FRDA instability region. RNA guided nucleases (RGNs) may be used for excising the instability region in FRDA patient cells. This approach requires 1) an RGN and guide RNA sequence that can be programmed to target the allele in the human genome; and 2) a delivery approach for the RGN and guide sequence. Many nucleases used for genome editing, such as the commonly used Cas9 nuclease from *S. pyogenes* (SpCas9), are too large to be packaged into adeno-associated viral (AAV) vectors, especially when considering the length of the SpCas9 gene and the guide RNA in addition to other genetic elements required for functional expression cassettes. This makes an approach using SpCas9 more difficult.

Certain RNA guided nucleases of the invention are well suited for packaging into an AAV vector along with a guide RNA. Packing two guide RNAs would likely require a second vector, but this approach still compares favorably to what would be required of a larger nuclease such as SpCas9, which may require splitting the protein sequence between two vectors. The present invention encompasses a strategy using RGNs of the invention in which a region of genomic instability is removed. Such a strategy is applicable to other diseases and disorders which have a similar genetic basis, such as Huntington's Disease. Similar strategies using RGNs of the invention may also be applicable to similar diseases and disorders in non-human animals of agronomic or economic importance, including dogs, cats, horses, pigs, cows, sheep, chickens, donkeys, snakes, ferrets, and fish including salmon and shrimp.

Modifying Causal Mutations by Targeted Mutagenesis

RGNs of the invention could also be to introduce disruptive mutations that may result in a beneficial effect. Genetic defects in the genes encoding hemoglobin, particularly the beta globin chain (the HBB gene), can be responsible for a number of diseases known as hemoglobinopathies, including sickle cell anemia and thalassemias.

In adult humans, hemoglobin is a heterotetramer comprising two alpha ($\alpha$)-like globin chains and two beta ($\beta$)-like globin chains and 4 heme groups. In adults the $\alpha2\beta2$ tetramer is referred to as Hemoglobin A (HbA) or adult hemoglobin. Typically, the alpha and beta globin chains are synthesized in an approximate 1:1 ratio and this ratio seems to be critical in terms of hemoglobin and red blood cell (RBC) stabilization. In a developing fetus, a different form of hemoglobin, fetal hemoglobin (HbF), is produced which has a higher binding affinity for oxygen than Hemoglobin A such that oxygen can be delivered to the baby's system via the mother's blood stream. Fetal hemoglobin also contains two $\alpha$ globin chains, but in place of the adult $\beta$-globin chains, it has two fetal gamma ($\gamma$)-globin chains (i.e., fetal hemoglobin is $\alpha2\gamma2$). The regulation of the switch from production of gamma- to beta-globin is quite complex, and primarily involves a down-regulation of gamma globin transcription with a simultaneous up-regulation of beta globin transcription. At approximately 30 weeks of gestation, the synthesis of gamma globin in the fetus starts to drop while the production of beta globin increases. By approximately 10 months of age, the newborn's hemoglobin is nearly all $\alpha2\beta2$ although some HbF persists into adulthood (approximately 1-3% of total hemoglobin). In the majority of patients with hemoglobinopathies, the genes encoding gamma globin remain present, but expression is relatively low due to normal gene repression occurring around parturition as described above.

Sickle cell disease is caused by a V6E mutation in the $\beta$ globin gene (HBB) (a GAG to GTG at the DNA level), where the resultant hemoglobin is referred to as "hemoglobinS" or "HbS." Under lower oxygen conditions, HbS molecules aggregate and form fibrous precipitates. These aggregates cause the abnormality or 'sickling' of the RBCs, resulting in a loss of flexibility of the cells. The sickling RBCs are no longer able to squeeze into the capillary beds and can result in vaso-occlusive crisis in sickle cell patients. In addition, sickled RBCs are more fragile than normal RBCs, and tend towards hemolysis, eventually leading to anemia in the patient.

Treatment and management of sickle cell patients is a life-long proposition involving antibiotic treatment, pain management and transfusions during acute episodes. One approach is the use of hydroxyurea, which exerts its effects in part by increasing the production of gamma globin. Long term side effects of chronic hydroxyurea therapy are still unknown, however, and treatment gives unwanted side effects and can have variable efficacy from patient to patient. Despite an increase in the efficacy of sickle cell treatments, the life expectancy of patients is still only in the mid to late 50's and the associated morbidities of the disease have a profound impact on a patient's quality of life.

Thalassemias (alpha thalassemias and beta thalassemia) are also diseases relating to hemoglobin and typically involve a reduced expression of globin chains. This can occur through mutations in the regulatory regions of the genes or from a mutation in a globin coding sequence that results in reduced expression or reduced levels or functional globin protein. Treatment of thalassemias usually involves blood transfusions and iron chelation therapy. Bone marrow transplants are also being used for treatment of people with severe thalassemias if an appropriate donor can be identified, but this procedure can have significant risks.

One approach that has been proposed for the treatment of both SCD and beta thalassemias is to increase the expression of gamma globin so that HbF functionally replaces the aberrant adult hemoglobin. As mentioned above, treatment of SCD patients with hydroxyurea is thought to be successful in part due to its effect on increasing gamma globin expression (DeSimone (1982) Proc Nat'l Acad Sci USA 79(14):4428-31; Ley, et al., (1982) N. Engl. J. Medicine, 307: 1469-1475; Ley, et al., (1983) Blood 62: 370-380; Constantoulakis et al., (1988) Blood 72(6):1961-1967, all herein incorporated by reference). Increasing the expression of HbF involves identification of genes whose products play a role in the regulation of gamma globin expression. One such gene is BCL11A. BCL11A encodes a zinc finger protein that expressed in adult erythroid precursor cells, and down-regulation of its expression leads to an increase in gamma globin expression (Sankaran et at (2008) Science 322: 1839, herein incorporated by reference). Use of an inhibitory RNA targeted to the BCL11A gene has been proposed (e.g., U.S. Patent Publication 2011/0182867, herein incorporated by reference) but this technology has several potential drawbacks, including that complete knock down may not be achieved, delivery of such RNAs may be problematic, and the RNAs must be present continuously, requiring multiple treatments for life.

RGNs of the invention may be used to target the BCL11A enhancer region to disrupt expression of BCL11A, thereby increasing gamma globin expression. This targeted disruption can be achieved by non-homologous end joining (NHEJ), whereby an RGN of the invention targets to a particular sequence within the BCL11A enhancer region, makes a double-stranded break, and the cell's machinery repairs the break, typically simultaneously introducing deleterious mutations. Similar to what is described for other disease targets, RGNs of the invention may have advantages over other known RGNs due to their relatively small size, which enables packaging expression cassettes for the RGN and its guide RNA into a single AAV vector for in vivo delivery. Similar strategies using RGNs of the invention may also be applicable to similar diseases and disorders in both humans and in non-human animals of agronomic or economic importance.

IX. Cells Comprising a Polynucleotide Genetic Modification

Provided herein are cells and organisms comprising a target sequence of interest that has been modified using a process mediated by an RGN, crRNA, and/or tracrRNA as described herein. In some of these embodiments, the RGN comprises the amino acid sequence of SEQ ID NO: 1, 9, 16, 23, 30, 38, 46, 54, 61, 69, 75, 82, 89, 95, 103, 110, 117, 137, or 235, or an active variant or fragment thereof. In various embodiments, the guide RNA comprises a CRISPR repeat sequence comprising the nucleotide sequence of SEQ ID NO: 2, 10, 17, 24, 31, 39, 47, 55, 62, 70, 76, 83, 90, 96, 104, 111, 118, 240, 273, or 287, or an active variant or fragment thereof. In particular embodiments, the guide RNA comprises a tracrRNA comprising the nucleotide sequence of SEQ ID NO: 3, 11, 18, 25, 32, 40, 48, 56, 63, 71, 77, 84, 91, 97, 105, 112, 119, 241, 274, or 286, or an active variant or fragment thereof. The guide RNA of the system can be a single guide RNA or a dual-guide RNA.

The modified cells can be eukaryotic (e.g., mammalian, plant, insect cell) or prokaryotic. Also provided are organelles and embryos comprising at least one nucleotide sequence that has been modified by a process utilizing an RGN, crRNA, and/or tracrRNA as described herein. The genetically modified cells, organisms, organelles, and embryos can be heterozygous or homozygous for the modified nucleotide sequence.

The chromosomal modification of the cell, organism, organelle, or embryo can result in altered expression (up-regulation or down-regulation), inactivation, or the expression of an altered protein product or an integrated sequence. In those instances wherein the chromosomal modification results in either the inactivation of a gene or the expression of a non-functional protein product, the genetically modified cell, organism, organelle, or embryo is referred to as a "knock out". The knock out phenotype can be the result of a deletion mutation (i.e., deletion of at least one nucleotide), an insertion mutation (i.e., insertion of at least one nucleotide), or a nonsense mutation (i.e., substitution of at least one nucleotide such that a stop codon is introduced).

Alternatively, the chromosomal modification of a cell, organism, organelle, or embryo can produce a "knock in", which results from the chromosomal integration of a nucleotide sequence that encodes a protein. In some of these embodiments, the coding sequence is integrated into the chromosome such that the chromosomal sequence encoding the wild-type protein is inactivated, but the exogenously introduced protein is expressed.

In other embodiments, the chromosomal modification results in the production of a variant protein product. The expressed variant protein product can have at least one amino acid substitution and/or the addition or deletion of at least one amino acid. The variant protein product encoded by the altered chromosomal sequence can exhibit modified characteristics or activities when compared to the wild-type protein, including but not limited to altered enzymatic activity or substrate specificity.

In yet other embodiments, the chromosomal modification can result in an altered expression pattern of a protein. As a non-limiting example, chromosomal alterations in the regulatory regions controlling the expression of a protein product can result in the overexpression or downregulation of the protein product or an altered tissue or temporal expression pattern.

X. Kits and Methods for Detecting Target DNA or Single-Stranded DNA

Some RGNs (e.g., APG09106.1 and APG09748, set forth as SEQ ID NOs: 54 and 137) can promiscuously cleave non-targeted single-stranded DNA (ssDNA) once activated by detection of a target DNA. Thus, provided herein are compositions and methods for detecting a target DNA (double-stranded or single-stranded) in a sample. In some embodiments, the desired target may exist as RNA, such as the genome or part of a genome of an RNA virus, such as for example a coronavirus. In some embodiments, the coronavirus may be a SARS-like coronavirus. In further embodiments, the coronavirus may be SARS-CoV-2, SARS-CoV, or a bat SARS-like coronavirus such as bat-SL-CoVZC45 (accession MG772933). In embodiments where the target exists as RNA, the target may be reverse-transcribed into a DNA molecule which can be effectively targeted by the RGN. Reverse-transcription may be followed by an amplification step, such as RT-PCR methods known in the art, which involve thermocycling, or may be by isothermal methods such as RT-LAMP (reverse transcription loop-mediated isothermal amplification) (Notomi et al., *Nucleic Acids Res* 28: E63, (2000)).

These compositions and methods involve the use of a detector ssDNA that does not hybridize with the guideRNA and is a non-target ssDNA. In some embodiments, the detector ssDNA comprises a detectable label that provides a detectable signal after cleavage of the detector ssDNA. A non-limiting example is a detector ssDNA that comprises a fluorophore/quencher pair wherein the fluorophore does not fluoresce when the detector ssDNA is whole (i.e., uncleaved) as its signal is suppressed by the presence of the quencher in close proximity. Cleavage of the detector ssDNA results in removal of the quencher and the fluorescent label can then be detected. Non-limiting examples of fluorescent labels or dyes include Cy5, fluorescein (e.g., FAM, 6 FAM, 5(6) FAM, FITC), Cy3, Alexa Fluor® dyes, and Texas Red. Non-limiting examples of quenchers include Iowa Black® FQ, Iowa Black® RQ, a Qx1 quencher, an ATTO quencher, and a QSY dye. In some embodiments, the detector ssDNA comprises a second quencher, such as an internal quencher like ZEN™, TAO™, and Black Hole Quencher®, which can lower background and increase signal detection.

In other embodiments, the detector ssDNA comprises a detectable label that provides a detectable signal before cleavage of the detector ssDNA and cleavage of the ssDNA inhibits or prevents detection of the signal. A non-limiting example of such a scenario is a detector ssDNA that comprises a fluorescence resonance energy transfer (FRET) pair. FRET is a process by which radiationless transfer of energy occurs from an excited state of a first (donor) fluorophore to a second (acceptor) fluorophore in close proximity. The emission spectrum of the donor fluorophore overlaps with the excitation spectrum of the acceptor fluorophore. Thus, the acceptor fluorophore will fluoresce when the detector ssDNA is whole (i.e., uncleaved) and the acceptor fluorophore will no longer fluoresce when the detector ssDNA is cleaved because the donor and acceptor fluorophore will no longer be in close proximity to one another. FRET donor and acceptor fluorophores are known in the art and include, but are not limited to cyan fluorescent protein (CFP)/green fluorescent protein (GFP), Cy3/Cy5, and GFP/yellow fluorescent protein (YFP).

In some embodiments, the detector ssDNA has a length of from about 2 nucleotides to about 30 nucleotides, including but not limited to about 2, about 3, about 4, about 5, about 6, about 7, about 8, about 9, about 10, about 11, about 12, about 13, about 14, about 15, about 16, about 17, about 18, about 19, about 20, about 21, about 22, about 23, about 24, about 25 nucleotides, about 26 nucleotides, about 27 nucleotides, about 28 nucleotides, about 29 nucleotides, and about 30 nucleotides.

Methods of detecting a target DNA of a DNA molecule comprise contacting a sample with an RGN, a guide RNA capable of hybridizing with the RGN and a target DNA sequence in a DNA molecule, and a detector single-stranded DNA (ssDNA) that does not hybridize with the guide RNA, followed by measuring a detectable signal produced by cleavage of the ssDNA by the RGN, thereby detecting the target DNA sequence of the DNA molecule. In some embodiments, the method can comprise a step of amplification of the nucleic acid molecules within a sample, either before or simultaneously with contact with the RGN and guideRNA. In some of these embodiments, specific sequences to which the guide RNA will hybridize can be amplified in order to increase sensitivity of a detection method.

The sample in which a target DNA can be detected using these compositions and methods comprising a detector ssDNA include any sample comprising or believed to comprise a nucleic acid (e.g., DNA or RNA molecule). The sample can be derived from any source including a synthetic combination of purified nucleic acids or a biological sample such as respiratory swab (e.g., nasopharyngeal swab) extracts, a cell lysate, a patient sample, cells, tissues, saliva, blood, serum, plasma, urine, aspirate, biopsy samples, cerebral spinal fluid, or organism (e.g., bacteria, virus).

The contacting of the sample with the RGN, guide RNA, and detector ssDNA can include contacting in vitro, ex vivo, or in vivo. In some embodiments, the detector ssDNA and/or the RGN and/or guide RNA is immobilized on for example, a lateral flow device, wherein the sample contacts the immobilized detector ssDNA and/or RGN and/or guide RNA. In some embodiments, antibodies against antigen moieties on the detector ssDNA are immobilized on, for example, a lateral flow device in a manner that allows differentiation of cleaved detector ssDNA from intact detector ssDNA.

In some embodiments, the methods can further comprise determining the amount of the target DNA present in the sample. The measurement of the detectable signal in the test sample can be compared to a reference measurement (e.g., a measurement of a reference sample or series thereof comprising a known amount of target DNA).

Non-limiting examples of applications of the compositions and methods include single-nucleotide polymorphism (SNP) detection, cancer screening, detection of a bacterial infection, detection of antibiotic resistance, and detection of a viral infection.

The detectable signal produced by cleavage of the ssDNA by the RGN can be measured using any suitable method known in the art including but not limited to measuring fluorescent signal, a visual analysis of bands on a gel, a colorimetric change, and the presence or absence of an electrical signal.

The present invention provides kits for detecting a target DNA of a DNA molecule in a sample, wherein the kit comprises an RGN polypeptide, a guide RNA capable of hybridizing with the RGN and a target DNA sequence in a DNA molecule, and a detector ssDNA that does not hybridize with the guide RNA.

Also provided herein are methods of cleaving single-stranded DNAs by contacting a population of nucleic acids, wherein the population comprises a target DNA sequence of a DNA molecule and a plurality of non-target ssDNAs with an RGN and a guide RNA capable of hybridizing with the RGN and the target DNA sequence.

The article "a" and "an" are used herein to refer to one or more than one (i.e., to at least one) of the grammatical object of the article. By way of example, "a polypeptide" means one or more polypeptides.

All publications and patent applications mentioned in the specification are indicative of the level of those skilled in the art to which this disclosure pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended embodiments.

NON-LIMITING EMBODIMENTS INCLUDE

1. A nucleic acid molecule comprising a polynucleotide encoding an RNA-guided nuclease (RGN) polypeptide, wherein said polynucleotide comprises a nucleotide sequence encoding an RGN polypeptide comprising an amino acid sequence having at least 95% sequence identity to SEQ ID NO: 1, 9, 16, 23, 30, 38, 46, 54, 61, 69, 75, 82, 89, 95, 103, 110, or 117;

wherein said RGN polypeptide is capable of binding a target DNA sequence of a DNA molecule in an RNA-guided sequence specific manner when bound to a guide RNA (gRNA) capable of hybridizing to said target DNA sequence, and wherein said polynucleotide encoding an RGN polypeptide is operably linked to a promoter heterologous to said polynucleotide.

2. The nucleic acid molecule of embodiment 1, wherein said RGN polypeptide is capable of cleaving said target DNA sequence upon binding.

3. The nucleic acid molecule of embodiment 2, wherein said RGN polypeptide is capable of generating a double-stranded break.

4. The nucleic acid molecule of embodiment 2, wherein said RGN polypeptide is capable of generating a single-stranded break.

5. The nucleic acid molecule of embodiment 2, wherein said RGN polypeptide is nuclease inactive.

6. The nucleic acid molecule of any one of embodiments 1-5, wherein the RGN polypeptide is operably fused to a base-editing polypeptide.

7. The nucleic acid molecule of embodiment 6, wherein the base-editing polypeptide is a deaminase.

8. The nucleic acid molecule of embodiment 7, wherein the deaminase is a cytidine deaminase or an adenosine deaminase.

9. The nucleic acid molecule of any one of embodiments 1-8, wherein the RGN polypeptide comprises one or more nuclear localization signals.

10. The nucleic acid molecule of any one of embodiments 1-9, wherein the RGN polypeptide is codon optimized for expression in a eukaryotic cell.

11. The nucleic acid molecule of any one of embodiments 1-10, wherein said target DNA sequence is located adjacent to a protospacer adjacent motif (PAM).

12. A vector comprising the nucleic acid molecule of any one of embodiments 1-11.

13. The vector of embodiment 12, further comprising at least one nucleotide sequence encoding said gRNA capable of hybridizing to said target DNA sequence.

14. The vector of embodiment 13, wherein the guide RNA comprises a CRISPR RNA comprising a CRISPR repeat sequence having at least 95% sequence identity to SEQ ID NO: 2, 10, 17, 24, 31, 39, 47, 55, 62, 70, 76, 83, 90, 96, 104, 111, or 118.

15. The vector of embodiment 13 or 14, wherein said gRNA comprises a tracrRNA.

16. The vector of embodiment 15, wherein the tracrRNA has at least 95% sequence identity to SEQ ID NO: 3, 11, 18, 25, 32, 40, 48, 56, 63, 71, 77, 84, 91, 97, 105, 112, or 119.

17. The vector of embodiment 15 or 16, where said gRNA is a single guide RNA.

18. The vector of embodiment 15 or 16, wherein said gRNA is a dual-guide RNA.

19. A cell comprising the nucleic acid molecule of any one of embodiments 1-11 or the vector of any one of embodiments 12-18.

20. A method for making an RGN polypeptide comprising culturing the cell of embodiment 18 under conditions in which the RGN polypeptide is expressed.

21. A method for making an RGN polypeptide comprising introducing into a cell a heterologous nucleic acid molecule comprising a nucleotide sequence encoding an RNA-guided nuclease (RGN) polypeptide comprising an amino acid sequence having at least 95% sequence identity to SEQ ID NO: 1, 9, 16, 23, 30, 38, 46, 54, 61, 69, 75, 82, 89, 95, 103, 110, or 117;

wherein said RGN polypeptide is capable of binding a target DNA sequence of a DNA molecule in an RNA-guided sequence specific manner when bound to a guide RNA (gRNA) capable of hybridizing to said target DNA sequence;

and culturing said cell under conditions in which the RGN polypeptide is expressed.

22. The method of embodiment 20 or 21, further comprising purifying said RGN polypeptide.

23. The method of embodiment 20 or 21, wherein said cell further expresses one or more guide RNAs that binds to said RGN polypeptide to form an RGN ribonucleoprotein complex.

24. The method of embodiment 23, further comprising purifying said RGN ribonucleoprotein complex.

25. A nucleic acid molecule comprising a polynucleotide encoding a CRISPR RNA (crRNA), wherein said crRNA comprises a spacer sequence and a CRISPR repeat sequence, wherein said CRISPR repeat sequence comprises a nucleotide sequence having at least 95% sequence identity to SEQ ID NO: 2, 10, 17, 24, 31, 39, 47, 55, 62, 70, 76, 83, 90, 96, 104, 111, or 118;

wherein a guide RNA comprising:

a) said crRNA; and optionally, b) a trans-activating CRISPR RNA (tracrRNA) capable of hybridizing to said CRISPR repeat sequence of said crRNA;

is capable of hybridizing to a target DNA sequence of a DNA molecule in a sequence specific manner through the spacer sequence of said crRNA when said guide RNA is bound to an RNA-guided nuclease (RGN) polypeptide, and wherein said polynucleotide encoding a crRNA is operably linked to a promoter heterologous to said polynucleotide.

26. A vector comprising the nucleic acid molecule of embodiment 25.

27. The vector of embodiment 26, wherein said vector further comprises a polynucleotide encoding said tracrRNA.

28. The vector of embodiment 27, wherein said tracrRNA comprises a nucleotide sequence having at least 95% sequence identity to SEQ ID NO: 3, 11, 18, 25, 32, 40, 48, 56, 63, 71, 77, 84, 91, 97, 105, 112, or 119.

29. The vector of embodiment 27 or 28, wherein said polynucleotide encoding said crRNA and said polynucleotide encoding said tracrRNA are operably linked to the same promoter and are encoded as a single guide RNA.

30. The vector of embodiment 27 or 28, wherein said polynucleotide encoding said crRNA and said polynucleotide encoding said tracrRNA are operably linked to separate promoters.

31. The vector of any one of embodiments 26-30, wherein said vector further comprises a polynucleotide encoding said RGN polypeptide, wherein said RGN polypeptide comprises an amino acid sequence having at least 95% sequence identity to SEQ ID NO: 1, 9, 16, 23, 30, 38, 46, 54, 61, 69, 75, 82, 89, 95, 103, 110, or 117.

32. A nucleic acid molecule comprising a polynucleotide encoding a trans-activating CRISPR RNA (tracrRNA) comprising a nucleotide sequence having at least 95% sequence identity to SEQ ID NO: 3, 11, 18, 25, 32, 40, 48, 56, 63, 71, 77, 84, 91, 97, 105, 112, or 119;

wherein a guide RNA comprising:

a) said tracrRNA; and b) a crRNA comprising a spacer sequence and a CRISPR repeat sequence, wherein said tracrRNA is capable of hybridizing with said CRISPR repeat sequence of said crRNA;

is capable of hybridizing to a target DNA sequence of a DNA molecule in a sequence specific manner through the spacer sequence of said crRNA when said guide RNA is bound to an RNA-guided nuclease (RGN) polypeptide, and wherein said polynucleotide encoding a tracrRNA is operably linked to a promoter heterologous to said polynucleotide.

33. A vector comprising the nucleic acid molecule of embodiment 32.

34. The vector of embodiment 33, wherein said vector further comprises a polynucleotide encoding said crRNA.

35. The vector of embodiment 34, wherein the CRISPR repeat sequence of said crRNA comprises a nucleotide sequence having at least 95% sequence identity to SEQ ID NO: 2, 10, 17, 24, 31, 39, 47, 55, 62, 70, 76, 83, 90, 96, 104, 111, or 118.

36. The vector of embodiment 34 or 35, wherein said polynucleotide encoding said crRNA and said polynucleotide encoding said tracrRNA are operably linked to the same promoter and are encoded as a single guide RNA.

37. The vector of embodiment 34 or 35, wherein said polynucleotide encoding said crRNA and said polynucleotide encoding said tracrRNA are operably linked to separate promoters.

38. The vector of any one of embodiments 33-37, wherein said vector further comprises a polynucleotide encoding said RGN polypeptide, wherein said RGN polypeptide comprises an amino acid sequence having at least 95% sequence identity to SEQ ID NO: 1, 9, 16, 23, 30, 38, 46, 54, 61, 69, 75, 82, 89, 95, 103, 110 or 117.

39. A system for binding a target DNA sequence of a DNA molecule, said system comprising:

a) one or more guide RNAs capable of hybridizing to said target DNA sequence or one or more polynucleotides comprising nucleotide sequences encoding the one or more guide RNAs (gRNAs); and b) an RNA-guided nuclease (RGN) polypeptide comprising an amino acid sequence having at least 95% sequence identity to SEQ ID NO: 1, 9, 16, 23, 30, 38, 46, 54, 61, 69, 75, 82, 89, 95, 103, 110, or 117; or a polynucleotide comprising a nucleotide sequence encoding the RGN polypeptide;

wherein said nucleotide sequences encoding the one or more guide RNAs and encoding the RGN polypeptide are each operably linked to a promoter heterologous to said nucleotide sequence; and wherein the one or more guide RNAs are capable of forming a complex with the RGN polypeptide, in order to direct said RGN polypeptide to bind to said target DNA sequence of the DNA molecule.

40. The system of embodiment 39, wherein said gRNA comprises a CRISPR repeat sequence comprising a nucleotide sequence having at least 95% sequence identity to SEQ ID NO: 2, 10, 17, 24, 31, 39, 47, 55, 62, 70, 76, 83, 90, 96, 104, 111, or 118.

41. The system of embodiment 39 or 40, wherein said gRNA comprises a tracrRNA.

42. The system of embodiment 41, wherein said tracrRNA comprises a nucleotide sequence having at least 95% sequence identity to SEQ ID NO: 3, 11, 18, 25, 32, 40, 48, 56, 63, 71, 77, 84, 91, 97, 105, 112, or 119.

43. The system of embodiment 41 or 42, wherein said gRNA is a single guide RNA (sgRNA).

44. The system of embodiment 41 or 42, wherein said gRNA is a dual-guide RNA.

45. The system of any one of embodiments 39-44, wherein said target DNA sequence is located adjacent to a protospacer adjacent motif (PAM).

46. The system of any one of embodiments 39-45, wherein the target DNA sequence is within a cell.

47. The system of embodiment 46, wherein the cell is a eukaryotic cell.

48. The system of embodiment 47, wherein the eukaryotic cell is a plant cell.

49. The system of embodiment 47, wherein the eukaryotic cell is a mammalian cell.

50. The system of embodiment 47, wherein the eukaryotic cell is an insect cell.

51. The system of embodiment 46, wherein the cell is a prokaryotic cell.

52. The system of any one of embodiments 39-51, wherein when transcribed the one or more guide RNAs is capable of hybridizing to the target DNA sequence and the guide RNA is capable of forming a complex with the RGN polypeptide to direct cleavage of the target DNA sequence.

53. The system of embodiment 52, wherein said RGN polypeptide is capable of generating a double-stranded break.

54. The system of embodiment 52, wherein said RGN polypeptide is capable of generating a single-stranded break.

55. The system of embodiment 52, wherein said RGN polypeptide is nuclease inactive.

56. The system of any one of embodiments 39-55, wherein the RGN polypeptide is operably linked to a base-editing polypeptide.

57. The system of embodiment 56, wherein the base-editing polypeptide is a deaminase.

58. The system of embodiment 57, wherein the deaminase is a cytidine deaminase or an adenosine deaminase.

59. The system of any one of embodiments 39-58, wherein the RGN polypeptide comprises one or more nuclear localization signals.

60. The system of any one of embodiments 39-59, wherein the RGN polypeptide is codon optimized for expression in a eukaryotic cell.

61. The system of any one of embodiments 39-60, wherein polynucleotides comprising the nucleotide sequences encoding the one or more guide RNAs and the polynucleotide comprising the nucleotide sequence encoding an RGN polypeptide are located on one vector.

62. The system of any one of embodiments 39-61, wherein said system further comprises one or more donor polynucleotides or one or more nucleotide sequences encoding the one or more donor polynucleotides.

63. A method for binding a target DNA sequence of a DNA molecule comprising delivering a system according to any one of embodiments 39-62, to said target DNA sequence or a cell comprising the target DNA sequence.

64. The method of embodiment 63, wherein said RGN polypeptide or said guide RNA further comprises a detectable label, thereby allowing for detection of said target DNA sequence.

65. The method of embodiment 63, wherein said guide RNA or said RGN polypeptide further comprises an expression modulator, thereby modulating expression of said target DNA sequence or a gene under transcriptional control by said target DNA sequence.

66. A method for cleaving or modifying a target DNA sequence of a DNA molecule comprising delivering a system according to any one of embodiments 39-62, to said target DNA sequence or a cell comprising the DNA molecule and cleavage or modification of said target DNA sequence occurs.

67. The method of embodiment 66, wherein said modified target DNA sequence comprises insertion of heterologous DNA into the target DNA sequence.

68. The method of embodiment 66, wherein said modified target DNA sequence comprises deletion of at least one nucleotide from the target DNA sequence.

69. The method of embodiment 66, wherein said modified target DNA sequence comprises mutation of at least one nucleotide in the target DNA sequence.

70. A method for binding a target DNA sequence of a DNA molecule, said method comprising:
  a) assembling an RNA-guided nuclease (RGN) ribonucleotide complex in vitro by combining:
    i) one or more guide RNAs capable of hybridizing to the target DNA sequence; and
    ii) an RGN polypeptide comprising an amino acid having at least 95% sequence identity to SEQ ID NO: 1, 9, 16, 23, 30, 38, 46, 54, 61, 69, 75, 82, 89, 95, 103, 110, or 117 under conditions suitable for formation of the RGN ribonucleotide complex; and
  b) contacting said target DNA sequence or a cell comprising said target DNA sequence with the in vitro-assembled RGN ribonucleotide complex;
  wherein the one or more guide RNAs hybridize to the target DNA sequence, thereby directing said RGN polypeptide to bind to said target DNA sequence.

71. The method of embodiment 70, wherein said RGN polypeptide or said guide RNA further comprises a detectable label, thereby allowing for detection of said target DNA sequence.

72. The method of embodiment 70, wherein said guide RNA or said RGN polypeptide further comprises an expression modulator, thereby allowing for the modulation of expression of said target DNA sequence.

73. A method for cleaving and/or modifying a target DNA sequence of a DNA molecule, comprising contacting the DNA molecule with:
  a) an RNA-guided nuclease (RGN) polypeptide, wherein said RGN comprises an amino acid having at least 95% sequence identity to SEQ ID NO: 1, 9, 16, 23, 30, 38, 46, 54, 61, 69, 75, 82, 89, 95, 103, 110, or 117; and
  b) one or more guide RNAs capable of targeting the RGN of (a) to the target DNA sequence;
  wherein the one or more guide RNAs hybridize to the target DNA sequence, thereby directing said RGN polypeptide to bind to said target DNA sequence and cleavage and/or modification of said target DNA sequence occurs.

74. The method of embodiment 73, wherein the cleavage by said RGN polypeptide generates a double-stranded break.

75. The method of embodiment 73, wherein the cleavage by said RGN polypeptide generates a single-stranded break.

76. The method of embodiment 73, wherein said RGN polypeptide is nuclease inactive.

77. The method of any one of embodiments 73-76, wherein said RGN polypeptide is operably linked to a base-editing polypeptide.

78. The method of embodiment 77, wherein said base-editing polypeptide comprises a deaminase. 79. The method of embodiment 78, wherein said deaminase is a cytidine deaminase or an adenosine deaminase.

80. The method of any one of embodiments 73-79, wherein said modified target DNA sequence comprises insertion of heterologous DNA into the target DNA sequence.

81. The method of any one of embodiments 73-79, wherein said modified target DNA sequence comprises deletion of at least one nucleotide from the target DNA sequence.

82. The method of any one of embodiments 73-79, wherein said modified target DNA sequence comprises mutation of at least one nucleotide in the target DNA sequence.

83. The method of any one of embodiments 70-82, wherein said gRNA comprises a CRISPR repeat sequence comprising a nucleotide sequence having at least 95% sequence identity to SEQ ID NO: 2, 10, 17, 24, 31, 39, 47, 55, 62, 70, 76, 83, 90, 96, 104, 111, or 118.

84. The method of any one of embodiments 70-83, wherein said gRNA comprises a tracrRNA.

85. The method of embodiment 84, wherein said tracrRNA comprises a nucleotide sequence having at least 95% sequence identity to SEQ ID NO: 3, 11, 18, 25, 32, 40, 48, 56, 63, 71, 77, 84, 91, 97, 105, 112, or 119.

86. The method of embodiment 84 or 85, wherein said gRNA is a single guide RNA (sgRNA).

87. The method of embodiment 84 or 85, wherein said gRNA is a dual-guide RNA.

88. The method of any one of embodiments 63-87, wherein said target DNA sequence is located adjacent to a protospacer adjacent motif (PAM).

89. The method of any one of embodiments 63-88, wherein the target DNA sequence is within a cell.

90. The method of embodiment 89, wherein the cell is a eukaryotic cell.

91. The method of embodiment 90, wherein the eukaryotic cell is a plant cell.

92. The method of embodiment 90, wherein the eukaryotic cell is a mammalian cell.

93. The method of embodiment 90, wherein the eukaryotic cell is an insect cell.

94. The method of embodiment 89, wherein the cell is a prokaryotic cell.

95. The method of any one of embodiments 89-94, further comprising culturing the cell under conditions in which the RGN polypeptide is expressed and cleaves the target DNA sequence to produce a DNA molecule comprising a modified DNA sequence; and selecting a cell comprising said modified target DNA sequence.

96. A cell comprising a modified target DNA sequence according to the method of embodiment 95.

97. The cell of embodiment 96, wherein the cell is a eukaryotic cell.

98. The cell of embodiment 97, wherein the eukaryotic cell is a plant cell.

99. A plant comprising the cell of embodiment 98.

100. A seed comprising the cell of embodiment 98.

101. The cell of embodiment 97, wherein the eukaryotic cell is a mammalian cell.

102. The cell of embodiment 98, wherein the eukaryotic cell is an insect cell.

103. The cell of embodiment 96, wherein the cell is a prokaryotic cell.

104. A method for producing a genetically modified cell with a correction in a causal mutation for a genetically inherited disease, the method comprising introducing into the cell:
  a) an RNA-guided nuclease (RGN) polypeptide, wherein the RGN polypeptide comprises an amino acid sequence having at least 95% sequence identity to SEQ ID NO: 1, 9, 16, 23, 30, 38, 46, 54, 61, 69, 75, 82, 89, 95, 103, 110, or 117; or a polynucleotide encoding said RGN polypeptide, wherein said polynucleotide encoding the RGN polypeptide is operably linked to a promoter to enable expression of the RGN polypeptide in the cell; and b) a guide RNA (gRNA), wherein the gRNA comprises a CRISPR repeat sequence comprising a nucleotide sequence having at least 95% sequence identity to SEQ ID NO: 2, 10, 17, 24, 31, 39, 47, 55, 62, 70, 76, 83, 90, 96, 104, 111, or 118, or a polynucleotide encoding said gRNA, wherein said polynucleotide encoding the gRNA is operably linked to a promoter to enable expression of the gRNA in the cell whereby the RGN and gRNA target to the genomic location of the causal mutation and modify the genomic sequence to remove the causal mutation.

105. The method of embodiment 104, wherein the RGN is operably linked to a base-editing polypeptide.

106. The method of embodiment 105, wherein the base-editing polypeptide is a deaminase.

107. The method of embodiment 106, wherein the deaminase is a cytidine deaminase or an adenosine deaminase.

108. The method of any one of embodiments 104-107, wherein the cell is an animal cell.

109. The method of any one of embodiments 104-107, wherein the cell is a mammalian cell.

110. The method of embodiment 108, wherein the cell is derived from a dog, cat, mouse, rat, rabbit, horse, cow, pig, or human.

111. The method of embodiment 108, wherein the genetically inherited disease is caused by a single nucleotide polymorphism.

112. The method of embodiment 111, wherein the genetically inherited disease is Hurler Syndrome.

113. The method of embodiment 112, wherein the gRNA further comprises a spacer sequence that targets a region proximal to the causal single nucleotide polymorphism.

114. A method for producing a genetically modified cell with a deletion in a disease-causing genomic region of instability, the method comprising introducing into the cell:

a) an RNA-guided nuclease (RGN) polypeptide, wherein the RGN polypeptide comprises an amino acid sequence having at least 95% sequence identity to SEQ ID NO: 1, 9, 16, 23, 30, 38, 46, 54, 61, 69, 75, 82, 89, 95, 103, 110, or 117; or a polynucleotide encoding said RGN polypeptide, wherein said polynucleotide encoding the RGN polypeptide is operably linked to a promoter to enable expression of the RGN polypeptide in the cell; and b) a guide RNA (gRNA), wherein the gRNA comprises a CRISPR repeat sequence comprising a nucleotide sequence having at least 95% sequence identity to SEQ ID NO: 2, 10, 17, 24, 31, 39, 47, 55, 62, 70, 76, 83, 90, 96, 104, 111, or 118, or a polynucleotide encoding said gRNA, wherein said polynucleotide encoding the gRNA is operably linked to a promoter to enable expression of the gRNA in the cell, and further wherein the gRNA comprises a spacer sequence that targets the 5' flank of the genomic region of instability; and c) a second guide RNA (gRNA), wherein the gRNA comprises a CRISPR repeat sequence comprising a nucleotide sequence having at least 95% sequence identity to SEQ ID NO: 2, 10, 17, 24, 31, 39, 47, 55, 62, 70, 76, 83, 90, 96, 104, 111, or 118, or a polynucleotide encoding said gRNA, wherein said polynucleotide encoding the gRNA is operably linked to a promoter to enable expression of the second gRNA in the cell, and further wherein said second gRNA comprises a spacer sequence that targets the 3' flank of the genomic region of instability;

whereby the RGN and the two gRNAs target to the genomic region of instability and at least a portion of the genomic region of instability is removed.

115. The method of embodiment 114, wherein the cell is an animal cell.

116. The method of embodiment 114, wherein the cell is a mammalian cell.

117. The method of embodiment 115, wherein the cell is derived from a dog, cat, mouse, rat, rabbit, horse, cow, pig, or human.

118. The method of embodiment 115, wherein the genetically inherited disease is Friedrich's Ataxia or Huntington's Disease.

119. The method of embodiment 118, wherein the first gRNA further comprises a spacer sequence that targets a region within or proximal to the genomic region of instability.

120. The method of embodiment 118, wherein the second gRNA further comprises a spacer sequence that targets a region within or proximal to genomic region of instability.

121. A method for producing a genetically modified mammalian hematopoietic progenitor cell having decreased BCL11A mRNA and protein expression, the method comprising introducing into an isolated human hematopoietic progenitor cell:

a) an RNA-guided nuclease (RGN) polypeptide, wherein the RGN polypeptide comprises an amino acid sequence having at least 95% sequence identity to SEQ ID NO: 1, 9, 16, 23, 30, 38, 46, 54, 61, 69, 75, 82, 89, 95, 103, 110, or 117; or a polynucleotide encoding said RGN polypeptide, wherein said polynucleotide encoding the RGN polypeptide is operably linked to a promoter to enable expression of the RGN polypeptide in the cell; and b) a guide RNA (gRNA), wherein the gRNA comprises a CRISPR repeat sequence comprising a nucleotide sequence having at least 95% sequence identity to SEQ ID NO: 2, 10, 17, 24, 31, 39, 47, 55, 62, 70, 76, 83, 90, 96, 104, 111, or 118, or a polynucleotide encoding said gRNA, wherein said polynucleotide encoding the gRNA is operably linked to a promoter to enable expression of the gRNA in the cell, whereby the RGN and gRNA are expressed in the cell and cleave at the BCL11A enhancer region, resulting in genetic modification of the human hematopoietic progenitor cell and reducing the mRNA and/or protein expression of BCL11A.

122. The method of embodiment 121, wherein the gRNA further comprises a spacer sequence that targets a region within or proximal to the BCL11A enhancer region.

123. The method of any one of embodiments 104-122, wherein the guide RNA comprises a tracrRNA comprising a nucleotide sequence having at least 95% sequence identity to SEQ ID NO: 3, 11, 18, 25, 32, 40, 48, 56, 63, 71, 77, 84, 91, 97, 105, 112, or 119.

124. A system for binding a target DNA sequence of a DNA molecule, said system comprising:

a) one or more guide RNAs capable of hybridizing to said target DNA sequence or one or more polynucleotides comprising one or more nucleotide sequences encoding the one or more guide RNAs (gRNAs); and b) an RNA-guided nuclease (RGN) polypeptide comprising an amino acid sequence having at least 95% sequence identity to SEQ ID NO: 1, 9, 16, 23, 30, 38, 46, 54, 61, 69, 75, 82, 89, 95, 103, 110, or 117;

wherein the one or more guide RNAs are capable of hybridizing to the target DNA sequence, and wherein the one or more guide RNAs are capable of forming a complex with the RGN polypeptide, in order to direct said RGN polypeptide to bind to said target DNA sequence of the DNA molecule.

125. The system of embodiment 124, wherein said RGN polypeptide is nuclease inactive or capable of functioning as a nickase.

126. The system of embodiment 124 or 125, wherein said RGN polypeptide is operably fused to a base-editing polypeptide.

127. The system of embodiment 126, wherein the base-editing polypeptide is a deaminase. 128. The system of embodiment 127, wherein the deaminase is a cytidine deaminase or an adenosine deaminase.

129. A method of detecting a target DNA sequence of a DNA molecule in a sample, the method comprising:

a) contacting the sample with:
   i) an RNA-guided nuclease (RGN) polypeptide comprising an amino acid sequence having at least 95% sequence identity to SEQ ID NO: 1, 9, 16, 23, 30, 38, 46, 54, 61, 69, 75, 82, 89, 95, 103, 110, 117, or 137, wherein said RGN polypeptide is capable of binding said target DNA sequence of a DNA molecule in an RNA-guided sequence specific manner when bound to a guide RNA capable of hybridizing to said target DNA sequence;
   ii) said guide RNA; and
   iii) a detector single-stranded DNA (ssDNA) that does not hybridize with the guide RNA; and b) measuring a detectable signal produced by cleavage of the detector ssDNA by the RGN, thereby detecting the target DNA.

130. The method of embodiment 129, wherein said sample comprises DNA molecules from a cell lysate.

131. The method of embodiment 129, wherein said sample comprises cells.

132. The method of embodiment 131, wherein said cells are eukaryotic cells.

133. The method of embodiment 129, wherein the DNA molecule comprising the target DNA sequence is produced by reverse-transcription of an RNA template molecule present in a sample comprising RNA.

134. The method of embodiment 133, wherein the RNA template molecule is an RNA virus.

135. The method of embodiment 134, wherein the RNA virus is a coronavirus.

136. The method of embodiment 135, wherein the coronavirus is a bat SARS-like coronavirus, SARS-CoV, or SARS-CoV-2.

137. The method of any one of embodiments 133-136, wherein the sample comprising RNA is derived from a sample comprising cells.

138. The method of any one of embodiments 129-137, wherein said detector ssDNA comprises a fluorophore/quencher pair.

139. The method of any one of embodiments 129-137, wherein said detector ssDNA comprises a fluorescence resonance energy transfer (FRET) pair.

140. The method of any one of embodiments 129-139, wherein said guide RNA comprises a CRISPR repeat sequence comprising a nucleotide sequence having at least 95% sequence identity to SEQ ID NO: 2, 10, 17, 24, 31, 39, 47, 55, 62, 70, 76, 83, 90, 96, 104, 111, 118, or 273.

141. The method of any one of embodiments 129-140, wherein said guide RNA comprises a tracrRNA.

142. The method of embodiment 141, wherein said tracrRNA comprises a nucleotide sequence having at least 95% sequence identity to SEQ ID NO: 3, 11, 18, 25, 32, 40, 48, 56, 63, 71, 77, 84, 91, 97, 105, 112, 119, or 274.

143. The method of embodiment 141 or 142, wherein said guide RNA is a single guide RNA.

144. The method of embodiment 141 or 142, wherein said guide RNA is a dual-guide RNA.

145. The method of any one of embodiments 129-144, wherein said method further comprises amplifying nucleic acids in the sample prior to or together with the contacting of step a).

146. The method of embodiment 145, wherein the amplification is of a DNA molecule produced by reverse transcription of an RNA molecule.

147. A kit for detecting a target DNA sequence of a DNA molecule in a sample, the kit comprising:

a) an RNA-guided nuclease (RGN) polypeptide comprising an amino acid sequence having at least 95% sequence identity to SEQ ID NO: 1, 9, 16, 23, 30, 38, 46, 54, 61, 69, 75, 82, 89, 95, 103, 110, 117, or 137, wherein said RGN polypeptide is capable of binding said target DNA sequence of a DNA molecule in an RNA-guided sequence specific manner when bound to a guide RNA capable of hybridizing to said target DNA sequence;

b) said guide RNA; and c) a detector single-stranded DNA (ssDNA) that does not hybridize with the guide RNA.

148. The kit of embodiment 147, wherein said detector ssDNA comprises a fluorophore/quencher pair.

149. The kit of embodiment 147, wherein said detector ssDNA comprises a fluorescence resonance energy transfer (FRET) pair.

150. The kit of any one of embodiments 147-149, wherein said guide RNA comprises a CRISPR repeat sequence comprising a nucleotide sequence having at least 95% sequence identity to SEQ ID NO: 2, 10, 17, 24, 31, 39, 47, 55, 62, 70, 76, 83, 90, 96, 104, 111, 118, or 273.

151. The kit of any one of embodiments 147-150, wherein said guide RNA comprises a tracrRNA.

152. The kit of embodiment 151, wherein said tracrRNA comprises a nucleotide sequence having at least 95% sequence identity to SEQ ID NO: 3, 11, 18, 25, 32, 40, 48, 56, 63, 71, 77, 84, 91, 97, 105, 112, 119, or 274.

153. The kit of embodiment 151 or 152, wherein said guide RNA is a single guide RNA.

154. The kit of embodiment 151 or 152, wherein said guide RNA is a dual-guide RNA.

155. A method of cleaving single-stranded DNAs, the method comprising contacting a population of nucleic acids, wherein said population comprises a DNA molecule comprising a target DNA sequence and a plurality of non-target ssDNAs with:

a) an RNA-guided nuclease (RGN) polypeptide comprising an amino acid sequence having at least 95% sequence identity to SEQ ID NO: 1, 9, 16, 23, 30, 38, 46, 54, 61, 69, 75, 82, 89, 95, 103, 110, 117, or 137, wherein said RGN polypeptide is capable of binding said target DNA sequence in an RNA-guided sequence specific manner when bound to a guide RNA capable of hybridizing to said target DNA sequence; and b) said guide RNA;

wherein the RGN polypeptide cleaves non-target ssDNAs of said plurality.

156. The method of embodiment 155, wherein said population of nucleic acids are within a cell lysate.

157. The method of embodiment 155 or 156, wherein said guide RNA comprises a CRISPR repeat sequence comprising a nucleotide sequence having at least 95% sequence identity to SEQ ID NO: 2, 10, 17, 24, 31, 39, 47, 55, 62, 70, 76, 83, 90, 96, 104, 111, 118, or 273.

158. The method of any one of embodiments 155-157, wherein said guide RNA comprises a tracrRNA.

159. The method of embodiment 158, wherein said tracrRNA comprises a nucleotide sequence having at least 95% sequence identity to SEQ ID NO: 3, 11, 18, 25, 32, 40, 48, 56, 63, 71, 77, 84, 91, 97, 105, 112, 119, or 274.

160. The method of embodiment 158 or 159, wherein said guide RNA is a single guide RNA.

161. The method of embodiment 158 or 159, wherein said guide RNA is a dual-guide RNA.

162. A nucleic acid molecule comprising a polynucleotide encoding a CRISPR RNA (crRNA), wherein said crRNA comprises a spacer sequence and a CRISPR repeat sequence, wherein said CRISPR repeat sequence comprises a nucleotide sequence having at least 95% sequence identity to SEQ ID NO: 240;

wherein a guide RNA comprising:

a) said crRNA; and optionally b) a trans-activating CRISPR RNA (tracrRNA) capable of hybridizing to said CRISPR repeat sequence of said crRNA;

is capable of hybridizing to a target DNA sequence of a DNA molecule in a sequence specific manner through the spacer sequence of said crRNA when said guide RNA is bound to an RNA-guided nuclease (RGN) polypeptide, and wherein said polynucleotide encoding a crRNA is operably linked to a promoter heterologous to said polynucleotide.

163. A vector comprising the nucleic acid molecule of embodiment 162.

164. The vector of embodiment 163, wherein said vector further comprises a polynucleotide encoding said tracrRNA.

165. The vector of embodiment 164, wherein said tracrRNA comprises a nucleotide sequence having at least 95% sequence identity to SEQ ID NO: 241.

166. The vector of embodiment 164 or 165, wherein said polynucleotide encoding said crRNA and said polynucleotide encoding said tracrRNA are operably linked to the same promoter and are encoded as a single guide RNA.

167. The vector of embodiment 164 or 165, wherein said polynucleotide encoding said crRNA and said polynucleotide encoding said tracrRNA are operably linked to separate promoters.

168. The vector of any one of embodiments 163-167, wherein said vector further comprises a polynucleotide encoding said RGN polypeptide, wherein said RGN polypeptide comprises an amino acid sequence having at least 95% sequence identity to SEQ ID NO: 235.

169. A nucleic acid molecule comprising a polynucleotide encoding a trans-activating CRISPR RNA (tracrRNA) comprising a nucleotide sequence having at least 95% sequence identity to SEQ ID NO: 241;

wherein a guide RNA comprising:

a) said tracrRNA; and b) a crRNA comprising a spacer sequence and a CRISPR repeat sequence, wherein said tracrRNA is capable of hybridizing with said CRISPR repeat sequence of said crRNA;

is capable of hybridizing to a target DNA sequence of a DNA molecule in a sequence specific manner through the spacer sequence of said crRNA when said guide RNA is bound to an RNA-guided nuclease (RGN) polypeptide, and wherein said polynucleotide encoding a tracrRNA is operably linked to a promoter heterologous to said polynucleotide.

170. A vector comprising the nucleic acid molecule of embodiment 169.

171. The vector of embodiment 170, wherein said vector further comprises a polynucleotide encoding said crRNA.

172. The vector of embodiment 171, wherein the CRISPR repeat sequence of said crRNA comprises a nucleotide sequence having at least 95% sequence identity to SEQ ID NO: 240.

173. The vector of embodiment 171 or 172, wherein said polynucleotide encoding said crRNA and said polynucleotide encoding said tracrRNA are operably linked to the same promoter and are encoded as a single guide RNA.

174. The vector of embodiment 171 or 172, wherein said polynucleotide encoding said crRNA and said polynucleotide encoding said tracrRNA are operably linked to separate promoters.

175. The vector of any one of embodiments 170-174, wherein said vector further comprises a polynucleotide encoding said RGN polypeptide, wherein said RGN polypeptide comprises an amino acid sequence having at least 95% sequence identity to SEQ ID NO: 235.

The following examples are offered by way of illustration and not by way of limitation.

EXAMPLES

Example 1. Identification of RNA-Guided Nucleases

Seventeen distinct CRISPR-associated RNA-guided nucleases (RGN's) were identified and are described in Table 1 below. Table 1 provides the name of each RGN, its amino acid sequence, the source from which it was derived, and processed crRNA and tracrRNA sequences (see Example 2 for methods of identification). Table 1 further provides a generic single guide RNA (sgRNA) sequence, where the poly-N indicates the location of the spacer sequence which determines the nucleic acid target sequence of the sgRNA. RGN systems APG05733.1, APG06207.1, APG01647.1, APG08032.1, APG02675.1, APG01405.1, APG06250.1, APG04293.1, and APG01308.1) had the conserved sequence in the base of the hairpin stem of the tracrRNA of UNANNA (SEQ ID NO: 8). For APG05712.1, the sequence in the same location is CNANNG (SEQ ID NO: 37). For APG01658.1, the sequence in the same location is CNANNU (SEQ ID NO: 45). For RGN systems APG06498.1 and APG06877.1, the conserved sequence in the base of the hairpin stem of the tracrRNA is UNANNG (SEQ ID NO: 53). For APG09882.1 and APG06646.1, the sequence in the same location is UNANNC (SEQ ID NO: 68). For APG09053.1, the sequence in the same location is CNANNU (SEQ ID NO: 102).

TABLE 1

| | | | crRNA repeat seq (SEQ ID NO) | tracrRNA (SEQ ID NO) | sgRNA (SEQ ID NO) |
|---|---|---|---|---|---|
| RGN ID | SEQ ID NO | Source | | | |
| APG05733.1 | 1 | *Bacillus* sp. | 2 | 3 | 4 |
| APG06207.1 | 9 | *Chryseobacterium* sp. | 10 | 11 | 12 |
| APG01647.1 | 16 | *Sphingobacterium* sp. | 17 | 18 | 19 |
| APG08032.1 | 23 | *Chryseobacterium* sp. | 24 | 25 | 26 |
| APG05712.1 | 30 | *Brucella* sp. | 31 | 32 | 33 |
| APG01658.1 | 38 | *Staphylococcus* sp. | 39 | 40 | 41 |
| APG06498.1 | 46 | *Bacillus* sp. | 47 | 48 | 49 |
| APG09106.1 | 54 | *Brevibacillus* sp. | 55 | 56 | 57 |
| APG09882.1 | 61 | *Enterococcus* sp. | 62 | 63 | 64 |
| APG02675.1 | 69 | *Sphingobacterium* sp. | 70 | 71 | 72 |
| APG01405.1 | 75 | *Chryseobacterium* sp. | 76 | 77 | 78 |
| APG06250.1 | 82 | *Chryseobacterium* sp. | 83 | 84 | 85 |
| APG06877.1 | 89 | *Bacillus* sp. | 90 | 91 | 92 |
| APG09053.1 | 95 | *Rhizobium* sp. | 96 | 97 | 98 |
| APG04293.1 | 103 | *Myroides* sp. | 104 | 105 | 106 |
| APG01308.1 | 110 | *Chryseobacterium* sp. | 111 | 112 | 113 |
| APG06646.1 | 117 | *Bacillus* sp. | 118 | 119 | 120 |

Example 2: Guide RNA Identification and sgRNA Construction

Cultures of bacteria that natively express the RNA-guided nuclease system under investigation were grown to mid-log phase (0D600 of 0.600), pelleted, and flash frozen. RNA was isolated from the pellets using a mirVANA miRNA Isolation Kit (Life Technologies, Carlsbad, CA), and sequencing libraries were prepared from the isolated RNA using an NEBNext Small RNA Library Prep kit (NEB, Beverly, MA). The library prep was fractionated on a 6% polyacrylamide gel to capture the RNA species less than 200 nt to detect crRNAs and tracrRNAs, respectively. Deep sequencing (75 bp paired-end) was performed on a Next Seq 500 (High Output kit) by a service provider (MoGene, St. Louis, MO). Reads were quality trimmed using Cutadapt and mapped to reference genomes using Bowtie2. A custom RNAseq pipeline was written in python to detect the crRNA and tracrRNA transcripts. Processed crRNA boundaries were determined by sequence coverage of the native repeat spacer array. The anti-repeat portion of the tracrRNA was identified using permissive BLASTn parameters. RNA sequencing depth confirmed the boundaries of the processed tracrRNA by identifying the transcript containing the anti-repeat. Manual curation of RNAs was performed using secondary structure prediction by NUPACK, an RNA folding software. sgRNA cassettes were prepared by DNA synthesis and were generally designed as follows (5'→3'): 20-30 bp spacer sequence, operably linked at its 3' end to the processed repeat portion of the crRNA, operably linked to a 4 bp noncomplementary linker (AAAG; SEQ ID NO: 123), operably linked at its 3' end to the processed tracrRNA. Other 4 bp noncomplementary linkers may also be used.

For in vitro assays, sgRNAs were synthesized by in vitro transcription of the sgRNA cassettes with a GeneArt™ Precision gRNA Synthesis Kit (ThermoFisher). Processed crRNA and tracrRNA sequences for each of the RGN polypeptides are identified and are set forth in Table 1. See below for the sgRNAs constructed for PAM libraries 1 and 2.

Example 3: Determination of PAM Requirements for Each RGN

PAM requirements for each RGN were determined using a PAM depletion assay essentially adapted from Kleinstiver et al. (2015) Nature 523:481-485 and Zetsche et al. (2015) Cell 163:759-771. Briefly, two plasmid libraries (L1 and L2) were generated in a pUC18 backbone (ampR), with each containing a distinct 30 bp protospacer (target) sequence flanked by 8 random nucleotides (i.e., the PAM region). The target sequence and flanking PAM region of library 1 and library 2 for each RGN are set forth in Table 2.

The libraries were separately electroporated into *E. coli* BL21(DE3) cells harboring pRSF-1b expression vectors containing an RGN of the invention (codon optimized for *E. coli*) along with a cognate sgRNA containing a spacer sequence corresponding to the protospacer in L1 or L2. Sufficient library plasmid was used in the transformation reaction to obtain $>10^6$ CFU. Both the RGN and sgRNA in the pRSF-1b backbone were under the control of T7 promoters. The transformation reaction was allowed to recover for 1 hr after which it was diluted into LB media containing carbenicillin and kanamycin and grown overnight. The following day the mixture was diluted into self-inducing Overnight Express™ Instant TB Medium (Millipore Sigma) to allow expression of the RGN and sgRNA, and grown for an additional 4 h or 20 h after which the cells were spun down and plasmid DNA was isolated with a Mini-prep kit (Qiagen, Germantown, MD). In the presence of the appropriate sgRNA, plasmids containing a PAM that is recognizable by the RGN will be cleaved resulting in their removal from the population. Plasmids containing PAMs that are not recognizable by the RGN, or that are transformed into bacteria not containing an appropriate sgRNA, will survive and replicate. The PAM and protospacer regions of uncleaved plasmids were PCR-amplified and prepared for sequencing following published protocols (16s-metagenomic library prep guide 15044223B, Illumina, San Diego, CA). Deep sequencing (75 bp single end reads) was performed on a MiSeq (Illumina) by a service provider (MoGene, St. Louis, MO). Typically, 1-4M reads were obtained per amplicon. PAM regions were extracted, counted, and normalized to total reads for each sample. PAMs that lead to plasmid cleavage were identified by being underrepresented when compared to controls (i.e., when the library is transformed into *E. coli* containing the RGN but lacking an appropriate sgRNA). To represent PAM requirements for a novel RGN, the depletion ratios (frequency in sample/ frequency in control) for all sequences in the region in question were converted to enrichment values with a –log base 2 transformation. Sufficient PAMs were defined as those with enrichment values >2.3 (which corresponds to depletion ratios <~0.2). PAMs above this threshold in both libraries were collected and used to generate web logos, which for example can be generated using a web-based service on the internet known as "weblogo". PAM sequences were identified and reported when there was a consistent pattern in the top enriched PAMs. A consensus PAM (having an enrichment factor (EF)>2.3) for each RGN is provided in Table 2. The PAM orientation is also indicated in Table 2. As noted elsewhere in this application, APG06646.1 and APG04293.1 nucleases do not possess PAM-interacting domains. The results in Table 2 show that they also do not possess the typical PAM requirement, which is 2-5 nucleotides. APG06646.1 and APG04293.1 were shown to have single nucleotide requirements for cleavage.

TABLE 2

| | PAM or PAM-like determination | | | |
|---|---|---|---|---|
| RGN ID | sgRNA L1 (SEQ ID NO) | sgRNA L2 (SEQ ID NO) | PAM (SEQ ID NO) | PAM orientation |
| APG05733.1 | 5 | 6 | 7 | 5'-target-PAM-3' |
| APG06207.1 | 13 | 14 | 15 | 5'-target-PAM-3' |
| APG01647.1 | 20 | 21 | 22 | 5'-target-PAM-3' |
| APG08032.1 | 27 | 28 | 29 | 5'-target-PAM-3' |
| APG05712.1 | 34 | 35 | 36 | 5'-target-PAM-3' |
| APG01658.1 | 42 | 43 | 44 | 5'-target-PAM-3' |
| APG06498.1 | 50 | 51 | 52 | 5'-target-PAM-3' |
| APG09106.1 | 58 | 59 | 60 | 5'-PAM-target-3' |
| APG09882.1 | 65 | 66 | 67 | 5'-target-PAM-3' |
| APG02675.1 | 73 | 74 | 15 | 5'-target-PAM-3' |
| APG01405.1 | 79 | 80 | 81 | 5'-target-PAM-3' |
| APG06250.1 | 86 | 87 | 88 | 5'-target-PAM-3' |
| APG06877.1 | 93 | 94 | 7 | 5'-target-PAM-3' |
| APG09053.1 | 99 | 100 | 101 | 5'-target-PAM-3' |
| APG04293.1 | 107 | 108 | 109 | 5'-target-PAM-3' |
| APG01308.1 | 114 | 115 | 116 | 5'-target-PAM-3' |
| APG06646.1 | 121 | 122 | 109 | 5'-target-PAM-3' |

Example 4: Engineering the Guide RNA to Increase Nuclease Activity 4.1 RGNs APG09748 and APG09106.1

For RGNs APG09748 (set forth as SEQ ID NO: 137, and APG09748 crRNA repeat sequence, tracrRNA sequence, and generic sgRNA sequence are set forth as SEQ ID NOs: 273, 274, and 275, respectively; all sequences are described in International Appl. No. PCT/US2019/068079, which is incorporated by reference in its entirety) and APG09106.1, which have very high sequence identity and have the same PAM, RNA folding predictions were used to determine regions in the guide RNA that can be altered to optimize nuclease activity. The stability of the crRNA:tracrRNA base pairing in the repeat:antirepeat region was increased by shortening the repeat:antirepeat region, adding G-C base pairs, and removing G-U wobble pairs. "Optimized" guide variants were tested and compared to the wild-type gRNA using the RGN APG09748 in in vitro cleavage assays.

To produce RGNs for RNP formation, expression plasmids containing an RGN fused to a C-terminal His6 (SEQ ID NO: 276) or His10 (SEQ ID NO: 277) tag were constructed and transformed into BL21 (DE3) strains of *E. coli*. Expression was performed using Magic Media (Thermo Fisher) supplemented with 50 μg/mL kanamycin. After lysis and clarification, the protein was purified by immobilized metal affinity chromatography and quantified using the Qubit protein quantitation kit (Thermo Fisher) or by UV-vis using a calculated extinction coefficient.

Ribonucleoprotein (RNP) was prepared by incubating the purified RGN with sgRNA at a ~2:1 ratio for 20 min at room temperature. For in vitro cleavage reactions, RNPs were incubated with plasmids or linear dsDNA containing the targeted protospacer flanked by a preferred PAM sequence for >30 min at room temperature. Two target nucleic acid sequences within the TRAC locus, TRAC11 (SEQ ID NO: 278) and TRAC14 (SEQ ID NO: 279), were tested. gRNAs were assayed both for targeted activity with the correct target nucleic acid sequence (for example, the gRNA has TRAC11 spacer sequence and the assayed target is TRAC11) and without the correct target nucleic acid sequence (for example, the gRNA has TRAC11 spacer sequence and the assayed target is TRAC14). Activity determined by plasmid cleavage is assessed by agarose gel electrophoresis. Results are shown in Table 3. Guide variants are listed as SEQ ID NOs: 280-283, and are provided with spacer sequences. These guide sequences use a noncomplementary nucleotide linker of AAAA (SEQ ID NO: 284). The optimized gRNA (SEQ ID NO: 285; poly-N indicates location of spacer sequence), with increased repeat:antirepeat binding, has optimized tracrRNA (SEQ ID NO: 286) and optimized crRNA (SEQ ID NO: 287) components. The optimized guide variant was able to cleave two loci where previously no cleavage was detected using the wild-type guide RNA. Through optimization of hybridization in the repeat:antirepeat region, in vitro cleavage of APG09748 increased from 0% cleavage to 100% cleavage for multiple targets in the TRAC locus.

TABLE 3

| | Editing efficiency of APG09748 with engineered guide variants | | | | | |
|---|---|---|---|---|---|---|
| gRNA variant | Guide | Assayed | Gel 1 - 2 μL load | | Gel 2 - 1 μL load | |
| (SEQ ID NO.) | Design | Target | % intact | % cleaved | % intact | % cleaved |
| 280 | Optimized | TRAC11 | 68 | 32 | 57 | 43 |
| 280 | Optimized | TRAC14 | 100 | 0 | 100 | 0 |
| 281 | Optimized | TRAC11 | 100 | 0 | 100 | 0 |
| 281 | Optimized | TRAC14 | 70 | 30 | 69 | 31 |
| 282 | WT | TRAC11 | 100 | 0 | 100 | 0 |
| 282 | WT | TRAC14 | 100 | 0 | 100 | 0 |
| 283 | WT | TRAC11 | 100 | 0 | 100 | 0 |
| 283 | WT | TRAC14 | 100 | 0 | 100 | 0 |
| None | | TRAC11 | 100 | 0 | 100 | 0 |
| None | | TRAC14 | 100 | 0 | 100 | 0 |

Additional optimized gRNA variants were designed and assayed. Further, different lengths of spacer sequence were also tested to determine how spacer length might affect cleavage efficiency. The sgRNA outside of the spacer sequence is referred to as the "backbone" in this assay. In Table 4, these are denoted as "WT" (SEQ ID NO: 288, the wild type sequence), and the three optimized sgRNAs: V1 (SEQ ID NO: 289), V2 (SEQ ID NO: 290) and V3 (SEQ ID NO: 291). All of these sequences have a poly-N to indicate the location of the spacer sequence. Guides were expressed as sgRNAs by in vitro transcription (IVT). Compared to the wild-type sgRNA backbone, V1 is 87.8% identical, V2 is 92.4% identical, and V3 is 85.5% identical. Synthetic tracrRNA:crRNA duplexes ("synthetic") representing dual-guide RNAs but otherwise similar to the wild type and optimized sgRNAs recited above were also produced and tested.

For this set of assays, RGN APG09106.1 was used; otherwise, methods for in vitro cleavage reactions were similar to what is described above. The targeted nucleic acid sequences were Target 1 (SEQ ID NO: 292) and Target 2 (SEQ ID NO: 293). The results are shown in Table 4.

TABLE 4

Editing efficiency of APG09106.1 with engineered guide variants

| RNA Source | Target | Spacer Length | Backbone | Spacer SEQ ID NO. | Cleavage % |
|---|---|---|---|---|---|
| Synthetic | 2 | 18 | WT | 294 | 12.3 |
| Synthetic | 1 | 20 | WT | 295 | 0 |
| Synthetic | 2 | 20 | WT | 296 | 55.0 |
| Synthetic | 1 | 25 | WT | 297 | 0 |
| Synthetic | 2 | 25 | WT | 298 | 61.4 |
| IVT | 2 | 25 | VI | 299 | 1.1 |
| IVT | 2 | 25 | V2 | 300 | 0.9 |
| IVT | 2 | 25 | V3 | 301 | 0.7 |
| IVT | 2 | 20 | V3 | 302 | 21.0 |
| IVT | 1 | 25 | V3 | 303 | 2.0 |

4.2 RGN APG07433.1

RNA folding predictions were used to determine regions in the guide RNA for APG07433.1 (set forth as SEQ ID NO: 235 and described in U.S. Appl. Publ. No. 2019/0367949 and International Appl. Publ. No. WO 2019/236566, each of which is herein incorporated by reference in its entirety) that can be altered to optimize nuclease activity and shorten guide RNA for packaging into viral vectors. Two areas were identified as potential locations to make alterations: the repeat:antirepeat pairing between the crRNA and tracrRNA region and the terminal hairpins in the tracrRNA. The repeat:antirepeat region was truncated to 7 (APG07433.1-7 bp, SEQ ID NOs: 238 and 239), 13 (APG07433.1-13 bp, SEQ ID NOs: 250 and 251), and 15 base pairs in length (APG07433.1-15 bp, SEQ ID NOs: 242 and 243). Additionally, a fourth variant was tested that altered the sequence of the repeat:antirepeat region and reduced the pairing to 11 basepairs in length (APG07433.1-11 bp-syn, SEQ ID NOs: 240 and 241), with an introduction of a smaller RNA bulge compared to the wildtype guide. Truncations were also made to the terminal hairpins in the tracrRNA, including a reduction of the native sequence to 40 (APG07433.1-40ntTHP, SEQ ID NOs: 254 and 255) and 42 (APG07433.1-42ntTHP, SEQ ID NOs: 244 and 245) nucleotides in length. Altered stem-loops were designed to shorten these to 35 (APG07433.1-35ntTHP-syn, SEQ ID NOs: 248 and 249) and 39 (APG07433.1-39ntTHP-syn, SEQ ID NOs: 246 and 247) nucleotides as well. One guide combined the 13-base-pair shortened repeat:antirepeat region and the 42-nucleo-tide shortened terminal hairpin (APG07433.1-13bp42ntTH, SEQ ID NOs: 252 and 253). The effects of spacer length on cleavage was also tested. Spacer lengths of 25 (APG07433.1-native[25], SEQ ID NOs: 236 and 237; spacer sequence is set forth as SEQ ID NO: 271) and 18 (APG07433.1-native[18], SEQ ID NOs: 256 and 257; spacer sequence is set forth as SEQ ID NO: 272) nucleotides on the wild type guide RNA backbone were also tested.

The following dual guide RNAs were prepared by anneal-ing crRNAs and tracrRNAs by preparing a solution con-taining 20 μM crRNA and 10 μM tracrRNA in annealing buffer (Synthego), then heating to 78° C. for 10 min and then at 37° C. for 30 min. RNPs were formed by incubation with purified APG07433.1 protein at 0.5 μM and the dual guide RNA at 1 μM in phosphate buffered saline for 20 minutes. The guide RNAs used in this experiment are shown in Table 5.

TABLE 5

Dual guide RNAs

| Dual gRNA Name | crRNA SEQ ID NO | tracrRNA SEQ ID NO |
|---|---|---|
| APG07433.1-native[25] | 236 | 237 |
| APG07433.1-7bp | 238 | 239 |
| APG07433.1-11bp-syn | 240 | 241 |
| APG07433.1-15bp | 242 | 243 |
| APG07433.1-42ntTHP | 244 | 245 |
| APG07433.1-39ntTHP-syn | 246 | 247 |
| APG07433.1-35ntTHP-syn | 248 | 249 |
| APG07433.1-13bp | 250 | 251 |
| APG07433.1-13bp42ntTH | 252 | 253 |
| APG07433.1-40ntTHP | 254 | 255 |
| APG07433.1-native[18] | 256 | 257 |
| APG07433.1cr-13bp tr-35ntTHP | 258 | 259 |

These RNPs were incubated with a PCR product contain-ing the appropriate target sequence (SEQ ID NO: 260) produced by amplification using FAM and Cy3 labeled primers, to facilitate accurate and sensitive quantitation of cleavage product. The reactions contained 250 nM RNP, produced as above, and 150 nM of the FAM and Cy3 labeled PCR product in 1× Cutsmart buffer (New England Biolabs). The reaction was allowed to proceed for 15 min at 37° C. and was terminated by adding RNase A to 0.1 mg/mL and EDTA to 45 mM. The quenched reaction was heated at 50° C. for 30 min and 95° C. for 5 minutes. The samples were then analyzed using native acrylamide gel electrophoresis on a 5% TBE gel (Bio-rad). These were imaged on a ChemiDoc MP imager. Each of the two dyes could be used for quan-titation, and each sample was performed in duplicate. The results of this experiment are shown in Table 6.

TABLE 6

Cleavage results

| | % Cleaved | | | | |
| | Cy3 Channel | | FAM channel | | Overall |
| RNP | Rep 1 | Rep 2 | Rep 1 | Rep 2 | average |
|---|---|---|---|---|---|
| Nuclease only (no guide) | 0 | 0 | 0 | 0 | 0 |
| APG07433.1-native [25] | 66.41 | 61.16 | 68.81 | 56.85 | 63.3 |
| APG07433.1-7bp | 0 | 3.38 | 2.83 | 0 | 1.6 |
| APG07433.1-11bp-syn | 66.33 | 76.38 | 66.73 | 68 | 69.4 |
| APG07433.1-15bp | 50.7 | 65.61 | 54.62 | 59.95 | 57.7 |
| APG07433.1-42ntTHP | 44.81 | 50.59 | 48.84 | 51.77 | 49.0 |
| APG07433.1-39ntTHP-syn | 19.16 | 32.88 | 24.91 | 33.43 | 27.6 |
| APG07433.1-35ntTHP-syn | 26.77 | 38.61 | 32.09 | 40.2 | 34.4 |
| APG07433.1-13bp | 44.36 | 33.03 | 42.93 | 35.22 | 38.9 |
| APG07433.1-13bp42ntTHP | 35.91 | 36.74 | 33.84 | 39.2 | 36.4 |
| APG07433.1-40ntTHP | 44.52 | 57.14 | 48.34 | 57.84 | 52.0 |
| APG07433.1-native [18] | 11.1 | 9.76 | 12.93 | 13.24 | 11.8 |
| APG07433.1cr-13bp tr-35ntTHP | 10.66 | 12.25 | 12.65 | 13.54 | 12.3 |

This analysis demonstrates that the native backbone out-performs most of the shortened variants, and a variant containing a shortened target sequence (APG07433.1-native [18], SEQ ID NOs: 256 and 257). Of the shortened backbone sequences, that with the highest level of cleavage is the sequence named APG07433.1-11 bp-syn, which comprises a 25 nt targeting sequence (spacer; SEQ ID NO: 271), SEQ ID NO: 240 for the crRNA and SEQ ID NO: 241 as the tracrRNA. This guide variant included an altered repeat: antirepeat stem loop with an engineered bulge in the stem.

Example 5: Demonstration of Gene Editing Activity in Mammalian Cells

RGN expression cassettes were produced and introduced into vectors for mammalian expression. RGNs APG09748, APG09106.1, APG05712.1, APG01658.1, APG05733.1, APG06498.1, APG06646.1, APG09882.1, APG01405.1, and APG01308.1 were each codon-optimized for mammalian expression (SEQ ID NOs: 304, 305, and 411-418, respectively), and the expressed proteins were operably fused at the N-terminal end to an SV40 nuclear localization sequence (NLS; SEQ ID NO: 125) and to 3×FLAG tags (SEQ ID NO: 126), and operably fused at the C-terminal end to nucleoplasmin NLS sequences (SEQ ID NO: 127). Two copies of the NLS sequence were used, operably fused in tandem. Each expression cassette was under control of a cytomegalovirus (CMV) promoter (SEQ ID NO: 306). It is known in the art that the CMV transcription enhancer (SEQ ID NO: 307) may also be included in constructs comprising the CMV promoter. Guide RNA expression constructs encoding a single gRNA each under the control of a human RNA polymerase III U6 promoter (SEQ ID NO: 308) were produced and introduced into an expression vector. Guides targeted regions of selected genes, including RelA, AurkB, GAPDH, LINC01509, HBB, CFTR, HPRT1, TRA, EMX1, and VEGFA, as shown in Table 7. For RNA-guided nuclease APG09106.1, specific residues were mutated to increase nuclease activity of the protein, specifically the T849 residue of APG09106 was mutated to arginine (SEQ ID NO: 309). This point mutation increased editing rates in mammalian cells.

The constructs described above were introduced into mammalian cells. One day prior to transfection, 1×10⁵HEK293T cells (Sigma) were plated in 24-well dishes in Dulbecco's modified Eagle medium (DMEM) plus 10% (vol/vol) fetal bovine serum (Gibco) and 1% Penicillin-Streptomycin (Gibco). The next day when the cells were at 50-60% confluency, 500 ng of a RGN expression plasmid plus 500 ng of a single gRNA expression plasmid were co-transfected using 1.5 µL, of Lipofectamine 3000 (Thermo Scientific) per well, following the manufacturer's instructions. After 48 hours of growth, total genomic DNA was harvested using a genomic DNA isolation kit (Machery-Nagel) according to the manufacturer's instructions.

The total genomic DNA was then analyzed to determine the rate of editing in the targeted gene. Oligonucleotides were produced to be used for PCR amplification and subsequent analysis of the amplified genomic target site (SEQ ID NOs: 310 and 311). All PCR reactions were performed using 10 µL, of 2× Master Mix Phusion High-Fidelity DNA polymerase (Thermo Scientific) in a 20 µL reaction including 0.5 µM of each primer. Large genomic regions encompassing each target gene were first amplified using PCR #1 primers (SEQ ID NOs: 310 and 311), using a program of: 98° C., 1 min; 30 cycles of [98° C., 10 sec; 62° C., 15 sec; 72° C., 5 min]; 72° C., 5 min; 12° C., forever.

One microliter of this PCR reaction was then further amplified using primers specific for each guide (PCR #2 primers; SEQ ID NOs: 365-370), using a program of: 98° C., 1 min; 35 cycles of [98° C., 10 sec; 67° C., 15 sec; 72° C., 30 sec]; 72° C., 5 min; 12° C., forever. Primers for PCR #2 include Nextera Read 1 and Read 2 Transposase Adapter overhang sequences for Illumina sequencing.

Following the second PCR amplification, DNA was cleaned using a PCR cleanup kit (Zymo) according to the manufacturer's instructions and eluted in water. 200-500 ng of purified PCR #2 product was combined with 2 µL, of 10×NEB Buffer 2 and water in a 20 µL, reaction and annealed to form heteroduplex DNA using a program of: 95° C., 5 min; 95-85° C., cooled at a rate of 2° C./sec; 85-25° C., cooled at a rate of 0.1° C./sec.; 12° C., forever. Following annealing, 5 µL, of DNA was removed as a no enzyme control, and 1 µL of T7 Endonuclease I (NEB) was added and the reaction incubated at 37° C. for 1 hr. After incubation, 5× FlashGel loading dye (Lonza) was added and 5 µL, of each reaction and controls were analyzed by a 2.2% agarose FlashGel (Lonza) using gel electrophoresis. Following visualization of the gel, the percentage of non-homologous end joining (NHEJ) was determined using the following equation: % NHEJ events=100×[1−(1−fraction cleaved) (½)], where (fraction cleaved) is defined as: (density of digested products)/(density of digested products+undigested parental band).

For some samples, SURVEYOR® was used to analyze the results following expression in mammalian cells. Cells were incubated at 37° C. for 72 h post-transfection before genomic DNA extraction. Genomic DNA was extracted using the QuickExtract DNA Extraction Solution (Epicentre) following the manufacturer's protocol. The genomic region flanking the RGN target site was PCR amplified, and products were purified using QiaQuick Spin Column (Qiagen) following the manufacturer's protocol. 200-500 ng total of the purified PCR products were mixed with 1 µl 10× Taq DNA Polymerase PCR buffer (Enzymatics) and ultra-pure water to a final volume of 10 µl, and subjected to a re-annealing process to enable heteroduplex formation: 95° C. for 10 min, 95° C. to 85° C. ramping at −2° C./s, 85° C. to 25° C. at −0.25° C./s, and 25° C. hold for 1 min.

After reannealing, products were treated with SURVEYOR® nuclease and SURVEYOR® enhancer S (Integrated DNA Technologies) following the manufacturer's recommended protocol and analyzed on 4-20% Novex TBE polyacrylamide gels (Life Technologies). Gels were stained with SYBR Gold DNA stain (Life Technologies) for 10 min and imaged with a Gel Doc gel imaging system (Bio-rad). Quantification was based on relative band intensities. Indel percentage was determined by the formula, 100×(1−(1−(b+c)/(a+b+c))½), where a is the integrated intensity of the undigested PCR product, and b and c are the integrated intensities of each cleavage product.

Additionally, products from PCR #2 containing Illumina overhang sequences underwent library preparation following the Illumina 16S Metagenomic Sequencing Library protocol. Deep sequencing was performed on an Illumina Mi-Seq platform by a service provider (MOGene). Typically, 200,000 of 250 bp paired-end reads (2×100,000 reads) are generated per amplicon. The reads were analyzed using CRISPResso (Pinello, et al. 2016 Nature Biotech, 34:695-697) to calculate the rates of editing. Output alignments were hand-curated to confirm insertion and deletion sites as well as identify microhomology sites at the recombination sites. The overall rates of editing, as well as the deletion rate and insertion rate in each sample, are shown in Table 7. All experiments were performed in human cells. The "target" is the targeted sequence within the gene target. For each target sequence, the guide RNA comprised the complementary RNA spacer sequence and the appropriate sgRNA depending on the RGN used. A selected breakdown of experiments by guide RNA is shown in Tables 8.1 and 8.2.

TABLE 7

| | | | | Overall | | |
| RGN | Gene Target | Guide RNA (SEQ ID NO.) | Target (SEQ ID NO.) | Editing Rate | Deletion Rate | Insertion Rate |
| --- | --- | --- | --- | --- | --- | --- |
| APG09106.1 | AurkB | 316 | 314 | 0.55% | 100% | |
| APG09106.1 | AurkB | 312 | 315 | 0.60% | 54% | 46% |
| APG09106.1 T849R | AurkB | 316 | 314 | 2.97% | 98% | 2.00% |
| APG09106.1 T849R | AurkB | 312 | 315 | 2.36% | 100% | |
| APG05712.1 | RelA | 419 | 482 | 0.36% | 72.33% | 27.67% |
| APG05712.1 | AurkB | 420 | 483 | 1.39% | 25.94% | 75.12% |
| APG05712.1 | RelA | 421 | 484 | 1.04% | 32.10% | 70.33% |
| APG05712.1 | RelA | 422 | 485 | 0.28% | 64.13% | 35.87% |
| APG01658.1 | RelA | 423 | 486 | 10.03% | 70.66% | 29.33% |
| APG01658.1 | GAPDH | 424 | 487 | 5.60% | 76.96% | 25.97% |
| APG01658.1 | LINC01509 | 425 | 488 | 9.87% | 75.10% | 26.61% |
| APG01658.1 | HBB | 426 | 489 | 0.42% | 63.86% | 36.13% |
| APG01658.1 | CFTR | 427 | 490 | 6.06% | 75.42% | 27.86% |
| APG01658.1 | AurkB | 428 | 491 | 13.07% | 88.02% | 13.14% |
| APG05733.1 | HPRT1 | 429 | 492 | 0.36% | | 100% |
| APG05733.1 | AurkB | 430 | 493 | 5.01% | 86.40% | 13.60% |
| APG05733.1 | RelA | 431 | 494 | 0.76% | | 100% |
| APG05733.1 | HPRT1 | 432 | 495 | 0.17% | 38.42% | 61.58% |
| APG05733.1 | RelA | 433 | 496 | 0.96% | 77.52% | 22.48% |
| APG06498.1 | TRA | 434 | 497 | 35.35% | 92.25% | 8.29% |
| APG06498.1 | TRA | 435 | 498 | 21.04% | 84.87% | 16.34% |
| APG06498.1 | TRA | 436 | 499 | 10.16% | 89.44% | 10.69% |
| APG06498.1 | TRA | 437 | 500 | 13.21% | 87.24% | 15.00% |
| APG06498.1 | TRA | 438 | 501 | 13.56% | 86.73% | 13.66% |
| APG06498.1 | TRA | 439 | 502 | 9.62% | 95.85% | 19.90% |
| APG06498.1 | TRA | 440 | 503 | 1.51% | 75.89% | 24% |
| APG06498.1 | TRA | 441 | 504 | 2.63% | 88.81% | 11.76% |
| APG06498.1 | TRA | 442 | 505 | 4.27% | 52.09% | 47.90% |
| APG06646.1 | TRA | 443 | 497 | 0.33% | 0% | 100% |
| APG06646.1 | VEGFA | 444 | 506 | 4.52% | 40.83% | 63.79% |
| APG06646.1 | AurkB | 445 | 507 | 0.66% | 69.38% | 30.62% |
| APG06646.1 | AurkB | 446 | 508 | 6.55% | 79.97% | 20.37% |
| APG06646.1 | TRA | 447 | 509 | 2.47% | 73.40% | 40.81% |
| APG06646.1 | TRA | 448 | 510 | 0.14% | 34.46% | 65.55% |
| APG06646.1 | TRA | 449 | 511 | 0.61% | 0% | 100% |
| APG06646.1 | AurkB | 450 | 493 | 7.94% | 67.95% | 32.40% |
| APG06646.1 | TRA | 451 | 512 | 7.03% | 86.95% | 14.03% |
| APG06646.1 | TRA | 452 | 513 | 0.50% | 21.80% | 78.10% |
| APG06646.1 | TRA | 453 | 514 | 3.53% | 86.42% | 16.28% |
| APG06646.1 | RelA | 454 | 515 | 6.22% | 80.39% | 45.34% |
| APG06646.1 | TRA | 455 | 516 | 0.38% | 0% | 100% |
| APG06646.1 | TRA | 456 | 517 | 0.34% | 66.76% | 48.22% |
| APG06646.1 | RelA | 457 | 518 | 3.78% | 75.25% | 67.90% |
| APG06646.1 | TRA | 458 | 519 | 0.42% | 69.61% | 30.39% |
| APG06646.1 | TRA | 459 | 520 | 0.08% | 100.00% | 0.00% |
| APG06646.1 | AurkB | 460 | 521 | 1.09% | 30.18% | 69.81% |
| APG06646.1 | AurkB | 461 | 522 | 0.28% | 86.60% | 21.78% |
| APG06646.1 | AurkB | 462 | 523 | 10.92% | 78.87% | 22.05% |
| APG06646.1 | TRA | 463 | 504 | 0.08% | 0% | 100% |
| APG06646.1 | TRA | 464 | 505 | 2.84% | 38.26% | 61.47% |
| APG06646.1 | TRA | 465 | 524 | 0.43% | 71.67% | 28.33% |
| APG06646.1 | TRA | 466 | 525 | 0.03% | 0.00% | 100.00% |
| APG06646.1 | TRA | 467 | 526 | 0.08% | 100% | 0% |
| APG09882.1 | RelA | 468 | 482 | 0.32% | 100.00% | 0.00% |
| APG09882.1 | EMX1 | 469 | 527 | 12.84% | 82.46% | 17.79% |
| APG09882.1 | VEGFA | 470 | 528 | 14.76% | 92.56% | 7.77% |
| APG09882.1 | TRA | 471 | 529 | 14.66% | 94.19% | 7.33% |
| APG09882.1 | TRA | 472 | 530 | 7.84% | 95.07% | 5.75% |
| APG09882.1 | VEGFA | 473 | 531 | 24.45% | 88.96% | 11.57% |
| APG09882.1 | TRA | 474 | 532 | 14.43% | 90.24% | 10.96% |
| APG01405.1 | RelA | 475 | 482 | 0.06% | 0% | 100% |
| APG01405.1 | AurkB | 476 | 533 | 6.81% | 80.58% | 20.27% |
| APG01405.1 | AurkB | 477 | 534 | 0.54% | 33.83% | 66.16% |
| APG01405.1 | HPRT1 | 478 | 535 | 1.07% | 42.14% | 57.87% |
| APG01405.1 | RelA | 479 | 484 | 0.55% | 2.07% | 97.93% |
| APG01308.1 | HPRT1 | 480 | 536 | 1.19% | 80.57% | 19.43% |
| APG01308.1 | AurkB | 481 | 537 | 0.90% | 94.97% | 6.46% |

Specific insertions and deletions for respective guides are shown in Tables 8.1 and 8.2. In these tables, the target sequence is identified by bold upper case letters. The 8mer PAM regions are double underlined, with the main recognized nucleotides in bold. Insertions are identified by lowercase letters. Deletions are indicated with dashes (---). The INDEL location is calculated from the PAM proximal edge of the target sequence, with the edge being location 0. The location is positive (+) if the location is on the target side of the edge; the location is negative (−) if the location is on the PAM side of the edge.

TABLE 8.1

| Edited target sequence | # Reads | % Reads | % of INDELs | Type | INDEL Location | Size |
|---|---|---|---|---|---|---|
| Specific insertions and deletions for Guide 831 using RGN APG09106.1 | | | | | | |
| GTCTGATTGCCTGTCGTTGCCCCTCCCAGATCAT GGAGGAGTTGGCAGA (wild type; SEQ ID NO: 316) | 92294 | 99.40 | | | | |
| GTCTGATTGCCTGTCGTTGCCCCTCCCA------ --AGGAGTTGGCAGA (SEQ ID NO: 317) | 263 | 0.28 | 54.22 | Deletion | +19 | 8 |
| GTCTGATTGCCTGTCGTTGCCCctaagtgtatta agcattgtctcagagattttGGAGGAGTTGGCAG A (SEQ ID NO: 318) | 222 | 0.24 | 45.77 | Insertion | +13 | 20 |

TABLE 8.2

| Edited target sequence | # Reads | % Reads | % of INDELs | Type | INDEL Location | Size |
|---|---|---|---|---|---|---|
| Specific insertions and deletions for Guide 831 using APG09106.1 T849R | | | | | | |
| GTCTGATTGCCTGTCGTTGCCCCTCCCAGATCAT GGAGGAGTTGGCAGA (wild type; SEQ ID NO: 316) | 189881 | 97.64 | | | | |
| GTCTGATTGCCCTGTCGTTGCCCC---------- TGGAGGAGTTGGCAGA (SEQ ID NO: 319) | 602 | 0.309 | 13.129 | Deletion | +14 | 10 |
| GTCTGATTGCCTGTCGTTGCCCCTCCCAGATC- GGAGGAGTTGGCAGA (SEQ ID NO: 320) | 394 | 0.202 | 8.593 | Deletion | +23 | 2 |
| GTCTGATTGCCTGTCGTTGCCCCTCCCAGAT--- --AGGAGTTGGCAGA (SEQ ID NO: 321) | 399 | 0.205 | 8.702 | Deletion | +22 | 5 |
| GTCTGATTGCCTGTCGTTGCCCaTC-------- TG GGAGTTGGCAGA (SEQ ID NO: 322) | 379 | 0.194 | 8.266 | Deletion & Mutation | +16 | 10 |
| GTCTGATTGCCTGTCGTTGCCCCTC-------- TGGAGGAGTTGGCAGA (SEQ ID NO: 323) | 350 | 0.179 | 7.633 | Deletion | +16 | 8 |
| GTCTGAT------------------------ TGGAGGAGTTGGCAGA (SEQ ID NO: 324) | 309 | 0.158 | 6.739 | Deletion | −1 | 26 |
| GTCTGATTGCCTGTCGTTGCCCCTC--------- GGAGGAGTTGGCAGA (SEQ ID NO: 325) | 280 | 0.143 | 6.106 | Deletion | +16 | 9 |
| GTCTGATTGCCTGTCGTTGCCCCTCC------- aGGAGGAGTTGGCAGA (SEQ ID NO: 326) | 274 | 0.140 | 5.976 | Deletion & Mutation | +17 | 7 |
| GTCTGATTGCCTGTCGTTGCCC----------- GGAGTTGGCAGA (SEQ ID NO: 327) | 251 | 0.129 | 5.474 | Deletion | +13 | 15 |
| GTCTGATTGCCTGTCGTTGCCC------- ATCATGGAGGAGTTGGCAGA (SEQ ID NO: 328) | 250 | 0.128 | 5.452 | Deletion | +13 | 7 |
| GTCTGATTGCCTGTCGTTGCCCCTC------ CATGGAGGAGTTGGCAGA (SEQ ID NO: 329) | 231 | 0.118 | 5.038 | Deletion | +16 | 6 |
| GTCTGATTGCCTGTCGTTGCCCCTCCCA------ ----------------------GTACT (SEQ ID NO: 330) | 218 | 0.112 | 4.754 | Deletion | +19 | 30 |
| GTCTGATTGCCTGTCGTTGCCCC----- aATCtTGGAGGAGTTGGCAGA (SEQ ID NO: 331) | 206 | 0.105 | 4.492 | Deletion & Mutation | +14 | 5 |

TABLE 8.2-continued

| | | | | | INDEL | |
|---|---|---|---|---|---|---|
| Edited target sequence | # Reads | % Reads | % of INDELs | Type | Location | Size |

Specific insertions and deletions for Guide 831 using APG09106.1 T849R

| Edited target sequence | # Reads | % Reads | % of INDELs | Type | INDEL Location | Size |
|---|---|---|---|---|---|---|
| gTCTGATTGCCTGTCGTTGCCC--------<br>TgggATGGAGGAGTTGGCAGA (SEQ ID NO: 332) | 162 | 0.083 | 3.533 | Deletion & Mutation | +13 | 8 |
| gTCTGATTGCCTGTCGTTGCCCCTC---------<br>-----AGTTGGCAGA (SEQ ID NO: 333) | 158 | 0.081 | 3.446 | Deletion | +16 | 14 |
| gTCTGATTGCCTGTCGTTGCCCC-------<br>TCATGGAGGAGTTGGCAGA (SEQ ID NO: 334) | 122 | 0.062 | 2.660 | Deletion | +14 | 7 |

Example 6: Demonstration of Gene Editing Activity in Plant Cells

RNA-guided nuclease activity of an RGN of the invention is demonstrated in plant cells using protocols adapted from Li, et al., 2013 (*Nat. Biotech.* 31:688-691). Briefly, a plant codon optimized version of an RGN of the invention (SEQ ID NO: 1, 9, 16, 23, 30, 38, 46, 54, 61, 69, 75, 82, 89, 95, 103, 110, or 117) operably linked to a nucleic acid sequence encoding for an N-terminal SV40 nuclear localization signal are cloned behind the strong constitutive 35S promoter in a transient transformation vector. sgRNAs targeting one or more sites in the plant PDS gene that flank an appropriate PAM sequence are cloned behind a plant U6 promoter in a second transient expression vector. The expression vectors are introduced into *Nicotiana benthamiana* mesophyll protoplasts using PEG-mediated transformation. The transformed protoplasts are incubated in the dark for up to 36 hr. Genomic DNA is isolated from the protoplasts using a DNeasy Plant Mini Kit (Qiagen). The genomic region flanking the RGN target site is PCR amplified, and products are purified using QiaQuick Spin Column (Qiagen) following the manufacturer's protocol. 200-500 ng total of the purified PCR products are mixed with 1 µl 10× Taq DNA Polymerase PCR buffer (Enzymatics) and ultrapure water to a final volume of 10 µl, and subjected to a re-annealing process to enable heteroduplex formation: 95° C. for 10 min, 95° C. to 85° C. ramping at −2° C./s, 85° C. to 25° C. at −0.25° C./s, and 25° C. hold for 1 min.

After reannealing, products are treated with SURVEYOR nuclease and SURVEYOR enhancer S (Integrated DNA Technologies) following the manufacturer's recommended protocol and analyzed on 4-20% Novex TBE polyacrylamide gels (Life Technologies). Gels are stained with SYBR Gold DNA stain (Life Technologies) for 10 min and imaged with a Gel Doc gel imaging system (Bio-rad). Quantification is based on relative band intensities. Indel percentage is determined by the formula, $100 \times (1 - (1 - (b+c)/(a+b+c))^{1/2})$, where a is the integrated intensity of the undigested PCR product, and b and c are the integrated intensities of each cleavage product.

Example 7: Identification of Disease Targets

A database of clinical variants was obtained from NCBI ClinVar database, which is available through the world wide web at the NCBI ClinVar website. Pathogenic Single Nucleotide Polymorphisms (SNPs) were identified from this list. Using the genomic locus information, CRISPR targets in the region overlapping and surrounding each SNP were identified. A selection of SNPs that can be corrected using base editing in combination with an RGN system comprising APG09748 or APG09106.1 to target the causal mutation ("Casl Mut.") is listed in Table 9.1. A selection of SNPs that can be corrected using base editing in combination with an RGN system comprising APG06646.1 or APG01658.1 to target the causal mutation ("Casl Mut.") is listed in Table 9.2. In both Table 9.1 and 9.2, only one alias of each disease is listed. The "RS #" corresponds to the RS accession number through the SNP database at the NCBI website. The Chromosome Accession number provides accession reference information found through the NCBI website. Tables 9.1 and 9.2 also provide genomic target sequence information suitable for RGN systems APG09748 or APG09106.1 (in Table 9.1), or APG06646.1 or APG01658.1 (in Table 9.2) for each disease. The target sequence information also provides protospacer sequence for the production of the necessary sgRNA for the corresponding RGN of the invention.

TABLE 9.1

Disease Targets for APG09748 and APG09106.1

| Disease | RS# | Casl Mut. | Chromosome Accession | Gene Symbol | Target (SEQ ID NO.) |
|---|---|---|---|---|---|
| Stargardt disease 1 | 1800728 | A > G | NC_000001.10, NC_000001.11 | ABCA4 | 313 |
| Glycogen storage disease type 1A | 1801175 | C > T | NC_000017.10, NC_000017.11 | G6PC | 335 |
| Severe combined immunodeficiency disease | 3218716 | C > T | NC_000014.8, NC_000014.9 | MYH7 | 336 |
| Phenylketonuria | 5030858 | G > A | NC_000012.11, NC_000012.12 | PAH | 337 |
| Hyperphenylalaninemia | 5030860 | T > C | NC_000012.11, NC_000012.12 | PAH | 338 |
| Alpha-1-antitrypsin deficiency | 28929474 | C > T | NC_000014.8, NC_000014.9 | SERPINA1 | 339 |
| MECP2-Related Disorders | 28934906 | G > A | NC_000023.10, NC_000023.11 | MECP2 | 340 |
| Inclusion body myopathy 2 | 28937594 | A > G | NC_000009.11, NC_000009.12 | GNE | 341 |

TABLE 9.1-continued

Disease Targets for APG09748 and APG09106.1

| Disease | RS# | CasI Mut. | Chromosome Accession | Gene Symbol | Target (SEQ ID NO.) |
|---|---|---|---|---|---|
| Von Willebrand disease | 41276738 | C > T | NC_000012.11, NC_000012.12 | VWF | 342 |
| Breast and/or ovarian cancer | 41293455 | G > A | NC_000017.10, NC_000017.11 | BRCA1 | 343 |
| MECP2-Related Disorders | 61750240 | G > A | NC_000023.10, NC_000023.11 | MECP2 | 344 |
| MEFV-Related Disorder | 61752717 | T > C | NC_000016.9, NC_000016.10 | MEFV | 345 |
| Breast and/or ovarian cancer | 62625307 | G > A | NC_000017.10, NC_000017.11 | BRCA1 | 346 |
| Breast and/or ovarian cancer | 62625308 | G > A | NC_000017.10, NC_000017.11 | BRCA1 | 347 |
| Hereditary cancer-predisposing syndrome | 63749795 | C > T | NC_000003.11 , NC_000003.12 | MLH1 | 348 |
| Hereditary cancer-predisposing syndrome | 63749849 | C > T | NC_000002.11, NC_000002.12 | MSH2 | 349 |
| Hereditary cancer-predisposing syndrome | 63750636 | C > T | NC_000002.11, NC_000002.12 | MSH2 | 350 |
| Carnitine palmitoyltransferase II deficiency | 74315294 | C > T | NC_000001.10, NC_000001.11 | CPT2 | 351 |
| Cystic fibrosis | 74597325 | C > T | NC_000007.13, NC_000007.14 | CFTR | 352 |
| Deficiency of UDPglucose-hexose-1-phosphate uridylyltransferase | 75391579 | A > G | NC_000009.11, NC_000009.12 | GALT | 353 |
| Cystic fibrosis | 75527207 | G > A | NC_000007.13, NC_000007.14 | CFTR | 354 |
| Amyloidogenic transthyretin amyloidosis | 76992529 | G > A | NC_000018.9, NC_000018.10 | TTR | 355 |
| Cystic fibrosis | 77010898 | G > A | NC_000007.13, NC_000007.14 | CFTR | 356 |
| Metachromatic leukodystrophy | 80338815 | C > T | NC_000022.10, NC_000022.11 | ARSA | 357 |
| Cowden syndrome 3 | 80338844 | C > T | NC_000011.9, NC_000011.10 | SDHD | 358 |
| Smith-Lemli-Opitz syndrome | 80338853 | G > A | NC_000011.9, NC_000011.10 | DHCR7 | 359 |
| Breast and/or ovarian cancer | 80356962 | C > T | NC_000017.10, NC_000017.11 | BRCA1 | 360 |
| Breast and/or ovarian cancer | 80357123 | G > A | NC_000017.10, NC_000017.11 | BRCA1 | 361 |
| Inborn genetic diseases | 80358259 | A > G | NC_000018.9, NC_000018.10 | NPC1 | 362 |
| Breast and/or ovarian cancer | 80359212 | C > T | NC_000013.10, NC_000013.11 | BRCA2 | 363 |
| Fanconi anemia | 104886457 | G > A | NC_000009.11, NC_000009.12 | FANCC | 364 |
| SLC26A2-Related Disorders | 104893915 | C > T | NC_000005.9, NC_000005.10 | SLC26A2 | 365 |
| Cardiomyopathy | 104894368 | C > T | NC_000012.11, NC_000012.12 | MYL2 | 366 |
| Deafness, X-linked | 104894396 | C > T | NC_000013.10, NC_000013.11 | GJB2 | 367 |
| Inborn genetic diseases | 104894635 | C > T | NC_000017.10, NC_000017.11 | SGSH | 368 |
| Familial Mediterranean fever | 104895097 | C > T | NC_000016.9, NC_000016.10 | MEFV | 369 |
| Familial dysautonomia | 111033171 | A > G | NC_000009.11, NC_000009.12 | ELP1 | 370 |
| Shwachman syndrome | 113993993 | A > G | NC_000007.13, NC_000007.14 | SBDS | 371 |
| RYR1-Related Disorders | 118192172 | C > T | NC_000019.9, NC_000019.10 | RYR1 | 372 |
| Ceroid lipofuscinosis neuronal 2 | 119455955 | G > A | NC_000011.9, NC_000011.10 | TPP1 | 373 |
| Medium-chain acyl-coenzyme A dehydrogenase deficiency | 121434274 | G > A | NC_000001.10, NC_000001.11 | ACADM | 374 |
| Primary hyperoxaluria | 121908529 | G > A | NC_000002.11, NC_000002.12 | AGXT | 375 |
| Cardiomyopathy | 121908987 | C > T | NC_000007.13, NC_000007.14 | PRKAG2 | 376 |
| Cowden syndrome | 121909219 | C > T | NC_000010.10, NC_000010.11 | PTEN | 377 |
| Cardiomyopathy | 121913628 | C > T | NC_000014.8, NC_000014.9 | MYH7 | 378 |
| Inborn genetic diseases | 121918243 | G > A | NC_000001.10, NC_000001.11 | MMACHC | 379 |
| PTRN11-related disorder | 121918457 | C > T | NC_000012.11, NC_000012.12 | PTPN11 | 380 |
| Juvenile myelomonocytic leukemia | 121918462 | C > T | NC_000012.11, NC_000012.12 | PTPN11 | 381 |
| Juvenile myelomonocytic leukemia | 121918466 | A > G | NC_000012.11, NC_000012.12 | PTPN11 | 382 |
| Mucopolysaccharidosis type I | 121965020 | C > T | NC_000004.11, NC_000004.12 | IDUA | 383 |
| Ceroid lipofuscinosis neuronal 1 | 137852700 | G > A | NC_000001.10, NC_000001.11 | PPT1 | 384 |
| CHEK2-Related Cancer Susceptibility | 137853007 | G > A | NC_000022.10, NC_000022.11 | CHEK2 | 385 |
| Colorectal cancer | 137854568 | C > T | NC_000005.9, NC_000005.10 | APC | 386 |
| Familial hypercholesterolemia | 137929307 | G > A | NC_000019.9, NC_000019.10 | LDLR | 387 |
| Cardio-facio-cutaneous syndrome | 180177035 | T > C | NC_000007.13, NC_000007.14 | BRAF | 388 |
| Familial cancer of breast | 180177083 | G > A | NC_000016.10, NC_000016.9 | PALB2 | 389 |
| MYBPC3-Related Disorders | 200411226 | C > T | NC_000011.9, NC_000011.10 | MYBPC3 | 390 |
| RYR1-Related Disorders | 200563280 | C > T | NC_000019.9, NC_000019.10 | RYR1 | 391 |
| MYBPC3-Related Disorders | 387907267 | G > A | NC_000011.9, NC_000011.10 | MYBPC3 | 392 |
| Desmoid disease, hereditary | 397515734 | C > T | NC_000005.9, NC_000005.10 | APC | 393 |
| Marfan Syndrome/Loeys-Dietz Syndrome/Familial Thoracic Aortic Aneurysms and Dissections | 397515757 | C > T | NC_000015.9, NC_000015.10 | FBN1 | 394 |
| Immunodeficiency 14 | 397518423 | G > A | NC_000001.10, NC_000001.11 | PIK3CD | 395 |
| Inborn genetic diseases | 398123009 | C > T | NC_000011.9, NC_000011.10 | PACS1 | 396 |
| B lymphoblastic leukemia lymphoma, no ICD-O subtype | 529008617 | G > A | NC_000001.10, NC_000001.11 | MUTYH | 397 |
| Familial cancer of breast | 587780021 | G > A | NC_000002.11, NC_000002.12 | BARD1 | 398 |
| Familial hypercholesterolemia | 746118995 | C > T | NC_000019.9, NC_000019.10 | LDLR | 399 |
| Familial hypercholesterolemia | 769370816 | G > A | NC_000019.10, NC_000019.9 | LDLR | 400 |

TABLE 9.2

Disease Targets for APG6646.1 or APG01658.1

| Disease | RGN | RS# | Casl Mut. | Chromosome Accession | Gene Symbol | Target (SEQ ID NO.) |
|---|---|---|---|---|---|---|
| Stargardt disease 1 | APG01658.1 | 1800553 | C > T | NC_000001.10, NC_000001.11 | ABCA4 | 538 |
| Stargardt disease 1 | APG06646.1 | 1800553 | C > T | NC_000001.10, NC_000001.11 | ABCA4 | 539 |
| Hereditary cancer-predisposing syndrome | APG01658.1 | 5030804 | A > G | NC_000003.11, NC_000003.12 | VHL | 540 |
| Hereditary cancer-predisposing syndrome | APG06646.1 | 5030804 | A > G | NC_000003.11, NC_000003.12 | VHL | 541 |
| Phenylketonuria | APG01658.1 | 5030851 | G > A | NC_000012.11, NC_000012.12 | PAH | 542 |
| Phenylketonuria | APG06646.1 | 5030851 | G > A | NC_000012.11, NC_000012.12 | PAH | 543 |
| Melanoma and myeloma | APG01658.1 | 11547328 | G > A | NC_000012.11, NC_000012.12 | CDK4 | 544 |
| Melanoma and myeloma | APG06646.1 | 11547328 | G > A | NC_000012.11, NC_000012.12 | CDK4 | 545 |
| Familial hypercholesterolemia | APG01658.1 | 11547917 | C > T | NC_000019.9, NC_000019.10 | LDLR | 546 |
| Familial hypercholesterolemia | APG06646.1 | 11547917 | C > T | NC_000019.9, NC_000019.10 | LDLR | 547 |
| Charcot-Marie-Tooth disease | APG01658.1 | 61444459 | G > A | NC_000001.10, NC_000001.11 | LMNA | 548 |
| Charcot-Marie-Tooth disease | APG06646.1 | 61444459 | G > A | NC_000001.10, NC_000001.11 | LMNA | 549 |
| Angelman syndrome | APG01658.1 | 61751362 | G > A | NC_000023.10, NC_000023.11 | MECP2 | 550 |
| Angelman syndrome | APG06646.1 | 61751362 | G > A | NC_000023.10, NC_000023.11 | MECP2 | 551 |
| Phenylketonuria | APG01658.1 | 62514895 | C > T | NC_000012.11, NC_000012.12 | PAH | 552 |
| Phenylketonuria | APG06646.1 | 62514895 | C > T | NC_000012.11, NC_000012.12 | PAH | 553 |
| Phenylketonuria | APG01658.1 | 62516152 | C > T | NC_000012.11, NC_000012.12 | PAH | 554 |
| Phenylketonuria | APG06646.1 | 62516152 | C > T | NC_000012.11, NC_000012.12 | PAH | 555 |
| Lynch syndrome | APG01658.1 | 63749795 | C > T | NC_000003.11, NC_000003.12 | MLH1 | 556 |
| Lynch syndrome | APG06646.1 | 63749795 | C > T | NC_000003.11, NC_000003.12 | MLH1 | 557 |
| Hereditary cancer | APG01658.1 | 63749843 | C > T | NC_000002.11, NC_000002.12 | MSH6 | 558 |
| Hereditary cancer | APG06646.1 | 63749843 | C > T | NC_000002.11, NC_000002.12 | MSH6 | 559 |
| Hereditary cancer-predisposing syndrome | APG01658.1 | 63749849 | C > T | NC_000002.11, NC_000002.12 | MSH2 | 560 |
| Hereditary cancer-predisposing syndrome | APG06646.1 | 63749849 | C > T | NC_000002.11, NC_000002.12 | MSH2 | 561 |
| Hereditary cancer-predisposing syndrome | APG01658.1 | 63750508 | C > T | NC_000002.11, NC_000002.12 | MSH2 | 562 |
| Hereditary cancer-predisposing syndrome | APG06646.1 | 63750508 | C > T | NC_000002.11, NC_000002.12 | MSH2 | 563 |
| Hereditary cancer-predisposing syndrome | APG01658.1 | 63750636 | C > T | NC_000002.11, NC_000002.12 | MSH2 | 564 |
| Hereditary cancer-predisposing syndrome | APG06646.1 | 63750636 | C > T | NC_000002.11, NC_000002.12 | MSH2 | 565 |
| Hereditary cancer-predisposing syndrome | APG06646.1 | 63750871 | G > A | NC_000007.13, NC_000007.14 | PMS2 | 566 |
| Lynch syndrome | APG01658.1 | 63751194 | C > T | NC_000003.11, NC_000003.12 | MLH1 | 567 |
| Lynch syndrome | APG06646.1 | 63751194 | C > T | NC_000003.11, NC_000003.12 | MLH1 | 568 |
| Lynch syndrome | APG01658.1 | 63751711 | G > A | NC_000003.11, NC_000003.12 | MLH1 | 569 |
| Lynch syndrome | APG06646.1 | 63751711 | G > A | NC_000003.11, NC_000003.12 | MLH1 | 570 |
| Cystic fibrosis | APG01658.1 | 75039782 | C > T | NC_000007.13, NC_000007.14 | CFTR | 571 |
| Cystic fibrosis | APG06646.1 | 75039782 | C > T | NC_000007.13, NC_000007.14 | CFTR | 572 |
| Deafness | APG01658.1 | 76434661 | C > T | NC_000013.10, NC_000013.11 | GJB2 | 573 |
| Deafness | APG06646.1 | 76434661 | C > T | NC_000013.10, NC_000013.11 | GJB2 | 574 |
| Cystic fibrosis | APG01658.1 | 76713772 | G > A | NC_000007.13, NC_000007.14 | CFTR | 575 |
| Cystic fibrosis | APG06646.1 | 76713772 | G > A | NC_000007.13, NC_000007.14 | CFTR | 576 |
| Cardiomyopathy | APG01658.1 | 76992529 | G > A | NC_000018.9, NC_000018.10 | TTR | 577 |
| Cardiomyopathy | APG06646.1 | 76992529 | G > A | NC_000018.9, NC_000018.10 | TTR | 578 |
| Cystic fibrosis | APG01658.1 | 77010898 | G > A | NC_000007.13, NC_000007.14 | CFTR | 579 |
| Cystic fibrosis | APG06646.1 | 77010898 | G > A | NC_000007.13, NC_000007.14 | CFTR | 580 |
| Cystic fibrosis | APG01658.1 | 80224560 | G > A | NC_000007.13, NC_000007.14 | CFTR | 581 |
| Cystic fibrosis | APG06646.1 | 80224560 | G > A | NC_000007.13, NC_000007.14 | CFTR | 582 |
| Cowden syndrome | APG01658.1 | 80338844 | C > T | NC_000011.9, NC_000011.10 | SDHD | 583 |
| Cowden syndrome | APG06646.1 | 80338844 | C > T | NC_000011.9, NC_000011.10 | SDHD | 584 |
| SLC26A4-Related Disorders | APG01658.1 | 80338849 | G > A | NC_000007.13, NC_000007.14 | SLC26A4 | 585 |
| SLC26A4-Related Disorders | APG06646.1 | 80338849 | G > A | NC_000007.13, NC_000007.14 | SLC26A4 | 586 |
| Breast-ovarian cancer | APG01658.1 | 80356885 | C > T | NC_000017.10, NC_000017.11 | BRCA1 | 587 |
| Breast-ovarian cancer | APG06646.1 | 80356885 | C > T | NC_000017.10, NC_000017.11 | BRCA1 | 588 |
| Breast-ovarian cancer | APG01658.1 | 80358557 | C > T | NC_000013.10, NC_000013.11 | BRCA2 | 589 |
| Breast-ovarian cancer | APG06646.1 | 80358557 | C > T | NC_000013.10, NC_000013.11 | BRCA2 | 590 |
| Breast-ovarian cancer | APG01658.1 | 80358650 | G > A | NC_000013.10, NC_000013.11 | BRCA2 | 591 |
| Breast-ovarian cancer | APG06646.1 | 80358650 | G > A | NC_000013.10, NC_000013.11 | BRCA2 | 592 |
| Breast-ovarian cancer | APG01658.1 | 80358659 | C > T | NC_000013.10, NC_000013.11 | BRCA2 | 593 |
| Breast-ovarian cancer | APG06646.1 | 80358659 | C > T | NC_000013.10, NC_000013.11 | BRCA2 | 594 |
| Breast-ovarian cancer | APG06646.1 | 80358663 | C > T | NC_000013.10, NC_000013.11 | BRCA2 | 595 |
| Breast-ovarian cancer | APG01658.1 | 80358871 | G > A | NC_000013.10, NC_000013.11 | BRCA2 | 596 |
| Breast-ovarian cancer | APG06646.1 | 80358871 | G > A | NC_000013.10, NC_000013.11 | BRCA2 | 597 |
| Breast-ovarian cancer | APG01658.1 | 80358920 | C > T | NC_000013.10, NC_000013.11 | BRCA2 | 598 |
| Breast-ovarian cancer | APG06646.1 | 80358920 | C > T | NC_000013.10, NC_000013.11 | BRCA2 | 599 |
| Breast-ovarian cancer | APG01658.1 | 80358972 | C > T | NC_000013.10, NC_000013.11 | BRCA2 | 600 |
| Breast-ovarian cancer | APG06646.1 | 80358972 | C > T | NC_000013.10, NC_000013.11 | BRCA2 | 601 |
| Breast-ovarian cancer | APG01658.1 | 80358981 | C > T | NC_000013.10, NC_000013.11 | BRCA2 | 602 |
| Breast-ovarian cancer | APG06646.1 | 80358981 | C > T | NC_000013.10, NC_000013.11 | BRCA2 | 603 |
| Breast-ovarian cancer | APG01658.1 | 80359003 | G > A | NC_000013.10, NC_000013.11 | BRCA2 | 604 |
| Breast-ovarian cancer | APG06646.1 | 80359003 | G > A | NC_000013.10, NC_000013.11 | BRCA2 | 605 |
| Breast-ovarian cancer | APG01658.1 | 80359004 | G > A | NC_000013.10, NC_000013.11 | BRCA2 | 606 |
| Breast-ovarian cancer | APG06646.1 | 80359004 | G > A | NC_000013.10, NC_000013.11 | BRCA2 | 607 |
| Breast-ovarian cancer | APG01658.1 | 80359013 | G > A | NC_000013.10, NC_000013.11 | BRCA2 | 608 |
| Breast-ovarian cancer | APG06646.1 | 80359013 | G > A | NC_000013.10, NC_000013.11 | BRCA2 | 609 |
| Breast-ovarian cancer | APG01658.1 | 80359027 | G > A | NC_000013.10, NC_000013.11 | BRCA2 | 610 |
| Breast-ovarian cancer | APG06646.1 | 80359027 | G > A | NC_000013.10, NC_000013.11 | BRCA2 | 611 |
| Breast-ovarian cancer | APG01658.1 | 80359071 | G > A | NC_000013.10, NC_000013.11 | BRCA2 | 612 |

TABLE 9.2-continued

Disease Targets for APG6646.1 or APG01658.1

| Disease | RGN | RS# | Casl Mut. | Chromosome Accession | Gene Symbol | Target (SEQ ID NO.) |
|---|---|---|---|---|---|---|
| Breast-ovarian cancer | APG06646.1 | 80359071 | G > A | NC_000013.10, NC_000013.11 | BRCA2 | 613 |
| Breast-ovarian cancer | APG01658.1 | 80359115 | C > T | NC_000013.10, NC_000013.11 | BRCA2 | 614 |
| Breast-ovarian cancer | APG06646.1 | 80359115 | C > T | NC_000013.10, NC_000013.11 | BRCA2 | 615 |
| Breast-ovarian cancer | APG01658.1 | 80359140 | C > T | NC_000013.10, NC_000013.11 | BRCA2 | 616 |
| Breast-ovarian cancer | APG06646.1 | 80359140 | C > T | NC_000013.10, NC_000013.11 | BRCA2 | 617 |
| Breast-ovarian cancer | APG06646.1 | 80359159 | C > T | NC_000013.10, NC_000013.11 | BRCA2 | 618 |
| Breast-ovarian cancer | APG01658.1 | 80359180 | C > T | NC_000013.10, NC_000013.11 | BRCA2 | 619 |
| Breast-ovarian cancer | APG06646.1 | 80359180 | C > T | NC_000013.10, NC_000013.11 | BRCA2 | 620 |
| Breast-ovarian cancer | APG01658.1 | 81002846 | G > A | NC_000013.10, NC_000013.11 | BRCA2 | 621 |
| Breast-ovarian cancer | APG06646.1 | 81002846 | G > A | NC_000013.10, NC_000013.11 | BRCA2 | 622 |
| Breast-ovarian cancer | APG06646.1 | 81002862 | A > G | NC_000013.10, NC_000013.11 | BRCA2 | 623 |
| Fanconi anemia | APG01658.1 | 104886457 | G > A | NC_000009.11, NC_000009.12 | FANCC | 624 |
| Fanconi anemia | APG06646.1 | 104886457 | G > A | NC_000009.11, NC_000009.12 | FANCC | 625 |
| Achondrogenesis | APG01658.1 | 104893915 | C > T | NC_000005.9, NC_000005.10 | SLC26A2 | 626 |
| Achondrogenesis | APG06646.1 | 104893915 | C > T | NC_000005.9, NC_000005.10 | SLC26A2 | 627 |
| RYR1-Related Disorders | APG01658.1 | 118192172 | C > T | NC_000019.9, NC_000019.10 | RYR1 | 628 |
| RYR1-Related Disorders | APG06646.1 | 118192172 | C > T | NC_000019.9, NC_000019.10 | RYR1 | 629 |
| CHEK2-Related Cancer Susceptibility | APG01658.1 | 137853007 | G > A | NC_000022.10, NC_000022.11 | CHEK2 | 630 |
| CHEK2-Related Cancer Susceptibility | APG06646.1 | 137853007 | G > A | NC_000022.10, NC_000022.11 | CHEK2 | 631 |
| Neurofibromatosis | APG06646.1 | 137854550 | A > G | NC_000017.10, NC_000017.11 | NF1 | 632 |
| Neurofibromatosis | APG01658.1 | 137854556 | G > A | NC_000017.10, NC_000017.11 | NF1 | 633 |
| Neurofibromatosis | APG06646.1 | 137854556 | G > A | NC_000017.10, NC_000017.11 | NF1 | 634 |
| Myopathy | APG01658.1 | 193922390 | C > T | NC_000014.8, NC_000014.9 | MYH7 | 635 |
| Myopathy | APG06646.1 | 193922390 | C > T | NC_000014.8, NC_000014.9 | MYH7 | 636 |
| Long QT syndrome | APG01658.1 | 199473428 | C > T | NC_000007.13, NC_000007.14 | KCNH2 | 637 |
| Long QT syndrome | APG06646.1 | 199473428 | C > T | NC_000007.13, NC_000007.14 | KCNH2 | 638 |
| Phenylketonuria | APG01658.1 | 199475575 | G > A | NC_000012.11, NC_000012.12 | PAH | 639 |
| Phenylketonuria | APG06646.1 | 199475575 | G > A | NC_000012.11, NC_000012.12 | PAH | 640 |
| Phenylketonuria | APG01658.1 | 199475679 | C > T | NC_000012.11, NC_000012.12 | PAH | 641 |
| Phenylketonuria | APG06646.1 | 199475679 | C > T | NC_000012.11, NC_000012.12 | PAH | 642 |
| MYBPC3-Related Disorders | APG01658.1 | 200411226 | C > T | NC_000011.9, NC_000011.10 | MYBPC3 | 643 |
| MYBPC3-Related Disorders | APG06646.1 | 200411226 | C > T | NC_000011.9, NC_000011.10 | MYBPC3 | 644 |
| Myopathy | APG06646.1 | 267606908 | T > C | NC_000014.8, NC_000014.9 | MYH7 | 645 |
| Cardiomyopathy | APG01658.1 | 267607003 | C > T | NC_000010.10, NC_000010.11 | RBM20 | 646 |
| Cardiomyopathy | APG06646.1 | 267607003 | C > T | NC_000010.10, NC_000010.11 | RBM20 | 647 |
| Noonan syndrome | APG01658.1 | 267607048 | A > G | NC_000010.10, NC_000010.11 | SHOC2 | 648 |
| Noonan syndrome | APG06646.1 | 267607048 | A > G | NC_000010.10, NC_000010.11 | SHOC2 | 649 |
| Familial hypercholesterolemia | APG01658.1 | 267607213 | G > A | NC_000019.9, NC_000019.10 | LDLR | 650 |
| Familial hypercholesterolemia | APG06646.1 | 267607213 | G > A | NC_000019.9, NC_000019.10 | LDLR | 651 |
| Lynch syndrome | APG01658.1 | 267607789 | G > A | NC_000003.11, NC_000003.12 | MLH1 | 652 |
| Lynch syndrome | APG06646.1 | 267607789 | G > A | NC_000003.11, NC_000003.12 | MLH1 | 653 |
| Lynch syndrome | APG01658.1 | 267607845 | G > A | NC_000003.11, NC_000003.12 | MLH1 | 654 |
| Lynch syndrome | APG06646.1 | 267607845 | G > A | NC_000003.11, NC_000003.12 | MLH1 | 655 |
| Hereditary cancer-predisposing syndrome | APG01658.1 | 267608098 | A > G | NC_000002.11, NC_000002.12 | MSH6 | 656 |
| Hereditary cancer-predisposing syndrome | APG06646.1 | 267608098 | A > G | NC_000002.11, NC_000002.12 | MSH6 | 657 |
| MYBPC3-Related Disorders | APG01658.1 | 387906397 | A > G | NC_000011.9, NC_000011.10 | MYBPC3 | 658 |
| MYBPC3-Related Disorders | APG06646.1 | 387906397 | A > G | NC_000011.9, NC_000011.10 | MYBPC3 | 659 |
| Breast-ovarian cancer | APG01658.1 | 387906843 | G > A | NC_000017.10, NC_000017.11 | RAD51D | 660 |
| Breast-ovarian cancer | APG06646.1 | 387906843 | G > A | NC_000017.10, NC_000017.11 | RAD51D | 661 |
| MYBPC3-Related Disorders | APG01658.1 | 387907267 | G > A | NC_000011.9, NC_000011.10 | MYBPC3 | 662 |
| MYBPC3-Related Disorders | APG06646.1 | 387907267 | G > A | NC_000011.9, NC_000011.10 | MYBPC3 | 663 |
| Breast-ovarian cancer | APG01658.1 | 397507389 | G > A | NC_000013.10, NC_000013.11 | BRCA2 | 664 |
| Breast-ovarian cancer | APG06646.1 | 397507389 | G > A | NC_000013.10, NC_000013.11 | BRCA2 | 665 |
| Breast-ovarian cancer | APG01658.1 | 397507404 | G > A | NC_000013.10, NC_000013.11 | BRCA2 | 666 |
| Breast-ovarian cancer | APG06646.1 | 397507404 | G > A | NC_000013.10, NC_000013.11 | BRCA2 | 667 |
| Leukemia | APG01658.1 | 397507545 | G > A | NC_000012.11, NC_000012.12 | PTPN11 | 668 |
| Leukemia | APG06646.1 | 397507545 | G > A | NC_000012.11, NC_000012.12 | PTPN11 | 669 |
| Leukemia | APG01658.1 | 397507547 | A > G | NC_000012.11, NC_000012.12 | PTPN11 | 670 |
| Leukemia | APG06646.1 | 397507547 | A > G | NC_000012.11, NC_000012.12 | PTPN11 | 671 |
| Breast-ovarian cancer | APG01658.1 | 397507922 | G > A | NC_000013.10, NC_000013.11 | BRCA2 | 672 |
| Breast-ovarian cancer | APG06646.1 | 397507922 | G > A | NC_000013.10, NC_000013.11 | BRCA2 | 673 |
| Marfan syndrome | APG01658.1 | 397515757 | C > T | NC_000015.9, NC_000015.10 | FBN1 | 674 |
| Marfan syndrome | APG06646.1 | 397515757 | C > T | NC_000015.9, NC_000015.10 | FBN1 | 675 |
| MYBPC3-Related Disorders | APG01658.1 | 397516074 | C > T | NC_000011.9, NC_000011.10 | MYBPC3 | 676 |
| MYBPC3-Related Disorders | APG06646.1 | 397516074 | C > T | NC_000011.9, NC_000011.10 | MYBPC3 | 677 |
| Cardiomyopathy | APG01658.1 | 397516354 | C > T | NC_000019.9, NC_000019.10 | TNNI3 | 678 |
| Cardiomyopathy | APG06646.1 | 397516354 | C > T | NC_000019.9, NC_000019.10 | TNNI3 | 679 |
| Immunodeficiency | APG01658.1 | 397518423 | G > A | NC_000001.10, NC_000001.11 | PIK3CD | 680 |
| Immunodeficiency | APG06646.1 | 397518423 | G > A | NC_000001.10, NC_000001.11 | PIK3CD | 681 |
| B lymphoblastic leukemia lymphoma | APG01658.1 | 529008617 | G > A | NC_000001.10, NC_000001.11 | MUTYH | 682 |
| B lymphoblastic leukemia lymphoma | APG06646.1 | 529008617 | G > A | NC_000001.10, NC_000001.11 | MUTYH | 683 |
| Familial hypercholesterolemia | APG01658.1 | 570942190 | C > T | NC_000019.9, NC_000019.10 | LDLR | 684 |
| Familial hypercholesterolemia | APG06646.1 | 570942190 | C > T | NC_000019.9, NC_000019.10 | LDLR | 685 |
| Ataxia-telangiectasia syndrome | APG01658.1 | 587776551 | G > A | NC_000011.10, NC_000011.9 | ATM | 686 |
| Ataxia-telangiectasia syndrome | APG06646.1 | 587776551 | G > A | NC_000011.10, NC_000011.9 | ATM | 687 |

TABLE 9.2-continued

Disease Targets for APG6646.1 or APG01658.1

| Disease | RGN | RS# | CasI Mut. | Chromosome Accession | Gene Symbol | Target (SEQ ID NO.) |
|---|---|---|---|---|---|---|
| Adenoid cystic carcinoma | APG01658.1 | 587778720 | C > T | NC_000017.10, NC_000017.11 | TP53 | 688 |
| Adenoid cystic carcinoma | APG06646.1 | 587778720 | C > T | NC_000017.10, NC_000017.11 | TP53 | 689 |
| Hereditary cancer-predisposing syndrome | APG01658.1 | 587779075 | C > T | NC_000002.11, NC_000002.12 | MSH2 | 690 |
| Hereditary cancer-predisposing syndrome | APG06646.1 | 587779075 | C > T | NC_000002.11, NC_000002.12 | MSH2 | 691 |
| Hereditary cancer-predisposing syndrome | APG06646.1 | 587779333 | T > C | NC_000007.13, NC_000007.14 | PMS2 | 692 |
| Ataxia-telangiectasia syndrome | APG01658.1 | 587779866 | A > G | NC_000011.10, NC_000011.9 | ATM | 693 |
| Ataxia-telangiectasia syndrome | APG06646.1 | 587779866 | A > G | NC_000011.10, NC_000011.9 | ATM | 694 |
| Breast cancer | APG01658.1 | 587780021 | G > A | NC_000002.11, NC_000002.12 | BARD1 | 695 |
| Breast cancer | APG06646.1 | 587780021 | G > A | NC_000002.11, NC_000002.12 | BARD1 | 696 |
| Breast-ovarian cancer | APG01658.1 | 587781629 | G > A | NC_000013.10, NC_000013.11 | BRCA2 | 697 |
| Breast-ovarian cancer | APG06646.1 | 587781629 | G > A | NC_000013.10, NC_000013.11 | BRCA2 | 698 |
| Hereditary cancer-predisposing syndrome | APG01658.1 | 587782144 | C > T | NC_000017.10, NC_000017.11 | TP53 | 699 |
| Hereditary cancer-predisposing syndrome | APG06646.1 | 587782144 | C > T | NC_000017.10, NC_000017.11 | TP53 | 700 |
| Marfan syndrome | APG01658.1 | 727503054 | A > G | NC_000015.9, NC_000015.10 | FBN1 | 701 |
| Marfan syndrome | APG06646.1 | 727503054 | A > G | NC_000015.9, NC_000015.10 | FBN1 | 702 |
| Noonan syndrome | APG01658.1 | 727503110 | T > C | NC_000012.11, NC_000012.12 | KRAS | 703 |
| Noonan syndrome | APG06646.1 | 727503110 | T > C | NC_000012.11, NC_000012.12 | KRAS | 704 |
| Familial hypercholesterolemia | APG01658.1 | 746118995 | C > T | NC_000019.9, NC_000019.10 | LDLR | 705 |
| Familial hypercholesterolemia | APG06646.1 | 746118995 | C > T | NC_000019.9, NC_000019.10 | LDLR | 706 |
| Familial hypercholesterolemia | APG01658.1 | 748944640 | G > A | NC_000019.9, NC_000019.10 | LDLR | 707 |
| Familial hypercholesterolemia | APG06646.1 | 748944640 | G > A | NC_000019.9, NC_000019.10 | LDLR | 708 |
| Familial hypercholesterolemia | APG01658.1 | 765696008 | G > A | NC_000019.10, NC_000019.9 | LDLR | 709 |
| Familial hypercholesterolemia | APG06646.1 | 765696008 | G > A | NC_000019.10, NC_000019.9 | LDLR | 710 |
| Familial hypercholesterolemia | APG01658.1 | 769370816 | G > A | NC_000019.10, NC_000019.9 | LDLR | 711 |
| Familial hypercholesterolemia | APG06646.1 | 769370816 | G > A | NC_000019.10, NC_000019.9 | LDLR | 712 |
| Familial hypercholesterolemia | APG01658.1 | 769737896 | C > T | NC_000019.10, NC_000019.9 | LDLR | 713 |
| Familial hypercholesterolemia | APG06646.1 | 769737896 | C > T | NC_000019.10, NC_000019.9 | LDLR | 714 |
| Familial hypercholesterolemia | APG01658.1 | 771019366 | A > G | NC_000019.10, NC_000019.9 | LDLR | 715 |
| Familial hypercholesterolemia | APG06646.1 | 771019366 | A > G | NC_000019.10, NC_000019.9 | LDLR | 716 |
| Paragangliomas | APG01658.1 | 772551056 | C > T | NC_000001.11, NC_000001.10 | SDHB | 717 |
| Paragangliomas | APG06646.1 | 772551056 | C > T | NC_000001.11, NC_000001.10 | SDHB | 718 |
| Hereditary cancer | APG01658.1 | 786201042 | C > T | NC_000002.12, NC_000002.11 | MSH6 | 719 |
| Hereditary cancer | APG06646.1 | 786201042 | C > T | NC_000002.12, NC_000002.11 | MSH6 | 720 |
| Familial hypercholesterolemia | APG01658.1 | 875989907 | G > A | NC_000019.9, NC_000019.10 | LDLR | 721 |
| Familial hypercholesterolemia | APG06646.1 | 875989907 | G > A | NC_000019.9, NC_000019.10 | LDLR | 722 |
| Familial hypercholesterolemia | APG01658.1 | 879254797 | G > A | NC_000019.10, NC_000019.9 | LDLR | 723 |
| Familial hypercholesterolemia | APG06646.1 | 879254797 | G > A | NC_000019.10, NC_000019.9 | LDLR | 724 |
| Familial hypercholesterolemia | APG01658.1 | 879254871 | C > T | NC_000019.10, NC_000019.9 | LDLR | 725 |
| Familial hypercholesterolemia | APG06646.1 | 879254871 | C > T | NC_000019.10, NC_000019.9 | LDLR | 726 |
| Familial hypercholesterolemia | APG01658.1 | 879255000 | T > C | NC_000019.10, NC_000019.9 | LDLR | 727 |
| Familial hypercholesterolemia | APG06646.1 | 879255000 | T > C | NC_000019.10, NC_000019.9 | LDLR | 728 |

Example 8: Targeting Mutations Responsible for Friedreich Ataxia

The expansion of the trinucleotide repeat sequence causing Friedreich's Ataxia (FRDA) occurs in a defined genetic locus within the FXN gene, referred to as the FRDA instability region. RNA guided nucleases (RGNs) may be used for excising the instability region in FRDA patient cells. This approach requires 1) an RGN and guide RNA sequence that can be programmed to target the allele in the human genome; and 2) a delivery approach for the RGN and guide sequence. Many nucleases used for genome editing, such as the commonly used Cas9 nuclease from *S. pyogenes* (SpCas9), are too large to be packaged into adeno-associated viral (AAV) vectors, especially when considering the length of the SpCas9 gene and the guide RNA in addition to other genetic elements required for functional expression cassettes. This makes a viable approach using SpCas9 unlikely.

The compact RNA guided nucleases of the invention, such as APG09748, APG09106.1, and APG06646.1, are uniquely well suited for the excision of the FRDA instability region. Each RGN has a PAM requirement that is in the vicinity of the FRDA instability region. Additionally, each of these RGNs can be packaged into an AAV vector along with a guide RNA. Packing two guide RNAs would likely require a second vector, but this approach still compares favorably to what would be required of a larger nuclease such as SpCas9, which would require splitting the protein sequence between two vectors.

Table 10 shows the location of genomic target sequences suitable for targeting APG09748, APG09106.1, or APG06646.1 to the 5' and 3' flanks of the FRDA instability region, as well as the sequence of the sgRNAs for the genomic targets. Once at the locus, the RGN would excise the FA instability region. Excision of the region can be verified with Illumina sequencing of the locus.

TABLE 10

Genomic target sequences for RGN systems

| Location relative to FRDA instability region | Genome target sequence for APG09748 or APG09106.1 (SEQ ID NO.) | sgRNA for APG09748 or APG09106.1 (SEQ ID NO.) | Genome target sequence for APG06646.1 (SEQ ID NO.) | sgRNA for APG06646.1 (SEQ ID NO.) |
|---|---|---|---|---|
| 5' | 401 | 405 | 729 | 733 |
| 5' | 402 | 406 | 730 | 734 |
| 3' | 403 | 407 | 731 | 735 |
| 3' | 404 | 408 | 732 | 736 |

Example 9: Targeting Mutations Responsible for Sickle Cell Diseases

Targeting sequences within the BCL11A enhancer region (SEQ ID NO: 220) may provide a mechanism for increasing fetal hemoglobulin (HbF) to either cure or alleviate the symptoms of sickle cell diseases. For example, genome wide association studies have identified a set of genetic variations at BCL11A that are associated with increased HbF levels. These variations are a collection of SNPs found in non-coding regions of BCL11A that function as a stage-specific, lineage-restricted enhancer region. Further investigation revealed that this BCL11A enhancer is required in erythroid cells for BCL11A expression (Bauer et al, (2013) *Science* 343:253-257, incorporated by reference herein). The enhancer region was found within intron 2 of the BCL11A gene, and three areas of DNaseI hypersensitivity (often indicative of a chromatin state that is associated with regulatory potential) in intron 2 were identified. These three areas were identified as "+62", "+58" and "+55" in accordance with the distance in kilobases from the transcription start site of BCL11A. These enhancer regions are roughly 350 (+55); 550 (+58); and 350 (+62) nucleotides in length (Bauer et al., 2013).

Example 9.1: Identifying Preferred RGN Systems

Here is described a potential treatment for beta-hemoglobinopathies using an RGN system that disrupts BCL11A binding to its binding site within the HBB locus, which is the gene responsible for making beta-globin in adult hemoglobin. This approach uses NHEJ which is more efficient in mammalian cells. In addition, this approach uses a nuclease of sufficiently small size that can be packaged into a single AAV vector for in vivo delivery.

The GATA1 enhancer motif in the human BCL11A enhancer region (SEQ ID NO: 220) is an ideal target for disruption using RNA guided nucleases (RGNs) to reduce BCL11A expression with concurrent re-expression of HbF in adult human erythrocytes (Wu et al. (2019) *Nat Med* 387:2554). Several PAM sequences compatible with APG09748 or APG09106.1 are readily apparent at the genetic locus surrounding this GATA1 site. These nucleases have a PAM sequence of 5'-DTTN-3' (SEQ ID NO: 60) and are compact in size, potentially allowing their delivery along with an appropriate guide RNA in a single AAV or adenoviral vector. In addition to its size, APG06646.1 has a minimal PAM requirement (SEQ ID NO: 109) which makes it well-suited for this approach. This delivery approach bestows multiple advantages relative to others, such as access to hematopoietic stem cells and a well-established safety profile and manufacturing techniques.

The commonly used Cas9 nuclease from *S. pyogenes* (SpyCas9) requires a PAM sequence of 5'-NGG-3', (SEQ ID NO: 101) several of which are present near the GATA1 motif. However, the size of SpyCas9 prevents packaging into a single AAV or adenoviral vector and thus forgoes the aforementioned advantages of this approach. While a dual delivery strategy may be employed, it would add significant manufacturing complexity and cost. Additionally, dual viral vector delivery significantly decreases the efficiency of gene correction, since a successful edit in a given cell requires infection with both vectors.

An expression cassette encoding a human codon optimized APG09748 (SEQ ID NO: 409), APG09106.1 (SEQ ID NO: 410), or APG06646.1 (SEQ ID NO: 415) is produced, similar to those described in Example 5. Expression cassettes which express guide RNAs for RGNs APG09748, APG09106.1, or APG06646.1 are also produced. These guide RNAs comprise: 1) a protospacer sequence that is complementary to either the non-coding or coding DNA strand within the BCL11A enhancer locus (the target sequence) and 2) an RNA sequence required for association of the guide RNA with the RGN. Because several potential PAM sequences for targeting by each RGN surround the BCL11A GATA1 enhancer motif, several potential guide RNA constructs are produced to determine the best protospacer sequence that produces robust cleavage and NHEJ mediated disruption of the BCL11A GATA1 enhancer sequence. The target genomic sequences in Table 11 are evaluated using the sgRNA provided in Table 11.

TABLE 11

Target Sequences for BCL11A GATA1 enhancer locus using APG06646.1

| Target genomic sequence for APG09748 or APG09106.1 (SEQ ID NO.) | sgRNA for APG09748 or APG09106.1 (SEQ ID NO.) | Target genomic sequence for APG06646.1 (SEQ ID NO.) | sgRNA for APG06646.1 (SEQ ID NO.) |
| --- | --- | --- | --- |
| 221 | 224 | 737 | 740 |
| 222 | 269 | 738 | 741 |
| 223 | 270 | 739 | 742 |

To evaluate the efficiency with which APG09748, APG09106.1, or APG06646.1 generates insertions or deletions that disrupt the BCL11A enhancer region, human cell lines such as human embryonic kidney cells (HEK cells) are used. A DNA vector comprising an RGN expression cassette (for example, as described in Example 5) is produced. A separate vector comprising an expression cassette comprising a coding sequence for a guide RNA sequence of Table 11 is also produced. Such an expression cassette may further comprise a human RNA polymerase III U6 promoter (SEQ ID NO: 308), as described in Example 5. Alternatively, a single vector comprising expression cassettes of both the RGN and guide RNA may be used. The vector is introduced into HEK cells using standard techniques such as those described in Example 5, and the cells are cultured for 1-3 days. Following this culture period, genomic DNA is isolated and the frequency of insertions or deletions is determined by using T7 Endonuclease I digestion and/or direct DNA sequencing, as described in Example 5.

A region of DNA encompassing the target BCL11A region is amplified by PCR with primers containing Illumina Nextera XT overhang sequences. These PCR amplicons are either examined for NHEJ formation using T7 Endonuclease I digestion or undergo library preparation following the Illumina 16S Metagenomic Sequencing Library protocol or a similar Next Generation Sequencing (NGS) library preparation. Following deep sequencing, the reads generated are analyzed by CRISPResso to calculate rates of editing. Output alignments are hand-curated to confirm insertion and deletion sites. This analysis identifies the preferred RGN and the corresponding preferred guide RNA (sgRNA). The analysis may result in either APG09748, APG09106.1, or APG06646.1 being equally preferred or that one RGN is most preferred. Additionally, the analysis may determine there is more than one preferred guide RNA, or that all target genomic sequences in Table 17 are equally preferred.

Example 9.2: Assay for Expression of Fetal Hemoglobin

In this example, APG09748, APG09106.1, or APG06646.1 generated insertions or deletions disrupting the BCL11A enhancer region are assayed for expression of fetal hemoglobin. Healthy human donor CD34$^+$ hematopoietic stem cells (HSCs) are used. These HSCs are cultured and vector(s) comprising expression cassettes comprising the coding regions of the preferred RGN and the preferred sgRNA are introduced using methods similar to those described in Example 5. Alternatively, electroporation may be used. Following electroporation, these cells are differentiated in vitro into erythrocytes using established protocols (for example, Giarratana et al. (2004) Nat Biotechnology 23:69-74, herein incorporated by reference). The expression of HbF is then measured using western blotting with an anti-human HbF antibody or quantified via High Performance Liquid Chromatography (HPLC). It is expected that successful disruption of the BCL11A enhancer locus will lead to an increase in HbF production when compared to HSCs electroporated with only the RGN but no guide.

Example 9.3: Assay for Decreased Sickle Cell Formation

In this example, APG09748, APG09106.1, or APG06646.1 generated insertions or deletions disrupting the BCL11A enhancer region are assayed for decreased sickle-cell formation. Donor CD34$^+$ hematopoietic stem cells (HSCs) from patients afflicted with sickle cell disease are used. These HSCs are cultured and vector(s) comprising expression cassettes comprising the coding regions of preferred RGN and the preferred sgRNA are introduced using methods similar to those described in Example 5. Alternatively, electroporation may be used. Following electroporation, these cells are differentiated in vitro into erythrocytes using established protocols (Giarratana et al. (2004) Nat Biotechnology 23:69-74). The expression of HbF is then measured using western blotting with an anti-human HbF antibody or quantified via High Performance Liquid Chromatography (HPLC). It is expected that successful disruption of the BCL11A enhancer locus will lead to an increase in HbF production when compared to HSCs electroporated with only the RGN but no guide.

Sickle cell formation is induced in these differentiated erythrocytes by the addition of metabisulfite. The numbers of sickled vs normal erythrocytes are counted using a microscope. It is expected that the numbers of sickled cells are less in cells treated with APG09748, APG09106.1, or APG06646.1 plus sgRNAs than with cells untreated, or treated with RGNs alone.

Example 9.4: Disease Treatment Validation in a Murine Model

To evaluate the efficacy of using APG09748, APG09106.1, or APG06646.1 disruption of the BCL11A locus, suitable humanized mouse models of sickle cell anemia are used. Expression cassettes encoding for the preferred RGN and for the preferred sgRNA are packaged into AAV vectors or adenovirus vectors. In particular, adenovirus type Ad5/35 is effective at targeting HSCs. A suitable mouse model containing a humanized HBB locus with sickle cell alleles is chosen such as B6; FVB-Tg(LCR-HBA2,LCR-HBB*E26K)53Hhb/J or B6.Cg-Hbatm1Paz Hbbtm1Tow Tg(HBA-HBBs)41Paz/HhbJ. These mice are treated with granulocyte colony-stimulating factor alone or in combination with plerixafor to mobilize HSCs into circulation. AAVs or adenoviruses carrying the RGN and guide plasmid are then injected intravenously, and the mice are allowed to recover for a week. Blood obtained from these mice is tested in an in vitro sickling assay using metabisulfite, and the mice are followed longitudinally to monitor mortality rates and hematopoietic function. It is expected that treatment with AAVs or adenoviruses carrying an RGN and guide RNA will reduce sickling, mortality, and improve hematopoietic function when compared to mice treated with viruses lacking both expression cassettes, or with viruses carrying the RGN expression cassette alone.

Example 10: Base Editing Activity in Mammalian Cells

An expression cassette that produces a cytidine deaminase-RGN fusion protein was constructed as follows. The coding sequence for RGNs (APG06646.1 described herein and APG08290.1, which was described in U.S. Appl. Publ. No. 2019/0367949 and International Appl. Publ. No. WO 2019/236566, each of which is herein incorporated by reference in its entirety) was codon optimized for mammalian expression and mutated to function as a nickase (SEQ ID NOs: 128 and 262, respectively). This coding sequence was introduced into an expression cassette which produces a fusion protein comprising an NLS at its N-terminal end (SEQ ID NO: 125), operably linked at its C-terminal end to a 3×FLAG tag (SEQ ID NO: 126), operably linked at its C-terminal end to a cytidine deaminase (SEQ ID NOs: 129-132, all of which are disclosed in International Appl. No. PCT/US2019/068079, which is herein incorporated by reference in its entirety) operably linked on its C-terminal end to an amino acid linker (SEQ ID NO: 133), operably linked on its C-terminal end to the RGN nickase, operably linked at its C-terminal end to a second NLS (SEQ ID NO: 127). These expression cassettes were each introduced into a pTwist CMV vector (Twist Bioscience) capable of driving expression of the fusion protein in mammalian cells. Separate vectors were also produced that expressed guide RNAs under control of the human U6 promoter, in mammalian cells. These guide RNAs (SEQ ID NOs: 134-136 for nAPG06646.1 and SEQ ID NOs: 263-265 for nAPG08290.1) are capable of guiding the deaminase-nRGN fusion proteins, or the RGN itself, to a targeted genomic sequence for base editing or gene editing, respectively.

500 ng of cytidine deaminase-RGN expression plasmids or standard RGN expression plasmid, and 500 ng of the guide RNA expression plasmids, were co-transfected into HEK293FT cells at 75-90% confluency in 24-well plates using Lipofectamine 2000 reagent (Life Technologies). Cells were then incubated at 37° C. for 72 h. Genomic DNA was then extracted using the NucleoSpin 96 Tissue (Macherey-Nagel) following the manufacturer's protocol. The genomic region flanking the guideRNA target site was PCR amplified, and products were purified using ZR-96 DNA Clean and Concentrator (Zymo Research) following the manufacturer's protocol. The purified PCR products were then sent for Next Generation Sequencing on Illumina MiSeq (2×250). Results were analyzed for indel formation or specific cytosine mutation.

Table 12 below shows cytidine base editing and indel formation of each construct and guide combination. Interestingly, when comparing the activity of the RGN APG06646.1 with that of cytidine deaminase-nAPG06646.1 using the same guide RNA, up to 20× higher cytidine base editing than gene editing was observed. These results demonstrate that an RGN that has low nuclease activity at a particular target site can still be an efficient base editor at that site. Furthermore, since indel formation in base editing applications is often an unwanted outcome, RGNs that have low nuclease activity at a site may be preferred for base editing applications.

TABLE 12

Cytidine base editing and gene editing of RGN and cytidine deaminase-nRGN

| RGN or Deaminase-RGN | Guide RNA | % Total Reads with Cytidine Base Editing | % Total Reads with INDEL Formation |
|---|---|---|---|
| ARM05-nAPG06646.1 | SGN000775 | 8.02 | 0.82 |
| ARM06CTD-nAPG06646.1 | SGN000775 | 0 | 0 |
| ARM08-nAPG06646.1 | SGN000775 | 5.15 | 0.46 |
| ARM11-nAPG06646.1 | SGN000775 | 0.66 | 0 |
| APG06646.1 | SGN000775 | 0 | 0.47 |
| ARM05-nAPG06646.1 | SGN000777 | 2.5 | 0.08 |
| ARM06CTD-nAPG06646.1 | SGN000777 | 0.53 | 0 |
| ARM08-nAPG06646.1 | SGN000777 | 8.12 | 0.25 |
| ARM11-nAPG06646.1 | SGN000777 | 3.52 | 1.04 |
| APG06646.1 | SGN000777 | 0 | 1.44 |
| ARM05-nAPG06646.1 | SGN000781 | 13.51 | 0.27 |
| ARM06CTD-nAPG06646.1 | SGN000781 | 2.69 | 0.13 |
| ARM08-nAPG06646.1 | SGN000781 | 12.97 | 0.12 |
| ARM11-nAPG06646.1 | SGN000781 | 4.7 | 0.14 |
| APG06646.1 | SGN000781 | 0 | 0.65 |
| ARM05-nAPG08290.1 | SGN000143 | 1.35 | 7.04 |
| ARM06CTD-nAPG08290.1 | SGN000143 | 1.36 | 3.17 |
| ARM08-nAPG08290.1 | SGN000143 | 2.59 | 10.98 |
| ARM11-nAPG08290.1 | SGN000143 | 4.78 | 5.77 |
| APG08290.1 | SGN000143 | 0 | 6.21 |
| ARM05-nAPG08290.1 | SGN000169 | 4.26 | 12.87 |
| ARM06CTD-nAPG08290.1 | SGN000169 | 1.63 | 8.29 |
| ARM08-nAPG08290.1 | SGN000169 | 6.99 | 14.27 |
| ARM11-nAPG08290.1 | SGN000169 | 4.99 | 6.39 |
| APG08290.1 | SGN000169 | 0 | 11.85 |
| ARM05-nAPG08290.1 | SGN000173 | 3.26 | 5.51 |
| ARM06CTD-nAPG08290.1 | SGN000173 | 0.72 | 0.96 |
| ARM08-nAPG08290.1 | SGN000173 | 6.6 | 6.06 |
| ARM11-nAPG08290.1 | SGN000173 | 2.83 | 4.82 |
| APG08290.1 | SGN000173 | 0 | 2.58 |

Example 11: Trans ssDNA Cleavage 11.1 Determining Assay Conditions for Trans DNA Cleavage Purified APG09748 (set forth as SEQ ID NO: 137 and described in International Appl. No. PCT/US2019/068079, which is incorporated by reference in its entirety) was incubated with single guide RNA (sgRNA) in Cutsmart buffer (New England Biolabs B7204S) at a final concentration of either 50 nM nuclease and 100 nM sgRNA or 200 nM nuclease and 400 nM sgRNA for 10 min. These RNP solutions were added to solutions of ssDNA—a target or mismatched negative control ssDNA—at a final concentration of 10 nM and reporter probes at a final concentration of 250 nM in 1.5× Cutsmart buffer (New England Biolabs B7204S). The reporter probes (TB0125 and TB0089, set forth as SEQ ID NOs: 138 and 139, respectively) contain a fluorescent dye at the 5' end (56-FAM for TB0125 and Cy5 for TB0089), a quencher at the 3' end (3IABkFQ for TB0125 and 3IAbRQSp for TB0089), and optionally an internal quencher (the internal quencher ZEN is only present on TB0125). Cleavage of the reporter probe results in dequenching of the fluorescent dye and thus an increase in fluorescence signal. To monitor fluorescence intensity, 10 μl of each reaction was incubated in a Corning low volume 384-well microplate at 30° C. in a microplate reader (CLAR-IOstar Plus).

A number of conditions were scouted in order to determine suitable parameters for this assay. In order to determine if there are effects of quenched probe design or fluorophore characteristics, two such reporters were included as a mixture in each reaction. They were at the same concentration as each other in any given reaction. In all cases, the control or target ssDNA concentration (LE201 or LE205, set forth as SEQ ID NOs: 140 and 141, respectively) was 10 nM. The RNP names signify the nuclease and the target as indicated in Table 13 below.

TABLE 13

Ribonucleoprotein complexes

| RNP Name | Nuclease | sgRNA | Intended Target |
|---|---|---|---|
| APG09748.1 | APG09748 | 27sg.1 (SEQ ID NO: 144) | LE201 (SEQ ID NO: 140) |
| APG09748.2 | APG09748 | 27sg.2 (SEQ ID NO: 145) | LE205 (SEQ ID NO: 141) |

The results are shown in Table 14 below.

TABLE 14

Results of trans DNA cleavage assays

| | | | | Slope (RFU/min) | |
|---|---|---|---|---|---|
| RNP Name | [RNP] (nM) | [reporters] (nM) | Target | Cy5 channel | FAM channel |
| APG09748.1 | 25 nM | 0 | LE201 | −0.30 | −2.40 |
| APG09748.1 | 25 nM | 50 | LE201 | 420.00 | 46.20 |
| APG09748.1 | 25 nM | 250 | LE201 | 1040.40 | 47.40 |
| APG09748.1 | 25 nM | 500 | LE201 | 1090.20 | 57.00 |
| APG09748.1 | 25 nM | 750 | LE201 | 996.60 | 36.60 |
| APG09748.1 | 25 nM | 1000 | LE201 | 770.40 | 36.00 |
| APG09748.1 | 25 nM | 0 | LE205 | 0.60 | −1.80 |
| APG09748.1 | 25 nM | 50 | LE205 | 6.00 | −1.20 |
| APG09748.1 | 25 nM | 250 | LE205 | 16.80 | −3.00 |
| APG09748.1 | 25 nM | 500 | LE205 | 33.00 | 1.80 |
| APG09748.1 | 25 nM | 750 | LE205 | 18.00 | 3.00 |
| APG09748.1 | 25 nM | 1000 | LE205 | −21.60 | −51.60 |
| APG09748.2 | 25 nM | 0 | LE201 | −0.18 | −1.80 |
| APG09748.2 | 25 nM | 50 | LE201 | 4.20 | 1.20 |
| APG09748.2 | 25 nM | 250 | LE201 | 42.60 | 3.00 |
| APG09748.2 | 25 nM | 500 | LE201 | 70.80 | 10.20 |
| APG09748.2 | 25 nM | 750 | LE201 | 67.80 | 10.80 |
| APG09748.2 | 25 nM | 1000 | LE201 | 55.80 | 7.80 |
| APG09748.2 | 25 nM | 0 | LE205 | 0.06 | −2.40 |
| APG09748.2 | 25 nM | 50 | LE205 | 321.00 | 64.20 |
| APG09748.2 | 25 nM | 250 | LE205 | 669.60 | 63.00 |
| APG09748.2 | 25 nM | 500 | LE205 | 706.80 | 52.20 |
| APG09748.2 | 25 nM | 750 | LE205 | 627.00 | 55.20 |
| APG09748.2 | 25 nM | 1000 | LE205 | 534.60 | 46.80 |
| APG09748.1 | 100 nM | 0 | LE201 | −0.42 | −1.80 |
| APG09748.1 | 100 nM | 50 | LE201 | 1063.80 | 155.40 |
| APG09748.1 | 100 nM | 250 | LE201 | 2386.20 | 144.00 |
| APG09748.1 | 100 nM | 500 | LE201 | 3058.80 | 108.60 |
| APG09748.1 | 100 nM | 750 | LE201 | 2974.20 | 99.00 |
| APG09748.1 | 100 nM | 1000 | LE201 | 3282.00 | 113.40 |
| APG09748.1 | 100 nM | 0 | LE205 | 1.20 | −0.36 |
| APG09748.1 | 100 nM | 50 | LE205 | 6.60 | 0.18 |
| APG09748.1 | 100 nM | 250 | LE205 | 27.00 | 1.80 |
| APG09748.1 | 100 nM | 500 | LE205 | 52.80 | 12.60 |
| APG09748.1 | 100 nM | 750 | LE205 | 57.60 | 9.00 |
| APG09748.1 | 100 nM | 1000 | LE205 | 73.80 | 16.20 |
| APG09748.2 | 100 nM | 0 | LE201 | 0.06 | −0.48 |
| APG09748.2 | 100 nM | 50 | LE201 | 25.80 | 9.00 |
| APG09748.2 | 100 nM | 250 | LE201 | 198.00 | 15.00 |
| APG09748.2 | 100 nM | 500 | LE201 | 265.80 | 16.20 |
| APG09748.2 | 100 nM | 750 | LE201 | 277.20 | 19.20 |
| APG09748.2 | 100 nM | 1000 | LE201 | 258.00 | 7.80 |
| APG09748.2 | 100 nM | 0 | LE205 | 0.12 | 0.00 |
| APG09748.2 | 100 nM | 50 | LE205 | 844.80 | 257.40 |
| APG09748.2 | 100 nM | 250 | LE205 | 2091.60 | 270.60 |
| APG09748.2 | 100 nM | 500 | LE205 | 2551.80 | 196.80 |
| APG09748.2 | 100 nM | 750 | LE205 | 2490.60 | 186.00 |
| APG09748.2 | 100 nM | 1000 | LE205 | 2511.00 | 138.00 |

From this experiment, it was concluded that the 100 nM concentration of RNP results generally in a higher cleavage rate of the reporter probe than the 25 nM RNP concentration. In general, reporter cleavage rates are higher at higher concentrations of the reporter oligonucleotides up to 250 to 500 nM reporter concentration, with little benefit observed from further increase in reporter concentrations. Notably, for the TB0089 reporter (detected in the Cy5 channel), there are substantially higher levels of background activity that interfere with target differentiation, especially at reporter concentrations higher than 250 nM. Therefore, it was concluded that reporter concentrations higher than 250 nM would not be beneficial. Both probes seem suitable for observation of target recognition by the RNP.

11.2 APG09748 Trans DNA Cleavage and Effect of Purification on Non-Specific Activity Purified APG09748 was incubated with single guide RNA (sgRNA) in 1× Cutsmart buffer (New England Biolabs B7204S) at a final concentration of 200 nM nuclease and 400 nM sgRNA for 10 min at 37° C. These RNP solutions are then added to solutions of ssDNA—a target or mismatched negative control ssDNA—at a final concentration of 10 nM and a reporter probe (TP0003) at a final concentration of 250 nM in 1.5× Cutsmart buffer (New England Biolabs B7204S). The reporter probe contains a fluorescent dye at the 5' end and a quencher at the 3' end. Cleavage of the reporter probe results in dequenching of the fluorescent dye and thus an increase in fluorescence signal. To monitor fluorescence intensity, 10 µl of each reaction was incubated in a Corning low volume 384-well microplate at 37° C. in a microplate reader (CLARIOstar Plus).

Incubation with target sequences resulted in a substantial increase in fluorescence intensity as a function of time relative to the negative control. The rate of cleavage is summarized as the slope of the linear portion of the fluorescence vs. time function as shown in Table 15.

TABLE 15

| Results of trans DNA cleavage assay | |
| --- | --- |
| ssDNA substrate sequence | Slope (RFU/min) |
| Mismatch (LE111; SEQ ID NO: 142) | 549 |
| Match (LE113; SEQ ID NO: 143) | 7724 |

These data show differentiation of the target sequence from the negative control by the RNPs that is clearly detectable using the cleaved reporter probe.

11.3 PAM Determination Using a Parallel Plasmid DNA Library

Oligonucleotides (LE00680 and LE00688 set forth as SEQ ID NOs: 266 and 267, respectively) containing a target sequence preceded by a 5 nt degenerate PAM sequence) were annealed and cloned into double digested pUC19 plasmid using NEBuilder HiFi DNA Assembly Master Mix (New England Biolabs). Each colony resulting from the transformation of this reaction corresponds to a clonal plasmid DNA sequence so that preparations of plasmid DNA from cultures deriving from single colonies are unique plasmid preparations sampled from the original library. Plasmid preparations were obtained from a sampling of 96 colonies. These preparations were individually subjected to Sanger sequencing to verify their PAM sequence.

Purified APG09748 was incubated with sgRNA (27sg.2) in 1× Cutsmart buffer (New England Biolabs B7204S) at a final concentration of 200 nM nuclease and 400 nM sgRNA for 20 minutes at room temperature.

These RNP solutions were added at a final concentration of 100 nM to solutions of plasmid DNA targets at a final concentration of 8.3 nM and TB0125 and TB0089 reporters (set forth as SEQ ID NOs: 138 and 139, respectively) at 250 nM and 50 nM respectively in 1.5× Cutsmart buffer (New England Biolabs B7204S). To monitor fluorescence intensity, 10 µl of each reaction was incubated in a Corning low volume 384-well microplate at 37° C. in a microplate reader (CLARIOstar Plus).

The plasmid concentration in a minority of samples was either below the target for concentration normalization or the volume of the solution was insufficient to deliver the intended target amount to the reaction well. These samples were not excluded from analysis and are thus expected to contribute to error through inconsistencies between duplicates. Samples which used plasmids that, upon evaluation by Sanger sequencing, were determined to have cross contamination (multiple traces apparent in the PAM region) or alterations in the target sequence were removed from the analysis and their results are not shown below. The results of the analysis are shown in Table 16 below in descending order by slope in the FAM channel

TABLE 16

| PAM sequences | | | |
| --- | --- | --- | --- |
| | | Slope (RFU/min) | |
| PAM | SEQ ID NO | Cy5 channel | FAM channel |
| ATATG | 147 | 111.52 | 1728.13 |
| ATATG | 147 | 102.42 | 1612.86 |
| TATTG | 148 | 137.15 | 846.12 |
| TATTG | 148 | 148.61 | 799.82 |
| CGTTC | 149 | 151.06 | 744.18 |
| CGTTC | 149 | 134.61 | 735.35 |
| TTTTT | 150 | 167.71 | 731.11 |
| TTTTT | 150 | 149.83 | 711.78 |
| CAATC | 151 | 120.84 | 675.71 |
| AATCT | 152 | 134.67 | 622.52 |
| AATCT | 152 | 134.1 | 620.2 |
| CAATC | 151 | 96.94 | 608.58 |
| AAATT | 153 | 152.6 | 607.24 |
| AAATT | 153 | 150.57 | 591.77 |
| CATCC | 154 | 97.34 | 588.7 |
| AGATA | 155 | 214.69 | 579.56 |
| TATTC | 156 | 124.22 | 570.81 |
| ATTTT | 157 | 134.72 | 551.91 |
| AGATA | 155 | 198.45 | 544.81 |
| TATTC | 156 | 108.57 | 538.18 |
| TCTTT | 158 | 141.66 | 532.87 |
| ATTTT | 157 | 107.9 | 526.75 |
| AGATC | 159 | 106.93 | 497.71 |

TABLE 16-continued

| PAM sequences | | | |
|---|---|---|---|
| | | Slope (RFU/min) | |
| PAM | SEQ ID NO | Cy5 channel | FAM channel |
| AATAA | 160 | 78.94 | 484.67 |
| TCTTT | 158 | 117.19 | 484.13 |
| GATCC | 161 | 112.85 | 479.91 |
| GATCC | 161 | 105.04 | 474.94 |
| AGATC | 159 | 106.5 | 473.98 |
| ATTCA | 162 | 115.03 | 473.24 |
| AATAA | 160 | 77.43 | 465.75 |
| AAAAT | 163 | 78.3 | 458.23 |
| TTATC | 164 | 102.14 | 456.73 |
| TATCA | 165 | 106.45 | 448.78 |
| TCACT | 166 | 167.02 | 429.36 |
| CTTAT | 167 | 82.9 | 418.38 |
| TATTG | 148 | 116.08 | 417.94 |
| TCACT | 166 | 160.29 | 415.64 |
| AAAAT | 163 | 56.43 | 411.26 |
| TGATA | 168 | 89.02 | 406.14 |
| TGATA | 168 | 85.99 | 395.57 |
| TACTA | 169 | 90.61 | 391.06 |
| ATTTT | 157 | 113.18 | 382.59 |
| TACTA | 169 | 74.33 | 364.56 |
| ATTTT | 157 | 106.72 | 364.02 |
| TATTG | 148 | 93.95 | 341.36 |
| CTTAT | 167 | 76.12 | 336.8 |
| ATATA | 170 | 83.39 | 326.86 |
| ATATA | 170 | 72.98 | 318.2 |
| TATCA | 165 | 65.41 | 317.53 |
| GACTC | 171 | 56.56 | 302.2 |
| GCTCA | 172 | 22.1 | 293.68 |
| TAACC | 173 | 56.08 | 283.99 |
| CGTGT | 174 | 66.57 | 268.89 |
| TAACC | 173 | 56.55 | 265.45 |
| TTTCG | 175 | 59.55 | 262.91 |
| CGTGT | 174 | 50.71 | 262.37 |
| TTTCG | 175 | 61.42 | 261.65 |
| CAGTA | 176 | 51.81 | 240.09 |
| GCTCA | 172 | 19.08 | 228.08 |
| CAGTA | 176 | 51.09 | 220.25 |

TABLE 16-continued

| PAM sequences | | | |
|---|---|---|---|
| | | Slope (RFU/min) | |
| PAM | SEQ ID NO | Cy5 channel | FAM channel |
| CCCTT | 177 | 17.83 | 136.69 |
| CCTAT | 178 | 40.4 | 125.81 |
| TCCCT | 179 | 39.93 | 124.6 |
| AGGTT | 180 | 40.96 | 117.18 |
| AGGTT | 180 | 40.81 | 114.79 |
| TAACG | 181 | 32.53 | 94.68 |
| AACAG | 182 | 8.19 | 91.72 |
| CCTAT | 178 | 34.51 | 87.57 |
| TGAAC | 183 | 10.22 | 86.38 |
| TAAGT | 184 | 19.35 | 85.12 |
| TCCCT | 179 | 26.67 | 83.02 |
| TAACG | 181 | 27.62 | 79.17 |
| TAACG | 181 | 28.89 | 78.55 |
| TAACG | 181 | 22.23 | 78.36 |
| CTGTA | 185 | 23.27 | 77.06 |
| AGGGG | 186 | 30.8 | 74.4 |
| GCTGT | 187 | 28.3 | 71.54 |
| ATCTA | 188 | 18.73 | 69.15 |
| GCTGT | 187 | 25.61 | 69.06 |
| TTATC | 164 | 22.8 | 68.13 |
| AACAG | 182 | 23.98 | 67.27 |
| TCAGG | 189 | 17.25 | 67.04 |
| ATGTC | 190 | 13.91 | 65.93 |
| TGCTA | 191 | 26.33 | 65.73 |
| TAAAA | 192 | 17.32 | 65.43 |
| ATCTA | 188 | 16.88 | 65.3 |
| CTGTA | 185 | 21.81 | 64.15 |
| GACTC | 171 | 24.05 | 64.02 |
| ATTCA | 162 | 25.04 | 63.87 |
| TGAAC | 183 | 24.53 | 63.64 |
| CCCTT | 177 | 21.35 | 61.95 |
| ATGTC | 190 | 12.99 | 60.6 |
| ATCAG | 193 | 22.32 | 59.63 |
| ATCAG | 193 | 18.55 | 56.58 |
| CGGGG | 194 | 27.86 | 56.28 |
| TAAAA | 192 | 17.72 | 56.03 |
| TTCTC | 195 | 25.7 | 55.83 |

TABLE 16-continued

| PAM sequences | | | |
|---|---|---|---|
| | | Slope (RFU/min) | |
| PAM | SEQ ID NO | Cy5 channel | FAM channel |
| GTCAT | 196 | 23.07 | 55.76 |
| GCGTG | 197 | 17.36 | 55.12 |
| GCGTG | 197 | 22.02 | 55.02 |
| GCAAT | 198 | 15.47 | 54.91 |
| TTCTC | 199 | 21.89 | 54.89 |
| GTCAT | 196 | 17.22 | 54.34 |
| GCAAT | 198 | 17.36 | 53.32 |
| AGCAT | 200 | 22.47 | 52.23 |
| GTCAA | 201 | 14.14 | 52.12 |
| AGAGC | 202 | 19.62 | 51.79 |
| AGAGC | 202 | 15.99 | 50.37 |
| GTGGG | 203 | 22.38 | 50.1 |
| CTGAA | 204 | 21.24 | 49.45 |
| CTGAT | 205 | 12.05 | 49.32 |
| ATGAA | 206 | 17.93 | 49.15 |
| ACCTT | 207 | 19.66 | 49.12 |
| ACCTT | 207 | 22.74 | 49.12 |
| GTCAA | 201 | 13 | 48.21 |
| AACCA | 208 | 17.81 | 48.04 |
| AACCA | 208 | 15.75 | 47.87 |
| GTAAA | 209 | 16.3 | 47.85 |
| TAGGA | 210 | 18.68 | 47.73 |
| CCGAA | 211 | 20.24 | 47.58 |
| AGCAT | 200 | 22.95 | 47.52 |
| CGGGG | 194 | 20.94 | 47.41 |
| GTCAT | 196 | 15.17 | 47.24 |
| CTGAA | 204 | 20.4 | 46.36 |
| GTGGG | 203 | 19.98 | 46.25 |
| TACGA | 212 | 16.79 | 46.18 |
| TGGCT | 213 | 14.81 | 45.75 |
| GTCAT | 196 | 15.55 | 45.51 |
| ATGAA | 206 | 19.11 | 45.09 |
| TAGGA | 210 | 21.65 | 44.94 |
| TTCTC | 199 | 21.44 | 44.76 |
| CCAAG | 214 | 16.98 | 44.61 |
| GTAAA | 209 | 15.35 | 44.59 |
| TGCTT | 215 | 15.79 | 44.54 |

TABLE 16-continued

| PAM sequences | | | |
|---|---|---|---|
| | | Slope (RFU/min) | |
| PAM | SEQ ID NO | Cy5 channel | FAM channel |
| CTAAA | 216 | 12.72 | 44.28 |
| TGCTA | 191 | 16 | 44.14 |
| TACGA | 212 | 16.07 | 44.06 |
| TCGAT | 217 | 22.28 | 43.96 |
| TTCTC | 199 | 15.94 | 42.55 |
| CTGAT | 205 | 16.13 | 42.27 |
| TCAGG | 189 | 11.38 | 41.9 |
| CCAAG | 214 | 11.28 | 41.45 |
| AGGGG | 186 | 16.04 | 41.44 |
| TCGAT | 217 | 18.68 | 40.5 |
| CCGAA | 211 | 15.39 | 39.09 |
| CTAAA | 216 | 10.72 | 30.37 |
| GTAAC | 218 | 4.36 | 9.51 |
| TGCTT | 215 | −0.32 | −0.7 |
| TAAGT | 184 | −0.57 | 1.3 |
| CATCC | 154 | 0.47 | −1.95 |
| TGGCT | 213 | −0.03 | −2.2 |
| GTAAC | 219 | −0.46 | −2.3 |

Sequences with the highest slope appear to comply with the predicted PAM (DTTN set forth as SEQ ID NO: 60) determined by the plasmid depletion assay previously described in International Appl. No. PCT/US2019/068079, which is incorporated by reference in its entirety. In particular, we see a strong preference for "T" in the position two nucleotides 5' of the target. Surprisingly, the most active PAM site observed in this assay (ATATG, SEQ ID NO: 147) did not exactly match the consensus of DTTN (SEQ ID NO: 60), suggesting some level of flexibility in this recognition site.

11.4. Trans ssDNA Cleavage Activity in the Presence of PCR Amplified DNA

PCR amplified targets were generated from genomic DNA (TRAC and VEGF amplicons set forth as SEQ ID NOs: 225 and 226, respectively) using appropriate primers. The VEGF target (set forth as SEQ ID NO: 227) was PCR amplified from HEK293T cell genomic DNA by primers with sequences LE573 and LE578 (set forth as SEQ ID NOs: 228 and 229, respectively). The TRAC target (set forth as SEQ ID NO: 230) was PCR amplified by LE257 and LE258 (set forth as SEQ ID NOs: 231 and 232, respectively).

RNPs were formed by incubation of APG09106.1 nuclease described herein and sgRNA at 0.5 μM and 1 μM respectively in 1×NEBuffer 2 (New England Biolabs) and incubated at room temperature for 20 minutes.

TABLE 17

| Ribonucleoprotein complexes | | | |
| --- | --- | --- | --- |
| RNP | Nuclease | Guide RNA | Intended target |
| APG09106.2 | APG09106.1 | 27sg.2 (SEQ ID NO: 145) | LET 126 amplicon Randomized PAM amplicon |
| APG09106.836 | APG09106.1 | 27sg.836 (SEQ ID NO: 233) | VEGF amplicon |
| APG09106.838 | APG09106.1 | 27sg.838 (SEQ ID NO: 234) | TRAC amplicon |

The cleavage reaction was performed in 1.5×NEBuffer 2 with 1.5 μM ssDNA oligonucleotide reporter with a 5' TEX615 label and a 3' Iowa Black FQ quencher and 100 nM of the respective PCR product. Cleavage of the reporter probe results in dequenching of the fluorescent dye and thus an increase in fluorescence signal. To monitor fluorescence intensity, 10 μl of each reaction was incubated in a Corning low volume 384-well microplate at 37° C. in a microplate reader (CLARIOstar Plus). The results of kinetic analysis are shown in Table 18.

TABLE 18

| Results of trans DNA cleavage assay | | | |
| --- | --- | --- | --- |
| RNP | Target Conc. (nM) | Target | Slope (RFU/min) |
| 28.836 | 30 | TRAC amplicon | 1204 |
| 28.838 | 30 | TRAC amplicon | 8436 |
| 28.838 | 30 | VEGF amplicon | 766 |
| 28.836 | 30 | VEGF amplicon | 3484 |

These results indicate specific activation of trans ssDNA cleavage activity in the presence of PCR amplified DNA from various sources. The activity is dependent on the concentration of the PCR amplified substrate.

11.5 Use of ssDNA Cleavage as a Diagnostic

Due to the capability of these nucleases to generate an optically detectable signal in the presence of a target DNA sequence, they promise utility for implementation into diagnostic devices for the detection of genetic disease or agents of infectious disease, such as bacteria, viruses, or fungi.

A diagnostic procedure may include isolation or amplification of nucleic acids from a sample to be tested. It may also be suitable to use some samples without performing any isolation or purification of nucleic acids, as they may be present in the sample at high enough quantities to be detectable without amplification (such as PCR) or free of materials that interfere with detection or signal production.

RNPs formed as described in the other examples could then be exposed to the sample (or processed sample as described in the preceding paragraph) along with a reporter, such as the fluorophore and quencher modified ssDNA oligonucleotides used in previous examples, or some other sort of ssDNA substrate that produces a visible or otherwise easily detectable signal when cleaved. If using fluorophore-quencher conjugated DNA oligonucleotides (as in the previously described examples), these can be detected using a fluorimeter as described in previous examples. To simplify detection, an endpoint assay can be performed instead of the kinetic assays described above, meaning that the assays can be performed for a fixed time and read out at the end of this elapsed time, relative to positive and negative controls.

These reagents may also be integrated into a lateral flow testing device which allows for the detection of a given disease-causing agent or specific nucleic acid sequence (such as a diseased allele in an individual) with very little instrumentation. In this assay, the ssDNA reporter would be conjugated to multiple molecules suitable for antibody or affinity reagent capture, such as fluorescein, biotin, and/or digoxigenin.

That which is claimed:

1. A nucleic acid molecule comprising a polynucleotide encoding an RNA-guided nuclease (RGN) polypeptide, wherein said RGN polypeptide is selected from the group consisting of:
a) an RGN polypeptide comprising an amino acid sequence having at least 95% sequence identity to SEQ ID NO: 117, 30, 75, 1, 9, 16, 23, 38, 46, 61, 69, 82, 89, 95, 103, or 110; and
b) an RGN polypeptide comprising the amino acid sequence set forth as SEQ ID NO: 54;
wherein said polynucleotide encoding an RGN polypeptide is operably linked to a promoter heterologous to said polynucleotide.

2. The nucleic acid molecule of claim 1, wherein said RGN polypeptide of a) is nuclease inactive or is capable of functioning as a nickase.

3. The nucleic acid molecule of claim 1, wherein the RGN polypeptide is operably fused to a base-editing polypeptide.

4. A vector comprising the nucleic acid molecule of claim 1.

5. The vector of claim 4, further comprising at least one nucleotide sequence encoding a guide RNA (gRNA) capable of hybridizing to a target DNA sequence, and wherein the RNA comprises a CRISPR RNA comprising a CRISPR repeat sequence having at least 95% sequence identity to SEQ ID NO: 118, 31, 76, 2, 10, 17, 24, 39, 47, 55, 62, 70, 83, 90, 96, 104, or 111.

6. The vector of claim 5, wherein said gRNA comprises a tracrRNA having at least 95% sequence identity to SEQ ID NO: 119, 32, 77, 3, 11, 18, 25, 40, 48, 56, 63, 71, 84, 91, 97, 105, or 112.

7. A cell comprising the nucleic acid molecule of claim 1.

8. A nucleic acid molecule comprising
(A) a polynucleotide encoding a CRISPR RNA (crRNA), wherein said crRNA comprises a spacer sequence and a CRISPR repeat sequence, wherein said CRISPR repeat sequence comprises a nucleotide sequence having at least 95% sequence identity to SEQ ID NO: 118, 31, 76, 2, 10, 17, 24, 39, 47, 55, 62, 70, 83, 90, 96, 104, or 111, and wherein said CRISPR repeat sequence is capable of hybridizing to a trans-activating CRISPR RNA (tracrRNA);
or
(B) a polynucleotide encoding a tracrRNA comprising a nucleotide sequence having at least 95% sequence identity to SEQ ID NO: 119, 32, 77, 3, 11, 18, 25, 40, 48, 56, 63, 71, 84, 91, 97, 105, or 112, wherein said tracrRNA of (B) is capable of hybridizing to a CRISPR repeat sequence of a crRNA;

wherein a guide RNA comprising:
i) said crRNA of (A);
or
ii) said tracrRNA of (B) and a crRNA comprising a spacer sequence and a CRISPR repeat sequence that is capable of hybridizing to the tracrRNA of (B)
is capable of hybridizing to a target DNA sequence of a DNA molecule in a sequence specific manner through the spacer sequence of said crRNA of (A) or (B) when said guide RNA is bound to an RNA-guided nuclease (RGN) polypeptide, and
wherein said polynucleotide encoding said crRNA of (A) or said tracrRNA of (B) is operably linked to a promoter heterologous to said polynucleotide.

9. A vector comprising the nucleic acid molecule of claim 8.

10. A system for binding a target DNA sequence of a DNA molecule, said system comprising:
a) a guide RNA (gRNA), or a polynucleotide comprising a nucleotide sequence encoding the gRNA, wherein the gRNA is capable of hybridizing to said target DNA sequence; and
b) an RNA-guided nuclease (RGN) polypeptide comprising an amino acid sequence selected from the group consisting of:
i) an amino acid sequence having at least 95% sequence identity to SEQ ID NO: 117, 30, 75, 1, 9, 16, 23, 38, 46, 61, 69, 82, 89, 95, 103, or 110; and
ii) the amino acid sequence set forth as SEQ ID NO: 54;
or a polynucleotide comprising a nucleotide sequence encoding the RGN polypeptide;
wherein at least one of said nucleotide sequence encoding the gRNA and encoding the RGN polypeptide is operably linked to a promoter heterologous to said nucleotide sequence.

11. The system of claim 10, wherein the target DNA sequence is within a eukaryotic cell.

12. The system of claim 10, wherein said RGN polypeptide of b) i) is nuclease inactive or is capable of functioning as a nickase.

13. The system of claim 10, wherein said system further comprises one or more donor polynucleotides or one or more nucleotide sequences encoding the one or more donor polynucleotides.

14. A method for binding a target DNA sequence of a DNA molecule comprising delivering a system according to claim 10, to said target DNA sequence or a cell comprising the target DNA sequence.

15. A method for cleaving or modifying a target DNA sequence of a DNA molecule comprising delivering a system according to claim 10, to said target DNA sequence or a cell comprising the DNA molecule and cleavage or modification of said target DNA sequence occurs.

16. A method for cleaving and/or modifying a target DNA sequence of a DNA molecule, comprising contacting the DNA molecule with:

a) an RNA-guided nuclease (RGN) polypeptide, wherein said RGN comprises an amino acid sequence selected from the group consisting of:

i) an amino acid sequence having at least 95% sequence identity to SEQ ID NO: 117, 30, 75, 1, 9, 16, 23, 38, 46, 61, 69, 82, 89, 95, 103, or 110; and ii) the amino acid sequence set forth as SEQ ID NO: 54; and b) one or more guide RNAs capable of targeting the RGN of (a) to the target DNA sequence;

wherein the one or more guide RNAs hybridize to the target DNA sequence, thereby directing said RGN polypeptide to bind to said target DNA sequence and cleavage and/or modification of said target DNA sequence occurs.

17. The method of claim 16, wherein said RGN polypeptide is nuclease inactive or functions as a nickase.

18. The method of claim 16, wherein the target DNA sequence is within a eukaryotic cell.

19. The method of claim 16, further comprising culturing a cell comprising said target DNA sequence under conditions in which the RGN polypeptide is expressed and cleaves the target DNA sequence to produce a DNA molecule comprising a modified DNA sequence; and selecting a cell comprising said modified target DNA sequence.

20. The nucleic acid molecule of claim 1, wherein the RGN polypeptide comprises the amino acid sequence of SEQ ID NO: 117, 30, 75, 1, 9, 16, 23, 38, 46, 61, 69, 82, 89, 95, 103, or 110.

21. The nucleic acid molecule of claim 3, wherein the base-editing polypeptide is a deaminase.

22. The nucleic acid molecule of claim 1, wherein the RGN polypeptide is operably fused to an effector domain.

23. The nucleic acid molecule of claim 22, wherein the effector domain is a cleavage domain, a deaminase domain, or an expression modulator domain.

24. The nucleic acid molecule of claim 23, wherein the expression modulator domain is an epigenetic modification domain, a transcriptional repressor domain, or a transcriptional activation domain.

25. The nucleic acid molecule of claim 22, wherein the effector domain is operably fused at the N-terminus or at the C-terminus of the RGN polypeptide.

26. The nucleic acid molecule of claim 22, wherein the effector domain is operably fused at an internal location of the RGN polypeptide.

27. The system of claim 10, wherein the RGN polypeptide comprises the amino acid sequence of SEQ ID NO: 117, 30, 75, 1, 9, 16, 23, 38, 46, 61, 69, 82, 89, 95, 103, or 110.

28. The system of claim 10, wherein the RGN polypeptide is operably linked to a base-editing polypeptide.

29. The system of claim 28, wherein the base-editing polypeptide is a deaminase.

30. The system of claim 10, wherein the RGN polypeptide is operably fused to an effector domain.

31. The system of claim 30, wherein the effector domain is a cleavage domain, a deaminase domain, or an expression modulator domain.

32. The system of claim 31, wherein the expression modulator domain is an epigenetic modification domain, a transcriptional repressor domain, or a transcriptional activation domain.

33. The system of claim 30, wherein the effector domain is operably fused at the N-terminus or at the C-terminus of the RGN polypeptide.

34. The system of claim 30, wherein the effector domain is operably fused at an internal location of the RGN polypeptide.

35. The method of claim 14, wherein the target DNA sequence is cleaved and/or modified.

36. The method of claim 14, wherein the target DNA sequence is not cleaved and/or modified.

37. The method of claim 16, wherein the RGN polypeptide comprises the amino acid sequence of SEQ ID NO: 117, 30, 75, 1, 9, 16, 23, 38, 46, 61, 69, 82, 89, 95, 103, or 110.

38. The method of claim 16, wherein the RGN polypeptide is operably linked to a base-editing polypeptide.

* * * * *